(12) United States Patent
Herold et al.

(10) Patent No.: US 7,842,688 B2
(45) Date of Patent: Nov. 30, 2010

(54) ORGANIC COMPOUNDS

(75) Inventors: Peter Herold, Basel (CH); Robert Mah, Muttenz (CH); Stefan Stutz, Basel (CH); Aleksandar Stojanovic, Basel (CH); Vincenzo Tschinke, Binningen (CH); Nathalie Jotterand, Basel (CH)

(73) Assignee: Novartis Pharma AG, Basel (CH)

( * ) Notice: Subject to any disclaimer, the term of this patent is extended or adjusted under 35 U.S.C. 154(b) by 66 days.

(21) Appl. No.: 12/068,443

(22) Filed: Feb. 6, 2008

(65) Prior Publication Data

US 2009/0012055 A1 Jan. 8, 2009

Related U.S. Application Data

(62) Division of application No. 10/574,108, filed as application No. PCT/EP2004/052389 on Sep. 30, 2004.

(30) Foreign Application Priority Data

Oct. 1, 2003 (CH) .................... 1669/03
Feb. 27, 2004 (CH) .................... 0343/04

(51) Int. Cl.
*C07D 401/12* (2006.01)
*A61K 31/4427* (2006.01)

(52) U.S. Cl. ............ 514/230.5; 544/90; 544/105

(58) Field of Classification Search ............ 544/90, 544/105; 514/230.5
See application file for complete search history.

(56) References Cited

U.S. PATENT DOCUMENTS

| 6,051,712 | A | 4/2000 | Binggeli et al. |
| 6,150,526 | A | 11/2000 | Binggeli et al. |
| 6,197,959 | B1 | 3/2001 | Breu et al. |
| 6,376,672 | B1 | 4/2002 | Breu et al. |
| 2002/0087002 | A1 | 7/2002 | Breu et al. |
| 2004/0204455 | A1 | 10/2004 | Cody et al. |

FOREIGN PATENT DOCUMENTS

| WO | 97/09311 | 3/1997 |
| WO | 00/64873 | 11/2000 |
| WO | 00/64887 | 11/2000 |
| WO | 2004/002466 | 1/2004 |
| WO | 2004/089903 | 10/2004 |

OTHER PUBLICATIONS

International Search Report issued on Mar. 1, 2005 in the International (PCT) Application PCT/EP2004/052389, on which the parent application of the present divisional application is based.
Eric Vieira et al., "Substituted Piperidines—Highly Potent Renin Inhibitors Due to Induced Fit Adaptation of the Active Site", Bioorganic & Medicinal Chemistry Letters, vol. 9, pp. 1397-1402, XP002317176, 1999.
Rolf Güller et al., "Piperidine-Renin Inhibitors Compounds with Improved Physicochemical Properties", Bioorganic & Medicinal Chemistry Letters, ISSN: 0960-894X, vol. 9, No. 10, pp. 1403-1408, XP002317171, 1999.
H.P. Märki et al., "Piperidine renin inhibitors: from leads to drug candidates", Farmaco, 56(1-2) ISSN: 0014-827X, pp. 21-27, XP002317172, 2001.
Daiga M. Helmeste et al., "Serotonin uptake inhibitors modulate intracellular Ca2+ mobilization in platelets", European Journal of Pharmacology, vol. 288, pp. 373-377, XP002317173, 1995.
Matthew G. Bursavich et al., "From Peptides to Non-Peptide Peptidomimetics: Design and Synthesis of New Piperidine Inhibitors of Aspartic Peptidases", Organic Letters, vol. 3, No. 15, pp. 2317-2320, XP002317174, 2001.
Matthew G. Bursavich et al., "Solid-Phase Synthesis of Aspartic Peptidase Inhibitors: 3-Alkoxy-4-Aryl Piperidines", Organic Letters, vol. 3, No. 17, pp. 2625-2628, XP002317175, 2001.

*Primary Examiner*—Kahsay T Habte
(74) *Attorney, Agent, or Firm*—Wenderoth, Lind & Ponack, L.L.P.

(57) ABSTRACT

Novel substituted piperidines of the general formulae (I) and (II)

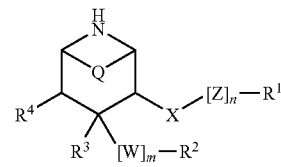

(I)

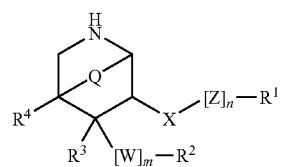

(II)

with the substituent definitions as explained in detail in the description are described. The compounds are suitable in particular as renin inhibitors and are highly potent.

14 Claims, No Drawings

ORGANIC COMPOUNDS

This application is a Divisional application of Ser. No. 10/574,108, filed Mar. 31, 2006, which is 371 application of PCT/EP2004/052389, filed Sep. 30, 2004.

The present invention relates to novel substituted piperidines, to processes for their preparation and to the use of the compounds as medicaments, in particular as renin inhibitors.

Piperidine derivatives for use as medicaments are disclosed, for example, by WO 97/09311. However, with regard especially to renin inhibition, there is still a need for highly potent active ingredients. In this context, the improvement of the pharmacokinetic properties is at the forefront. These properties directed to better bioavailability are, for example, absorption, metabolic stability, solubility or lipophilicity.

The invention therefore provides substituted piperidines of the general formulae (I) and (II)

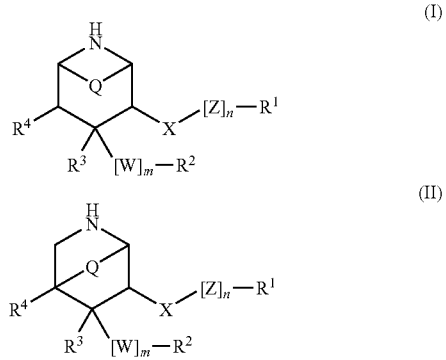

where (A) $R^1$ in formula (I) is substituted or unsubstituted oxazolyl, indolyl, pyrrolyl, pyrazolyl, triazinyl, 2-oxodihydrobenzo[d][1,3]oxazinyl, 4-oxodihydroimidazolyl, 5-oxo-4H-[1,2,4]triazinyl, 3-oxo-4H-benzo[1,4]thiazinyl, tetrahydroquinoxalinyl, 1,1,3-trioxodihydro-2H-1$\lambda^6$-benzo[1,4]thiazinyl, 1-oxo-pyridyl, dihydro-2H-benzo[1,4]oxazinyl, 2-oxotetrahydrobenzo[e][1,4]diazepinyl, 2-oxodihydrobenzo[e][1,4]diazepinyl, 1H-pyrrolizinyl, phthalazinyl, 1-oxo-3H-isobenzofuranyl, 4-oxo-3H-thieno[2,3-d]pyrimidinyl, 3-oxo-4H-benzo[1,4]oxazinyl, [1,5]naphthyridyl, dihydro-2H-benzo[1,4]thiazinyl, 1,1-dioxodihydro-2H-benzo[1,4]thiazinyl, 2-oxo-1H-pyrido[2,3-b][1,4]oxazinyl, dihydro-1H-pyrido[2,3-b][1,4]oxazinyl, 1H-pyrrolo[2,3-b]pyridyl, benzo[1,3]dioxolyl, benzooxazolyl, 2-oxobenzooxazolyl, 2-oxo-1,3-dihydroindolyl, 2,3-dihydroindolyl, indazolyl, benzofuranyl, dihydrobenzofuranyl, tetrahydropyranyl, 2-oxopiperidinyl or 2-oxoazepanyl; or (B) $R^1$ in formula (I) is aryl or heterocyclyl which is substituted by at least one substituent selected from $C_{1-6}$-alkoxy-$C_{1-6}$-alkoxy-$C_{1-6}$-alkyl, $C_{3-8}$-cycloalkyl-$C_{1-6}$-alkyl, $C_{1-6}$-alkoxycarbonyl, $C_{0-6}$-alkylcarbonylamino, $C_{0-6}$-alkylcarbonylamino-$C_{1-6}$-alkyl, $C_{1-6}$-alkylcarbonylamino-$C_{1-6}$-alkoxy, (N—$C_{1-6}$-alkyl)-$C_{0-6}$-alkylcarbonylamino-$C_{1-6}$-alkyl, (N—$C_{1-6}$-alkyl)-$C_{1-6}$-alkylcarbonylamino-$C_{1-6}$-alkoxy, $C_{3-8}$-cycloalkylcarbonylamino-$C_{1-6}$-alkyl, $C_{3-8}$-cycloalkylcarbonylamino-$C_{1-6}$-alkoxy, $C_{1-6}$-alkoxy-$C_{1-6}$-alkyl, hydroxy-$C_{1-6}$-alkyl, hydroxy-$C_{1-6}$-alkoxy-$C_{1-6}$-alkyl, hydroxy-$C_{1-6}$-alkoxy-$C_{1-6}$-alkoxy, $C_{1-6}$-alkoxycarbonylamino-$C_{1-6}$-alkyl, $C_{1-6}$-alkoxycarbonylamino-$C_{1-6}$-alkoxy, $C_{1-6}$-alkylaminocarbonylamino-$C_{1-6}$-alkyl, $C_{1-6}$-alkylaminocarbonylamino-$C_{1-6}$-alkoxy, $C_{1-6}$-alkylaminocarbonyl-$C_{1-6}$-alkyl, $C_{1-6}$-alkylaminocarbonyl-$C_{1-6}$-alkoxy, $C_{1-6}$-alkylaminocarbonyl-$C_{1-6}$-alkoxy-$C_{1-6}$-alkyl, di-$C_{1-6}$-alkylaminocarbonyl-$C_{1-6}$-alkyl, di-$C_{1-6}$-alkylaminocarbonyl-$C_{1-6}$-alkoxy, $C_{1-6}$-alkylcarbonyloxy-$C_{1-6}$-alkyl, $C_{1-6}$-alkoxycarbonyloxy-$C_{1-6}$-alkyl, $C_{1-6}$-alkylcarbonyloxy-$C_{1-6}$-alkoxy, cyano-$C_{1-6}$-alkyl, cyano-$C_{1-6}$-alkoxy, $C_{1-6}$-alkoxycarbonyl-$C_{1-6}$-alkyl, $C_{1-6}$-alkoxycarbonyl-$C_{1-6}$-alkoxy, $C_{1-6}$-alkylsulphonylamino-$C_{1-6}$-alkyl, $C_{1-6}$-alkylsulphonylamino-$C_{1-6}$-alkoxy, (N—$C_{1-6}$-alkyl)-$C_{1-6}$-alkylsulphonylamino-$C_{1-6}$-alkyl, (N—$C_{1-6}$-alkyl)-$C_{1-6}$-alkylsulphonylamino-$C_{1-6}$-alkoxy, amino-$C_{1-6}$-alkyl, amino-$C_{1-6}$-alkoxy, $C_{1-6}$-alkylamino-$C_{1-6}$-alkyl, $C_{1-6}$-alkylamino-$C_{1-6}$-alkoxy, di-$C_{1-6}$-alkylamino-$C_{1-6}$-alkyl, di-$C_{1-6}$-alkylamino-$C_{1-6}$-alkoxy, $C_{1-6}$-alkylsulphonyl-$C_{1-6}$-alkyl, $C_{1-6}$-alkylsulphonyl-$C_{1-6}$-alkoxy, carboxy-$C_{1-6}$-alkyl, carboxy-$C_{1-6}$-alkoxy, carboxy-$C_{1-6}$-alkoxy-$C_{1-6}$-alkyl, $C_{1-6}$-alkoxy-$C_{1-6}$-alkylcarbonyl, acyl-$C_{1-6}$-alkoxy-$C_{1-6}$-alkyl, (N—$C_{1-6}$-alkyl)-$C_{1-6}$-alkoxycarbonylamino, (N-hydroxy)-$C_{1-6}$-alkylaminocarbonyl-$C_{1-6}$-alkyl, (N-hydroxy)-$C_{1-6}$-alkylaminocarbonyl-$C_{1-6}$-alkoxy, (N-hydroxy)aminocarbonyl-$C_{1-6}$-alkyl, (N-hydroxy)aminocarbonyl-$C_{1-6}$-alkoxy, $C_{1-6}$-alkoxyaminocarbonyl-$C_{1-6}$-alkyl, $C_{1-6}$-alkoxyaminocarbonyl-$C_{1-6}$-alkoxy, (N—$C_{1-6}$-alkoxy)-$C_{1-6}$-alkylaminocarbonyl-$C_{1-6}$-alkyl, (N—$C_{1-6}$-alkoxy)-$C_{1-6}$-alkylaminocarbonyl-$C_{1-6}$-alkoxy, (N-acyl)-$C_{1-6}$-alkoxy-$C_{1-6}$-alkylamino, $C_{1-6}$-alkoxy-$C_{1-6}$-alkylcarbamoyl, (N—$C_{1-6}$-alkyl)-$C_{1-6}$-alkoxy-$C_{1-6}$-alkylcarbamoyl, $C_{1-6}$-alkoxy-$C_{1-6}$-alkylcarbonyl, $C_{1-6}$-alkoxy-$C_{1-6}$-alkylcarbonylamino, (N—$C_{1-6}$-alkyl)-$C_{1-6}$-alkoxy-$C_{1-6}$-alkylcarbonylamino, carbamoyl-$C_{1-6}$-alkyl, carbamoyl-$C_{1-6}$-alkoxy, $C_{1-6}$-alkylcarbamoyl, di-$C_{1-6}$-alkylcarbamoyl, $C_{1-6}$-alkylsulphonyl, $C_{1-6}$-alkylamidinyl, acetamidinyl-$C_{1-6}$-alkyl, O-methyloximyl-$C_{1-6}$-alkyl and O,N-dimethylhydroxylamino-$C_{1-6}$-alkyl; or (C) $R^1$ in formula (I) is aryl or heterocyclyl which is substituted by at least one substituent selected from [1,2,4]-triazol-1-ylalkyl, [1,2,4]-triazol-1-ylalkoxy, [1,2,4]-triazol-4-ylalkyl, [1,2,4]-triazol-4-ylalkoxy, [1,2,4]-oxadiazol-5-ylalkyl, [1,2,4]-oxadiazol-5-ylalkoxy, 3-methyl-[1,2,4]-oxadiazol-5-ylalkyl, 3-methyl-[1,2,4]-oxadiazol-5-ylalkoxy, 5-methyl-[1,2,4]-oxadiazol-3-ylalkyl, 5-methyl-[1,2,4]-oxadiazol-3-ylalkoxy, tetrazol-1-ylalkyl, tetrazol-1-ylalkoxy, tetrazol-2-ylalkyl, tetrazol-2-ylalkoxy, tetrazol-5-ylalkyl, tetrazol-5-ylalkoxy, 5-methyltetrazol-1-ylalkyl, 5-methyltetrazol-1-ylalkoxy, thiazol-4-ylalkyl, thiazol-4-ylalkoxy, oxazol-4-ylalkyl, oxazol-4-ylalkoxy, 2-oxopyrrolidinylalkyl, 2-oxopyrrolidinylalkoxy, imidazolylalkyl, imidazolylalkoxy, 2-methylimidazolylalkyl, 2-methylimidazolylalkoxy, dioxolanyl, dioxanyl, dithiolanyl, dithianyl, pyrrolidinyl, piperidinyl, piperazinyl, pyrrolyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 3-acetamidomethylpyrrolidinyl, 3-$C_{1-6}$-alkoxy-$C_{1-6}$-alkylpyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxoimidazolidinyl, 2-oxooxazolidinyl, 2-oxopyrrolidinyl, 2-oxo-[1,3]oxazinyl, 2-oxotetrahydropyrimidinyl, 2-oxooxazolidinyl-$C_{1-6}$-alkyl, 2-oxooxazolidinyl-$C_{1-6}$-alkoxy, 1-$C_{1-6}$-alkoxy-$C_{1-6}$-alkylimidazol-2-yl, 1-$C_{1-6}$- alkoxy-$C_{1-6}$-alkyltetrazol-5-yl, 5-$C_{1-6}$-alkoxy-$C_{1-6}$-alkyltetrazol-1-yl and 2-$C_{1-6}$-alkoxy-$C_{1-6}$-alkyl-4-oxoimidazol-1-yl; or (D) $R^1$ in formula (I) is aryl or heterocyclyl if n is 0 and X is —O—CH—$R^{11}$—CO—$NR^9$—, or if n and m are each 0 and X is —O—CH—$R^{11}$— and $R^2$ is phenyl substituted by $C_{1-6}$-alkoxybenzyloxy-$C_{1-6}$-alkoxy; or (E) $R^1$ in formula (I) is aryl or heterocyclyl if n is 1 and Z is -alk-$NR^9$—, where alk is $C_{1-6}$-alkylene; or (F) $R^1$ in formula (I) is aryl or heterocyclyl if $R^2$ is tetrazolyl or imidazolyl which may be substituted by 1-3 halogen, hydroxyl, cyano, trifluoromethyl, $C_{1-6}$-alkyl, halo-$C_{1-6}$-alkyl, hydroxy-$C_{1-6}$-alkyl, $C_{1-6}$-alkoxy-$C_{1-6}$-alkyl, cyano-$C_{1-6}$-alkyl, carboxy-$C_{1-6}$-alkyl, $C_{1-6}$-alkanoyloxy-$C_{1-6}$-alkyl, $C_{1-6}$-alkoxycarbonyloxy-$C_{1-6}$-alkyl, $C_{1-6}$-alkoxycarbonyl, or $C_{1-6}$-alkoxy groups, or a $C_{1-6}$-alkylenedioxy group, and/or may be substituted by an L1-T1-L2-T2-L3-T3-L4-T4-L5-U radical; or (G) $R^1$ in formula (II) is aryl or heterocyclyl;

$R^2$ is phenyl, naphthyl, acenaphthyl, cyclohexyl, pyridyl, pyrimidinyl, pyrazinyl, oxopyridinyl, diazinyl, triazolyl, thienyl, oxazolyl, oxadiazolyl, thiazolyl, pyrrolyl, furyl, tetrazolyl or imidazolyl which radicals may be substituted by 1-3 halogen, hydroxyl, cyano, trifluoromethyl, $C_{1-6}$-alkyl, halo-$C_{1-6}$-alkyl, hydroxy-$C_{1-6}$-alkyl, $C_{1-6}$-alkoxy-$C_{1-6}$-alkyl, cyano-$C_{1-6}$-alkyl, carboxy-$C_{1-6}$-alkyl, $C_{1-6}$-alkanoyloxy-$C_{1-6}$-alkyl, $C_{1-6}$-alkoxycarbonyloxy-$C_{1-6}$-alkyl, $C_{1-6}$-alkoxycarbonyl, or $C_{1-6}$-alkoxy groups, or a $C_{1-6}$-alkylenedioxy group, and/or by an L1-T1-L2-T2-L3-T3-L4-T4-L5-U radical;

L1, L2, L3, L4 and L5 are each independently a bond, $C_{1-8}$-alkylene, $C_{2-8}$-alkenylene or $C_{2-8}$-alkynylene, or are absent;

T1, T2, T3 and T4 are each independently (a) a bond, or are absent, or are one of the groups (b) —CH(OH)—

(c) —CH($OR^6$)—

(d) —CH($NR^5R^6$)—

(e) —CO—

(f) —$CR^7R^{11}$—

(g) —O— or —$NR^6$—

(h) —S(O)$_{0-2}$—

(i) —$SO_2NR^6$—

(j) —$NR^6SO_2$—

(k) —$CONR^6$—

(l) —$NR^6CO$—

(m) —O—CO—

(n) —CO—O—

(o) —O—CO—O—

(p) O—CO—$NR^6$—

(q) —N($R^6$)—CO—N($R^6$)—

(r) —N($R^6$)—CO—O—

(s) pyrrolidinylene, piperidinylene or piperazinylene (t) —C($R^{11}$)($R^{12}$)—, where the bonds starting from (b)-(t) lead to a saturated or aromatic carbon atom of the adjacent group if the bond starts from a heteroatom, and where not more than two (b)-(f) groups, three (g)-(h) groups and one (i)-(t) group are present;

$R^3$ is hydrogen, hydroxyl, $C_{1-6}$-alkoxy or $C_{2-6}$-alkenyloxy;

$R^4$ is hydrogen, $C_{1-6}$-alkyl, $C_{2-6}$-alkenyl, $C_{1-6}$-alkoxy, hydroxy-$C_{1-6}$-alkyl, $C_{1-6}$-alkoxy-$C_{1-6}$-alkyl, benzyl, oxo, or a $R^{4a}$—Z1-X1 group where $R^{4a}$ is (a) H—

(b) $C_{1-6}$-alkyl- (c) $C_{2-6}$-alkenyl- (d) hydroxy-$C_{1-6}$-alkyl- (e) polyhydroxy-$C_{1-6}$-alkyl- (f) $C_{1-6}$-alkyl-O—$C_{1-6}$-alkyl- (g) aryl- (h) heterocyclyl- (i) arylalkyl- (j) heterocyclylalkyl- (k) aryloxyalkyl- (l) heterocyclyloxyalkyl- (m) ($R^5,R^6$)N—($CH_2$)$_{1-3}$—

(n) ($R^5,R^6$)N—

(o) $C_{1-6}$-alkyl-S(O)$_{0-2}$—

(p) aryl-S(O)$_{0-2}$—

(q) heterocyclyl-S(O)$_{0-2}$—

(r) HO—$SO_3$— or salts thereof (s) $H_2N$—C(NH)—NH—

(t) NC— and the bonds starting from (n)-(t) lead to a carbon atom of the adjacent group and this carbon atom is saturated if the bond starts from a heteroatom;

Z1

(a) is a bond, is absent, or is one of the groups (b) $C_{1-6}$-alkylene- (c) $C_{2-6}$-alkenylene- (d) —O—, —N($R^{11}$)—, —S(O)$_{0-2}$—

(e) —CO—

(f) —CO—CO—

(g) —O—CO—O—

(h) —O—CO—N($R^{11}$)—

(i) —N($R^{11}$)—CO—O—

(j) —CO—N($R^{11}$)—

(k) —N($R^{11}$)—CO—

(l) —N($R^{11}$)—CO—N($R^{11}$)—

(m) —CH($OR^9$)— and the bonds starting from (d) and (f)-(m) lead to a carbon atom of the adjacent group and this carbon atom is saturated if the bond starts from a heteroatom;

X1

(a) is a bond, is absent, or is one of the groups (b) —O—

(c) —N($R^{11}$)—

(d) —S(O)$_{0-2}$—

(e) —(CH$_2$)$_{1-3}$—;

or $R^3$ and $R^4$ in formula (I) together are a bond;

$R^5$ and $R^6$ are each independently hydrogen, $C_{1-6}$-alkyl, $C_{2-6}$-alkenyl, aryl-$C_{1-6}$-alkyl or acyl, or, together with the nitrogen atom to which they are bonded, are a 5- or 6-membered heterocyclic ring which may contain an additional nitrogen, oxygen or sulphur atom or a —SO— or —SO$_2$— group, and the additional nitrogen atom may optionally be substituted by C: 6-alkyl radicals;

$R^7$ and $R^8$, together with the carbon atom to which they are bonded, are a 3-7-membered ring which may contain one or two —O— or —S— atoms or —SO— or —SO$_2$— groups;

$R^9$ is hydrogen, C: 6-alkyl, $C_{1-6}$-alkoxy-$C_{1-6}$-alkyl, acyl or arylalkyl;

$R^{10}$ is carboxyalkyl, alkoxycarbonylalkyl, alkyl or hydrogen;

$R^{11}$ is hydrogen or $C_{1-6}$-alkyl;

$R^{12}$ is hydrogen or $C_{1-6}$-alkyl;

U is hydrogen, $C_{1-6}$-alkyl, $C_{3-8}$-cycloalkyl, cyano, optionally substituted $C_{3-8}$-cycloalkyl, aryl, or heterocyclyl;

Q is ethylene or is absent (formula I) or is ethylene or methylene (formula II);

X is a bond, oxygen or sulphur, or is a >CH—$R^{11}$, >CHO$R^9$, —O—CO—, >CO, >C=NO$R^{10}$, —O—CH$R^{11}$— or —O—CH$R^{11}$—CO—N$R^9$— group and the bond starting from an oxygen or sulphur atom leads to a saturated carbon atom of the Z group or to $R^1$;

W is oxygen or sulphur;

Z is $C_{1-6}$-alkylene, $C_{2-6}$-alkenylene, hydroxy-$C_{1-6}$-alkylidene, —O—, —S—, —O-alk-, —S-alk-, -alk-O—, -alk-S— or -alk-N$R^9$—, where alk is $C_{1-6}$-alkylene; and where (a) if Z is —O— or —S—, X is >CH—$R^{11}$ and either $R^2$ contains an L1-T1-L2-T2-L3-T3-L4-T4-L5-U substituent or $R^4$ is a substituent other than hydrogen as defined above;

(b) if Z is —O-alk- or —S-alk-, X is >CH—$R^{11}$; and (c) if X is a bond, Z is $C_{2-6}$-alkenylene, -alk-O— or -alk-S—, n is 0 or 1;

m is 0 or 1;

and pharmaceutically usable salts thereof.

Examples of alkyl and alkoxy radicals are $C_{1-6}$-alkyl and $C_{1-6}$-alkoxy radicals such as methyl, ethyl, n-propyl, isopropyl, n-butyl, isobutyl, sec-butyl, tert-butyl, pentyl, hexyl, and methoxy, ethoxy, propoxy, isopropoxy, butoxy, isobutoxy, sec-butoxy and tert-butoxy respectively. $C_{1-6}$-Alkylenedioxy radicals are preferably methylenedioxy, ethylenedioxy and propylenedioxy. Examples of $C_{1-6}$-alkanoyl radicals are acetyl, propionyl and butyryl. Cycloalkyl is a saturated, cyclic hydrocarbon radical having 3-12 carbon atoms, i.e. cyclopropyl, cyclobutyl, cyclopentyl, cyclohexyl, cycloheptyl, bicyclo[2.2.1]heptyl, cyclooctyl, bicyclo[2.2.2]octyl and adamantyl. $C_{1-8}$-Alkylene radicals are, for example, methylene, ethylene, propylene, 2-methylpropylene, tetra-, penta- and hexamethylene; $C_{2-4}$-alkenylene radicals are, for example, vinylene and propenylene; $C_{2-8}$-alkynylene radicals are, for example, ethynylene; acyl radicals are alkanoyl radicals, preferably $C_{1-6}$-alkanoyl radicals, or aroyl radicals such as benzoyl. Aryl denotes mono- or polycyclic aromatic radicals which may be mono- or polysubstituted, for example phenyl, substituted phenyl, naphthyl, substituted naphthyl, tetrahydronaphthyl or substituted tetrahydronaphthyl. Examples of substituents on such aryl radicals or on heterocyclyl radicals are $C_{1-6}$-alkyl, trifluoromethyl, trifluoromethoxy, nitro, amino, $C_{2-6}$-alkenyl, $C_{1-6}$-alkoxy, $C_{1-6}$-alkylsulphinyl, $C_{1-6}$-alkylcarbonyloxy, hydroxyl, halogen, cyano, carbamoyl, carboxyl and $C_{1-6}$-alkylenedioxy, and also phenyl, phenoxy, phenylthio, phenyl-$C_{1-6}$-alkyl or phenyl-$C_{1-6}$-alkoxy each optionally substituted by halogen, $C_{1-6}$-alkyl, $C_{1-6}$-alkoxy or dihydroxy-$C_{1-6}$-alkylaminocarbonyl. Further examples of substituents on aryl or on heterocyclyl radicals are oxo, $C_{1-6}$-alkoxycarbonylphenyl, hydroxy-$C_{1-6}$-alkylphenyl, benzyloxy, pyridylcarbonylamino-$C_{1-6}$-alkyl, $C_{2-6}$-alkenyloxy, $C_{1-6}$-alkoxy-$C_{1-6}$-alkoxy, $C_{1-6}$-alkoxy-$C_{1-6}$-alkoxy-$C_{1-6}$-alkyl, hydroxy-$C_{1-6}$-alkoxy, di-$C_{1-6}$-alkylamino, 2,3-dihydroxypropoxy, 2,3-dihydroxypropoxy-$C_{1-6}$-alkoxy, 2,3-dimethoxypropoxy, methoxybenzyloxy, hydroxybenzyloxy, phenethyloxy, methylenedioxybenzyloxy, dioxolanyl-$C_{1-6}$-alkoxy, cyclopropyl-$C_{1-6}$-alkyl, cyclopropyl-$C_{1-6}$-alkoxy, hydroxy-$C_{1-6}$-alkoxy, carbamoyloxy-$C_{1-6}$-alkoxy, pyridylcarbamoyloxy-$C_{1-6}$-alkoxy, benzoyloxy-$C_{1-6}$-alkoxy, picolyloxy, $C_{1-6}$-alkoxycarbonyl, $C_{0-6}$-alkylcarbonylamino, $C_{0-6}$-alkylcarbonylamino-$C_{1-6}$-alkyl, $C_{0-6}$-alkylcarbonylamino-$C_{1-6}$-alkoxy, (N—$C_{1-6}$-alkyl)-$C_{0-6}$-alkylcarbonylamino-$C_{1-6}$-alkyl, (N—$C_{1-6}$-alkyl)-$C_{1-6}$ alkylcarbonylamino-$C_{1-6}$-alkoxy, $C_{3-8}$-cycloalkylcarbonylamino-$C_{1-6}$-alkyl, $C_{3-8}$-cycloalkylcarbonylamino-$C_{1-6}$-alkoxy, $C_{1-6}$-alkoxy-$C_{1-6}$-alkyl, hydroxy-$C_{1-6}$-alkyl, hydroxy-$C_{1-6}$-alkoxy-$C_{1-6}$-alkyl, hydroxy-$C_{1-6}$-alkoxy-$C_{1-6}$-alkoxy, $C_{1-6}$-alkoxycarbonylamino-$C_{1-6}$-alkyl, $C_{1-6}$-alkoxycarbonylamino-$C_{1-6}$-alkoxy, $C_{1-6}$-alkylaminocarbonylamino-$C_{1-6}$-alkyl, $C_{1-6}$-alkylaminocarbonylamino-$C_{1-6}$-alkoxy, $C_{1-6}$-alkylaminocarbonyl-$C_{1-6}$-alkyl, $C_{1-6}$-alkylaminocarbonyl-$C_{1-6}$-alkoxy, $C_{1-6}$-alkylaminocarbonyl-$C_{1-6}$-alkoxy-$C_{1-6}$-alkyl, di-$C_{1-6}$-alkylaminocarbonyl-$C_{1-6}$-alkyl, di-$C_{1-6}$-alkylaminocarbonyl-$C_{1-6}$-alkoxy, $C_{1-6}$-alkoxycarbonyloxy-$C_{1-6}$-alkyl, $C_{1-6}$-alkylcarbonyloxy-$C_{1-6}$-alkyl, $C_{1-6}$-alkoxycarbonyloxy-$C_{1-6}$-alkoxy, cyano-$C_{1-6}$-alkyl, cyano-$C_{1-6}$-alkoxy, 2-oxooxazolidinyl-$C_{1-6}$-alkyl, 2-oxooxazolidinyl-$C_{1-6}$-alkoxy, $C_{1-6}$-alkoxycarbonyl-$C_{1-6}$-alkyl, $C_{1-6}$-alkoxycarbonyl-$C_{1-6}$-alkoxy, $C_{1-6}$-alkylsulphonylamino-$C_{1-6}$-alkyl, $C_{1-6}$-alkylsulphonylamino-$C_{1-6}$-alkoxy, (N—$C_{1-6}$-alkyl)-$C_{1-6}$-alkylsulphonylamino-$C_{1-6}$-alkyl, (N—$C_{1-6}$-alkyl)-$C_{1-6}$-alkylsulphonylamino-$C_{1-6}$-alkoxy, amino-$C_{1-6}$-alkyl, amino-$C_{1-6}$-alkoxy, $C_{1-6}$-alkylamino-$C_{1-6}$-alkyl, $C_{1-6}$-alkylamino-$C_{1-6}$-alkoxy, di-$C_{1-6}$-alkylamino-$C_{1-6}$-alkyl, di-$C_{1-6}$-alkylamino-$C_{1-6}$-alkoxy, $C_{1-6}$-alkylsulphonyl-$C_{1-6}$-alkyl, $C_{1-6}$-alkylsulphonyl-$C_{1-6}$-alkoxy, carboxy-$C_{1-6}$-alkyl, carboxy-$C_{1-6}$-alkoxy, carboxy-$C_{1-6}$-alkoxy-$C_{1-6}$-alkyl, $C_{1-6}$-alkoxy-$C_{1-6}$-alkylcarbonyl, acyl-$C_{1-6}$-alkoxy-$C_{1-6}$-alkyl, (N—$C_{1-6}$-alkyl)-$C_{1-6}$-alkoxycarbonylamino, (N-hydroxy)-$C_{1-6}$-alkylaminocarbonyl-$C_{1-6}$-alkyl, (N-hydroxy)-$C_{1-6}$-alkylaminocarbonyl-$C_{1-6}$-alkoxy, (N-hydroxy)aminocarbonyl-$C_{1-6}$-alkyl, (N-hydroxy)aminocarbonyl-$C_{1-6}$-alkoxy, $C_{1-6}$-alkoxyaminocarbonyl-$C_{1-6}$-alkyl, $C_{1-6}$-alkoxyaminocarbonyl-$C_{1-6}$-alkoxy, (N—$C_{1-6}$-alkoxy)-$C_{1-6}$-alkylaminocarbonyl-$C_{1-6}$-alkyl, (N—$C_{1-6}$-alkoxy)-$C_{1-6}$-alkylaminocarbonyl-$C_{1-6}$-alkoxy, (N-acyl)-$C_{1-6}$-alkoxy-$C_{1-6}$-alkylamino, $C_{1-6}$-alkoxy-$C_{1-6}$-alkylcarbamoyl, (N—$C_{1-6}$-alkyl)-$C_{1-6}$-alkoxy-$C_{1-6}$-alkylcarbamoyl, $C_{1-6}$-alkoxy-$C_{1-6}$- alkylcarbonyl, $C_{1-6}$-alkoxy-$C_{1-6}$-alkylcarbonylamino, (N—$C_{1-6}$-alkyl)-$C_{1-6}$-alkoxy-$C_{1-6}$-alkylcarbonylamino, 1-$C_{1-6}$-alkoxy-$C_{1-6}$-alkylimidazol-2-yl, 1-$C_{1-6}$-alkoxy-$C_{1-6}$-alkyltetrazol-5-yl, 5-$C_{1-6}$-alkoxy-$C_{1-6}$-alkyltetrazol-1-yl, 2-$C_{1-6}$-alkoxy-$C_{1-6}$-alkyl-4-oxo-imidazol-1-yl, carbamoyl-$C_{1-6}$-alkyl, carbamoyl-$C_{1-6}$-alkoxy, $C_{1-6}$-alkylcarbamoyl, di-$C_{1-6}$-alkylcarbamoyl, $C_{1-6}$-alkylsulphonyl, $C_{1-6}$-alkylamidinyl, acetamidinyl-$C_{1-6}$-alkyl, O-methyloximyl-$C_{1-6}$-alkyl, O,N-dimethylhydroxylamino-$C_{1-6}$-alkyl, $C_{3-8}$-cycloalkyl-$C_{1-6}$-alkanoyl, aryl-$C_{1-6}$-alkanoyl, heterocyclyl-$C_{1-6}$-alkanoyl; and also pyridyl, pyridyloxy, pyridylthio, pyridylamino, pyridyl-$C_{1-6}$-alkyl, pyridyl-$C_{1-6}$-alkoxy, pyrimidinyl, pyrimidinyloxy, pyrimidinylthio, pyrimidinylamino, pyrimidinyl-$C_{1-6}$-alkyl, pyrimidinyl-$C_{1-6}$-alkoxy, thienyl, thienyl-$C_{1-6}$-alkyl, thienyl-$C_{1-6}$-alkoxy, furyl, furyl-$C_{1-6}$-alkyl, furyl-$C_{1-6}$-alkoxy each optionally substituted by halogen, $C_{1-6}$-alkyl, $C_{1-6}$-alkoxy or dihydroxy-$C_{1-6}$-alkylaminocarbonyl.

The term heterocyclyl denotes mono- or bicyclic, saturated and unsaturated heterocyclic radicals having from 1 to 4 nitrogen and/or 1 or 2 sulphur or oxygen atoms and which may be mono- or polysubstituted, especially by (in the case of unsaturated heterocyclyl radicals) alkyl, hydroxyl, alkoxy, nitrogen or halogen, or by substituents as defined above for aryl radicals, or (in the case of saturated heterocyclyl radicals) may be substituted by alkyl or alkoxy. Examples of heterocyclyl radicals are pyridyl, thienyl, pyrazinyl, triazolyl, imidazolyl, benzothiazolyl, furyl, pyranyl, tetrahydropyranyl, azetidinyl, pyrimidinyl, morpholinyl, quinazolinyl, quinolyl, quinoxalinyl, isoquinolyl, tetrahydroquinolyl, tetrahydroisoquinolyl, benzo[b]thienyl, isobenzofuranyl, benzoimidazolyl, 2-oxobenzoimidazolyl, oxazolyl, thiazolyl, indolyl, pyrrolyl, 2-oxodihydrobenzo[d][1,3]oxazinyl, 4-oxodihydroimidazolyl, 5-oxo-4H-[1,2,4]triazinyl, 3-oxo-4H-benzo[1,4]thiazinyl, tetrahydroquinoxalinyl, 1,1,3-trioxodihydro-2H-1$\lambda^6$-benzo[1,4]thiazinyl, 1-oxopyridyl, dihydro-2H-benzo[1,4]oxazinyl, 2-oxotetrahydrobenzo[e][1,4]diazepinyl, 2-oxodihydrobenzo[e][1,4]diazepinyl, 1H-pyrrolizinyl, phthalazinyl, 1-oxo-3H-isobenzofuranyl, 4-oxo-3H-thieno[2,3-d]pyrimidinyl, 3-oxo-4H-benzo[1,4]oxazinyl, [1,5]naphthyridyl, dihydro-2H-benzo[1,4]thiazinyl, 1,1-dioxodihydro-2H-benzo[1,4]thiazinyl, 2-oxo-1H-pyrido[2,3-b][1,4]oxazinyl, dihydro-1H-pyrido[2,3-b][1,4]oxazinyl, 1H-pyrrolo[2,3-b]pyridyl, benzo[1,3]dioxolyl, benzooxazolyl, 2-oxobenzooxazolyl, 2-oxo-1,3-dihydroindolyl, 2,3-dihydroindolyl, 2-oxodihydro-1H-quinazolinyl, indazolyl or benzofuranyl. Examples of substituted heterocyclyl radicals are nitrobenzothiazolyl, phenyltetrazolyl, phenyloxadiazolyl, phenylpiperidinyl, phenylpiperazinyl, phenylpyrrolidinyl, thienyloxadiazolyl, furanyloxadiazolyl, benzyloxadiazolyl or phenyloxazolyl. Examples of substituted heterocyclyl radicals are dioxolanyl, dioxanyl, dithiolanyl, dithianyl, pyrrolidinyl, piperidinyl, piperazinyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, tetrahydropyranyl, 2-oxoimidazolidinyl, 2-oxooxazolidinyl, 2-oxopiperidinyl, 2-oxopyrrolidinyl, 2-oxo-[1,3]oxazinyl, 2-oxoazepanyl, 2-oxotetrahydropyrimidinyl and the like.

In the case of $R^1$, $R^{4a}$ and $R^9$, the aryl, aroyl and heterocyclyl radicals may additionally be substituted by heterocyclylalkoxy, heterocyclylalkoxyalkyl or heterocyclyl for example piperidinoalkyl, piperidinoalkoxy, piperidinoalkoxyalkyl, morpholinoalkyl, morpholinoalkoxy, morpholinoalkoxyalkyl, piperazinoalkyl, piperazinoalkoxy, piperazinoalkoxyalkyl, [1,2,4]-triazol-1-ylalkyl, [1,2,4]-triazol-1-ylalkoxy, [1,2,4]-triazol-4-ylalkyl, [1,2,4]-triazol-4-ylalkoxy, [1,2,4]-oxadiazol-5-ylalkyl, [1,2,4]-oxadiazol-5-ylalkoxy, 3-methyl-[1,2,4]-oxadiazol-5-ylalkyl, 3-methyl-[1,2,4]-oxadiazol-5-ylalkoxy, 5-methyl-[1,2,4]-oxadiazol-3-ylalkyl, 5-methyl-[1,2,4]-oxadiazol-3-ylalkoxy, tetrazol-1-ylalkyl, tetrazol-1-ylalkoxy, tetrazol-2-ylalkyl, tetrazol-2-ylalkoxy, tetrazol-5-ylalkyl, tetrazol-5-ylalkoxy, 5-methyltetrazol-1-ylalkyl, 5-methyltetrazol-1-ylalkoxy, thiazol-4-ylalkyl, thiazol-4-ylalkoxy, oxazol-4-ylalkyl, oxazol-4-ylalkoxy, 2-oxopyrrolidinylalkyl, 2-oxopyrrolidinylalkoxy, imidazolylalkyl, imidazolylalkoxy, 2-methylimidazolylalkyl, 2-methylimidazolylalkoxy, N-methylpiperazinoalkyl, N-methylpiperazinoalkoxy, N-methylpiperazinoalkoxyalkyl, and also alkylaminoalkyl, alkylaminoalkoxy, alkylaminoalkoxyalkyl, mono- and polyhydroxyalkyl, -alkoxy, -alkoxyalkyl and -alkoxyalkoxy, carbamoylalkyloxy, $C_{1-6}$-alkoxy, amino-$C_{1-6}$-alkoxy, hydroxy-$C_{1-6}$-alkoxy, dioxolanyl, dioxanyl, dithiolanyl, dithianyl, pyrrolidinyl, piperidinyl, piperazinyl, pyrrolyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 3-acetamidomethylpyrrolidinyl, 3-$C_{1-6}$-alkoxy-$C_{1-6}$-alkylpyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxoimidazolidinyl, 2-oxooxazolidinyl, 2-oxopyrrolidinyl, 2-oxo[1,3]oxazinyl, 2-oxotetrahydropyrimidinyl and the like, or by the —O—$CH_2CH(OH)CH_2NRx$ radical where NRx is a mono- or di-$C_{1-6}$-alkylamino, piperidino, morpholino, piperazino or N-methylpiperazino radical.

Examples of 5- and 6-membered heterocyclic rings represented by $NR^5R^6$ are pyrrolidinyl, piperidinyl, piperazinyl, morpholinyl, thiomorpholinyl, 2-hydroxymethylpyrrolidinyl, 3-hydroxypyrrolidinyl, 3,4-dihydroxypyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxoimidazolidinyl, 2-oxooxazolidinyl, 2-oxopyrrolidinyl, 2-oxo-[1,3]oxazinyl, 2-oxotetrahydropyrimidinyl and the like. Examples of 3-7-membered rings represented by $CR^7R^8$ are cyclopentyl, cyclohexyl, cycloheptyl, 1,3-dioxolanyl, 1,3-dioxanyl, 1,3-dithiolanyl and 1,3-dithianyl.

The term polyhydroxyalkyl denotes $C_1$-$C_7$-alkyl radicals which may be substituted by 2-6 hydroxyl groups, for example glyceryl, arabityl, sorbityl, etc.

Halogen or halo denotes, for example, fluorine, chlorine or bromine, or a radical singly, multiply or fully substituted by fluorine, chlorine or bromine.

The compounds of the formula (I) or formula (II) have at least one or two asymmetric carbon atoms and may therefore be, in the latter case, in the form of optically pure diastereomers, diastereomer mixtures, diastereomeric racemates, mixtures of diastereomeric racemates or as meso compounds. The invention encompasses all of these forms. Diastereomer mixtures, diastereomeric racemates or mixtures of diastereomeric racemates may be separated by customary methods, for example by column chromatography, thin-layer chromatography, HPLC and the like.

The term "pharmaceutically useable salts" encompasses salts with inorganic or organic acids, such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like.

The compounds of the formulae (I) and (II) also include those compounds in which one or more atoms are replaced by their stable, non-radioactive isotopes; for example a hydrogen atom by deuterium.

The compound groups mentioned hereinbelow are not to be regarded as closed, but rather it is possible in a sensible manner, for example to replace general by more specific definitions, for parts of these groups of compounds to be exchanged with one another or for the definitions given above or to be omitted.

Preferred inventive compounds are those of the general formulae (IA) or (IIA)

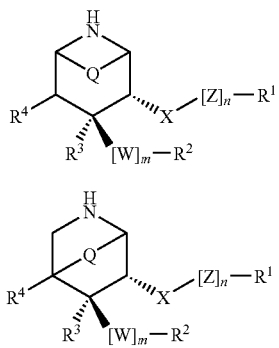

where $R^1$, $R^2$, $R^3$, $R^4$, Q, W, X and Z, n and m are each as defined above for the compounds of the formulae (I) and (II).

A further, preferred group of compounds of the formula (I) or (II), or more preferably of the formula (IA) or (IIA), are compounds where $R^1$ is as defined for (A), (B), (C), (D), (E), (F) or (G), more preferably as specified for (A), (B), (C) or (D) and most preferably as specified for (A); $R^2$ is phenyl, cyclohexyl, tetrazolyl, unsubstituted or substituted by halogen, hydroxyl, cyano, trifluoromethyl, $C_{1-6}$-alkyl, halo-$C_{1-6}$-alkyl, hydroxy-$C_{1-6}$-alkyl, $C_{1-6}$-alkoxy-$C_{1-6}$-alkyl, cyano-$C_{1-6}$-alkyl, carboxy-$C_{1-6}$-alkyl, $C_{1-6}$-alkanoyloxy-$C_{1-6}$-alkyl, $C_{1-6}$-alkoxycarbonyloxy-$C_{1-6}$-alkyl, $C_{1-6}$-alkoxycarbonyl, $C_{1-6}$-alkoxy, $C_{1-6}$-alkylenedioxy, or by an L1-T1-L2-T2-L3-T3-L4-T4-L5-U radical; or naphthyl or acenaphthyl;

L1, L2, L3, L4 and L5 are each independently a bond, $C_{1-8}$-alkylene, $C_{2-8}$-alkenylene or $C_{2-8}$ alkynylene, or are absent;

T1, T2, T3 and T4 are each independently (a) a bond, or are absent, or are one of the groups (b) —CH(OH)—

(c) —CH(OR$^6$)—

(d) —CH(NR$^5$R$^6$)—

(e) —CO—

(f) —CR$^7$R$^8$—

(g) —O— or —NR$^6$—

(h) —S(O)$_{0-2}$—

(i) —SO$_2$NR$^6$—

(j) —NR$^6$SO$_2$—

(k) —CONR$^6$—

(l) —NR$^6$CO—

(m) —O—CO—

(n) —CO—O—

(o) —O—CO—O—

(p) —O—CO—NR—

(q) —N(R$^6$)—CO—N(R$^6$)—

(r) —N(R$^6$)—CO—O—

(s) pyrrolidinylene, piperidinylene or piperazinylene (t) —C(R$^{11}$)(R$^{12}$)—, where the bonds starting from (b)-(t) lead to a saturated or aromatic carbon atom of the adjacent group if the bond starts from a heteroatom, and where not more than two (b)-(f) groups, three (g)-(h) groups and one (i)-(t) group are present;

$R^3$ is hydrogen, hydroxyl, $C_{1-6}$-alkoxy or $C_{2-6}$-alkenyloxy;

$R^4$ is hydrogen, $C_{1-6}$-alkyl, $C_{2-6}$-alkenyl, $C_{1-6}$-alkoxy, hydroxy-$C_{1-6}$-alkyl, $C_{1-6}$-alkoxy-$C_{1-6}$-alkyl or benzyl;

$R^5$ and $R^6$ are each independently hydrogen, $C_{1-6}$-alkyl or acyl, or, together with the nitrogen atom to which they are bonded, are a 5- or 6-membered heterocyclic ring which may contain an additional nitrogen, oxygen or sulphur atom;

$R^7$ and $R^8$, together with the carbon atom to which they are bonded, are a 3-7-membered ring which may contain one or two —O— or —S— atoms;

$R^9$ is hydrogen, $C_{1-6}$-alkyl, acyl or arylalkyl;

U is hydrogen, $C_{1-6}$-alkyl, $C_{3-8}$-cycloalkyl, cyano, aryl or heterocyclyl;

Q is ethylene or is absent (formula (I)) and is ethylene or methylene (formula (II));

X is oxygen, sulphur or a >CH$_2$, >CHOR$^9$, —O—CO—, >CO or —O—CH—R$^{11}$—CO—NR$^9$— group;

W is oxygen or sulphur if $R^3$ is hydrogen;

Z is $C_{1-6}$-alkylene or -alk-O—;

n is 0 or 1;

m is 0 or 1;

and pharmaceutically useable salts thereof.

Preference is further given to compounds of the formulae (I), (IA), (II) and (IIA) in which W is absent (m is 0), and to those of the formulae (I) and (IA) in which Q is absent.

Preferred $R^1$ radicals, especially in compounds of groups (D), (E), (F) or (G) are phenyl and phenyl substituted by 1-3 radicals selected from $C_{1-6}$-alkyl, $C_{1-6}$-alkoxy, halogen, hydroxyl, hydroxy-$C_{1-6}$-alkyl, $C_{1-6}$-alkoxy-$C_{1-6}$-alkoxy, $C_{1-6}$-alkylsulphinyl, carbamoyl, cyano, trifluoromethyl, trifluoromethoxy, carboxyl, $C_{1-6}$-alkoxycarbonyl, $C_{1-6}$-alkoxy-$C_{1-6}$-alkoxy-$C_{1-6}$-alkyl, $C_{0-6}$-alkylcarbonylamino, $C_{0-6}$-alkylcarbonylamino-$C_{1-6}$-alkyl, $C_{0-6}$-alkylcarbonylamino-$C_{1-6}$-alkoxy, (N—$C_{1-6}$-alkyl)-$C_{0-6}$-alkylcarbonylamino-$C_{1-6}$-alkyl, (N—$C_{1-6}$-alkyl)-$C_{0-6}$-alkylcarbonylamino-$C_{1-6}$-alkoxy, $C_{3-8}$-cycloalkylcarbonylamino-$C_{1-6}$-alkyl, $C_{3-8}$-cycloalkylcarbonylamino-$C_{1-6}$-oxy, $C_{1-6}$-alkoxy-$C_{1-6}$-yl, hydroxy-$C_{1-6}$-yl, hydroxy-$C_{1-6}$-oxy-$C_{1-6}$-yl, hydroxy-$C_{1-6}$-alkoxy-$C_{1-6}$-oxy, $C_{1-6}$-alkoxycarbonylamino-$C_{1-6}$-alkyl, $C_{1-6}$-alkoxycarbonylamino-$C_{1-6}$-alkoxy, $C_{1-6}$-alkylaminocarbonylamino-$C_{1-6}$-alkyl, $C_{1-6}$-alkylaminocarbonylamino-$C_{1-6}$-alkoxy, $C_{1-6}$-ylaminocarbonyl-$C_{1-6}$-alkyl, $C_{1-6}$-alkylaminocarbonyl-$C_{1-6}$-oxy, $C_{1-6}$-ylaminocarbonyl-$C_{1-6}$-oxy-$C_{1-6}$-alkyl, di-$C_{1-6}$-alkylaminocarbonyl-$C_{1-6}$-alkyl, di-$C_{1-6}$-alkylaminocarbonyl-$C_{1-6}$-alkoxy, $C_{1-6}$-alkylcarbonyloxy-$C_{1-6}$-alkyl, $C_{1-6}$-alkylcarbonyloxy-$C_{1-6}$-alkoxy, cyano-$C_{1-6}$-alkyl, cyano-$C_{1-6}$-alkoxy, 2-oxooxazolidinyl-$C_{1-6}$-alkyl, 2-oxooxazolidinyl-$C_{1-6}$-alkoxy, $C_{1-6}$-alkoxycarbonyl-$C_{1-6}$-yl, $C_{1-6}$-alkoxycarbonyl-$C_{1-6}$-alkoxy, $C_{1-6}$-alkylsulphonylamino-$C_{1-6}$-yl, $C_{1-6}$-ylsulphonylamino-$C_{1-6}$-oxy, (N—$C_{1-6}$-alkyl)-$C_{1-6}$-alkylsulphonylamino-$C_{1-6}$-yl, (N—$C_{1-6}$-alkyl)-$C_{1-6}$-alkylsulphonylamino-$C_{1-6}$-alkoxy, amino-$C_{1-6}$-alkyl, amino-$C_{1-6}$-oxy, $C_{1-6}$-alkylamino-$C_{1-6}$-alkyl, $C_{1-6}$-alkylamino-$C_{1-6}$-oxy, di-$C_{1-6}$-alkylamino-$C_{1-6}$-alkyl, di-$C_{1-6}$-alkylamino-$C_{1-6}$-alkoxy, $C_{1-6}$-alkylsulphonyl-$C_{1-6}$-alkyl, $C_{1-6}$-alkylsulphonyl-$C_{1-6}$-alkoxy, carboxy-$C_{1-6}$-alkyl, carboxy-$C_{1-6}$-alkoxy, carboxy-$C_{1-6}$-oxy-$C_{1-6}$-alkyl, $C_{1-6}$-oxy-$C_{1-6}$-alkylcarbonyl, acyl-$C_{1-6}$-alkoxy-$C_{1-6}$-yl, (N—$C_{1-6}$-alkyl)-$C_{1-6}$-alkoxycarbonylamino, (N-hydroxy)-$C_{1-6}$-alkylaminocarbonyl-$C_{1-6}$-alkyl, (N-hydroxy)-$C_{1-6}$-alkylaminocarbonyl-$C_{1-6}$-alkoxy, (N-hydroxy)aminocarbonyl-$C_{1-6}$-alkyl, (N-hydroxy)aminocarbonyl-$C_{1-6}$-alkoxy, $C_{1-6}$-alkoxyaminocarbonyl-$C_{1-6}$-alkyl, $C_{1-6}$-oxyaminocarbonyl-$C_{1-6}$-alkoxy, (N—$C_{1-6}$-alkoxy)-$C_{1-6}$-alkylaminocarbonyl-$C_{1-6}$-yl, (N—$C_{1-6}$-alkoxy)-$C_{1-6}$-alkylaminocarbonyl-$C_{1-6}$-alkoxy, (N-acyl)-$C_{1-6}$-alkoxy-$C_{1-6}$-alkylamino, $C_{1-6}$-alkoxy-$C_{1-6}$-ylcarbamoyl, (N—$C_{1-6}$-alkyl)-$C_{1-6}$-alkoxy-$C_{1-6}$-alkylcarbamoyl, $C_{1-6}$-alkoxy-$C_{1-6}$-alkylcarbonyl, $C_{1-6}$-alkoxy-$C_{1-6}$-alkylcarbonylamino, (N—$C_{1-6}$-alkyl)-$C_{1-6}$-alkoxy-$C_{1-6}$-ylcarbonylamino, 1-$C_{1-6}$-oxy-$C_{1-6}$-alkylimidazol-2-yl, 1-$C_{1-6}$-oxy-$C_{1-6}$-alkyltetrazol-5-yl, 5-$C_{1-6}$-alkoxy-$C_{1-6}$-alkyltetrazol-1-yl, 2-$C_{1-6}$-alkoxy-$C_{1-6}$-alkyl-4-oxoimidazol-1-yl, carbamoyl-$C_{1-6}$-alkyl, carbamoyl-$C_{1-6}$-alkoxy, $C_{1-6}$-ylcarbamoyl, di-$C_{1-6}$-alkylcarbamoyl, $C_{1-6}$-alkylsulphonyl, piperidinoalkyl, piperidinoalkoxy, piperidinoalkoxyalkyl, morpholinoalkyl, morpholinoalkoxy, morpholinoalkoxyalkyl, piperazinoalkyl, piperazinoalkoxy, piperazinoalkoxyalkyl, [1,2,4]-triazol-1-ylalkyl, [1,2,4]-triazol-1-ylalkoxy, [1,2,4]-triazol-4-ylalkyl, [1,2,4]-triazol-4-ylalkoxy, [1,2,4]-oxadiazol-5-ylalkyl, [1,2,4]-oxadiazol-5-ylalkoxy, 3-methyl-[1,2,4]-oxadiazol-5-ylalkyl, 3-methyl-[1,2,4]-oxadiazol-5-ylalkoxy, 5-methyl-[1,2,4]-oxadiazol-3-ylalkyl, 5-methyl-[1,2,4]-oxadiazol-3-ylalkoxy, tetrazol-1-ylalkyl, tetrazol-1-ylalkoxy, tetrazol-2-ylalkyl, tetrazol-2-ylalkoxy, tetrazol-5-ylalkyl, tetrazol-5-ylalkoxy, 5-methyltetrazol-1-ylalkyl, 5-methyltetrazol-1-ylalkoxy, thiazol-4-ylalkyl, thiazol-4-ylalkoxy, oxazol-4-ylalkyl, oxazol-4-ylalkoxy, 2-oxopyrrolidinylalkyl, 2-oxopyrrolidinylalkoxy, imidazolylalkyl, imidazolylalkoxy, 2-methylimidazolylalkyl, 2-methylimidazolylalkoxy, N-methylpiperazinoalkyl, N-methylpiperazinoalkoxy, N-methylpiperazinoalkoxyalkyl, pyrrolidinyl, piperidinyl, piperazinyl, pyrrolyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 3-acetamidomethylpyrrolidinyl, 3-$C_{1-6}$-alkoxy-$C_{1-6}$-alkylpyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxoimidazolidinyl, 2-oxooxazolidinyl, 2-oxopyrrolidinyl, 2-oxo[1,3]oxazinyl and 2-oxotetrahydropyrimidinyl.

Further preferred $R^1$ radicals, especially in compounds of groups (D), (E), (F) or (G) are naphthyl, and naphthyl substituted by 1-3 radicals selected from hydroxyl, oxo, halogen, carbamoyl, carboxyl, $C_{1-6}$-alkoxy, hydroxy-$C_{1-6}$-alkoxy, $C_{1-6}$-alkoxy-$C_{1-6}$-alkoxy, di-$C_{1-6}$-alkylamino, 2,3-dihydroxypropoxy, 2,3-dihydroxypropoxy-$C_{1-6}$-alkoxy, 2,3-dimethoxypropoxy, methoxybenzyloxy, hydroxybenzyloxy, phenethyloxy, methylenedioxybenzyloxy, dioxolanyl-$C_{1-6}$-alkoxy, cyclopropyl-$C_{1-6}$-alkoxy, hydroxy-$C_{1-6}$-alkoxy, pyridylcarbamoyloxy-$C_{1-6}$-alkoxy, 3-morpholino-2-hydroxypropoxy, benzyloxy-$C_{1-6}$-alkoxy, picolyloxy, $C_{1-6}$-alkoxycarbonyl, $C_{1-6}$-alkoxy-$C_{1-6}$-alkoxy-$C_{1-6}$-alkyl, $C_{0-6}$-alkylcarbonylamino, $C_{0-6}$-alkylcarbonylamino-$C_{1-6}$-alkyl, $C_{0-6}$-alkylcarbonylamino-$C_{1-6}$-alkoxy, (N—$C_{1-6}$-alkyl)-$C_{0-6}$-alkylcarbonylamino-$C_{1-6}$-alkyl, (N—$C_{1-6}$-alkyl)-$C_{0-6}$-alkylcarbonylamino-$C_{1-6}$-alkoxy, $C_{3-8}$-cycloalkylcarbonylamino-$C_{1-6}$-alkyl, $C_{3-8}$-cycloalkylcarbonylamino-$C_{1-6}$-alkoxy, $C_{1-6}$-alkoxy-$C_{1-6}$-alkyl, hydroxy-$C_{1-6}$-alkyl, hydroxy-$C_{1-6}$-alkoxy-$C_{1-6}$-alkyl, hydroxy-$C_{1-6}$-alkoxy-$C_{1-6}$-alkoxy, $C_{1-6}$-alkoxycarbonylamino-$C_{1-6}$-alkyl, $C_{1-6}$-alkoxycarbonylamino-$C_{1-6}$-alkoxy, $C_{1-6}$-alkylaminocarbonylamino-$C_{1-6}$-alkyl, $C_{1-6}$-alkylaminocarbonylamino-$C_{1-6}$-alkoxy, $C_{1-6}$-alkylaminocarbonyl-$C_{1-6}$-alkyl, $C_{1-6}$-alkylaminocarbonyl-$C_{1-6}$-alkoxy, $C_{1-6}$-alkylaminocarbonyl-$C_{1-6}$-alkoxy-$C_{1-6}$-alkyl, di-$C_{1-6}$-alkylaminocarbonyl-$C_{1-6}$-alkyl, di-$C_{1-6}$-alkylaminocarbonyl-$C_{1-6}$-alkoxy, $C_{1-6}$-alkylcarbonyloxy-$C_{1-6}$-alkyl, $C_{1-6}$-alkylcarbonyloxy-$C_{1-6}$-alkoxy, cyano-$C_{1-6}$-alkyl, cyano-$C_{1-6}$-alkoxy, 2-oxooxazolidinyl-$C_{1-6}$-alkyl, 2-oxooxazolidinyl-$C_{1-6}$-alkoxy, $C_{1-6}$-alkoxycarbonyl-$C_{1-6}$-alkyl, $C_{1-6}$-alkoxycarbonyl-$C_{1-6}$-alkoxy, $C_{1-6}$-alkylsulphonylamino-$C_{1-6}$-alkyl, $C_{1-6}$-alkylsulphonylamino-$C_{1-6}$-alkoxy, (N—$C_{1-6}$-alkyl)-$C_{1-6}$-alkylsulphonylamino-$C_{1-6}$-alkyl, (N—$C_{1-6}$-alkyl)-$C_{1-6}$-alkylsulphonylamino-$C_{1-6}$-alkoxy, amino-$C_{1-6}$-alkyl, amino-$C_{1-6}$-alkoxy, $C_{1-6}$-alkylamino-$C_{1-6}$-alkyl, $C_{1-6}$-alkylamino-$C_{1-6}$-alkoxy, di-$C_{1-6}$-alkylamino-$C_{1-6}$-alkyl, di-$C_{1-6}$-alkylamino-$C_{1-6}$-alkoxy, $C_{1-6}$-alkylsulphonyl-$C_{1-6}$-alkyl, $C_{1-6}$-alkylsulphonyl-$C_{1-6}$-alkoxy, carboxy-$C_{1-6}$-alkyl, carboxy-$C_{1-6}$-alkoxy, carboxy-$C_{1-6}$-alkoxy-$C_{1-6}$-alkyl, $C_{1-6}$-alkoxy-$C_{1-6}$-alkylcarbonyl, acyl-$C_{1-6}$-alkoxy-$C_{1-6}$-alkyl, (N—$C_{1-6}$-alkyl)-$C_{1-6}$-alkoxycarbonylamino, (N-hydroxy)-$C_{1-6}$-alkylaminocarbonyl-$C_{1-6}$-alkyl, (N-hydroxy)-$C_{1-6}$-alkylaminocarbonyl-$C_{1-6}$-alkoxy, (N-hydroxy)aminocarbonyl-$C_{1-6}$-alkyl, (N-hydroxy)aminocarbonyl-$C_{1-6}$-alkoxy, $C_{1-6}$-alkoxyaminocarbonyl-$C_{1-6}$-alkyl, $C_{1-6}$-alkoxyaminocarbonyl-$C_{1-6}$-alkoxy, (N—$C_{1-6}$-alkoxy)-$C_{1-6}$-alkylaminocarbonyl-$C_{1-6}$-alkyl, (N—$C_{1-6}$-alkoxy)-$C_{1-6}$-alkylaminocarbonyl-$C_{1-6}$-alkoxy, (N-acyl)-$C_{1-6}$-alkoxy-$C_{1-6}$-alkylamino, $C_{1-6}$-alkoxy-$C_{1-6}$-alkylcarbamoyl, (N—$C_{1-6}$-alkyl)-$C_{1-6}$-alkoxy-$C_{1-6}$-alkylcarbamoyl, $C_{1-6}$-alkoxy-$C_{1-6}$-alkylcarbonyl, $C_{1-6}$-alkoxy-$C_{1-6}$-alkylcarbonylamino, (N—$C_{1-6}$-alkyl)-$C_{1-6}$-alkoxy-$C_{1-6}$-alkyl-carbonylamino, 1-$C_{1-6}$-alkoxy-$C_{1-6}$-alkylimidazol-2-yl, 1-$C_{1-6}$-alkoxy-$C_{1-6}$-alkyltetrazol-5-yl, 5-$C_{1-6}$-alkoxy-$C_{1-6}$-alkyltetrazol-1-yl, 2-$C_{1-6}$-alkoxy-$C_{1-6}$-alkyl-4-oxoimidazol-1-yl, carbamoyl-$C_{1-6}$-alkyl, carbamoyl-$C_{1-6}$-alkoxy, $C_{1-6}$-alkylcarbamoyl, di-$C_{1-6}$-alkylcarbamoyl, $C_{1-6}$-alkylsulphonyl, piperidinoalkyl, piperidinoalkoxy, piperidinoalkoxyalkyl, morpholinoalkyl, morpholinoalkoxy, morpholinoalkoxyalkyl, piperazinoalkyl, piperazinoalkoxy, piperazinoalkoxyalkyl, [1,2,4]-triazol-1-ylalkyl, [1,2,4]-triazol-1-ylalkoxy, [1,2,4]-triazol-4-ylalkyl, [1,2,4]-triazol-4-ylalkoxy, [1,2,4]-oxadiazol-5-ylalkyl, [1,2,4]-oxadiazol-5-ylalkoxy, 3-methyl-[1,2,4]-oxadiazol-5-ylalkyl, 3-methyl-[1,2,4]-oxadiazol-5-ylalkoxy, 5-methyl-[1,2,4]-oxadiazol-3-ylalkyl, 5-methyl-[1,2,4]-oxadiazol-3-ylalkoxy, tetrazol-1-ylalkyl, tetrazol-1-ylalkoxy, tetrazol-2-ylalkyl, tetrazol-2-ylalkoxy, tetrazol-5-ylalkyl, tetrazol-5-ylalkoxy, 5-methyltetrazol-1-ylalkyl, 5-methyltetrazol-1-ylalkoxy, thiazol-4-ylalkyl, thiazol-4-ylalkoxy, oxazol-4-ylalkyl, oxazol-4-ylalkoxy, 2-oxopyrrolidinylalkyl, 2-oxopyrrolidinylalkoxy, imidazolylalkyl, imidazolylalkoxy, 2-methylimidazolylalkyl, 2-methylimidazolylalkoxy, N-methylpiperazinoalkyl, N-methylpiperazinoalkoxy, N-methylpiperazinoalkoxyalkyl, pyrrolidinyl, piperidinyl, piperazinyl, pyrrolyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 3-acetamidomethylpyrrolidinyl, 3-$C_{1-6}$-alkoxy-$C_{1-6}$-alkylpyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxoimidazolidinyl, 2-oxooxazolidinyl, 2-oxopyrrolidinyl, 2-oxo-[1,3]oxazinyl and 2-oxotetrahydropyrimidinyl; tetrahydronaphthyl or methyl-substituted tetrahydronaphthyl and indanyl.

A group of particularly preferred $R^1$ radicals encompasses the abovementioned substituted phenyl and naphthyl radicals, and also tetrahydronaphthyl and methyl-substituted tetrahydronaphthyl.

$R^1$ radicals which are likewise preferred, especially in compounds of groups (D), (E), (F) or (G) are pyridyl, benzoimidazolyl, di-$C_{1-6}$-alkoxypyrimidinyl, 2- and 5-benzo[b]thienyl, 6- and 7-quinolyl, 6- and 7-isoquinolyl, 6- and 7-tetrahydroquinolyl, 6- and 7-tetrahydroisoquinolyl, 6-quinoxalinyl, 6- and 7-quinazolinyl, indolyl, dihydro-2H-benzo[1,4]oxazinyl, 3-oxo-4H-benzo[1,4]oxazinyl, 2-oxobenzooxazolyl, 2-oxo-1,3-dihydroindolyl, 2,3-dihydroindolyl, indazolyl and benzofuranyl, and also 6- and 7-quinolyl, 6- and 7-isoquinolyl, 6- and 7-tetrahydroquinolyl, 6- and 7-tetrahydroisoquinolyl, 6-quinoxalinyl, 6- and 7-quinazolinyl, indolyl, dihydro-2H-benzo[1,4]oxazinyl, 3-oxo-4H-benzo[1,4]oxazinyl, 2-oxobenzooxazolyl, 2-oxo-1,3-dihydroindolyl, 2,3-dihydroindolyl, indazolyl and benzofuranyl each substituted by 1-3 radicals selected from hydroxyl, oxo, halogen, carbamoyl, carboxyl, $C_{1-6}$-alkoxy, hydroxy-$C_{1-6}$-alkoxy, $C_{1-6}$-alkoxy-$C_{1-6}$-alkoxy, di-$C_{1-6}$-alkylamino, 2,3-dihydroxypropoxy, 2,3-dihydroxypropoxy-$C_{1-6}$-alkoxy, 2,3-dimethoxypropoxy, methoxybenzyloxy, hydroxybenzyloxy, phenethyloxy, methylenedioxybenzyloxy, dioxolanyl-$C_{1-6}$-alkoxy, cyclopropyl-$C_{1-6}$-alkoxy, hydroxy-$C_{1-6}$-alkoxy, pyridylcarbamoyloxy-$C_{1-6}$-alkoxy, 3-morpholino-2-hydroxypropoxy, benzyloxy-$C_{1-6}$-alkoxy, picolyloxy, $C_{1-6}$-alkoxycarbonyl, $C_{1-6}$-alkoxy-$C_{1-6}$-alkoxy-$C_{1-6}$-alkyl, $C_{1-6}$-alkylcarbonylamino, $C_{0-6}$-alkylcarbonylamino-$C_{1-6}$-alkyl, $C_{0-6}$-alkylcarbonylamino-$C_{1-6}$-alkoxy, (N—$C_{1-6}$-alkyl)-$C_{0-6}$-alkylcarbonylamino-$C_{1-6}$-alkyl, (N—$C_{1-6}$-alkyl)-$C_{0-6}$-ylcarbonylamino-$C_{1-6}$-alkoxy, $C_{3-8}$-cycloalkylcarbonylamino-$C_{1-6}$-alkyl, $C_{3-8}$-cycloalkylcarbonylamino-$C_{1-6}$-alkoxy, $C_{1-6}$-alkoxy-$C_{1-6}$-alkyl, hydroxy-$C_{1-6}$-alkyl, hydroxy-$C_{1-6}$-alkoxy-$C_{1-6}$-alkyl, hydroxy-$C_{1-6}$-alkoxy-$C_{1-6}$-alkoxy, $C_{1-6}$-alkoxycarbonylamino-$C_{1-6}$-alkyl, $C_{1-6}$-alkoxycarbonylamino-$C_{1-6}$-alkoxy, $C_{1-6}$-alkylaminocarbonylamino-$C_{1-6}$-alkyl, $C_{1-6}$-alkylaminocarbonylamino-$C_{1-6}$-alkoxy, $C_{1-6}$-alkylaminocarbonyl-$C_{1-6}$-alkyl, $C_{1-6}$-alkylaminocarbonyl-$C_{1-6}$-alkoxy, $C_{1-6}$-alkylaminocarbonyl-$C_{1-6}$-alkoxy-$C_{1-6}$-alkyl, di-$C_{1-6}$-alkylaminocarbonyl-$C_{1-6}$-alkyl, di-$C_{1-6}$-alkylaminocarbonyl-$C_{1-6}$-alkoxy, $C_{1-6}$-alkylcarbonyloxy-$C_{1-6}$-alkyl, $C_{1-6}$-alkylcarbonyloxy-$C_{1-6}$-alkoxy, cyano-$C_{1-6}$-alkyl, cyano-$C_{1-6}$-alkoxy, 2-oxooxazolidinyl-$C_{1-6}$-alkyl, 2-oxooxazolidinyl-$C_{1-6}$-alkoxy, $C_{1-6}$-alkoxycarbonyl-$C_{1-6}$-alkyl, $C_{1-6}$-alkoxycarbonyl-$C_{1-6}$-alkoxy, $C_{1-6}$-alkylsulphonylamino-$C_{1-6}$-alkyl, $C_{1-6}$-alkylsulphonylamino-$C_{1-6}$-alkoxy, (N—$C_{1-6}$-alkyl)-$C_{1-6}$-alkylsulphonylamino-$C_{1-6}$-alkyl, (N—$C_{1-6}$-alkyl)-$C_{1-6}$-alkylsulphonylamino-$C_{1-6}$-alkoxy, amino-$C_{1-6}$-alkyl, amino-$C_{1-6}$-alkoxy, $C_{1-6}$-alkylamino-$C_{1-6}$-yl, $C_{1-6}$-alkylamino-$C_{1-6}$-alkoxy, di-$C_{1-6}$-alkylamino-$C_{1-6}$-alkyl, di-$C_{1-6}$-alkylamino-$C_{1-6}$-alkoxy, $C_{1-6}$-alkylsulphonyl-$C_{1-6}$-alkyl, $C_{1-6}$-alkylsulphonyl-$C_{1-6}$-alkoxy, carboxy-$C_{1-6}$-alkyl, carboxy-$C_{1-6}$-alkoxy, carboxy-$C_{1-6}$-alkoxy-$C_{1-6}$-alkyl, $C_{1-6}$-alkoxy-$C_{1-6}$-alkylcarbonyl, acyl-$C_{1-6}$-alkoxy-$C_{1-6}$-alkyl, (N—$C_{1-6}$-alkyl)-$C_{1-6}$-alkoxycarbonylamino, (N-hydroxy)-$C_{1-6}$-alkylaminocarbonyl-$C_{1-6}$-alkyl, (N-hydroxy)-$C_{1-6}$-alkylaminocarbonyl-$C_{1-6}$-alkoxy, (N-hydroxy)-aminocarbonyl-$C_{1-6}$-alkyl, (N-hydroxy)aminocarbonyl-$C_{1-6}$-alkoxy, $C_{1-6}$-alkoxyaminocarbonyl-$C_{1-6}$-alkyl, $C_{1-6}$-alkoxyaminocarbonyl-$C_{1-6}$-alkoxy, (N—$C_{1-6}$-alkoxy)-$C_{1-6}$-alkylaminocarbonyl-$C_{1-6}$-alkyl, (N—$C_{1-6}$-alkoxy)-$C_{1-6}$-alkylaminocarbonyl-$C_{1-6}$-alkoxy, (N-acyl)-$C_{1-6}$-alkoxy-$C_{1-6}$-alkylamino, $C_{1-6}$-alkoxy-$C_{1-6}$-alkylcarbamoyl, (N—$C_{1-6}$-alkyl)-$C_{1-6}$-alkoxy-$C_{1-6}$-alkylcarbamoyl, $C_{1-6}$-alkoxy-$C_{1-6}$-alkylcarbonyl, $C_{1-6}$-alkoxy-$C_{1-6}$-alkylcarbonylamino, (N—$C_{1-6}$-alkyl)-$C_{1-6}$-alkoxy-$C_{1-6}$-alkylcarbonylamino, 1-$C_{1-6}$-alkoxy-$C_{1-6}$-alkylimidazol-2-yl, 1-$C_{1-6}$-alkoxy-$C_{1-6}$-alkyltetrazol-5-yl, 5-$C_{1-6}$-alkoxy-$C_{1-6}$-alkyltetrazol-1-yl, 2-$C_{1-6}$-alkoxy-$C_{1-6}$-alkyl-4-oxoimidazol-1-yl, carbamoyl-$C_{1-6}$-alkyl, carbamoyl-$C_{1-6}$-alkoxy, $C_{1-6}$-alkylcarbamoyl, di-$C_{1-6}$-alkylcarbamoyl, $C_{1-6}$-alkylsulphonyl, piperidinoalkyl, piperidinoalkoxy, piperidinoalkoxyalkyl, morpholinoalkyl, morpholinoalkoxy, morpholinoalkoxyalkyl, piperazinoalkyl, piperazinoalkoxy, piperazinoalkoxyalkyl, [1,2,4]-triazol-1-ylalkyl, [1,2,4]-triazol-1-ylalkoxy, [1,2,4]-triazol-4-ylalkyl, [1,2,4]-triazol-4-ylalkoxy, [1,2,4]-oxadiazol-5-ylalkyl, [1,2,4]-oxadiazol-5-ylalkoxy, 3-methyl-[1,2,4]-oxadiazol-5-ylalkyl, 3-methyl-[1,2,4]-oxadiazol-5-ylalkoxy, 5-methyl-[1,2,4]-oxadiazol-3-ylalkyl, 5-methyl-[1,2,4]-oxadiazol-3-ylalkoxy, tetrazol-1-ylalkyl, tetrazol-1-ylalkoxy, tetrazol-2-ylalkyl, tetrazol-2-ylalkoxy, tetrazol-5-ylalkyl, tetrazol-5-ylalkoxy, 5-methyltetrazol-1-ylalkyl, 5-methyltetrazol-1-ylalkoxy, thiazol-4-ylalkyl, thiazol-4-ylalkoxy, oxazol-4-ylalkyl, oxazol-4-ylalkoxy, 2-oxopyrrolidinylalkyl, 2-oxopyrrolidinylalkoxy, imidazolylalkyl, imidazolylalkoxy, 2-methylimidazolylalkyl, 2-methylimidazolylalkoxy, N-methylpiperazinoalkyl, N-methylpiperazinoalkoxy, N-methylpiperazinoalkoxyalkyl, pyrrolidinyl, piperidinyl, piperazinyl, pyrrolyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 3-acetamidomethylpyrrolidinyl, 3-$C_{1-6}$-alkoxy-$C_{1-6}$-alkylpyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxoimidazolidinyl, 2-oxooxazolidinyl, 2-oxopyrrolidinyl, 2-oxo-[1,3]oxazinyl and 2-oxotetrahydropyrimidinyl.

Preferred $R^2$ radicals are phenyl and phenyl substituted by halogen, hydroxyl, cyano, trifluoromethyl, $C_{1-6}$-alkyl, halo-$C_{1-6}$-alkyl, hydroxy-$C_{1-6}$-alkyl, $C_{1-6}$-alkoxy-$C_{1-6}$-alkyl, cyano-$C_{1-6}$-alkyl, carboxy-$C_{1-6}$-alkyl, $C_{1-6}$-alkylcarbonyloxy-$C_{1-6}$-alkyl, $C_{1-6}$-alkoxycarbonyloxy-$C_{1-6}$-alkyl, $C_{1-6}$-alkoxycarbonyl, $C_{1-6}$-alkoxy or $C_{1-6}$-alkylenedioxy.

$R^2$ radicals which are likewise preferred are phenyl or halophenyl substituted by an L1-T1-L2-T2-L3-T3-L4-T4-L5-U radical where L1 and L2 are preferably absent or $C_{1-8}$-alkylene and L3 is absent and U is hydrogen, $C_{1-6}$-alkyl, $C_{3-8}$-cycloalkyl, phenylpiperidinyl, phenylpiperazinyl, phenylpyrrolidinyl, phenyl, is phenyl or phenylpyrrolidinyl each substituted by $C_{1-6}$-alkyl, $C_{1-6}$-alkoxy, $C_{1-6}$-alkylthio, $C_{1-6}$-alkylsulphinyl, $C_{1-6}$-alkylenedioxy, halogen, benzoyl-$C_{1-6}$-alkyl, halogen-$C_{1-6}$-alkyl, $C_{1-6}$-alkanoyloxy or hydroxyl, or is naphthyl, pyridyl, thienyl, pyrazinyl, triazolyl, imidazolyl, phenyloxadiazolyl, thienyloxadiazolyl, furyloxadiazolyl, phenyloxazolyl, benzthiazolyl, furyl, pyrimidinyl, nitrobenzthiazolyl, phenyltetrazolyl, piperidinyl, tetrahydropyranyl, morpholinyl or indolyl.

In the groups T1-T4, preference is given to the definitions (a)-(c), (e)-(h), (k)-(n) and (r)-(t).

Examples of particularly preferred $R^2$ radicals are phenyl and phenyl or halophenyl substituted by 2-benzothiazolylthio-$C_{1-6}$-alkyl, 2-benzyloxy-3-methoxypropoxy, 2-benzoyloxy-3-methoxypropoxy, 2,3-dihydroxypropoxy, 2-hydroxy-3-benzylamino-propoxy, 2-hydroxy-3-phenoxypropoxy, 2-hydroxy-3-phenylthiopropoxy, 2-methoxy-3-phenoxypropoxy, 2-methoxy-3-benzyloxypropoxy, 2-methyl-3-fluorophenylbutyryloxy-$C_{1-6}$-alkoxy, 2-methyl-3-phenoxypropoxy, 2-$C_{1-6}$-alkenyloxy-4-phenylbutyl, 3,4,5-trimethoxyphenyloxadiazolyl-$C_{1-6}$-alkoxy, 6-nitro-2-benzothiazolylthio-$C_{1-6}$-alkyl, benzamido-$C_{1-6}$-alkoxy, benzamido-$C_{1-66}$-alkyl, benzo[1,3]dioxolyloxy-$C_{1-6}$-alkoxy, benzoyl-$C_{1-6}$-alkoxy and ketals thereof, benzoyl-$C_{1-6}$-yl and ketals thereof, benzoyl-$C_{1-6}$-alkylaminocarbonyl-$C_{1-6}$-alkyl, benzoyl-$C_{1-6}$-alkoxycarbonyl-$C_{1-6}$-alkyl, benzoyl-$C_{1-6}$-ylaminocarbonyl, benzoyloxy, benzoyloxy-$C_{1-6}$-alkylbenzoyloxy-$C_{1-6}$-alkoxy, benzoyloxy-$C_{1-6}$-alkoxy, benzoyloxy-$C_{1-6}$-alkyl, benzthiazolylthio-$C_{1-6}$-alkoxy, benzthiazolylthio-$C_{1-6}$-alkyl, benzylcarbamoyl-$C_{1-6}$-alkoxy, benzyloxy-$C_{1-6}$-oxycarbonyloxy-$C_{1-6}$-alkyl, benzyloxy-$C_{1-6}$-oxy, benzylthio-$C_{1-6}$-alkoxy, carbamoyloxy-$C_{1-6}$-alkoxy, carbamoyloxy-$C_{1-6}$-alkyl, carboxy-$C_{1-6}$-alkoxy, carboxy-$C_{1-6}$-alkyl, cyano, cyano-$C_{1-6}$-oxy, cyano-$C_{1-6}$-alkyl, cyanophenyl-$C_{1-6}$-alkoxy, cyclohexylcarbonyloxy-$C_{1-6}$-alkyl, cyclohexyloxy-$C_{1-6}$-alkoxy, cyclopropylcarbonyloxy-$C_{1-6}$-alkyl, dioxolanyl-$C_{1-6}$-oxy, furyloxadiazolyl-$C_{1-6}$-alkoxy, furopyloxy-$C_{1-6}$-alkoxy, halophenoxy-$C_{1-6}$-yl, halobenzoyl-$C_{1-6}$-alkoxy, halobenzoyloxy-$C_{1-6}$-alkyl, halobenzoyloxy-$C_{1-6}$-alkoxy, halobenzoyloxy-$C_{1-6}$-alkoxy, halogen, halogen-$C_{1-6}$-alkyl, halophenoxy, halophenoxy-$C_{1-6}$-alkoxy, halophenyloxadiazolyl-$C_{1-6}$-alkoxy, hydroxyl, hydroxybenzoyloxy-$C_{1-6}$-alkyl, hydroxybenzoyloxy-$C_{1-6}$-alkoxy, hydroxy-$C_{1-6}$-alkoxy, hydroxy-$C_{1-6}$-yl, imidazolylcarbonyloxy-$C_{1-6}$-alkyl, methoxybenzoyl-$C_{1-6}$-alkyl, methoxybenzyloxy-$C_{1-6}$-alkoxy, methylenedioxybenzoyl-$C_{1-6}$-alkoxy, morpholino-$C_{1-6}$-alkoxy, morpholinocarbonyloxy-$C_{1-6}$-alkoxy, morpholinocarbonyloxy-$C_{1-6}$-alkyl, N-methylaminophenylcarbonyloxy-$C_{1-6}$-alkyl, N-methylbenzylamino-$C_{1-6}$-alkoxy, N-methylpyrrolylcarbonyloxy-$C_{1-6}$-alkoxy, N—$C_{1-6}$-alkylbenzamido-$C_{1-6}$-alkyl, naphthyl-$C_{1-6}$-alkoxy, nicotinoyloxy-$C_{1-6}$-alkoxy, nicotinoyloxy-$C_{1-6}$-alkyl, $C_{1-6}$-alkanoylbenzoyloxy-$C_{1-6}$-alkyl, $C_{1-6}$-alkanoyloxy-$C_{1-6}$-alkoxy, $C_{1-6}$-alkanoyloxy-$C_{1-6}$-alkyl, $C_{1-6}$-alkenylbenzyloxy-$C_{1-6}$-oxy, $C_{1-6}$-alkenyloxy, $C_{1-6}$-alkenyloxybenzyloxy-$C_{1-6}$-oxy, $C_{1-6}$-alkoxy, $C_{1-6}$-alkoxybenzoyloxy-$C_{1-6}$-alkyl, $C_{1-6}$-alkoxycarbonyl, $C_{1-6}$-alkoxy-$C_{1-6}$-alkyl, $C_{1-6}$-oxybenzoylamino-$C_{1-6}$-alkyl, $C_{1-6}$-alkoxybenzylcarbonyloxy-$C_{1-6}$-alkyl, $C_{1-6}$-alkoxybenzyloxy-$C_{1-6}$-alkoxy, $C_{1-6}$-alkoxybenzylthio-$C_{1-6}$-alkoxy, $C_{1-6}$-alkoxycarbonyl-$C_{1-6}$-alkoxy, $C_{1-6}$-alkoxycarbonyl-$C_{1-6}$-alkyl, $C_{1-6}$-alkoxyphenyloxadiazolyl-$C_{1-6}$-alkoxy, $C_{1-6}$-alkoxyphenyloxy-$C_{1-6}$-alkoxy, $C_{1-6}$-alkyl, $C_{1-6}$-alkylbenzyloxy-$C_{1-6}$-alkoxy, $C_{1-6}$-alkylphenoxy-$C_{1-6}$-alkoxy, $C_{1-6}$-alkylenedioxy, $C_{1-6}$-alkylenedioxybenzyloxy-$C_{1-6}$-alkoxy, $C_{1-6}$-alkylsulphonylbenzoyl-$C_{1-6}$-oxy, $C_{1-6}$-alkylthiobenzoyloxy-$C_{1-6}$-oxy, $C_{1-6}$-alkylthiobenzyloxy-$C_{1-6}$-alkoxy, benzoyloxybenzyl-$C_{1-6}$-alkoxy, hydroxybenzyl-$C_{1-6}$-oxy, $C_{1-6}$-alkoxybenzyl-$C_{1-6}$-alkoxy, $C_{1-6}$-alkoxybenzylcarbonyloxy-$C_{1-6}$-alkoxy, phenoxybenzyloxy-$C_{1-6}$-alkoxy, phenoxycarbonyl-$C_{1-6}$-alkyl, phenoxy-$C_{1-6}$-alkenyloxy, phenoxy-$C_{1-6}$-alkinyloxy, phenyl-$C_{1-6}$-alkanoylamino-$C_{1-6}$-alkyl, phenyl-$C_{1-6}$-alkenyloxy, phenyl-$C_{1-6}$-oxy, phenyl-$C_{1-6}$-alkyl, phenyl-$C_{1-6}$-alkylaminocarbonyl, phenyl-$C_{1-6}$-alkylcarbonyl-$C_{1-6}$-alkoxy, phenyl-$C_{1-6}$-alkylaminocarbonyl-$C_{1-6}$-alkyl, phenylaminocarbonyloxy-$C_{1-6}$-alkoxy, phenylaminocarbonyloxy-$C_{1-6}$-alkyl, phenylhydroxy-$C_{1-6}$-alkyl, phenyloxadiazolyl-$C_{1-6}$-alkoxy, phenyloxadiazolyl-$C_{1-6}$-alkyl, phenyloxadiazolyl-$C_{1-6}$-alkoxy, phenyloxy-$C_{1-6}$-alkoxy, phenylsulphamoyl-$C_{1-6}$-alkyl, phenylsulphinyl-$C_{1-6}$-alkyl, phenylsulphonyl-$C_{1-6}$-alkoxy, phenylsulphonyl-$C_{1-6}$-alkyl, phenyltetrazolylthio-$C_{1-6}$-alkyl, phenylthio-$C_{1-6}$-alkoxy, phenylthio-$C_{1-6}$-alkyl, pyrazinylcarbonyloxy-$C_{1-6}$-alkyl, pyridylaminocarbonyloxy-$C_{1-6}$-alkoxy, pyridylaminocarbonyloxy-$C_{1-6}$-alkyl, pyridylcarbamoyloxy, pyridyl-$C_{1-66}$-alkoxy-$C_{1-6}$-alkoxy, pyridyl-$C_{1-6}$-alkoxy-$C_{1-6}$-alkyl, pyridyloxadiazolyl-$C_{1-6}$-alkoxy, pyridylthio-$C_{1-6}$-alkyl, pyrimidinyloxy-$C_{1-6}$-alkoxy, pyrimidinylthio-$C_{1-6}$-alkyl, thienoyloxy-$C_{1-6}$-alkoxy, thienoyloxy-$C_{1-6}$-alkyl, thienyloxadiazolyl-$C_{1-6}$-alkoxy, triazolyl-$C_{1-6}$-alkoxy, trifluoromethylbenzyloxy-$C_{1-6}$-alkoxy, or trifluoromethyl.

Particularly preferred $R^1$ radicals, especially in compounds of groups (D), (E), (F) or (G) are acetamidophenyl, $C_{1-6}$-alkoxyphenyl, $C_{1-6}$-alkylaminophenyl, $C_{1-6}$-alkylphenyl, 1H-benzoimidazolyl, carbamoylphenyl, di-$C_{1-6}$-alkylaminophenyl, 3,4-dihydro-1H-quinolin-2-onyl, 2-furanylphenyl, halophenyl, 2-Methylpyrimidinyl, morpholinylphenyl, phenyl, pyrrolidinonylphenyl and pyrrolidinylphenyl which is substituted by 1-3 hydrogen, $C_{1-6}$-alkoxy-$C_{1-6}$-alkoxy, $C_{1-6}$-alkoxy-$C_{1-6}$-alkyl, N-acetyl-$C_{1-6}$-alkoxy-$C_{1-6}$-alkylamino, $C_{1-6}$-alkanoylamido-$C_{1-6}$-alkyl, N—$C_{1-6}$-alkyl-$C_{1-6}$-alkanoylamido-$C_{1-6}$-alkyl, $C_{1-6}$-alkoxy-$C_{1-6}$-alkoxy-$C_{1-6}$-alkyl, triazol-1-yl-$C_{1-6}$-alkyl, tetrazol-1-yl-$C_{1-6}$-alkyl, tetrazol-2-yl-$C_{1-6}$-alkyl, tetrazol-5-yl-$C_{1-6}$-alkyl, $C_{1-6}$-alkoxycarboxyl-$C_{1-6}$-alkyl, pyrrolidinonyl-$C_{1-6}$-alkyl, imidazolyl-$C_{1-6}$-alkyl, cyano-$C_{1-6}$-alkyl, carboxy-$C_{1-6}$-carboxy-$C_{1-6}$-alkoxy, $C_{1-6}$-alkoxycarbonyl-$C_{0-6}$-alkyl, $C_{1-6}$-alkylsulphonamidyl-$C_{1-6}$-alkyl, $C_{1-6}$-alkoxy-$C_{1-6}$-alkanoylamido, $C_{1-6}$-alkoxy-$C_{1-6}$-alkanoylamido-$C_{1-6}$-alkyl, N—($C_{1-6}$-alkyl)-$C_{1-6}$-alkoxy-$C_{1-6}$-alkanoylamido, N—$C_{1-6}$-alkylcarbamoyl-$C_{1-6}$-alkyl, $C_{3-8}$-cycloalkanoylamido-$C_{1-6}$-alkyl, $C_{1-6}$-alkylaminocarbonylamino-$C_{1-6}$-alkyl, $C_{1-6}$-alkanoylamidomethylpyrrolidinyl, N—($C_{1-6}$-alkoxy-$C_{1-6}$-alkyl)carbamoyl, N—($C_{1-6}$-alkoxy-$C_{1-6}$-alkyl)-N—($C_{1-6}$-alkyl)carbamoyl, N—($C_{1-6}$-alkoxy-$C_{1-6}$-alkyl)imidazol-2-yl, hydroxy-$C_{1-6}$-alkyl, hydroxy-$C_{1-6}$-alkoxy, hydroxy-$C_{1-6}$-alkoxy-$C_{1-6}$-alkyl, $C_{1-6}$-alkoxycarbonylamido-$C_{1-6}$-alkyl, amino-$C_{1-6}$-alkyl or $C_{1-6}$-alkylamino-$C_{1-6}$-alkyl.

Examples of particularly preferred $R^1$ radicals, especially in compounds of groups (A), (D), (E), (F) or (G) are 3-$C_{1-6}$-alkylindolyl, benzofuranyl, 4H-benzo[1,4]oxazin-3-onyl, 3,4-dihydro-2H-benzo[1,4]oxazinyl, 3,4-dihydro-2H-benzo[1,4]thiazinyl, 3,3-di-$C_{1-6}$-alkyl-1,3-dihydroindol-2-onyl, 3,3-di-$C_{1-6}$-alkyl-1,3-dihydroindolyl, indolyl, 3-methylindolyl and spiro[cyclopropane-1,3']-2,3-dihydro-1H-indolyl which may be substituted as specified above, especially by at least one substituent selected from $C_{1-6}$-alkoxy-$C_{1-6}$-alkoxy, $C_{1-6}$-alkoxy-$C_{1-6}$-alkyl, N-acetyl-$C_{1-6}$-alkoxy-$C_{1-6}$-alkylamino, $C_{1-6}$-alkanoylamido-$C_{1-6}$-alkyl, N—$C_{1-6}$-alkyl-$C_{1-6}$-alkanoylamido-$C_{1-6}$-alkyl, $C_{1-6}$-alkoxy-$C_{1-6}$-alkoxy-$C_{1-6}$-alkyl, triazol-1-yl-$C_{1-6}$-alkyl, tetrazol-1-yl-$C_{1-6}$-alkyl, tetrazol-2-yl-$C_{1-6}$-alkyl, tetrazol-5-yl-$C_{1-6}$-alkyl, $C_{1-6}$-alkoxycarboxyl-$C_{1-6}$-alkyl, pyrrolidinonyl-$C_{1-6}$-alkyl, imidazolyl-$C_{1-6}$-alkyl, cyano-$C_{1-6}$-alkyl, carboxy-$C_{1-6}$-alkyl, carboxy-$C_{1-6}$-alkoxy, $C_{1-6}$-alkoxycarbonyl-$C_{0-6}$-alkyl, $C_{1-6}$-alkylsulphonamidyl-$C_{1-6}$-alkyl, $C_{1-6}$-alkoxy-$C_{1-6}$-alkanoylamido, $C_{1-6}$-alkoxy-$C_{1-6}$-alkanoylamido-$C_{1-6}$-alkyl, N—($C_{1-6}$-alkyl)-$C_{1-6}$-alkoxy-$C_{1-6}$-alkanoylamido, N—$C_{1-6}$-alkylcarbamoyl-$C_{1-6}$-alkyl, $C_{3-8}$-cycloalkanoylamido-$C_{1-6}$-alkyl, $C_{1-6}$-alkylaminocarbonylamino-$C_{1-6}$-alkyl, $C_{1-6}$-alkanoylamidomethylpyrrolidinyl, N—($C_{1-6}$-alkoxy-$C_{1-6}$-alkyl)carbamoyl, N—($C_{1-6}$-alkoxy-$C_{1-6}$-alkyl)-N—($C_{1-6}$-alkyl)carbamoyl, N—($C_{1-6}$-alkoxy-$C_{1-6}$-alkyl)imidazol-2-yl, hydroxy-$C_{1-6}$-alkyl, hydroxy-$C_{1-6}$-alkoxy, hydroxy-$C_{1-6}$-alkoxy-$C_{1-6}$-alkyl, $C_{1-6}$-alkoxycarbonylamido-$C_{1-6}$-alkyl, amino-$C_{1-6}$-alkyl and $C_{1-6}$-alkylamino-$C_{1-6}$-alkyl.

Examples of very particularly preferred $R^1$ radicals, especially in compounds of groups (A), (D), (E), (F) or (G), are 4H-benzo[1,4]oxazin-3-on-6-yl, 3,4-dihydro-2H-benzo[1,4]oxazin-6-yl, 3,4-dihydro-2H-benzo[1,4]thiazin-6-yl, 2,2-dimethyl-3,4-dihydro-2H-benzo[1,4]oxazin-6-yl, 2,2-dimethyl-4H-benzo[1,4]oxazin-3-on-6-yl, 4,4-dimethyl-1,4-dihydrobenzo[d][1,3]oxazin-2-on-8-yl, 3,3-dimethyl-1,3-dihydroindol-2-on-6-yl, 3,3-dimethyl-1,3-dihydroindol-2-on-7-yl, 3,3-dimethyl-1,3-dihydroindol-6-yl, 3-methylindol-6-yl and spiro[cyclopropane-1,3']-2,3-dihydro-1H-indol-6-yl which may be substituted as specified above, especially by at least one substituent selected from $C_{1-6}$-alkoxy-$C_{1-6}$-alkoxy, $C_{1-6}$-alkoxy-$C_{1-6}$-alkyl, N-acetyl-$C_{1-6}$-alkoxy-$C_{1-6}$-alkylamino, $C_{1-6}$-alkylcarbonylamino-$C_{1-6}$-alkyl, $C_{1-6}$-alkylcarbonylamino-$C_{1-6}$-alkoxy, N—$C_{1-6}$-alkyl-$C_{1-6}$-alkanoylamido-$C_{1-6}$-alkyl, $C_{1-6}$-alkoxy-$C_{1-6}$-alkoxy-$C_{1-6}$-alkyl, triazol-1-yl-$C_{1-6}$-alkyl, tetrazol-1-yl-$C_{1-6}$-alkyl, tetrazol-2-yl-$C_{1-6}$-alkyl, tetrazol-5-yl-$C_{1-6}$-alkyl, $C_{1-6}$-alkoxycarboxyl-$C_{1-6}$-alkyl, pyrrolidinonyl-$C_{1-6}$-alkyl, imidazolyl-$C_{1-6}$-alkyl, cyano-$C_{1-6}$-alkyl, carboxy-$C_{1-6}$-alkyl, carboxy-$C_{1-6}$-alkoxy, $C_{1-6}$-alkoxycarbonyl-$C_{0-6}$-alkyl, $C_{1-6}$-alkylsulphonamidyl-$C_{1-6}$-alkyl, $C_{1-6}$-alkoxy-$C_{1-6}$-alkanoylamido, $C_{1-6}$-alkoxy-$C_{1-6}$-alkanoylamido-$C_{1-6}$-alkyl, N—($C_{1-6}$-alkyl)-$C_{1-6}$-alkoxy-$C_{1-6}$-alkanoylamido, N—$C_{1-6}$-alkylcarbamoyl-$C_{1-6}$-alkyl, $C_{3-8}$-cycloalkanoylamido-$C_{1-6}$-alkyl, $C_{1-6}$-alkylaminocarbonylamino-$C_{1-6}$-alkyl, $C_{1-6}$-alkanoylamidomethylpyrrolidinyl, N—($C_{1-6}$-alkoxy-$C_{1-6}$-alkyl)carbamoyl, N—($C_{1-6}$-alkoxy-$C_{1-6}$-alkyl)-N—($C_{1-6}$-alkyl)carbamoyl, N—($C_{1-6}$-alkoxy-$C_{1-6}$-alkyl)imidazol-2-yl, hydroxy-$C_{1-6}$-alkyl, hydroxy-$C_{1-6}$-oxy, hydroxy-$C_{1-6}$-alkoxy-$C_{1-6}$-alkyl, $C_{1-6}$-oxycarbonylamino-$C_{1-6}$-alkyl, amino-$C_{1-6}$-alkyl and $C_{1-6}$-alkylamino-$C_{1-6}$-alkyl.

Further examples of very particularly preferred $R^1$ radicals, especially in compounds of groups (B), (C), (D), (E), (F) or (G) are 3,4-dihydro-1H-quinolin-2-on-7-yl, 4,4-dimethyl-3,4-dihydro-1H-quinolin-2-on-8-yl and phenyl which is substituted as specified above, especially by at least one substituent selected from N-acetyl-$C_{1-6}$-alkoxy-$C_{1-6}$-alkylamino, $C_{1-6}$-alkylcarbonylamino-$C_{1-6}$-alkyl, $C_{1-6}$-alkylcarbonylamino-$C_{1-6}$-alkoxy, N—$C_{1-6}$-alkyl-$C_{1-6}$-alkanoylamido-$C_{1-6}$-alkyl, $C_{1-6}$-alkoxy-$C_{1-6}$-alkoxy-$C_{1-6}$-alkyl, triazol-1-yl-$C_{1-6}$-alkyl, tetrazol-1-yl-$C_{1-6}$-alkyl, tetrazol-2-yl-$C_{1-6}$-alkyl, tetrazol-5-yl-$C_{1-6}$-yl, $C_{1-6}$-alkoxycarboxyl-$C_{1-6}$-alkyl, pyrrolidinonyl-$C_{1-6}$-alkyl, imidazolyl-$C_{1-6}$-alkyl, cyano-$C_{1-6}$-alkyl, carboxy-$C_{1-6}$-alkyl, carboxy-$C_{1-6}$-alkoxy, $C_{1-6}$-alkoxycarbonyl-$C_{1-6}$-yl, $C_{1-6}$-alkylsulphonamidyl-$C_{1-6}$-alkyl, $C_{1-6}$-alkoxy-$C_{1-6}$-alkanoylamido, $C_{1-6}$-alkoxy-$C_{1-6}$-alkanoylamido-$C_{1-6}$-yl, N—($C_{1-6}$-alkyl)-$C_{1-6}$-alkoxy-$C_{1-6}$-alkanoylamido, N—$C_{1-6}$-ylcarbamoyl-$C_{1-6}$-alkyl, $C_{3-8}$-cycloalkanoylamido-$C_{1-6}$-yl, $C_{1-6}$-alkylaminocarbonylamino-$C_{1-6}$-alkyl, $C_{1-6}$-alkanoylamidomethylpyrrolidinyl, N—($C_{1-6}$-alkoxy-$C_{1-6}$-alkyl)carbamoyl, N—($C_{1-6}$-alkoxy-$C_{1-6}$-alkyl)-N—($C_{1-6}$-alkyl)carbamoyl, N—($C_{1-6}$-alkoxy-$C_{1-6}$-alkyl)imidazol-2-yl, hydroxy-$C_{1-6}$-alkyl, hydroxy-$C_{1-6}$-alkoxy-$C_{1-6}$-alkyl, $C_{1-6}$-alkoxycarbonylamido-$C_{1-6}$-alkyl, amino-$C_{1-6}$-alkyl and $C_{1-6}$-alkylamino-$C_{1-6}$-alkyl.

Examples of particularly preferred $R^2$ radicals are phenyl or halophenyl each substituted by ($C_{1-6}$-alkanoyl)aminophenoxy-$C_{1-6}$-alkyl, $C_{1-6}$-alkoxy, $C_{1-6}$-alkoxy-$C_{1-6}$-alkoxy, $C_{1-6}$-oxy-$C_{1-6}$-alkoxy-$C_{1-6}$-alkyl, $C_{1-6}$-alkoxy-$C_{1-6}$-alkyl, $C_{1-6}$-alkoxybenzyl-$C_{1-6}$-alkoxy, $C_{1-6}$-alkoxybenzyloxy-$C_{1-6}$-alkoxy, $C_{1-6}$-alkoxybenzyloxy-$C_{1-6}$-alkoxy-$C_{1-6}$-alkyl, $C_{1-6}$-alkoxymethylbenzyloxy-$C_{1-6}$-alkoxy, $C_{1-6}$-alkoxyphenoxy-$C_{1-6}$-alkoxy, $C_{1-6}$-alkoxyphenoxy-$C_{1-6}$-alkyl, $C_{1-6}$-alkoxyphenyl-$C_{1-6}$-alkoxy-$C_{1-6}$-alkoxy, N—($C_{1-6}$-alkoxyphenyl-$C_{1-6}$-alkyl)amino-$C_{1-6}$-alkoxy, N—($C_{1-6}$-alkoxyphenyl)azetidinyloxy, N—($C_{1-6}$-alkoxyphenyl)pyrrolidinyloxy, $C_{1-6}$-alkoxypyrimidinylamino-$C_{1-6}$-alkoxy, $C_{1-6}$-alkoxypyridylamino-$C_{1-6}$-alkoxy, (N—($C_{1-6}$-alkyl)-N-(benzoyl)amino)pyrrolidin-1-yl, $C_{1-6}$-alkylbenzyloxy-$C_{1-6}$-alkoxy, N—($C_{1-6}$-alkyl)carbamoyl-$C_{1-6}$-alkyl, (N—($C_{1-6}$-alkyl)carbamoyl-$C_{1-6}$-alkyl)phenoxy-$C_{1-6}$-alkyl, $C_{1-6}$-alkylindolyl-$C_{1-6}$-alkoxy, N—($C_{1-6}$-alkyl)indol-4-yloxy-$C_{1-6}$-alkyl, $C_{1-6}$-alkylphenoxy, $C_{1-6}$-alkylphenoxy-$C_{1-6}$-alkoxy, $C_{1-6}$-alkylphenoxy-$C_{1-6}$-alkyl, N—($C_{1-6}$-alkyl)-N-(phenoxy-$C_{1-6}$-alkyl)aminocarbonyl, azetidin-1-yl, benzo[1,3]dioxolyloxy-$C_{1-6}$-alkoxy, N-(benzoyl)azetidinyloxy, N-(benzyl)azetidinyloxy, benzyloxy, (carbamoyl-$C_{1-6}$-alkyl)phenoxy-$C_{1-6}$-alkyl, cyanophenoxy-$C_{1-6}$-alkoxy, N—($C_{3-8}$-cycloalkanoyl)pyrrolidinyloxy, N—($C_{3-8}$-cycloalkyl-$C_{1-6}$-alkanoyl)pyrrolidinyloxy, $C_{3-8}$-cycloalkoxy, $C_{3-8}$-cycloalkoxy-$C_{1-6}$-alkoxy, $C_{3-8}$-cycloalkyl-$C_{1-6}$-alkoxy, $C_{3-8}$-cycloalkyl-$C_{1-6}$-alkoxy-$C_{1-6}$-alkyl, N—($C_{3-6}$-cycloalkyl-$C_{0-6}$-alkyl)amino-$C_{1-6}$-alkoxy, N—($C_{3-8}$-cycloalkyl)pyrrolidinyloxy, N,N-(di-$C_{1-6}$-alkyl)amino-$C_{1-6}$-alkoxy, 3,4-dihydroquinolin-2-on-5-yloxy-$C_{1-6}$-alkyl, 3,4-dihydro-1H-isoquinolin-2-yl-$C_{1-6}$-alkoxy, halobenzoylamido-$C_{1-6}$-alkoxy, N-(halobenzyl)amino-$C_{1-6}$-alkoxy, halobenzyloxy-$C_{1-6}$-alkoxy, halophenoxy, halophenoxy-$C_{1-6}$-alkoxy, halophenoxy-$C_{1-6}$-alkoxy-$C_{1-6}$-alkyl, halophenoxy-$C_{1-6}$-alkyl, halophenoxy-$C_{1-6}$-alkylamino, N-(halophenoxy-$C_{1-6}$-alkyl)amino-$C_{1-6}$-alkyl, halophenyl-$C_{1-6}$-alkoxy-$C_{1-6}$-alkoxy, N-(halophenyl-$C_{1-6}$-alkyl)amino-$C_{1-6}$-alkoxy, N-(halophenyl)amino-$C_{1-6}$-alkoxy, N-(halophenyl)azetidinyloxy, N-(halophenyl)pyrrolidinyloxy, N-(heteroaryl)azetidinyloxy, N-(heteroaryl)pyrrolidinyloxy, hydroxy-$C_{1-6}$-alkoxy, (hydroxy)phenoxy-$C_{1-6}$-alkoxy, imidazol-1-yl-$C_{1-6}$-alkyl, imidazol-4-ylphenoxy-$C_{1-6}$-alkyl, indol-4-yloxy-$C_{1-6}$-alkyl, phenoxy, phenoxy-$C_{1-6}$-alkyl, phenoxy-$C_{1-6}$-alkoxy, phenoxy-($C_{1-6}$-alkoxy)-$C_{1-6}$-alkoxy, phenoxy-($C_{1-6}$-alkyl)-$C_{1-6}$-alkoxy, N-(phenoxy-$C_{1-6}$-alkyl)aminocarbonyl, (phenoxy)azetidin-1-ylcarbonyl, phenoxy(halo)-$C_{1-6}$-alkoxy, phenoxy(hydroxy)-$C_{1-6}$-alkoxy, (phenoxy)pyrrolidin-1-yl-$C_{1-6}$-alkyl, (phenoxy)pyrrolidin-1-ylcarbonyl, phenyl(amino)-$C_{1-6}$-alkoxy, N-(phenyl)-$C_{1-6}$-alkylpyrrolidinyloxy, phenylazetidinyl-$C_{1-6}$-alkyl, phenylazetidinyloxy, N-(phenyl)azetidinyloxy-$C_{1-6}$-alkyl, phenyl-($C_{3-8}$-cycloalkyl)-$C_{1-6}$-alkoxy-$C_{1-6}$-alkoxy, N4-(phenyl)piperazin-1-yl-$C_{1-6}$-alkyl, N4-(phenyl)piperazin-1-ylcarbonyl, phenylpiperidinyloxy, phenylpyrrolidin-1-yl-$C_{1-6}$-alkoxy, phenylpyrrolidin-1-yl-$C_{1-6}$-alkyl, N—(N-phenylpyrrolidinyl)amino-$C_{1-6}$-alkyl, (phenyl)pyrrolidin-1-ylcarbonyl, (phenyl)pyrrolidin-1-ylcarbonyl-$C_{1-6}$-alkyl, (phenyl)pyrrolidin-1-ylcarbonyloxy, N-(phenyl)pyrrolidinonyloxy, N-(phenyl)pyrrolidinyloxy, N-(phenyl)pyrrolidinyloxy-$C_{1-6}$-alkyl, piperidinyloxy-$C_{1-6}$-alkoxy, pyridyloxy-$C_{1-6}$-alkoxy, N-(pyridyl)pyrrolidinyloxy, pyrrolidin-1-yl, tetrahydrofuranyloxy, tetrahydrofuranyloxy-$C_{1-6}$-alkyl, N-(tetrahydropyranylcarbonyl)piperidinyloxy, tetrahydropyranyloxy, tetrahydropyranyloxy-$C_{1-6}$-alkoxy, tetrahydropyranyloxy-$C_{1-6}$-alkyl or trifluoromethylphenoxy-$C_{1-6}$-alkoxy.

Examples of very particularly preferred $R^2$ radicals are phenyl or halophenyl each substituted by $C_{1-6}$-alkoxybenzyloxy-$C_{1-6}$-alkoxy, $C_{1-6}$-alkoxyphenyl-$C_{1-6}$-alkoxy-$C_{1-6}$-alkoxy, $C_{1-6}$-alkylphenoxy-$C_{1-6}$-alkoxy, halobenzyloxy-$C_{1-6}$-alkoxy, halophenoxy-$C_{1-6}$-alkoxy, halophenoxy-$C_{1-6}$-alkoxy-$C_{1-6}$-alkyl, N-(halophenyl)pyrrolidin-3-yloxy and indol-4-yloxy-$C_{1-6}$-alkyl.

Examples of preferred X radicals are oxygen, —O—$CH_2$—CO—NH—, —O—$CH_2$—CO—N($CH_3$)— and —O—CH($CH_3$)—CO—NH—.

Particularly preferred for X is oxygen.

Particularly preferred Z radicals are methylene, —($CH_2$)$_2$—O— and —CH($CH_3$)—.

Very particularly preferred are the compounds of Example numbers 2, 5, 13, 14, 58, 59, 60, 64, 76, 79, 100, 108, 109, 110, 111, 112, 113, 115, 119, 121, 140, 141, 142, 143, 180, 182, 185, 187, 194, 196, 245, 270, 273, 278 and 346.

The compounds of the formula (I) or (II) may be prepared in a similar manner to the preparation processes disclosed in the literature. Similar preparation processes are described, for example, in WO 97/09311. Details on the specific preparation variants can be taken from the examples.

The compounds of the formula (I) or (II) may also be prepared in optically pure form. The separation into antipodes can be effected by methods known per se, either preferably at an earlier synthetic stage by salt formation with an optically active acid, for example (+)- or (−)-mandelic acid and separation of the diastereomeric salts by fractional crystallization, or preferably at a relatively late stage by derivatizing with a chiral auxiliary building block, for example (+)- or (−)-camphanoyl chloride, and separation of the diastereomeric products by chromatography and/or crystallization and subsequent cleavage of the bonds to give the chiral auxiliary. The pure diastereomeric salts and derivatives may be analysed to determine the absolute configuration of the piperidine present with common spectroscopic methods, and X-ray spectroscopy on single crystals constitutes a particularly suitable method.

Prodrug derivatives of the compounds described in the present context are derivatives thereof which, on in vivo application, release the original compound by a chemical or physiological process. A prodrug may be converted to the original compound, for example, when a physiological pH is attained or by enzymatic conversion. Prodrug derivatives may, for example, be esters of freely available carboxylic acids, S- and O-acyl derivatives of thiols, alcohols or phenols, and the acyl group is as defined in the present context. Preference is given to pharmaceutically useable ester derivatives which are converted by solvolysis in physiological medium to the original carboxylic acid, for example lower alkyl esters, cycloalkyl esters, lower alkenyl esters, benzyl esters, mono- or disubstituted lower alkyl esters such as lower ω-(amino, mono- or dialkylamino, carboxyl, lower alkoxycarbonyl)-alkyl esters or such as lower α-(alkanoyloxy, alkoxycarbonyl or dialkylaminocarbonyl)-alkyl esters; as such, pivaloyloxymethyl esters and similar esters are utilized in a conventional manner.

Owing to the close relationship between a free compound, a prodrug derivative and a salt compound, a certain compound in this invention also encompasses its prodrug derivative and salt form, where these are possible and appropriate.

The compounds of the formulae (I) and (II), respectively of the formulae (IA) and (IIA), and their pharmaceutically useable salts have inhibiting action on the natural enzyme renin. The latter passes from the kidneys into the blood and there brings about the cleavage of angiotensinogen to form the decapeptide angiotensin I which is then cleaved in the lung, the kidneys and other organs to the octapeptide angiotensin II. Angiotensin II increases the blood pressure both directly by arterial constriction and indirectly by the release of the hormone aldosterone which inhibits the release of the sodium ion from the adrenal glands, which is associated with a rise in the extracellular liquid volume. This rise can be attributed to the action of angiotensin II itself or of the heptapeptide angiotensin III formed therefrom as a cleavage product. Inhibitors of the enzymatic activity of renin bring about a reduction in the formation of angiotensin I and, as a consequence thereof, the formation of a smaller amount of angiotensin II. The reduced concentration of this active peptide hormone is the immediate cause of the hypotensive action of renin inhibitors.

One experimental method of detecting the action of renin inhibitors is by means of in vitro tests, in which the reduction of the formation of angiotensin I in different systems (human plasma, purified human renin together with synthetic or natural renin substrate) is measured. One in vitro test which is used is the one according to Nussberger et. al (1987) J. Cardiovascular Pharmacol., Vol. 9, p. 39-44 which follows. This test measures the formation of angiotensin I in human plasma. The amount of angiotensin I formed is determined in a subsequent radioimmunoassay. Which action inhibitors have on the formation of angiotensin I is tested in this system by the addition of different concentrations of these substances. The $IC_{50}$ refers to that concentration of the particular inhibitor which reduces the formation of angiotensin I by 50%. The compounds of the present invention exhibit inhibiting actions in the in vitro systems at minimum concentrations of about $10^{-6}$ to about $10^{-10}$ mol/l.

In salt-depleted animals, renin inhibitors bring about a blood pressure decrease. Human renin differs from renin of other species. To test inhibitors of human renin, primates (marmosets, Callithrixjacchus) are used, because human renin and primate renin are substantially homologous in the enzymatically active region. One in vivo test which is used is as follows: the test compounds are tested on normotensive marmosets of both genders and having a body weight of about 350 g which are conscious, able to move freely and in their normal cages. Blood pressure and heart rate are measured using a catheter in the descending aorta and recorded radiometrically. The endogenous release of renin is stimulated by the combination of a 1-week low-salt diet with a single intramuscular injection of furosemide (5-(aminosulphonyl)-4-chloro-2-[(2-furanylmethyl)amino]benzoic acid) (5 mg/kg). 16 hours after the injection of furosemide, the test substances are administered either directly into the femoral artery by means of an injection cannular or into the stomach by gavage as a suspension or solution, and their effect on blood pressure and heart rate was evaluated. The compounds of the present invention effectively reduce blood pressure in the in vivo test described at doses of about 0.003 to about 0.3 mg/kg i.v. and at doses of about 0.3 to about 30 mg/kg p.o.

The compounds of the formula (I) or (II), or preferably of the formula (IA) or (IIA), and their pharmaceutically useable salts may find use as medicaments, for example in the form of pharmaceutical preparations. The pharmaceutical preparations may be administered enterally, such as orally, for example in the form of tablets, coated tablets, sugar-coated tablets, hard and soft gelatine capsules, solutions, emulsions or suspensions, nasally, for example in the form of nasal sprays, rectally, for example in the form of suppositories, or transdermally, for example in the form of ointments or patches. The administration may also be parenteral, such as intramuscular or intravenous, for example in the form of injection solutions.

To prepare tablets, coated tablets, sugar-coated tablets and hard gelatine capsules, the compounds of the formula (I) or (II), or preferably of the formula (IA) or (IIA), and pharmaceutically useable salts thereof, may be processed with pharmaceutically inert, inorganic or organic excipients. Such excipients used, for example for tablets, coated tablets and hard gelatine capsules, may be lactose, corn starch, or derivatives thereof, talc, stearic acid or salts thereof etc.

Suitable excipients for soft gelatine capsules are, for example, vegetable oils, waxes, fats, semisolid and liquid polyols, etc.

Suitable excipients for preparing solutions and syrups are, for example, water, polyols, sucrose, invert sugar, glucose, etc.

Suitable excipients for injection solutions are, for example, water, alcohols, polyols, glycerol, vegetable oils, bile acids, lecithin, etc.

Suitable excipients for suppositories are, for example, natural or hardened oils, waxes, fats, semisolid or liquid polyols, etc.

The pharmaceutical preparations may additionally also comprise preservatives, solubilizers, viscosity-increasing substances, stabilizers, wetting agents, emulsifiers, sweeteners, colorants, flavourings, salts for altering the osmotic pressure, buffers, coatings or antioxidants. They may also comprise other therapeutically valuable substances.

The present invention further provides the use of the compounds of the formula (I) or (II), or preferably of the formula (IA) or (IIA), and the pharmaceutically useable salts thereof, in the treatment or prevention of hypertension and heart failure, and also glaucoma, cardiac infarction, kidney failure and restenoses of mammals, especially of human beings.

The compounds of the formula (I) or (II), or preferably of the formula (IA) or (IIA), and the pharmaceutically useable salts thereof, may also be administered in combination with one or more agents having cardiovascular action, for example α- and β-blockers such as phentolamine, phenoxybenzamine, prazosin, terazosin, tolazine, atenolol, metoprolol, nadolol, propranolol, timolol, carteolol etc.; vasodilators such as hydralazine, minoxidil, diazoxide, nitroprusside, flosequinan etc.; calcium antagonists such as aminone, bencyclan, diltiazem, fendiline, flunarizine, nicardipine, nimodipine, perhexylene, verapamil, gallopamil, nifedipine etc.; ACE inhibitors such as cilazapril, captopril, enalapril, lisinopril etc.; potassium activators such as pinacidil; anti-serotoninergics such as ketanserin; thromboxane-synthetase inhibitors; neutral endopeptidase inhibitors (NEP inhibitors); angiotensin II antagonists; and also diuretics such as hydrochlorothiazide, chlorothiazide, acetazolamide, amiloride, bumetamide, benzthiazide, ethacrynic acid, furosemide, indacrinone, metolazone, spironolactone, triamteren, chlorthalidone etc.; sympatholytics such as methyldopa, clonidine, guanabenz, reserpine; and other agents which are suitable for the treatment of hypertension, heart failure or vascular diseases in humans and animals which are associated with diabetes or renal disorders such as acute or chronic renal failure. Such combinations may be employed separately or in preparations which comprise a plurality of components.

Further substances which can be used in combination with the compounds of the formulae (I), (IA), (II) or (IIA) are the compounds of classes (i) to (ix) on page 1 of WO 02/40007 (and also the preferences and examples further listed therein) and the substances specified on pages 20 and 21 of WO 03/027091.

The dose may vary within wide limits and has of course to be adapted to the individual circumstances in each individual case. In general, for oral administration, a daily dose of about 3 mg to about 3 g, preferably about 10 mg to about 1 g, for example about 300 mg, per adult (70 kg), divided into preferably 1-3 individual doses which may, for example, be of equal size, may be appropriate, although the upper limit specified may also be exceeded if this should be found to be appropriate; typically, children receive a lower dose according to their age and body weight.

The examples which follow illustrate the present invention. All temperatures are reported in degrees Celsius, pressures in mbar. Unless stated otherwise, the reactions takes place at room temperature. The abbreviation "Rf=xx (A)" means, for example, that the Rf value xx is obtained in the solvent system A. The ratio of the solvents relative to one another is always reported in parts by volume. Chemical names of end products and intermediates were obtained with the aid of the program AutoNom 2000 (Automatic Nomenclature). Unless stated otherwise, the absolute stereochemistry of the 3-alkoxy-4-phenylpiperidine unit is (3R,4R).

HPLC gradients on Hypersil BDS C-18 (5 µm); column: 4×125 mm

90% water*/10% acetonitrile* to 0% water /100% acetonitrile* in 5 minutes+2.5 minutes (1.5 ml/min); *: containing 0.1% trifluoroacetic acid     I 95% water*/5% acetonitrile* to 0% water/100% acetonitrile* in 40 minutes (0.8 ml/min); *: containing 0.1% trifluoroacetic acid The following abbreviations are used:

Rf ratio of distance which a substance travels to distance of the eluent front from the start point in thin layer chromatography Rt retention time of a substance in HPLC (in minutes)

m.p. melting point (temperature)

General Method A: (N—BOC Deprotection)

The solution of 1 mmol of "N—BOC derivative" in 5 ml of chloroform is admixed successively with 15 ml of methanol and 2.5 ml of 2N HCl and stirred at 60° C. over 18 hours. The reaction mixture is cooled to room temperature, poured onto 1M aqueous sodium hydrogencarbonate solution (40 ml) and extracted with tert-butyl methyl ether (2×60 ml). The organic phases are washed with brine (1×60 ml), dried over sodium sulphate and concentrated by evaporation. The title compound is obtained from the residue by means of flash chromatography ($SiO_2$ 60F).

General Method B: (N-Cbz Deprotection)

The solution of 1 mmol of "N-Cbz derivative" in 15 ml of tetrahydrofuran is hydrogenated in the presence of 100-200 mg of 10% Pd/C at 15-20° C. over 2-20 hours. The reaction mixture is clarified by filtration and the filtrate is concentrated by evaporation. The title compound is obtained from the residue by means of flash chromatography ($SiO_2$ 60F).

General Method C: (9-BBN Reduction)

The solution of 1 mmol of "lactam" in 3 ml of tetrahydrofuran is admixed with 9-BBN (0.5M in tetrahydrofuran) (3.2-6.4 equiv.) and stirred at reflux over 1-2 hours (checking of conversion with HPLC). The reaction mixture is cooled to room temperature, admixed with ethanolamine (3.2-6.4 equiv) and concentrated by evaporation. The residue is stirred in 1:1 ethyl acetate-heptane (30 ml) at 0° C. overnight and clarified by filtration, and the filtrate is concentrated by evaporation. The title compound is obtained from the residue by means of flash chromatography ($SiO_2$ 60F).

General Method D: (O-alkylation)

The solution of 1 mmol of "alcohol", 1.0-2.0 mmol of "benzyl halide" in 2.0 ml N,N-dimethylformamide is admixed with stirring at −10° C. with 1.1 mmol of sodium hydride dispersion (60%). The reaction mixture is stirred at −10° C. over 1 hour and at room temperature over 18 hours. The mixture is poured onto 1M aqueous sodium hydrogencarbonate solution (50 ml) and extracted with tert-butyl methyl ether (2×50 ml). The organic phases are washed successively with water (1×50 ml) and brine (1×60 ml), dried over sodium sulphate and concentrated by evaporation. The title compound is obtained from the residue by means of flash chromatography ($SiO_2$ 60F).

General Method E: (Chlorination)

The solution of 40 mmol of "benzyl alcohol" in 6.40 ml of pyridine and 100 ml of dichloromethane is slowly added dropwise at 0-5° C. to the precooled solution of 7.65 ml of thionyl chloride in 20 ml of dichloromethane. The reaction mixture is stirred at 0° C. and then at room temperature for 1 hour each and subsequently poured onto 200 ml of ice-water. The mixture is extracted with dichloromethane (2×200 ml). The organic phases are washed successively with 1M aqueous sodium hydrogencarbonate solution (2×200 ml) and brine, dried over sodium sulphate and concentrated by evaporation. The title compound is obtained from the residue by means of flash chromatography ($SiO_2$ 60F).

General Method F: (Phenol Alkylation I)

The mixture of 20 mmol of "phenol" in 60 ml of N,N-dimethylformamide is stirred with 4.15 g of potassium carbonate and 30 mmol of "halide" or "tosylate" at 100° C. over 24 hours. The reaction mixture is then concentrated by evaporation. The residue is admixed with 1M aqueous sodium hydrogencarbonate solution (40 ml) and extracted with ethyl acetate (2×60 ml). The organic phases are washed with brine (1×60 ml), dried over sodium sulphate and concentrated by evaporation. The title compound is obtained from the residue by means of flash chromatography ($SiO_2$ 60F).

General Method G: (Phenol Alkylation II)

A suspension of 1 mmol of "tosylate", 2 mmol of "phenol", 2 mmol of potassium carbonate and 20 ml of acetonitrile is stirred at 90° C. over 24 h. The reaction mixture is then concentrated by evaporation. The residue is then admixed with saturated aqueous sodium hydrogencarbonate solution and extracted with ethyl acetate (2×). The organic phases are washed with brine, dried over sodium sulphate and concentrated by evaporation. The title compound is obtained from the residue by means of flash chromatography ($SiO_2$ 60F).

General Method H: (Tosylation)

A solution of 12 mmol of p-toluenesulphonyl chloride in 15 ml of dichloromethane is added dropwise at 0° C. to the solution of 10 mmol of "alcohol", 15 mmol of triethylamine, 1 mmol of 4-dimethylaminopyridine in 90 ml of dichloromethane. The reaction mixture is stirred at room temperature over 2-18 hours. The reaction mixture is diluted with dichloromethane and subsequently washed with water and brine, dried over sodium sulphate and concentrated by evaporation. The title compound is obtained from the residue by means of flash chromatography ($SiO_2$ 60F).

General Method I: (Phenol Alkylation III)

A suspension of 1 mmol of "phenol", 1.0-1.5 mmol of "tosylate" or "bromide", 1.5 mmol of caesium carbonate and 2 ml of acetonitrile is stirred at 80° C. over 2 hours. The reaction mixture is cooled, poured onto water and extracted with ethyl acetate (2×). The organic phases are washed with brine, dried over sodium sulphate and concentrated by evaporation. The title compound is obtained from the residue by means of flash chromatography ($SiO_2$ 60F).

EXAMPLE 1

4-{4-[3-(2-Methoxybenzyloxy)propoxy]phenyl}-3-[3-methoxy-5-(3-methoxypropoxy)benzyloxy]piperidine Analogously to Method A, 0.215 g of tert-butyl 4-[4-(3-benzyloxypropoxy)phenyl]-3-[3-(3-methoxypropoxy)benzyloxy]piperidine-1-carboxylate was used to prepare the title compound.

The starting materials were prepared as follows:

a) tert-butyl 4-[4-(3-benzyloxypropoxy)phenyl]-3-[3-(3-methoxypropoxy)benzyloxy]piperidine-1-carboxylate Analogously to Method D, 0.238 g of tert-butyl 3-hydroxy-4-{4-[3-(2-methoxybenzyloxy)propoxy]phenyl}piperidine-1-carboxylate and 0.122 g of 1-chloromethyl-3-methoxy-5-(3-methoxypropoxy)benzene are reacted. The title compound is obtained as a colourless oil. Rf=0.42 (1:1 EtOAc-heptane); Rt=6.19.

b) 1-Chloromethyl-3-methoxy-5-(3-methoxypropoxy)benzene

Analogously to Method E, 1.13 g of [3-methoxy-5-(3-methoxypropoxy)phenyl]methanol are reacted. The title compound is obtained as a slightly yellowish oil. Rf=0.50 (1:1 EtOAc-heptane).

c) [3-Methoxy-5-(3-methoxypropoxy)phenyl]methanol

Analogously to Method F, 3.15 g of 3-hydroxymethyl-5-methoxyphenol are reacted with 1-chloro-3-methoxypropane. The title compound is obtained as a slightly yellowish oil. Rf=0.27 (1:1 EtOAc-heptane). Rt=3.23.

EXAMPLE 2

6-(4-{4-[3-(2-Methoxybenzyloxy)propoxy]phenyl}piperidin-3-yloxymethyl)-4-(3-methoxypropyl)-4H-benzo[1,4]oxazin-3-one Analogously to Method A, 0.143 g of tert-butyl 4-{4-[3-(2-methoxybenzyloxy)propoxy]phenyl}-3-[4-(3-methoxypropyl)-3-oxo-3,4-dihydro-2H-benzo[1,4]oxazin-6-ylmethoxy]piperidine-1-carboxylate is used to prepare the title compound.

The starting materials are prepared as follows:

a) tert-Butyl 4-{4-[3-(2-methoxybenzyloxy)propoxy]phenyl}-3-[4-(3-methoxypropyl)-3-oxo-3,4-dihydro-2H-benzo[1,4]oxazin-6-ylmethoxy]piperidine-1-carboxylate Analogously to Method D, 0.340 g of tert-butyl 3-hydroxy-4-{4-[3-(2-methoxybenzyloxy)propoxy]phenyl}piperidine-1-carboxylate and 0.193 g of 6-chloromethyl-4-(3-methoxypropyl)-4H-benzo[1,4]oxazin-3-one are reacted. The title compound is obtained as a colourless oil. Rf=0.30 (1:1 EtOAc-heptane); Rt=5.99.

b) 6-Chloromethyl-4-(3-methoxypropyl)-4H-benzo[1,4]oxazin-3-one

Analogously to Method E, 0.37 g of 6-hydroxymethyl-4-(3-methoxypropyl)-4H-benzo[1,4]oxazin-3-one is reacted. The title compound is obtained as a colourless oil. Rf=0.60 (2:1 EtOAc-heptane). Rt=4.05.

c) 6-Hydroxymethyl-4-(3-methoxypropyl)-4H-benzo[1,4]oxazin-3-one

The suspension of 1.79 g of 6-hydroxymethyl-4H-benzo[1,4]oxazin-3-one, 2.20 ml of 1-chloro-3-methoxypropane, 10 g of KF on alumina and 0.033 g of potassium iodide in 150 ml of acetonitrile is stirred at reflux over 72 hours. The reaction mixture is cooled and clarified by filtration, and the filtrate is concentrated by evaporation to dryness. The title compound is obtained from the residue by means of flash chromatography (SiO$_2$ 60F). Rf=0.60 (9:1 dichloromethane-methanol); Rt=2.74.

d) 6-Hydroxymethyl-4H-benzo[1,4]oxazin-3-one

The mixture of 6.9 g of methyl 3-oxo-3,4-dihydro-2H-benzo[1,4]oxazine-6-carboxylate and 230 ml of tetrahydrofuran is cooled to −40° C. Over 30 minutes, 88.9 ml of diisobutylaluminium hydride (1.5M in toluene) are added dropwise at −40° C. The reaction mixture is stirred at from −40° C. to −20° C. over 1.5 hours and subsequently poured cautiously onto 150 ml of 2N HCl (cold). The organic phase is removed and the water phase extracted with tetrahydrofuran (5×100 ml). The organic phases are washed with brine (1×100 ml), filtered through cottonwool and concentrated by evaporation. The title compound is obtained as beige crystals from the residue by crystallization (from ethanol). Rf (2:1 EtOAc-heptane)=0.16; Rt=2.23; m.p.: 186-187° C.

EXAMPLE 3

2(R,S)-(4-{4-[3-(2-Methoxybenzyloxy)propoxy]phenyl}piperidin-3-yloxy)-N-[2-(3-methoxypropoxy)phenyl]propionamide Analogously to Method A, 0.075 g of tert-butyl 4-{4-[3-(2-methoxybenzyloxy)propoxy]phenyl}-3-{1-[2(R,S)-(3-methoxypropoxy)phenylcarbamoyl]ethoxy}piperidine-1-carboxylate is used to prepare the title compound.

The starting materials are prepared as follows:

a) tert-Butyl 4-{4-[3-(2-methoxybenzyloxy)propoxy]phenyl}-3-{1-[2(R,S)-(3-methoxypropoxy)phenylcarbamoyl]ethoxy}piperidine-1-carboxylate 0.07 ml of 4-methylmorpholine and a solution of 0.12 ml of diethyl cyanphosphonate in 2 ml of N,N-dimethylformamide are added dropwise to the solution of 0.29 g of tert-butyl 3-(1(R,S)-carboxyethoxy)-4-{4-[3-(2-methoxybenzyloxy)propoxy]phenyl}-piperidine-1-carboxylate and 0.13 g of 2-(3-methoxypropoxy)phenylamine in 5 ml of N,N-dimethylformamide. The reaction mixture is stirred at room temperature over 18 hours and then partitioned between ethyl acetate and water. The organic phase is washed with saturated sodium carbonate solution, water, 1N HCl and brine, dried over sodium sulphate and concentrated by evaporation. The title compound is obtained as a yellowish oil from the residue by means of flash chromatography (SiO$_2$ 60F). Rf=0.57 (200:20:0.5 dichloromethane-methanol-25% conc. ammonia); Rt=6.13.

b) tert-Butyl 3-(1(R,S)-carboxyethoxy)-4-{4-[3-(2-methoxybenzyloxy)propoxy]phenyl}piperidine-1-carboxylate A solution of 0.33 g of tert-butyl 3-(1(R,S)-ethoxycarbonylethoxy)-4-{4-[3-(2-methoxybenzyloxy)propoxy]phenyl}piperidine-1-carboxylate in 4 ml of methanol and 1 ml of 2N NaOH is stirred at room temperature over 18 hours. The reaction mixture is admixed with 1.5 ml of 4N HCl and extracted with EtOAc. The organic phase is washed with brine, dried over sodium sulphate and concentrated by evaporation. The crude title compound is obtained as a yellowish oil from the residue. Rt=5.33.

c) tert-Butyl 3-(1(R,S)-ethoxycarbonylethoxy)-4-{4-[3-(2-methoxybenzyloxy)propoxy]phenyl}piperidine-1-carboxylate Analogously to Method D, 0.5 g of tert-butyl 3-hydroxy-4-{4-[3-(2-methoxybenzyloxy)propoxy]phenyl}piperidine-1-carboxylate and 0.15 ml of ethyl 2-bromopropionate are reacted. The title compound is obtained as a slightly yellowish oil. Rf=0.40 (1:1 EtOAc-heptane); Rt=5.93/6.0.

d) 2-(3-Methoxypropoxy)phenylamine

A suspension of 2.55 g of 1-(3-methoxypropoxy)-2-nitrobenzene, 3.72 g of ammonium formate in 25 ml of methanol is hydrogenated at reflux in the presence of 0.26 g of 10% Pd/C over 1.5 hours. The reaction mixture is cooled and clarified by filtration, and the filtrate is concentrated by evaporation. The residue is dissolved in diethyl ether, washed with water (2×) and brine, dried over sodium sulphate and concentrated by evaporation. The title compound is obtained as a red oil from the residue by means of flash chromatography (SiO$_2$ 60F). Rf=0.30 (1:2 EtOAc-heptane); Rt=2.28.

e) 1-(3-Methoxypropoxy)-2-nitrobenzene

A suspension of 2.00 g of 2-nitrophenol, 1.72 g of 1-chloro-3-methoxypropane and 3.04 g potassium carbonate in 20 ml of N,N-dimethylformamide is stirred at reflux over 23 hours. The reaction mixture is concentrated by evaporation. The residue is partitioned between ethyl acetate and a 9:1 water/brine mixture. The water phase is extracted using ethyl acetate (2×). The organic phases are washed with brine, dried over sodium sulphate and concentrated by evaporation. The title compound is obtained as a yellow oil from the residue by means of flash chromatography (SiO$_2$ 60F). Rf=0.33 (1:2 EtOAc-heptane); Rt=4.08.

EXAMPLE 5

6-(4-{4-[3-(2-Methoxybenzyloxy)propoxy]phenyl}piperidin-3-yloxymethyl)-4-(3-methoxypropyl)-3,4-dihydro-2H-benzo[1,4]oxazine Analogously to Method C, 0.220 g of 6-(4-{4-[3-(2-methoxybenzyloxy)propoxy]phenyl}piperidin-3-yloxymethyl)-4-(3-methoxypropyl)-4H-benzo[1,4]oxazin-3-one (Example 2) is used to prepare the title compound.

EXAMPLE 6

5-(4-{4-[3-(2-Methoxybenzyloxy)propoxy]phenyl}piperidin-3-yloxymethyl)-3-(3-methoxypropyl)-3H benzoxazol-2-one Analogously to Method A, 0.098 g of tert-butyl 4-{4-[3-(2-methoxybenzyloxy)propoxy]phenyl}-3-[3-(3-methoxypropyl)-2-oxo-2,3-dihydrobenzoxazol-5-ylmethoxy]piperidine-1-carboxylate is used to prepare the title compound.

The starting materials are prepared as follows:

a) tert-Butyl 4-{4-[3-(2-methoxybenzyloxy)propoxy]phenyl}-3-[3-(3-methoxypropyl)-2-oxo-2,3-dihydrobenzoxazol-5-ylmethoxy]piperidine-1-carboxylate The solution of 0.206 g of tert-butyl 4-{4-[3-(2-methoxybenzyloxy)propoxy]phenyl}-(3R,4R)-3-(2-oxo-2,3-dihydrobenzoxazol-5-ylmethoxy)piperidine-1-carboxylate in 2 ml of N,N-dimethylformamide is cooled to 0° C. with stirring and admixed with 12 mg of sodium hydride dispersion (60%). The mixture is stirred at 0° C. for 30 minutes and subsequently admixed with 0.048 ml of 1-chloro-3-methoxypropane and 5 mg of sodium iodide. The reaction mixture is stirred at 80° C. for 14 hours, cooled and poured onto water (40 ml). The mixture is extracted with ethyl acetate (2×40 ml). The organic phases are washed successively with water (2×40 ml) and brine (1×40 ml), dried over sodium sulphate and concentrated by evaporation. The title compound is obtained from the residue as a slightly yellowish oil by means of flash chromatography ($SiO_2$ 60F). Rf=0.25 (2:1 toluene-EtOAc); Rt=6.03.

b) tert-Butyl 4-{4-[3-(2-methoxybenzyloxy)propoxy]phenyl}-(3R,4R)-3-(2-oxo-2,3-dihydrobenzoxazol-5-ylmethoxy)piperidine-1-carboxylate 0.133 ml of phenyl chloroformate are added dropwise to the stirred emulsion of 0.640 g of tert-butyl 3-(3-amino-4-hydroxybenzyloxy)-4-{4-[3-(2-methoxybenzyloxy)propoxy]phenyl}piperidine-1-carboxylate and 0.086 g of sodium hydrogencarbonate in 4 ml of methanol and 4 ml of water. The reaction mixture is stirred over 15 minutes and then admixed with 2 ml of methanol. After a further 15 minutes, it is admixed with 0.51 ml of 2N NaOH. After a further 10 minutes, the mixture is admixed with 20 ml of 0.5N HCl and extracted with tert-butyl methyl ether (2×30 ml). The organic phases are washed successively with water (30 ml) and brine (30 ml), dried over sodium sulphate, filtered and concentrated by evaporation. The title compound is obtained as a slightly yellowish oil from the residue by means of flash chromatography ($SiO_2$ 60F). Rf=0.52 (3:1 EtOAc-heptane); Rt=5.56.

c) tert-Butyl 3-(3-amino-4-hydroxybenzyloxy)-4-{4-[3-(2-methoxybenzyloxy)propoxy]-phenyl}piperidine-1-carboxylate The solution of 2.16 g of tert-butyl 3-(4-allyloxy-3-nitrobenzyloxy)-4-{4-[3-(2-methoxybenzyloxy)propoxy]phenyl}piperidine-1-carboxylate in 15 ml of tetrahydrofuran is admixed with stirring at room temperature with 0.025 g of bis(triphenylphosphine)palladium(II) acetate and 0.075 g of lithium borohydride and stirred at room temperature for 2.5 hours. The reaction mixture is poured onto 1M sodium hydrogencarbonate (50 ml) and extracted with tert-butyl methyl ether (2×50 ml). The organic phases are washed with water (50 ml) and brine (50 ml), dried over sodium sulphate, filtered and concentrated by evaporation. The title compound is obtained as a slightly yellowish oil from the residue by means of flash chromatography ($SiO_2$ 60F). Rf=0.38 (1:1 EtOAc-heptane); Rt=6.02.

d) tert-Butyl 3-(4-allyloxy-3-nitrobenzyloxy)-4-{4-[3-(2-methoxybenzyloxy)propoxy]phenyl}piperidine-1-carboxylate Analogously to Method D, 2.0 g of tert-butyl 3-hydroxy-4-{4-[3-(2-methoxybenzyloxy)propoxy]phenyl}piperidine-1-carboxylate and 1.06 g of 1-allyloxy-4-chloromethyl-2-nitrobenzene are reacted. The title compound is obtained as a slightly yellowish oil. Rf=0.31 (1:1 EtOAc-heptane); Rt=6.99.

e) 1-Allyloxy-4-chloromethyl-2-nitrobenzene

Analogously to Method E, 2.0 g of (4-allyloxy-3-nitrophenyl)methanol are reacted. The title compound is obtained as a colourless oil. Rf=0.44 (1:1 EtOAc-heptane); Rt=4.44.

f) (4-Allyloxy-3-nitrophenyl)methanol

The solution of 2.4 g of 4-allyloxy-3-nitrobenzaldehyde in 30 ml of methanol is cooled to 0° C. with stirring and subsequently admixed with 0.48 g of sodium borohydride in portions over 5 minutes. The reaction mixture is stirred further at 0° C. over 30 minutes, then poured onto cooled 2N HCl (100 ml) and extracted with tert-butyl methyl ether (2×100 ml). The organic phases are washed with water (100 ml), 1M sodium hydrogencarbonate solution (100 ml) and brine (100 ml), dried over sodium sulphate, filtered and concentrated by evaporation. The title compound is obtained as a slightly yellowish oil from the residue by means of flash chromatography ($SiO_2$ 60F). Rf=0.12 (1:1 EtOAc-heptane); Rt=3.37.

g) 4-Allyloxy-3-nitrobenzaldehyde

Analogously to Method F, 25 g of 4-hydroxy-3-nitrobenzaldehyde and 25.1 ml of allyl bromide are reacted. The title compound is obtained as a slightly yellowish solid. Rf=0.30 (1:2 EtOAc-heptane). Rt=4.00.

EXAMPLE 7

4-{4-[3-(2-Methoxybenzyloxy)propoxy]phenyl}-3-[7-(3-methoxypropoxy)benzofuran-2-ylmethoxy]piperidine Analogously to Method A, the title compound is prepared from 0.135 g of tert-butyl 4-{4-[3-(2-methoxybenzyloxy)propoxy]phenyl}-3-[7-(3-methoxypropoxy)benzofuran-2-ylmethoxy]piperidine-1-carboxylate.

The starting materials are prepared as follows:

a) tert-Butyl 4-{4-[3-(2-methoxybenzyloxy)propoxy]phenyl}-3-[7-(3-methoxypropoxy)benzofuran-2-ylmethoxy]piperidine-1-carboxylate Analogously to Method D, 0.339 g of tert-butyl 3-hydroxy-4-{4-[3-(2-methoxybenzyloxy)propoxy]phenyl}piperidine-1-carboxylate and 0.215 g of 2-chloromethyl-7-(3-methoxypropoxy)benzofuran are reacted. The title compound is obtained as a yellow oil. Rf=0.37 (1:2 EtOAc-heptane); Rt=6.26.

b) 2-Chloromethyl-7-(3-methoxypropoxy)benzofuran

Analogously to Method E, 0.222 g of [7-(3-methoxypropoxy)benzofuran-2-yl]methanol is reacted. The crude title compound is obtained as an orange-yellow oil. Rt=4.71.

c) 7-(3-Methoxypropoxy)benzofuran-2-yl]methanol 2.24 ml of diisobutylaluminum hydride (1.5M in toluene) are added dropwise at 0° C. to the solution of 0.42 g of ethyl 7-(3-methoxypropoxy)benzofuran-2-carboxylate in 25 ml of dichloromethane. After 3 hours at 0° C., the reaction mixture is admixed cautiously with 2 ml of ethyl acetate and stirred over 1 hour. Subsequently, 3.5 ml of 1M sodium potassium tartrate solution are added. The mixture is stirred over one hour and the dichloromethane is subsequently concentrated by evaporation. The residue is admixed with water and extracted with ethyl acetate (3×). The combined organic phases are washed with 1N HCl and brine, dried over sodium sulphate and concentrated by evaporation. The title compound is obtained as a yellow oil from the residue by means of flash chromatography (SiO$_2$ 60F). Rf=0.20 (1:1 EtOAc-heptane); Rt=3.56.

d) Ethyl 7-(3-methoxypropoxy)benzofuran-2-carboxylate

A suspension of 1.95 g of 2-hydroxy-3-(3-methoxypropoxy)benzaldehyde, 1.16 ml of ethyl chloroacetate and 2.51 g of potassium carbonate in 100 ml of N,N-dimethylformamide is stirred at reflux over 19 hours. The reaction mixture is cooled, poured onto water (at 0° C.), stirred and subsequently extracted with dichloromethane (2×). The combined organic phases are dried over sodium sulphate and concentrated by evaporation. The title compound is obtained as a yellow oil from the residue by means of flash chromatography (SiO$_2$ 60F). Rf=0.50 (1:1 EtOAc-heptane); Rt=4.72.

e) 2-Hydroxy-3-(3-methoxypropoxy)benzaldehyde

A solution of 5.00 g of 2,3-dihydroxybenzaldehyde in 10 ml of dimethyl sulphoxide is added dropwise at room temperature to the suspension of 3.77 g of sodium hydride dispersion (55%) in 28 ml of dimethyl sulphoxide. The reaction mixture is stirred over 1 hour and then admixed with a solution of 3.81 g of 1-chloro-3-methoxypropane in 2 ml of dimethyl sulphoxide. After 2 hours, 0.50 g of sodium iodide is added. After 16 hours, the reaction mixture is poured onto water, acidified to pH 2 with 4N HCl and extracted with dichloromethane (7×). The combined organic phases are washed with 0.5N HCl (2×), dried over sodium sulphate and concentrated by evaporation. The title compound is obtained as a yellow oil from the residue by means of flash chromatography (SiO$_2$ 60F). Rf=0.23 (95:5 dichloromethane-methanol); Rt=3.60.

EXAMPLE 8

N-[5-(4-{4-[3-(2-Methoxybenzyloxy)propoxy]phenyl}piperidin-3-yloxymethyl)-2-methylphenyl]-N-(3-methoxypropyl)acetamide Analogously to Method A, 0.225 g of tert-butyl 3-{3-[acetyl-(3-methoxypropyl)amino]-4-methylbenzyloxy}-4-{4-[3-(2-methoxybenzyloxy)propoxy]phenyl}piperidine-1-carboxylate is used to prepare the title compound.

The starting materials are prepared as follows:

a) tert-Butyl 3-{3-[acetyl-(3-methoxypropyl)amino]-4-methylbenzyloxy}-4-{4-[3-(2-methoxybenzyloxy)propoxy]phenyl}piperidine-1-carboxylate Analogously to Method D, 0.238 g of tert-butyl 3-hydroxy-4-{4-[3-(2-methoxybenzyloxy)propoxy]phenyl}piperidine-1-carboxylate and 0.147 g of N-(5-chloromethyl-2-methylphenyl)-N-(3-methoxypropyl)acetamide are reacted. The title compound is obtained as a slightly yellowish oil. Rf=0.12 (1:1 EtOAc-heptane); Rt=5.90.

b) N-(5-Chloromethyl-2-methylphenyl)-N-(3-methoxypropyl)acetamide

Analogously to Method E, 0.40 g of N-(5-hydroxymethyl-2-methylphenyl)-N-(3-methoxypropyl)acetamide is reacted. The title compound is obtained as a slightly brownish oil. Rf=0.38 (3:1 EtOAc-heptane); Rt=3.86.

c) N-(5-Hydroxymethyl-2-methylphenyl)-N-(3-methoxypropyl)acetamide

The solution of 0.892 g of N-(5-hydroxymethyl-2-methylphenyl)acetamide in 8 ml of N,N-dimethylformamide is cooled to 0° C. with stirring and admixed with 0.16 g of sodium hydride dispersion (60%). The mixture is stirred at 0° C. over 30 minutes and subsequently admixed with 0.489 ml of 1-chloro-3-methoxypropane and 60 mg of sodium iodide. The reaction mixture is stirred at 80° C. over 48 hours and poured onto water (50 ml). The mixture is extracted with ethyl acetate (2×50 ml). The organic phases are washed successively with water (2×50 ml) and brine (1×50 ml), dried over sodium sulphate and concentrated by evaporation. The title compound is obtained as an orange oil from the residue by means of flash chromatography (SiO$_2$ 60F). Rt=2.73.

d) N-(5-Hydroxymethyl-2-methylphenyl)acetamide

The solution of 11.3 g of (3-amino-4-methylphenyl)methanol in 500 ml of chloroform is cooled to 0° C. with stirring and admixed with 13.4 ml of triethylamine. 6.03 ml of acetyl chloride are slowly added dropwise. Subsequently, the mixture is stirred at 0° C. over 2 hours. The reaction mixture is poured onto water (1 l) and extracted with dichloromethane (2×350 ml). The organic phases are washed with brine (350 ml), dried over sodium sulphate and concentrated by evaporation. The title compound is obtained as a slightly brownish solid from the residue by means of flash chromatography (SiO$_2$ 60F). Rf=0.10 (1:2 dichloromethane-diethyl ether); Rt=2.14.

EXAMPLE 9

N-[3-(4-{4-[3-(2-Methoxybenzyloxy)propoxy]phenyl}piperidin-3-yloxymethyl)phenyl]-N-(3-methoxypropyl)acetamide Analogously to Method A, 0.222 g of tert-butyl 3-{3-[acetyl-(3-methoxypropyl)amino]benzyloxy}-4-{4-[3-(2-methoxybenzyloxy)propoxy]phenyl}piperidine-1-carboxylate is used to prepare the title compound.

The starting materials are prepared as follows:

a) tert-Butyl 3-{3-[acetyl-(3-methoxypropyl)amino] benzyloxy}-4-{4-[3-(2-methoxybenzyloxy)propoxy] phenyl}piperidine-1-carboxylate Analogously to Method D, 0.238 g of tert-butyl 3-hydroxy-4-{4-[3-(2-methoxybenzyloxy)-propoxy] phenyl}piperidine-1-carboxylate and 0.128 g of N-(3-chloromethylphenyl)-N-(3-methoxypropyl)acetamide are reacted. The title compound is obtained as a slightly yellowish oil. Rf=0.20 (2:1 EtOAc-heptane); Rt=5.80.

b) N-(3-Chloromethylphenyl)-N-(3-methoxypropyl) acetamide

Analogously to Method E, 0.300 g of N-(3-hydroxymethylphenyl)-N-(3-methoxypropyl)acetamide is reacted. The title compound is obtained as a slightly brownish oil. Rf=0.54 (6:1 EtOAc-heptane); Rt=3.65.

c) N-(3-Hydroxymethylphenyl)-N-(3-methoxypropyl)acetamide

Analogously to Example 8c, 0.40 g of N-(3-hydroxymethylphenyl)acetamide and 0.978 ml of 1-chloro-3-methoxypropane are reacted. The title compound is obtained as a beige oil. Rf=0.17 (6:1 EtOAc-heptane); Rt=2.55.

d) N-(3-Hydroxymethylphenyl)acetamide

Analogously to Example 8d, 10.16 g of (3-aminophenyl) methanol are reacted. The title compound is obtained as a beige solid. Rf=0.21 (4:1 EtOAc-heptane); Rt=2.07.

EXAMPLE 10

6-(4-{4-[3-(2-Methoxybenzyloxy)propoxy] phenyl}piperidin-3-yloxymethyl)-1-(3-methoxypropyl)-1H-indole Analogously to Method B, 0.116 g of benzyl 4-{4-[3-(2-methoxybenzyloxy)propoxy]phenyl}-3-[1-(3-methoxypropyl)-1H-indol-6-ylmethoxy]piperidine-1-carboxylate is used to prepare the title compound.

The starting materials are prepared as follows:

a) Benzyl 4-{4-[3-(2-Methoxybenzyloxy)propoxy] phenyl}-3-[1-(3-methoxypropyl)-1H-indol-6-ylmethoxy]piperidine-1-carboxylate The solution of 0.155 g of benzyl 3-(1H-indol-6-ylmethoxy)-4-{4-[3-(2-methoxybenzyloxy)propoxy] phenyl}piperidine-1-carboxylate in 1.5 ml of DMPU is admixed with stirring at room temperature with 0.015 g of sodium hydride dispersion (60%). The mixture is stirred over 5 minutes and subsequently admixed with 0.081 ml of 1-chloro-3-methoxypropane and 0.007 g of tetrabutylammonium iodide. The reaction mixture is stirred at room temperature over 24 hours, cooled and poured onto water (20 ml). The mixture is extracted with tert-butyl methyl ether (2×20 ml). The organic phases are washed successively with water (2×20 ml) and brine (1×20 ml), dried over sodium sulphate and concentrated by evaporation. The title compound is obtained as an orange oil from the residue by means of flash chromatography (SiO₂ 60F). Rf=0.25 (1:1 EtOAc-heptane); Rt=27.51 (II).

b1) Benzyl 3-(H-indol-6-ylmethoxy)-4-{4-[3-(2-methoxybenzyloxy)propoxy]phenyl}piperidine-1-carboxylate b2) Benzyl 3-(1H-indol-4-ylmethoxy)-4-{4-[3-(2-methoxybenzyloxy)propoxy]phenyl}piperidine-1-carboxylate The solution of 0.507 g of the regioisomer mixture consisting of benzyl 3-(1H-indol-6-ylmethoxy)-4-{4-[3-(2-methoxybenzyloxy)propoxy]phenyl}piperidine-1-carboxylate (45%) and benzyl 3-(1H-indol-4-ylmethoxy)-4-{4-[3-(2-methoxybenzyloxy)propoxy]phenyl}piperidine-1-carboxylate (55%) in 15 ml of methanol is admixed with 0.030 g of sodium hydroxide (solid) and stirred at room temperature over 30 minutes. The reaction mixture is poured onto 20 ml of water, admixed with 2.0 ml of 0.5N HCl (cold) and extracted with ethyl acetate (2×30 ml). The organic phases are washed with brine (1×30 ml), dried over sodium sulphate and concentrated by evaporation. The title compounds are obtained as slightly yellowish oils by means of flash chromatography (SiO₂ 60F). b1: Rf=0.91 (4:1 dichloromethane-diethyl ether); Rt=25.65 (II). b2: Rf=0.88 (4:1 dichloromethane-diethyl ether); Rt=25.28 (II).

c) Benzyl 3-(1-acetyl-1H-indol-6-ylmethoxy)-4-{4-[3-(2-methoxybenzyloxy)propoxy]-phenyl}piperidine-1-carboxylate (content: 45%) and benzyl 3-(1-acetyl-1H-indol-4-ylmethoxy)-4-{4-[3-(2-methoxybenzyloxy)propoxy]phenyl}piperidine-1-carboxylate (content: 55%): regioisomer mixture The solution of 0.640 g of benzyl 3-[3-(acetylhydroxyamino)benzyloxy]-4-{4-[3-(2-methoxybenzyloxy) propoxy]phenyl}piperidine-1-carboxylate in 6.56 ml of vinyl acetate is heated at 35° C. with stirring, admixed with 0.100 g of lithium tetrachloropalladate(II) and stirred at 55° C. over 20 hours. The reaction mixture is cooled, poured onto water (40 ml) and extracted with ethyl acetate (2×40 ml). The organic phases are washed successively with water (1×40 ml) and brine (1×40 ml), dried over sodium sulphate and concentrated by evaporation. The title compounds (regioisomer mixture) are obtained as a slightly yellowish oil from the residue by means of flash chromatography (SiO₂ 60F). Rf=0.38 (2:1 EtOAc-heptane); Rt=26.04 (45%)/26.16 (55%) (II).

d) Benzyl 3-[3-(acetylhydroxyamino)benzyloxy]-4-{4-[3-(2-methoxybenzyloxy)propoxy]-phenyl}piperidin-1-carboxylate The mixture of 40 mg of 5% Pt/C and 2.0 ml of tetrahydrofuran is prehydrogenated over 30 minutes. After the solution of 0.630 g of benzyl 4-{4-[3-(2-methoxybenzyloxy)propoxy]phenyl}-3-(3-nitrobenzyloxy)piperidine-1-carboxylate in 8.0 ml of tetrahydrofuran, 0.080 ml of dimethyl sulphoxide and 0.060 ml of aqueous ammonia (25%) has been added, the reaction mixture is hydrogenated at 15° C. over 2 hours. Subsequently, the mixture is clarified by filtration and the filtrate is concentrated. The residue is dissolved in 10 ml of tetrahydrofuran, cooled to 0° C. and admixed successively with 1.0 ml of water, 0.124 g of sodium hydrogencarbonate and 0.070 ml of acetyl chloride. The reaction mixture is stirred at 0° C. for 30 minutes, poured onto water (40 ml) and extracted with ethyl acetate (2×40 ml). The organic phases are washed successively with water (1×40 ml) and brine (1×40 ml), dried over sodium sulphate and concentrated by evaporation. The crude title compounds are obtained as a slightly yellowish oil from the residue. Rf=0.32 (2:1 EtOAc-heptane); Rt=5.36.

e) Benzyl 4-{4-[3-(2-methoxybenzyloxy)propoxy]phenyl}-3-(3-nitrobenzyloxy)piperidine-1-carboxylate The solution of 0.512 g of benzyl 3-hydroxy-4-{4-[3-(2-methoxybenzyloxy)propoxy]phenyl}piperidine-1-carboxylate and 0.355 g of 3-nitrobenzyl chloride in 3.0 ml of N,N-dimethylformamide is admixed with stirring at −10° C. with 0.022 g of sodium hydride dispersion (60%). The reaction mixture is stirred at −10° C. over 2.5 hours, then poured onto 1M aqueous sodium hydrogencarbonate solution (25 ml) and extracted with ethyl acetate (2×25 ml). The organic phases are washed successively with water (2×25 ml) and brine (1×25 ml), dried over sodium sulphate and concentrated by evaporation. The title compound is obtained as a yellow oil from the residue by means of flash chromatography (SiO$_2$ 60F). Rf=0.35 (1:1 EtOAc-heptane); Rt=5.94.

f) Benzyl 3-hydroxy-4-{4-[3-(2-methoxybenzyloxy)propoxy]phenyl}piperidine-1-carboxylate The solution of 3.0 g of 4-{4-[3-(2-methoxybenzyloxy)propoxy]phenyl}piperidin-3-ol in 30 ml of ethyl acetate is cooled to 0° C. with stirring and admixed with 30 ml of saturated aqueous sodium carbonate solution. At 0-5° C., 1.32 ml of benzyl formate are added dropwise. After 10 minutes, the reaction mixture is poured onto water (250 ml) and extracted with ethyl acetate (2×250 ml). The organic phases are washed with brine (1×250 ml), dried over sodium sulphate and concentrated by evaporation. The title compound is obtained as a yellow oil from the residue by means of flash chromatography (SiO$_2$ 60F). Rf=0.35 (1:1 EtOAc-heptane); Rt=5.94. m.p. 71-73° C.

g) 4-{4-[3-(2-Methoxybenzyloxy)propoxy]phenyl}piperidin-3-ol

Analogously to Method A, 4.10 g of tert-butyl 3-hydroxy-4-{4-[3-(2-methoxybenzyloxy)propoxy]phenyl}piperidine-1-carboxylate are reacted. The title compound is obtained as a white solid. Rf=0.24 (200:20:1 dichloromethane-methanol-25% conc. ammonia); Rt=3.56.

EXAMPLE 11

4-(4-{4-[3-(2-Methoxybenzyloxy)propoxy]phenyl}piperidin-3-yloxmethyl)-1-(3-methoxypropyl)-1H-indole Analogously to Method B 0.155 g of benzyl 4-{4-[3-(2-methoxybenzyloxy)propoxy]phenyl}-3-[1-(3-methoxypropyl)-1H-indol-4-ylmethoxy]piperidine-1-carboxylate is used to prepare the title compound.

The starting material is prepared as follows:

a) Benzyl 4-{4-[3-(2-methoxybenzyloxy)propoxy]phenyl}-3-[1-(3-methoxypropyl)-1H-indol-4-ylmethoxy]piperidine-1-carboxylate Analogously to Example 10a, 0.148 g of benzyl 3-(1H-indol-4-ylmethoxy)-4-{4-[3-(2-methoxybenzyloxy)propoxy]phenyl}piperidine-1-carboxylate (Example 10b2) and 0.110 ml of 1-chloro-3-methoxypropane are reacted. The title compound is obtained as a slightly yellowish oil. Rf=0.25 (1:1 EtOAc-heptane); Rt=27.24 min (II).

EXAMPLE 12

4-{4-[3-(2-Methoxybenzyloxy)propoxy]phenyl}-3-[3-(3-methoxypropoxy)-4-methylbenzyloxy]piperidine Analogously to Method A, 0.210 g of tert-butyl 4-{4-[3-(2-methoxybenzyloxy)propoxy]phenyl}-3-[3-(3-methoxypropoxy)-4-methylbenzyloxy]piperidine-1-carboxylate is used to prepare the title compound.

The starting materials are prepared as follows:

a) tert-Butyl 4-{4-[3-(2-methoxybenzyloxy)propoxy]phenyl}-3-[3-(3-methoxypropoxy)-4-methylbenzyloxy]piperidine-1-carboxylate Analogously to Method D, 0.238 g of tert-butyl 3-hydroxy-4-{4-[3-(2-methoxybenzyloxy)propoxy]phenyl}piperidine-1-carboxylate and 0.125 g of 4-chloromethyl-2-(3-methoxypropoxy)-1-methylbenzene are reacted. The title compound is obtained as a slightly yellowish oil. Rt=6.39.

b) 4-Chloromethyl-2-(3-methoxypropoxy)-1-methylbenzene

Analogously to Method E, 1.0 g of [3-(3-methoxypropoxy)-4-methylphenyl]methanol is reacted. The title compound is obtained as a slightly yellowish oil. Rf=0.53 (1:1 EtOAc-heptane); Rt=4.93.

c) [3-(3-Methoxypropoxy)-4-methylphenyl]methanol

The solution of 7.70 g of 3-methoxypropyl 3-(3-methoxypropoxy)-4-methylbenzoate in 20 ml of tetrahydrofuran is added dropwise at 20-60° C. to the stirred mixture of 1.02 g of lithium aluminium hydride in 20 ml of tetrahydrofuran. The reaction mixture is stirred at reflux over 3 hours and subsequently cooled to room temperature. 2 ml of water, 2 ml of 2N NaOH and once again 2 ml of water are successively added dropwise. The suspension is stirred at room temperature over 14 hours. The reaction mixture is poured onto 250 ml of 2N HCl (cold) and extracted with ethyl acetate (2×200 ml). The organic phases are washed successively with 2N HCl (100 ml), water (100 ml) and brine (1×100 ml), dried over sodium sulphate, filtered and concentrated by evaporation. The title compound is obtained as a slightly yellowish oil from the residue by means of flash chromatography (SiO$_2$ 60F). Rf=0.23 (1:1 EtOAc-heptane); Rt=3.59.

d) 3-Methoxypropyl 3-(3-methoxypropoxy)-4-methylbenzoate

The mixture of 5.0 g of 3-hydroxy-4-methylbenzoic acid and 12.95 g of potassium carbonate in 80 ml of N,N-dimethylformamide is admixed with 7.45 g of 1-chloro-3-methoxypropane and stirred at 100° C. over 24 hours. The reaction mixture is concentrated by evaporation, admixed with a 1:1 water/brine mixture (1×250 ml) and extracted with ethyl acetate (2×250 ml). The organic phases are washed successively with a 1:1 water/brine mixture (1×250 ml) and brine (1×250 ml), dried over sodium sulphate, filtered and concentrated by evaporation. The title compound is obtained as a slightly yellowish oil from the residue by means of flash chromatography (SiO$_2$ 60F). Rf=0.38 (1:1 EtOAc-heptane); Rt=4.83.

EXAMPLE 13

7-(4-{4-[3-(2-Methoxybenzyloxy)propoxy]
phenyl}piperidin-3-yloxymethyl)-1-(3-methoxypropyl)-3,4-dihydro-1H-quinolin-2-one Analogously to Method A, 0.400 g of tert-butyl 4-{4-[3-(2-methoxybenzyloxy)propoxy]phenyl}-3-[1-(3-methoxypropyl)-2-oxo-1,2,3,4-tetrahydroquinolin-7-ylmethoxy]piperidine-1-carboxylate is used to prepare the title compound. The starting materials are prepared as follows:

a) tert-Butyl 4-{4-[3-(2-methoxybenzyloxy)propoxy]phenyl}-3-[1-(3-methoxypropyl)-2-oxo-1,2,3,4-tetrahydroquinolin-7-ylmethoxy]piperidine-1-carboxylate Analogously to Method D, 0.477 g of tert-butyl 3-hydroxy-4-{4-[3-(2-methoxybenzyloxy)propoxy]phenyl}piperidine-1-carboxylate and 0.268 g of 7-chloromethyl-1-(3-methoxypropyl)-3,4-dihydro-1H-quinolin-2-one are reacted. The title compound is obtained as a slightly yellowish oil. Rf=0.11 (1:1 EtOAc-heptane); Rt=5.89.

b) 7-Chloromethyl-1-(3-methoxypropyl)-3,4-dihydro-1H-quinolin-2-one

Analogously to Method E, 0.870 g of 7-hydroxymethyl-1-(3-methoxypropyl)-3,4-dihydro-1H-quinolin-2-one is reacted. The title compound is obtained as a slightly yellowish oil. Rf=0.48 (2:1 EtOAc-heptane); Rt=3.95.

c) 7-Hydroxymethyl-1-(3-methoxypropyl)-3,4-dihydro-1H-quinolin-2-one

Analogously to Example 2c, 1.28 g of 7-hydroxymethyl-3,4-dihydro-1H-quinolin-2-one are reacted with 1.59 ml of 1-chloro-3-methoxypropane. The title compound is obtained as a slightly yellowish oil. Rf=0.24 (dichloromethane-methanol=95:5); Rt=2.71.

d) 7-Hydroxymethyl-3,4-dihydro-1H-quinolin-2-one

Analogously to Example 2d, 1.90 g of ethyl 2-oxo-1,2,3,4-tetrahydroquinoline-7-carboxylate are reacted. The title compound is obtained as a beige solid. Rf=0.14 (dichloromethane-methanol=9:1); Rt=2.25.

e) Ethyl 2-oxo-1,2,3,4-tetrahydroquinoline-7-carboxylate

The solution of 2.80 g of ethyl 4-(2-methoxycarbonylvinyl)-3-nitrobenzoic acid in 20 ml of glacial acetic acid is hydrogenated in the presence of 0.288 g of 10% Pd/C at room temperature over 16 hours. The reaction mixture is stirred at 70° C. over 1 hour and subsequently concentrated by evaporation to dryness. The residue is admixed with 250 ml of 1M sodium hydrogencarbonate and extracted with ethyl acetate (2×250 ml). The organic phases are washed with water (250 ml), dried over sodium sulphate, filtered and concentrated by evaporation. The title compound is obtained as a white solid from the residue by means of crystallization (ethyl acetate-hexane). Rf=0.24 (1:1 EtOAc-heptane).

f) Ethyl 4-(2-methoxycarbonylvinyl)-3-nitrobenzoic acid

The solution of 3.20 g of ethyl 4-(2-chloro-2-methoxycarbonylethyl)-3-nitrobenzoate in 130 ml of tetrahydrofuran is admixed with 6.46 ml of triethylamine and stirred at reflux over 18 hours. The reaction mixture is cooled, poured onto water (300 ml) and extracted with tert-butyl methyl ether (2×300 ml). The organic phases are washed successively with water (2×300 ml) and brine (150 ml), dried over sodium sulphate, filtered and concentrated by evaporation. The crude title compound is obtained as a slightly yellowish solid from the residue. Rf=0.30 (1:2 EtOAc-heptane). Rt=4.50.

EXAMPLE 14

N-(2-{2-[2-(4-{4-[3-(2-Methoxybenzyloxy)propoxy]phenyl}piperidin-3-yloxy)ethoxy]phenyl}-ethyl)acetamide Analogously to Method A, 0.098 g of tert-butyl 3-{2-[2-(2-acetylaminoethyl)phenoxy]ethoxy}-4-{4-[3-(2-methoxybenzyloxy)propoxy]phenyl}piperidine-1-carboxylate is used to prepare the title compound.

The starting materials are prepared as follows:

a) tert-Butyl 3-{2-[2-(2-acetylaminoethyl)phenoxy]ethoxy}-4-{4-[3-(2-methoxybenzyloxy)propoxy]phenyl}piperidine-1-carboxylate Analogously to Method G, 0.30 g of tert-butyl 4-{4-[3-(2-methoxybenzyloxy)propoxy]phenyl}-3-[2-(toluene-4-sulphonyloxy)ethoxy]piperidine-1-carboxylate and 0.16 g of N-[2-(2-hydroxyphenyl)ethyl]acetamide are reacted. The title compound is obtained as a colourless oil. Rf=0.17 (3:1 EtOAc-heptane); Rt=5.65.

b) tert-Butyl 4-{4-[3-(2-methoxybenzyloxy)propoxy]phenyl}-3-[2-(toluene-4-sulphonyloxy)ethoxy]piperidine-1-carboxylate Analogously to Method H, 2.00 g of tert-butyl 3-(2-hydroxyethoxy)-4-{4-[3-(2-methoxybenzyloxy)propoxy]phenyl}piperidine-1-carboxylate are used to prepare the title compound as a yellow oil. Rf=0.46 (1:2 EtOAc-heptane). Rt=5.99.

c) tert-Butyl 3-(2-hydroxyethoxy)-4-{4-[3-(2-methoxybenzyloxy)propoxy]phenyl}piperidine-1-carboxylate 8.54 g of tert-butyl 3-allyloxy-4-{4-[3-(2-methoxybenzyloxy)propoxy]phenyl}piperidine-1-carboxylate are initially charged in a 3:1 tetrahydrofuran/water mixture (52 ml) with stirring at room temperature and admixed with 2.07 ml of osmium tetroxide (2.5% by wt. in tert-BuOH). Subsequently, 9.00 g of sodium periodate are added in portions. The reaction mixture is stirred further over 2 hours. The reaction mixture is concentrated by evaporation. The residue is suspended in a 1:1 dichloromethane/methanol mixture (150 ml), cooled to 5° C. and admixed with 3.96 g of sodium borohydride in portions. The reaction mixture is stirred at 5° C. for 1.5 hours and subsequently concentrated by evaporation. The residue is stirred in 200 ml of dichloromethane, filtered through glass fibre filter and washed with dichloromethane. The filtrate is washed with a 1:1 brine/water mixture, filtered through cotton wool, dried over sodium sulphate and concentrated by evaporation. The title compound is obtained as a colourless oil from the residue by means of flash chromatography (SiO$_2$ 60F). Rf=0.17 (1:1 EtOAc-heptane). Rt=5.22.

d) tert-Butyl 3-allyloxy-4-{4-[3-(2-methoxybenzyloxy)propoxy]phenyl}piperidine-1-carboxylate Analogously to Method D, 9.53 g of tert-butyl 3-hydroxy-4-{4-[3-(2-methoxybenzyloxy)propoxy]phenyl}piperidine-1-carboxylate and 3.42 ml of allylbromide are reacted. The title compound is obtained as a slightly yellowish oil. Rf=0.31 (1:2 EtOAc-heptane); Rt=6.03.

EXAMPLE 16

7-(4-{4-[3-(2-Methoxybenzyloxy)propoxy]phenyl}piperidin-3-yloxymethyl)-1-(3-methoxypropyl)-1H-quinolin-2-one Analogously to Method A, 0.185 g of tert-butyl 4-{4-[3-(2-methoxybenzyloxy)propoxy]phenyl}-3-[1-(3-methoxypropyl)-2-oxo-1,2-dihydroquinolin-7-ylmethoxy]piperidine-1-carboxylate is used to prepare the title compound.

The starting materials are prepared as follows:

a) tert-Butyl 4-{4-[3-(2-methoxybenzyloxy)propoxy]phenyl}-3-[1-(3-methoxypropyl)-2-oxo-1,2-dihydroquinolin-7-ylmethoxy]piperidine-1-carboxylate Analogously to Method D, 0.262 g of tert-butyl 3-hydroxy-4-{4-[3-(2-methoxybenzyloxy)propoxy]phenyl}piperidine-1-carboxylate and 0.148 g of 7-chloromethyl-1-(3-methoxypropyl)-1H-quinolin-2-one are reacted. The title compound is obtained as a slightly yellowish oil. Rf=0.28 (2:1 EtOAc-heptane); Rt=5.91.

b) 7-Chloromethyl-1-(3-methoxypropyl)-1H-quinolin-2-one

Analogously to Method E, 0.500 g of 7-hydroxymethyl-1-(3-methoxypropyl)-1H-quinolin-2-one is reacted. The title compound is obtained as a slightly yellowish solid. Rf=0.65 (10:1 dichloromethane-methanol); Rt=3.76.

c1) 7-Hydroxymethyl-1-(3-methoxypropyl)-1H-quinolin-2-one c2) [2-(3-Methoxypropoxy)quinolin-7-yl]methanol Analogously to Example 2c, 2.66 g of 7-hydroxymethyl-1H-quinolin-2-one are reacted with 3.34 ml of 1-chloro-3-methoxypropane. The title compounds are obtained as slightly yellowish oils.
c1: Rf=0.23 (20:1 dichloromethane-methanol); Rt=2.58.
c2: Rf=0.30 (20:1 dichloromethane-methanol); Rt=2.76.

d) 7-Hydroxymethyl-1H-quinolin-2-one

Analogously to Example 2d, 0.439 g of ethyl 2-oxo-1,2-dihydroquinoline-7-carboxylate is reacted. The title compound is obtained as a slightly yellowish solid. Rf=0.10 (10:1 dichloromethane-methanol); Rt=2.14.

EXAMPLE 17

7-(4-{4-[3-(2-Methoxybenzyloxy)propoxy]phenyl}piperidin-3-yloxymethyl)-2-(3-methoxypropoxy)quinoline Analogously to Method A, 0.258 g of tert-butyl 4-{4-[3-(2-methoxybenzyloxy)propoxy]phenyl}-3-[2-(3-methoxypropoxy)quinolin-7-ylmethoxy]piperidine-1-carboxylate is used to prepare the title compound.

The starting materials are prepared as follows:

a) tert-Butyl 4-{4-[3-(2-methoxybenzyloxy)propoxy]phenyl}-3-[2-(3-methoxypropoxy)quinolin-7-ylmethoxy]piperidine-1-carboxylate Analogously to Method D, 0.300 g of tert-butyl 3-hydroxy-4-{4-[3-(2-methoxybenzyloxy)propoxy]phenyl}piperidine-1-carboxylate and 0.181 g of 7-chloromethyl-2-(3-methoxypropoxy)quinoline are reacted. The title compound is obtained as a slightly yellowish oil. Rf=0.42 (1:1 EtOAc-heptane); Rt=6.33.

b) 7-Chloromethyl-2-(3-methoxypropoxy)quinoline

Analogously to Method E, 0.690 g of [2-(3-methoxypropoxy)quinolin-7-yl]methanol (Example 16c2) is reacted. The title compound is obtained as a slightly yellowish solid. Rf=0.50 (1:2 EtOAc-heptane); Rt=4.64.

EXAMPLE 18

6-(4-{4-[3-(2-Methoxybenzyloxy)propoxy]phenyl}piperidin-3-yloxymethyl)-1'-(3-methoxypropyl)spiro[cyclopropane-1,3'-[3H]indol]-2'(1'H)one Analogously to Method A, 0.595 g of tert-butyl 4-{4-[3-(2-methoxybenzyloxy)propoxy]phenyl}-3-[1'-(3-methoxypropyl)-2'-oxo)spiro[cyclopropane-1,3'-[3H]indol]-6-ylmethoxy]piperidine-1-carboxylate is used to prepare the title compound.

The starting materials are prepared as follows:

a) tert-Butyl 4-{4-[3-(2-methoxybenzyloxy)propoxy]phenyl}-3-[1'-(3-methoxypropyl)-2'-oxo)spiro[cyclopropane-1,3'-[3H]indol]-6-ylmethoxy]piperidine-1-carboxylate Analogously to Method D, 0.500 g of tert-butyl 3-hydroxy-4-{4-[3-(2-methoxybenzyloxy)propoxy]phenyl}piperidine-1-carboxylate and 0.504 g of 6-bromomethyl-1'-(3-methoxypropyl)spiro[cyclopropane-1,3'-[3H]indol]-2'(1'H)-one are reacted. The title compound is obtained as a slightly yellowish oil. Rf=0.13 (1:1 EtOAc-heptane); Rt=6.05.

b) 6-Bromomethyl-1'-(3-methoxypropyl)spiro[cyclopropane-1,3'-[3H]indol]-2'(1'H)-one The mixture of 1.43 g of 6-methyl-1'-(3-methoxypropyl)spiro[cyclopropane-1,3'-[3H]indol]-2'(1'H)-one, 1.06 g of N-bromosuccinimide, 0.019 g of 2,2'-azobis(2-methylpropionitrile) and 0.028 g of dibenzoyl peroxide in 60 ml of carbon tetrachloride is heated to reflux with stirring. The reaction vessel is irradiated with a 150 W lamp over the reaction time. After 1 hour, 0.019 g of 2,2'-azobis(2-methylpropionitrile) and 0.028 g of dibenzoyl peroxide are again added. Stirring is continued over 1 hour (succinimide crystallizes out). The reaction mixture is cooled and clarified by filtration, and the filtrate is concentrated by evaporation. The title compound is obtained as a slightly orange oil from the residue by means of flash chromatography (SiO$_2$ 60F). Rf=0.38 (1:1 EtOAc-heptane); Rt=16.40 (II).

c) 6-Methyl-1'-(3-methoxypropyl)spiro[cyclopropane-1,3'-[3H]indol]-2'(1'H)-one The solution, prepared under argon, of 0.161 g of 1,3-bis (2,6-di-L-propylphenyl)imidazolium chloride and 0.194 g of dipalladiumtris(dibenzylidenacetone)-chloroform complex in 80 ml of tetrahydrofuran is admixed with stirring with the solution of 4.67 g of N-(2-bromo-5-methylphenyl)-N-(3-methoxypropyl)cyclopropanecarboxamide in 40 ml of tetrahydrofuran. Over 10 minutes, 28.9 ml of lithium bis(trimethylsilyl)amide (1M in tetrahydrofuran) are added dropwise. Subsequently, the mixture is stirred at 68° C. over 48 hours. The reaction mixture is cooled, poured onto ice-water (150 ml) and extracted with tert-butyl methyl ether (2×150 ml). The organic phases are washed successively with water (2×150 ml) and brine (1×150 ml) dried over sodium sulphate, filtered and concentrated. The title compound is obtained as a slightly yellowish oil from the residue by means of flash chromatography (SiO$_2$ 60F). Rf=0.25 (1:1 EtOAc-heptane); Rt=15.69 (II).

d) N-2-Bromo-5-methylphenyl)-N-3-(methoxypropyl)cyclopropanecarboxamide

Analogously to Example 8c, 15.5 g of N-(2-bromo-5-methylphenyl)cyclopropanecarboxamide and 7.33 ml of 1-chloro-3-methoxypropane are reacted. The title compound is obtained as slightly yellowish oil. Rf=0.09 (1:4 EtOAc-heptane); Rt=4.56.

e) N-(2-Bromo-5-methylphenyl)cyclopropanecarboxamide

The solution of 13.95 g of 2-bromo-5-methylphenylamine in 250 ml of chloroform is cooled to 0° C. with stirring and admixed with 12.6 ml of triethylamine. 7.56 ml of cyclopropanecarbonyl chloride are slowly added dropwise. The mixture is stirred for 1 hour each at 0° C. and at room temperature. The reaction mixture is poured onto water (400 ml) and extracted with dichloromethane (1×250 ml). The organic phases are washed with brine (350 ml), dried over sodium sulphate and concentrated by evaporation. The title compound is obtained as a white solid from the residue by means of crystallization from ethyl acetate. Rf=0.37 (1:4 EtOAc-heptane); Rt=4.19.

EXAMPLE 19

4-{4-[3-(2-Methoxybenzyloxy)propoxy]phenyl}-3-[7-(3-methoxypropoxy)-2,3-dihydrobenzofuran-2(R,S)-ylmethoxy]piperidine Analogously to Method A, 0.093 g of tert-butyl 4-{4-[3-(2-methoxybenzyloxy)propoxy]phenyl}-3-[7-(3-methoxypropoxy)-2,3-dihydrobenzofuran-2(R,S)-ylmethoxy]piperidine-1-carboxylate is used to prepare the title compound.

The starting materials are prepared as follows:

a) tert-Butyl 4-{4-[3-(2-methoxybenzyloxy)propoxy]phenyl}-3-[7-(3-methoxypropoxy)-2,3-dihydrobenzofuran-2(R,S)-ylmethoxy]piperidine-1-carboxylate 0.035 ml of formic acid are added to the suspension of 0.20 g of tert-butyl 4-{4-[3-(2-methoxybenzyloxy)propoxy]phenyl}-3-[7-(3-methoxypropoxy)benzofuran-2-ylmethoxy]piperidine-1-carboxylate (Example 7a) and 0.20 g of 10% Pd/C in 3 ml of acetone. After 15 minutes, 0.16 ml of triethylamine is added in portions. The reaction mixture is stirred at room temperature over 20 hours and clarified by filtration, and the filtrate is concentrated by evaporation. The title compound is obtained as a colourless oil from the residue by means of flash chromatography (SiO$_2$ 60F). Rf=0.34 (1:2 EtOAc-heptane); Rt=6.24.

EXAMPLE 20

3-[4-Fluoro-3-(3-methoxypropoxy)benzyloxy]-4-{4-[3-(2-methoxybenzyloxy)propoxy]phenyl}piperidine Analogously to Method A, 0.220 g of tert-butyl 3-[4-fluoro-3-(3-methoxypropoxy)benzyloxy]-4-{4-[3-(2-methoxybenzyloxy)propoxy]phenyl}piperidine-1-carboxylate is used to prepare the title compound.

The starting materials are prepared as follows:

a) tert-Butyl 3-[4-fluoro-3-(3-methoxypropoxy)benzyloxy]-4-{4-[3-(2-methoxybenzyloxy)propoxy]phenyl}piperidine-1-carboxylate Analogously to Method D, 0.213 g of tert-butyl 3-hydroxy-4-{4-[3-(2-methoxybenzyloxy)propoxy]phenyl}piperidine-1-carboxylate and 0.114 g of 4-chloromethyl-1-fluoro-2-(3-methoxypropoxy)benzene are reacted. The title compound is obtained as a colourless oil. Rt=6.28.

b) 4-Chloromethyl-1-fluoro-2-(3-methoxypropoxy)benzene

Analogously to Method E, 1.0 g of [4-fluoro-3-(3-methoxypropoxy)phenyl]methanol is reacted. The title compound is obtained as a slightly yellowish oil. Rt=4.62.

c) [4-Fluoro-3-(3-methoxypropoxy)phenyl]methanol

Analogously to Example 12c, 9.0 g of 3-methoxypropyl 4-fluoro-3-(3-methoxypropoxy)benzoate are reacted. The title compound is obtained as a colourless oil. Rt=3.28.

d) 3-Methoxypropyl 4-fluoro-3-(3-methoxypropoxy)benzoate

Analogously to Example 12d, 5.0 g of 4-fluoro-3-hydroxybenzoic acid are reacted. The title compound is obtained as a colourless oil. Rt=4.55.

EXAMPLE 21

6-(4-{4-[3-(2-Methoxybenzyloxy)propoxy]phenyl}piperidin-3-yloxymethyl)-1-(3-methoxypropyl)-3-methyl-1H-indole The solution of 0.150 g of benzyl 3-[7-bromo-1-(3-methoxypropyl)-3-methyl-1H-indol-6-ylmethoxy]-4-{4-[3-(2-methoxybenzyloxy)propoxy]phenyl}piperidine-1-carboxylate in 5.0 ml of methanol is admixed with 0.027 ml of triethylamine and hydrogenated in the presence of 30 mg of 5% Pd/C at room temperature over 16 hours. The reaction mixture is clarified by filtration and the filtrate is concentrated by evaporation. The title compound is obtained from the residue by means of flash chromatography (SiO$_2$ 60F).

The starting materials are prepared as follows:

a) Benzyl 3-[7-bromo-1-(3-methoxypropyl)-3-methyl-1H-indol-6-yl methoxy]-4-{4-[3-(2-methoxybenzyloxy)propoxy]phenyl}piperidine-1-carboxylate The solution of 0.208 g benzyl 3-(7-bromo-3-methyl-1H-indol-6-ylmethoxy)-4-{4-[3-(2-methoxybenzyloxy)propoxy]phenyl}piperidine-1-carboxylate in 2.0 ml of N,N-dimethylformamide is cooled to 0° C., admixed with 0.023 g of sodium hydride dispersion (60%) and stirred over 10 minutes. The mixture is admixed successively with 0.126 ml of 1-chloro-3-methoxypropane and 0.011 g of tetrabutylammonium iodide and subsequently stirred at room temperature over 18 h. The reaction mixture is poured onto 1M sodium hydrogencarbonate solution (30 ml) and extracted with tert-butyl methyl ether (2×30 ml). The organic phases are washed with water (30 ml) and brine (30 ml), dried over sodium sulphate and concentrated by evaporation. The title compound is obtained as a slightly yellowish oil from the residue by means of flash chromatography (SiO$_2$ 60F). Rf=0.17 (1:2 EtOAc-heptane); Rt=6.60.

b) Benzyl 3-(7-bromo-3-methyl-1H-indol-6-ylmethoxy)-4-{4-[3-(2-methoxybenzyloxy)propoxy]phenyl}piperidine-1-carboxylate The solution of 0.500 g of benzyl 3-(2-bromo-3-nitrobenzyloxy)-4-{4-[3-(2-methoxybenzyloxy)propoxy]phenyl}piperidine-1-carboxylate in 6.5 ml of tetrahydrofuran is cooled to −45° C. under argon and admixed slowly with 4.0 ml of 1-propenylmagnesium bromide (0.5M in tetrahydrofuran). The reaction mixture is stirred over 15 minutes, subsequently poured onto saturated aqueous ammonium chloride solution (10 ml) and extracted with tert-butyl methyl ether (2×25 ml). The organic phases are washed with water (25 ml) and brine (25 ml), dried over sodium sulphate and concentrated by evaporation. The title compound is obtained as a slightly yellowish oil from the residue by means of flash chromatography (SiO$_2$ 60F). Rf=0.21 (1:2 EtOAc-heptane); Rt=6.17.

c) Benzyl 3-(2-bromo-3-nitrobenzyloxy)-4-{4-[3-(2-methoxybenzyloxy)propoxy]phenyl}piperidine-1-carboxylate Analogously to Method D, 1.30 g of benzyl 3-hydroxy-4-{4-[3-(2-methoxybenzyloxy)propoxy]-phenyl}piperidine-1-carboxylate (Example 10f) and 1.0 g of 2-bromo-1-bromomethyl-3-nitrobenzene are reacted. The title compound is obtained as a yellowish oil. Rf=0.29 (1:1 EtOAc-heptane); Rt=6.12.

EXAMPLE 22

6-(4-{4-[3-(2-Methoxybenzyloxy)propoxy]phenyl}piperidin-3-yloxymethyl)-1-(3-methoxypropyl)-2-methyl-1H-indole Analogously to Example 21, 0.165 g of benzyl 3-[7-bromo-1-(3-methoxypropyl)-2-methyl-1H-indol-6-ylmethoxy]-4-{4-[3-(2-methoxybenzyloxy)propoxy]phenyl}piperidine-1-carboxylate is reacted to obtain the title compound.

The starting materials are prepared as follows:

a) Benzyl 3-[7-bromo-1-(3-methoxypropyl)-2-methyl-1H-indol-6-ylmethoxy]-4-{4-[3-(2-methoxybenzyloxy)propoxy]phenyl}piperidine-1-carboxylate Analogously to Example 21a, 0.295 g of benzyl 3-(7-bromo-2-methyl-1H-indol-6-ylmethoxy)-4-{4-[3-(2-methoxybenzyloxy)propoxy]phenyl}piperidine-1-carboxylate is reacted. The title compound is obtained as a slightly yellowish oil. Rf=0.16 (1:2 EtOAc-heptane); Rt=6.52.

b) Benzyl 3-(7-bromo-2-methyl-1H-indol-6-ylmethoxy)-4-{4-[3-(2-methoxybenzyloxy)propoxy]phenyl}piperidine-1-carboxylate Analogously to Example 21b, 0.350 g of benzyl 3-(2-bromo-3-nitrobenzyloxy)-4-{4-[3-(2-methoxybenzyloxy)propoxy]phenyl}piperidine-1-carboxylate (Example 21c) and 2.84 ml of isopropylmagnesium bromide (0.5M in tetrahydrofuran) are reacted. The title compound is obtained as a white foam. Rf=0.23 (1:2 EtOAc-heptane); Rt=6.13.

EXAMPLE 23

6-(4-{4-[3-(2-Methoxybenzyloxy)propoxy]phenyl}piperidin-3-yloxymethyl)-1-(3-methoxypropyl)-1H-indazole Analogously to Method A, 0.415 g of tert-butyl 4-{4-[3-(2-methoxybenzyloxy)propoxy]phenyl}-3-[1-(3-methoxypropyl)-1H-indazol-6-ylmethoxy]piperidine-1-carboxylate is used to prepare the title compound.

The starting materials are prepared as follows:

a) tert-Butyl 4-{4-[3-(2-methoxybenzyloxy)propoxy]phenyl}-3-[1-(3-methoxypropyl)-1H-indazol-6-ylmethoxy]piperidine-1-carboxylate Analogously to Method D, 0.390 g of tert-butyl 3-hydroxy-4-{4-[3-(2-methoxybenzyloxy)propoxy]phenyl}piperidine-1-carboxylate and 0.199 g of 6-chloromethyl-1-(3-methoxypropyl)-1H-indazole are reacted. The title compound is obtained as a colourless oil. Rf=0.31 (2:1 EtOAc-heptane); Rt=6.12.

b) Chloromethyl-1-(3-methoxypropyl)-1H-indazole

Analogously to Method E, 0.345 g of [1-(3-methoxypropyl)-1H-indazol-6-yl]methanol is reacted. The title compound is obtained as a slightly yellowish oil. Rf=0.50 (EtOAc-heptane=9:1); Rt=4.15.

c) [1-(3-Methoxypropyl)-1H-indazol-6-yl]methanol

Analogously to Example 2d, 0.440 g of methyl 1-(3-methoxypropyl)-1H-indazole-6-carboxylate (Example 23d1) is reacted. The title compound is obtained as a slightly yellowish oil. Rf=0.27 (EtOAc); Rt=2.74.

d1) Methyl 1-(3-methoxypropyl)-1H-indazole-6-carboxylate d2) Methyl 2-(3-methoxypropyl)-2H-indazole-6-carboxylate Analogously to Example 8c, 1.0 g of methyl 1H-indazole-6-carboxylate and 1.16 g of 1-chloro-3-methoxypropane are reacted. The title compounds are obtained as yellowish oils.
d1: Rf=0.27 (1:1 EtOAc-heptane); Rt=3.87.
d2: Rf=0.14 (1:1 EtOAc-heptane); Rt=3.49.

EXAMPLE 24

6-(4-{4-[3-(2-Methoxybenzyloxy)propoxy]phenyl}piperidin-3-yloxymethyl)-2-(3-methoxypropyl)-2H-indazole Analogously to Method A, 0.206 g of tert-butyl 4-{4-[3-(2-methoxybenzyloxy)propoxy]phenyl}-3-[2-(3-methoxypropyl)-2H-indazol-6-ylmethoxy]piperidine-1-carboxylate is used to prepare the title compound.

The starting materials are prepared as follows:

a) tert-Butyl 4-{4-[3-(2-methoxybenzyloxy)propoxy]phenyl}-3-[2-(3-methoxypropyl)-2H-indazol-6-ylmethoxy]piperidine-1-carboxylate Analogously to Method D, 0.178 g of tert-butyl 3-hydroxy-4-{4-[3-(2-methoxybenzyloxy)propoxy]phenyl}piperidine-1-carboxylate and 0.090 g of 6-chloromethyl-2-(3-methoxypropyl)-2H-indazole are reacted. The title compound is obtained as a colourless oil. Rf=0.15 (2:1 EtOAc-heptane); Rt=5.80.

b) 6-Chloromethyl-2-(3-methoxypropyl)-2H-indazole

Analogously to Method E, 0.205 g of [2-(3-methoxypropyl)-2H-indazol-6-yl]methanol is reacted. The title compound is obtained as a slightly yellowish oil. Rf=0.31 (EtOAc-heptane=9:1); Rt=3.78.

c) [2-(3-Methoxypropyl)-2H-indazol-6-yl]methanol

Analogously to Example 2d, 0.295 g of methyl 2-(3-methoxypropyl)-2H-indazole-6-carboxylate (Example 23d2) is reacted. The title compound is obtained as a slightly yellowish oil. Rf=0.11 (EtOAc); Rt=2.45.

EXAMPLE 25

7-(4-{4-[4-(2-Methoxyphenoxy)butoxy]phenyl}piperidin-3-yloxymethyl)-1-(3-methoxypropyl)-3,4-dihydro-1H-quinolin-2-one Analogously to Method A, 0.228 g of tert-butyl 4-{4-[4-(2-methoxyphenoxy)butoxy]phenyl}-3-[1-(3-methoxypropyl)-2-oxo-1,2,3,4-tetrahydroquinolin-7-ylmethoxy]piperidine-1-carboxylate is used to prepare the title compound.

The starting materials are prepared as follows:

a) tert-Butyl 4-{4-[4-(2-methoxyphenoxy)butoxy]phenyl}-3-[1-(3-methoxypropyl)-2-oxo-1,2,3,4-tetrahydroquinolin-7-ylmethoxy]piperidine-1-carboxylate Analogously to Method D, 0.200 g of tert-butyl 3-hydroxy-4-{4-[4-(2-methoxyphenoxy)butoxy]phenyl}piperidine-1-carboxylate and 0.125 g of 7-chloromethyl-1-(3-methoxypropyl)-3,4-dihydro-1H-quinolin-2-one (Example 13b) are reacted. The title compound is obtained as a colourless oil. Rf=0.12 (1:1 EtOAc-heptane); Rt=5.86.

b) tert-Butyl 3-hydroxy-4-{4-[4-(2-methoxyphenoxy)butoxy]phenyl}piperidine-1-carboxylate Analogously to Method F, 5.86 g of tert-butyl 3-hydroxy-4-(4-hydroxyphenyl)piperidin-1-carboxylate and 6.33 g of 1-(4-bromobutoxy)-2-methoxybenzene are reacted. The title compound is obtained as a solid. Rf=0.12 (1:2 EtOAc-heptane); Rt=5.15.

EXAMPLE 26

4-{4-[3-(2-Methoxybenzyloxy)propoxy]phenyl}-3-{2-[2-(2-[1,2,4]triazol-1-ylethyl)phenoxy]ethoxy}piperidine Analogously to Method A, 0.066 g of tert-butyl 4-{4-[3-(2-methoxybenzyloxy)propoxy]phenyl}-3-{2-[2-(2-[1,2,4]triazol-1-ylethyl)phenoxy]ethoxy}piperidine-1-carboxylate is used to prepare the title compound.

The starting materials are prepared as follows:

a) tert-Butyl 4-{4-[3-(2-methoxybenzyloxy)propoxy]phenyl}-3-{2-[2-(2-[1.2.4]triazol-1-ylethyl)phenoxy]ethoxy}piperidine-1-carboxylate 0.051 g of sodium 1,2,4-triazolide is admixed with a solution of 0.10 g of tert-butyl 4-{4-[3-(2-methoxybenzyloxy)propoxy]phenyl}-3-(2-{2-[2-(toluene-4-sulphonyloxy)ethyl]phenoxy}-ethoxy)piperidine-1-carboxylate in 3 ml of N,N-dimethylformamide. The reaction mixture is stirred at 90° C. over 40 minutes. The mixture is cooled to room temperature, diluted with tert-butyl methyl ether and washed with water. The water phase is extracted with tert-butyl methyl ether. The combined organic phases are dried over sodium sulphate and concentrated by evaporation. The title compound is obtained as a colourless oil from the residue by means of flash chromatography (SiO$_2$ 60F). Rf=0.13 (2:1 EtOAc-heptane); Rt=5.66.

b) tert-Butyl 4-{4-[3-(2-methoxybenzyloxy)propoxy]phenyl}-3-(2-{2-[2-(toluene-4-sulphonyloxy)ethyl]phenoxy}ethoxy)piperidine-1-carboxylate Analogously to Method H, 3.5 g of tert-butyl 3-{2-[2-(2-hydroxyethyl)phenoxy]ethoxy}-4-{4-[3-(2-methoxybenzyloxy)propoxy]phenyl}piperidine-1-carboxylate are used to prepare the title compound as a colourless oil. Rf=0.19 (1:2 EtOAc-heptane). Rt=6.30.

c) tert-Butyl 3-{2-[2-(2-hydroxyethyl)phenoxy]ethoxy}-4-{4-[3-(2-methoxybenzyloxy)propoxy]phenyl}piperidine-1-carboxylate Analogously to Method G, 5.00 g of tert-butyl 4-{4-[3-(2-methoxybenzyloxy)propoxy]phenyl}-3-[2-(toluene-4-sulphonyloxy)ethoxy]piperidine-1-carboxylate (Example 14b) and 0.99 g of 2-(2-hydroxyethyl)phenol are reacted. The title compound is obtained as a colourless oil. Rf=0.08 (1:2 EtOAc-heptane); Rt=5.81.

EXAMPLE 27

4-{4-[3-(2-Methoxybenzyloxy)propoxy]phenyl}-3-{2-[2-(2-tetrazol-1-ylethyl)phenoxy]ethoxy}piperidine Analogously to Method A, 0.091 g of tert-butyl 4-{4-[3-(2-methoxybenzyloxy)propoxy]phenyl}-3-{2-[2-(2-tetrazol-1-ylethyl)phenoxy]ethoxy}piperidin-1-carboxylate is used to prepare the title compound.

The starting materials are prepared as follows:

a1) tert-Butyl 4-{4-[3-(2-methoxybenzyloxy)propoxy]phenyl}-3-{2-[2-(2-tetrazol-1-ylethyl)phenoxy]ethoxy}piperidin-1-carboxylate a2) tert-Butyl 4-{4-[3-(2-methoxybenzyloxy)propoxy]phenyl}-3-{2-[2-(2-tetrazol-2-ylethyl)phenoxy]ethoxy}piperidin-1-carboxylate 3.6 ml of 1H-tetrazole solution (0.45 M in acetonitrile) are concentrated fully. The residue is dissolved in 10 ml of N,N-dimethylformamide and admixed at room temperature with 0.057 g of sodium hydride dispersion (55%). The reaction mixture is stirred at room temperature over 15 minutes and subsequently heated to 65° C. A solution of 0.248 g of tert-butyl 4-{4-[3-(2-methoxybenzyloxy)propoxy]phenyl}-3-(2-{2-[2-(toluene-4-sulphonyloxy)ethyl]phenoxy}-ethoxy)piperidine-1-carboxylate (Example 26b) in 10 ml of N,N-dimethylformamide is added dropwise to this mixture. The reaction mixture is stirred at 65° C. over 16 h, cooled to room temperature, admixed with 5 ml of water and subsequently almost fully concentrated by evaporation. The residue is partitioned between water and tert-butyl methyl ether. The organic phase is washed with 1N potassium bisulphate solution and 0.1N NaOH, dried over sodium sulphate and concentrated by evaporation. The title compounds are obtained as colourless oils from the residue by means of flash chromatography (SiO$_2$ 60F).

a1: Rf=0.09 (1:1.5 EtOAc-heptane); Rt=5.82.

a2: Rf=0.29 (1:1.5 EtOAc-heptane); Rt=6.03.

EXAMPLE 28

4-{4-[3-(2-Methoxybenzyloxy)propoxy]phenyl}-3-{2-[2-(2-tetrazol-2-ylethyl)phenoxy]ethoxy}piperidine Analogously to Method A, 0.104 g of tert-butyl 4-{4-[3-(2-methoxybenzyloxy)propoxy]phenyl}-3-{2-[2-(2-tetrazol-2-ylethyl)phenoxy]ethoxy}piperidine-1-carboxylate (Example 27a2) is used to prepare the title compound.

EXAMPLE 29

Methyl 4-(4-{4-[3-(2-methoxybenzyloxy)propoxy]phenyl}piperidin-3-yloxymethyl)-2-(3-methoxypropoxy)benzoate Analogously to Method B, 0.178 g of benzyl 4-{4-[3-(2-methoxybenzyloxy)propoxy]phenyl}-3-[4-methoxycarbonyl-3-(3-methoxypropoxy)benzyloxy]piperidine-1-carboxylate is used to prepare the title compound.

The starting materials are prepared as follows:

a) Benzyl 4-{4-[3-(2-methoxybenzyloxy)propoxy]phenyl}-3-[4-methoxycarbonyl-3-(3-methoxypropoxy)benzyloxy]piperidine-1-carboxylate Analogously to Method D, 3.25 g of benzyl 3-hydroxy-4-{4-[3-(2-methoxybenzyloxy)propoxy]-phenyl}piperidine-1-carboxylate (Example 10f) and 4.05 g of methyl 4-bromomethyl-2-(3-methoxypropoxy)benzoate are reacted. The title compound is obtained as a slightly yellowish oil. Rf=0.30 (1:2 toluene-EtOAc); Rt=6.00.

b) Methyl 4-bromomethyl-2-(3-methoxypropoxy)benzoate

The mixture of 25.0 g of methyl 2-(3-methoxypropoxy)-4-methylbenzoate, 18.4 g of N-bromosuccinimide, 1.65 g of 2,2'-azobis(2-methylpropionitrile) and 2.46 g of dibenzoyl peroxide in 1.2 l of carbon tetrachloride is heated to reflux with stirring and stirred over 3 hours (succinimide crystallizes out). The reaction mixture is cooled and clarified by filtration, and the filtrate is concentrated by evaporation. The title compound is obtained as a slightly orange oil from the residue by means of flash chromatography (SiO$_2$ 60F). Rf=0.30 (1:1 EtOAc-heptane); Rt=17.10 (II).

c) Methyl 2-(3-methoxypropoxy)-4-methylbenzoate

Analogously to Method F, 103.7 g of methyl 2-hydroxy-4-methylbenzoate are reacted with 95.8 g of 1-chloro-3-methoxypropane. The title compound is obtained as slightly beige oil. Rf=0.27 (1:2 EtOAc-heptane); Rt=4.22.

EXAMPLE 30

N-(2-{2-[2-(4-{4-[3-(2-Methoxybenzyloxy)propoxy]phenyl}piperidin-3-yloxy)ethoxy]phenyl}ethyl)-N-methylacetamide Analogously to Method A, 0.055 g of tert-butyl 3-(2-{2-[2-(acetylmethylamino)ethyl]phenoxy}ethoxy)-4-{4-[3-(2-methoxybenzyloxy)propoxy]phenyl}piperidine-1-carboxylate is used to prepare the title compound.

The starting material is prepared as follows:

a) tert-Butyl 3-(2-{2-[2-(acetylmethylamino)ethyl]phenoxy}ethoxy)-4-{4-[3-(2-methoxybenzyloxy)propoxy]phenyl}piperidine-1-carboxylate A solution of 0.099 g of tert-butyl 3-{2-[2-(2-acetylaminoethyl)phenoxy]ethoxy}-4-{4-[3-(2-methoxybenzyloxy)propoxy]phenyl}piperidine-1-carboxylate (Example 14a) in 3 ml of N,N-dimethylformamide is admixed with stirring at room temperature with 0.023 g of sodium hydride dispersion (55%). After 30 minutes at room temperature, a solution of 0.055 ml of methyl iodide in 0.4 ml of N,N-dimethylformamide is added dropwise. The reaction mixture is stirred at 75° C. over 18 hours, cooled, poured onto water and extracted with tert-butyl methyl ether (2×). The combined organic phases are dried with sodium sulphate and concentrated by evaporation. The title compound is obtained as a yellow oil from the residue by means of flash chromatography (SiO$_2$ 60F). Rf=0.09 (1.5:1 EtOAc-heptane); Rt=5.84.

EXAMPLE 31

3-[4-Chloro-3-(3-methoxypropoxy)benzyloxy]-4-{4-[3-(2-methoxybenzyloxy)propoxy]phenyl}piperidine Analogously to Method A, 0.110 g of tert-butyl 3-[4-chloro-3-(3-methoxypropoxy)benzyloxy]-4-{4-[3-(2-methoxybenzyloxy)propoxy]phenyl}piperidine-1-carboxylate is used to prepare the title compound.

The starting materials are prepared as follows:

a) tert-Butyl 3-[4-chloro-3-(3-methoxypropoxy)benzyloxy]-4-{4-[3-(2-methoxybenzyloxy)propoxy]phenyl}piperidine-1-carboxylate The solution of 0.150 g of tert-butyl 3-(4-chloro-3-hydroxybenzyloxy)-4-{4-[3-(2-methoxybenzyloxy)propoxy]phenyl}piperidine-1-carboxylate in 1.5 ml of N,N-dimethylformamide is admixed successively with 0.104 g of potassium carbonate, 0.082 ml of 1-chloro-3-methoxypropane and 0.004 mg of potassium iodide, and stirred at 80° C. over 20 hours. The reaction mixture is admixed with 1M aqueous sodium hydrogencarbonate solution (25 ml) and extracted with ethyl acetate (2×25 ml). The organic phases are washed with water (2×25 ml) and brine (1×25 ml), dried over sodium sulphate, filtered and concentrated by evaporation. The title compound is obtained as a colourless oil from the residue by means of flash chromatography (SiO$_2$ 60F). Rt=6.44.

b) tert-Butyl 3-(4-chloro-3-hydroxybenzyloxy)-4-{4-[3-(2-methoxybenzyloxy)propoxy]-phenyl}piperidine-1-carboxylate The solution of 1.53 g of tert-butyl 3-(3-allyloxy-4-chlorobenzyloxy)-4-{4-[3-(2-methoxybenzyloxy)propoxy]phenyl}piperidine-1-carboxylate in 15 ml of tetrahydrofuran is admixed with stirring successively with 0.018 g of bis(triphenylphosphine)palladium(II) acetate and 0.053 g of lithium borohydride. The reaction mixture is stirred at room temperature over 16 hours, subsequently poured onto saturated aqueous sodium hydrogencarbonate solution and extracted with tert-butyl methyl ether (2×100 ml). The organic phases are washed with water (100 ml) and brine (100 ml), dried over sodium sulphate, filtered and concentrated by evaporation. The title compound is obtained as a slightly yellowish oil from the residue by means of flash chromatography (SiO$_2$ 60F). Rf=0.45 (1:1 EtOAc-heptane); Rt=5.88.

c) tert-Butyl 3-(3-allyloxy-4-chlorobenzyloxy)-4-{4-[3-(2-methoxybenzyloxy)propoxy]phenyl}-piperidine-1-carboxylate Analogously to Method D, 2.00 g of tert-butyl 3-hydroxy-4-{4-[3-(2-methoxybenzyloxy)propoxy]phenyl}piperidine-1-carboxylate and 2-allyloxy-1-chloro-4-chloromethylbenzene are reacted. The title compound is obtained as a colourless oil. Rf=0.18 (1:4 EtOAc-heptane); Rt=6.44.

d) Allyloxy-1-chloro-4-chloromethylbenzene

Analogously to Method E, 5.10 g of (3-allyloxy-4-chlorophenyl)methanol are reacted. The title compound is obtained as a slightly brownish oil. Rf=0.70 (1:1 EtOAc-heptane); Rt=5.06.

e) (3-Allyloxy-4-chlorophenyl)methanol

Analogously to Example 12c, 7.01 g of allyl 3-allyloxy-4-chlorobenzoate are reacted. The title compound is obtained as a slightly brownish oil. Rf=0.06 (1:10 EtOAc-heptane); Rt=3.86.

f) Allyl 3-allyloxy-4-chlorobenzoate

The mixture of 5.0 g of 4-chloro-3-hydroxybenzoic acid and 12.0 g of potassium carbonate in 60 ml of N,N-dimethylformamide is admixed with 5.82 ml of allyl bromide and stirred at 100° C. over 20 hours. The reaction mixture is concentrated by evaporation, admixed with water (1×200 ml) and extracted with tert-butyl methyl ether (2×200 ml). The organic phases are washed successively with water (2×200 ml) and brine (1×250 ml), dried over sodium sulphate, filtered and concentrated by evaporation. The title compound is obtained as a slightly yellowish oil from the residue by means of flash chromatography (SiO$_2$ 60F). Rt=5.18.

EXAMPLE 32

2-{2-[2-(4-{4-[3-(2-Methoxybenzyloxy)propoxy]phenyl}piperidin-3-yloxy)ethoxy]phenyl}ethyl methyl carbonate Analogously to Method A, 0.080 g of tert-butyl 3-(2-{2-[2-(imidazole-1-carbonyloxy)ethyl]-phenoxy}ethoxy)-4-{4-[3-(2-methoxybenzyloxy)propoxy]phenyl}piperidine-1-carboxylate is used to prepare the title compound.

The starting material is prepared as follows:

a) tert-Butyl 3-(2-{2-[2-(imidazole-1-carbonyloxy)ethyl]phenoxy}ethoxy)-4-{4-[3-(2-methoxybenzyloxy)propoxy]phenyl}piperidine-1-carboxylate A solution of 0.100 g of tert-butyl 3-{2-[2-(2-hydroxyethyl)phenoxy]ethoxy}-4-{4-[3-(2-methoxybenzyloxy)propoxy]phenyl}piperidine-1-carboxylate (Example 26c) and 0.049 g of diimidazol-1-ylmethanone in 4 ml of acetonitrile is stirred at reflux over 5 hours. The reaction mixture is cooled at room temperature, diluted with tert-butyl methyl ether, washed with 1N HCl and 0.5N NaOH, dried over sodium sulphate and concentrated by evaporation. The crude title compound is obtained as a yellow oil from the residue. Rf=0.41 (2:1 EtOAc-heptane); Rt=5.61.

EXAMPLE 33

2-(4-m{4-[3-(2-Methoxybenzyloxy)propoxy]phenyl}piperidin-3-yloxymethyl)-1-(3-methoxypropyl)-1H-indole Analogously to Method B, 0.130 g of benzyl 4-{4-[3-(2-methoxybenzyloxy)propoxy]phenyl}-3-[1-(3-methoxypropyl)-1H-indol-2-ylmethoxy]piperidine-1-carboxylate is used to prepare the title compound.

The starting materials are prepared as follows:

a) Benzyl 4-{4-[3-(2-methoxybenzyloxy)propoxy]phenyl}-3-[1-(3-methoxypropyl)-1H-indol-2-ylmethoxy]piperidine-1-carboxylate Analogously to Example 10a, 0.134 g of benzyl 3-(1H-indol-2-ylmethoxy)-4-{4-[3-(2-methoxybenzyloxy)propoxy]phenyl}piperidine-1-carboxylate is reacted. The title compound is obtained as a slightly brownish oil. Rf=0.25 (1:1 EtOAc-heptane); Rt=6.28.

b) Benzyl 3-(1H-indol-2-ylmethoxy)-4-{4-[3-(2-methoxybenzyloxy)propoxy]phenyl}piperidine-1-carboxylate The solution of 0.160 g of benzyl 3-(1-methanesulphonyl-1H-indol-2-ylmethoxy)-4-{4-[3-(2-methoxybenzyloxy)propoxy]phenyl}piperidine-1-carboxylate in 11 ml of tetrahydrofuran is admixed with 0.44 ml of tetrabutylammonium fluoride solution (1M in tetrahydrofuran) and stirred at reflux over 20 hours. The reaction mixture is cooled, poured onto brine (40 ml) and extracted with ethyl acetate (2×40 ml). The organic phases are washed with brine (1×40 ml), dried over sodium sulphate, filtered and concentrated by evaporation. The title compound is obtained as an orange oil from the residue by means of flash chromatography (SiO$_2$ 60F). Rf=0.18 (1:2 EtOAc-heptane); Rt=26.90 (II).

c) Benzyl 3-(1-methanesulphonyl-1H-indol-2-yl-methoxy)-4-{4-[3-(2-methoxybenzyloxy)propoxy]phenyl}piperidine-1-carboxylate The solution of 0.108 g of benzyl 4-{4-[3-(2-methoxybenzyloxy)propoxy]phenyl}-3-prop-2-ynyloxypiperidine-1-carboxylate, 0.098 g of N-(2-iodophenyl)methanesulphonamide in 0.5 ml of N,N-dimethylformamide and 1.0 ml of triethylamine are admixed with stirring with 0.011 g of bis(triphenylphosphine)palladium(II) chloride and 0.005 g of copper(I) iodide. The reaction mixture is stirred at 80° C. over 20 hours, then cooled, admixed with water (5 ml) and extracted with ethyl acetate (3×5 ml). The organic phases are washed with brine (1×5 ml), dried over sodium sulphate, filtered and concentrated by evaporation. The title compound is obtained as an orange oil from the residue by means of flash chromatography (SiO$_2$ 60F). Rf=0.13 (1:2 EtOAc-heptane); Rt=6.07.

d) Benzyl 4-{4-[3-(2-methoxybenzyloxy)propoxy]phenyl}-3-prop-2-ynyloxypiperidine-1-carboxylate Analogously to Method D, 0.255 g of benzyl 3-hydroxy-4-{4-[3-(2-methoxybenzyloxy)propoxy]phenyl}piperidine-1-carboxylate (Example 10f) and 0.022 g of propargyl bromide are reacted. The title compound is obtained as a colourless oil. Rf=0.40 (1:1 EtOAc-heptane); Rt=5.58.

EXAMPLE 34

N-[2-(2-Acetylaminoethyl)phenyl]-2-(4-{4-[3-(2-methoxybenzyloxy)propoxy]phenyl}piperidin-3-yloxy)acetamide Analogously to Method A, 0.135 g of tert-butyl 3-{[2-(2-acetylaminoethyl)phenylcarbamoyl]methoxy}-4-{4-[3-(2-methoxybenzyloxy)propoxy]phenyl}piperidine-1-carboxylate is used to prepare the title compound.
The starting materials are prepared as follows:

a) tert-Butyl 3-{[2-(2-acetylaminoethyl)phenylcarbamoyl]methoxy}-4-{4-[3-(2-methoxybenzyloxy)propoxy]phenyl}piperidine-1-carboxylate Analogously to Example 3a, 0.138 g of tert-butyl 3-carboxymethoxy-4-{4-[3-(2-methoxybenzyloxy)propoxy]phenyl}piperidine-1-carboxylate and 0.061 g of N-[2-(2-aminophenyl)ethyl]acetamide. The title compound is obtained as a yellow oil. Rf=0.21 (95:5 dichloromethane-methanol); Rt=5.22.

b) tert-Butyl 3-carboxymethoxy-4-{4-[3-(2-methoxybenzyloxy)propoxy]phenyl}piperidine-1-carboxylate A solution of 0.953 g of tert-butyl 3-hydroxy-4-{4-[3-(2-methoxybenzyloxy)propoxy]phenyl}piperidine-1-carboxylate in 10 ml of N,N-dimethylformamide is admixed with stirring at room temperature with 0.16 g of sodium hydride dispersions (60%). The reaction mixture is stirred at 60° C. over 10 minutes, admixed with 0.191 g of chloroacetic acid and then stirred at 60° C. over 24 hours. The reaction mixture is admixed with 0.5N HCl and extracted with ethyl acetate (2×). The combined organic phases are washed with brine, dried over sodium sulphate and concentrated by evaporation. The title compound is obtained as a yellow oil from the residue by means of flash chromatography (SiO$_2$ 60F). Rf=0.20 (95:5 dichloromethane-methanol); Rt=5.18.

c) N-[2-(2-Aminophenyl)ethyl]acetamide

A solution of 0.95 g of N-[2-(2-nitrophenyl)ethyl]acetamide in 30 ml of ethanol is hydrogenated in the presence of 0.112 g of 10% Pd/C at room temperature over 3.5 hours. The reaction mixture is clarified by filtration and the filtrate is concentrated by evaporation. The crude title compound is obtained as a light brown solid from the residue. Rf=0.50 (9:1 dichloromethane-methanol); Rt=1.86.

EXAMPLE 35

N-[2-(2-Acetylaminoethyl)phenyl]-2(S)-(4-{4-[3-(2-methoxybenzyloxy)propoxy]phenyl}piperidin-3-yloxy)propionamide Analogously to Method A, 0.102 g of tert-butyl 3-(1(S)-[2-(2-acetylaminoethyl)phenylcarbamoyl]ethoxy-4-{4-[3-(2-methoxybenzyloxy)propoxy]phenyl}piperidine-1-carboxylate is used to prepare the title compound.
The starting materials are prepared as follows:

a) tert-Butyl 3-{1(S)-[2-(2-acetylaminoethyl)phenylcarbamoyl]ethoxy}-4-{4-[3-(2-methoxybenzyloxy)propoxy]phenyl}piperidine-1-carboxylate Analogously to Example 3a, 0.175 g of tert-butyl 3-(1(S)-carboxyethoxy)-4-{4-[3-(2-methoxybenzyloxy)propoxy]phenyl}piperidine-1-carboxylate and 0.065 g of N-[2-(2-aminophenyl)ethyl]acetamide (Example 34c) are reacted. The title compound is obtained as a brown oil. Rf=0.35 (95:5 dichloromethane-methanol); Rt=5.32.

b) tert-Butyl 3-(1(S)-carboxyethoxy)-4-{4-[3-(2-methoxybenzyloxy)propoxy]phenyl}piperidine-1-carboxylate Analogously to Example 3b, 0.467 g of tert-butyl 3-(1(S)-ethoxycarbonylethoxy)-4-{4-[3-(2-methoxybenzyloxy)propoxy]phenyl}piperidine-1-carboxylate is reacted. The title compound is obtained as a yellow oil. Rt=5.33.

c) tert-Butyl 3-(1(S)-ethoxycarbonylethoxy)-4-{4-[3-(2-methoxybenzyloxy)propoxy]phenyl}piperidine-1-carboxylate 0.32 ml of ethyl 2(R)-trifluoromethanesulphonyloxypropionic acid and 0.075 g of sodium hydride dispersion (55%) are added at −45° C. to the solution of 0.733 g of tert-butyl 3-hydroxy-4-{4-[3-(2-methoxybenzyloxy)propoxy]phenyl}piperidine-1-carboxylate in 5 ml of tetrahydrofuran. The reaction mixture is stirred at room temperature over 5 hours and subsequently poured onto water. The mixture is extracted with ethyl acetate (2×). The combined organic phases are washed with brine, dried over sodium sulphate and concentrated by evaporation. The title compound is obtained as a colourless oil from the residue by means of flash chromatography (SiO₂ 60F). Rf=0.26 (1:3 EtOAc-heptane); Rt=6.01.

EXAMPLE 36

N-[2-(2-Acetylaminoethyl)phenyl]-2(R)-(4-{4-[3-(2-methoxybenzyloxy)propoxy]phenyl}piperidin-3-yloxy)propionamide Analogously to Method A, 0.136 g of tert-butyl 3-{1(R)-[2-(2-acetylaminoethyl)phenylcarbamoyl]ethoxy}-4-{4-[3-(2-methoxybenzyloxy)propoxy]phenyl}piperidine-1-carboxylate is used to prepare the title compound.

The starting materials are prepared as follows:

a) tert-Butyl 3-{1(R)-[2-(2-acetylaminoethyl)phenylcarbamoyl]ethoxy}-4-{4-[3-(2-methoxybenzyloxy)propoxy]phenyl}piperidine-1-carboxylate Analogously to Example 3a, 0.165 g of tert-butyl 3-(1(R)-carboxyethoxy)-4-{4-[3-(2-methoxybenzyloxy)propoxy]phenyl}piperidine-1-carboxylate and 0.066 g of N-[2-(2-aminophenyl)ethyl]acetamide (Example 34c) are reacted. The title compound is obtained as a yellow oil. Rf=0.22 (95:5 dichloromethane-methanol); Rt=5.34.

b) tert-Butyl 3-(1(R)-carboxyethoxy)-4-{4-[3-(2-methoxybenzyloxy)propoxy]phenyl}piperidine-1-carboxylate Analogously to Example 3b, 0.290 g of tert-butyl 3-(1(R)-ethoxycarbonylethoxy)-4-{4-[3-(2-methoxybenzyloxy)propoxy]phenyl}piperidine-1-carboxylate is reacted. The title compound is obtained as a yellow oil. Rt=5.32.

c) tert-Butyl 3-(1(R)-ethoxycarbonylethoxy)-4-{4-[3-(2-methoxybenzyloxy)propoxy]phenyl}piperidine-1-carboxylate Analogously to Example 35c, 0.32 ml of ethyl 2(S)-trifluoromethanesulphonyloxypropionate and 0.734 g of tert-butyl 3-hydroxy-4-{4-[3-(2-methoxybenzyloxy)propoxy]phenyl}piperidine-1-carboxylate are reacted. The title compound is obtained as a colourless oil. Rf=0.19 (1:3 EtOAc-heptane); Rt=5.93.

EXAMPLE 37

N-[2-(2-{2-[4-(4-Methoxyphenyl)piperidin-3-yloxy]ethoxy}phenyl)ethyl]acetamide

Analogously to Method A, 0.156 g of tert-butyl 3-{2-[2-(2-acetylaminoethyl)phenoxy]ethoxy}-4-(4-methoxyphenyl)piperidine-1-carboxylate is used to prepare the title compound.

The starting materials are prepared as follows:

a) tert-Butyl 3-{2-[2-(2-acetylaminoethyl)phenoxy]ethoxy}-4-(4-methoxyphenyl)piperidine-1-carboxylate Analogously to Method G, 0.24 g of tert-butyl 4-(4-methoxyphenyl)-3-[2-(toluene-4-sulphonyloxy)ethoxy]piperidine-1-carboxylate and 0.17 g of N-[2-(2-hydroxyphenyl)ethyl]acetamide are reacted. The title compound is obtained as an orange oil. Rf=0.50 (200:20:1 dichloromethane-methanol-25% conc. ammonia); Rt=4.85.

b) tert-Butyl 4-(4-methoxyphenyl)-3-[2-(toluene-4-sulphonyloxy)ethoxy]piperidine-1-carboxylate Analogously to Method H, 0.21 g of tert-butyl 3-(2-hydroxyethoxy)-4-(4-methoxyphenyl)piperidine-1-carboxylate is reacted. The title compound is obtained as a yellow oil. Rf=0.10 (1:3 EtOAc-heptane); Rt=5.40.

c) tert-Butyl 3-(2-hydroxyethoxy)-4-(4-methoxyphenyl)piperidine-1-carboxylate

A solution of 1.01 g of tert-butyl 3-hydroxy-4-(4-methoxyphenyl)piperidine-1-carboxylate in 40 ml of N,N-dimethylformamide is added at 0° C. to the suspension of 0.26 g of sodium hydride dispersion (60%) in 40 ml of N,N-dimethylformamide. After 30 minutes, the reaction mixture is admixed with 0.83 g of [1,3,2]dioxathiolane 2,2-dioxide and stirred at room temperature over 18 hours. The reaction mixture is cooled to 0° C., admixed with water and concentrated by evaporation. The residue is stirred in a 1:10 mixture of 0.1 M H₂SO₄/dioxane at 50° C. over 60 hours, neutralized with saturated aqueous sodium hydrogencarbonate solution and concentrated by evaporation. The residue is dissolved in ethyl acetate, washed with water and brine, dried over sodium sulphate and concentrated by evaporation. The title compound is obtained as a yellow oil from the residue by means of flash chromatography (SiO₂ 60F). Rf=0.20 (1:1 EtOAc-heptane); Rt=4.24.

d) tert-Butyl 3-hydroxy-4-(4-methoxyphenyl)piperidine-1-carboxylate

A suspension of 15.07 g of tert-butyl 3-hydroxy-4-(4-hydroxyphenyl)piperidine-1-carboxylate and 10.10 g of potassium carbonate in 260 ml of acetone is admixed with 5.43 ml of dimethyl sulphate and stirred at reflux over 7 hours. The reaction mixture is cooled to room temperature and concentrated by evaporation. The residue is partitioned between diethyl ether and a 1:1 25% conc. ammonia-water mixture. The organic phase is washed with water, 2N NaOH (2×) and brine, dried over sodium sulphate and concentrated by evaporation. The crude title compound is obtained as a white solid from the residue. Rf=0.30 (1:1 EtOAc-heptane); Rt=4.22.

EXAMPLE 38

N-(2-{2-[2-(4-{4-[4-(2-Methoxyphenoxy)butoxy]phenyl}piperidin-3-yloxy)ethoxy]phenyl}ethyl)acetamide Analogously to Method A, 0.095 g of tert-butyl 3-{2-[2-(2-acetylaminoethyl)phenoxy]ethoxy}-4-{4-[4-(2-methoxyphenoxy)butoxy]phenyl}piperidine-1-carboxylate is used to prepare the title compound.

The starting materials are prepared as follows:

a) tert-Butyl 3-{2-[2-(2-acetylaminoethyl)phenoxy]ethoxy}-4-{4-[4-(2-methoxyphenoxy)butoxy]phenyl}piperidine-1-carboxylate Analogously to Method G, 0.090 g of tert-butyl 4-{4-[4-(2-methoxyphenoxy)butoxy]phenyl}-3-[2-(toluene-4-sulphonyloxy)ethoxy]piperidine-1-carboxylate and 0.048 g of N-[2-(2-hydroxyphenyl)ethyl]acetamide are reacted. The title compound is obtained as a yellow oil. Rf=0.48 (200:20:1 dichloromethane-methanol-25% conc. ammonia); Rt=5.57.

b) tert-Butyl 4-{4-[4-(2-methoxyphenoxy)butoxy]phenyl}-3-[2-(toluene-4-sulphonyloxy)ethoxy]piperidine-1-carboxylate Analogously to Method H, 0.125 g of tert-butyl 3-(2-hydroxyethoxy)-4-{4-[4-(2-methoxyphenoxy)butoxy]phenyl}piperidine-1-carboxylate is reacted. The title compound is obtained as a yellow oil. Rf=0.10 (1:3 EtOAc-heptane); Rt=5.90.

c) tert-Butyl 3-(2-hydroxyethoxy)-4-{4-[4-(2-methoxyphenoxy)butoxy]phenyl}piperidine-1-carboxylate Analogously to Example 37c, 0.997 g of tert-butyl 3-hydroxy-4-{4-[4-(2-methoxyphenoxy)butoxy]phenyl}piperidine-1-carboxylate (Example 25b) is reacted. The title compound is obtained as a yellow solid. Rf=0.20 (1:1 EtOAc-heptane); Rt=5.19.

EXAMPLE 39

1-(2-{2-[2-(4-{4-[3-(2-Methoxybenzyloxy)propoxy]phenyl}piperidin-3-yloxy)ethoxy]phenyl}-ethyl)pyrrolidin-2-one Analogously to Method A, 0.095 g of tert-butyl 4-{4-[3-(2-methoxybenzyloxy)propoxy]phenyl}-3-(2-{2-[2-(2-oxopyrrolidin-1-yl)ethyl]phenoxy}ethoxy)piperidine-1-carboxylate is used to prepare the title compound.

The starting material is prepared as follows:

a) tert-Butyl 4-{4-[3-(2-methoxybenzyloxy)propoxy]phenyl}-3-(2-{2-[2-(2-oxopyrrolidin-1-yl)ethyl]phenoxy}ethoxy)piperidine-1-carboxylate Analogously to Example 27a, 0.20 g of tert-butyl 4-{4-[3-(2-methoxybenzyloxy)propoxy]phenyl}-3-(2-{2-[2-(toluene-4-sulphonyloxy)ethyl]phenoxy}ethoxy)piperidine-1-carboxylate (Example 26b) and 0.19 ml of pyrrolidin-2-one are reacted. The title compound is obtained as a colourless oil. Rf=0.10 (2:1 EtOAc-heptane); Rt=5.88.

EXAMPLE 40

3-{2-[2-(2-Imidazol-1-ylethyl)phenoxy]ethoxy}-4-{4-[3-(2-methoxybenzyloxy)propoxy]phenyl}piperidine Analogously to Method A, 0.095 g of tert-butyl 3-{2-[2-(2-imidazol-1-ylethyl)phenoxy]ethoxy}-4-{4-[3-(2-methoxybenzyloxy)propoxy]phenyl}piperidine-1-carboxylate is used to prepare the title compound.

The starting material is prepared as follows:

a) tert-Butyl 3-{2-[2-(2-imidazol-1-ylethyl)phenoxy]ethoxy}-4-{4-[3-(2-methoxybenzyloxy)propoxy]phenyl}piperidine-1-carboxylate Analogously to Example 27a, 0.20 g of tert-butyl 4-{4-[3-(2-methoxybenzyloxy)propoxy]phenyl}-3-(2-{2-[2-(toluene-4-sulphonyloxy)ethyl]phenoxy}ethoxy)piperidine-1-carboxylate (Example 26b) and 0.34 g of 1H-imidazole are reacted. The title compound is obtained as a colourless oil. Rf=0.55 (200:20:1 dichloromethane-methanol-25% conc. ammonia); Rt=5.37.

EXAMPLE 41

3-{2-[2-(4-{4-[3-(2-Methoxybenzyloxy)propoxy]phenyl}piperidin-3-yloxy)ethoxy]phenyl}propionitrile Analogously to Method A, 0.137 g of tert-butyl 3-{2-[2-(2-cyanoethyl)phenoxy]ethoxy}-4-{4-[3-(2-methoxybenzyloxy)propoxy]phenyl}piperidine-1-carboxylate is used to prepare the title compound.

The starting material is prepared as follows:

a) tert-Butyl 3-{2-[2-(2-cyanoethyl)phenoxy]ethoxy}-4-{4-[3-(2-methoxybenzyloxy)propoxy]phenyl}piperidine-1-carboxylate A solution of 0.20 g of tert-butyl 4-{4-[3-(2-methoxybenzyloxy)propoxy]phenyl}-3-(2-{2-[2-(toluene-4-sulphonyloxy)ethyl]phenoxy}ethoxy)piperidine-1-carboxylate (Example 26b) and 0.33 g of potassium cyanide in 4 ml of N,N-dimethylformamide is stirred at 65° C. over 10 hours. The reaction mixture is cooled to room temperature, diluted with 0.1N NaOH and extracted with tert-butyl methyl ether (2×) and ethyl acetate. The combined organic phases are dried over sodium sulphate and concentrated by evaporation. The title compound is obtained as a colourless oil from the residue by means of flash chromatography ($SiO_2$ 60F). Rf=0.44 (1:1 EtOAc-heptane); Rt=6.02.

EXAMPLE 42

3-(2-{2-[2-(4-{4-[3-(2-Methoxybenzyloxy)propoxy]phenyl}piperidin-3-yloxy)ethoxy]phenyl}-ethyl)oxazolidin-2-one Analogously to Method A, 0.117 g of tert-butyl 4-{4-[3-(2-methoxybenzyloxy)propoxy]phenyl}-3-(2-{2-[2-(2-oxooxazolidin-3-yl)ethyl]phenoxy}ethoxy)piperidine-1-carboxylate is used to prepare the title compound.

The starting material is prepared as follows:

a) tert-Butyl 4-{4-[3-(2-methoxybenzyloxy)ethoxy]phenyl}-3-(2-{2-[2-(2-oxooxazolidin-3-yl)ethyl]phenoxy}ethoxy)piperidine-1-carboxylate Analogously to Example 27a, 0.20 g of tert-butyl 4-{4-[3-(2-methoxybenzyloxy)propoxy]phenyl}-3-(2-{2-[2-(toluene-4-sulphonyloxy)ethyl]phenoxy}ethoxy)piperidine-1-carboxylate (Example 26b) and 0.44 g of oxazolidin-2-one are reacted. The title compound is obtained as a colourless oil. Rf=0.27 (2:1 EtOAc-heptane).

EXAMPLE 43

3-[4-Ethyl-3-(3-methoxypropoxy)benzyloxy]-4-{4-[3-(2-methoxybenzyloxy)propoxy]phenyl}piperidine Analogously to Method A, 0.022 g of tert-butyl 3-[4-ethyl-3-(3-methoxypropoxy)benzyloxy]-4-{4-[3-(2-methoxybenzyloxy)propoxy]phenyl}piperidine-1-carboxylate is used to prepare the title compound.

The starting materials are prepared as follows:

a) tert-Butyl 3-[4-ethyl-3-(3-methoxypropoxy)benzyloxy]-4-{4-[3-(2-methoxybenzyloxy)propoxy]phenyl}piperidine-1-carboxylate The solution of 0.090 g of tert-butyl 4-{4-[3-(2-methoxybenzyloxy)propoxy]phenyl}-3-[3-(3-methoxypropoxy)-4-vinylbenzyloxy]piperidine-1-carboxylate in 0.090 ml of triethylamine and 5.0 ml of methanol is hydrogenated in the presence of 10 mg of 10% Pd/C over 16 hours. The reaction mixture is clarified by filtration and the filtrate is concentrated by evaporation. The title compound is obtained as an orange oil from the residue by means of flash chromatography (SiO$_2$ 60F). Rf=0.23 (1:2 EtOAc-heptane); Rt=30.02 (II).

b) tert-Butyl 4-{4-[3-(2-methoxybenzyloxy)propoxy]phenyl}-3-[3-(3-methoxypropoxy)-4-vinylbenzyloxy]piperidine-1-carboxylate The solution of 0.155 g of tert-butyl 3-[4-chloro-3-(3-methoxypropoxy)benzyloxy]-4-{4-[3-(2-methoxybenzyloxy)propoxy]phenyl}piperidine-1-carboxylate (Example 31a), 0.008 g of caesium fluoride and vinyl tributyl tin in 1.0 ml of dioxane is initially charged under argon in a Schlenk apparatus with stirring. The mixture is admixed with the solution of 0.0027 g of tris(dibenzylidenacetone)dipalladium (II) and 0.0026 g of tri-tert-butylphosphine in 0.20 ml of dioxane (prepared in a Schlenk apparatus under argon). The reaction mixture is stirred at 100° C. over 24 hours, then cooled, admixed with 1M sodium hydrogencarbonate solution (20 ml) and extracted with tert-butyl methyl ether (2×25 ml). The organic phases are washed with brine (1×5 ml), dried over sodium sulphate, filtered and concentrated by evaporation. The title compound is obtained as an orange oil from the residue by means of flash chromatography (SiO$_2$ 60F). Rf=0.16 (6:1 toluene-methanol); Rt=29.41 (II).

EXAMPLE 44

1-(3-Methoxypropyl)-7-(4-{4-[3-(1-phenylethoxy)propoxy]phenyl}piperidin-3-yloxymethyl)-3,4-dihydro-1H-quinolin-2-one Analogously to Method B, 0.0245 g of benzyl 3-[1-(3-methoxypropyl)-2-oxo-1,2,3,4-tetrahydroquinolin-7-ylmethoxy]-4-{4-[3-(1-phenylethoxy)propoxy]phenyl}piperidine-1-carboxylate is used to prepare the title compound.

The starting materials are prepared as follows:

a) Benzyl 3-[1-(3-methoxypropyl)-2-oxo-1,2,3,4-tetrahydroquinolin-7-ylmethoxy]-4-{4-[3-(1-phenylethoxy)propoxy]phenyl}piperidine-1-carboxylate The mixture of 0.200 g of benzyl 4-(4-hydroxyphenyl)-3-[1-(3-methoxypropyl)-2-oxo-1,2,3,4-tetrahydroquinolin-7-ylmethoxy]piperidine-1-carboxylate, 0.157 g of 3-(1-phenylethoxy)propyl toluene-4-sulphonate and 0.173 g of caesium carbonate in 2.5 ml of acetonitrile is stirred at 80° C. over 2 hours. The reaction mixture is subsequently cooled, poured onto water (25 ml) and extracted with tert-butyl methyl ether (2×25 ml). The organic phases are washed with brine (1×25 ml), dried over sodium sulphate, filtered and concentrated by evaporation. The title compound is obtained as a yellowish oil from the residue by means of flash chromatography (SiO$_2$ 60F). Rf=0.19 (2:1 EtOAc-heptane); Rt=6.03.

b) Benzyl 4-(4-hydroxyphenyl)-3-[1-(3-methoxypropyl)-2-oxo-1,2,3,4-tetrahydroquinolin-7-ylmethoxy]piperidine-1-carboxylate Analogously to Example 10f, 0.190 g of 7-[4-(4-hydroxyphenyl)piperidin-3-yloxymethyl]-1-(3-methoxypropyl)-3,4-dihydro-1H-quinolin-2-one and 0.070 ml of benzyl formate are reacted. The title compound is obtained as a white foam. Rf=0.19 (2:1 EtOAc-heptane); Rt=6.03.

c) 7-[4-(4-Hydroxyphenyl)piperidin-3-yloxymethyl]-1-(3-methoxypropyl)-3,4-dihydro-1H-quinolin-2-one Analogously to Method A, 0.250 g of tert-butyl 4-(4-hydroxyphenyl)-3-[1-(3-methoxypropyl)-2-oxo-1,2,3,4-tetrahydroquinolin-7-ylmethoxy]piperidine-1-carboxylate is reacted. The title compound is obtained as a white foam. Rf=0.10 (200:20:1 dichloromethane-methanol-conc. ammonia); Rt=2.70.

d) tert-Butyl 4-(4-hydroxyphenyl)-3-[1-(3-methoxypropyl)-2-oxo-1,2,3,4-tetrahydroquinolin-7-ylmethoxy]piperidine-1-carboxylate Analogously to Example 31b, 0.584 g of tert-butyl 4-(4-allyloxyphenyl)-3-[1-(3-methoxypropyl)-2-oxo-1,2,3,4-tetrahydroquinolin-7-ylmethoxy]piperidine-1-carboxylate is reacted. The title compound is obtained as a white foam. Rf=0.16 (2:1 EtOAc-heptane); Rt=4.54.

e) tert-Butyl 4-(4-allyloxyphenyl)-3-[1-(3-methoxypropyl)-2-oxo-1,2,3,4-tetrahydroquinolin-7-ylmethoxy]piperidine-1-carboxylate Analogously to Method D, 3.26 g of tert-butyl 4-(4-allyloxyphenyl)-3-hydroxypiperidine-1-carboxylate and 2.62 g of 7-chloromethyl-1-(3-methoxypropyl)-3,4-dihydro-1H-quinolin-2-one are reacted. The title compound is obtained as a slightly yellowish oil. Rf=0.16 (1:1 EtOAc-heptane); Rt=5.50.

f) 3-(1-Phenylethoxy)propyl toluene-4-sulphonate

Analogously to Method H, 5.0 g of 3-[1-(2-methoxyphenyl)ethoxy]propan-1-ol are reacted. The title compound is obtained as a slightly yellowish oil. Rf=0.43 (1:2 EtOAc-heptane); Rt=5.24.

g) 3-[1-(2-Methoxyphenyl)ethoxy]propan-1-ol

The solution of 61.9 g of 2-(2-methoxyphenyl)-2-methyl-[1,3]dioxane in 450 ml of toluene is cooled to 0° C. with stirring and admixed at 0-10° C. with 487 ml of diisobutylaluminum hydride (1.5M in toluene) over 1 hour. The mixture is stirred over 2.5 hours and subsequently poured onto the stirred solution of 382 g of citric acid monohydrate in 2 l of water. The organic phase is removed and the water phase extracted with tert-butyl methyl ether (1 l). The organic phases are washed with brine (1 l), dried over sodium sulphate, filtered and concentrated by evaporation. The title compound is obtained as a yellowish oil from the residue by means of flash chromatography (SiO$_2$ 60F). Rf=0.12 (1:2 EtOAc-heptane); Rt=3.56.

h) 2-(2-Methoxyphenyl)-2-methyl-[1,3]dioxane

The solution of 55.5 g of 2-methoxyacetophenone in hexane is admixed with stirring with 31.7 ml of 1,3-propanediol and 0.92 g of pyridinium-p-toluenesulphonate. The mixture is stirred under reflux (with water separator) over 4 days. The reaction mixture is cooled to room temperature, concentrated by evaporation, admixed with 1M sodium hydrogencarbonate (0.5 l) and extracted with dichloromethane (2×0.5 l). The organic phases are washed with water (0.5 l), dried over sodium sulphate, filtered and concentrated by evaporation. The title compound is obtained as a yellowish oil and used crude in Example 44g.

EXAMPLE 45

7-[4-(4-{2-[2-(2-Methoxyphenyl)ethoxy]ethoxy}phenyl)piperidin-3-yloxymethyl]-1-(3-methoxypropyl)-3,4-dihydro-1H-quinolin-2-one Analogously to Method A, 0.125 g of tert-butyl 4-(4-{2-[2-(2-methoxyphenyl)ethoxy]ethoxy}phenyl)-3-[1-(3-methoxypropyl)-2-oxo-1,2,3,4-tetrahydroquinolin-7-ylmethoxy]piperidine-1-carboxylate is used to prepare the title compound.

The starting materials are prepared as follows:

a) tert-Butyl 4-(4-{2-[2-(2-methoxyphenyl)ethoxy]ethoxy}phenyl)-3-[1-(3-methoxypropyl)-2-oxo-1,2,3,4-tetrahydroquinolin-7-ylmethoxy]piperidine-1-carboxylate The mixture of 0.133 g of tert-butyl 4-(4-hydroxyphenyl)-3-[1-(3-methoxypropyl)-2-oxo-1,2,3,4-tetrahydroquinolin-7-ylmethoxy]piperidine-1-carboxylate (Example 44d), 0.106 g of 2-[2-(2-methoxyphenyl)ethoxy]ethyl toluene-4-sulphonate and 0.173 g of potassium carbonate in 2.5 ml of N,N-dimethylformamide is stirred at 60° C. for 20 hours. The reaction mixture is subsequently cooled, poured onto water (25 ml) and extracted with tert-butyl methyl ether (2×25 ml). The organic phases are washed with brine (25 ml), dried over sodium sulphate, filtered and concentrated by evaporation. The title compound is obtained as a yellowish oil from the residue by means of flash chromatography (SiO$_2$ 60F). Rf=0.20 (2:1 EtOAc-heptane); Rt=5.87.

b) 2-[2-(2-Methoxyphenyl)ethoxy]ethyl toluene-4-sulphonate

The solution of 7.50 g of 2-[2-(2-methoxyphenyl)ethoxy]ethanol in 75 ml of dichloromethane is admixed successively with 8.5 ml of pyridine, 0.519 g of 4-dimethylaminopyridine and 9.10 g of p-toluenesulphonyl chloride, and stirred at room temperature over 16 hours. The reaction mixture is washed with brine (2×200 ml). The organic phase is dried with sodium sulphate, filtered and concentrated by evaporation. The title compound is obtained as a slightly yellowish oil from the residue by means of flash chromatography (SiO$_2$ 60F). Rf=0.26 (1:2 EtOAc-heptane); Rt=5.02.

c) 2-[2-(2-Methoxyphenyl)ethoxy]ethanol

The solution of 10.1 g of [2-(2-methoxyphenyl)ethoxy]acetic acid in 50 ml of tetrahydrofuran is added dropwise at 0-5° C. to the stirred mixture of 1.76 g of lithium aluminium hydride in 50 ml of tetrahydrofuran. The reaction mixture is stirred at reflux over 5 hours and subsequently cooled to room temperature. 4 ml of water, 4 ml of 2N NaOH and once again 4 ml of water are successively added dropwise. The reaction mixture is poured onto 200 ml of 0.5 M HCl (cold) and extracted with ethyl acetate (2×200 ml). The organic phases are washed successively with water (200 ml) and brine (1×200 ml), dried over sodium sulphate, filtered and concentrated by evaporation. The title compound is obtained as a slightly yellowish oil from the residue by means of flash chromatography (SiO$_2$ 60F). Rf=0.19 (1:1 EtOAc-heptane); Rt=3.32.

d) [2-(2-Methoxyphenyl)ethoxy]acetic acid

The solution of 10.0 g of 2-(2-methoxyphenyl)ethanol in 130 ml of dimethyl sulphoxide is admixed with stirring with sodium hydride dispersion (60%) and stirred at 60° C. over 10 min. The suspension is admixed slowly with 6.20 g of chloroacetic acid and subsequently stirred at 80° C. over 2 hours. The reaction mixture is cooled, poured onto ice-water (0.5 l) and washed with ethyl acetate (1×250 ml). The aqueous phase is acidified with 2M HCl and extracted with ethyl acetate (2×250 ml). The organic phases are washed successively with water (250 ml) and brine (1×250 ml), dried over sodium sulphate, filtered and concentrated. The title compound is obtained as a slightly yellowish oil from the residue by means of flash chromatography (SiO$_2$ 60F). Rf=0.04 (200:20:1 dichloromethane-methanol-conc. ammonia); Rt=3.44.

EXAMPLE 46

7-{4-[4-(3-Hydroxypropoxy)phenyl]piperidin-3-yloxymethyl}-1-(3-methoxypropyl)-3,4-dihydro-1H-quinolin-2-one Analogously to Method A, 0.204 g of tert-butyl 4-(4-{3-[1-(2-methoxyphenyl)ethoxy]propoxy}phenyl)-3-[1-(3-methoxypropyl)-2-oxo-1,2,3,4-tetrahydroquinolin-7-ylmethoxy]piperidine-1-carboxylate is used to prepare the title compound.

The starting material is prepared as follows:

a) tert-Butyl 4-(4-[3-{1-(2-methoxyphenyl)ethoxy]propoxy}phenyl)-3-[1-(3-methoxypropyl)-2-oxo-1,2,3,4-tetrahydroquinolin-7-ylmethoxy]piperidine-1-carboxylate Analogously to Method I, 0.160 g of tert-butyl 4-(4-hydroxyphenyl)-3-[1-(3-methoxypropyl)-2-oxo-1,2,3,4-tetrahydroquinolin-7-ylmethoxy]piperidine-1-carboxylate (Example 44d) and 0.133 g of 3-(1-phenylethoxy)propyl toluene-4-sulphonate (Example 44f) are reacted. The title compound is obtained as a colourless oil. Rf=0.26 (2:1 EtOAc-heptane); Rt=27.11 (II).

EXAMPLE 47

3-{2-[2-(4-{4-[3-(2-methoxybenzyloxy)propoxy]phenyl}piperidin-3-yloxy)ethoxy]phenyl}propionic acid A mixture of 0.057 g of methyl 3-{2-[2-(4-{4-[3-(2-Methoxybenzyloxy)propoxy]phenyl}piperidin-3-yloxy)ethoxy]phenyl}propionate (Example 52) in 1 ml of dioxane and 0.2 ml of 2N NaOH is stirred at 80° C. over 40 minutes. The reaction mixture is cooled to room temperature and made neutral with 0.5N HCl. The mixture is subsequently extracted with ethyl acetate (3×). The combined organic phases are dried over sodium sulphate and concentrated by evaporation. The crude title compound is obtained as a yellow solid from the residue. Rt=4.26.

EXAMPLE 48

1-(3-Methoxypropyl)-7-{4-[4-(4-o-tolyloxybutoxy)phenyl]piperidin-3-yloxymethyl}-3,4-dihydro-1H-quinolin-2-one Analogously to Method A, 0.195 g of tert-butyl 3-[1-(3-methoxypropyl)-2-oxo-1,2,3,4-tetrahydroquinolin-7-ylmethoxy]-4-[4-(4-o-tolyloxybutoxy)phenyl]piperidine-1-carboxylate is used to prepare the title compound.

The starting material is prepared as follows:

a) tert-Butyl 3-[1-(3-methoxypropyl)-2-oxo-1,2,3,4-tetrahydroquinolin-7-ylmethoxy]-4-[4-(4-o-tolyloxybutoxy)phenyl]piperidine-1-carboxylate Analogously to Method I, 0.160 g of tert-butyl 4-(4-hydroxyphenyl)-3-[1-(3-methoxypropyl)-2-oxo-1,2,3,4-tetrahydroquinolin-7-ylmethoxy]piperidine-1-carboxylate (Example 44d) and 0.099 g of 1-(4-bromobutoxy)-2-methylbenzene are reacted. The title compound is obtained as a colourless oil. Rf=0.33 (2:1 EtOAc-heptane); Rt=6.34.

EXAMPLE 49

7-(4-{4-[4-(2-Fluorophenoxy)butoxy]phenyl}piperidin-3-yloxymethyl)-1-(3-methoxypropyl)-3,4-dihydro-1H-quinolin-2-one Analogously to Method A, 0.195 g of tert-butyl 4-{4-[4-(2-fluorophenoxy)butoxy]phenyl}-3-[1-(3-methoxypropyl)-2-oxo-1,2,3,4-tetrahydroquinolin-7-ylmethoxy]piperidine-1-carboxylate is used to prepare the title compound.

The starting materials are prepared as follows:

a) tert-Butyl 4-{4-[4-(2-fluorophenoxy)butoxy]phenyl}-3-[1-(3-methoxypropyl)-2-oxo-1,2,3,4-tetrahydroquinolin-7-ylmethoxy]piperidine-1-carboxylate Analogously to Method I, 0.160 g of tert-butyl 4-(4-hydroxyphenyl)-3-[1-(3-methoxypropyl)-2-oxo-1,2,3,4-tetrahydroquinolin-7-ylmethoxy]piperidine-1-carboxylate (Example 44d) and 0.093 g of 1-(4-bromobutoxy)-2-fluorobenzene are reacted. The title compound is obtained as a colourless oil. Rf=0.28 (2:1 EtOAc-heptane); Rt=6.00.

EXAMPLE 50

7-(4-{4-[4-(2-Ethylphenoxy)butoxy]phenyl}piperidin-3-yloxymethyl)-1-(3-methoxypropyl)-3,4-dihydro-1H-quinolin-2-one Analogously to Method A, 0.200 g of tert-butyl 4-{4-[4-(2-ethylphenoxy)butoxy]phenyl}-3-[1-(3-methoxypropyl)-2-oxo-1,2,3,4-tetrahydroquinolin-7-ylmethoxy]piperidine-1-carboxylate is used to prepare the title compound.

The starting materials are prepared as follows:

a) tert-Butyl 4-{4-[4-(2-ethylphenoxy)butoxy]phenyl}-3-[1-(3-methoxypropyl)-2-oxo-1,2,3,4-tetrahydroquinolin-7-ylmethoxy]piperidine-1-carboxylate Analogously to Method I, 0.160 g of tert-butyl 4-(4-hydroxyphenyl)-3-[1-(3-methoxypropyl)-2-oxo-1,2,3,4-tetrahydroquinolin-7-ylmethoxy]piperidine-1-carboxylate (Example 44d) and 0.101 g of 1-(4-bromobutoxy)-2-ethylbenzene are reacted. The title compound is obtained as a colourless oil. Rf=0.35 (2:1 EtOAc-heptane); Rt=6.48.

b) 1-(4-Bromobutoxy)-2-ethylbenzene

The solution of 19.04 ml of 2-ethylphenol in 24 ml of 1,4-dibromobutane is heated to 100° C. with stirring and admixed slowly with 99.2 ml of 1.6M NaOH. The emulsion is stirred at 100° C. over 20 h. The reaction mixture is cooled and extracted with tert-butyl methyl ether (2×150 ml). The organic phases are washed successively with 2M NaOH (1×150 ml), water (1×150 ml) and brine (1×150 ml), dried over sodium sulphate, filtered and concentrated by evaporation. The title compound is obtained as a slightly yellowish oil from the residue by means of distillation. b.p. 132° C. (1.1 mbar); Rt=5.75.

EXAMPLE 51

2-[4-(4-{3-[1-(3-Methoxypropyl)-2-oxo-1,2,3,4-tetrahydroquinolin-7-ylmethoxy]piperidin-4-yl}phenoxy)butoxy]benzonitrile Analogously to Method A, 0.200 g of tert-butyl 4-{4-[4-(2-cyanophenoxy)butoxy]phenyl}-3-[1-(3-methoxypropyl)-2-oxo-1,2,3,4-tetrahydroquinolin-7-ylmethoxy]piperidine-1-carboxylate is used to prepare the title compound.

The starting material is prepared as follows:

a) tert-Butyl 4-{4-[4-(2-cyanophenoxy)butoxy]phenyl}-3-[1-(3-methoxypropyl)-2-oxo-1,2,3,4-tetrahydroquinolin-7-ylmethoxy]piperidine-1-carboxylate Analogously to Method I, 0.160 g of tert-butyl 4-(4-hydroxyphenyl)-3-[1-(3-methoxypropyl)-2-oxo-1,2,3,4-tetrahydroquinolin-7-ylmethoxy]piperidine-1-carboxylate (Example 44d) and 0.105 g of 2-(4-bromobutoxy)benzonitrile are reacted. The title compound is obtained as a colourless oil. Rf=0.18 (2:1 EtOAc-heptane); Rt=5.73.

EXAMPLE 52

Methyl 3-{2-[2-(4-{4-[3-(2-methoxybenzyloxy)propoxy]phenyl}piperidin-3-yloxy)ethoxy]phenyl}propionate Analogously to Method A, 0.140 g of tert-butyl 4-{4-[3-(2-methoxybenzyloxy)propoxy]phenyl}-3-{2-[2-(2-methoxycarbonylethyl)phenoxy]ethoxy}piperidine-1-carboxylate is used to prepare the title compound.

The starting material is prepared as follows:

a) tert-Butyl 4-{4-[3-(2-methoxybenzyloxy)propoxy]phenyl}-3-{2-[2-(2-methoxycarbonylethyl)phenoxy]ethoxy}piperidine-1-carboxylate Analogously to Method F, 0.30 g of tert-butyl 4-{4-[3-(2-methoxybenzyloxy)propoxy]phenyl}-3-[2-(toluene-4-sulphonyloxy)ethoxy]piperidine-1-carboxylate (Example 14b) and methyl 3-(2-hydroxyphenyl)propionate are used to prepare the title compound as a colourless oil. Rf=0.23 (1:2 EtOAc-heptane); Rt=6.20.

EXAMPLE 53

1-(3-Methoxypropyl)-7-(4-{4-[4-(3-methylindol-1-yl)butoxy]phenyl}piperidin-3-yloxymethyl)-3,4-dihydro-1H-quinolin-2-one Analogously to Method A, 0.196 g of tert-butyl 3-[1-(3-methoxypropyl)-2-oxo-1,2,3,4-tetrahydroquinolin-7-ylmethoxy]-4-{4-[4-(3-methylindol-1-yl)butoxy]phenyl}piperidine-1-carboxylate is used to prepare the title compound.

The starting materials are prepared as follows:

a) tert-Butyl 3-[1-(3-methoxypropyl)-2-oxo-1,2,3,4-tetrahydroquinolin-7-ylmethoxy]-4-{4-[4-(3-methylindol-1-yl)butoxy]phenyl}piperidine-1-carboxylate Analogously to Method I, 0.160 g of tert-butyl 4-(4-hydroxyphenyl)-3-[1-(3-methoxypropyl)-2-oxo-1,2,3,4-tetrahydroquinolin-7-ylmethoxy]piperidine-1-carboxylate (Example 44d) and 0.149 g of 1-(4-bromobutyl)-3-methyl-1H-indole are reacted. The title compound is obtained as a colourless oil. Rf=0.21 (2:1 EtOAc-heptane); Rt=6.27.

b) 1-(4-Bromobutyl)-3-methyl-1H-indole

The solution of 5.0 g of 2-methylindole in 70 ml of DMPU is admixed with stirring at 0° C. with 3.30 g of sodium hydride dispersion (60%) and stirred at room temperature over 2 hours. Subsequently, 20 ml of 1,4-dibromobutane and 1.40 g of tetrabutylammonium iodide are added (exothermic reaction). The mixture is stirred at room temperature over 20 hours. The reaction mixture is poured onto water (200 ml) and extracted with tert-butyl methyl ether (2×200 ml). The organic phases are washed successively with water (4×200 ml) and brine (1×200 ml), dried over sodium sulphate, filtered and concentrated by evaporation. The excess of 1,4-dibromobutane is evaporated out of the residue under high vacuum and the title compound is obtained as a slightly yellowish oil by means of flash chromatography (SiO$_2$ 60F). Rf=0.79 (1:1 EtOAc-heptane); Rt=5.43.

EXAMPLE 55

4-{2-[2-(4-{4-[3-(2-Methoxybenzyloxy)propoxy]phenyl}piperidin-3-yloxy)ethoxy]phenyl}butyronitrile Analogously to Method A, 0.140 g of tert-butyl 3-{2-[2-(3-cyanopropyl)phenoxy]ethoxy}-4-{4-[3-(2-methoxybenzyloxy)propoxy]phenyl}piperidine-1-carboxylate is used to prepare the title compound.

The starting materials are prepared as follows:

a) tert-Butyl 3-{2-[2-(3-cyanopropyl)phenoxy]ethoxy}-4-{4-[3-(2-methoxybenzyloxy)propoxy]phenyl}piperidine-1-carboxylate Analogously to Example 41a, 0.20 g of tert-butyl 4-{4-[3-(2-methoxybenzyloxy)propoxy]phenyl}-3-(2-{2-[3-(toluene-4-sulphonyloxy)propyl]phenoxy}ethoxy)piperidine-1-carboxylate is reacted. The title compound is obtained as a colourless oil. Rf=0.18 (1:2 EtOAc-heptane); Rt=6.11.

b) tert-Butyl 4-{4-[3-(2-methoxybenzyloxy)propoxy]phenyl}-3-(2-{2-[3-(toluene-4-sulphonyloxy)propyl]phenoxy}ethoxy)piperidine-1-carboxylate Analogously to Method H, 1.40 g of tert-butyl 3-{2-[2-(3-hydroxypropyl)phenoxy]ethoxy}-4-{4-[3-(2-methoxybenzyloxy)propoxy]phenyl}piperidine-1-carboxylate are reacted. The title compound is obtained as a colourless oil. Rf=0.17 (1:2 EtOAc-heptane); Rt=6.36.

c) tert-Butyl 3-{2-[2-(3-hydroxypropyl)phenoxy]ethoxy}-4-{4-[3-(2-methoxybenzyloxy)propoxy]phenyl}piperidine-1-carboxylate Analogously to Method F, 2.24 g of tert-butyl 4-{4-[3-(2-methoxybenzyloxy)propoxy]phenyl}-3-[2-(toluene-4-sulphonyloxy)ethoxy]piperidine-1-carboxylate (Example 14b) and 1.28 g of 2-(3-hydroxypropyl)phenol are reacted. The title compound is obtained as a colourless oil. Rf=0.41 (2:1 EtOAc-heptane); Rt=5.90.

EXAMPLE 56

N-(2-{2-[2-(4-{4-[3-(2-Methoxybenzyloxy)propoxy]phenyl}piperidin-3-yloxy)ethoxy]phenyl}ethyl)methanesulphonamide Analogously to Method A, 0.191 g of tert-butyl 3-{2-[2-(2-methanesulphonylaminoethyl)phenoxy]ethoxy}-4-{4-[3-(2-methoxybenzyloxy)propoxy]phenyl}piperidine-1-carboxylate is used to prepare the title compound.

The starting materials are prepared as follows:

a) tert-Butyl 3-{2-[2-(2-methanesulphonylaminoethyl)phenoxy]ethoxy}-4-{4-[3-(2-methoxybenzyloxy)propoxy]phenyl}piperidine-1-carboxylate A solution of 0.25 g of tert-butyl 3-{2-[2-(2-aminoethyl)phenoxy]ethoxy}-4-{4-[3-(2-methoxybenzyloxy)propoxy]phenyl}piperidine-1-carboxylate in 12 ml of dichloromethane is admixed at room temperature with a solution of 0.12 ml of triethylamine in 1 ml of dichloromethane. Subsequently, a solution of 0.034 ml of methanesulphonyl chloride in 1 ml of dichloromethane is added dropwise. After stirring for 2 hours, the reaction mixture is diluted with dichloromethane, washed with 1M aqueous potassium bisulphate solution (2×), dried over sodium sulphate and concentrated by evaporation. The title compound is obtained as a colourless oil from the residue by means of flash chromatography (SiO$_2$ 60F). Rf=0.07 (1:2 EtOAc-heptane); Rt=5.78.

b) tert-Butyl 3-{2-[2-(2-aminoethyl)phenoxy]ethoxy}-4-{4-[3-(2-methoxybenzyloxy)propoxy]phenyl}piperidine-1-carboxylate A solution of 2.85 g of tert-butyl 3-{2-[2-(2-azidoethyl)phenoxy]ethoxy}-4-{4-[3-(2-methoxybenzyloxy)propoxy]phenyl}piperidine-1-carboxylate in 12.5 ml of tetrahydrofuran and 2.5 ml of water is admixed at room temperature with a solution of 1.2 ml of 25% conc. ammonia in 11.2 ml of methanol. After 1.7 g of triphenylphosphine have been added, the reaction mixture is stirred at room temperature over 16 hours. The mixture is diluted with ethyl acetate and washed with semisaturated aqueous sodium hydrogencarbonate solution (2×), dried over sodium sulphate and concentrated by evaporation. The title compound is obtained as a colourless oil from the residue by means of flash chromatography (SiO$_2$ 60F). Rf=0.26 (200:20:1 dichloromethane-methanol-25% conc. ammonia); Rt=5.17.

c) tert-Butyl 3-{2-[2-(2-azidoethyl)phenoxy] ethoxy}-4-{4-[3-(2-methoxybenzyloxy)propoxy] phenyl}piperidine-1-carboxylate A solution of 2.0 g of tert-butyl 4-{4-[3-(2-methoxybenzyloxy)propoxy]phenyl}-3-(2-{2-[2-(toluene-4-sulphonyloxy)ethyl]phenoxy}ethoxy)piperidine-1-carboxylate (Example 26b) and 1.32 g of sodium azide in 20 ml of N,N-dimethylformamide is stirred at 65° C. over 90 minutes. The reaction mixture is diluted with semisaturated aqueous sodium hydrogencarbonate solution and extracted with tert-butyl methyl ether (3×). The combined organic phases are dried over sodium sulphate and concentrated by evaporation. The crude title compound is obtained as a colourless oil from the residue. Rf=0.43 (1:1 EtOAc-heptane); Rt=6.40.

EXAMPLE 57

4-Methoxy-N-[2-(4-{4-[3-(2-methoxybenzyloxy) propoxy]phenyl}piperidin-3-yloxymethyl)phenyl] butyramide Analogously to Method A, 0.135 g of tert-butyl 4-{4-[3-(2-methoxybenzyloxy)propoxy]phenyl}-3-[2-(4-methoxybutyrylamino)benzyloxy]piperidine-1-carboxylate is used to prepare the title compound.

The starting materials are prepared as follows:

a) tert-Butyl 4-{4-[3-(2-methoxybenzyloxy)propoxy] phenyl}-3-[2-(4-methoxybutyrylamino)benzyloxy] piperidine-1-carboxylate Analogously to Example 116b, 0.135 g of tert-butyl 3-(2-aminobenzyloxy)-4-{4-[3-(2-methoxybenzyloxy)propoxy] phenyl}piperidine-1-carboxylate and 0034 g of 4-methoxybutyryl chloride are reacted. The title compound is obtained as a beige oil. Rf=0.10 (1:1 EtOAc-heptane); Rt=5.86.

b) tert-Butyl 3-(2-aminobenzyloxy)-4-{4-[3-(2-methoxybenzyloxy)propoxy]phenyl}piperidine-1-carboxylate Analogously to Example 116c, 0.900 g of tert-butyl 3-(2-bromobenzyloxy)-4-{4-[3-(2-methoxybenzyloxy)propoxy] phenyl}piperidine-1-carboxylate is used to prepare the title compound as a colourless oil. Rf=0.23 (1:2 EtOAc-heptane); Rt=5.30.

c) tert-Butyl 3-(2-bromobenzyloxy)-4-{4-[3-(2-methoxybenzyloxy)propoxy]phenyl}piperidine-1-carboxylate Analogously to Method D, 0.953 g of tert-butyl 3-hydroxy-4-{4-[3-(2-methoxybenzyloxy)propoxy]phenyl}piperidine-1-carboxylate and 0.510 g of 2-bromobenzylbromide are reacted. The title compound is obtained as a beige oil. Rf=0.31 (1:2 EtOAc-heptane); Rt=6.46.

EXAMPLE 58

6-(4-{4-[3-(2-Methoxybenzyloxy)propoxy] phenyl}piperidin-3-yloxymethyl)-1-(3-methoxypropyl)-3,3-dimethyl-1,3-dihydroindol-2-one Analogously to Method A, 0.990 g of tert-butyl 4-{4-[3-(2-methoxybenzyloxy)propoxy]phenyl}-3-[1-(3-methoxypropyl)-3,3-dimethyl-2-oxo-2,3-dihydro-1H-indol-6-ylmethoxy]piperidine-1-carboxylate is used to prepare the title compound.

The starting materials are prepared as follows:

a) tert-Butyl 4-{4-[3-(2-methoxybenzyloxy)propoxy] phenyl}-3-[1-(3-methoxypropyl)-3,3-dimethyl-2-oxo-2,3-dihydro-1H-indol-6-ylmethoxy]piperidine-1-carboxylate Analogously to Method D, 0.853 g of tert-butyl 3-hydroxy-4-{4-[3-(2-methoxybenzyloxy)propoxy]phenyl}piperidine-1-carboxylate and 0.504 g of 6-bromomethyl-1-(3-methoxypropyl)-3,3-dimethyl-1,3-dihydroindol-2-one are reacted. The title compound is obtained as a slightly yellowish oil. Rf=0.14 (1:1 EtOAc-heptane); Rt=6.13.

b) 6-Bromomethyl-1-(3-methoxypropyl)-3,3-dimethyl-1,3-dihydroindol-2-one

The mixture of 1.08 g of 1-(3-methoxypropyl)-3,3,6-trimethyl-1,3-dihydroindol-2-one, 0.801 g of N-bromosuccinimide, 0.014 g of 2,2'-azobis(2-methylpropionitrile) and 0.021 g of dibenzoyl peroxide in 50 ml of carbon tetrachloride is heated to reflux with stirring. The reaction mixture is stirred at reflux over 1 hour (succinimide crystallizes out) and subsequently cooled to room temperature. The succinimide is filtered off and the filtrate is concentrated by evaporation. The title compound is obtained as a slightly orange oil from the residue by means of flash chromatography (SiO$_2$ 60F). Rf=0.40 (dichloromethane-diethyl ether); Rt=17.22 (II).

c) 1-(3-Methoxypropyl)-3,3,6-trimethyl-1,3-dihydroindol-2-one

The solution, prepared under argon, of 0.226 g of 1,3-bis (2,6-Di-L-propylphenyl)imidazolium chloride, 0.116 g of palladium(II) acetate and 1.497 g of sodium tert-butoxide in 90 ml of dioxane is admixed with stirring with the solution of 3.34 g of N-(2-bromo-5-methylphenyl)-N-(3-methoxypropyl)isobutyramide in 10 ml of dioxane and stirred at 50° C. over 22 hours. The reaction mixture is cooled, poured onto ice-water (250 ml) and extracted with tert-butyl methyl ether (2×250 ml). The organic phases are washed successively with water (2×250 ml) and brine (1×250 ml), dried over sodium sulphate, filtered and concentrated by evaporation. The title compound is obtained as a slightly yellowish oil from the residue by means of flash chromatography (SiO$_2$ 60F). Rf=0.26 (1:1 EtOAc-heptane); Rt=16.60 (II).

d) N-(2-Bromo-5-methylphenyl)-N-(3-methoxypropyl)isobutyramide

Analogously to Example 8c, 16.50 g of N-(2-bromo-5-methylphenyl)isobutyramide and 8.59 ml of 1-chloro-3-methoxypropane are reacted. The title compound is obtained as a slightly yellowish oil. Rf=0.13 (1:1 EtOAc-heptane); Rt=18.54 (II).

e) N-(2-Bromo-5-methylphenyl)isobutyramide

Analogously to Example 18e, 12.20 g of 2-bromo-5-methylaniline are reacted with 7.77 ml of isobutyryl chloride. The title compound is obtained as a white solid. Rt=4.29.

EXAMPLE 59

6-(4-{4-[3-(2-Methoxybenzyloxy)propoxy]phenyl}piperidin-3-yloxymethyl)-1'-(3-methoxypropyl)spiro[cyclopropane-1,3']-2,3-dihydro-1H-indole The solution of 0.069 g of 6-(4-{4-[3-(2-methoxybenzyloxy)propoxy]phenyl}piperidin-3-yloxymethyl)-1'-(3-methoxypropyl)spiro[cyclopropane-1,3'-[3H]indol]-2'(1'H)one (Example 18) in 1.0 ml of toluene is admixed with 0.080 ml of sodium dihydridobis(2-methoxyethoxy)aluminate solution (3.5 M in toluene) and subsequently stirred at reflux over 1 hour. The reaction mixture is cooled, poured cautiously onto 1N NaOH (15 ml) and extracted with tert-butyl methyl ether (2×15 ml). The organic phases are washed successively with water (1×15 ml) and brine (1×15 ml), dried over sodium sulphate, filtered and concentrated by evaporation. The title compound is obtained as a slightly yellowish oil from the residue by means of flash chromatography (SiO$_2$ 60F). Rf=0.19 (200:20:1 dichloromethane-methanol-conc. ammonia); Rt=4.46.

EXAMPLE 60

6-(4-{4-[3-(2-Methoxybenzyloxy)propoxy]phenyl}piperidin-3-yloxymethyl)-1-(3-methoxypropyl)-3,3-dimethyl-2,3-dihydro-1H-indole Analogously to Example 59, 0.250 g of tert-butyl 4-{4-[3-(2-methoxybenzyloxy)propoxy]phenyl}3-[1-(3-methoxypropyl)-3,3-dimethyl-2,3-dihydro-1H-indol-6-ylmethoxy]piperidine-1-carboxylate (Example 58) is used to prepare the title compound.

EXAMPLE 61

4-Methoxy-N-[2-(4-{4-[3-(2-methoxybenzyloxy)propoxy]phenyl}piperidin-3-yloxymethyl)phenyl]-N-methylbutyramide Analogously to Method A, 0.143 g of tert-butyl 4-{4-[3-(2-methoxybenzyloxy)propoxy]phenyl}-3-{2-[(4-methoxybutyryl)methylamino]benzyloxy}piperidine-1-carboxylate is used to prepare the title compound.

The starting material is prepared as follows:

a) tert-Butyl 4-{4-[3-(2-methoxybenzyloxy)propoxy]phenyl}-3-{2-[(4-methoxybutyryl)methylamino]benzyloxy}piperidine-1-carboxylate Analogously to Example 116a, tert-butyl 4-{4-[3-(2-methoxybenzyloxy)propoxy]phenyl}-3-[2-(4-methoxybutyrylamino)benzyloxy]piperidine-1-carboxylate (Example 57a) is used to obtain the title compound as a yellow oil. Rf=0.19 (2:1 EtOAc-heptane); Rt=27.71 (II).

EXAMPLE 62

2-(4-{4-[3-(2-Methoxybenzyloxy)propoxy]phenyl}piperidin-3-yloxy)-N-(3-methoxypropyl)-N-phenylacetamide Analogously to Method A, 0.297 g of tert-butyl 4-{4-[3-(2-methoxybenzyloxy)propoxy]phenyl}-3-{[(3-methoxypropyl)phenylcarbamoyl]methoxy}piperidine-1-carboxylate is used to prepare the title compound.

The starting materials are prepared as follows:

a) tert-Butyl 4-{4-[3-(2-methoxybenzyloxy)propoxy]phenyl}-3-{[(3-methoxypropyl)phenylcarbamoyl]methoxy}piperidine-1-carboxylate Analogously to Example 2c, 0.50 g of tert-butyl 4-{4-[3-(2-methoxybenzyloxy)propoxy]phenyl}-3-phenylcarbamoylmethoxypiperidine-1-carboxylate is reacted. The title compound is obtained as a colourless oil. Rf=0.17 (1:1 EtOAc-heptane); Rt=5.83.

b) tert-Butyl 4-{4-[3-(2-methoxybenzyloxy)propoxy]phenyl}-3-phenylcarbamoylmethoxypiperidine-1-carboxylate Analogously to Example 3a, 3.06 g of tert-butyl 3-carboxymethoxy-4-{4-[3-(2-methoxybenzyloxy)propoxy]phenyl}piperidine-1-carboxylate (Example 34b) and 0.63 ml of aniline are reacted. The title compound is obtained as a colourless oil. Rf=0.50 (1:1 EtOAc-heptane); Rt=5.89.

EXAMPLE 63

N-{2-[2-(4-{4-[3-(2-Methoxybenzyloxy)propoxy]phenyl}piperidin-3-yloxymethyl)benzofuran-7-yl]ethyl}acetamide Analogously to Method A, 0.401 g of tert-butyl 3-[7-(2-acetylaminoethyl)benzofuran-2-ylmethoxy]-4-{4-[3-(2-methoxybenzyloxy)propoxy]phenyl}piperidine-1-carboxylate is used to prepare the title compound.

The starting materials are prepared as follows:

a) tert-Butyl 3-[7-(2-acetylaminoethyl)benzofuran-2-ylmethoxy]-4-{4-[3-(2-methoxybenzyloxy)propoxy]phenyl}piperidine-1-carboxylate Analogously to Method D, 1.18 g of tert-butyl 3-hydroxy-4-{4-[3-(2-methoxybenzyloxy)propoxy]phenyl}piperidine-1-carboxylate and 0.64 g of N-[2-(2-chloromethylbenzofuran-7-yl)ethyl]acetamide are reacted. The title compound is obtained as a yellow oil. Rf=0.12 (3:1 EtOAc-heptane); Rt=5.65.

b) N-[2-(2-Chloromethylbenzofuran-7-yl)ethyl]acetamide

Analogously to Method E, 1.15 g of N-[2-(2-hydroxymethylbenzofuran-7-yl)ethyl]acetamide are reacted. The title compound is obtained as a white solid. Rf=0.25 (3:1 EtOAc-heptane); Rt=3.59.

c) N-[2-(2-Hydroxymethylbenzofuran-7-yl)ethyl]acetamide

A solution of 1.41 g of methyl 7-(2-acetylaminoethyl)benzofuran-2-carboxylate in 40 ml of tetrahydrofuran is admixed at 0° C. with 0.30 g of lithium borohydride. The reaction mixture is stirred at room temperature over 4 hours and then admixed slowly with 20 ml of 2N HCl. The mixture is concentrated by evaporation. The residue is taken up in methanol (2×) and once more concentrated by evaporation. The title compound is obtained as an orange oil from the residue by means of flash chromatography ($SiO_2$ 60F). Rf=0.47 (9:1 dichloromethane-methanol); Rt=2.67.

d) Methyl 7-(2-acetylaminoethyl)benzofuran-2-carboxylate

A suspension of 1.07 g of sodium acetate, 2.00 g of methyl 7-cyanomethylbenzofuran-2-carboxylate in 10.4 ml of acetic anhydride is hydrogenated in the presence of 0.22 g of Raney nickel at 50° C. over 5 hours. The reaction mixture is clarified by filtration and the filtrate is concentrated by evaporation. The residue is dissolved in ethyl acetate, washed with saturated aqueous sodium hydrogencarbonate solution, water and brine, dried over sodium sulphate and concentrated by evaporation. The title compound is obtained as a white solid from the residue by means of flash chromatography ($SiO_2$ 60F). Rf=0.20 (6:1 EtOAc-heptane); Rt=3.23.

e) Methyl 7-cyanomethylbenzofuran-2-carboxylate

A solution of 11.92 g of methyl 7-bromomethylbenzofuran-2-carboxylate and 5.57 g of sodium cyanide in 150 ml of dimethyl sulphoxide is stirred at room temperature over 1 hour. The reaction mixture is poured onto water and extracted with ethyl acetate (3×). The combined organic phases are washed with water and brine, dried over sodium sulphate and concentrated by evaporation. The title compound is obtained as a white solid from the residue by means of flash chromatography ($SiO_2$ 60F). Rf=0.23 (dichloromethane); Rt=3.86.

f) Methyl 7-bromomethylbenzofuran-2-carboxylate

A solution of 7.38 g of methyl 7-methylbenzofuran-2-carboxylate in 300 ml of carbon tetrachloride is admixed at 70° C. with 6.96 g of N-bromosuccinimide and 1.42 g of dibenzoyl peroxide, heated to reflux with stirring and kept at reflux for 2 hours (succinimide crystallizes out). The reaction mixture is cooled and clarified by filtration, and the filtrate is concentrated by evaporation. The title compound is obtained as a red-orange oil from the residue by means of flash chromatography ($SiO_2$ 60F). Rf=0.60 (dichloromethane); Rt=17.83 (II).

g) Methyl 7-methylbenzofuran-2-carboxylate

A solution of 4.32 g of 7-methylbenzofuran-2-carboxylic acid in 150 ml of methanol and 1 ml of conc. $H_2SO_4$ is stirred at reflux over 9 hours. The reaction mixture is cooled and concentrated by evaporation. The residue is dissolved in diethyl ether and washed with water, saturated aqueous sodium hydrogencarbonate solution and brine, dried over sodium sulphate and concentrated by evaporation. The crude title compound is obtained as a red-brown oil from the residue. Rf=0.32 (1:6 EtOAc-heptane); Rt=4.51.

EXAMPLE 64

Methyl (2-{2-[2-(4-{4-[3-(2-methoxybenzyloxy)propoxy]phenyl}piperidin-3-yloxy)ethoxy]phenyl}ethyl)carbamate Analogously to Method A, 0.165 g of tert-butyl 4-{4-[3-(2-methoxybenzyloxy)propoxy]phenyl}-3-{2-[2-(2-methoxycarbonylaminoethyl)phenoxy]ethoxy}piperidine-1-carboxylate is used to prepare the title compound.

The starting material is prepared as follows:

a) tert-Butyl 4-{4-[3-(2-methoxybenzyloxy)propoxy]phenyl}-3-{2-[2-(2-methoxycarbonylaminoethyl)phenoxy]ethoxy}piperidine-1-carboxylate A solution of 0.25 g of tert-butyl 3-{2-[2-(2-aminoethyl)phenoxy]ethoxy}-4-{4-[3-(2-methoxybenzyloxy)propoxy]phenyl}piperidine-1-carboxylate (Example 56b) in 13 ml of dichloromethane and 0.12 ml of triethylamine is admixed at room temperature with a solution of 0.034 ml of methyl chloroformate in 1 ml of dichloromethane and stirred at room temperature over 2 hours. The reaction mixture is diluted with dichloromethane, washed with 1M potassium bisulphate solution (2×), dried over sodium sulphate and concentrated by evaporation. The title compound is obtained as a colourless oil from the residue by means of flash chromatography ($SiO_2$ 60F). Rf=0.15 (1:2 EtOAc-heptane); Rt=5.95.

EXAMPLE 65

4-(4-{4-[3-(2-Methoxybenzyloxy)propoxy]phenyl}piperidin-3-yloxymethyl)-2-(3-methoxypropoxy)benzoic acid The solution of 0.025 g of methyl 4-(4-{4-[3-(2-methoxybenzyloxy)propoxy]phenyl}piperidin-3-yloxymethyl)-2-(3-methoxypropoxy)benzoic acid (Example 29) in 0.200 ml of methanol is admixed with 0.200 ml of 1M NaOH and stirred at 65° C. over 1 hour. The reaction mixture is cooled, admixed with 0.100 ml of 2M HCl and extracted with ethyl acetate (3×2 ml). The organic phases are concentrated by evaporation. The title compound is obtained as a slightly yellowish oil from the residue by means of flash chromatography ($SiO_2$ 60F). Rf=0.19 (750:270:50:5 dichloromethane-methanol-water-AcOH); Rt=4.08.

EXAMPLE 66

(3-{2-[2-(4-{4-[3-(2-Methoxybenzyloxy)propoxy]phenyl}piperidin-3-yloxy)ethoxy]phenyl}-propyl)dimethylamine Analogously to Method A, 0.154 g of tert-butyl 3-{2-[2-(3-dimethylaminopropyl)phenoxy]ethoxy}-4-{4-[3-(2-methoxybenzyloxy)propoxy]phenyl}piperidine-1-carboxylate is used to prepare the title compound.

The starting material is prepared as follows:

a) tert-Butyl 3-{2-[2-(3-dimethylaminopropyl)phenoxy]ethoxy}-4-{4-[3-(2-methoxybenzyloxy)propoxy]phenyl}piperidine-1-carboxylate A solution of 0.40 g of tert-butyl 4-{4-[3-(2-methoxybenzyloxy)propoxy]phenyl}-3-(2-{2-[2-(toluene-4-sulphonyloxy)ethyl]phenoxy}ethoxy)piperidine-1-carboxylate (Example 26b), 0.82 g of dimethylamine hydrochloride and 1.39 ml of triethylamine in 4 ml of N,N-dimethylformamide is stirred at 65° C. over 16 hours. The reaction mixture is cooled to room temperature, diluted with tert-butyl methyl ether, washed with 1N HCl (2×) and 0.5N NaOH, dried over sodium sulphate and concentrated by evaporation. The title compound is obtained as a colourless oil from the residue by means of flash chromatography ($SiO_2$ 60F). Rf=0.33 (1:2 EtOAc-heptane); Rt=5.47.

EXAMPLE 67

4-(4-{4-[3-(2-Methoxybenzyloxy)propoxy]phenyl}piperidin-3-yloxymethyl)-2-(3-methoxypropoxy)benzonitrile Analogously to Method A, 0.036 g of tert-butyl 3-[4-cyano-3-(3-methoxypropoxy)benzyloxy]-4-{4-[3-(2-methoxybenzyloxy)propoxy]phenyl}piperidine-1-carboxylate is used to prepare the title compound.

The starting materials are prepared as follows:

a) tert-Butyl 3-[4-cyano-3-(3-methoxypropoxy)benzyloxy]-4-{4-[3-(2-methoxybenzyloxy)propoxy]phenyl}piperidine-1-carboxylate The mixture, prepared under argon, of 0.280 g of tert-butyl 3-[4-chloro-3-(3-methoxypropoxy)benzyloxy]-4-{4-[3-(2-methoxybenzyloxy)propoxy]phenyl}piperidine-1-carboxylate (Example 31a), 0.080 g of sodium cyanide and 0.005 ml of 15-crown-5 in 2 ml of toluene is initially charged at room temperature with stirring and admixed with 0.75 ml of Ni-catalyst solution (preparation described below). The reaction mixture is stirred at 80° C. for 24 hours and then admixed with a further 0.75 ml of Ni catalyst solution. The reaction mixture is stirred at 80° C. over a further 24 hours and then admixed once more with 0.75 ml of Ni catalyst solution. After stirring for a further 24 hours, the mixture is cooled, admixed with water (30 ml) and extracted with ethyl acetate (2×30 ml). The organic phases are washed with brine (1×30 ml), dried over sodium sulphate, filtered and concentrated by evaporation. The title compound is obtained as a colourless oil from the residue by means of flash chromatography ($SiO_2$ 60F). Rf=0.38 (2:1 EtOAc-heptane); Rt=6.10.

of the Catalyst Solution (in a 10 ml Schlenk Flask):

The stirred mixture of 21 mg of nickel acetyl acetonate and 108 mg of triphenylphosphine is admixed under argon with 2.0 ml of toluene and cooled to 0° C. By means of a syringe, 0.13 ml of triethylaluminum (1.8 M in toluene) is added dropwise. Subsequently, the mixture is stirred at room temperature over a further 30 minutes. This provides the catalyst solution used above.

EXAMPLE 68

3-{2-[2-(3-Methanesulphonylpropyl)phenoxy]ethoxy}-4-{4-[3-(2-methoxybenzyloxy)propoxy]phenyl}piperidine Analogously to Method A, 0.25 g of tert-butyl 3-{2-[2-(3-methanesulphonylpropyl)phenoxy]ethoxy}-4-{4-[3-(2-methoxybenzyloxy)propoxy]phenyl}piperidine-1-carboxylate is used to prepare the title compound.

The starting materials are prepared as follows:

a) tert-Butyl 3-{2-[2-(3-methanesulphonylpropyl)phenoxy]ethoxy}-4-{4-[3-(2-methoxybenzyloxy)propoxy]phenyl}piperidine-1-carboxylate A solution of 0.41 g of tert-butyl 4-{4-[3-(2-methoxybenzyloxy)propoxy]phenyl}-3-{2-[2-(3-methylsulphanylpropyl)phenoxy]ethoxy}piperidine-1-carboxylate and 0.297 g of 3-chloroperbenzoic acid (70%) in 22 ml of chloroform is stirred at room temperature over 1.5 hours. The reaction mixture is diluted with chloroform, washed with 0.5N NaOH (2×), dried over sodium sulphate and concentrated by evaporation. The title compound is obtained as a colourless oil from the residue by means of flash chromatography ($SiO_2$ 60F). Rf=0.09 (1:1.5 EtOAc-heptane); Rt=5.96.

b) tert-Butyl 4-{4-[3-(2-methoxybenzyloxy)propoxy]phenyl}-3-[2-{2-(3-methylsulphanylpropyl)phenoxy]ethoxy}piperidine-1-carboxylate A solution of 0.50 g of tert-butyl 4-{4-[3-(2-methoxybenzyloxy)propoxy]phenyl}-3-(2-{2-[2-(toluene-4-sulphonyloxy)ethyl]phenoxy}ethoxy)piperidine-1-carboxylate (Example 26b) and 0.55 g of sodium methanethiolate in 5 ml of N,N-dimethylformamide is stirred at 90° C. over 1 hour. The reaction mixture is cooled to room temperature, diluted with tert-butyl methyl ether, washed with saturated aqueous sodium bicarbonate solution, dried with sodium sulphate and concentrated by evaporation. The crude title compound is obtained as a colourless oil from the residue. Rt=6.53.

EXAMPLE 69

4-(4-{4-[3-(2-Methoxybenzyloxy)propoxy]phenyl}piperidin-3-yloxymethyl)-2-(3-methoxypropoxy)benzamide Analogously to Method B, 0.212 g of benzyl 3-[4-carbamoyl-3-(3-methoxypropoxy)benzyloxy]-4-{4-[3-(2-methoxybenzyloxy)propoxy]phenyl}piperidin-1-carboxylate is used to prepare the title compound.

The starting materials are prepared as follows:

a) Benzyl 3-[4-carbamoyl-3-(3-methoxypropoxy)benzyloxy]-4-{4-[3-(2-methoxybenzyloxy)propoxy]phenyl}piperidin-1-carboxylate The solution of 0.290 g of benzyl 3-[4-chlorocarbonyl-3-(3-methoxypropoxy)benzyloxy]-4-{4-[3-(2-methoxybenzyloxy)propoxy]phenyl}piperidine-1-carboxylate in 1.0 ml of toluene is added dropwise slowly to 2.30 ml of ammonia solution (7M in methanol, precooled to 0° C.). After 15 minutes, the reaction solution is poured onto water (20 ml) and extracted with tert-butyl methyl ether (2×20 ml). The organic phases are washed with brine (1×30 ml), dried over sodium sulphate, filtered and concentrated by evaporation. The title compound is obtained as a colourless oil from the residue by means of flash chromatography (SiO$_2$ 60F). Rf=0.06 (2:1 EtOAc-heptane); Rt=5.56.

b) Benzyl 3-[4-chlorocarbonyl-3-(3-methoxypropoxy)benzyloxy]-4-{4-[3-(2-methoxybenzyloxy)propoxy]phenyl}piperidine-1-carboxylate The solution of 0.80 g of benzyl 3-[4-carboxy-3-(3-methoxypropoxy)benzyloxy]-4-{4-[3-(2-methoxybenzyloxy)propoxy]phenyl}piperidine-1-carboxylate in 15 ml of dichloromethane is cooled to 0° C. with stirring and admixed successively with 0.190 ml of oxalyl chloride and 0.008 ml of N,N-dimethylformamide. The reaction mixture is stirred at 0° C. over 6 hours. The reaction mixture is subsequently concentrated by evaporation at room temperature to obtain the crude title compound.

c) Benzyl 3-[4-carboxy-3-(3-methoxypropoxy)benzyloxy]-4-{4-[3-(2-methoxybenzyloxy)propoxy]phenyl}piperidine-1-carboxylate The mixture of 1.90 g of benzyl 4-{4-[3-(2-methoxybenzyloxy)propoxy]phenyl}-3-[4-methoxycarbonyl-3-(3-methoxypropoxy)benzyloxy]piperidine-1-carboxylate (Example 29a) in 15 ml of methanol and 5.0 ml of 1N NaOH is stirred at reflux over 2 hours. The reaction mixture is cooled, admixed with water (100 ml) and 2N HCl (3.0 ml), and extracted with tert-butyl methyl ether (2×100 ml). The organic phases are dried with sodium sulphate, filtered, concentrated by evaporation. This gives the crude title compound as a yellowish oil. Rt=5.72.

EXAMPLE 70

4-(4-{4-[3-(2-Methoxybenzyloxy)propoxy]phenyl}piperidin-3-yloxymethyl)-2-(3-methoxypropoxy)-N-methylbenzamide Analogously to Method B, 0.170 g of benzyl 4-{4-[3-(2-methoxybenzyloxy)propoxy]phenyl}-3-[3-(3-methoxypropoxy)-4-methylcarbamoylbenzyloxy]piperidine-1-carboxylate is used to prepare the title compound.

The starting material is prepared as follows:

a) Benzyl 4-{4-[3-(2-methoxybenzyloxy)propoxy]phenyl}-3-[3-(3-methoxypropoxy)-4-methylcarbamoylbenzyloxy]piperidine-1-carboxylate The solution of 0.290 g of benzyl 3-[4-chlorocarbonyl-3-(3-methoxypropoxy)benzyloxy]-4-{4-[3-(2-methoxybenzyloxy)propoxy]phenyl}piperidine-1-carboxylate (Example 69b) in 1.0 ml of toluene is slowly added dropwise to 1.5 ml of methylamine solution (approx. 10M in ethanol, precooled to 0° C.). After 15 minutes, the reaction solution is poured onto water (20 ml) and extracted with tert-butyl methyl ether (2×20 ml). The organic phases are washed with brine (1×30 ml), dried over sodium sulphate, filtered and concentrated by evaporation. The title compound is obtained as a colourless oil from the residue by means of flash chromatography (SiO$_2$ 60F). Rf=0.11 (2:1 EtOAc-heptane); Rt=5.72.

EXAMPLE 71

4-(4-{4-[3-(2-Methoxybenzyloxy)propoxy]phenyl}piperidin-3-yloxymethyl)-2-(3-methoxypropoxy)-N,N-dimethylbenzamide Analogously to Method B, 0.215 g of benzyl 3-[4-dimethylcarbamoyl-3-(3-methoxypropoxy)benzyloxy]-4-{4-[3-(2-methoxybenzyloxy)propoxy]phenyl}piperidine-1-carboxylate is used to prepare the title compound.

The starting material is prepared as follows:

a) Benzyl 3-[4-dimethylcarbamoyl-3-(3-methoxypropoxy)benzyloxy]-4-{4-[3-(2-methoxybenzyloxy)propoxy]phenyl}piperidine-1-carboxylate The solution of 0.290 g of benzyl 3-[4-chlorocarbonyl-3-(3-methoxypropoxy)benzyloxy]-4-{4-[3-(2-methoxybenzyloxy)propoxy]phenyl}piperidine-1-carboxylate (Example 69b) in 1.0 ml of toluene is slowly added dropwise to 2.4 ml of dimethylamine solution (5.6M in ethanol, precooled to 0° C.). After 15 minutes, the reaction solution is poured onto water (20 ml) and extracted with tert-butyl methyl ether (2×20 ml). The organic phases are washed with brine (1×30 ml), dried over sodium sulphate, filtered and concentrated by evaporation. The title compound is obtained as a colourless oil from the residue by means of flash chromatography (SiO$_2$ 60F). Rf=0.06 (2:1 EtOAc-heptane); Rt=5.67.

EXAMPLE 72

3-{2-[2-(4-{4-[3-(2-Methoxybenzyloxy)propoxy]phenyl}piperidin-3-yloxy)ethoxy]phenyl}-N-methylpropionamide Analogously to Method A, 0.15 g of tert-butyl 4-{4-[3-(2-methoxybenzyloxy)propoxy]phenyl}-3-{2-[2-(2-methylcarbamoylethyl)phenoxy]ethoxy}piperidine-1-carboxylate is used to prepare the title compound.

The starting material is prepared as follows:

a) tert-Butyl 4-{4-[3-(2-methoxybenzyloxy)propoxy]phenyl}-3-{2-[2-(2-methylcarbamoylethyl)phenoxy]ethoxy}piperidine-1-carboxylate Analogously to Method G, 0.30 g tert-butyl 4-{4-[3-(2-methoxybenzyloxy)propoxy]phenyl}-3-[2-(toluene-4-sulphonyloxy)ethoxy]piperidine-1-carboxylate (Example 14b) and 0.16 g of 3-(2-hydroxyphenyl)-N-methylpropionamide are reacted. The title compound is obtained as a colourless oil. Rf=0.20 (3:1 EtOAc-heptane); Rt=5.61.

EXAMPLE 73

N-{2-[2(R,S)-(4-{4-[3-(2-Methoxybenzyloxy)propoxy]phenyl}piperidin-3-yloxymethyl)-2,3-dihydrobenzofuran-7-yl]ethyl}acetamide Analogously to Method A, 0.255 g of tert-butyl 3-[7-(2-acetylaminoethyl)-2,3-dihydrobenzofuran-2(R,S)-yl-methoxy]-4-{4-[3-(2-methoxybenzyloxy)propoxy]phenyl}piperidine-1-carboxylate is used to prepare the title compound.

The starting material is prepared as follows:

a) tert-Butyl 3-[7-(2-acetylaminoethyl)-2,3-dihydrobenzofuran-2(R,S)-ylmethoxy]-4-{4-[3-(2-methoxybenzyloxy)propoxy]phenyl}piperidine-1-carboxylate Analogously to Example 19a, 0.40 g of tert-butyl 3-[7-(2-acetylaminoethyl)benzofuran-2-ylmethoxy]-4-{4-[3-(2-methoxybenzyloxy)propoxy]phenyl}piperidine-1-carboxylate (Example 63a) is reacted. The title compound is obtained as a colourless oil. Rf=0.40 (EtOAc); Rt=5.73.

EXAMPLE 74

2-(4-{4-[3-(2-Methoxybenzyloxy)propoxy]phenyl}piperidin-3-yloxy)-N-[2-(3-methoxypropyl)phenyl]acetamide Analogously to Method A, 0.35 g of tert-butyl 4-{4-[3-(2-methoxybenzyloxy)propoxy]phenyl}-3-{[2-(3-methoxypropyl)phenylcarbamoyl]methoxy}piperidine-1-carboxylate is used to prepare the title compound.

The starting material is prepared as follows:

a) tert-Butyl 4-{4-[3-(2-methoxybenzyloxy)propoxy]phenyl}-3-{[2-(3-methoxypropyl)phenylcarbamoyl]methoxy}piperidine-1-carboxylate Analogously to Example 3a, 0.537 g of tert-butyl 3-carboxymethoxy-4-{4-[3-(2-methoxybenzyloxy)propoxy]phenyl}piperidine-1-carboxylate (Example 34b) and 0.207 g of 2-(3-methoxypropyl)phenylamine are reacted. The title compound is obtained as a yellow oil. Rf=0.19 (1:1 EtOAc-heptane); Rt=5.94.

EXAMPLE 75

2-(4-{4-[3-(2-Methoxybenzyloxy)propoxy]phenyl}piperidin-3-yloxy)-N-[2-(4-methoxybutyl)phenyl]acetamide Analogously to Method A, 0.29 g of tert-butyl 4-{4-[3-(2-methoxybenzyloxy)propoxy]phenyl}-3-{[2-(4-methoxybutyl)phenylcarbamoyl]methoxy}piperidine-1-carboxylate is used to prepare the title compound.

The starting materials are prepared as follows:

a) tert-Butyl 4-{4-[3-(2-methoxybenzyloxy)propoxy]phenyl}-3-{[2-(4-methoxybutyl)phenylcarbamoyl]methoxy}piperidine-1-carboxylate Analogously to Example 3a, 0.537 g of tert-butyl 3-carboxymethoxy-4-{4-[3-(2-methoxybenzyloxy)propoxy]phenyl}piperidine-1-carboxylate (Example 34b) and 0.296 g of 2-(4-methoxybutyl)phenylamine are reacted. The title compound is obtained as a yellow oil. Rf=0.27 (1:1 EtOAc-heptane); Rt=5.98.

b) 2-(4-Methoxybutyl)phenylamine

Analogously to Example 34c, 0.995 g of 1-(4-methoxybut-1-ynyl)-2-nitrobenzene is reacted. The title compound is obtained as a yellow oil. Rf=0.26 (1:1 EtOAc-heptane); Rt=2.57.

c) 1-(4-Methoxybut-1-ynyl)-2-nitrobenzene

A solution of 2.9 g of 4-(2-nitrophenyl)but-3-yn-1-ol in 750 ml of acetonitrile is admixed at room temperature with 17.5 g of silver oxide and 9.4 ml of methyl iodide and stirred at 50° C. over 70 hours. The reaction mixture is clarified by filtration and the filtrate is concentrated by evaporation. The title compound is obtained as a yellow oil from the residue by means of flash chromatography (SiO$_2$ 60F). Rf=0.34 (1:2 EtOAc-heptane); Rt=4.17.

EXAMPLE 76

N-{2-[6-(4-{4-[3-(2-Methoxybenzyloxy)propoxy]phenyl}piperidin-3-yloxymethyl)-3-methylindol-1-yl]ethyl}acetamide Analogously to Example 21, 0.165 g of benzyl 3-[1-(2-acetylaminoethyl)-7-bromo-3-methyl-1H-indol-6-ylmethoxy]-4-{4-[3-(2-methoxybenzyloxy)propoxy]phenyl}piperidine-1-carboxylate is used to prepare the title compound.

The starting materials are prepared as follows:

a) Benzyl 3-[1-(2-acetylaminoethyl)-7-bromo-3-methyl-1H-indol-6-ylmethoxy]-4-{4-[3-(2-methoxybenzyloxy)propoxy]phenyl}piperidine-1-carboxylate The solution of 0.185 g of benzyl 3-[1-(2-aminoethyl)-7-bromo-3-methyl-1H-indol-6-ylmethoxy]-4-{4-[3-(2-methoxybenzyloxy)propoxy]phenyl}piperidine-1-carboxylate in 1.1 ml of dichloromethane is admixed successively with 0.50 ml of pyridine and 0.21 ml of acetic anhydride and stirred at room temperature for 2 hours. The reaction mixture is poured onto water (40 ml) and extracted with ethyl acetate (2×40 ml). The organic phases are washed successively with 1M sodium hydrogencarbonate solution (40 ml) and brine (40 ml), dried over sodium sulphate, filtered and concentrated by evaporation. The title compound is obtained as a white foam from the residue by means of flash chromatography (SiO$_2$ 60F). Rf=0.17 (EtOAc-heptane=4:1); Rt=5.89.

b) Benzyl 3-[1-(2-aminoethyl)-7-bromo-3-methyl-1H-indol-6-ylmethoxy]-4-{4-[3-(2-methoxybenzyloxy)propoxy]phenyl}piperidine-1-carboxylate The solution of 0.240 g of benzyl 3-(7-bromo-1-cyanomethyl-3-methyl-1H-indol-6-ylmethoxy)-4-{4-[3-(2-methoxybenzyloxy)propoxy]phenyl}piperidine-1-carboxylate in 1.5 ml of tetrahydrofuran is cooled to 0° C. with stirring and admixed with 1.22 ml of diborane (1M in tetrahydrofuran). The reaction mixture is stirred at 0° C. over 1 hour and subsequently admixed cautiously with 1.0 ml of methanol and concentrated by evaporation. The title compound is obtained as a yellow oil from the residue by means of flash chromatography (SiO$_2$ 60F). Rf=0.46 (200:20:1 dichloromethane-methanol-conc. ammonia); Rt=5.45.

c) Benzyl 3-(7-bromo-1-cyanomethyl-3-methyl-1H-indol-6-ylmethoxy)-4-{4-[3-(2-methoxybenzyloxy)propoxy]phenyl}piperidine-1-carboxylate The solution of 3.38 g of benzyl 3-(7-bromo-3-methyl-1H-indol-6-ylmethoxy)-4-{4-[3-(2-methoxybenzyloxy)propoxy]phenyl}piperidine-1-carboxylate (Example 21b) in 46 ml of DMPU is admixed with stirring at 0° C. with 0.367 g of sodium hydride dispersion (60%). The mixture is stirred at 0° C. over 30 minutes and then admixed with 0.323 ml of chloroacetonitrile and 0.172 g of tetrabutylammonium iodide. The reaction mixture is stirred at room temperature over 16 hours, poured onto 1M ammonium chloride solution and extracted with tert-butyl methyl ether (2×300 ml). The organic phases are washed successively with water (300 ml) and brine (300 ml), dried over sodium sulphate, filtered and concentrated by evaporation. The title compound is obtained as a white foam from the residue by means of flash chromatography (SiO$_2$ 60F). Rf=0.33 (1:1 EtOAc-heptane); Rt=6.10.

EXAMPLE 77

N-(2-{1-[2-(4-{4-[3-(2-Methoxybenzyloxy)propoxy]phenyl}piperidin-3-yloxy)ethyl]-1H-indol-3-yl}ethyl)acetamide Analogously to Method A, 0.265 g of tert-butyl 3-{2-[3-(2-acetylaminoethyl)indol-1-yl]ethoxy}-4-{4-[3-(2-methoxybenzyloxy)propoxy]phenyl}piperidine-1-carboxylate is used to prepare the title compound.

The starting material is prepared as follows:

a) tert-Butyl 3-{2-[3-(2-acetylaminoethyl)indol-1-yl]ethoxy}-4-{4-[3-(2-methoxybenzyloxy)propoxy]phenyl}piperidine-1-carboxylate A suspension of 0.20 g of tert-butyl 4-{4-[3-(2-methoxybenzyloxy)propoxy]phenyl}-3-[2-(toluene-4-sulphonyloxy)ethoxy]piperidine-1-carboxylate (Example 14b) and 0.067 g of N-[2-(1H-indol-3-yl)ethyl]acetamide in 7 ml of N,N-dimethylformamide is admixed at 0° C. with 0.024 g of sodium hydride dispersion (60%) and stirred at room temperature over 20 hours. The reaction mixture is poured onto saturated aqueous sodium bicarbonate solution and extracted with ethyl acetate (2×). The combined organic phases are washed with brine, dried over sodium sulphate and concentrated by evaporation. The title compound is obtained as a yellow oil from the residue by means of flash chromatography (SiO$_2$ 60F). Rf=0.35 (EtOAc); Rt=5.69.

EXAMPLE 78

2-(4-{4-[3-(2-Methoxybenzyloxy)propoxy]phenyl}piperidin-3-yloxy)-N-(4-methoxybutyl)-N-phenylacetamide Analogously to Method A, 0.38 g of tert-butyl 4-{4-[3-(2-methoxybenzyloxy)propoxy]phenyl}-3-{[(4-methoxybutyl)phenylcarbamoyl]methoxy}piperidine-1-carboxylate is used to prepare the title compound.

The starting material is prepared as follows:

a) tert-Butyl 4-{4-[3-(2-methoxybenzyloxy)propoxy]phenyl}-3-{[(4-methoxybutyl)phenylcarbamoyl]methoxy}piperidine-1-carboxylate Analogously to Example 2c, 0.49 g of tert-butyl 4-{4-[3-(2-methoxybenzyloxy)propoxy]phenyl}-3-phenylcarbamoylmethoxypiperidine-1-carboxylate (Example 62b) and 0.37 g of 1-chloro-4-methoxybutane are reacted. The title compound is obtained as a yellow oil. Rf=0.20 (1:1 EtOAc-heptane); Rt=5.89.

EXAMPLE 79

4-{4-[3-(2-Methoxybenzyloxy)propoxy]phenyl}-3-[3-(3-methoxypropoxy)-4-pyrrolidin-1-ylbenzyloxy]piperidine Analogously to Method B, 0.312 g of benzyl 4-{4-[3-(2-methoxybenzyloxy)propoxy]phenyl}-3-[3-(3-methoxypropoxy)-4-pyrrolidin-1-ylbenzyloxy]piperidine-1-carboxylate is used to prepare the title compound.

The starting materials are prepared as follows:

a) Benzyl 4-{4-[3-(2-methoxybenzyloxy)propoxy]phenyl}-3-[3-(3-methoxypropoxy)-4-pyrrolidin-1-ylbenzyloxy]piperidine-1-carboxylate The mixture of 0.019 g of 2-(di-t-butylphosphino)biphenyl, 0.005 g of palladium(II) acetate and 0.134 g of sodium tert-butoxide is admixed under argon with the solution of 0.831 g of benzyl 3-[4-bromo-3-(3-methoxypropoxy)benzyloxy]-4-{4-[3-(2-methoxybenzyloxy)propoxy]phenyl}piperidine-1-carboxylate and 0.100 ml of pyrrolidine in 7.0 ml of toluene. The reaction mixture is stirred at 90° C. over 16 hours, subsequently cooled, poured onto water (40 ml) and extracted with tert-butyl methyl ether (2×40 ml). The organic phases are washed with brine (40 ml), dried over sodium sulphate, filtered and concentrated by evaporation. The title compound is obtained as a white foam from the residue by means of flash chromatography (SiO$_2$ 60F). Rf=0.22 (1:1 EtOAc-heptane); Rt=5.40.

b) Benzyl 3-[4-bromo-3-(3-methoxypropoxy)benzyloxy]-4-{4-[3-(2-methoxybenzyloxy)propoxy]phenyl}piperidine-1-carboxylate Analogously to Method D, 2.0 g of benzyl 3-hydroxy-4-{4-[3-(2-methoxybenzyloxy)propoxy]-phenyl}piperidine-1-carboxylate (Example 10f and 1.77 g of 1-bromo-4-bromomethyl-2-(3-methoxypropoxy)benzene are used to obtain the title compound as a slightly yellowish oil. Rf=0.34 (1:1 EtOAc-heptane); Rt=6.23.

c) 1-Bromo-4-bromomethyl-2-(3-methoxypropoxy)benzene

Analogously to Example 29b, 13.0 g of 1-bromo-2-(3-methoxypropoxy)-4-methylbenzene are used to obtain the title compound as a yellowish oil. Rf=0.26 (1:4 EtOAc-heptane); Rt=5.01.

d) 1-Bromo-2-(3-methoxypropoxy)-4-methylbenzene

Analogously to Method F, 10.0 g of 2-bromo-5-methylphenol and 11.6 g of 1-chloro-3-methoxypropane are reacted. The title compound is obtained as a slightly orange oil. Rf=0.31 (1:4 EtOAc-heptane); Rt=5.01.

EXAMPLE 80

4-[4-(4-{4-[3-(2-Methoxybenzyloxy)propoxy]phenyl}piperidin-3-yloxymethyl)-2-(3-methoxypropoxy)phenyl]morpholine Analogously to Method A, 0.082 g of tert-butyl 4-{4-[3-(2-methoxybenzyloxy)propoxy]phenyl}-3-[3-(3-methoxypropoxy)-4-morpholin-4-ylbenzyloxy]piperidine-1-carboxylate is used to prepare the title compound.

The starting material is prepared as follows:

a) tert-Butyl 4-{4-[3-(2-methoxybenzyloxy)propoxy]phenyl}-3-[3-(3-methoxypropoxy)-4-morpholin-4-ylbenzyloxy]piperidine-1-carboxylate The mixture of 0.0074 g of 2-(di-t-butylphosphino)biphenyl, 0.017 g of dipalladiumtris (dibenzylidenacetone)-chloroform complex and 0.055 g of sodium tert-butoxide is admixed under argon with the solution of 0.280 g of tert-butyl 3-[4-chloro-3-(3-methoxypropoxy)benzyloxy]-4-{4-[3-(2-methoxybenzyloxy)propoxy]phenyl}piperidine-1-carboxylate (Example 31a) and 0.043 ml of morpholine in 2.0 ml of toluene. The reaction mixture is stirred at 110° C. over 16 hours, subsequently cooled, poured onto water (20 ml) and extracted with ethyl acetate (2×20 ml). The organic phases are washed with brine (20 ml), dried over sodium sulphate, filtered and concentrated by evaporation. The title compound is obtained as a white foam from the residue by means of flash chromatography (SiO$_2$ 60F). Rf=0.23 (2:1 EtOAc-heptane); Rt=5.46.

EXAMPLE 81

N-{2-[6-(4-{4-[3-(2-Methoxybenzyloxy)propoxy]phenyl}piperidin-3-yloxymethyl)-3-methylindol-1-yl]ethyl}cyclopropanecarboxamide Analogously to Example 21, 0.170 g of benzyl 3-{7-bromo-1-[2-(cyclopropanecarbonylamino)ethyl]-3-methyl-1H-indol-6-ylmethoxy}-4-{4-[3-(2-methoxybenzyloxy)propoxy]phenyl}piperidine-1-carboxylate is used to prepare the title compound.

The starting material is prepared as follows:

a) Benzyl 3-{7-bromo-1-[2-(cyclopropanecarbonylamino)ethyl]-3-methyl-1H-indol-6-ylmethoxy}-4-{4-[3-(2-methoxybenzyloxy)propoxy]phenyl}piperidine-1-carboxylate The solution of 0.400 g of benzyl 3-[1-(2-aminoethyl)-7-bromo-3-methyl-1H-indol-6-ylmethoxy]-4-{4-[3-(2-methoxybenzyloxy)propoxy]phenyl}piperidine-1-carboxylate (Example 76b) in 2.5 ml of dichloromethane is admixed successively with 0.74 ml of pyridine and 0.43 ml of cyclopropanecarbonyl chloride, and stirred at room temperature over 30 minutes. The reaction mixture is poured onto water (50 ml) and extracted with dichloromethane (2×40 ml). The organic phases are washed successively with 1M sodium hydrogencarbonate solution (40 ml) and brine (40 ml), dried over sodium sulphate, filtered and concentrated by evaporation. The title compound is obtained as a white foam from the residue by means of flash chromatography (SiO$_2$ 60F). Rf=0.16 (1:1 EtOAc-heptane); Rt=6.02.

EXAMPLE 82

N-{2-[6-(4-{4-[3-(2-Methoxybenzyloxy)propoxy]phenyl}piperidin-3-yloxymethyl)-3-methylindol-1-yl]ethyl}propionamide Analogously to Example 21, 0.110 g of benzyl 3-[7-bromo-3-methyl-1-(2-propionylaminoethyl)-1H-indol-6-ylmethoxy]-4-{4-[3-(2-methoxybenzyloxy)propoxy]phenyl}piperidine-1-carboxylate is used to prepare the title compound.

The starting material is prepared as follows:

a) Benzyl 3-[7-bromo-3-methyl-1-(2-propionylaminoethyl)-1H-indol-6-ylmethoxy]-4-{4-[3-(2-methoxybenzyloxy)propoxy]phenyl}piperidine-1-carboxylate Analogously to Example 76a, 0.285 g of benzyl 3-[1-(2-aminoethyl)-7-bromo-3-methyl-1H-indol-6-ylmethoxy]-4-{4-[3-(2-methoxybenzyloxy)propoxy]phenyl}piperidine-1-carboxylate (Example 76b) and 0.051 ml of propionic anhydride are reacted. The title compound is obtained as a yellowish oil. Rf=0.11 (1:1 EtOAc-heptane); Rt=6.00.

EXAMPLE 83

N-(2-{2-[2-(4-{4-[3-(2-Methoxybenzyloxy)propoxy]phenyl}piperidin-3-yloxy)ethoxy]phenyl}ethyl)propionamide Analogously to Method A, 0.72 g of tert-butyl 4-{4-[3-(2-methoxybenzyloxy)propoxy]phenyl}-3-{2-[2-(2-propionylaminoethyl)phenoxy]ethoxy}piperidine-1-carboxylate is used to prepare the title compound.

The starting material is prepared as follows:

a) tert-Butyl 4-{4-[3-(2-methoxybenzyloxy)propoxy]phenyl}-3-{2-[2-(2-propionylaminoethyl)phenoxy]ethoxy}piperidine-1-carboxylate Analogously to Example 76a, 0.80 g of tert-butyl 3-{2-[2-(2-aminoethyl)phenoxy]ethoxy}-4-{4-[3-(2-methoxybenzyloxy)propoxy]phenyl}piperidine-1-carboxylate (Example 56b) and 0.15 ml of propionic anhydride are reacted. The title compound is obtained as a colourless oil. Rf=0.19 (1:1 EtOAc-heptane); Rt=5.76.

EXAMPLE 84

N-(2-{2-[2-(4-{4-[3-(2-methoxybenzyloxy)propoxy]phenyl}piperidin-3-yloxy)ethoxy]phenyl}ethyl)cyclopropanecarboxamide Analogously to Method A, 0.56 g of tert-butyl 3-(2-{2-[2-(cyclopropanecarbonylamino)ethyl]-phenoxy}ethoxy)-4-{4-[3-(2-methoxybenzyloxy)propoxy]phenyl}piperidine-1-carboxylate is used to prepare the title compound.

The starting material is prepared as follows:

a) tert-Butyl 3-(2-{2-[2-(cyclopropanecarbonylamino)ethyl]phenoxy}ethoxy)-4-{4-[3-(2-methoxybenzyloxy)propoxy]phenyl}piperidine-1-carboxylate Analogously to Example 81a, 0.80 g of tert-butyl 3-{2-[2-(2-aminoethyl)phenoxy]ethoxy}-4-{4-[3-(2-methoxybenzyloxy)propoxy]phenyl}piperidine-1-carboxylate (Example 56b) is reacted. The title compound is obtained as a colourless oil. Rf=0.29 (1:1 EtOAc-heptane); Rt=5.82.

EXAMPLE 85

1-(2-{2-[2-(4-{4-[3-(2-Methoxybenzyloxy)propoxy]phenyl}piperidin-3-yloxy)ethoxy]phenyl}ethyl)-3-methylurea Analogously to Method A, 0.37 g of tert-butyl 4-{4-[3-(2-methoxybenzyloxy)propoxy]phenyl}-3-(2-{2-[2-(3-methylureido)ethyl]phenoxy}ethoxy)piperidine-1-carboxylate is used to prepare the title compound.

The starting material is prepared as follows:

a) tert-Butyl 4-{4-[3-(2-methoxybenzyloxy)propoxy]phenyl}-3-(2-{2-[2-(3-methylureido)ethyl]phenoxy}ethoxy)piperidine-1-carboxylate Analogously to Example 99a, 0.50 g of tert-butyl 3-{2-[2-(2-aminoethyl)phenoxy]ethoxy}-4-{4-[3-(2-methoxybenzyloxy)propoxy]phenyl}piperidine-1-carboxylate (Example 56b) is reacted. The title compound is obtained as a colourless oil. Rf=0.16 (4:1 EtOAc-heptane); Rt=5.53.

EXAMPLE 86

7-(4-{4-[3-(2,6-Dimethoxyphenoxy)propoxy]phenyl}piperidin-3-yloxymethyl)-1-(3-methoxypropyl)-3,4-dihydro-1H-quinolin-2-one Analogously to Method A, 0.120 g of tert-butyl 4-{4-[3-(2,6-dimethoxyphenoxy)propoxy]phenyl}-3-[1-(3-methoxypropyl)-2-oxo-1,2,3,4-tetrahydroquinolin-7-ylmethoxy]piperidine-1-carboxylate is used to prepare the title compound.

The starting material is prepared as follows:

a) tert-Butyl 4-{4-[3-(2,6-dimethoxyphenoxy)propoxy]phenyl}-3-[1-(3-methoxypropyl)-2-oxo-1,2,3,4-tetrahydroquinolin-7-ylmethoxy]piperidine-1-carboxylate Analogously to Method I, 0.100 g of tert-butyl 4-(4-hydroxyphenyl)-3-[1-(3-methoxypropyl)-2-oxo-1,2,3,4-tetrahydroquinolin-7-ylmethoxy]piperidine-1-carboxylate (Example 44d) and 0.067 g of 2-(3-bromopropoxy)-1,3-dimethoxybenzene are used to prepare the title compound. Rf=0.20 (2:1 EtOAc-heptane); Rt=5.83.

EXAMPLE 87

7-(4-{4-[4-(2,6-Dimethoxyphenoxy)butoxy]phenyl}piperidin-3-yloxymethyl)-1-(3-methoxypropyl)-3,4-dihydro-1H-quinolin-2-one Analogously to Method A, 0.098 g of tert-butyl 4-{4-[4-(2,6-dimethoxyphenoxy)butoxy]phenyl}-3-[1-(3-methoxypropyl)-2-oxo-1,2,3,4-tetrahydroquinolin-7-ylmethoxy]piperidine-1-carboxylate is used to prepare the title compound.

The starting material is prepared as follows:

a) tert-Butyl 4-{4-[4-(2,6-dimethoxyphenoxy)butoxy]phenyl}-3-[1-(3-methoxypropyl)-2-oxo-1,2,3,4-tetrahydroquinolin-7-ylmethoxy]piperidine-1-carboxylate Analogously to Method I, 0.100 g of tert-butyl 4-(4-hydroxyphenyl)-3-[1-(3-methoxypropyl)-2-oxo-1,2,3,4-tetrahydroquinolin-7-ylmethoxy]piperidine-1-carboxylate (Example 44d) and 0.066 g of 2-(4-bromobutoxy)-1,3-dimethoxybenzene are used to prepare the title compound. Rf=0.22 (2:1 EtOAc-heptane); Rt=5.73.

EXAMPLE 88

7-(4-{4-[3-(2-Chlorophenoxy)propoxy]phenyl}piperidin-3-yloxymethyl)-1-(3-methoxypropyl)-3,4-dihydro-1H-quinolin-2-one Analogously to Method A, 0.144 g of tert-butyl 4-{4-[3-(2-chlorophenoxy)propoxy]phenyl}-3-[1-(3-methoxypropyl)-2-oxo-1,2,3,4-tetrahydroquinolin-7-ylmethoxy]piperidine-1-carboxylate is used to prepare the title compound.

The starting material is prepared as follows:

a) tert-Butyl 4-{4-[3-(2-chlorophenoxy)propoxy]phenyl}-3-[1-(3-methoxypropyl)-2-oxo-1,2,3,4-tetrahydroquinolin-7-ylmethoxy]piperidine-1-carboxylate Analogously to Method I, 0.100 g of tert-butyl 4-(4-hydroxyphenyl)-3-[1-(3-methoxypropyl)-2-oxo-1,2,3,4-tetrahydroquinolin-7-ylmethoxy]piperidine-1-carboxylate (Example 44d) and 0.062 g of 1-(3-bromopropoxy)-2-chlorobenzene are used to prepare the title compound. Rf=0.27 (2:1 EtOAc-heptane); Rt=6.07.

EXAMPLE 89

2-[3-(4-[3-{1-(3-Methoxypropyl)-2-oxo-1,2,3,4-tetrahydroquinolin-7-ylmethoxy]piperidin-4-yl}phenoxy)propoxy]benzonitrile Analogously to Method A, 0.130 g of tert-butyl 4-{4-[3-(2-cyanophenoxy)propoxy]phenyl}-3-[1-(3-methoxypropyl)-2-oxo-1,2,3,4-tetrahydroquinolin-7-ylmethoxy]piperidine-1-carboxylate is used to prepare the title compound.

The starting material is prepared as follows:

a) tert-Butyl 4-{4-[3-(2-cyanophenoxy)propoxy]phenyl}-3-[1-(3-methoxypropyl)-2-oxo-1,2,3,4-tetrahydroquinolin-7-ylmethoxy]piperidine-1-carboxylate Analogously to Method I, 0.100 g of tert-butyl 4-(4-hydroxyphenyl)-3-[1-(3-methoxypropyl)-2-oxo-1,2,3,4-tetrahydroquinolin-7-ylmethoxy]piperidine-1-carboxylate (Example 44d) and 0.057 g of 2-(3-bromopropoxy)benzonitrile are used to prepare the title compound. Rf=0.18 (2:1 EtOAc-heptane); Rt=5.58.

EXAMPLE 90

7-(4-{4-[4-(2-Chlorophenoxy)butoxy]phenyl}piperidin-3-yloxymethyl)-1-(3-methoxypropyl)-3,4-dihydro-1H-quinolin-2-one Analogously to Method A, 0.130 g of tert-butyl 4-{4-[4-(2-chlorophenoxy)butoxy]phenyl}-3-[1-(3-methoxypropyl)-2-oxo-1,2,3,4-tetrahydroquinolin-7-ylmethoxy]piperidine-1-carboxylate is used to prepare the title compound.

The starting material is prepared as follows:

a) tert-Butyl 4-{4-[4-(2-chlorophenoxy)butoxy]phenyl}-3-[1-(3-methoxypropyl)-2-oxo-1,2,3,4-tetrahydroquinolin-7-ylmethoxy]piperidine-1-carboxylate Analogously to Method I, 0.100 g of tert-butyl 4-(4-hydroxyphenyl)-3-[1-(3-methoxypropyl)-2-oxo-1,2,3,4-tetrahydroquinolin-7-ylmethoxy]piperidine-1-carboxylate (Example 44d) and 0.060 g of 1-(4-bromobutoxy)-2-chlorobenzene are used to prepare the title compound. Rf=0.28 (2:1 EtOAc-heptane); Rt=6.17.

EXAMPLE 91

7-(4-{4-[3-(2-Methoxy-6-methylphenoxy)propoxy]phenyl}piperidin-3-(3-methoxypropyl)-3,4-dihydro-1H-quinolin-2-one Analogously to Method A, 0.150 g of tert-butyl 4-{4-[3-(2-methoxy-6-methylphenoxy)propoxy]phenyl}-3-[1-(3-methoxypropyl)-2-oxo-1,2,3,4-tetrahydroquinolin-7-ylmethoxy]piperidine-1-carboxylate is used to prepare the title compound.

The starting materials are prepared as follows:

a) tert-Butyl 4-{4-[3-(2-methoxy-6-methylphenoxy)propoxy]phenyl}-3-[1-(3-methoxypropyl)-2-oxo-1,2,3,4-tetrahydroquinolin-7-ylmethoxy]piperidine-1-carboxylate Analogously to Method I, 0.100 g of tert-butyl 4-(4-hydroxyphenyl)-3-[1-(3-methoxypropyl)-2-oxo-1,2,3,4-tetrahydroquinolin-7-ylmethoxy]piperidine-1-carboxylate (Example 44d) and 0.065 g of 2-(3-bromopropoxy)-1-methoxy-3-methylbenzene are used to prepare the title compound. Rf=0.26 (2:1 EtOAc-heptane); Rt=6.05.

b) 2-(3-Bromopropoxy)-1-methoxy-3-methylbenzene

The mixture of 2.50 g of 2-methoxy-6-methylphenol, 3.75 g of potassium carbonate and 18.3 ml of 1,3-dibromopropane in 50 ml of acetonitrile is stirred at reflux with stirring over 16 hours. The reaction mixture is cooled, diluted with 200 ml of water and extracted with tert-butyl methyl ether (2×200 ml). The organic phases are washed successively with water (200 ml) and brine (200 ml), dried over sodium sulphate, filtered and concentrated by evaporation. The title compound is obtained as a yellowish oil from the residue by means of flash chromatography (SiO$_2$ 60F). Rf=0.59 (1:1 EtOAc-heptane); Rt=5.10.

EXAMPLE 92

7-(4-{4-[4-(2-Methoxy-6-methylphenoxy)butoxy]phenyl}piperidin-3-yloxymethyl)-1-(3-methoxypropyl)-3,4-dihydro-1H-quinolin-2-one Analogously to Method A, 0.087 g of tert-butyl 4-{4-[4-(2-methoxy-6-methylphenoxy)butoxy]phenyl}-3-[1-(3-methoxypropyl)-2-oxo-1,2,3,4-tetrahydroquinolin-7-ylmethoxy]piperidine-1-carboxylate is used to prepare the title compound.

The starting materials are prepared as follows:

a) tert-Butyl 4-{4-[4-(2-methoxy-6-methylphenoxy)butoxy]phenyl}-3-[1-(3-methoxypropyl)-2-oxo-1,2,3,4-tetrahydroquinolin-7-ylmethoxy]piperidine-1-carboxylate Analogously to Method I, 0.100 g of tert-butyl 4-(4-hydroxyphenyl)-3-[1-(3-methoxypropyl)-2-oxo-1,2,3,4-tetrahydroquinolin-7-ylmethoxy]piperidine-1-carboxylate (Example 44d) and 0.081 g of 2-(4-bromobutoxy)-1-methoxy-3-methylbenzene are used to prepare the title compound. Rf=0.28 (2:1 EtOAc-heptane); Rt=6.15.

b) 2-(4-Bromobutoxy)-1-methoxy-3-methylbenzene

Analogously to Example 50b, 2.50 g of 2-methoxy-6-methylphenol and 2.67 ml of 1,4-dibromobutane are used to prepare the title compound. Rf=0.58 (1:1 EtOAc-heptane); Rt=5.28.

EXAMPLE 93

7-(4-{4-[4-(3-Chlorophenoxy)butoxy]phenyl}piperidin-3-yloxymethyl)-1-(3-methoxypropyl)-3,4-dihydro-1H-quinolin-2-one Analogously to Method A, 0.080 g of tert-butyl 4-{4-[4-(3-chlorophenoxy)butoxy]phenyl}-3-[1-(3-methoxypropyl)-2-oxo-1,2,3,4-tetrahydroquinolin-7-ylmethoxy]piperidine-1-carboxylate are used to prepare the title compound.

The starting material is prepared as follows:

a) tert-Butyl 4-{4-[4-(3-chlorophenoxy)butoxy]phenyl}-3-[1-(3-methoxypropyl)-2-oxo-1,2,3,4-tetrahydroquinolin-7-ylmethoxy]piperidine-1-carboxylate Analogously to Method I, 0.100 g of tert-butyl 4-(4-hydroxyphenyl)-3-[1-(3-methoxypropyl)-2-oxo-1,2,3,4-tetrahydroquinolin-7-ylmethoxy]piperidine-1-carboxylate (Example 44d) and 0.065 g of 1-(4-bromobutoxy)-3-chlorobenzene are used to prepare the title compound. Rf=0.29 (2:1 EtOAc-heptane); Rt=6.16.

EXAMPLE 94

N-{2-[6-(4-{4-[3-(2-Methoxybenzyloxy)propoxy]phenyl}piperidin-3-yloxymethyl)-3,3-dimethyl-2,3-dihydroindol-1-yl]ethyl}acetamide Analogously to Method A, 0.240 g of tert-butyl 3-[1-(2-acetylaminoethyl)-3,3-dimethyl-2,3-dihydro-1H-indol-6-ylmethoxy]-4-{4-[3-(2-methoxybenzyloxy)propoxy]phenyl}piperidine-1-carboxylate is used to prepare the title compound.

The starting materials are prepared as follows:

a) tert-Butyl 3-[1-(2-acetylaminoethyl)-3,3-dimethyl-2,3-dihydro-1H-indol-6-ylmethoxy]-4-{4-[3-(2-methoxybenzyloxy)propoxy]phenyl}piperidine-1-carboxylate The solution of 0.268 g of tert-butyl 3-[1-(2-aminoethyl)-3,3-dimethyl-2,3-dihydro-1H-indol-6-ylmethoxy]-4-{4-[3-(2-methoxybenzyloxy)propoxy]phenyl}piperidine-1-carboxylate in 0.061 ml of triethylamine and 9.0 ml of dichloromethane is cooled to 0° C. and admixed slowly with the solution of 0.033 ml of acetyl chloride in 1.0 ml of dichloromethane. The reaction solution is stirred over a further 30 minutes, poured onto ice-water (20 ml) and extracted with tert-butyl methyl ether (2×20 ml). The organic phases are washed successively with water (20 ml) and brine (20 ml), dried over sodium sulphate, filtered and concentrated by evaporation. The title compound is obtained as a yellowish oil from the residue by means of flash chromatography (SiO$_2$ 60F). Rf=0.73 (200:20:1 dichloromethane-methanol-conc. ammonia); Rt=5.82.

b) tert-Butyl 3-[1-(2-aminoethyl)-3,3-dimethyl-2,3-dihydro-1H-indol-6-ylmethoxy]-4-{4-[3-(2-methoxybenzyloxy)propoxy]phenyl}piperidine-1-carboxylate The solution of 0.347 g of tert-butyl 3-[1-(2-azidoethyl)-3,3-dimethyl-2,3-dihydro-1H-indol-6-ylmethoxy]-4-{4-[3-(2-methoxybenzyloxy)propoxy]phenyl}piperidine-1-carboxylate in 1.5 ml of tetrahydrofuran is admixed with stirring at room temperature successively with 0.32 ml of water, 1.40 ml of methanol, 0.32 ml of conc. ammonia and 0.210 g of triphenylphosphine, and stirred over 1 hour. The reaction mixture is admixed with water (40 ml) and extracted with tert-butyl methyl ether (2×40 ml). The organic phases are washed successively with water (40 ml) and brine (40 ml), dried over sodium sulphate, filtered and concentrated by evaporation. The title compound is obtained as a yellowish oil from the residue by means of flash chromatography ($SiO_2$ 60F). Rf=0.41 (200:20:1 dichloromethane-methanol-conc. ammonia); Rt=5.54.

c) tert-Butyl 3-[1-(2-azidoethyl)-3,3-dimethyl-2,3-dihydro-1H-indol-6-ylmethoxy]-4-{4-[3-(2-methoxybenzyloxy)propoxy]phenyl}piperidine-1-carboxylate The solution of 0.455 g of tert-butyl 3-{3,3-dimethyl-1-[2-(toluene-4-sulphonyloxy)ethyl]-2,3-dihydro-1H-indol-6-ylmethoxy}-4-{4-[3-(2-methoxybenzyloxy)propoxy]phenyl}piperidine-1-carboxylate in 5.0 ml of N,N-dimethylformamide is admixed with 0.286 g of sodium azide and stirred at 65° C. over 1.5 hours. The reaction mixture is cooled, admixed with water (40 ml) and extracted with tert-butyl methyl ether (2×40 ml). The organic phases are washed successively with water (40 ml) and brine (40 ml), dried over sodium sulphate, filtered and concentrated by evaporation. The title compound is obtained as a yellowish oil from the residue by means of flash chromatography ($SiO_2$ 60F). Rf=0.33 (1:2 EtOAc-heptane); Rt=6.56.

d) tert-Butyl 3-{3,3-dimethyl-1-[2-(toluene-4-sulphonyloxy)ethyl]-2,3-dihydro-1H-indol-6-ylmethoxy}-4-{4-[3-(2-methoxybenzyloxy)propoxy]phenyl}piperidine-1-carboxylate The solution of 0.457 g of tert-butyl 3-[1-(2-hydroxyethyl)-3,3-dimethyl-2,3-dihydro-1H-indol-6-ylmethoxy]-4-{4-[3-(2-methoxybenzyloxy)propoxy]phenyl}piperidine-1-carboxylate, 0.274 ml of triethylamine and 0.008 g of 4-dimethylaminopyridine in 10 ml of dichloromethane is admixed with stirring at 0° C. with 0.301 g of p-toluenesulphonyl chloride and stirred at room temperature over 18 hours. The reaction mixture is admixed with water (40 ml) and extracted with tert-butyl methyl ether (2×40 ml). The organic phases are washed successively with water (40 ml) and brine (40 ml), dried over sodium sulphate, filtered and concentrated by evaporation. The title compound is obtained as a yellowish oil from the residue by means of flash chromatography ($SiO_2$ 60F). Rf=0.42 (1:1 EtOAc-heptane); Rt=6.46.

e) tert-Butyl 3-[1-(2-hydroxyethyl)-3,3-dimethyl-2,3-dihydro-1H-indol-6-ylmethoxy]-4-{4-[3-(2-methoxybenzyloxy)propoxy]phenyl}piperidine-1-carboxylate The solution of 0.595 g of tert-butyl 3-[3,3-dimethyl-1-(2-triisopropylsilanyloxyethyl)-2,3-dihydro-1H-indol-6-ylmethoxy]-4-{4-[3-(2-methoxybenzyloxy)propoxy]phenyl}piperidine-1-carboxylate in 8.0 ml of tetrahydrofuran is admixed with tetrabutylammonium fluoride solution (1M in tetrahydrofuran) and stirred at 60° C. over 1 hour. The reaction mixture is cooled, admixed with water (15 ml) and extracted with tert-butyl methyl ether (2×15 ml). The organic phases are washed successively with water (15 ml) and brine (15 ml), dried over sodium sulphate, filtered and concentrated by evaporation. The title compound is obtained as a yellowish oil from the residue by means of flash chromatography ($SiO_2$ 60F). Rf=0.13 (1:1 EtOAc-heptane); Rt=5.72.

f) tert-Butyl 3-[3,3-dimethyl-1-(2-triisopropylsilanyloxyethyl)-2,3-dihydro-1H-indol-6-ylmethoxy]-4-{4-[3-(2-methoxybenzyloxy)propoxy]phenyl}piperidine-1-carboxylate Analogously to Example 59, 0.580 g of tert-butyl 3-[3,3-dimethyl-2-oxo-1-(2-triisopropylsilanyloxyethyl)-2,3-dihydro-1H-indol-6-ylmethoxy]-4-{4-[3-(2-methoxybenzyloxy)propoxy]phenyl}piperidine-1-carboxylate is used to obtain the title compound. Rf=0.29 (1:2 EtOAc-heptane).

g) tert-Butyl 3-[3,3-dimethyl-2-oxo-1-(2-triisopropylsilanyloxyethyl)-2,3-dihydro-1H-indol-6-ylmethoxy]-4-{4-[3-(2-methoxybenzyloxy)propoxy]phenyl}piperidine-1-carboxylate Analogously to Example 58c, 1.52 g of tert-butyl 3-{4-bromo-3-[isobutyryl-(2-triisopropylsilanyloxyethyl)amino]benzyloxy}-4-{4-[3-(2-methoxybenzyloxy)propoxy]phenyl}piperidine-1-carboxylate is used to obtain the title compound. Rf=0.38 (1:2 EtOAc-heptane). Rt=7.65.

h) tert-Butyl 3-{4-bromo-3-[isobutyryl-(2-triisopropylsilanyloxyethyl)amino]benzyloxy}-4-{4-[3-(2-methoxybenzyloxy)propoxy]phenyl}piperidine-1-carboxylate The solution of 3.50 g of tert-butyl 3-(4-bromo-3-isobutyrylaminobenzyloxy)-4-{4-[3-(2-methoxybenzyloxy)propoxy]phenyl}piperidine-1-carboxylate in 25 ml of N,N-dimethylformamide is cooled to 0° C. with stirring and admixed with sodium hydride dispersion (60%). After 30 minutes, the mixture is admixed with 1.66 g of (2-iodoethoxy)triisopropylsilane and stirred at room temperature over 16 hours. The reaction mixture is admixed with cold 1N HCl (100 ml) and extracted with tert-butyl methyl ether (2×100 ml). The organic phases are washed successively with water (100 ml) and brine (100 ml), dried over sodium sulphate, filtered and concentrated by evaporation. The title compound is obtained as a yellowish oil from the residue by means of flash chromatography ($SiO_2$ 60F). Rt=7.60.

i) tert-Butyl 3-(4-bromo-3-isobutyrylaminobenzyloxy)-4-{4-[3-(2-methoxybenzyloxy)propoxy]phenyl}piperidine-1-carboxylate Analogously to Example 18e, 4.30 g of tert-butyl 3-(3-amino-4-bromobenzyloxy)-4-{4-[3-(2-methoxybenzyloxy)propoxy]phenyl}piperidine-1-carboxylate are reacted with 0.78 ml of isobutyryl chloride. The title compound is obtained as a colourless oil. Rt=6.12.

k) tert-Butyl 3-(3-amino-4-bromobenzyloxy)-4-{4-[3-(2-methoxybenzyloxy)propoxy]phenyl}piperidine-1-carboxylate The solution of 10.8 g of tert-butyl 3-(4-bromo-3-nitrobenzyloxy)-4-{4-[3-(2-methoxybenzyloxy)propoxy]phenyl}piperidine-1-carboxylate in 250 ml of benzene is admixed with stirring at 10° C. with the solution of 4.08 g of nickel chloride hexahydrate in 150 ml of benzene. At approx. 5° C., the mixture is admixed with 2.0 g of sodium borohydride in small portions over 1 hour. The reaction mixture is stirred for a further 1 hour, poured onto water (500 ml) and extracted with tert-butyl methyl ether (2×500 ml). The organic phases are washed successively with water (500 ml) and brine (500 ml), dried over sodium sulphate, filtered and concentrated by evaporation. The title compound is obtained as a yellowish oil from the residue by means of flash chromatography (SiO$_2$ 60F). Rt=6.03.

l) tert-Butyl 3-(4-bromo-3-nitrobenzyloxy)-4-{4-[3-(2-methoxybenzyloxy)propoxy]phenyl}piperidine-1-carboxylate Analogously to Method D, 12.60 g of tert-butyl 3-hydroxy-4-{4-[3-(2-methoxybenzyloxy)propoxy]phenyl}piperidine-1-carboxylate and 1-bromo-4-bromomethyl-2-nitrobenzene are reacted. The title compound is obtained as a yellow oil. Rf=0.21 (1:2 EtOAc-heptane); Rt=27.96 (II).

EXAMPLE 95

2-(4-{4-[3-(2-Methoxybenzyloxy)propoxy]phenyl}piperidin-3-yloxy)-N-[2-(3-methoxypropyl)phenyl]-N-methylacetamide Analogously to Method A, 0.416 g of tert-butyl 4-{4-[3-(2-methoxybenzyloxy)propoxy]phenyl}-3-({[2-(3-methoxypropyl)phenyl]methylcarbamoyl}methoxy)piperidine-1-carboxylate is used to prepare the title compound.

The starting material is prepared as follows:

a) tert-Butyl 4-{4-[3-(2-methoxybenzyloxy)propoxy]phenyl}-3-({[2-(3-methoxypropyl)phenyl]methylcarbamoyl}methoxy)piperidine-1-carboxylate A solution of 0.50 g of tert-butyl 4-{4-[3-(2-methoxybenzyloxy)propoxy]phenyl}-3-{[2-(3-methoxypropyl)phenylcarbamoyl]methoxy}piperidine-1-carboxylate (Example 74a) in 7 ml of N,N-dimethylformamide is admixed at room temperature with 0.056 g of sodium hydride dispersion (60%) and stirred for 45 minutes. After 0.26 ml of methyl iodide has been added, the reaction mixture is stirred at 75° C. over 15 hours. The reaction mixture is cooled to room temperature and partitioned between tert-butyl methyl ether and brine. The organic phase is washed once more with brine, dried over sodium sulphate and concentrated by evaporation. The title compound is obtained as a yellow oil from the residue by means of flash chromatography (SiO$_2$ 60F). Rf=0.25 (2:1 EtOAc-heptane); Rt=5.84.

EXAMPLE 96

2-(4-{4-[3-(2-Methoxybenzyloxy)propoxy]phenyl}piperidin-3-yloxy)-N-[2-(4-methoxybutyl)phenyl]-N-methylacetamide Analogously to Method A, 0.395 g tert-butyl 4-{4-[3-(2-methoxybenzyloxy)propoxy]phenyl}-3-({[2-(4-methoxybutyl)phenyl]methylcarbamoyl}methoxy)piperidine-1-carboxylate is used to prepare the title compound.

The starting material is prepared as follows:

a) tert-Butyl 4-{4-[3-(2-methoxybenzyloxy)propoxy]phenyl}-3-({[2-(4-methoxybutyl)phenyl]methylcarbamoyl}methoxy)piperidine-1-carboxylate Analogously to Example 95a, 0.51 g of tert-butyl 4-{4-[3-(2-methoxybenzyloxy)propoxy]phenyl}-3-{[2-(4-methoxybutyl)phenylcarbamoyl]methoxy}piperidine-1-carboxylate (Example 75a) is reacted. The title compound is obtained as a yellow oil. Rf=0.29 (2:1 EtOAc-heptane); Rt=5.95.

EXAMPLE 97

N-[2-(2-{2-[4-(4-{2-[2-(2-Methoxyphenyl)ethoxy]ethoxy}phenyl)piperidin-3-yloxy]ethoxy}phenyl)ethyl]acetamide Analogously to Method A, 0.365 g of tert-butyl 3-{2-[2-(2-acetylaminoethyl)phenoxy]ethoxy}-4-(4-{2-[2-(2-methoxyphenyl)ethoxy]ethoxy}phenyl)piperidine-1-carboxylate is used to prepare the title compound.

The starting materials are prepared as follows:

a) tert-Butyl 3-{2-[2-(2-acetylaminoethyl)phenoxy]ethoxy}-4-(4-{2-[2-(2-methoxyphenyl)ethoxy]ethoxy}phenyl)piperidine-1-carboxylate Analogously to Method G, 0.50 g of tert-butyl 4-(4-{2-[2-(2-Methoxyphenyl)ethoxy]ethoxy}phenyl)-3-[2-(toluene-4-sulphonyloxy)ethoxy]piperidine-1-carboxylate and 0.27 g of N-[2-(2-hydroxyphenyl)ethyl]acetamide are reacted. The title compound is obtained as a colourless oil. Rf=0.45 (EtOAc); Rt=5.52.

b) tert-Butyl 4-(4-{2-[2-(2-Methoxyphenyl)ethoxy]ethoxy}phenyl)-3-[2-(toluene-4-sulphonyloxy)ethoxy]piperidine-1-carboxylate Analogously to Method H, 1.01 g of tert-butyl 3-(2-hydroxyethoxy)-4-(4-{2-[2-(2-methoxyphenyl)ethoxy]ethoxy}phenyl)piperidine-1-carboxylate are reacted. The title compound is obtained as a colourless oil. Rf=0.30 (1:2 EtOAc-heptane); Rt=5.86.

c) tert-Butyl 3-(2-hydroxyethoxy)-4-(4-{2-[2-(2-methoxyphenyl)ethoxy]ethoxy}phenyl)piperidine-1-carboxylate Analogously to Example 14c, 3.70 g of tert-butyl 3-allyloxy-4-(4-{2-[2-(2-methoxyphenyl)ethoxy]ethoxy}phenyl)piperidine-1-carboxylate are reacted. The title compound is obtained as a yellow oil. Rf=0.33 (1:1 EtOAc-heptane); Rt=5.12.

d) tert-Butyl 3-allyloxy-4-(4-{2-[2-(2-methoxyphenyl)ethoxy]ethoxy}phenyl)piperidine-1-carboxylate Analogously to Example 14d, 4.49 g of tert-butyl 3-hydroxy-4-(4-{2-[2-(2-methoxyphenyl)ethoxy]ethoxy}phenyl)piperidine-1-carboxylate are reacted. The title compound is obtained as a yellow oil. Rf=0.70 (1:1 EtOAc-heptane); Rt=5.87.

e) tert-Butyl 3-hydroxy-4-(4-{2-[2-(2-methoxyphenyl)ethoxy]ethoxy}phenyl)piperidine-1-carboxylate Analogously to Method I, 2.80 g of tert-butyl 3-hydroxy-4-(4-hydroxyphenyl)piperidine-1-carboxylate and 3.71 g of 2-[2-(2-methoxyphenyl)ethoxy]ethyl toluene-4-sulphonate (Example 45b) are reacted. The title compound is obtained as a colourless oil. Rf=0.47 (1:1 EtOAc-heptane); Rt=5.11.

EXAMPLE 98

N-{1-[2-(4-{4-[3-(2-Methoxybenzyloxy)propoxy]phenyl}piperidin-3-yloxymethyl)phenyl]pyrrolidin-3R-ylmethyl}acetamide Analogously to Method D, 0.148 g of benzyl 3-{2-[3R-(acetylaminomethyl)pyrrolidin-1-yl]benzyloxy}-4-{4-[3-(2-methoxybenzyloxy)propoxy]phenyl}piperidine-1-carboxylate is used to prepare the title compound.
The starting materials are prepared as follows:

a) Benzyl 3-{2-[3R-(acetylaminomethyl)pyrrolidin-1-yl]benzyloxy}-4-{4-[3-(2-methoxybenzyloxy)propoxy]phenyl}piperidine-1-carboxylate The solution of 0.161 g of benzyl 3-[2-(3R-cyanopyrrolidin-1-yl)benzyloxy]-4-{4-[3-(2-methoxybenzyloxy)propoxy]phenyl}piperidine-1-carboxylate in 4 ml of methanol is admixed with stirring at room temperature with 0.057 g of nickel chloride hexahydrate. The resulting solution is cooled to 0° C. and admixed with 0.30 g of sodium borohydride in small portions over 6 hours. 0.20 ml of acetic anhydride is added and the mixture is stirred at room temperature over a further 15 minutes. The reaction mixture is concentrated by evaporation and the residue is admixed with saturated sodium hydrogencarbonate solution (20 ml) and ethyl acetate (40 ml). The resulting mixture is clarified by filtration through Hyflo, and the organic phase is removed, dried over sodium sulphate, filtered and concentrated by evaporation. The title compound is obtained as a colourless oil from the residue by means of flash chromatography (SiO$_2$ 60F). Rf=0.25 (dichloromethane-methanol=97:3); Rt=4.87.

b) Benzyl 3-[2-(3R-cyanopyrrolidin-1-yl)benzyloxy]-4-{4-[3-(2-methoxybenzyloxy)propoxy]phenyl}piperidine-1-carboxylate The mixture of 0.551 g of benzyl 3-[2-(3S-methanesulphonyloxypyrrolidin-1-yl)benzyloxy]-4-{4-[3-(2-methoxybenzyloxy)propoxy]phenyl}piperidine-1-carboxylate, 0.191 g of tetrabutylammonium cyanide and 0.177 g of sodium cyanide in 5.0 ml of dimethyl sulphoxide is kept at 60° C. while stirring over 18 hours. The reaction mixture is cooled, admixed with saturated sodium hydrogencarbonate solution (40 ml) and extracted with tert-butyl methyl ether (2×40 ml). The organic phases are washed with brine (40 ml), dried over sodium sulphate, filtered and concentrated by evaporation. The crude title compound is obtained as a yellowish oil from the residue. Rt=5.77.

c) Benzyl 3-[2-(3S-methanesulphonyloxypyrrolidin-1-yl)benzyloxy]-4-{4-[3-(2-methoxybenzyloxy)propoxy]phenyl}piperidine-1-carboxylate The solution of 0.515 g of benzyl 3-[2-(3S-hydroxypyrrolidin-1-yl)benzyloxy]-4-{4-[3-(2-methoxybenzyloxy)propoxy]phenyl}piperidine-1-carboxylate and 0.16 ml of triethylamine in 5.0 ml of tetrahydrofuran is cooled to −10° C. with stirring and admixed slowly with 0.072 ml of methanesulphonyl chloride. The reaction mixture is stirred at −10° C. over 1 hour, subsequently admixed with water (20 ml) and extracted with tert-butyl methyl ether. The organic phases are washed with brine (20 ml), dried over sodium sulphate, filtered and concentrated by evaporation. The crude title compound is obtained as a brown oil from the residue. Rf=0.23 (1:2 EtOAc-heptane); Rt=5.96.

d) Benzyl 3-[2-(3S-hydroxypyrrolidin-1-yl)benzyloxy]-4-{4-[3-(2-methoxybenzyloxy)propoxy]phenyl}piperidine-1-carboxylate The mixture of 3.0 g of benzyl 3-(2-bromobenzyloxy)-4-{4-[3-(2-methoxybenzyloxy)propoxy]-phenyl}piperidine-1-carboxylate, 0.660 g of (S)-3-pyrrolidinol hydrochloride, 0.138 g of (±)-2,2'-bis(diphenylphosphine)-1,1'-binaphthyl, 1.03 g of sodium tert-butoxide and 0.112 g of dipalladiumtris(dibenzylidenacetone)-chloroform complex in 40 ml of toluene is stirred at 70° C. under argon over 48 hours. The reaction mixture is cooled, admixed with brine (20 ml) and extracted with ethyl acetate (2×40 ml). The organic phases are washed successively with 0.1M HCl (40 ml) and brine (20 ml), dried over sodium sulphate, filtered and concentrated by evaporation. The title compound is obtained as a brown oil from the residue by means of flash chromatography (SiO$_2$ 60F). Rf=0.18 (EtOAc-heptane=1:1); Rt=5.08.

e) Benzyl 3-(2-bromobenzyloxy)-4-{4-[3-(2-methoxybenzyloxy)propoxy]phenyl}piperidine-1-carboxylate Analogously to Method D, 3.0 g of benzyl 3-hydroxy-4-{4-[3-(2-methoxybenzyloxy)propoxy]-phenyl}piperidine-1-carboxylate (Example 10f) and 2-bromobenzyl bromide are reacted. The title compound is obtained as a colourless oil. Rf=0.58 (1:1 EtOAc-heptane); Rt=6.36.

EXAMPLE 99

1-{2-[6-(4-{4-[3-(2-Methoxybenzyloxy)propoxy]phenyl}piperidin-3-yloxymethyl)-3-methylindol-1-yl]ethyl}-3-methylurea Analogously to Example 21, 0.075 g of benzyl 3-{7-bromo-3-methyl-1-[2-(3-methylureido)ethyl]-1H-indol-6-ylmethoxy}-4-{4-[3-(2-methoxybenzyloxy)propoxy]phenyl}piperidine-1-carboxylate is used to prepare the title compound.
The starting material is prepared as follows:

a) Benzyl 3-{7-bromo-3-methyl-1-[2-(3-methylureido)ethyl]-1H-indol-6-ylmethoxy}-4-{4-[3-(2-methoxybenzyloxy)propoxy]phenyl}piperidine-1-carboxylate The solution of 0.270 g of benzyl 3-[1-(2-aminoethyl)-7-bromo-3-methyl-1H-indol-6-ylmethoxy]-4-{4-[3-(2-methoxybenzyloxy)propoxy]phenyl}piperidine-1-carboxylate (Example 76b) in 1.5 ml of N,N-dimethylformamide is cooled to 0° C. and admixed successively with 0.066 g of N-succinimidyl N-methyl carbamate and 0.043 ml of triethylamine. The reaction mixture is stirred at room temperature over 2 hours, subsequently poured onto water (40 ml) and extracted with dichloromethane (2×40 ml). The organic phases are washed successively with water (40 ml), 1M sodium hydrogencarbonate solution (40 ml) and brine (40 ml), dried over sodium sulphate, filtered and concentrated by evaporation. The title compound is obtained as a brown oil from the residue by means of flash chromatography ($SiO_2$ 60F). Rf=0.10 (2:1 EtOAc-heptane); Rt=5.76.

EXAMPLE 100

6-[4-(4-{2-[2-(2-Methoxyphenyl)ethoxy]ethoxy}phenyl)piperidin-3-yloxymethyl]-4-(3-methoxypropyl)-3,4-dihydro-2H-benzo[1,4]oxazine Analogously to Method C, 0.300 g of 6-[4-(4-{2-[2-(2-methoxyphenyl)ethoxy]ethoxy}phenyl)piperidin-3-yloxymethyl]-4-(3-methoxypropyl)-4H-benzo[1,4]oxazin-3-one is used to prepare the title compound.

The starting materials are prepared as follows:

a) 6-[4-(4-{2-[2-(2-Methoxyphenyl)ethoxy]ethoxy}phenyl)piperidin-3-yloxymethyl]-4-(3-methoxypropyl)-4H-benzo[1,4]oxazin-3-one Analogously to Method A, 0.447 g of tert-butyl 4-(4-{2-[2-(2-methoxyphenyl)ethoxy]ethoxy}phenyl)-3-[4-(3-methoxypropyl)-3-oxo-3,4-dihydro-2H-benzo[1,4]oxazin-6-ylmethoxy]piperidine-1-carboxylate is used to prepare the title compound. Rf=0.27 (200:20:1 dichloromethane-methanol-conc. ammonia); Rt=4.22.

b) tert-Butyl 4-(4-{2-[2-(2-methoxyphenyl)ethoxy]ethoxy}phenyl)-3-[4-(3-methoxypropyl)-3-oxo-3,4-dihydro-2H-benzo[1,4]oxazin-6-ylmethoxy]piperidine-1-carboxylate Analogously to Method D, 0.500 g of tert-butyl 3-hydroxy-4-(4-{2-[2-(2-methoxyphenyl)ethoxy]ethoxy}phenyl)piperidine-1-carboxylate and 0.314 g of 6-chloromethyl-4-(3-methoxypropyl)-4H-benzo[1,4]oxazin-3-one (Example 2b) are reacted. The title compound is obtained as an opaque oil. Rf=0.24 (1:1 EtOAc-heptane); Rt=5.82.

c) tert-Butyl 3-hydroxy-4-(4-{2-[2-(2-methoxyphenyl)ethoxy]ethoxy}phenyl)piperidine-1-carboxylate Analogously to Method I, 0.610 g of tert-butyl 3-hydroxy-4-(4-hydroxyphenyl)piperidine-1-carboxylate and 0.808 g of 2-[2-(2-methoxyphenyl)ethoxy]ethyl toluene-4-sulphonate (Example 45b) are reacted. The title compound is obtained as a slightly yellowish oil. Rt=5.10.

EXAMPLE 101

7-[4-(4-{2-[2-(2-Methoxyphenyl)ethoxy]ethoxy}phenyl)piperidin-3-yloxymethyl]-1-(3-methoxypropyl)-1,2,3,4-tetrahydroquinoline Analogously to Method C, 0.355 g of 7-[4-(4-{2-[2-(2-methoxyphenyl)ethoxy]ethoxy}phenyl)piperidin-3-yloxymethyl]-1-(3-methoxypropyl)-3,4-dihydro-1H-quinolin-2-one is used to prepare the title compound.

The starting materials are prepared as follows:

a) 7-[4-(4-{2-[2-(2-Methoxyphenyl)ethoxy]ethoxy}phenyl)piperidin-3-yloxymethyl]-1-(3-methoxypropyl)-3,4-dihydro-1H-quinolin-2-one Analogously to Method A, 0.480 g of tert-butyl 4-(4-{2-[2-(2-methoxyphenyl)ethoxy]ethoxy}phenyl)-3-[1-(3-methoxypropyl)-2-oxo-1,2,3,4-tetrahydroquinolin-7-ylmethoxy]piperidine-1-carboxylate is used to prepare the title compound. Rf=0.47 (200:20:1 dichloromethane-methanol-conc. ammonia); Rt=4.16.

b) tert-Butyl 4-(4-{2-[2-(2-methoxyphenyl)ethoxy]ethoxy}phenyl)-3-[1-(3-methoxypropyl)-2-oxo-1,2,3,4-tetrahydroquinolin-7-ylmethoxy]piperidine-1-carboxylate Analogously to Method D, 0.500 g of tert-butyl 3-hydroxy-4-(4-{2-[2-(2-methoxyphenyl)ethoxy]ethoxy}phenyl)piperidine-1-carboxylate (Example 100c) and 0.312 g of 7-chloromethyl-1-(3-methoxypropyl)-3,4-dihydro-1H-quinolin-2-one (Example 13b) are reacted. The title compound is obtained as an opaque oil. Rf=0.21 (1:1 EtOAc-heptane); Rt=5.80.

EXAMPLE 102

1-(3-Methoxypropyl)-7-(4-{4-[3-(2-methylbenzyloxy)propoxy]phenyl}piperidin-3-yloxymethyl)-3,4-dihydro-1H-quinolin-2-one Analogously to Method A, 0.180 g of tert-butyl 3-[1-(3-methoxypropyl)-2-oxo-1,2,3,4-tetrahydroquinolin-7-ylmethoxy]-4-{4-[3-(2-methylbenzyloxy)propoxy]phenyl}piperidine-1-carboxylate is used to prepare the title compound.

The starting materials are prepared as follows:

a) tert-Butyl 3-[1-(3-methoxypropyl)-2-oxo-1,2,3,4-tetrahydroquinolin-7-ylmethoxy]-4-{4-[3-(2-methylbenzyloxy)propoxy]phenyl}piperidine-1-carboxylate Analogously to Method I, 0.150 g of tert-butyl 4-(4-hydroxyphenyl)-3-[1-(3-methoxypropyl)-2-oxo-1,2,3,4-tetrahydroquinolin-7-ylmethoxy]piperidine-1-carboxylate (Example 44d) and 0.808 g of 3-(2-methylbenzyloxy)propyl toluene-4-sulphonate are reacted. The title compound is obtained as a slightly yellowish oil. Rf=0.47 (2:1 EtOAc-heptane); Rt=6.04.

b) 3-(2-Methylbenzyloxy)propyl toluene-4-sulphonate

Analogously to Method H, 5.0 g of 3-(2-methylbenzyloxy)propan-1-ol are used to obtain the title compound as a yellowish oil. Rf=0.81 (2:1 EtOAc-heptane); Rt=5.15.

c) 3-(2-Methylbenzyloxy)propan-1-ol

Analogously to Example 44g, 37.8 g of 2-o-tolyl-[1,3]dioxane are used to obtain the crude title compound as a yellowish oil. Rt=3.44.

EXAMPLE 103

3-[4-Furan-2-yl-3-(3-methoxypropoxy)benzyloxy]-4-{4-[3-(2-methoxybenzyloxy)propoxy]phenyl}piperidine Analogously to Method A, 0.450 g of tert-butyl 3-[4-furan-2-yl-3-(3-methoxypropoxy)benzyloxy]-4-{4-[3-(2-methoxybenzyloxy)propoxy]phenyl}piperidine-1-carboxylate is used to prepare the title compound.

The starting materials are prepared as follows:

a) tert-Butyl 3-[4-furan-2-yl-3-(3-methoxypropoxy)benzyloxy]-4-{4-[3-(2-methoxybenzyloxy)propoxy]phenyl}piperidine-1-carboxylate The mixture of 0.500 g of tert-butyl 3-[4-bromo-3-(3-methoxypropoxy)benzyloxy]-4-{4-[3-(2-methoxybenzyloxy)propoxy]phenyl}piperidine-1-carboxylate and 0.023 g of tetrakis(triphenylphosphine)palladium(0) in 6.0 ml of 1,2-dimethoxyethane is stirred at room temperature over 10 minutes, then admixed with 0.114 g of 2-furanboric acid, 0.70 ml of ethanol and 0.68 ml of 2M sodium carbonate solution and stirred at 80° C. over 16 hours. The reaction mixture is cooled, poured onto 1M sodium hydrogencarbonate solution (40 ml) and extracted with tert-butyl methyl ether (2×40 ml). The organic phases are washed successively with water (40 ml) and brine (40 ml), dried over sodium sulphate, filtered and concentrated by evaporation. The title compound is obtained as a brown oil from the residue by means of flash chromatography ($SiO_2$ 60F). Rf=0.43 (1:1 EtOAc-heptane); Rt=6.32.

b) tert-Butyl 3-[4-bromo-3-(3-methoxypropoxy)benzyloxy]-4-{4-[3-(2-methoxybenzyloxy)propoxy]phenyl}piperidine-1-carboxylate Analogously to Method D, 3.35 g of tert-butyl 3-hydroxy-4-{4-[3-(2-methoxybenzyloxy)propoxy]phenyl}piperidine-1-carboxylate and 3.17 g of 1-bromo-4-bromomethyl-2-(3-methoxypropoxy)benzene (Example 79c) are used to obtain the title compound as a slightly yellowish oil. Rf=0.35 (1:1 EtOAc-heptane); Rt=6.42.

EXAMPLE 104

N-[4-(4-{4-[3-(2-Methoxybenzyloxy)propoxy]phenyl}piperidin-3-yloxymethyl)-2-(3-methoxypropoxy)phenyl]acetamide Analogously to Method A, 0.280 g of tert-butyl 3-[4-acetylamino-3-(3-methoxypropoxy)benzyloxy]-4-{4-[3-(2-methoxybenzyloxy)propoxy]phenyl}piperidine-1-carboxylate is used to prepare the title compound.

The starting materials are prepared as follows:

a) tert-Butyl 3-[4-acetylamino-3-(3-methoxypropoxy)benzyloxy]-4-{4-[3-(2-methoxybenzyloxy)propoxy]phenyl}piperidine-1-carboxylate The solution of 0.380 g of tert-butyl 3-[4-amino-3-(3-methoxypropoxy)benzyloxy]-4-{4-[3-(2-methoxybenzyloxy)propoxy]phenyl}piperidine-1-carboxylate in 0.168 ml of triethylamine and 10.0 ml of dichloromethane is cooled to 0° C. and admixed slowly with the solution of 0.090 ml of acetyl chloride in 1.0 ml of dichloromethane. The reaction solution is stirred over 2 hours, poured onto ice-water (20 ml) and extracted with tert-butyl methyl ether (2×20 ml). The organic phases are washed with successively with water (20 ml) and brine (20 ml), dried over sodium sulphate, filtered and concentrated by evaporation. The title compound is obtained as a yellowish oil from the residue by means of flash chromatography ($SiO_2$ 60F). Rf=0.10 (1:1 EtOAc-heptane); Rt=5.73.

b) tert-Butyl 3-[4-amino-3-(3-methoxypropoxy)benzyloxy]-4-{4-[3-(2-methoxybenzyloxy)propoxy]phenyl}piperidine-1-carboxylate Analogously to Example 116c, 0.730 g of tert-butyl 3-[4-bromo-3-(3-methoxypropoxy)benzyloxy]-4-{4-[3-(2-methoxybenzyloxy)propoxy]phenyl}piperidine-1-carboxylate (Example 103b) is used to obtain the title compound as a slightly yellowish oil. Rf=0.17 (1:1 EtOAc-heptane); Rt=5.12.

EXAMPLE 105

N-[2-(2-Acetylaminoethyl)phenyl]-2-(4-{4-[3-(2-methoxybenzyloxy)propoxy]phenyl}piperidin-3-yloxy)-N-methylacetamide Analogously to Method A, 0.32 g of tert-butyl 3-({[2-(2-acetylaminoethyl)phenyl]methylcarbamoyl}methoxy)-4-{4-[3-(2-methoxybenzyloxy)propoxy]phenyl}piperidine-1-carboxylate is used to prepare the title compound.

The starting materials are prepared as follows:

a) tert-Butyl 3-({[2-(2-acetylaminoethyl)phenyl]methylcarbamoyl}methoxy)-4-{4-[3-(2-methoxybenzyloxy)propoxy]phenyl}piperidine-1-carboxylate A solution of 0.49 g of tert-butyl 3-({[2-(2-aminoethyl)phenyl]methylcarbamoyl}methoxy)-4-{4-[3-(2-methoxybenzyloxy)propoxy]phenyl}piperidine-1-carboxylate in 10 ml of dichloromethane and 0.22 ml of triethylamine is admixed at 0° C. with 0.15 ml of acetyl chloride and stirred at room temperature over 17 hours. The reaction mixture is diluted with dichloromethane, washed with 1N HCl (2×), dried over sodium sulphate and concentrated by evaporation. The title compound is obtained as a colourless oil from the residue by means of flash chromatography ($SiO_2$ 60F). Rf=0.09 (EtOAc); Rt=5.10.

b) tert-Butyl 3-({[2-(2-aminoethyl)phenyl]methylcarbamoyl}methoxy)-4-{4-[3-(2-methoxybenzyloxy)propoxy]phenyl}piperidine-1-carboxylate Analogously to Example 56b, 0.70 g of tert-butyl 3-({[2-(2-azidoethyl)phenyl]methylcarbamoyl}methoxy)-4-{4-[3-(2-methoxybenzyloxy)propoxy]phenyl}piperidine-1-carboxylate is reacted. The title compound is obtained as a colourless oil. Rf=0.28 (200:20:1 dichloromethane-methanol-25% conc. ammonia); Rt=4.83.

c) tert-Butyl 3-({[2-(2-azidoethyl)phenyl]methylcarbamoyl}methoxy)-4-{4-[3-(2-methoxybenzyloxy)propoxy]phenyl}piperidine-1-carboxylate Analogously to Example 56c, 1.0 g of tert-butyl 4-{4-[3-(2-methoxybenzyloxy)propoxy]phenyl}-3-[(methyl-{2-[2-(toluene-4-sulphonyloxy)ethyl]phenyl}carbamoyl)methoxy]piperidine-1-carboxylate is reacted. The title compound is obtained as a colourless oil. Rf=0.22 (1:1 EtOAc-heptane); Rt=5.77.

d) tert-Butyl 4-{4-[3-(2-methoxybenzyloxy)propoxy]phenyl}-3-[(methyl-{2-[2-(toluene-4-sulphonyloxy)ethyl]phenyl}carbamoyl)methoxy]piperidine-1-carboxylate Analogously to Method H, 1.2 g of tert-butyl 3-({[2-(2-hydroxyethyl)phenyl]methylcarbamoyl}methoxy)-4-{4-[3-(2-methoxybenzyloxy)propoxy]phenyl}piperidine-1-carboxylate are reacted. The title compound is obtained as a yellow oil. Rf=0.21 (1:1 EtOAc-heptane); Rt=5.88.

e) tert-Butyl 3-({[2-(2-hydroxyethyl)phenyl] methylcarbamoyl}methoxy)-4-{4-[3-(2-methoxy-benzyloxy)propoxy]phenyl}piperidine-1-carboxylate Analogously to Example 3a, 2.0 g of tert-butyl 3-carboxymethoxy-4-{4-[3-(2-methoxybenzyloxy)propoxy]phenyl}piperidine-1-carboxylate (Example 34b) and 0.68 g of 2-(2-methylaminophenyl)ethanol are reacted. The title compound is obtained as a colourless oil. Rf=0.30 (3:1 EtOAc-heptane); Rt=5.25.

EXAMPLE 106

3-(4-{4-[3-(2-Methoxybenzyloxy)propoxy] phenyl}piperidin-3-yloxymethyl)-N-(2-methoxyethyl)-N-methylbenzamide Analogously to Method A, 0.255 g of tert-butyl 4-{4-[3-(2-methoxybenzyloxy)propoxy]phenyl}-3-{3-[(2-methoxyethyl)methylcarbamoyl]benzyloxy}piperidine-1-carboxylate is used to prepare the title compound.

The starting materials are prepared as follows:

a) tert-Butyl 4-{4-[3-(2-methoxybenzyloxy)propoxy] phenyl}-3-{3-[(2-methoxyethyl)methylcarbamoyl] benzyloxy}piperidine-1-carboxylate Analogously to Example 127a, 0.355 g tert-butyl 3-(3-chlorocarbonylbenzyloxy)-4-{4-[3-(2-methoxybenzyloxy) propoxy]phenyl}piperidine-1-carboxylate and 0.106 g of 2-methoxy-N-methylethylamine are reacted. The title compound is obtained as a colourless oil. Rf=0.10 (1:1 EtOAc-heptane); Rt=5.65.

b) tert-Butyl 3-(3-chlorocarbonylbenzyloxy)-4-{4-[3-(2-methoxybenzyloxy)propoxy] phenyl}piperidine-1-carboxylate Analogously to Example 127b, 1.42 g of tert-butyl 3-(3-carboxybenzyloxy)-4-{4-[3-(2-methoxybenzyloxy)propoxy]phenyl}piperidine-1-carboxylate are used to obtain the crude title compound as a yellow oil.

c) tert-Butyl 3-(3-carboxybenzyloxy)-4-{4-[3-(2-methoxybenzyloxy)propoxy]phenyl}piperidine-1-carboxylate Analogously to Example 65, 1.54 g of tert-butyl 4-{4-[3-(2-methoxybenzyloxy)propoxy]phenyl}-3-(3-methoxycarbonylbenzyloxy)piperidine-1-carboxylate are used to obtain the title compound as a white foam. Rt=5.52.

d) tert-Butyl 4-{4-[3-(2-methoxybenzyloxy)propoxy]phenyl}-3-(3-methoxycarbonylbenzyloxy)piperidine-1-carboxylate Analogously to Method D, 2.08 g of tert-butyl 3-hydroxy-4-{4-[3-(2-methoxybenzyloxy)propoxy]phenyl}piperidine-1-carboxylate and 1.13 g of methyl 3-(bromomethyl)benzoate are used to obtain the title compound as a slightly yellowish oil. Rf=0.31 (1:2 EtOAc-heptane); Rt=6.06.

EXAMPLE 107

3-(4-{4-[3-(2-Methoxybenzyloxy)propoxy] phenyl}piperidin-3-yloxymethyl)-N-(2-methoxyethyl)benzamide Analogously to Method A, 0.245 g of tert-butyl 4-{4-[3-(2-methoxybenzyloxy)propoxy]phenyl}-3-[3-(2-methoxyethylcarbamoyl)benzyloxy]piperidine-1-carboxylate is used to prepare the title compound.

The starting material is prepared as follows:

a) tert-Butyl 4-{4-[3-(2-methoxybenzyloxy)propoxy] phenyl}-3-[3-(2-methoxyethylcarbamoyl)benzyloxy] piperidine-1-carboxylate Analogously to Example 127a, 0.355 g of tert-butyl 3-(3-chlorocarbonylbenzyloxy)-4-{4-[3-(2-methoxybenzyloxy) propoxy]phenyl}piperidine-1-carboxylate (Example 106b) and 0.087 g of 2-methoxyethylamine are reacted. The title compound is obtained as a colourless oil. Rf=0.10 (1:1 EtOAc-heptane); Rt=5.51.

EXAMPLE 108

N-(2-{3-Fluoro-2-[2-(4-{4-[3-(2-methoxybenzyloxy)propoxy]phenyl}piperidin-3-yloxy)ethoxy] phenyl}ethyl)acetamide Analogously to Method A, 0.298 g of tert-butyl 3-{2-[2-(2-acetylaminoethyl)-6-fluorophenoxy]ethoxy}-4-{4-[3-(2-methoxybenzyloxy)propoxy]phenyl}piperidine-1-carboxylate is used to prepare the title compound.

The starting materials are prepared as follows:

a) tert-Butyl 3-{2-[2-(2-acetylaminoethyl)-6-fluorophenoxy]ethoxy}-4-{4-[3-(2-methoxybenzyloxy) propoxy]phenyl}piperidine-1-carboxylate Analogously to Method G, 0.45 g of tert-butyl 4-{4-[3-(2-methoxybenzyloxy)propoxy]phenyl}-3-[2-(toluene-4-sulphonyloxy)ethoxy]piperidine-1-carboxylate (Example 14b) and 0.26 g of N-[2-(3-fluoro-2-hydroxyphenyl)ethyl]acetamide are reacted. The title compound is obtained as a yellow oil. Rf=0.42 (EtOAc); Rt=5.65.

b) N-[2-(3-Fluoro-2-hydroxyphenyl)ethyl]acetamide

A solution of 1.54 g of (3-fluoro-2-hydroxyphenyl)acetonitrile, 1.87 ml of acetic anhydride and 2.41 g of nickel chloride hexahydrate in 75 ml of methanol is admixed at 0° C. with 2.72 g of sodium borohydride in portions and stirred at room temperature over 22 hours. The reaction mixture is concentrated by evaporation, and the residue is diluted with ethyl acetate and saturated aqueous sodium bicarbonate solution and clarified by filtration. The aqueous phase is extracted with ethyl acetate (3×). The combined organic phases are dried with sodium sulphate and concentrated by evaporation. The title compound is obtained as a beige solid from the residue by means of flash chromatography ($SiO_2$ 60F). Rf=0.23 (95:5 dichloromethane-methanol); Rt=2.60.

c) (3-Fluoro-2-hydroxyphenyl)acetonitrile

A solution of 4.89 g of 2-fluoro-6-hydroxymethylphenol and 2.08 g of sodium cyanide in 120 ml of N,N-dimethylformamide is stirred at 120° C. over 24 hours. The reaction mixture is cooled, diluted with water and concentrated by evaporation. The residue is diluted with water and neutralized with conc. acetic acid (caution! hydrocyanic acid). The mixture is extracted with dichloromethane (3×). The combined organic phases are washed with water and brine, dried over sodium sulphate and concentrated by evaporation. The title compound is obtained as a violet solid from the residue by means of flash chromatography ($SiO_2$ 60F). Rf=0.32 (1:2 EtOAc-heptane); Rt=3.12.

EXAMPLE 109

N-(2-{2-[2-(4-{4-[3-(2-Methoxybenzyloxy)propoxy]phenyl}piperidin-3-yloxy)ethoxy]-6-methylphenyl}ethyl)acetamide Analogously to Method A, 0.249 g of tert-butyl 3-{2-[2-(2-acetylaminoethyl)-3-methylphenoxy]ethoxy}-4-{4-[3-(2-methoxybenzyloxy)propoxy]phenyl}piperidine-1-carboxylate is used to prepare the title compound.

The starting materials are prepared as follows:

a) tert-Butyl 3-{2-[2-(2-acetylaminoethyl)-3-methylphenoxy]ethoxy}-4-{4-[3-(2-methoxybenzyloxy)propoxy]phenyl}piperidine-1-carboxylate Analogously to Method G, 0.44 g of tert-butyl 4-{4-[3-(2-methoxybenzyloxy)propoxy]phenyl}-3-[2-(toluene-4-sulphonyloxy)ethoxy]piperidine-1-carboxylate (Example 14b) and 0.25 g of N-[2-(2-hydroxy-6-methylphenyl)ethyl]acetamide are reacted. The title compound is obtained as a colourless oil. Rf=0.50 (EtOAc); Rt=5.77.

b) N-[2-(2-hydroxy-6-methylphenyl)ethyl]acetamide

Analogously to Example 108b, 0.67 g of (2-hydroxy-6-methylphenyl)acetonitrile is reacted. The title compound is obtained as a yellow-orange solid. Rf=0.20 (95:5 dichloromethane-methanol); Rt=2.81.

c) (2-Hydroxy-6-methylphenyl)acetonitrile

Analogously to Example 108c, 0.97 g of 2-hydroxymethyl-3-methylphenol is reacted. The title compound is obtained as an orange-brown solid. Rf=0.38 (1:2 EtOAc-heptane); Rt=3.36.

EXAMPLE 110

N-(2-{2-[2-(4-{4-[3-(2-Methoxybenzyloxy)propoxy]phenyl}piperidin-3-yloxy)ethoxy]-3-methylphenyl}ethyl)acetamide Analogously to Method A, 0.278 g of tert-butyl 3-{2-[2-(2-acetylaminoethyl)-6-methylphenoxy]ethoxy}-4-{4-[3-(2-methoxybenzyloxy)propoxy]phenyl}piperidine-1-carboxylate is used to prepare the title compound.

The starting materials are prepared as follows:

a) tert-Butyl 3-{2-[2-(2-acetylaminoethyl)-6-methylphenoxy]ethoxy}-4-{4-[3-(2-methoxybenzyloxy)propoxy]phenyl}piperidine-1-carboxylate Analogously to Method G, 0.36 g of tert-butyl 4-{4-[3-(2-methoxybenzyloxy)propoxy]phenyl}-3-[2-(toluene-4-sulphonyloxy)ethoxy]piperidine-1-carboxylate (Example 14b) and 0.21 g of N-[2-(2-hydroxy-3-methylphenyl)ethyl]acetamide are reacted. The title compound is obtained as a yellow oil. Rf=0.47 (EtOAc); Rt=5.75.

b)
N-[2-(2-Hydroxy-3-methylphenyl)ethyl]acetamide

Analogously to Example 108b, 2.7 g of (2-hydroxy-3-methylphenyl)acetonitrile are reacted. The title compound is obtained as an orange solid. Rf=0.16 (1:1 EtOAc-heptane); Rt=2.79.

c) (2-Hydroxy-3-methylphenyl)acetonitrile

Analogously to Example 108c, 8.79 g of 2-hydroxymethyl-6-methylphenol are reacted. The title compound is obtained as a yellow solid. Rf=0.42 (1:2 EtOAc-heptane); Rt=3.42.

EXAMPLE 111

N-(2-{2-[2-(4-{4-[3-(2-Methoxybenzyloxy)propoxy]phenyl}piperidin-3-yloxy)ethoxy]-5-methylphenyl}ethyl)acetamide Analogously to Method A, 0.265 g of tert-butyl 3-{2-[2-(2-acetylaminoethyl)-4-methylphenoxy]ethoxy}-4-{4-[3-(2-methoxybenzyloxy)propoxy]phenyl}piperidine-1-carboxylate is used to prepare the title compound.

The starting materials are prepared as follows:

a) tert-Butyl 3-{2-[2-(2-acetylaminoethyl)-4-methylphenoxy]ethoxy}-4-{4-[3-(2-methoxybenzyloxy)propoxy]phenyl}piperidine-1-carboxylate Analogously to Method G, 0.45 g of tert-butyl 4-{4-[3-(2-methoxybenzyloxy)propoxy]phenyl}-3-[2-(toluene-4-sulphonyloxy)ethoxy]piperidine-1-carboxylate (Example 14b) and 0.26 g of N-[2-(2-hydroxy-3-methylphenyl)ethyl]acetamide are reacted. The title compound is obtained as a yellow oil. Rf=0.60 (EtOAc); Rt=5.78.

b)
N-[2-(2-Hydroxy-3-methylphenyl)ethyl]acetamide

Analogously to Example 108b, 1.24 g of (2-hydroxy-5-methylphenyl)acetonitrile are reacted. The title compound is obtained as a yellow solid. Rf=0.17 (1:1 EtOAc-heptane); Rt=2.80.

c) (2-Hydroxy-5-methylphenyl)acetonitrile

Analogously to Example 108c, 6.72 g of 2-hydroxymethyl-4-methylphenol are reacted. The title compound is obtained as a brown oil. Rf=0.36 (1:2 EtOAc-heptane); Rt=3.41.

EXAMPLE 112

N-(2-{4-Fluoro-2-[2-(4-{4-[3-(2-methoxybenzyloxy)propoxy]phenyl}piperidin-3-yloxy)ethoxy]phenyl}ethyl)acetamide Analogously to Method A, 0.265 g of tert-butyl 3-{2-[2-(2-acetylaminoethyl)-5-fluorophenoxy]ethoxy}-4-{4-[3-(2-methoxybenzyloxy)propoxy]phenyl}piperidine-1-carboxylate is used to prepare the title compound.

The starting materials are prepared as follows:

a) tert-Butyl 3-{2-[2-(2-acetylaminoethyl)-5-fluorophenoxy]ethoxy}-4-{4-[3-(2-methoxybenzyloxy)propoxy]phenyl}piperidine-1-carboxylate Analogously to Method G, 0.45 g of tert-butyl 4-{4-[3-(2-methoxybenzyloxy)propoxy]phenyl}-3-[2-(toluene-4-sulphonyloxy)ethoxy]piperidine-1-carboxylate (Example 14b) and 0.27 g of N-[2-(4-fluoro-2-hydroxyphenyl)ethyl]acetamide are reacted. The title compound is obtained as a yellow oil. Rf=0.63 (EtOAc); Rt=5.61.

b) N-[2-(4-fluoro-2-hydroxyphenyl)ethyl]acetamide

Analogously to Example 108b, 2.68 g of (4-fluoro-2-hydroxyphenyl)acetonitrile are reacted. The title compound is obtained as a yellow solid. Rf=0.12 (1:1 EtOAc-heptane); Rt=2.71.

c) (4-Fluoro-2-hydroxyphenyl)acetonitrile

Analogously to Example 108c, 5.06 g of 2-hydroxymethyl-4-methylphenol are reacted. The title compound is obtained as a brown oil. Rf=0.38 (1:2 EtOAc-heptane); Rt=3.25.

d) 2-Hydroxymethyl-4-methylphenol

A solution of 4.80 g of 4-fluoro-2-hydroxybenzoic acid in 100 ml of tetrahydrofuran is added dropwise at 0° C. to the suspension of 5.29 g of lithium aluminium hydride in 150 ml of tetrahydrofuran and stirred over 2 hours. The reaction mixture is admixed dropwise successively with 6 ml of water, 6 ml of 15% NaOH and 24 ml of water, and stirred over 1 hour. The mixture is filtered and the filtrate is concentrated by evaporation. The crude title compound is obtained as a red-orange oil from the residue. Rf=0.20 (1:1 EtOAc-heptane); Rt=2.47.

EXAMPLE 113

N-(2-{5-Fluoro-2-[2-(4-{4-[3-(2-methoxybenzyloxy)propoxy]phenyl}piperidin-3-yloxy)ethoxy]phenyl}ethyl)acetamide Analogously to Method A, 0.298 g of tert-butyl 3-{2-[2-(2-acetylaminoethyl)-4-fluorophenoxy]ethoxy}-4-{4-[3-(2-methoxybenzyloxy)propoxy]phenyl}piperidine-1-carboxylate is used to prepare the title compound.

The starting materials are prepared as follows:

a) tert-Butyl 3-{2-[2-(2-acetylaminoethyl)-4-fluorophenoxy]ethoxy}-4-{4-[3-(2-methoxybenzyloxy)propoxy]phenyl}piperidine-1-carboxylate Analogously to Method G, 0.45 g of tert-butyl 4-{4-[3-(2-methoxybenzyloxy)propoxy]phenyl}-3-[2-(toluene-4-sulphonyloxy)ethoxy]piperidine-1-carboxylate (Example 14b) and 0.27 g of N-[2-(5-fluoro-2-hydroxyphenyl)ethyl]acetamide are reacted. The title compound is obtained as a yellow oil. Rf=0.50 (EtOAc); Rt=5.59.

b) N-[2-(5-fluoro-2-hydroxyphenyl)ethyl]acetamide

Analogously to Example 108b, 1.35 g of (5-fluoro-2-hydroxyphenyl)acetonitrile are reacted. The title compound is obtained as a yellow solid. Rf=0.14 (1:1 EtOAc-heptane); Rt=2.63.

c) (5-Fluoro-2-hydroxyphenyl)acetonitrile

Analogously to Example 108c, 3.92 g of 4-fluoro-2-hydroxymethylphenol are reacted. The title compound is obtained as a brown oil. Rf=0.34 (1:2 EtOAc-heptane); Rt=3.18.

EXAMPLE 114

N-(2-{2-[2-(4-{4-[3-(2-Methoxybenzyloxy)propoxy]phenyl}piperidin-3-yloxy)ethoxy]-4-methylphenyl}ethyl)acetamide Analogously to Method A, 0.45 g of tert-butyl 3-{2-[2-(2-acetylaminoethyl)-5-methylphenoxy]ethoxy}-4-{4-[3-(2-methoxybenzyloxy)propoxy]phenyl}piperidine-1-carboxylate is used to prepare the title compound.

The starting materials are prepared as follows:

a) tert-Butyl 3-{2-[2-(2-acetylaminoethyl)-5-methylphenoxy]ethoxy}-4-{4-[3-(2-methoxybenzyloxy)propoxy]phenyl}piperidine-1-carboxylate Analogously to Method G, 0.45 g of tert-butyl 4-{4-[3-(2-methoxybenzyloxy)propoxy]phenyl}-3-[2-(toluene-4-sulphonyloxy)ethoxy]piperidine-1-carboxylate (Example 14b) and 0.26 g of N-[2-(2-hydroxy-4-methylphenyl)ethyl]acetamide are reacted. The title compound is obtained as a yellow oil. Rf=0.55 (EtOAc); Rt=5.73.

b) N-[2-(2-Hydroxy-4-methylphenyl)ethyl]acetamide

Analogously to Example 108b, 4.68 g of (2-hydroxy-4-methylphenyl)acetonitrile are reacted. The title compound is obtained as a yellow oil. Rf=0.21 (1:1 EtOAc-heptane); Rt=2.89.

c) (2-Hydroxy-4-methylphenyl)acetonitrile

Analogously to Example 108c, 8.28 g of 2-hydroxymethyl-5-methylphenol are reacted. The title compound is obtained as a yellow solid. Rf=0.44 (1:2 EtOAc-heptane); Rt=3.37.

EXAMPLE 115

N-(2-{2-Fluoro-6-[2-(4-{4-[3-(2-methoxybenzy-loxy)propoxy]phenyl}piperidin-3-yloxy)ethoxy]phenyl}ethyl)acetamide Analogously to Method A, 0.265 g of tert-butyl 3-{2-[2-(2-acetylaminoethyl)-3-fluorophenoxy]ethoxy}-4-{4-[3-(2-methoxybenzyloxy)propoxy]phenyl}piperidine-1-carboxylate is used to prepare the title compound.

The starting materials are prepared as follows:

a) tert-Butyl 3-{2-[2-(2-Acetylaminoethyl)-3-fluorophenoxy]ethoxy}-4-{4-[3-(2-methoxybenzyloxy)propoxy]phenyl}piperidine-1-carboxylate Analogously to Method G, 0.45 g of tert-butyl 4-{4-[3-(2-methoxybenzyloxy)propoxy]phenyl}-3-[2-(toluene-4-sulphonyloxy)ethoxy]piperidine-1-carboxylate (Example 14b) and 0.27 g of N-[2-(2-fluoro-6-hydroxyphenyl)ethyl]acetamide are reacted. The title compound is obtained as a yellow oil. Rf=0.58 (EtOAc); Rt=5.57.

b) N-[2-(2-Fluoro-6-hydroxyphenyl)ethyl]acetamide

Analogously to Example 108b, 2.15 g of (2-fluoro-6-hydroxyphenyl)acetonitrile are reacted. The title compound is obtained as a yellow solid. Rf=0.17 (1:1 EtOAc-heptane); Rt=2.67.

c) (2-Fluoro-6-hydroxyphenyl)acetonitrile

Analogously to Example 108c, 4.13 g of 3-fluoro-2-hydroxymethylphenol are reacted. The title compound is obtained as a yellow solid. Rf=0.32 (1:2 EtOAc-heptane); Rt=3.23.

d) 3-Fluoro-2-hydroxymethylphenol

Analogously to Example 112d, 4.85 g of 2-fluoro-6-hydroxybenzoic acid are reacted. The title compound is obtained as a yellow-green oil. Rf=0.25 (1:1 EtOAc-heptane); Rt=2.41.

EXAMPLE 116

4-Methoxy-N-[2-(4-{4-[3-(2-methoxybenzyloxy)propoxy]phenyl}piperidin-3-yloxymethyl)-5-methylphenyl]-N-methylbutyramide Analogously to Method A, 0.095 g of tert-butyl 4-{4-[3-(2-methoxybenzyloxy)propoxy]phenyl}-3-{2-[(4-methoxybutyryl)methylamino]-4-methylbenzyloxy}piperidine-1-carboxylate is used to prepare the title compound.

The starting materials are prepared as follows:

a) tert-Butyl 4-{4-[3-(2-methoxybenzyloxy)propoxy]phenyl}-3-{2-[(4-methoxybutyryl)methylamino]-4-methylbenzyloxy}piperidine-1-carboxylate The solution of 0.270 g of tert-butyl 4-{4-[3-(2-methoxybenzyloxy)propoxy]phenyl}-3-[2-(4-methoxybutyrylamino)-4-methylbenzyloxy]piperidine-1-carboxylate in 4.0 ml of N,N-dimethylformamide is admixed with 0.031 g of sodium hydride dispersion (60%) and stirred at room temperature over 45 minutes. The mixture is admixed with 0.148 ml of methyl iodide and stirred at 75° C. over 16 hours. The reaction mixture is cooled, poured onto water (25 ml) and extracted with tert-butyl methyl ether (2×25 ml). The organic phases are washed successively with water (25 ml) and brine (25 ml), dried over sodium sulphate, filtered and concentrated by evaporation. The title compound is obtained as a yellowish oil from the residue by means of flash chromatography (SiO₂ 60F). Rf=0.22 (1:1 EtOAc-heptane); Rt=5.91.

b) tert-Butyl 4-{4-[3-(2-methoxybenzyloxy)propoxy]phenyl}-3-[2-(4-methoxybutyrylamino)-4-methylbenzyloxy]piperidine-1-carboxylate The solution of 0.278 g of tert-butyl 3-(2-amino-4-methylbenzyloxy)-4-{4-[3-(2-methoxybenzyloxy)propoxy]phenyl}piperidine-1-carboxylate in 0.046 ml of pyridine and 2.3 ml of dichloromethane is cooled to 0° C. and admixed slowly with 0.078 g of 4-methoxybutyryl chloride. The reaction mixture is concentrated by evaporation. The title compound is obtained as a yellowish oil from the residue by means of flash chromatography (SiO₂ 60F). Rf=0.06 (1:1 EtOAc-heptane); Rt=5.86.

c) tert-Butyl 3-(2-amino-4-methylbenzyloxy)-4-{4-[3-(2-methoxybenzyloxy)propoxy]phenyl}piperidine-1-carboxylate The mixture of 0.800 g of tert-butyl 3-(2-bromo-4-methylbenzyloxy)-4-{4-[3-(2-methoxybenzyloxy)propoxy]phenyl}piperidine-1-carboxylate, 0.250 ml of benzophenone imine, 0.0037 g of dipalladiumtris(dibenzylidenacetone)-chloroform complex, 0.0051 g of (R)-(+)-2,2'-bis(diphenylphosphine)-1,1'-binaphthyl and 0.168 g of sodium tert-butoxide is admixed with 6.0 ml of toluene and stirred under argon at 80° C. over 72 hours. The reaction mixture is cooled, admixed with brine (20 ml) and extracted with ethyl acetate (2×80 ml). The organic phases are dried over sodium sulphate, filtered and concentrated by evaporation. The residue is dissolved in 6.0 ml of methanol, admixed with 0.090 g of 5% Pd/C and 1.15 g of ammonium formate, and stirred at 60° C. over 72 hours. The reaction mixture is diluted with methanol (20 ml) and clarified by filtration, and the filtrate is concentrated by evaporation. The residue is admixed with 0.1M NaOH (100 ml) and extracted with ethyl acetate (2×100 ml). The organic phases are washed successively with 0.1M NaOH (100 ml) and brine (100 ml), dried over sodium sulphate, filtered and concentrated by evaporation. The title compound is obtained as a yellowish oil from the residue by means of flash chromatography (SiO₂ 60F). Rf=0.30 (1:2 EtOAc-heptane); Rt=5.32.

d) tert-Butyl 3-(2-bromo-4-methylbenzyloxy)-4-{4-[3-(2-methoxybenzyloxy)propoxy]phenyl}piperidine-1-carboxylate Analogously to Method D, 1.45 g of tert-butyl 3-hydroxy-4-{4-[3-(2-methoxybenzyloxy)propoxy]phenyl}piperidine-1-carboxylate and 0.80 g of 2-bromo-1-chloromethyl-4-methylbenzene are used to obtain the title compound as a slightly yellowish oil. Rf=0.56 (1:1 EtOAc-heptane); Rt=6.53.

EXAMPLE 117

4-{4-[3-(2-Methoxybenzyloxy)propoxy]phenyl}-3-(2-{2-[3-(1H-tetrazol-5-yl)propyl]phenoxy}ethoxy)piperidine Analogously to Method A, 0.218 g of tert-butyl 4-{4-[3-(2-methoxybenzyloxy)propoxy]phenyl}-3-(2-{2-[3-(1H-tetrazol-5-yl)propyl]phenoxy}ethoxy)piperidine-1-carboxylate are used to prepare the title compound.

The starting material is prepared as follows:

a) tert-Butyl 4-{4-[3-(2-methoxybenzyloxy)propoxy]phenyl}-3-(2-{2-[3-(1H-tetrazol-5-yl)propyl]phenoxy}ethoxy)piperidine-1-carboxylate A solution of 0.40 g of tert-butyl 3-{2-[2-(3-cyanopropyl)phenoxy]ethoxy}-4-{4-[3-(2-methoxybenzyloxy)propoxy]phenyl}piperidine-1-carboxylate (Example 55a) and 0.34 ml of tributyltin azide in 8 ml of o-xylene is stirred at 145° C. over 19 hours. The reaction mixture is concentrated by evaporation, the residue is taken up in 12.5 ml of 40:10:1 dichloromethane-methanol-25% conc. ammonia and stirred at room temperature over 1 hour. The mixture is concentrated by evaporation. The title compound is obtained as a yellow resin from the residue by means of flash chromatography ($SiO_2$ 60F). Rf=0.65 (40:10:1 dichloromethane-methanol-25% conc. ammonia); Rt=5.61.

EXAMPLE 118

3-Methoxy-N-[3-(4-{4-[3-(2-methoxybenzyloxy)propoxy]phenyl}piperidin-3-yloxymethyl)phenyl]-N-methylpropionamide Analogously to Method A, 0.335 g of tert-butyl 4-{4-[3-(2-methoxybenzyloxy)propoxy]phenyl}-3-{3-[(3-methoxypropionyl)methylamino]benzyloxy}piperidine-1-carboxylate is used to prepare the title compound.

The starting materials are prepared as follows:

a) tert-Butyl 4-{4-[3-(2-methoxybenzyloxy)propoxy]phenyl}-3-{3-[(3-methoxypropionyl)methylamino]benzyloxy}piperidine-1-carboxylate Analogously to Example 116a, 0.645 g of tert-butyl 4-{4-[3-(2-methoxybenzyloxy)propoxy]phenyl}-3-[3-(3-methoxypropionylamino)benzyloxy]piperidine-1-carboxylate is used to obtain the title compound as a yellowish oil. Rf=0.12 (1:1 EtOAc-heptane); Rt=5.82.

b) tert-Butyl 4-{4-[3-(2-methoxybenzyloxy)propoxy]phenyl}-3-[3-(3-methoxypropionylamino)benzyloxy]piperidine-1-carboxylate Analogously to Example 116b, 0.610 g of tert-butyl 3-(3-aminobenzyloxy)-4-{4-[3-(2-methoxybenzyloxy)propoxy]phenyl}piperidine-1-carboxylate and 0.270 g of 3-methoxypropionyl chloride are reacted. The title compound is obtained as a beige oil. Rf=0.40 (1:1 EtOAc-heptane); Rt=5.56.

c) tert-Butyl 3-(3-aminobenzyloxy)-4-{4-[3-(2-methoxybenzyloxy)propoxy]phenyl}piperidine-1-carboxylate The solution of 0.710 g of tert-butyl 4-{4-[3-(2-methoxybenzyloxy)propoxy]phenyl}-3-(3-nitrobenzyloxy)piperidine-1-carboxylate in 10 ml of tetrahydrofuran is hydrogenated in the presence of 0.190 g of Raney nickel over 20 hours. The reaction mixture is filtered and the filtrate is concentrated by evaporation. The title compound is obtained as a yellowish oil from the residue by means of flash chromatography ($SiO_2$ 60F). Rf=0.14 (1:2 EtOAc-heptane); Rt=4.93.

d) tert-Butyl 4-{4-[3-(2-methoxybenzyloxy)propoxy]phenyl}-3-(3-nitrobenzyloxy)piperidine-1-carboxylate Analogously to Method D, 1.0 g of tert-butyl 3-hydroxy-4-{4-[3-(2-methoxybenzyloxy)propoxy]phenyl}piperidine-1-carboxylate and 0.417 g of 1-chloromethyl-3-nitrobenzene are used to obtain the title compound as a slightly yellowish oil. Rf=0.37 (1:2 EtOAc-heptane); Rt=6.05.

EXAMPLE 119

N-{2-[5-(4-{4-[3-(2-Methoxybenzyloxy)propoxy]phenyl}piperidin-3-yloxymethyl)-2-methylphenoxy]ethyl}acetamide Analogously to Method B, 0.222 g of benzyl 3-[3-(2-acetylaminoethoxy)-4-methylbenzyloxy]-4-{4-[3-(2-methoxybenzyloxy)propoxy]phenyl}piperidine-1-carboxylate is used to prepare the title compound.

The starting materials are prepared as follows:

a) Benzyl 3-[3-(2-acetylaminoethoxy)-4-methylbenzyloxy]-4-{4-[3-(2-methoxybenzyloxy)propoxy]phenyl}piperidine-1-carboxylate Analogously to Example 94a, 0.245 g of benzyl 3-[3-(2-aminoethoxy)-4-methylbenzyloxy]-4-{4-[3-(2-methoxybenzyloxy)propoxy]phenyl}piperidine-1-carboxylate is used to obtain the title compound as a white foam. Rf=0.67 (200:20:1 dichloromethane-methanol-conc. ammonia); Rt=5.58.

b) Benzyl 3-[3-(2-aminoethoxy)-4-methylbenzyloxy]-4-{4-[3-(2-methoxybenzyloxy)propoxy]phenyl}piperidine-1-carboxylate Analogously to Example 94b, 0.300 g of benzyl 3-[3-(2-azidoethoxy)-4-methylbenzyloxy]-4-{4-[3-(2-methoxybenzyloxy)propoxy]phenyl}piperidine-1-carboxylate is used to obtain the title compound as a yellowish oil. Rf=0.56 (200:20:1 dichloromethane-methanol-conc. ammonia); Rt=5.16.

c) Benzyl 3-[3-(2-azidoethoxy)-4-methylbenzyloxy]-4-{4-[3-(2-methoxybenzyloxy)propoxy]phenyl}piperidine-1-carboxylate Analogously to Example 94c, 0.364 g of benzyl 4-{4-[3-(2-methoxybenzyloxy)propoxy]phenyl}-3-{4-methyl-3-[2-(toluene-4-sulphonyloxy)ethoxy]benzyloxy}piperidine-1-carboxylate is used to obtain the title compound as a yellowish oil. Rf=0.26 (1:2 EtOAc-heptane); Rt=6.22.

d) Benzyl 4-{4-[3-(2-methoxybenzyloxy)propoxy] phenyl}-3-{4-methyl-3-[2-(toluene-4-sulphonyloxy) ethoxy]benzyloxy}piperidine-1-carboxylate Analogously to Example 94d, 0.339 g of benzyl 3-[3-(2-hydroxyethoxy)-4-methylbenzyloxy]-4-{4-[3-(2-methoxybenzyloxy)propoxy]phenyl}piperidine-1-carboxylate is used to obtain to the title compound as a yellowish oil. Rf=0.16 (1:2 EtOAc-heptane); Rt=6.19.

e) Benzyl 3-[3-(2-hydroxyethoxy)-4-methylbenzyloxy]-4-{4-[3-(2-methoxybenzyloxy)propoxy] phenyl}piperidine-1-carboxylate Analogously to Example 94e, 0.442 g of benzyl 4-{4-[3-(2-methoxybenzyloxy)propoxy]phenyl}-3-[4-methyl-3-(2-triisopropylsilanyloxyethoxy)benzyloxy]piperidine-1-carboxylate is used to obtain the title compound as a yellowish oil. Rf=0.08 (1:2 EtOAc-heptane 1:2); Rt=5.69.

f) Benzyl 4-{4-[3-(2-methoxybenzyloxy)propoxy] phenyl}-3-[4-methyl-3-(2-triisopropylsilanyloxyethoxy)benzyloxy]piperidine-1-carboxylate Analogously to Method D, 0.700 g of benzyl 3-hydroxy-4-{4-[3-(2-methoxybenzyloxy)propoxy]phenyl}piperidine-1-carboxylate (Example 10f) and [2-(5-chloromethyl-2-methylphenoxy)ethoxy]triisopropylsilane are reacted. The title compound is obtained as a colourless oil. Rf=0.41 (1:2 EtOAc-heptane); Rt=7.94.

g) [2-(5-Chloromethyl-2-methylphenoxy)ethoxy] triisopropylsilane

Analogously to Method E, 0.830 g of [4-methyl-3-(2-triisopropylsilanyloxyethoxy)phenyl]methanol is used to obtain the title compound as a yellowish oil. Rf=0.63 (1:3 EtOAc-heptane); Rt=6.83.

h) [4-Methyl-3-(2-triisopropylsilanyloxyethoxy)phenyl]methanol

The solution of 2.0 g of 2-triisopropylsilanyloxyethyl 4-methyl-3-(2-triisopropylsilanyloxyethoxy)benzoate in 6 ml of tetrahydrofuran is added dropwise at 20-40° C. to the stirred mixture of 0.149 g of lithium aluminium hydride in 6 ml of tetrahydrofuran. The reaction mixture is stirred at 40° C. over 4 hours and subsequently cooled to room temperature. 0.6 ml of water, 0.6 ml of 2N NaOH and once again 0.6 ml of water are added dropwise successively and the suspension is stirred at room temperature over 1 hour. The reaction mixture is poured onto 100 ml of 2N HCl (cold) and extracted with ethyl acetate (2×100 ml). The organic phases are washed successively with 2N HCl (100 ml), water (100 ml) and brine (1×100 ml), dried over sodium sulphate, filtered and concentrated by evaporation. The title compound is obtained as a slightly yellowish oil from the residue by means of flash chromatography (SiO$_2$ 60F). Rf=0.71 (1:1 EtOAc-heptane); Rt=6.30.

i) 2-Triisopropylsilanyloxyethyl 4-methyl-3-(2-triisopropylsilanyloxyethoxy)benzoate Analogously to Example 12d, 5.0 g of 3-hydroxy-4-methylbenzoic acid and 24.3 g of (2-iodoethoxy)triisopropylsilane are reacted. The title compound is obtained as a yellowish oil. Rf=0.66 (1:4 EtOAc-heptane); Rt=6.30.

EXAMPLE 120

4-{2-[2-(4-{4-[3-(2-Methoxybenzyloxy)propoxy] phenyl}piperidin-3-yloxy)ethoxy]phenyl}-N-methylbutyramide Analogously to Method A, 0.283 g of tert-butyl 4-{4-[3-(2-methoxybenzyloxy)propoxy]phenyl}-3-{2-[2-(3-methylcarbamoylpropyl)phenoxy]ethoxy}piperidine-1-carboxylate is used to prepare the title compound.

The starting materials are prepared as follows:

a) tert-Butyl 4-{4-[3-(2-methoxybenzyloxy)propoxy] phenyl}-3-[2-{2-(3-methylcarbamoylpropyl)phenoxy]ethoxy}piperidine-1-carboxylate Analogously to Method G, 0.40 g of tert-butyl 4-{4-[3-(2-methoxybenzyloxy)propoxy]phenyl}-3-[2-(toluene-4-sulphonyloxy)ethoxy]piperidine-1-carboxylate (Example 14b) and 0.23 g of 4-(2-hydroxyphenyl)-N-methylbutyramide are reacted. The title compound is obtained as a colourless resin. Rf=0.25 (200:20:1 dichloromethane-methanol-25% conc. ammonia); Rt=5.73.

b) 4-(2-Hydroxyphenyl)-N-methylbutyramide

A solution of 1.0 g of 4,5-dihydro-3H-benzo[b]oxepin-2-one and 40 ml of 10% methylamine in isopropanol is heated in an autoclave at 100° C. over 16 hours. The reaction mixture is cooled to room temperature and concentrated by evaporation. The title compound is obtained as white crystals from the residue by means of flash chromatography (SiO$_2$ 60F). Rf=0.20 (4:1 EtOAc-heptane); Rt=2.66.

EXAMPLE 121

6-(4-{4-[3-(2-Chlorophenoxy)propoxy] phenyl}piperidin-3-yloxymethyl)-4-(3-methoxypropyl)-3,4-dihydro-2H-benzo[1,4]oxazine Analogously to Method C, 0.565 g of 6-(4-{4-[3-(2-chlorophenoxy)propoxy]phenyl}piperidin-3-yloxymethyl)-4-(3-methoxypropyl)-4H-benzo[1,4]oxazin-3-one is used to prepare the title compound.

The starting materials are prepared as follows:

a) 6-(4-{4-[3-(2-Chlorophenoxy)propoxy] phenyl}piperidin-3-yloxymethyl)-4-(3-methoxypropyl)-4H-benzo[1,4]oxazin-3-one Analogously to Method A, 0.680 g of tert-butyl 4-{4-[3-(2-chlorophenoxy)propoxy]phenyl}-3-[4-(3-methoxypropyl)-3-oxo-3,4-dihydro-2H-benzo[1,4]oxazin-6-ylmethoxy] piperidine-1-carboxylate is used to obtain the title compound as a beige oil. Rf=0.12 (200:20:1 dichloromethane-methanol-conc. ammonia); Rt=4.40.

b) tert-Butyl 4-{4-[3-(2-chlorophenoxy)propoxy] phenyl}-3-[4-(3-methoxypropyl)-3-oxo-3,4-dihydro-2H-benzo[1,4]oxazin-6-ylmethoxy]piperidine-1-carboxylate Analogously to Method D, 0.495 g of tert-butyl 4-{4-[3-(2-chlorophenoxy)propoxy]phenyl}-3-hydroxypiperidine-1-carboxylate (Example 123e) and 0.318 g of 1-chloromethyl-3-methoxy-5-(3-methoxypropoxy)benzene (Example 2b) are reacted. The title compound is obtained as a colourless oil. Rf=0.17 (1:2 EtOAc-heptane); Rt=6.02.

EXAMPLE 122

N-(2-{4-[2-(4-{4-[3-(2-Methoxybenzyloxy)propoxy]phenyl}piperidin-3-yloxy)ethoxy]-2-methylpyrimidin-5-yl}ethyl)acetamide Analogously to Method A, 0.030 g of tert-butyl 3-{2-[5-(2-acetylaminoethyl)-2-methylpyrimidin-4-yloxy]ethoxy}-4-{4-[3-(2-methoxybenzyloxy)propoxy]phenyl}piperidine-1-carboxylate is used to prepare the title compound.

The starting materials are prepared as follows:

a) tert-Butyl 3-{2-[5-(2-acetylaminoethyl)-2-methylpyrimidin-4-yloxy]ethoxy}-4-{4-[3-(2-methoxybenzyloxy)propoxy]phenyl}piperidine-1-carboxylate A solution of 0.191 g of tert-butyl 3-{2-[5-(2-acetylaminoethyl)-6-chloro-2-methylpyrimidin-4-yloxy]ethoxy}-4-{4-[3-(2-methoxybenzyloxy)propoxy]phenyl}piperidine-1-carboxylate and 0.055 ml of triethylamine in 6 ml of ethanol is hydrogenated in the presence of 0.060 g of 10% Pd/C (added 4 times) at room temperature over 60 hours. The reaction mixture is clarified by filtration and the filtrate is concentrated by evaporation. The residue is taken up in ethyl acetate, washed with water and brine, dried over sodium sulphate and concentrated by evaporation. The title compound is obtained as a colourless oil from the residue by means of flash chromatography (SiO$_2$ 60F). Rf=0.22 (95:5 dichloromethane-methanol); Rt=4.54.

b) tert-Butyl 3-{2-[5-(2-acetylaminoethyl)-6-chloro-2-methylpyrimidin-4-yloxy]ethoxy}-4-{4-[3-(2-methoxybenzyloxy)propoxy]phenyl}piperidine-1-carboxylate A solution of 1.13 g of tert-butyl 3-{2-[5-(2-azidoethyl)-6-chloro-2-methylpyrimidin-4-yloxy]ethoxy}-4-{4-[3-(2-methoxybenzyloxy)propoxy]phenyl}piperidine-1-carboxylate in 25 ml of tetrahydrofuran is admixed at room temperature successively with 3.1 ml of water, 0.54 g of triphenylphosphine and 0.74 ml of acetic anhydride. The reaction mixture is stirred at room temperature over 16 hours and subsequently concentrated by evaporation. The title compound is obtained as a colourless oil from the residue by means of flash chromatography (SiO$_2$ 60F). Rf=0.10 (3:1 EtOAc-heptane); Rt=5.49.

c) tert-Butyl 3-{2-[5-(2-azidoethyl)-6-chloro-2-methylpyrimidin-4-yloxy]ethoxy}-4-{4-[3-(2-methoxybenzyloxy)propoxy]phenyl}piperidine-1-carboxylate Analogously to Example 56c, 1.15 g of tert-butyl 3-(2-{6-chloro-2-methyl-5-[2-(toluene-4-sulphonyloxy)ethyl]pyrimidin-4-yloxy}ethoxy)-4-{4-[3-(2-methoxybenzyloxy)propoxy]phenyl}piperidine-1-carboxylate are reacted. The title compound is obtained as a yellow oil. Rf=0.46 (1:1 EtOAc-heptane); Rt=6.31.

d) tert-Butyl 3-(2-{6-chloro-2-methyl-5-[2-(toluene-4-sulphonyloxy)ethyl]pyrimidin-4-yloxy}ethoxy)-4-{4-[3-(2-methoxybenzyloxy)propoxy]phenyl}piperidine-1-carboxylate Analogously to Method H, 1.10 g of tert-butyl 3-{2-[6-chloro-5-(2-hydroxyethyl)-2-methylpyrimidin-4-yloxy]ethoxy}-4-{4-[3-(2-methoxybenzyloxy)propoxy]phenyl}piperidine-1-carboxylate are reacted. The title compound is obtained as a colourless oil. Rf=0.40 (1:1 EtOAc-heptane); Rt=6.19.

e) tert-Butyl 3-{2-[6-chloro-5-(2-hydroxyethyl)-2-methylpyrimidin-4-yloxy]ethoxy}-4-{4-[3-(2-methoxybenzyloxy)propoxy]phenyl}piperidine-1-carboxylate 4.8 ml of diisobutylaluminium hydride (1.5M in toluene) are added dropwise at −70° C. over 10 minutes to the solution of 1.74 g of tert-butyl 3-[2-(6-chloro-5-methoxycarbonylmethyl-2-methylpyrimidin-4-yloxy)ethoxy]-4-{4-[3-(2-methoxybenzyloxy)propoxy]phenyl}piperidine-1-carboxylate in 20 ml of tetrahydrofuran. The reaction mixture is warmed slowly to −40° C. over 3 hours, admixed with 0.4 ml of methanol and subsequently warmed to room temperature. The reaction solution is admixed with 20 ml of 0.5N HCl and stirred vigorously over 10 minutes. The reaction mixture is extracted with tert-butyl methyl ether (2×). The combined organic phases are washed successively with 1M sodium potassium tartrate solution and brine, dried over sodium sulphate and concentrated by evaporation. The title compound is obtained as a colourless oil from the residue by means of flash chromatography (SiO$_2$ 60F). Rf=0.35 (2:1 EtOAc-heptane); Rt=5.75.

f) tert-Butyl 3-[2-(6-chloro-5-methoxycarbonylmethyl-2-methylpyrimidin-4-yloxy)ethoxy]-4-{4-[3-(2-methoxybenzyloxy)propoxy]phenyl}piperidine-1-carboxylate A solution of 1.95 g of tert-butyl 3-(2-hydroxyethoxy)-4-{4-[3-(2-methoxybenzyloxy)propoxy]-phenyl}piperidine-1-carboxylate (Example 14c) in 20 ml of 1,2-dimethoxyethane is admixed in portions at 0° C. with 0.195 g of sodium hydride dispersion (60%) and stirred for 30 minutes. A solution of 0.91 g of methyl (4,6-dichloro-2-methylpyrimidin-5-yl)acetate in 5 ml of dimethoxyethane is added dropwise and the reaction mixture is stirred at room temperature over 2.5 hours. The reaction mixture is admixed with water and extracted with tert-butyl methyl ether (3×). The combined organic phases are washed with brine, dried over sodium sulphate and concentrated by evaporation. The title compound is obtained as a colourless oil from the residue by means of flash chromatography (SiO$_2$ 60F). Rf=0.42 (1:1 EtOAc-heptane); Rt=6.10.

EXAMPLE 123

N-(2-{2-[2-(4-{4-[3-(2-Chlorophenoxy)propoxy]phenyl}piperidin-3-yloxy)ethoxy]-4-fluorophenyl}ethyl)acetamide Analogously to Method A, 0.25 g of tert-butyl 3-{2-[2-(2-acetylaminoethyl)-5-fluorophenoxy]ethoxy}-4-{4-[3-(2-chlorophenoxy)propoxy]phenyl}piperidine-1-carboxylate is used to prepare the title compound.

The starting materials are prepared as follows:

a) tert-Butyl 3-{2-[2-(2-acetylaminoethyl)-5-fluorophenoxy]ethoxy}-4-{4-[3-(2-chlorophenoxy)propoxy]phenyl}piperidine-1-carboxylate Analogously to Method G, 0.28 g of tert-butyl 4-{4-[3-(2-chlorophenoxy)propoxy]phenyl}-3-[2-(toluene-4-sulphonyloxy)ethoxy]piperidine-1-carboxylate and 0.17 g of N-[2-(4-fluoro-2-hydroxyphenyl)ethyl]acetamide (Example 112b) are reacted. The title compound is obtained as a yellow oil. Rf=0.58 (EtOAc); Rt=5.74.

b) tert-Butyl 4-{4-[3-(2-chlorophenoxy)propoxy]phenyl}-3-[2-(toluene-4-sulphonyloxy)ethoxy]piperidine-1-carboxylate Analogously to Method H, 0.41 g of tert-butyl 4-{4-[3-(2-chlorophenoxy)propoxy]phenyl}-3-(2-hydroxyethoxy)piperidine-1-carboxylate is reacted. The title compound is obtained as a yellow oil. Rf=0.34 (1:2 EtOAc-heptane); Rt=6.01.

c) tert-Butyl 4-{4-[3-(2-chlorophenoxy)propoxy]phenyl}-3-(2-hydroxyethoxy)piperidine-1-carboxylate Analogously to Example 14c, 1.64 g of tert-butyl 3-allyloxy-4-{4-[3-(2-chlorophenoxy)propoxy]phenyl}piperidine-1-carboxylate are reacted. The title compound is obtained as a yellow oil. Rf=0.54 (1:1 EtOAc-heptane); Rt=5.37.

d) tert-Butyl 3-allyloxy-4-{4-[3-(2-chlorophenoxy)propoxy]phenyl}piperidine-1-carboxylate Analogously to Method D, 2.01 g of tert-butyl 4-{4-[3-(2-chlorophenoxy)propoxy]phenyl}-3-hydroxypiperidine-1-carboxylate and 0.74 ml of allylbromide are reacted. The title compound is obtained as a colourless oil. Rf=0.80 (1:1 EtOAc-heptane); Rt=6.13.

e) tert-Butyl 4-{4-[3-(2-chlorophenoxy)propoxy]phenyl}-3-hydroxypiperidine-1-carboxylate Analogously to Method I, 5.84 g of tert-butyl 3-hydroxy-4-(4-hydroxyphenyl)piperidine-1-carboxylate and 6.00 g of 1-(3-bromopropoxy)-2-chlorobenzene are reacted. The title compound is obtained as a white solid. Rf=0.62 (1:2 EtOAc-heptane); Rt=5.33.

EXAMPLE 124

N-(2-{2-[2-(4-{4-[3-(2-Chlorophenoxy)propoxy]phenyl}piperidin-3-yloxy)ethoxy]phenyl}ethyl)acetamide Analogously to Method A, 0.137 g of tert-butyl 3-{2-[2-(2-acetylaminoethyl)phenoxy]ethoxy}-4-{4-[3-(2-chlorophenoxy)propoxy]phenyl}piperidine-1-carboxylate is used to prepare the title compound.

The starting material is prepared as follows:

a) tert-Butyl 3-{2-[2-(2-acetylaminoethyl)phenoxy]ethoxy}-4-{4-[3-(2-chlorophenoxy)propoxy]phenyl}piperidine-1-carboxylate Analogously to Method G, 0.28 g of tert-butyl 4-{4-[3-(2-chlorophenoxy)propoxy]phenyl}-3-[2-(toluene-4-sulphonyloxy)ethoxy]piperidine-1-carboxylate (Example 123b) and 0.15 g of N-[2-(2-hydroxyphenyl)ethyl]acetamide are reacted. The title compound is obtained as a yellow oil. Rf=0.65 (EtOAc); Rt=5.73.

EXAMPLE 125

1-(3-Methoxypropyl)-7-(4-{4-[4-(5-methoxypyrimidin-4-ylamino)butoxy]phenyl}piperidin-3-yloxymethyl)-3,4-dihydro-1H-quinolin-2-one Analogously to Method A, 0.130 g of tert-butyl 3-[1-(3-methoxypropyl)-2-oxo-1,2,3,4-tetrahydroquinolin-7-ylmethoxy]-4-{4-[4-(5-methoxypyrimidin-4-ylamino)butoxy]phenyl}piperidine-1-carboxylate is used to prepare the title compound.

The starting materials are prepared as follows:

a) tert-Butyl 3-[1-(3-methoxypropyl)-2-oxo-1,2,3,4-tetrahydroquinolin-7-ylmethoxy]-4-{4-[4-(5-methoxypyrimidin-4-ylamino)butoxy]phenyl}piperidine-1-carboxylate The mixture of 0.200 g of tert-butyl 4-[4-(4-aminobutoxy)phenyl]-3-[1-(3-methoxypropyl)-2-oxo-1,2,3,4-tetrahydroquinolin-7-ylmethoxy]piperidine-1-carboxylate, 0.058 g of 4-chloro-5-methoxypyrimidine, 0.0064 g of (±)-2,2'-bis(diphenylphosphine)-1,1'-binaphthyl, 0.387 g of sodium tert-butoxide and 0.0028 g of dipalladiumtris(dibenzylidenacetone)-chloroform complex in 10 ml of toluene is stirred under argon at 90° C. over 20 hours. The reaction mixture is cooled, admixed with brine (20 ml) and extracted with tert-butyl methyl ether (2×100 ml). The organic phases are washed successively with water (100 ml) and brine (100 ml), dried over sodium sulphate, filtered and concentrated by evaporation. The title compound is obtained as a brown oil from the residue by means of flash chromatography (SiO$_2$ 60F). Rf=0.25 (200:20:1 dichloromethane-methanol-conc. ammonia); Rt=4.60.

b) tert-Butyl 4-[4-(4-aminobutoxy)phenyl]-3-[1-(3-methoxypropyl)-2-oxo-1,2,3,4-tetrahydroquinolin-7-ylmethoxy]piperidine-1-carboxylate The solution of 0.650 g of tert-butyl 4-[4-(3-cyanopropoxy)phenyl]-3-[1-(3-methoxypropyl)-2-oxo-1,2,3,4-tetrahydroquinolin-7-ylmethoxy]piperidine-1-carboxylate in 10 ml of ammonia (2M in methanol) is hydrogenated in the presence of 0.65 g of Raney nickel at 45° C. over 3 hours. The reaction mixture is clarified by filtration and the filtrate is concentrated by evaporation. The title compound is obtained as a brown oil from the residue by means of flash chromatography (SiO$_2$ 60F). Rf=0.13 (200:20:1 dichloromethane-methanol-conc. ammonia); Rt=4.18.

c) tert-Butyl 4-[4-(3-cyanopropoxy)phenyl]-3-[1-(3-methoxypropyl)-2-oxo-1,2,3,4-tetrahydroquinolin-7-ylmethoxy]piperidine-1-carboxylate Analogously to Method I, 0.615 g of tert-butyl 4-(4-hydroxyphenyl)-3-[1-(3-methoxypropyl)-2-oxo-1,2,3,4-tetrahydroquinolin-7-ylmethoxy]piperidine-1-carboxylate (Example 44d) and 0.176 ml of 4-bromobutyronitrile are reacted. The title compound is obtained as a yellowish oil. Rf=0.16 (2:1 EtOAc-heptane); Rt=5.00.

EXAMPLE 126

1-(3-Methoxypropyl)-7-(4-{4-[4-(3-methoxypyridin-2-ylamino)butoxy]phenyl}piperidin-3-yloxymethyl-3,4-dihydro-1H-quinolin-2-one Analogously to Method A, 0.205 g of tert-butyl 3-[1-(3-methoxypropyl)-2-oxo-1,2,3,4-tetrahydroquinolin-7-ylmethoxy]-4-{4-[4-(3-methoxypyridin-2-ylamino)butoxy]phenyl}piperidine-1-carboxylate is used to prepare the title compound.

The starting material is prepared as follows:

a) tert-Butyl 3-[1-(3-methoxypropyl)-2-oxo-1,2,3,4-tetrahydroquinolin-7-ylmethoxy]-4-{4-[4-(3-methoxypyridin-2-ylamino)butoxy]phenyl}piperidine-1-carboxylate Analogously to Example 125a, 0.200 g of tert-butyl 4-[4-(4-aminobutoxy)phenyl]-3-[1-(3-methoxypropyl)-2-oxo-1,2,3,4-tetrahydroquinolin-7-ylmethoxy]piperidine-1-carboxylate (Example 125b) and 0.076 g of 2-bromo-3-methoxypyridine are reacted. The title compound is obtained as a colourless oil. Rf=0.34 (3:1:0.04 EtOAc-heptane-triethylamine); Rt=4.65.

EXAMPLE 127

5-(4-N-{4-[3-(2-Methoxybenzyloxy)propoxy]phenyl}piperidin-3-yloxymethyl)-N-(2-methoxyethyl)-2,N-dimethylbenzamide Analogously to Method A, 0.145 g of tert-butyl 4-{4-[3-(2-methoxybenzyloxy)propoxy]phenyl}-3-{3-[(2-methoxyethyl)methylcarbamoyl]-4-methylbenzyloxy}piperidine-1-carboxylate is used to prepare the title compound.

The starting materials are prepared as follows:

a) tert-Butyl 4-{4-[3-(2-methoxybenzyloxy)propoxy]phenyl}-3-{3-[(2-methoxyethyl)methylcarbamoyl]-4-methylbenzyloxy}piperidine-1-carboxylate The solution of 0.222 g of tert-butyl 3-(3-chlorocarbonyl-4-methylbenzyloxy)-4-{4-[3-(2-methoxybenzyloxy)propoxy]phenyl}piperidine-1-carboxylate in 6 ml of toluene is admixed at 0° C. with the solution of 0.129 g of 2-methoxy-N-methylethylamine in 6 ml of toluene. The reaction mixture is stirred at 0° C. over a further 1 hour and then concentrated by evaporation. The title compound is obtained as a colourless oil from the residue by means of flash chromatography (SiO₂ 60F). Rf=0.12 (1:2 EtOAc-heptane); Rt=5.72.

b) tert-Butyl 3-(3-chlorocarbonyl-4-methylbenzyloxy)-4-{4-[3-(2-methoxybenzyloxy)propoxy]phenyl}piperidine-1-carboxylate The solution of 0.474 g of tert-butyl 3-(3-carboxy-4-methylbenzyloxy)-4-{4-[3-(2-methoxybenzyloxy)propoxy]phenyl}piperidine-1-carboxylate in 12 ml of dichloromethane is admixed at 0° C. successively with 0.132 ml of oxalyl chloride and 0.005 ml of N,N-dimethylformamide. The reaction mixture is stirred over 1 hour and then concentrated by evaporation. The residue is dissolved once more in 20 ml of dichloromethane and concentrated by evaporation. This gives the crude title compound.

c) tert-Butyl 3-(3-carboxy-4-methylbenzyloxy)-4-{4-[3-(2-methoxybenzyloxy)propoxy]phenyl}piperidine-1-carboxylate Analogously to Method D, 1.68 g of tert-butyl 3-hydroxy-4-{4-[3-(2-methoxybenzyloxy)propoxy]phenyl}piperidine-1-carboxylate and 0.700 g of methyl 5-chloromethyl-2-methylbenzoate are reacted. The title compound is obtained as a white foam. Rf=0.07 (1:2 EtOAc-heptane); Rt=5.65.

d) Methyl 5-chloromethyl-2-methylbenzoate

Analogously to Method E, 1.20 g of methyl 5-hydroxymethyl-2-methylbenzoate are used to obtain the title compound as a colourless oil. Rf=0.52 (1:2 EtOAc-heptane); Rt=4.50.

EXAMPLE 128

5-(4-{4-[3-(2-Methoxybenzyloxy)propoxy]phenyl}piperidin-3-yloxymethyl)-N-(2-methoxyethyl)-2-methylbenzamide Analogously to Method A, 0.161 g of tert-butyl 4-{4-[3-(2-methoxybenzyloxy)propoxy]phenyl}-3-[3-(2-methoxyethylcarbamoyl)-4-methylbenzyloxy]piperidine-1-carboxylate is used to prepare the title compound.

The starting material is prepared as follows:

a) tert-Butyl 4-{4-[3-(2-methoxybenzyloxy)propoxy]phenyl}-3-[3-(2-methoxyethylcarbamoyl)-4-methylbenzyloxy]piperidine-1-carboxylate Analogously to Example 127a, 0.222 g of tert-butyl 3-(3-chlorocarbonyl-4-methylbenzyloxy)-4-{4-[3-(2-methoxybenzyloxy)propoxy]phenyl}piperidine-1-carboxylate (Example 127b) and 0.053 g of 2-methoxyethylamine are reacted. The title compound is obtained as a colourless oil. Rf=0.14 (1:2 EtOAc-heptane); Rt=5.54.

EXAMPLE 129

3-Methoxy-N-[5-(4-{4-[3-(2-methoxybenzyloxy)propoxy]phenyl}piperidin-3-yloxymethyl-2-methylphenyl]-N-methylpropionamide Analogously to Method A, 0.325 g of tert-butyl 4-{4-[3-(2-methoxybenzyloxy)propoxy]phenyl}-3-{3-[(3-methoxypropionyl)methylamino]-4-methylbenzyloxy}piperidine-1-carboxylate is used to prepare the title compound.

The starting materials are prepared as follows:

a) tert-Butyl 4-{4-[3-(2-methoxybenzyloxy)propoxy]phenyl}-3-{3-[(3-methoxypropionyl)methylamino]-4-methylbenzyloxy}piperidine-1-carboxylate Analogously to Method D, 0.477 g of tert-butyl 3-hydroxy-4-{4-[3-(2-methoxybenzyloxy)propoxy]phenyl}piperidine-1-carboxylate and 0.284 g of N-(5-chloromethyl-2-methylphenyl)-3-methoxy-N-methylpropionamide are reacted. The title compound is obtained as a yellowish oil. Rf=0.22 (1:1 EtOAc-heptane); Rt=5.82.

b) N-(5-Chloromethyl-2-methylphenyl)-3-methoxy-N-methylpropionamide

Analogously to Method E, 2.50 g of N-(5-hydroxymethyl-2-methylphenyl)-3-methoxy-N-methylpropionamide are used to obtain the title compound as a colourless oil. Rf=0.43 (3:1 EtOAc-heptane); Rt=3.73.

c) N-(5-Hydroxymethyl-2-methylphenyl)-3-methoxy-N-methylpropionamide

The solution of 4.50 g of 3-methoxy-N-methyl-N-[2-methyl-5-(tetrahydropyran-2-yloxymethyl)phenyl]propionamide in 70 ml of ethanol is admixed with 0.350 g of pyridinium p-toluenesulphonate and stirred at 60° C. over 2 hours. The reaction mixture is cooled and concentrated by evaporation. The title compound is obtained as a colourless oil from the residue by means of flash chromatography (SiO$_2$ 60F). Rf=0.15 (3:1 EtOAc-heptane); Rt=2.60.

d) 3-Methoxy-N-methyl-N-[2-methyl-5-(tetrahydropyran-2-yloxymethyl)phenyl]propionamide Analogously to Example 116a, 5.15 g of 3-methoxy-N-[2-methyl-5-(tetrahydropyran-2-yloxymethyl)phenyl]propionamide are used to obtain the title compound as a colourless oil. Rf=0.35 (2:1 EtOAc-heptane); Rt=3.91.

e) 3-Methoxy-N-[2-methyl-5-(tetrahydropyran-2-yloxymethyl)phenyl]propionamide

Analogously to Example 116b, 4.95 g of 2-methyl-5-(tetrahydropyran-2-yloxymethyl)phenylamine and 3.27 g of 3-methoxypropionyl chloride are reacted. The title compound is obtained as a white solid. Rf=0.33 (2:1 EtOAc-heptane); Rt=3.60.

f) 2-Methyl-5-(tetrahydropyran-2-yloxymethyl)phenylamine

The solution of 12.3 g of 2-(4-methyl-3-nitrobenzyloxy)tetrahydropyran in 150 ml of ethanol is hydrogenated in the presence of 1.25 g of 10% Pd/C over 24 hours. The reaction mixture is filtered and the filtrate is concentrated by evaporation. The title compound is obtained as a colourless oil from the residue by means of flash chromatography (SiO$_2$ 60F). Rf=0.19 (1:2 EtOAc-heptane); Rt=2.72.

g) 2-(4-Methyl-3-nitrobenzyloxy)tetrahydropyran

The solution of 9.85 g of 4-methyl-3-nitrobenzyl alcohol in 200 ml of dichloromethane is admixed successively with 10.9 ml of 3,4-dihydro-2H-pyran and 1.12 g of p-toluenesulphonic acid monohydrate. The reaction mixture is stirred at room temperature over 18 hours. The solution is poured onto 1M sodium hydrogencarbonate solution (300 ml) and extracted with tert-butyl methyl ether (2×300 ml). The organic phase is washed with brine (300 ml), dried over sodium sulphate, filtered and concentrated by evaporation. The title compound is obtained as a colourless oil from the residue by means of flash chromatography (SiO$_2$ 60F). Rf=0.49 (1:2 EtOAc-heptane); Rt=4.73.

EXAMPLE 130

N-Isopropyl-3-methoxy-N-[3-(4-{4-[3-(2-methoxybenzyloxy)propoxy]phenyl}piperidin-3-yloxymethyl)phenyl]propionamide Analogously to Method A, 0.400 g of tert-butyl 3-{3-[isopropyl-(3-methoxypropionyl)amino]benzyloxy}-4-{4-[3-(2-methoxybenzyloxy)propoxy]phenyl}piperidine-1-carboxylate is used to prepare the title compound.

The starting materials are prepared as follows:

a) tert-Butyl 3-{3-[isopropyl-(3-methoxypropionyl)amino]benzyloxy}-4-{4-[3-(2-methoxybenzyloxy)propoxy]phenyl}piperidine-1-carboxylate Analogously to Example 116b, 0.400 g of tert-butyl 3-(3-isopropylaminobenzyloxy)-4-{4-[3-(2-methoxybenzyloxy)propoxy]phenyl}piperidine-1-carboxylate and 0.270 g of 3-methoxypropionyl chloride are reacted. The title compound is obtained as a colourless oil. Rf=0.27 (1:1 EtOAc-heptane); Rt=5.97.

b) tert-Butyl 3-(3-isopropylaminobenzyloxy)-4-{4-[3-(2-methoxybenzyloxy)propoxy]phenyl}piperidine-1-carboxylate Analogously to Example 125a, 0.510 g of tert-butyl 3-(3-bromobenzyloxy)-4-{4-[3-(2-methoxybenzyloxy)propoxy]phenyl}piperidine-1-carboxylate and 0.086 ml of isopropylamine are reacted. The title compound is obtained as a yellowish oil. Rf=0.30 (1:2 EtOAc-heptane); Rt=5.18.

c) tert-Butyl 3-(3-bromobenzyloxy)-4-{4-[3-(2-methoxybenzyloxy)propoxy]phenyl}piperidine-1-carboxylate Analogously to Method D, 4.14 g of tert-butyl 3-hydroxy-4-{4-[3-(2-methoxybenzyloxy)propoxy]phenyl}piperidine-1-carboxylate and 2.31 g of 3-bromobenzyl bromide are reacted. The title compound is obtained as a yellowish oil. Rf=0.40 (1:2 EtOAc-heptane); Rt=6.45.

EXAMPLE 133

N-[4-Fluoro-2-(4-{4-[3-(2-methoxybenzyloxy)propoxy]phenyl}piperidin-3-yloxymethyl)phenyl]-4-methoxy-N-methylbutyramide Analogously to Method A, 0.400 g of tert-butyl 3-{5-fluoro-2-[(4-methoxybutyryl)methylamino]benzyloxy}-4-{4-[3-(2-methoxybenzyloxy)propoxy]phenyl}piperidine-1-carboxylate is used to prepare the title compound.

The starting materials are prepared as follows:

a) tert-Butyl 3-{5-fluoro-2-[(4-methoxybutyryl)methylamino]benzyloxy}-4-{4-[3-(2-methoxybenzyloxy)propoxy]phenyl}piperidine-1-carboxylate Analogously to Example 116a, 0.505 g of tert-butyl 3-[5-fluoro-2-(4-methoxybutyrylamino)benzyloxy]-4-{4-[3-(2-methoxybenzyloxy)propoxy]phenyl}piperidine-1-carboxylate is used to obtain the title compound as a beige oil. Rf=0.43 (2:1 EtOAc-heptane); Rt=5.87.

b) tert-Butyl 3-[5-fluoro-2-(4-methoxybutyrylamino)benzyloxy]-4-{4-[3-(2-methoxybenzyloxy)propoxy]phenyl}piperidine-1-carboxylate Analogously to Example 116b, 0.487 g of tert-butyl 3-(2-amino-5-fluorobenzyloxy)-4-{4-[3-(2-methoxybenzyloxy)propoxy]phenyl}piperidine-1-carboxylate and 0.322 g of 4-methoxybutyryl chloride are reacted. The title compound is obtained as a beige oil. Rf=0.22 (1:1 EtOAc-heptane); Rt=5.73.

c) tert-Butyl 3-(2-amino-5-fluorobenzyloxy)-4-{4-[3-(2-methoxybenzyloxy)propoxy]phenyl}piperidine-1-carboxylate Analogously to Example 116c, 1.81 g of tert-butyl 3-(2-bromo-5-fluorobenzyloxy)-4-{4-[3-(2-methoxybenzyloxy)propoxy]phenyl}piperidine-1-carboxylate are used to obtain the title compound as a yellow oil. Rf=0.16 (1:2 EtOAc-heptane); Rt=5.26.

d) tert-Butyl 3-(2-bromo-5-fluorobenzyloxy)-4-{4-[3-(2-methoxybenzyloxy)propoxy]phenyl}piperidine-1-carboxylate Analogously to Method D, 1.45 g of tert-butyl 3-hydroxy-4-{4-[3-(2-methoxybenzyloxy)propoxy]phenyl}piperidine-1-carboxylate and 0.816 g of 1-bromo-2-chloromethyl-4-fluorobenzene are reacted. The title compound is obtained as a yellowish oil. Rf=0.35 (1:2 EtOAc-heptane); Rt=6.39.

e) 1-Bromo-2-chloromethyl-4-fluorobenzene

Analogously to Method E, 4.80 g of (2-bromo-5-fluorophenyl)methanol are used to obtain the title compound. Rf=0.61 (1:3 EtOAc-heptane); Rt=4.77.

EXAMPLE 134

4-{4-[3-(2-Methoxybenzyloxy)propoxy]phenyl}-3-{3-[1-(3-methoxypropyl)-1H-imidazol-2-yl]benzyloxy}piperidine Analogously to Method A, 0.140 g of tert-butyl 4-{4-[3-(2-methoxybenzyloxy)propoxy]phenyl}-3-{3-[1-(3-methoxypropyl)-1H-imidazol-2-yl]benzyloxy}piperidine-1-Carboxylate is used to prepare the title compound.

The starting materials are prepared as follows:

a) tert-Butyl 4-{4-[3-(2-methoxybenzyloxy)propoxy]phenyl}-3-{3-[1-(3-methoxypropyl)-1H-imidazol-2-yl]benzyloxy}piperidine-1-carboxylate The mixture of 0.050 g of tetrakis(triphenylphosphine)palladium(0) in 1.0 ml of 1,2-dimethoxyethane is admixed with the solution of 0.319 g of tert-butyl 4-{4-[3-(2-methoxybenzyloxy)propoxy]phenyl}-3-[3-(4,4,5,5-tetramethyl-[1,3,2]dioxaborolan-2-yl)benzyloxy]piperidine-1-carboxylate and 0.144 g of 2-bromo-1-(3-methoxypropyl)-1H-imidazole in 2.0 ml of 1,2-dimethoxyethane and 0.3 ml of ethanol. The reaction mixture is admixed with 0.9 ml of 2M sodium carbonate solution and stirred at reflux over 20 hours. The resulting reaction solution is concentrated by evaporation, admixed with 1:1 water/brine mixture (30 ml) and extracted with ethyl acetate (2×30 ml). The organic phases are washed with brine (30 ml), dried over sodium sulphate, filtered and concentrated by evaporation. The title compound is obtained as a colourless oil from the residue by means of flash chromatography (SiO$_2$ 60F). Rf=0.15 (97:3 dichloromethane-methanol); Rt=5.23.

b) tert-Butyl 4-{4-[3-(2-methoxybenzyloxy)propoxy]phenyl}-3-[3-(4,4,5,5-tetramethyl-[1,3,2]dioxaborolan-2-yl)benzyloxy]piperidine-1-carboxylate The mixture of 0.532 g of tert-butyl 3-(3-bromobenzyloxy)-4-{4-[3-(2-methoxybenzyloxy)propoxy]phenyl}piperidine-1-carboxylate (Example 130c), 0.323 g of bis(pinacolato)diboron, 0.247 g of potassium acetate and 0.030 g of [1,1'-bis(diphenylphosphino)ferrocene]dichloropalladium(II) is admixed under argon with 4.0 ml of dimethyl sulphoxide and stirred at 80° C. over 20 hours. The reaction mixture is cooled, admixed with a water/brine mixture (30 ml) and extracted with tert-butyl methyl ether (2×20 ml). The organic phases are washed with brine (20 ml), dried over sodium sulphate, filtered and concentrated by evaporation. The title compound is obtained as a colourless oil from the residue by means of flash chromatography (SiO$_2$ 60F). Rf=0.16 (1:4 EtOAc-heptane); Rt=6.52.

c) 2-Bromo-1-(3-methoxypropyl)-1H-imidazole

The solution of 1.05 g of 1-(3-methoxypropyl)-1H-imidazole in 14 ml of tetrahydrofuran is cooled to −70° C. and admixed slowly with 4.6 ml of n-butyllithium (1.6M in hexane). The mixture is stirred at −70° C. over 1 hour and subsequently admixed slowly with the solution of 2.54 g of tetrabromomethane in 14 ml of tetrahydrofuran. After a further 30 minutes, the reaction mixture is admixed with 25 ml of saturated aqueous ammonium chloride solution and extracted with tert-butyl methyl ether (2×25 ml). The organic phases are washed with brine, (20 ml), dried over sodium sulphate, filtered and concentrated by evaporation. The title compound is obtained as a colourless oil from the residue by means of flash chromatography (SiO$_2$ 60F). Rf=0.51 (200:20:1 dichloromethane-methanol-conc. ammonia); Rt=1.78.

d) 1-(3-Methoxypropyl)-1H-imidazole

The mixture of 5.02 g of imidazole and 50 ml of N,N-dimethylformamide is admixed at 0° C. with 3.52 g of sodium hydride dispersion (69%) and stirred at room temperature over 1 hour. The solution of 8.36 g of 1-chloro-3-methoxypropane in 10 ml of N,N-dimethylformamide is added and the reaction solution is subsequently stirred at 60° C. over 2 hours. The reaction mixture is cooled, poured onto ice-water (150 ml) and extracted with ethyl acetate (3×150 ml). The organic phases are washed with water (3×150 ml) and brine (150 ml), dried over sodium sulphate, filtered and concentrated by evaporation. The title compound is obtained as a colourless oil from the residue by means of flash chromatography (SiO$_2$ 60F). Rf=0.25 (200:20:1 dichloromethane-methanol-conc. ammonia); Rt=1.55.

EXAMPLE 135

3-Methoxy-N-{2-[2-(4-{4-[3-(2-methoxybenzyloxy)propoxy]phenyl}piperidin-3-yloxy)ethoxy]phenyl}propionamide Analogously to Method A, 0.435 g of tert-butyl 4-{4-[3-(2-methoxybenzyloxy)propoxy]phenyl}-3-{2-[2-(3-methoxypropionylamino)phenoxy]ethoxy}piperidine-1-carboxylate is used to prepare the title compound.

The starting material is prepared as follows:

a) tert-Butyl 4-{4-[3-(2-methoxybenzyloxy)propoxy]phenyl}-3-{2-[2-(3-methoxypropionylamino)phenoxy]ethoxy}piperidine-1-carboxylate Analogously to Method G, 0.458 g of tert-butyl 4-{4-[3-(2-methoxybenzyloxy)propoxy]phenyl}-3-[2-(toluene-4-sulphonyloxy)ethoxy]piperidine-1-carboxylate (Example 14b) and 0.32 g of N-(2-hydroxyphenyl)-3-methoxypropionamide are reacted. The title compound is obtained as a colourless oil. Rf=0.50 (1:1 EtOAc-heptane); Rt=5.70.

EXAMPLE 136

2-[2-(4-{4-[3-(2-Methoxybenzyloxy)propoxy]phenyl}piperidin-3-yloxy)ethoxy]-N-(2 methoxyethyl)benzamide Analogously to Method A, 0.435 g of tert-butyl 4-{4-[3-(2-methoxybenzyloxy)propoxy]phenyl}-3-{2-[2-(2-methoxyethylcarbamoyl)phenoxy]ethoxy}piperidine-1-carboxylate is used to prepare the title compound.

The starting material is prepared as follows:

a) tert-Butyl 3-{2-[2-(2-cyanoethyl)phenoxy]ethoxy}-4-{4-[3-(2-methoxybenzyloxy)propoxy]phenyl}piperidine-1-carboxylate Analogously to Method G, 0.456 g of tert-butyl 4-{4-[3-(2-methoxybenzyloxy)propoxy]phenyl}-3-[2-(toluene-4-sulphonyloxy)ethoxy]piperidine-1-carboxylate (Example 14b) and 0.27 g of 2-hydroxy-N-(2-methoxyethyl)benzamide are reacted. The title compound is obtained as a yellow oil. Rf=0.40 (1:1 EtOAc-heptane); Rt=5.60.

EXAMPLE 137

Methyl 4-{2-[2-(4-{4-[3-(2-methoxybenzyloxy)propoxy]phenyl}piperidin-3-yloxy)ethoxy]phenyl}butyrate Analogously to Method A, 0.081 g of tert-butyl 3-{2-[2-(3-carboxypropyl)phenoxy]ethoxy}-4-{4-[3-(2-methoxybenzyloxy)propoxy]phenyl}piperidine-1-carboxylate is used to prepare the title compound.

The starting material is prepared as follows:

a) tert-Butyl 3-{2-[2-(3-carboxypropyl)phenoxy]ethoxy}-4-{4-[3-(2-methoxybenzyloxy)propoxy]phenyl}piperidine-1-carboxylate Analogously to Method G, 0.549 g of tert-butyl 4-{4-[3-(2-methoxybenzyloxy)propoxy]phenyl}-3-[2-(toluene-4-sulphonyloxy)ethoxy]piperidine-1-carboxylate (Example 14b) and 0.075 g of 4-(2-hydroxyphenyl)butyric acid are reacted. The yellow oil obtained after chromatography is dissolved in 9.5 ml of methanol and 3.2 ml of water, admixed with 1.5 ml of 1N NaOH and stirred at reflux over 2 hours. The reaction mixture is cooled to room temperature, diluted with ethyl acetate and water and acidified with 2N HCl. The aqueous phase is extracted with ethyl acetate. The combined organic phases are washed with water, dried over sodium sulphate and concentrated by evaporation. The title compound is obtained as a colourless resin from the residue by means of flash chromatography (SiO$_2$ 60F). Rf=0.20 (95:5 dichloromethane-methanol); Rt=5.86.

EXAMPLE 138

3-Ethoxy-N-[3-(4-{4-[3-(2-methoxybenzyloxy)propoxy]phenyl}piperidin-3-yloxymethyl)phenyl]-N-methylpropionamide Analogously to Method A, 0.507 g of tert-butyl 3-{3-[(3-ethoxypropionyl)methylamino]benzyloxy}-4-{4-[3-(2-methoxybenzyloxy)propoxy]phenyl}piperidine-1-carboxylate is used to prepare the title compound.

The starting materials are prepared as follows:

a) tert-Butyl 3-{3-[(3-ethoxypropionyl)methylamino]benzyloxy}-4-{4-[3-(2-methoxybenzyloxy)propoxy]phenyl}piperidine-1-carboxylate Analogously to Example 116a, 1.96 g of tert-butyl 3-[3-(3-ethoxypropionylamino)benzyloxy]-4-{4-[3-(2-methoxybenzyloxy)propoxy]phenyl}piperidine-1-carboxylate are used to prepare the title compound as a colourless oil. Rf=0.22 (1:1 EtOAc-heptane); Rt=5.82.

b) tert-Butyl 3-[3-(3-ethoxypropionylamino)benzyloxy]-4-{4-[3-(2-methoxybenzyloxy)propoxy]phenyl}piperidine-1-carboxylate Analogously to Example 116b, 1.81 g of tert-butyl 3-(3-aminobenzyloxy)-4-{4-[3-(2-methoxybenzyloxy)propoxy]phenyl}piperidine-1-carboxylate (Example 118c) and 0.612 g of 3-ethoxypropionyl chloride are reacted. The title compound is obtained as a colourless oil. Rf=0.22 (1:1 EtOAc-heptane); Rt=5.77.

EXAMPLE 139

6-(4-{4-[3-(3-Methoxyphenoxy)propoxy]phenyl}piperidin-3-yloxymethyl)-4-(3-methoxypropyl)-3,4-dihydro-2H-benzo[1,4]oxazine Analogously to Method C, 0.600 g of 6-(4-{4-[3-(3-methoxyphenoxy)propoxy]phenyl}piperidin-3-yloxymethyl)-4-(3-methoxypropyl)-4H-benzo[1,4]oxazin-3-one is used to prepare the title compound.

The starting materials are prepared as follows:

a) 6-(4-{4-[3-(3-Methoxyphenoxy)propoxy]phenyl}piperidin-3-yloxymethyl)-4-(3-methoxypropyl)-4H-benzo[1,4]oxazin-3-one Analogously to Method A, 0.720 g of tert-butyl 4-{4-[3-(3-methoxyphenoxy)propoxy]phenyl}-3-[4-(3-methoxypropyl)-3-oxo-3,4-dihydro-2H-benzo[1,4]oxazin-6-ylmethoxy]piperidine-1-carboxylate is used to obtain the title compound as a yellowish oil. Rf=0.10 (200:20:1 dichloromethane-methanol-conc. ammonia); Rt=4.11.

b) tert-Butyl 4-{4-[3-(3-methoxyphenoxy)propoxy]phenyl}-3-[4-(3-methoxypropyl)-3-oxo-3,4-dihydro-2H-benzo[1,4]oxazin-6-ylmethoxy]piperidine-1-carboxylate Analogously to Method D, 1.0 g of tert-butyl 3-hydroxy-4-{4-[3-(3-methoxyphenoxy)propoxy]-phenyl}piperidine-1-carboxylate and 0.608 g of 6-chloromethyl-4-(3-methoxypropyl)-4H-benzo[1,4]oxazin-3-one (Example 2a) are reacted. The title compound is obtained as an opaque oil. Rf=0.28 (1:1 EtOAc-heptane); Rt=5.90.

c) tert-Butyl 3-hydroxy-4-{4-[3-(3-methoxyphenoxy)propoxy]phenyl}piperidine-1-carboxylate Analogously to Method I, 0.750 g of tert-butyl 3-hydroxy-4-(4-hydroxyphenyl)piperidine-1-carboxylate and 0.808 g of 1-(3-bromopropoxy)-3-methoxybenzene are reacted. The title compound is obtained as a slightly yellowish oil. Rf=0.30 (1:2 EtOAc-heptane); Rt=5.18.

EXAMPLE 140

6-(4-{4-[3-(3-Fluorophenoxy)propoxy]phenyl}piperidin-3-yloxymethyl)-4-(3-methoxypropyl)-3,4-dihydro-2H-benzo[1,4]oxazine Analogously to Method C, 0.490 g of 6-(4-{4-[3-(3-fluorophenoxy)propoxy]phenyl}piperidin-3-yloxymethyl)-4-(3-methoxypropyl)-4H-benzo[1,4]oxazin-3-one is used to prepare the title compound.

The starting materials are prepared as follows:

a) 6-(4-{4-[3-(3-Fluorophenoxy)propoxy]phenyl}piperidin-3-yloxymethyl)-4-(3-methoxypropyl)-4H-benzo[1,4]oxazin-3-one Analogously to Method A, 0.860 g of tert-butyl 4-{4-[3-(3-fluorophenoxy)propoxy]phenyl}-3-[4-(3-methoxypropyl)-3-oxo-3,4-dihydro-2H-benzo[1,4]oxazin-6-ylmethoxy]piperidine-1-carboxylate is used to obtain the title compound as a yellowish oil. Rf=0.13 (200:20:1 dichloromethane-methanol-conc. ammonia); Rt=4.20.

b) tert-Butyl 4-{4-[3-(3-fluorophenoxy)propoxy]phenyl}-3-[4-(3-methoxypropyl)-3-oxo-3,4-dihydro-2H-benzo[1,4]oxazin-6-ylmethoxy]piperidine-1-carboxylate Analogously to Method D, 1.1 g of tert-butyl 4-{4-[3-(3-fluorophenoxy)propoxy]phenyl}-3-hydroxypiperidine-1-carboxylate and 0.687 g of 6-chloromethyl-4-(3-methoxypropyl)-4H-benzo[1,4]oxazin-3-one (Example 2a) are reacted. The title compound is obtained as an opaque oil. Rf=0.42 (1:1 EtOAc-heptane); Rt=5.97.

c) tert-Butyl 4-{4-[3-(3-fluorophenoxy)propoxy]phenyl}-3-hydroxypiperidine-1-carboxylate Analogously to Method I, 0.750 g of tert-butyl 3-hydroxy-4-(4-hydroxyphenyl)piperidine-1-carboxylate and 0.723 g of 1-(3-bromopropoxy)-3-fluorobenzene are reacted. The title compound is obtained as a slightly yellowish oil. Rf=0.30 (1:2 EtOAc-heptane); Rt=5.29.

EXAMPLE 141

6-(4-{4-[3-(2-Fluorophenoxy)propoxy]phenyl}piperidin-3-yloxymethyl)-4-(3-methoxypropyl)-3,4-dihydro-2H-benzo[1,4]oxazine Analogously to Method C, 0.333 g of 6-(4-{4-[3-(2-fluorophenoxy)propoxy]phenyl}piperidin-3-yloxymethyl)-4-(3-methoxypropyl)-4H-benzo[1,4]oxazin-3-one is used to prepare the title compound.

The starting materials are prepared as follows:

a) 6-(4-{4-[3-(2-Fluorophenoxy)propoxy]phenyl}piperidin-3-yloxymethyl)-4-(3-methoxypropyl)-4H-benzo[1,4]oxazin-3-one Analogously to Method A, 0.568 g of tert-butyl 4-{4-[3-(2-fluorophenoxy)propoxy]phenyl}-3-[4-(3-methoxypropyl)-3-oxo-3,4-dihydro-2H-benzo[1,4]oxazin-6-ylmethoxy]piperidine-1-carboxylate is used to obtain the title compound as a yellowish oil. Rf=0.28 (200:20:1 dichloromethane-methanol-conc. ammonia); Rt=4.11.

b) tert-Butyl 4-{4-[3-(2-fluorophenoxy)propoxy]phenyl}-3-[4-(3-methoxypropyl)-3-oxo-3,4-dihydro-2H-benzo[1,4]oxazin-6-ylmethoxy]piperidine-1-carboxylate Analogously to Method D, 1.08 g of tert-butyl 4-{4-[3-(2-fluorophenoxy)propoxy]phenyl}-3-hydroxypiperidine-1-carboxylate and 0.720 g of 6-chloromethyl-4-(3-methoxypropyl)-4H-benzo[1,4]oxazin-3-one (Example 2a) are reacted. The title compound is obtained as an opaque oil. Rf=0.30 (1:1 EtOAc-heptane); Rt=5.89.

c) tert-Butyl 4-{4-[3-(2-fluorophenoxy)propoxy]phenyl}-3-hydroxypiperidine-1-carboxylate Analogously to Method I, 0.750 g of tert-butyl 3-hydroxy-4-(4-hydroxyphenyl)piperidine-1-carboxylate and 0.753 g of 1-(3-bromopropoxy)-2-fluorobenzene are reacted. The title compound is obtained as a slightly yellowish oil. Rf=0.53 (2:1 EtOAc-heptane); Rt=5.10.

EXAMPLE 142

6-(4-{4-[3-(2,5-Difluorophenoxy)propoxy]phenyl}piperidin-3-yloxymethyl)-4-(3-methoxypropyl)-3,4-dihydro-2H-benzo[1,4]oxazine Analogously to Method C, 0.414 g of 6-(4-{4-[3-(2,5-difluorophenoxy)propoxy]phenyl}piperidin-3-yloxymethyl)-4-(3-methoxypropyl)-4H-benzo[1,4]oxazin-3-one is used to prepare the title compound.

The starting materials are prepared as follows:

a) 6-(4-{4-[3-(2,5-Difluorophenoxy)propoxy]phenyl}piperidin-3-yloxymethyl)-4-(3-methoxypropyl)-4H-benzo[1,4]oxazin-3-one Analogously to Method A, 0.585 g of tert-butyl 4-{4-[3-(2,5-difluorophenoxy)propoxy]phenyl}-3-[4-(3-methoxypropyl)-3-oxo-3,4-dihydro-2H-benzo[1,4]oxazin-6-ylmethoxy]piperidine-1-carboxylate is used to obtain the title compound as a yellowish oil. Rf=0.32 (200:20:1 dichloromethane-methanol-conc. ammonia); Rt=4.16.

b) tert-Butyl 4-{4-[3-(2,5-difluorophenoxy)propoxy]
phenyl}-3-[4-(3-methoxypropyl)-3-oxo-3,4-dihydro-
2H-benzo[1,4]oxazin-6-ylmethoxy]piperidine-1-
carboxylate Analogously to Method D, 1.09 g of tert-butyl 4-{4-[3-(2,5-difluorophenoxy)propoxy]phenyl}-3-hydroxypiperidine-1-carboxylate and 0.720 g of 6-chloromethyl-4-(3-methoxypropyl)-4H-benzo[1,4]oxazin-3-one (Example 2a) are reacted. The title compound is obtained as slightly yellowish oil. Rf=0.40 (1:1 EtOAc-heptane); Rt=5.90.

c) tert-Butyl 4-{4-[3-(2,5-difluorophenoxy)propoxy]
phenyl}-3-hydroxypiperidine-1-carboxylate Analogously to Method I, 0.750 g of tert-butyl 3-hydroxy-4-(4-hydroxyphenyl)piperidine-1-carboxylate and 0.812 g of 2-(3-bromopropoxy)-1,4-difluorobenzene are reacted. The title compound is obtained as a slightly yellowish oil. Rf=0.35 (1:1 EtOAc-heptane); Rt=5.14.

d) 2-(3-Bromopropoxy)-1,4-difluorobenzene

Analogously to Example 91b, 1.40 g of 2,5-difluorophenol and 21.5 g of 1,3-dibromopropane are reacted. The title compound is obtained as a colourless oil. Rf=0.59 (1:3 EtOAc-heptane); Rt=4.84.

EXAMPLE 143

4-(3-Methoxypropyl)-6-{4-[4-(3-o-tolyloxypropoxy)
phenyl]piperidin-3-yloxymethyl}-3,4-dihydro-2H-
benzo[1,4]oxazine Analogously to Method C, 0.358 g of 4-(3-methoxypropyl)-6-{4-[4-(3-o-tolyloxypropoxy)phenyl]piperidin-3-yloxymethyl}-4H-benzo[1,4]oxazin-3-one is used to prepare the title compound.

The starting materials are prepared as follows:

a) 4-(3-Methoxypropyl)-6-{4-[4-(3-o-tolyloxypropoxy)phenyl]piperidin-3-yloxymethyl}-4H benzo[1,4]oxazin-3-one Analogously to Method A, 0.580 g of tert-butyl 3-[4-(3-methoxypropyl)-3-oxo-3,4-dihydro-2H-benzo[1,4]oxazin-6-ylmethoxy]-4-[4-(3-o-tolyloxypropoxy)phenyl]piperidine-1-carboxylate is used to obtain the title compound as a yellowish oil. Rf=0.28 (200:20:1 dichloromethane-methanol-conc. ammonia); Rt=4.41.

b) tert-Butyl 3-[4-(3-methoxypropyl)-3-oxo-3,4-
dihydro-2H-benzo[1,4]oxazin-6-yl methoxy]-4-[4-
(3-o-tolyloxypropoxy)phenyl]piperidine-1-carboxy-
late Analogously to Method D, 1.04 g of tert-butyl 3-hydroxy-4-[4-(3-o-tolyloxypropoxy)phenyl]piperidine-1-carboxylate and 0.700 g of 6-chloromethyl-4-(3-methoxypropyl)-4H-benzo[1,4]oxazin-3-one (Example 2a) are reacted. The title compound is obtained as a colourless oil. Rf=0.40 (1:1 EtOAc-heptane); Rt=5.90.

c) tert-Butyl 3-hydroxy-4-[4-(3-o-tolyloxypropoxy)
phenyl]piperidine-1-carboxylate Analogously to Method I, 0.750 g of tert-butyl 3-hydroxy-4-(4-hydroxyphenyl)piperidine-1-carboxylate and 0.732 g of 1-(3-bromopropoxy)-2-methylbenzene are reacted. The title compound is obtained as a slightly yellowish oil. Rf=0.57 (1:2 EtOAc-heptane); Rt=5.45.

EXAMPLE 144

6-(4-{4-[3-(2-Methoxyphenoxy)propoxy]
phenyl}piperidin-3-yloxymethyl)-4-(3-methoxypro-
pyl)-3,4-dihydro-2H-benzo[1,4]oxazine Analogously to Method C, 0.328 g of 6-(4-{4-[3-(2-methoxyphenoxy)propoxy]phenyl}piperidin-3-yloxymethyl)-4-(3-methoxypropyl)-4H-benzo[1,4]oxazin-3-one is used to prepare the title compound.

The starting materials are prepared as follows:

a) 6-(4-{4-[3-(2-Methoxyphenoxy)propoxy]
phenyl}piperidin-3-yloxymethyl)-4-(3-methoxypro-
pyl)-4H-benzo[1,4]oxazin-3-one Analogously to Method A, 0.514 g of tert-butyl 4-{4-[3-(2-methoxyphenoxy)propoxy]phenyl}-3-[4-(3-methoxypropyl)-3-oxo-3,4-dihydro-2H-benzo[1,4]oxazin-6-ylmethoxy]piperidine-1-carboxylate is used to obtain the title compound as a yellowish oil. Rf=0.28 (200:20:1 dichloromethane-methanol-conc. ammonia); Rt=3.92.

b) tert-Butyl 4-{4-[3-(2-methoxyphenoxy)propoxy]
phenyl}-3-[4-(3-methoxypropyl)-3-oxo-3,4-dihydro-
2H-benzo[1,4]oxazin-6-ylmethoxy]piperidine-1-
carboxylate Analogously to Method D, 1.08 g of tert-butyl 3-hydroxy-4-{4-[3-(2-methoxyphenoxy)propoxy]phenyl}piperidine-1-carboxylate and 0.714 g of 6-chloromethyl-4-(3-methoxypropyl)-4H-benzo[1,4]oxazin-3-one (Example 2a) are reacted. The title compound is obtained as a colourless oil. Rf=0.33 (1:1 EtOAc-heptane); Rt=5.75.

c) tert-Butyl 3-hydroxy-4-{4-[3-(2-methoxyphe-
noxy)propoxy]phenyl}piperidine-1-carboxylate Analogously to Method I, 0.750 g of tert-butyl 3-hydroxy-4-(4-hydroxyphenyl)piperidine-1-carboxylate and 0.786 g of 1-(3-bromopropoxy)-2-methoxybenzene are reacted. The title compound is obtained as a slightly yellowish oil. Rf=0.25 (1:1 EtOAc-heptane); Rt=4.91.

EXAMPLE 145

6-(4-{4-[3-(3-Chlorophenoxy)propoxy]
phenyl}piperidin-3-yloxymethyl)-4-(3-methoxypro-
pyl)-3,4-dihydro-2H-benzo[1,4]oxazine Analogously to Method C, 0.480 g of 6-(4-{4-[3-(3-chlorophenoxy)propoxy]phenyl}piperidin-3-yloxymethyl)-4-(3-methoxypropyl)-4H-benzo[1,4]oxazin-3-one is used to prepare the title compound.

The starting materials are prepared as follows:

a) 6-(4-{4-[3-(3-Chlorophenoxy)propoxy]phenyl}piperidin-3-yloxymethyl)-4-(3-methoxypropyl)-4H-benzo[1,4]oxazin-3-one Analogously to Method A, 0.890 g of tert-butyl 4-{4-[3-(3-chlorophenoxy)propoxy]phenyl}-3-[4-(3-methoxypropyl)-3-oxo-3,4-dihydro-2H-benzo[1,4]oxazin-6-ylmethoxy]piperidine-1-carboxylate is used to obtain the title compound as a yellowish oil. Rf=0.35 (200:20:1 dichloromethane-methanol-conc. ammonia); Rt=4.44.

b) tert-Butyl 4-{4-[3-(3-Chlorophenoxy)propoxy]phenyl}-3-[4-(3-methoxypropyl)-3-oxo-3,4-dihydro-2H-benzo[1,4]oxazin-6-ylmethoxy]piperidine-1-carboxylate Analogously to Method D, 1.10 g of tert-butyl 4-{4-[3-(3-chlorophenoxy)propoxy]phenyl}-3-hydroxypiperidine-1-carboxylate and 0.662 g of 6-chloromethyl-4-(3-methoxypropyl)-4H-benzo[1,4]oxazin-3-one (Example 2a) are reacted. The title compound is obtained as a colourless oil. Rf=0.36 (1:1 EtOAc-heptane); Rt=6.19.

c) tert-Butyl 4-{4-[3-(3-chlorophenoxy)propoxy]phenyl}-3-hydroxypiperidine-1-carboxylate Analogously to Method I, 0.750 g of tert-butyl 3-hydroxy-4-(4-hydroxyphenyl)piperidine-1-carboxylate and 0.832 g of 1-(3-bromopropoxy)-3-chlorobenzene are reacted. The title compound is obtained as a slightly yellowish oil. Rf=0.30 (1:2 EtOAc-heptane); Rt=5.55.

EXAMPLE 146

4-(3-Methoxypropyl)-6-{4-[4-(3-m-tolyloxypropoxy)phenyl]piperidin-3-yloxymethyl}-3,4-dihydro-2H-benzo[1,4]oxazine Analogously to Method C, 0.690 g of 4-(3-methoxypropyl)-6-{4-[4-(3-m-tolyloxypropoxy)phenyl]piperidin-3-yloxymethyl}-4H-benzo[1,4]oxazin-3-one is used to prepare the title compound.

The starting materials are prepared as follows:

a) 4-(3-Methoxypropyl)-6-{4-[4-(3-m-tolyloxypropoxy)phenyl]piperidin-3-yloxymethyl}-4H-benzo[1,4]oxazin-3-one Analogously to Method A, 0.900 g of tert-butyl 3-[4-(3-methoxypropyl)-3-oxo-3,4-dihydro-2H-benzo[1,4]oxazin-6-ylmethoxy]-4-[4-(3-m-tolyloxypropoxy)phenyl]piperidine-1-carboxylate is used to obtain the title compound as a yellowish oil. Rf=0.15 (200:20:1 dichloromethane-methanol-conc. ammonia); Rt=4.35.

b) tert-Butyl 3-[4-(3-methoxypropyl)-3-oxo-3,4-dihydro-2H-benzo[1,4]oxazin-6-ylmethoxy]-4-[4-(3-m-tolyloxypropoxy)phenyl]piperidine-1-carboxylate Analogously to Method D, 1.10 g of tert-butyl 3-hydroxy-4-[4-(3-m-tolyloxypropoxy)phenyl]piperidine-1-carboxylate and 0.693 g 6-chloromethyl-4-(3-methoxypropyl)-4H-benzo[1,4]oxazin-3-one (Example 2a) are reacted. The title compound is obtained as a colourless oil. Rf=0.60 (1:1 EtOAc-heptane); Rt=6.14.

c) tert-Butyl 3-hydroxy-4-[4-(3-m-tolyloxypropoxy)phenyl]piperidine-1-carboxylate Analogously to Method I, 0.750 g of tert-butyl 3-hydroxy-4-(4-hydroxyphenyl)piperidine-1-carboxylate and 0.742 g of 1-(3-bromopropoxy)-3-methylbenzene are reacted. The title compound is obtained as a colourless oil. Rf=0.30 (1:2 EtOAc-heptane); Rt=5.46.

EXAMPLE 147

3-[4-Ethoxy-3-(3-methoxypropoxy)benzyloxy]-4-{4-[3-(2-methoxybenzyloxy)propoxy]phenyl}piperidine Analogously to Method A, 0.525 g of tert-butyl 3-[4-ethoxy-3-(3-methoxypropoxy)benzyloxy]-4-{4-[3-(2-methoxybenzyloxy)propoxy]phenyl}piperidine-1-carboxylate is used to obtain the title compound.

The starting materials are prepared as follows:

a) tert-Butyl 3-[4-ethoxy-3-(3-methoxypropoxy)benzyloxy]-4-{4-[3-(2-methoxybenzyloxy)propoxy]phenyl}piperidine-1-carboxylate Analogously to Method D, 0.496 g of tert-butyl 3-hydroxy-4-{4-[3-(2-methoxybenzyloxy)propoxy]phenyl}piperidine-1-carboxylate and 0.502 g of 4-bromomethyl-1-ethoxy-2-(3-methoxypropoxy)benzene are reacted. The title compound is obtained as a colourless oil. Rf=0.26 (1:2 EtOAc-heptane); Rt=6.20.

b) 4-Bromomethyl-1-ethoxy-2-(3-methoxypropoxy)benzene

The mixture of 2.01 g of 1-ethoxy-2-(3-methoxypropoxy)-4-methylbenzene, 1.76 g of N-bromosuccinimide and 0.150 g of 2,2'-azobis(2-methylpropionitrile) in 90 ml of carbon tetrachloride is kept at reflux with stirring over 1 hour. The reaction mixture is cooled and clarified by filtration, and the filtrate is concentrated by evaporation. The title compound is obtained as a beige solid from the residue by means of flash chromatography (SiO$_2$ 60F).

c) 1-Ethoxy-2-(3-methoxypropoxy)-4-methylbenzene

Analogously to Method F, 5.05 g of 2-ethoxy-5-methylphenol and 4.03 g of 1-chloro-3-methoxypropane are reacted. The title compound is obtained as a slightly orange oil. Rf=0.32 (1:4 EtOAc-heptane); Rt=4.60 d) 2-Ethoxy-5-methylphenol

The solution of 14.5 g of 1-(2-ethoxy-5-methylphenyl)ethanone in 800 ml of dichloromethane is admixed with 36.8 g of 3-chloroperbenzoic acid and stirred at room temperature over 72 hours. The reaction mixture is concentrated by evaporation, and the residue is admixed with 400 ml of saturated aqueous sodium thiosulphate solution and extracted with tert-butyl methyl ether (2×800 ml). The organic phases are washed successively with saturated aqueous sodium carbonate solution (1×500 ml) and brine (500 ml), dried over sodium sulphate, filtered and concentrated by evaporation. The residue is taken up in 75 ml of methanol, admixed with 25 ml of ammonia solution (25%) and stirred over 30 minutes. The reaction mixture is concentrated by evaporation, admixed with 0.5 M HCl (200 ml) and extracted with tert-butyl methyl ether (600 ml). The organic phase is washed with brine (500 ml), dried over sodium sulphate, filtered and concentrated by evaporation. The title compound is obtained as a brown solid from the residue by means of flash chromatography (SiO$_2$ 60F). Rt=3.89.

e) 1-(2-Ethoxy-5-methylphenyl)ethanone

The stirred solution of 20.0 g of 1-(2-hydroxy-5-methylphenyl)ethanone in 600 ml of ethanol is admixed with 8.0 g of sodium hydroxide. The resulting solution is admixed with 25.9 ml of diethyl sulphate and the mixture is kept at room temperature over 72 hours. The reaction mixture is concentrated by evaporation, and the residue is admixed with 1M NaOH (300 ml) and extracted with tert-butyl methyl ether (2×500 ml). The organic phases are washed with brine (300 ml), dried over sodium sulphate, filtered and concentrated by evaporation. The title compound is obtained as a brown solid from the residue by means of flash chromatography (SiO$_2$ 60F). Rt=4.49.

EXAMPLE 148

4-Methoxy-1-[2(R,S)-(4-{4-[3-(2-methoxybenzyloxy)propoxy]phenyl}piperidin-3-yloxymethyl)-2,3-dihydrobenzo[1,4]oxazin-4-yl]butan-1-one Analogously to Method A, 0.20 g of tert-butyl 4-{4-[3-(2-methoxybenzyloxy)propoxy]phenyl}-3-[4-(4-methoxybutyryl)-3,4-dihydro-2H-benzo[1,4]oxazin-2(R,S)-ylmethoxy]piperidine-1-carboxylate is used to prepare the title compound.

The starting materials are prepared as follows:

a) tert-Butyl 4-{4-[3-(2-methoxybenzyloxy)propoxy]phenyl}-3-[4-(4-methoxybutyryl)-3,4-dihydro-2H-benzo[1,4]oxazin-2(R,S)-ylmethoxy]piperidine-1-carboxylate A solution of 0.33 g of tert-butyl 3-(3,4-dihydro-2H-benzo[1,4]oxazin-2(R,S)-ylmethoxy)-4-{4-[3-(2-methoxybenzyloxy)propoxy]phenyl}piperidine-1-carboxylate in 40 ml of chloroform and 0.23 ml of triethylamine is admixed at room temperature with 0.23 g of 4-methoxybutyryl chloride and stirred over 30 minutes. The reaction mixture is washed successively with 1N HCl and 1N NaOH, dried over sodium sulphate and concentrated by evaporation. The title compound is obtained as a colourless oil from the residue by means of flash chromatography (SiO$_2$ 60F). Rf=0.27 (1:1.5 EtOAc-heptane); Rt=6.05.

b) tert-Butyl 3-(3,4-dihydro-2H-benzo[1,4]oxazin-2(R,S)-ylmethoxy)-4-{4-[3-(2-methoxybenzyloxy)propoxy]phenyl}piperidine-1-carboxylate A solution of 0.66 g of tert-butyl 4-{4-[3-(2-methoxybenzyloxy)propoxy]phenyl}-3-[4-(toluene-4-sulphonyl)-3,4-dihydro-2H-benzo[1,4]oxazin-2(R,S)-ylmethoxy]piperidine-1-carboxylate in 10 ml of methanol is treated in an ultrasound bath in the presence of 0.5 g of magnesium turnings over 30 minutes. The reaction mixture is decantered off from the magnesium, diluted with ethyl acetate, washed with 1N HCl (2×), dried over sodium sulphate and concentrated by evaporation. The title compound is obtained as a colourless oil from the residue by means of flash chromatography (SiO$_2$ 60F). Rf=0.26 (1:2 EtOAc-heptane); Rt=5.62.

c) tert-Butyl 4-{4-[3-(2-methoxybenzyloxy)propoxy]phenyl}-3-[4-(toluene-4-sulphonyl)-3,4-dihydro-2H-benzo[1,4]oxazin-2(R,S)-ylmethoxy]piperidine-1-carboxylate A solution of 1.04 g tert-butyl 3-{3-[(2-fluorophenyl)(toluene-4-sulphonyl)amino]-2(R,S)-hydroxypropoxy}-4-{4-[3-(2-methoxybenzyloxy)propoxy]phenyl}piperidine-1-carboxylate and 0.60 g of potassium tert-butoxide in 30 ml of tetrahydrofuran is stirred at reflux over 30 minutes. The reaction mixture is cooled to room temperature, diluted with 1N HCl and extracted with ethyl acetate (2×). The combined organic phases are dried over sodium sulphate and concentrated by evaporation. The title compound is obtained as a colourless oil from the residue by means of flash chromatography (SiO$_2$ 60F). Rf=0.30 (1:2 EtOAc-heptane); Rt=6.32.

d) tert-Butyl 3-{3-[(2-fluorophenyl)(toluene-4-sulphonyl)amino]-2(R,S)-hydroxypropoxy}-4-{4-[3-(2-methoxybenzyloxy)propoxy]phenyl}piperidine-1-carboxylate A suspension of 2.20 g of tert-butyl 4-{4-[3-(2-methoxybenzyloxy)propoxy]phenyl}-3-oxiranylmethoxypiperidine-1-carboxylate, 1.23 g of N-(2-fluorophenyl)-4-methylbenzenesulphonamide, 0.29 g of potassium carbonate, 0.35 g of benzyltriethylammonium bromide and 0.053 g of lithium chloride in 30 ml of dioxane is stirred at 90° C. over 17 hours. After 18 hours, another 0.20 g of lithium chloride, 0.50 g of potassium carbonate and 0.30 g of benzyltriethylammonium bromide are added. After a total of 40 hours, the reaction mixture is cooled to room temperature, diluted with 1N HCl and extracted with tert-butyl methyl ether (2×). The combined organic phases are dried over sodium sulphate and concentrated by evaporation. The title compound is obtained as a colourless oil from the residue by means of flash chromatography (SiO$_2$ 60F). Rf=0.14 (1:2 EtOAc-heptane); Rt=5.96.

e) tert-Butyl 4-{4-[3-(2-methoxybenzyloxy)propoxy]phenyl}-3-oxiranylmethoxypiperidine-1-carboxylate Analogously to Method D, 5.60 g of tert-butyl 3-hydroxy-4-{4-[3-(2-methoxybenzyloxy)propoxy]phenyl}piperidine-1-carboxylate and 2.05 ml of (R)-(−)-epichlorohydrin are reacted. The title compound is obtained as a colourless oil. Rf=0.12 (1:3 EtOAc-heptane); Rt=5.55.

EXAMPLE 149

N-(2-{4-Chloro-2-[2-(4-{4-[3-(2-methoxybenzyloxy)propoxy]phenyl}piperidin-3-yloxy)ethoxy]phenyl}ethyl)acetamide Analogously to Method A, 0.24 g of tert-butyl 3-{2-[2-(2-acetylaminoethyl)-5-chlorophenoxy]ethoxy}-4-{4-[3-(2-methoxybenzyloxy)propoxy]phenyl}piperidine-1-carboxylate is used to prepare the title compound.

The starting materials are prepared as follows:

a) tert-Butyl 3-{2-[2-(2-acetylaminoethyl)-5-chlorophenoxy]ethoxy}-4-{4-[3-(2-methoxybenzyloxy)propoxy]phenyl}piperidine-1-carboxylate Analogously to Method G, 0.458 g of tert-butyl 4-{4-[3-(2-methoxybenzyloxy)propoxy]phenyl}-3-[2-(toluene-4-sulphonyloxy)ethoxy]piperidine-1-carboxylate (Example 14b) and 0.30 g of N-[2-(4-chloro-2-hydroxyphenyl)ethyl]

acetamide are reacted. The title compound is obtained as a yellow oil. Rf=0.70 (EtOAc); Rt=5.75.

b) N-[2-(4-Chloro-2-hydroxyphenyl)ethyl]acetamide

Analogously to Example 108b, 2.72 g of (4-chloro-2-hydroxyphenyl)acetonitrile are reacted. The title compound is obtained as pink crystals. Rf=0.18 (2:1 EtOAc-heptane); Rt=3.04.

EXAMPLE 150

4-Methoxy-1-[2(R,S)-(4-{4-[3-(2-methoxybenzyloxy)propoxy]phenyl}piperidin-3-yloxymethyl)-2,3-dihydrobenzo[1,4]oxazin-4-yl]butan-1-one Analogously to Method A, 0.15 g of tert-butyl 4-{4-[3-(2-methoxybenzyloxy)propoxy]phenyl}-3-[4-(4-methoxybutyryl)-3,4-dihydro-2H-benzo[1,4]oxazin-2(R,S)-ylmethoxy]piperidine-1-carboxylate is used to prepare the title compound.

The starting materials are prepared as follows:

a) tert-Butyl 4-{4-[3-(2-methoxybenzyloxy)propoxy]phenyl}-3-[4-(4-methoxybutyryl)-3,4-dihydro-2H-benzo[1,4]oxazin-2(R,S)-ylmethoxy]piperidine-1-carboxylate Analogously to Example 148a, 0.39 g of tert-butyl 3-(3,4-dihydro-2H-benzo[1,4]oxazin-2(R,S)-ylmethoxy)-4-{4-[3-(2-methoxybenzyloxy)propoxy]phenyl}piperidine-1-carboxylate is reacted. The title compound is obtained as a colourless oil. Rf=0.27 (1:1.5 EtOAc-heptane); Rt=6.04.

b) tert-Butyl 3-(3,4-dihydro-2H-benzo[1,4]oxazin-2 (R,S)-ylmethoxy)-4-{4-[3-(2-methoxybenzyloxy) propoxy]phenyl}piperidine-1-carboxylate Analogously to Example 148b, 0.57 g of tert-butyl 4-{4-[3-(2-methoxybenzyloxy)propoxy]phenyl}-3-[4-(toluene-4-sulphonyl)-3,4-dihydro-2H-benzo[1,4]oxazin-2(R,S)-ylmethoxy]piperidine-1-carboxylate is reacted. The title compound is obtained as a colourless oil. Rf=0.26 (1:2 EtOAc-heptane); Rt=5.68.

c) tert-Butyl 4-{4-[3-(2-methoxybenzyloxy)propoxy]phenyl}-3-[4-(toluene-4-sulphonyl)-3,4-dihydro-2H-benzo[1,4]oxazin-2(R,S)-ylmethoxy]piperidine-1-carboxylate Analogously to Example 148c, 1.04 g of tert-butyl 3-{3-[(2-fluorophenyl)(toluene-4-sulphonyl)amino]-2(R,S)-hydroxypropoxy}-4-{4-[3-(2-methoxybenzyloxy)propoxy]phenyl}piperidine-1-carboxylate are reacted. The title compound is obtained as a colourless oil. Rf=0.32 (1:2 EtOAc-heptane); Rt=6.31.

d) tert-Butyl 3-{3-[(2-fluorophenyl)(toluene-4-sulphonyl)amino]-2(R,S)-hydroxypropoxy}-4-{4-[3-(2-methoxybenzyloxy)propoxy]phenyl}piperidine-1-carboxylate Analogously to Example 148d, 2.60 g of tert-butyl 4-{4-[3-(2-methoxybenzyloxy)propoxy]phenyl}-3-oxiranylmethoxypiperidine-1-carboxylate are reacted. The title compound is obtained as a colourless oil. Rf=0.14 (1:2 EtOAc-heptane); Rt=5.97.

e) tert-Butyl 4-{4-[3-(2-methoxybenzyloxy)propoxy]phenyl}-3-oxiranylmethoxypiperidine-1-carboxylate Analogously to Example 148e, 5.60 g of tert-butyl 3-hydroxy-4-{4-[3-(2-methoxybenzyloxy)propoxy]phenyl}piperidine-1-carboxylate and 2.05 ml of (S)-(+)-epichlorohydrin are reacted. The title compound is obtained as a colourless oil. Rf=0.24 (1:2 EtOAc-heptane); Rt=5.66.

EXAMPLE 151

4-(3-Methoxypropyl)-6-{4-[4-(3-phenoxypropoxy)phenyl]piperidin-3-yloxymethyl}-3,4-dihydro-2H benzo[1,4]oxazine Analogously to Method C, 0.700 g of 4-(3-methoxypropyl)-6-{4-[4-(3-phenoxypropoxy)phenyl]piperidin-3-yloxymethyl}-4H-benzo[1,4]oxazin-3-one is used to prepare the title compound.

The starting materials are prepared as follows:

a) 4-(3-Methoxypropyl)-6-{4-[4-(3-phenoxypropoxy)phenyl]piperidin-3-yloxymethyl}-4H-benzo[1,4]oxazin-3-one Analogously to Method A, 1.15 g of tert-butyl 3-[4-(3-methoxypropyl)-3-oxo-3,4-dihydro-2H-benzo[1,4]oxazin-6-ylmethoxy]-4-[4-(3-phenoxypropoxy)phenyl]piperidine-1-carboxylate are used to obtain the title compound as a yellowish oil. Rf=0.24 (200:20:1 dichloromethane-methanol-conc. ammonia); Rt=4.23.

b) tert-Butyl 3-[4-(3-methoxypropyl)-3-oxo-3,4-dihydro-2H-benzo[1,4]oxazin-6-ylmethoxy]-4-[4-(3-phenoxypropoxy)phenyl]piperidine-1-carboxylate Analogously to Method D, 1.05 g of tert-butyl 3-hydroxy-4-[4-(3-phenoxypropoxy)phenyl]piperidine-1-carboxylate and 0.735 g of 6-chloromethyl-4-(3-methoxypropyl)-4H-benzo[1,4]oxazin-3-one (Example 2a) are reacted. The title compound is obtained as a colourless oil. Rf=0.36 (1:1 EtOAc-heptane); Rt=5.84.

c) tert-Butyl 3-hydroxy-4-[4-(3-phenoxypropoxy) phenyl]piperidine-1-carboxylate

Analogously to Method I, 0.750 g of tert-butyl 3-hydroxy-4-(4-hydroxyphenyl)piperidine-1-carboxylate and 0.692 g of (3-bromopropoxy)benzene are reacted. The title compound is obtained as a slightly yellowish oil. Rf=0.24 (1:2 EtOAc-heptane); Rt=5.13.

EXAMPLE 152

4-{2-[2-(4-{4-[3-(2-Methoxybenzyloxy)propoxy]phenyl}piperidin-3-yloxy)ethoxy]phenyl}butyric acid A solution of 0.30 g of methyl 4-{2-[2-(4-{4-[3-(2-methoxybenzyloxy)propoxy]phenyl}piperidin-3-yloxy)ethoxy]phenyl}butyrate (Example 137) in 5 ml of dioxane and 2 ml of 2N NaOH is stirred at 80° C. over 7 hours. The reaction mixture is cooled to room temperature, diluted with water and washed with tert-butyl methyl ether. The combined organic phases are acidified to pH 6 with 1N HCl and subsequently extracted with ethyl acetate (2×). The combined organic phases are washed with brine, dried over sodium sulphate and concentrated by evaporation. The title compound is obtained as a yellow solid from the residue by means of flash chromatography (SiO₂ 60F). Rf=0.08 (200:20:1 dichloromethane-methanol-25% conc. ammonia); Rt=4.37.

EXAMPLE 153

4-{4-[3-(2-Methoxybenzyloxy)propoxy]phenyl}-3-[3-methoxy-2-(2-methoxyethoxy)benzyloxy]piperidine Analogously to Method A, 0.497 g of tert-butyl 4-{4-[3-(2-methoxybenzyloxy)propoxy]phenyl}-3-[3-methoxy-2-(2-methoxyethoxy)benzyloxy]piperidine-1-carboxylate is used to obtain the title compound.

The starting materials are prepared as follows:

a) tert-Butyl 4-{4-[3-(2-methoxybenzyloxy)propoxy]phenyl}-3-[3-methoxy-2-(2-methoxyethoxy)benzyloxy]piperidine-1-carboxylate Analogously to Method D, 0.417 g of tert-butyl 3-hydroxy-4-{4-[3-(2-methoxybenzyloxy)propoxy]phenyl}piperidine-1-carboxylate and 0.251 g of 1-chloromethyl-3-methoxy-2-(2-methoxyethoxy)benzene are reacted. The title compound is obtained as a colourless oil. Rf=0.20 (1:2 EtOAc-heptane); Rt=6.07.

b) 1-Chloromethyl-3-methoxy-2-(2-methoxyethoxy)benzene

Analogously to Method E, 1.76 g of [3-methoxy-2-(2-methoxyethoxy)phenyl]methanol are reacted. The title compound is obtained as a slightly yellowish oil. Rf=0.53 (1:1 EtOAc-heptane). Rt=4.27.

c) [3-Methoxy-2-(2-methoxyethoxy)phenyl]methanol

Analogously to Method F, 2.44 g of 2-hydroxymethyl-6-methoxyphenol and 2.56 g of 2-bromoethyl methyl ether are reacted and the title compound is obtained as a colourless oil. Rf=0.22 (1:1 EtOAc-heptane); Rt=2.91.

EXAMPLE 154

4-{4-[3-(2-Methoxybenzyloxy)propoxy]phenyl}-3-[3-methoxy-2-(3-methoxypropoxy)benzyloxy]piperidine Analogously to Method A, 0.497 g of tert-butyl 4-{4-[3-(2-methoxybenzyloxy)propoxy]phenyl}-3-[3-methoxy-2-(3-methoxypropoxy)benzyloxy]piperidine-1-carboxylate is used to obtain the title compound.

The starting materials are prepared as follows:

a) tert-Butyl 4-{4-[3-(2-methoxybenzyloxy)propoxy]phenyl}-3-[3-methoxy-2-(3-methoxypropoxy)benzyloxy]piperidine-1-carboxylate Analogously to Method D, 0.417 g of tert-butyl 3-hydroxy-4-{4-[3-(2-methoxybenzyloxy)propoxy]phenyl}piperidine-1-carboxylate and 0.278 g of 1-chloromethyl-3-methoxy-2-(3-methoxypropoxy)benzene are reacted. The title compound is obtained as a colourless oil. Rf=0.17 (1:2 EtOAc-heptane); Rt=6.19.

b) 1-Chloromethyl-3-methoxy-2-(3-methoxypropoxy)benzene

Analogously to Method E, 1.58 g of [3-methoxy-2-(3-methoxypropoxy)phenyl]methanol are reacted. The title compound is obtained as a slightly yellowish oil. Rf=0.53 (1:1 EtOAc-heptane). Rt=4.53.

c) [3-Methoxy-2-(2-methoxyethoxy)phenyl]methanol

Analogously to Method F, 2.67 g of 2-hydroxymethyl-6-methoxyphenol and 2.19 g of 1-chloro-3-methoxypropane are reacted. The title compound is obtained as a colourless oil. Rf=0.23 (1:1 EtOAc-heptane); Rt=3.08.

EXAMPLE 155

N-Hydroxy-3-{2-[2-(4-{4-[3-(2-methoxybenzyloxy)propoxy]phenyl}piperidin-3-yloxy)ethoxy]phenyl}-N methylpropionamide Analogously to Method B, 0.131 g of benzyl 3-(2-{2-[2-(hydroxymethylcarbamoyl)ethyl]phenoxy}ethoxy)-4-{4-[3-(2-methoxybenzyloxy)propoxy]phenyl}piperidine-1-carboxylate is used to prepare the title compound.

The starting materials are prepared as follows:

a) Benzyl 3-(2-{2-[2-(hydroxymethylcarbamoyl)ethyl]phenoxy}ethoxy)-4-{4-[3-(2-methoxybenzyloxy)propoxy]phenyl}piperidine-1-carboxylate A solution of 0.136 g of benzyl 3-{2-[2-(2-carboxyethyl)phenoxy]ethoxy}-4-{4-[3-(2-methoxybenzyloxy)propoxy]phenyl}piperidine-1-carboxylate in 3 ml of dichloromethane is admixed with 0.01 ml of N,N-dimethylformamide and 0.034 ml of oxalyl chloride and stirred at room temperature over 2 hours. The reaction mixture is concentrated by evaporation, and the residue is dissolved in 3 ml of tetrahydrofuran, cooled to 0° C. and added dropwise to the suspension of 0.033 g of N-methylhydroxylamine hydrochloride and 0.11 ml of triethylamine in a 4:1 tetrahydrofuran/water mixture (2 ml). The reaction mixture is stirred at room temperature over 14 hours, diluted with ethyl acetate, washed successively with 1N HCl, 1M aqueous sodium hydrogencarbonate solution and brine, dried over sodium sulphate and concentrated by evaporation. The title compound is obtained as a colourless oil from the residue by means of flash chromatography (SiO₂ 60F). Rf=0.40 (200:20:1 dichloromethane-methanol-25% conc. ammonia); Rt=5.53.

b) Benzyl 3-{2-[2-(2-carboxyethyl)phenoxy]ethoxy}-4-{4-[3-(2-methoxybenzyloxy)propoxy]phenyl}piperidine-1-carboxylate A solution of 0.16 g of benzyl 4-{4-[3-(2-methoxybenzyloxy)propoxy]phenyl}-3-{2-[2-(2-methoxycarbonylethyl)phenoxy]ethoxy}piperidine-1-carboxylate in 4 ml of dioxane is admixed with 0.4 ml of 2N NaOH and stirred at 80° C. over 3 hours. The reaction mixture is cooled to room temperature and acidified to pH 6 with 1N HCl. The solution is admixed with brine and extracted with ethyl acetate (2×). The combined organic phases are dried over sodium sulphate and concentrated by evaporation. The crude title compound is obtained as a yellow foam from the residue. Rt=5.64.

c) Benzyl 4-{4-[3-(2-methoxybenzyloxy)propoxy]
phenyl}-3-{2-[2-(2-methoxycarbonylethyl)phenoxy]
ethoxy}piperidine-1-carboxylate A solution of 0.15 g of methyl 3-{2-[2-(4-{4-[3-(2-methoxybenzyloxy)propoxy]phenyl}piperidin-3-yloxy)ethoxy]phenyl}propionate (Example 52) in 3 ml of ethyl acetate is admixed with 3 ml of saturated aqueous sodium bicarbonate solution. The mixture is cooled to 0° C. and admixed with 0.046 ml of benzyl chloroformate. After 1 hour, another 1 ml of saturated aqueous sodium bicarbonate solution and 0.020 ml of benzyl chloroformate are added. The aqueous phase is removed and extracted with ethyl acetate (2×). The combined organic phases are dried over sodium sulphate and concentrated by evaporation. The title compound is obtained as a colourless oil from the residue by means of flash chromatography ($SiO_2$ 60F). Rf=0.32 (2:5 EtOAc-heptane); Rt=6.07.

EXAMPLE 156

6-(4-{4-[3-(Benzo[1,3]dioxol-5-yloxy)propoxy]
phenyl}piperidin-3-yloxymethyl)-4-(3-methoxypropyl)-3,4-dihydro-2H-benzo[1,4]oxazine Analogously to Method C, 0.500 g of 6-(4-{4-[3-(benzo[1,3]dioxol-5-yloxy)propoxy]phenyl}piperidin-3-yloxymethyl)-4-(3-methoxypropyl)-4H-benzo[1,4]oxazin-3-one is used to prepare the title compound.

The starting materials are prepared as follows:

a) 6-(4-{4-[3-(Benzo[1,3]dioxol-5-yloxy)propoxy]
phenyl}piperidin-3-yloxymethyl)-4-(3-methoxypropyl)-4H-benzo[1,4]oxazin-3-one Analogously to Method A, 0.600 g of tert-butyl 4-{4-[3-(benzo[1,3]dioxol-5-yloxy)propoxy]phenyl}-3-[4-(3-methoxypropyl)-3-oxo-3,4-dihydro-2H-benzo[1,4]oxazin-6-ylmethoxy]piperidine-1-carboxylate is used to obtain the title compound as a yellowish oil. Rf=0.40 (200:20:1 dichloromethane-methanol-conc. ammonia); Rt=4.10.

b) tert-Butyl 4-{4-[3-(benzo[1,3]dioxol-5-yloxy)
propoxy]phenyl}-3-[4-(3-methoxypropyl)-3-oxo-3,
4-dihydro-2H-benzo[1,4]oxazin-6-ylmethoxy]piperidine-1-carboxylate Analogously to Method D, 0.600 g of tert-butyl 4-{4-[3-(benzo[1,3]dioxol-5-yloxy)propoxy]phenyl}-3-hydroxypiperidine-1-carboxylate and 0.385 g of 6-chloromethyl-4-(3-methoxypropyl)-4H-benzo[1,4]oxazin-3-one (Example 2a) are reacted. The title compound is obtained as a colourless oil. Rf=0.13 (1:2 EtOAc-heptane); Rt=5.68.

c) tert-Butyl 4-{4-[3-(benzo[1,3]dioxol-5-yloxy)
propoxy]phenyl}-3-hydroxypiperidine-1-carboxylate Analogously to Method I, 0.750 g of tert-butyl 3-hydroxy-4-(4-hydroxyphenyl)piperidine-1-carboxylate and 0.859 g of 5-(3-bromopropoxy)benzo[1,3]dioxole are reacted. The title compound is obtained as a slightly yellowish oil. Rf=0.10 (1:2 EtOAc-heptane); Rt=4.96.

EXAMPLE 157

6-(4-{4-[3-(2,4-Difluorophenoxy)propoxy]
phenyl}piperidin-3-yloxymethyl)-4-(3-methoxypropyl)-3,4-dihydro-2H-benzo[1,4]oxazine Analogously to Method C, 0.560 g of 6-(4-{4-[3-(2,4-difluorophenoxy)propoxy]phenyl}piperidin-3-yloxymethyl)-4-(3-methoxypropyl)-4H-benzo[1,4]oxazin-3-one is used to prepare the title compound.

The starting materials are prepared as follows:

a) 6-(4-{4-[3-(2,4-Difluorophenoxy)propoxy]
phenyl}piperidin-3-yloxymethyl)-4-(3-methoxypropyl)-4H-benzo[1,4]oxazin-3-one Analogously to Method A, 0.700 g of tert-butyl 4-{4-[3-(2,4-difluorophenoxy)propoxy]phenyl}-3-[4-(3-methoxypropyl)-3-oxo-3,4-dihydro-2H-benzo[1,4]oxazin-6-ylmethoxy]piperidine-1-carboxylate is used to prepare the title compound as a yellowish oil. Rf=0.42 (200:20:1 dichloromethane-methanol-conc. ammonia); Rt=4.25.

b) tert-Butyl 4-{4-[3-(2,4-difluorophenoxy)propoxy]
phenyl}-3-[4-(3-methoxypropyl)-3-oxo-3,4-dihydro-2H-benzo[1,4]oxazin-6-ylmethoxy]piperidine-1-
carboxylate Analogously to Method D, 0.600 g of tert-butyl 4-{4-[3-(2,4-difluorophenoxy)propoxy]phenyl}-3-hydroxypiperidine-1-carboxylate and 0.391 g of 6-chloromethyl-4-(3-methoxypropyl)-4H-benzo[1,4]oxazin-3-one (Example 2a) are reacted. The title compound is obtained as a colourless oil. Rf=0.17 (1:2 EtOAc-heptane); Rt=5.80.

c) tert-Butyl 4-{4-[3-(2,4-difluorophenoxy)propoxy]
phenyl}-3-hydroxypiperidine-1-carboxylate Analogously to Method I, 0.750 g of tert-butyl 3-hydroxy-4-(4-hydroxyphenyl)piperidine-1-carboxylate and 0.796 g of 1-(3-bromopropoxy)-2,4-difluorobenzene are reacted. The title compound is obtained as a slightly yellowish oil. Rf=0.13 (1:2 EtOAc-heptane); Rt=5.12.

EXAMPLE 158

6-(4-{4-[3-(2,3-Difluorophenoxy)propoxy]
phenyl}piperidin-3-yloxymethyl)-4-(3-methoxypropyl)-3,4-dihydro-2H-benzo[1,4]oxazine Analogously to Method C, 0.240 g of 6-(4-{4-[3-(2,3-difluorophenoxy)propoxy]phenyl}piperidin-3-yloxymethyl)-4-(3-methoxypropyl)-4H-benzo[1,4]oxazin-3-one is used to prepare the title compound.

The starting materials are prepared as follows:

a) 6-(4-{4-[3-(2,3-Difluorophenoxy)propoxy]
phenyl}piperidin-3-yloxymethyl)-4-(3-methoxypropyl)-4H-benzo[1,4]oxazin-3-one Analogously to Method A, 0.396 g of tert-butyl 4-{4-[3-(2,3-difluorophenoxy)propoxy]phenyl}-3-[4-(3-methoxypropyl)-3-oxo-3,4-dihydro-2H-benzo[1,4]oxazin-6-ylmethoxy]piperidine-1-carboxylate is used to obtain the title compound as a yellowish oil. Rf=0.40 (200:20:1 dichloromethane-methanol-conc. ammonia); Rt=4.26.

b) tert-Butyl 4-{4-[3-(2,3-difluorophenoxy)propoxy]phenyl}-3-[4-(3-methoxypropyl)-3-oxo-3,4-dihydro-2H-benzo[1,4]oxazin-6-ylmethoxy]piperidine-1-carboxylate Analogously to Method D, 0.600 g of tert-butyl 4-{4-[3-(2,3-difluorophenoxy)propoxy]phenyl}-3-hydroxypiperidine-1-carboxylate and 0.391 g of 6-chloromethyl-4-(3-methoxypropyl)-4H-benzo[1,4]oxazin-3-one (Example 2a) are reacted. The title compound is obtained as a yellowish oil. Rf=0.14 (1:2 EtOAc-heptane); Rt=5.81.

c) tert-Butyl 4-{4-[3-(2,3-difluorophenoxy)propoxy]phenyl}-3-hydroxypiperidine-1-carboxylate Analogously to Method I, 0.750 g of tert-butyl 3-hydroxy-4-(4-hydroxyphenyl)piperidine-1-carboxylate and 0.776 g of 1-(3-bromopropoxy)-2,3-difluorobenzene are reacted. The title compound is obtained as a slightly yellowish oil. Rf=0.11 (1:2 EtOAc-heptane); Rt=5.13.

d) 1-(3-Bromopropoxy)-2,3-difluorobenzene

Analogously to Example 91b, 2.00 g of 2,3-difluorophenol and 30.7 g of 1,3-dibromopropane are reacted. The title compound is obtained as a colourless oil. Rf=0.39 (1:10 EtOAc-heptane); Rt=4.82.

EXAMPLE 159

6-(4-{4-[3-(4-Fluorophenoxy)propoxy]phenyl}piperidin-3-yloxymethyl)-4-(3-methoxypropyl)-3,4-dihydro-2H-benzo[1,4]oxazine Analogously to Method C, 0.310 g of 6-(4-{4-[3-(4-fluorophenoxy)propoxy]phenyl}piperidin-3-yloxymethyl)-4-(3-methoxypropyl)-4H-benzo[1,4]oxazin-3-one is used to prepare the title compound.

The starting materials are prepared as follows:

a) 6-(4-{4-[3-(4-Fluorophenoxy)propoxy]phenyl}piperidin-3-yloxymethyl)-4-(3-methoxypropyl)-4H-benzo[1,4]oxazin-3-one Analogously to Method A, 0.510 g of tert-butyl 4-{4-[3-(4-fluorophenoxy)propoxy]phenyl}-3-[4-(3-methoxypropyl)-3-oxo-3,4-dihydro-2H-benzo[1,4]oxazin-6-ylmethoxy]piperidine-1-carboxylate is used to obtain the title compound as a yellowish oil. Rf=0.40 (200:20:1 dichloromethane-methanol-conc. ammonia); Rt=4.25.

b) tert-Butyl 4-{4-[3-(4-fluorophenoxy)propoxy]phenyl}-3-[4-(3-methoxypropyl)-3-oxo-3,4-dihydro-2H-benzo[1,4]oxazin-6-ylmethoxy]piperidine-1-carboxylate Analogously to Method D, 0.600 g of tert-butyl 4-{4-[3-(4-fluorophenoxy)propoxy]phenyl}-3-hydroxypiperidine-1-carboxylate and 0.408 g of 6-chloromethyl-4-(3-methoxypropyl)-4H-benzo[1,4]oxazin-3-one (Example 2a) are reacted. The title compound is obtained as a yellowish oil. Rf=0.17 (1:2 EtOAc-heptane); Rt=5.82.

c) tert-Butyl 4-{4-[3-(4-fluorophenoxy)propoxy]phenyl}-3-hydroxypiperidine-1-carboxylate Analogously to Method I, 0.750 g of tert-butyl 3-hydroxy-4-(4-hydroxyphenyl)piperidine-1-carboxylate and 0.758 g of 1-(3-bromopropoxy)-4-fluorobenzene are reacted. The title compound is obtained as a slightly yellowish oil. Rf=0.13 (1:2 EtOAc-heptane); Rt=5.12.

EXAMPLE 160

6-(4-{4-[3-(2,6-Difluorophenoxy)propoxy]phenyl}piperidin-3-yloxymethyl)-4-(3-methoxypropyl)-3,4-dihydro-2H-benzo[1,4]oxazine Analogously to Method C, 0.200 g of 6-(4-{4-[3-(2,6-difluorophenoxy)propoxy]phenyl}piperidin-3-yloxymethyl)-4-(3-methoxypropyl)-4H-benzo[1,4]oxazin-3-one is used to prepare the title compound.

The starting materials are prepared as follows:

a) 6-(4-{4-[3-(2,6-Difluorophenoxy)propoxy]phenyl}piperidin-3-yloxymethyl)-4-(3-methoxypropyl)-4H-benzo[1,4]oxazin-3-one Analogously to Method A, 0.390 g of tert-butyl 4-{4-[3-(2,6-difluorophenoxy)propoxy]phenyl}-3-[4-(3-methoxypropyl)-3-oxo-3,4-dihydro-2H-benzo[1,4]oxazin-6-ylmethoxy]piperidine-1-carboxylate is used to obtain the title compound as a yellowish oil. Rf=0.47 (200:20:1 dichloromethane-methanol-conc. ammonia); Rt=4.16.

b) tert-Butyl 4-{4-[3-(2,6-difluorophenoxy)propoxy]phenyl}-3-[4-(3-methoxypropyl)-3-oxo-3,4-dihydro-2H-benzo[1,4]oxazin-6-ylmethoxy]piperidine-1-carboxylate Analogously to Method D, 0.540 g of tert-butyl 4-{4-[3-(2,6-difluorophenoxy)propoxy]phenyl}-3-hydroxypiperidine-1-carboxylate and 0.350 g of 6-chloromethyl-4-(3-methoxypropyl)-4H-benzo[1,4]oxazin-3-one (Example 2a) are reacted. The title compound is obtained as a yellowish oil. Rf=0.18 (1:1 EtOAc-heptane); Rt=5.94.

c) tert-Butyl 4-{4-[3-(2,6-difluorophenoxy)propoxy]phenyl}-3-hydroxypiperidine-1-carboxylate Analogously to Method I, 0.750 g of tert-butyl 3-hydroxy-4-(4-hydroxyphenyl)piperidine-1-carboxylate and 0.820 g of 2-(3-bromopropoxy)-1,3-difluorobenzene are reacted. The title compound is obtained as a slightly yellowish oil. Rf=0.70 (1:1 EtOAc-heptane); Rt=5.26.

d) 2-(3-Bromopropoxy)-1,3-difluorobenzene

Analogously to Example 91b, 2.00 g of 2,6-difluorophenol and 30.7 g of 1,3-dibromopropane are reacted. The title compound is obtained as a colourless oil. Rf=0.70 (1:6 EtOAc-heptane); Rt=4.97.

EXAMPLE 161

6-(4-{4-[3-(3,4-Difluorophenoxy)propoxy]
phenyl}piperidin-3-yloxymethyl)-4-(3-methoxypropyl)-3,4-dihydro-2H-benzo[1,4]oxazine Analogously to Method C, 0.160 g of 6-(4-{4-[3-(3,4-difluorophenoxy)propoxy]phenyl}piperidin-3-yloxymethyl)-4-(3-methoxypropyl)-4H-benzo[1,4]oxazin-3-one is used to prepare the title compound.

The starting materials are prepared as follows:

a) 6-(4-{4-[3-(3,4-Difluorophenoxy)propoxy] phenyl}piperidin-3-yloxymethyl)-4-(3-methoxypropyl)-4H-benzo[1,4]oxazin-3-one Analogously to Method A, 0.480 g of tert-butyl 4-{4-[3-(3,4-difluorophenoxy)propoxy]phenyl}-3-[4-(3-methoxypropyl)-3-oxo-3,4-dihydro-2H-benzo[1,4]oxazin-6-ylmethoxy]piperidine-1-carboxylate is used to obtain the title compound as a yellowish oil. Rf=0.53 (200:20:1 dichloromethane-methanol-conc. ammonia); Rt=4.26.

b) tert-Butyl 4-{4-[3-(3,4-difluorophenoxy)propoxy] phenyl}-3-[4-(3-methoxypropyl)-3-oxo-3,4-dihydro-2H-benzo[1,4]oxazin-6-ylmethoxy]piperidine-1-carboxylate Analogously to Method D, 0.540 g of tert-butyl 4-{4-[3-(3,4-difluorophenoxy)propoxy]phenyl}-3-hydroxypiperidine-1-carboxylate and 0.353 g of 6-chloromethyl-4-(3-methoxypropyl)-4H-benzo[1,4]oxazin-3-one (Example 2a) are reacted. The title compound is obtained as a yellowish oil. Rf=0.26 (1:1 EtOAc-heptane); Rt=5.98.

c) tert-Butyl 4-{4-[3-(3,4-difluorophenoxy)propoxy] phenyl}-3-hydroxypiperidine-1-carboxylate Analogously to Method I, 0.750 g of tert-butyl 3-hydroxy-4-(4-hydroxyphenyl)piperidine-1-carboxylate and 0.820 g of 4-(3-bromopropoxy)-1,2-difluorobenzene are reacted. The title compound is obtained as a slightly yellowish oil. Rf=0.65 (1:1 EtOAc-heptane); Rt=5.30.

d) 4-(3-Bromopropoxy)-1,2-difluorobenzene

Analogously to Example 91b, 2.00 g of 3,4-difluorophenol and 31.0 g of 1,3-dibromopropane are reacted. The title compound is obtained as a colourless oil. Rf=0.66 (1:6 EtOAc-heptane); Rt=5.01.

EXAMPLE 162

6-(4-{4-[3-(3,5-Difluorophenoxy)propoxy]
phenyl}piperidin-3-yloxymethyl)-4-(3-methoxypropyl)-3,4-dihydro-2H-benzo[1,4]oxazine Analogously to Method C, 0.230 g of 6-(4-{4-[3-(3,5-difluorophenoxy)propoxy]phenyl}piperidin-3-yloxymethyl)-4-(3-methoxypropyl)-4H-benzo[1,4]oxazin-3-one is used to prepare the title compound.

The starting materials are prepared as follows:

a) 6-(4-{4-[3-(3,5-Difluorophenoxy)propoxy] phenyl}piperidin-3-yloxymethyl)-4-(3-methoxypropyl)-4H-benzo[1,4]oxazin-3-one Analogously to Method A, 0.490 g of tert-butyl 4-{4-[3-(3,5-difluorophenoxy)propoxy]phenyl}-3-[4-(3-methoxypropyl)-3-oxo-3,4-dihydro-2H-benzo[1,4]oxazin-6-ylmethoxy]piperidine-1-carboxylate is used to obtain the title compound as a yellowish oil. Rf=0.50 (200:20:1 dichloromethane-methanol-conc. ammonia); Rt=4.32.

b) tert-Butyl 4-{4-[3-(3,5-difluorophenoxy)propoxy] phenyl}-3-[4-(3-methoxypropyl)-3-oxo-3,4-dihydro-2H-benzo[1,4]oxazin-6-ylmethoxy]piperidine-1-carboxylate Analogously to Method D, 0.510 g of tert-butyl 4-{4-[3-(3,5-difluorophenoxy)propoxy]phenyl}-3-hydroxypiperidine-1-carboxylate and 0.323 g of 6-chloromethyl-4-(3-methoxypropyl)-4H-benzo[1,4]oxazin-3-one (Example 2a) are reacted. The title compound is obtained as a yellowish oil. Rf=0.23 (1:1 EtOAc-heptane); Rt=6.04.

c) tert-Butyl 4-{4-[3-(3,5-difluorophenoxy)propoxy] phenyl}-3-hydroxypiperidine-1-carboxylate Analogously to Method I, 0.750 g of tert-butyl 3-hydroxy-4-(4-hydroxyphenyl)piperidine-1-carboxylate and 0.820 g of 1-(3-bromopropoxy)-3,5-difluorobenzene are reacted. The title compound is obtained as a slightly yellowish oil. Rf=0.40 (1:1 EtOAc-heptane); Rt=5.39.

d) 1-(3-Bromopropoxy)-3,5-difluorobenzene

Analogously to Example 91b, 0.98 g of 3,5-difluorophenol and 15.2 g of 1,3-dibromopropane are reacted. The title compound is obtained as a colourless oil. Rf=0.70 (1:6 EtOAc-heptane); Rt=5.13.

EXAMPLE 163

4-(3-Methoxypropyl)-6-(4-{4-[3-(3-trifluoromethylphenoxy)propoxy]phenyl}piperidin-3-yloxymethyl)-3,4-dihydro-2H-benzo[1,4]oxazine Analogously to Method C, 0.240 g of 4-(3-methoxypropyl)-6-(4-{4-[3-(3-trifluoromethylphenoxy)propoxy]phenyl}piperidin-3-yloxymethyl)-4H-benzo[1,4]oxazin-3-one is used to prepare the title compound.

The starting materials are prepared as follows:

a) 4-(3-Methoxypropyl)-6-(4-{4-[3-(3-trifluoromethylphenoxy)propoxy]phenyl}piperidin-3-yloxymethyl)-4H-benzo[1,4]oxazin-3-one Analogously to Method A, 0.400 g of tert-butyl 3-[4-(3-methoxypropyl)-3-oxo-3,4-dihydro-2H-benzo[1,4]oxazin-6-ylmethoxy]-4-{4-[3-(3-trifluoromethylphenoxy)propoxy] phenyl}piperidine-1-carboxylate is used to obtain the title compound as a yellowish oil. Rf=0.46 (200:20:1 dichloromethane-methanol-conc. ammonia); Rt=4.50.

b) tert-Butyl 3-[4-(3-methoxypropyl)-3-oxo-3,4-dihydro-2H-benzo[1,4]oxazin-6-ylmethoxy]-4{4-[3-(3-trifluoromethylphenoxy)propoxy]phenyl}piperidine-1-carboxylate Analogously to Method D, 0.560 g of tert-butyl 3-hydroxy-4-{4-[3-(3-trifluoromethylphenoxy)propoxy]phenyl}piperidine-1-carboxylate and 0.339 g of 6-chloromethyl-4-(3-methoxypropyl)-4H-benzo[1,4]oxazin-3-one (Example 2a) are reacted. The title compound is obtained as a yellowish oil. Rf=0.30 (1:1 EtOAc-heptane); Rt=6.15.

c) tert-Butyl 3-hydroxy-4-{4-[3-(3-trifluoromethylphenoxy)propoxy]phenyl}piperidine-1-carboxylate Analogously to Method I, 0.750 g of tert-butyl 3-hydroxy-4-(4-hydroxyphenyl)piperidine-1-carboxylate and 0.924 g of 1-(3-bromopropoxy)-3-trifluoromethylbenzene are reacted. The title compound is obtained as a slightly yellowish oil. Rf=0.28 (1:1 EtOAc-heptane); Rt=5.43.

EXAMPLE 164

6-{4-[4-(3-Cyclohexyloxypropoxy)phenyl]piperidin-3-yloxymethyl}-4-(3-methoxypropyl)-3,4-dihydro-2H-benzo[1,4]oxazine Analogously to Method C, 0.330 g of 6-{4-[4-(3-cyclohexyloxypropoxy)phenyl]piperidin-3-yloxymethyl}-4-(3-methoxypropyl)-4H-benzo[1,4]oxazin-3-one is used to prepare the title compound.

The starting materials are prepared as follows:

a) 6-{4-[4-(3-Cyclohexyloxypropoxy)phenyl]piperidin-3-yloxymethyl}-4-(3-methoxypropyl)-4H-benzo[1,4]oxazin-3-one Analogously to Method A, 0.450 g of tert-butyl 4-[4-(3-cyclohexyloxypropoxy)phenyl]-3-[4-(3-methoxypropyl)-3-oxo-3,4-dihydro-2H-benzo[1,4]oxazin-6-ylmethoxy]piperidine-1-carboxylate is used to obtain the title compound as a yellowish oil. Rf=0.36 (200:20:1 dichloromethane-methanol-conc. ammonia); Rt=4.42.

b) tert-Butyl 4-[4-(3-cyclohexyloxypropoxy)phenyl]-3-[4-(3-methoxypropyl)-3-oxo-3,4-dihydro-2H-benzo[1,4]oxazin-6-ylmethoxy]piperidine-1-carboxylate Analogously to Method D, 0.470 g of tert-butyl 4-[4-(3-cyclohexyloxypropoxy)phenyl]-3-hydroxypiperidine-1-carboxylate and 0.324 g of 6-chloromethyl-4-(3-methoxypropyl)-4H-benzo[1,4]oxazin-3-one (Example 2a) are reacted. The title compound is obtained as a yellowish oil. Rf=0.46 (1:1 EtOAc-heptane); Rt=6.20.

c) tert-Butyl 4-[4-(3-cyclohexyloxypropoxy)phenyl]-3-hydroxypiperidine-1-carboxylate Analogously to Method I, 0.795 g of tert-butyl 3-hydroxy-4-(4-hydroxyphenyl)piperidine-1-carboxylate and 1.07 g of 3-cyclohexyloxypropyl toluene-4-sulphonate are reacted. The title compound is obtained as a slightly yellowish oil. Rf=0.39 (1:1 EtOAc-heptane); Rt=5.43.

d) 3-Cyclohexyloxypropyl toluene-4-sulphonate

Analogously to Method H, 0.620 g of 3-cyclohexyloxypropan-1-ol is used to obtain the title compound as a colourless oil. Rf=0.40 (1:3 EtOAc-heptane); Rt=5.18.

EXAMPLE 166

6-{4-[4-(2(R)-Methoxy-3(R)-phenoxypropoxy)phenyl]piperidin-3-yloxymethyl}-4-(3-methoxypropyl)-3,4-dihydro-2H-benzo[1,4]oxazine Analogously to Method C, 0.080 g of 6-{4-[4-(2(R)-methoxy-3-phenoxypropoxy)phenyl]piperidin-3-yloxymethyl}-4-(3-methoxypropyl)-4H-benzo[1,4]oxazin-3-one is used to prepared the title compound.

The starting materials are prepared as follows:

a) 6-{4-[4-(2(R)-Methoxy-3-phenoxypropoxy)phenyl]piperidin-3-yloxymethyl}-4-(3-methoxypropyl)-4H-benzo[1,4]oxazin-3-one Analogously to Method B, 0.160 g of benzyl 4-[4-(2(R)-methoxy-3-phenoxypropoxy)phenyl]-3-[4-(3-methoxypropyl)-3-oxo-3,4-dihydro-2H-benzo[1,4]oxazin-6-ylmethoxy]piperidine-1-carboxylate is used to obtain the title compound as a colourless oil. Rf=0.16 (200:20:1 dichloromethane-methanol-conc. ammonia); Rt=4.05.

b) Benzyl 4-[4-(2(R)-methoxy-3-phenoxypropoxy)phenyl]-3-[4-(3-methoxypropyl)-3-oxo-3,4-dihydro-2H-benzo[1,4]oxazin-6-ylmethoxy]piperidine-1-carboxylate The solution of 0.330 g of benzyl 4-[4-(2(R)-hydroxy-3-phenoxypropoxy)phenyl]-3-[4-(3-methoxypropyl)-3-oxo-3,4-dihydro-2H-benzo[1,4]oxazin-6-ylmethoxy]piperidine-1-carboxylate in 3.0 ml of tetrahydrofuran is cooled to 0° C. and admixed with stirring with 0.018 g of NaH dispersion (60%). The mixture is stirred at room temperature over 1.5 hours and subsequently admixed with 0.056 ml of methyl iodide. The reaction mixture is stirred for a further 2 hours, poured onto water (40 ml) and extracted with ethyl acetate (2×40 ml). The organic phases are washed with brine (40 ml), dried over sodium sulphate, filtered and concentrated by evaporation. The title compound is obtained as a colourless oil from the residue by means of flash chromatography (SiO$_2$ 60F). Rf=0.33 (1:1 EtOAc-heptane); Rt=5.54.

c) Benzyl 4-[4-(2(R)-hydroxy-3-phenoxypropoxy)phenyl]-3-[4-(3-methoxypropyl)-3-oxo-3,4-dihydro-2H-benzo[1,4]oxazin-6-ylmethoxy]piperidine-1-carboxylate The mixture of 0.280 g of benzyl 4-(4-hydroxyphenyl)-3-[4-(3-methoxypropyl)-3-oxo-3,4-dihydro-2H-benzo[1,4]oxazin-6-ylmethoxy]piperidine-1-carboxylate, 0.152 g of 2(S)-phenoxymethyloxirane and 0.0015 g of caesium fluoride is stirred at 130° C. over 3 hours. The reaction mixture is cooled and the title compound is obtained as a colourless oil by means of flash chromatography (SiO$_2$ 60F). Rf=0.13 (1:1 EtOAc-heptane); Rt=5.14.

d) Benzyl 4-(4-hydroxyphenyl)-3-[4-(3-methoxypropyl)-3-oxo-3,4-dihydro-2H-benzo[1,4]oxazin-6-ylmethoxy]piperidine-1-carboxylate The solution of 10.0 g of benzyl 4-(4-allyloxyphenyl)-3-[4-(3-methoxypropyl)-3-oxo-3,4-dihydro-2H-benzo[1,4]oxazin-6-ylmethoxy]piperidine-1-carboxylate in 160 ml of methanol is admixed successively with 0.57 g of tetrakis(triphenylphosphine)palladium(0) and potassium carbonate. The reaction mixture is stirred at room temperature over 2 hours and subsequently concentrated by evaporation. The residue is admixed slowly with 2M HCl (70 ml) and extracted with dichloromethane (2×250 ml). The organic phases are washed with water (150 ml) and brine (150 ml), dried over sodium sulphate, filtered and concentrated by evaporation. The title compound is obtained as a colourless oil from the residue by means of flash chromatography (SiO$_2$ 60F). Rf=0.20 (3:2 EtOAc-heptane); Rt=4.54.

e) Benzyl 4-(4-allyloxyphenyl)-3-[4-(3-methoxypropyl-1)-3-oxo-3,4-dihydro-2Hbenzo-[1,4]oxazin-6-ylmethoxy]piperidine-1-carboxylate Analogously to Method D, 20.0 g of benzyl 4-(4-allyloxyphenyl)-3-hydroxypiperidine-1-carboxylate and 15.6 g of 6-chloromethyl-4-(3-methoxypropyl)-4H-benzo[1,4]oxazin-3-one (Example 2a) are reacted. The title compound is obtained as a yellowish oil. Rf=0.20 (1:1 EtOAc-heptane); Rt=5.43.

f) Benzyl 4-(4-allyloxyphenyl)-3-hydroxypiperidine-1-carboxylate

Analogously to Example 10f, 29.45 g of 4-(4-allyloxyphenyl)piperidin-3-ol and 26.8 g of benzyl formate are reacted. The title compound is obtained as a white solid. Rt=4.62.

g) 4-(4-Allyloxyphenyl)piperidin-3-ol

Analogously to Method A, 6.3 g of tert-butyl 4-(4-allyloxyphenyl)-3-hydroxypiperidine-1-carboxylate is used to obtain the title compound as a white solid. Rt=2.72.

EXAMPLE 167

1-{2-[2-(4-{4-[3-(2-Methoxybenzyloxy)propoxy]phenyl}piperidin-3-yloxy)ethoxy]benzyloxy}propan-2(S)-ol Analogously to Method A, 0.036 g of tert-butyl 3-{2-[2-(2-hydroxypropoxymethyl)phenoxy]ethoxy}-4-{4-[3-(2-methoxybenzyloxy)propoxy]phenyl}piperidine-1-carboxylate is used to prepare the title compound.

The starting materials are prepared as follows:

a) tert-Butyl 3-{2-[2-(2-hydroxypropoxymethyl)phenoxy]ethoxy}-4-{4-[3-(2-methoxybenzyloxy)propoxy]phenyl}piperidine-1-carboxylate A solution of 0.34 g of tert-butyl 3-[2-(2-hydroxymethylphenoxy)ethoxy]-4-{4-[3-(2-methoxybenzyloxy)propoxy]phenyl}piperidine-1-carboxylate in 10 ml of N,N-dimethylformamide and 0.39 ml of (S)-(−)-propylene oxide (plus 0.3 ml after 2.5 hours, 1.0 ml after 5 hours) and one drop of 1,4-diazabicyclo[2.2.2]octane is stirred at 100° C. over 26 hours. The reaction mixture is cooled, diluted with 1N HCl and extracted with ethyl acetate (2×). The combined organic phases are dried over sodium sulphate and concentrated by evaporation. The title compound is obtained as a yellow oil from the residue by means of flash chromatography (SiO$_2$ 60F). Rf=0.38 (2:1 EtOAc-heptane); Rt=5.88.

b) tert-Butyl 3-[2-(2-hydroxymethylphenoxy)ethoxy]-4-{4-[3-(2-methoxybenzyloxy)propoxy]phenyl}piperidine-1-carboxylate Analogously to Method G, 1.0 g of tert-butyl 4-{4-[3-(2-methoxybenzyloxy)propoxy]phenyl}-3-[2-(toluene-4-sulphonyloxy)ethoxy]piperidine-1-carboxylate (Example 14b) and 0.37 g of 2-hydroxymethylphenol are reacted. The title compound is obtained as an opaque oil. Rf=0.16 (1:2 EtOAc-heptane); Rt=5.71.

According to the process described in Example 142, the following compounds are prepared in an analogous manner:

EXAMPLES

| | |
|---|---|
| 168 | 1-(4-{3-[4-(3-Methoxypropyl)-3,4-dihydro-2H-benzo[1,4]oxazin-6-ylmethoxy]piperidin-4-yl}phenoxy)-3-phenoxypropan-2(R)-ol |
| 169 | 4-(3-Methoxypropyl-6-{4-[4-(2(R)-methyl-3-phenoxypropoxy)phenyl]piperidin-3-yloxymethyl}-3,4-dihydro-2H-benzo[1,4]oxazine |
| 170 | 4-(3-Methoxypropyl)-6-(4-{4-[3-(piperidin-4-yloxy)propoxy]phenvl}piperidin-3-yloxymethyl)-3,4-dihydro-2H-benzo[1,4]oxazine |
| 171 | 4-(3-Methoxypropyl)-6-(4-{4-[3-(tetrahydropyran-4-yloxy)propoxy]phenyl}piperidin-3-yloxymethyl)-3,4-dihydro-2H-benzo[1,4]oxazine |
| 172 | 4-(3-Methoxypropyl)-6-(4-{4-[3-(pyridin-2-yloxy)propoxy]phenyl}piperidin-3-yloxymethyl)-3,4-dihydro-2H-benzo[1.4]oxazine |
| 173 | 3-[3-(4-{3-[4-(3-Methoxypropyl)-3,4-dihydro-2H-benzo[1,4]oxazin-6-ylmethoxy]piperidin-4-yl}phenoxy)propoxy]phenol |
| 174 | 4-(3-Methoxypropyl)-6-(4-{4-[2-(1-phenylcyclopropylmethoxy)ethoxy]phenyl}piperidin-3-yloxymethyl)-3,4-dihydro-2H-benzo[1,4]oxazine |
| 175 | 6-[4-(4-Methoxyphenyl)piperidin-3-yloxymethyl]-4-(3-methoxypropyl)-3,4-dihydro-2H-benzo[1,4]oxazine |

According to the process described in Example 79, the following compounds are prepared in an analogous manner:

EXAMPLES 176 4-{4-[3-(3-Fluorophenoxy)propoxy]phenyl}-3-[3-(3-methoxypropoxy)-4-pyrrolidin-1-ylbenzyloxy]piperidine
177 [4-(4-{4-[3-(2-Methoxybenzyloxy)propoxy]phenyl}piperidin-3-yloxymethyl)-2-(3-methoxypropoxy)phenyl]dimethylamine
178 1-[4-(4-{4-[3-(2-Methoxybenzyloxy)propoxy]phenyl}piperidin-3-yloxymethyl)-2-(3-methoxypropoxy)phenyl]pyrrolidin-2-one
179 [4-(4-{4-[3-(2-Methoxybenzyloxy)propoxy]phenyl}piperidin-3-yloxymethyl)-2-(3-methoxypropoxy)phenyl]methylamine

EXAMPLE 180

Methyl N-(2-{4-fluoro-2-[2-(4-{4-[3-(2-methoxybenzyloxy)propoxy]phenyl}piperidin-3-yloxy)ethoxy]phenyl}ethyl)carbamate Analogously to Method A, 0.425 g of tert-butyl 3-{2-[5-fluoro-2-(2-methoxycarbonylaminoethyl)phenoxy]ethoxy}-4-{4-[3-(2-methoxybenzyloxy)propoxy]phenyl}piperidine-1-carboxylate is used to prepare the title compound.

The starting materials are prepared as follows:

a) tert-Butyl 3-{2-[5-fluoro-2-(2-methoxycarbonylaminoethyl)phenoxy]ethoxy}-4-{4-[3-(2-methoxybenzyloxy)propoxy]phenyl}piperidine-1-carboxylate Analogously to Method G, 0.40 g of tert-butyl 4-{4-[3-(2-methoxybenzyloxy)propoxy]phenyl}-3-[2-(toluene-4-sulphonyloxy)ethoxy]piperidine-1-carboxylate (Example 14b) and 0.26 g of methyl N-[2-(4-fluoro-2-hydroxyphenyl)ethyl]carbamate are reacted. The title compound is obtained as a yellow oil. Rf=0.42 (1:1 EtOAc-heptane); Rt=5.93.

b) Methyl N-[2-(4-fluoro-2-hydroxyphenyl)ethyl]carbamate

A solution of 1.12 g of N-[2-(4-fluoro-2-hydroxyphenyl)ethyl]acetamide (Example 112b) in 10 ml of 6N HCl is stirred at reflux over 44 hours. The reaction mixture is cooled to room temperature and concentrated by evaporation. The residue is dissolved in 20 ml of 1:1 ethyl acetate/saturated sodium carbonate solution, admixed with 0.54 ml of methyl chloroformate and stirred at room temperature over 18 hours. The reaction mixture is partitioned between ethyl acetate and water—the water phase is extracted once more with ethyl acetate (2×). The combined organic phases are washed with brine, dried over sodium sulphate and concentrated by evaporation. The title compound is obtained as a beige solid from the residue by means of flash chromatography (SiO$_2$ 60F). Rf=0.33 (95:5 dichloromethane-methanol); Rt=3.29.

According to the process described in Example 180, the following compounds are prepared in an analogous manner:

EXAMPLES

181 Methyl (2-{3-fluoro-2-[2-(4-{4-[3-(2-methoxybenzyloxy)propoxy]phenyl}piperidin-3-yloxy)ethoxy]phenyl}ethyl)carbamate
182 Methyl (2-{5-fluoro-2-[2-(4-{4-[3-(2-methoxybenzyloxy)propoxy]phenyl}piperidin-3-yloxy)ethoxy]phenyl}ethyl)carbamate
183 Methyl (2-{2-fluoro-6-[2-(4-{4-[3-(2-methoxybenzyloxy)propoxy]phenyl}piperidin-3-yloxy)ethoxy]phenyl}ethyl)carbamate

EXAMPLE 184

3-Fluoro-N-[2-(4-{3-[4-(3-methoxypropyl)-3,4-dihydro-2H-benzo[1,4]oxazin-6-ylmethoxy]piperidin-4-yl}phenoxy)ethyl]benzamide Analogously to Method B, 0.295 g of benzyl 4-{4-[2-(3-fluorobenzoylamino)ethoxy]phenyl}-3-[4-(3-methoxypropyl)-3,4-dihydro-2H-benzo[1,4]oxazin-6-ylmethoxy]piperidine-1-carboxylate is used to prepare the title compound.
The starting materials are prepared as follows:

a) Benzyl 4-{4-[2-(3-fluorobenzoylamino)ethoxy]phenyl}-3-[4-(3-methoxypropyl)-3,4-dihydro-2H-benzo[1,4]oxazin-6-ylmethoxy]piperidine-1-carboxylate A solution of 0.375 g of benzyl 4-[4-(2-aminoethoxy)phenyl]-3-[4-(3-methoxypropyl)-3,4-dihydro-2H-benzo[1,4]oxazin-6-ylmethoxy]piperidine-1-carboxylate and 0.094 g of 3-fluorobenzoic acid in 6 ml of dichloromethane and 1.5 ml of N,N-dimethylformamide is admixed with 0.127 g of 3-dimethylaminopropyl ethyl carbodiimide hydrochloride and 0.167 g of 4-dimethylaminopyridine and stirred at room temperature over 18 hours. The reaction mixture is concentrated by evaporation and the residue partitioned between ethyl acetate and water. The organic phase is washed with 1N HCl, water and brine, dried over sodium sulphate and concentrated by evaporation. The title compound is obtained as a yellow oil from the residue by means of flash chromatography (SiO$_2$ 60F). Rf=0.39 (95:5 dichloromethane-methanol); Rt=5.25.

b) Benzyl 4-[4-(2-aminoethoxy)phenyl]-3-[4-(3-methoxypropyl)-3,4-dihydro-2H-benzo[1,4]oxazin-6-ylmethoxy]piperidine-1-carboxylate Analogously to Method C, 0.787 g of benzyl 4-[4-(2-aminoethoxy)phenyl]-3-[4-(3-methoxypropyl)-3-oxo-3,4-dihydro-2H-benzo[1,4]oxazin-6-ylmethoxy]piperidine-1-carboxylate is reacted. The title compound is obtained as a yellow oil. Rf=0.32 (200:20:1 dichloromethane-methanol-25% conc. ammonia); Rt=4.25.

c) Benzyl 4-[4-(2-aminoethoxy)phenyl]-3-[4-(3-methoxypropyl)-3-oxo-3,4-dihydro-2H-benzo[1,4]oxazin-6-ylmethoxy]piperidine-1-carboxylate Analogously to Method A, 1.06 g of benzyl 4-[4-(2-tert-butoxycarbonylaminoethoxy)phenyl]-3-[4-(3-methoxypropyl)-3-oxo-3,4-dihydro-2H-benzo[1,4]oxazin-6-ylmethoxy]piperidine-1-carboxylate are reacted. The title compound is obtained as a yellow oil. Rf=0.30 (200:20:1 dichloromethane-methanol-25% conc. ammonia); Rt=4.02.

d) Benzyl 4-[4-(2-tert-butoxycarbonylaminoethoxy)phenyl]-3-[4-(3-methoxypropyl)-3-oxo-3,4-dihydro-2H-benzo[1,4]oxazin-6-ylmethoxy]piperidine-1-carboxylate A solution of 1.197 g of benzyl 4-(4-hydroxyphenyl)-3-[4-(3-methoxypropyl)-3-oxo-3,4-dihydro-2H-benzo[1,4]oxazin-6-ylmethoxy]piperidine-1-carboxylate (Example 166c), 0.506 ml of tert-butyl (2-hydroxyethyl)carbamate and 0.848 g of triphenylphosphine in 10 ml of tetrahydrofuran at 0° C. is admixed dropwise with 0.66 ml of diisopropyl azodicarbonate. The reaction mixture is warmed to room temperature, stirred further for 22 hours and subsequently concentrated by evaporation. The title compound is obtained as a yellow oil from the residue by means of flash chromatography (SiO$_2$ 60F). Rf=0.50 (2:1 EtOAc-heptane); Rt=5.39.

EXAMPLE 185

N-{2-[6-(4-{4-[3-(2,5-Difluorophenoxy)propoxy]phenyl}piperidin-3-yloxymethyl)-2,3-dihydrobenzo[1,4]oxazin-4-yl]ethyl}acetamide Analogously to Method B, 0.134 g of benzyl 3-[4-(2-acetylaminoethyl)-3,4-dihydro-2H-benzo[1,4]oxazin-6-ylmethoxy]-4-{4-[3-(2,5-difluorophenoxy)propoxy]phenyl}piperidine-1-carboxylate is used to prepare the title compound.

The starting materials are prepared as follows:

a) Benzyl 3-[4-(2-acetylaminoethyl)-3,4-dihydro-2H-benzo[1,4]oxazin-6-ylmethoxy]-4-{4-[3-(2,5-difluorophenoxy)propoxy]phenyl}piperidine-1-carboxylate The solution of 0.220 g of benzyl 3-[4-(2-aminoethyl)-3,4-dihydro-2H-benzo[1,4]oxazin-6-ylmethoxy]-4-{4-[3-(2,5-difluorophenoxy)propoxy]phenyl}piperidine-1-carboxylate in 7.5 ml of dichloromethane is cooled to 0° C. with stirring and admixed with 0.042 ml of triethylamine. 0.023 ml of acetyl chloride in 0.50 ml of dichloromethane are slowly added dropwise. Subsequently, the mixture is stirred at 0° C. over 1 hour. The reaction mixture is poured onto ice-water (20 ml) and extracted with tert-butyl methyl ether (2×20 ml). The organic phases are washed with brine (20 ml), dried over sodium sulphate and concentrated by evaporation. The title compound is obtained as a white foam from the residue by means of flash chromatography (SiO$_2$ 60F). Rf=0.75 (200:20:1 dichloromethane-methanol-25% conc. ammonia); Rt=5.46.

b) Benzyl 3-[4-(2-aminoethyl)-3,4-dihydro-2H-benzo[1,4]oxazin-6-ylmethoxy]-4-{4-[3-(2,5-difluorophenoxy)propoxy]phenyl}piperidine-1-carboxylate Analogously to Method C, 0.585 g of benzyl 3-[4-(2-aminoethyl)-3-oxo-3,4-dihydro-2H-benzo[1,4]oxazin-6-ylmethoxy]-4-{4-[3-(2,5-difluorophenoxy)propoxy]phenyl}piperidine-1-carboxylate is reacted. The title compound is obtained as a yellowish oil. Rf=0.44 (200:20:1 dichloromethane-methanol-25% conc. ammonia); Rt=21.49 (II)

c) Benzyl 3-[4-(2-aminoethyl)-3-oxo-3,4-dihydro-2H-benzo[1,4]oxazin-6-ylmethoxy]-4-{4-[3-(2,5-difluorophenoxy)propoxy]phenyl}piperidine-1-carboxylate A solution of 0.660 g of benzyl 3-[4-(2-azidoethyl)-3-oxo-3,4-dihydro-2H-benzo[1,4]oxazin-6-ylmethoxy]-4-{4-[3-(2,5-difluorophenoxy)propoxy]phenyl}piperidine-1-carboxylate in 2.5 ml of tetrahydrofuran and 0.55 ml of water is admixed at room temperature with a solution of 0.55 ml of 25% conc. ammonia in 2.4 ml of methanol. After 0.357 g of triphenylphosphine has been added, the reaction mixture is stirred at room temperature over 16 hours. The reaction mixture is poured onto water (40 ml) and extracted with tert-butyl methyl ether (3×40 ml). The organic phases are washed with brine (20 ml), dried over sodium sulphate and concentrated by evaporation. The title compound is obtained as a slightly yellowish oil from the residue by means of flash chromatography (SiO$_2$ 60F). Rf=0.31 (200:20:1 dichloromethane-methanol-25% conc. ammonia); Rt=5.01.

d) Benzyl 3-[4-(2-azidoethyl)-3-oxo-3,4-dihydro-2H-benzo[1,4]oxazin-6-ylmethoxy]-4-{4-[3-(2,5-difluorophenoxy)propoxy]phenyl}piperidine-1-carboxylate A solution of 0.880 g of benzyl 4-{4-[3-(2,5-difluorophenoxy)propoxy]phenyl}-3-{3-oxo-4-[2-(toluene-4-sulphonyloxy)ethyl]-3,4-dihydro-2H-benzo[1,4]oxazin-6-ylmethoxy}piperidine-1-carboxylate and 0.532 g of sodium azide in 10 ml of N,N-dimethylformamide is stirred at 65° C. over 90 minutes. The reaction mixture is poured onto water (40 ml) and extracted with tert-butyl methyl ether (2×40 ml). The organic phases are washed with brine (20 ml), dried over sodium sulphate and concentrated by evaporation. The title compound is obtained as a slightly yellowish oil from the residue by means of flash chromatography (SiO$_2$ 60F). Rf=0.11 (1:2 EtOAc-heptane). Rt=5.82 e) Benzyl 4-{4-[3-(2,5-difluorophenoxy)propoxy]
phenyl}-3-{3-oxo-4-[2-(toluene-4-sulphonyloxy)
ethyl]-3,4-dihydro-2H-benzo[1,4]oxazin-6-
ylmethoxy}piperidine-1-carboxylate Analogously to Method H, 0.890 g of benzyl 4-{4-[3-(2,5-difluorophenoxy)propoxy]phenyl}-3-[4-(2-hydroxyethyl)-3-oxo-3,4-dihydro-2H-benzo[1,4]oxazin-6-ylmethoxy]piperidine-1-carboxylate is reacted. The title compound is obtained as a white foam. Rf=0.51 (2:1 EtOAc-heptane). Rt=5.93.

f) Benzyl 4-{4-[3-(2,5-difluorophenoxy)propoxy]
phenyl}-3-[4-(2-hydroxyethyl)-3-oxo-3,4-dihydro-
2H-benzo[1,4]oxazin-6-ylmethoxy]piperidine-1-
carboxylate The solution of 2.0 g of benzyl 4-{4-[3-(2,5-difluorophenoxy)propoxy]phenyl}-3-[3-oxo-4-(2-triisopropylsilanyloxyethyl)-3,4-dihydro-2H-benzo[1,4]oxazin-6-ylmethoxy]piperidine-1-carboxylate in 30 ml of tetrahydrofuran is admixed with 2.30 ml of tetrabutylammonium fluoride solution (1M in tetrahydrofuran) and stirred at 60° C. over 30 minutes. The reaction mixture is cooled, poured onto water (100 ml) and extracted with tert-butyl methyl ether (2×100 ml). The organic phases are washed with brine (1×100 ml), dried over sodium sulphate, filtered and concentrated by evaporation. The title compound is obtained as a white foam from the residue by means of flash chromatography (SiO$_2$ 60F). Rf=0.10 (1:1 EtOAc-heptane); Rt=5.43.

g) Benzyl 4-{4-[3-(2,5-difluorophenoxy)propoxy]
phenyl}-3-[3-oxo-4-(2-triisopropylsilanyloxyethyl)-
3,4-dihydro-2H-benzo[1,4]oxazin-6-ylmethoxy]piperidine-1-carboxylate Analogously to Method D, 1.34 g of benzyl 4-{4-[3-(2,5-difluorophenoxy)propoxy]phenyl}-3-hydroxypiperidine-1-carboxylate and 1.43 g of 6-chloromethyl-4-(2-triisopropylsilanyloxyethyl)-4H-benzo[1,4]oxazin-3-one are reacted. The title compound is obtained as a slightly yellowish oil. Rf=0.55 (1:1 EtOAc-heptane); Rt=7.03.

h) Benzyl 4-{4-[3-(2,5-difluorophenoxy)propoxy]
phenyl}-3-hydroxypiperidine-1-carboxylate Analogously to Method I, 1.20 g of benzyl 3-hydroxy-4-(4-hydroxyphenyl)piperidine-1-carboxylate and 1.00 g of 2-(3-bromopropoxy)-1,4-difluorobenzene (Example 142d) are reacted. The title compound is obtained as a colourless oil. Rf=0.24 (1:1 EtOAc-heptane). Rt=3.29.

i) 6-Chloromethyl-4-(2-triisopropylsilanyloxyethyl)-
4H-benzo[1,4]oxazin-3-one

Analogously to Method E, 4.66 g of 6-hydroxymethyl-4-(2-triisopropylsilanyloxyethyl)-4H-benzo[1,4]oxazin-3-one are reacted. The title compound is obtained as a colourless oil. Rf=0.66 (1:1 EtOAc-heptane). Rt=6.40.

k) 6-Hydroxymethyl-4-(2-triisopropylsilanyloxy-
ethyl)-4H-benzo[1,4]oxazin-3-one The solution of 7.24 g of 6-(tetrahydropyran-2-yloxymethyl)-4-(2-triisopropylsilanyloxyethyl)-4H-benzo[1,4]oxazin-3-one in 130 ml of ethanol is admixed with 0.392 g of pyridinium p-toluenesulphonate and stirred at 60° C. over 3 hours. The reaction mixture is cooled and concentrated by evaporation. The title compound is obtained as a colourless oil from the residue by means of flash chromatography (SiO$_2$ 60F). Rf=0.48 (1:1 EtOAc-heptane); Rt=5.51.

l) 6-(Tetrahydropyran-2-yloxymethyl)-4-(2-triisopro-
pylsilanyloxyethyl)-4H-benzo[1,4]oxazin-3-one The solution of 5.50 g of 6-(tetrahydropyran-2-yloxymethyl)-4H-benzo[1,4]oxazin-3-one and 100 ml of N,N-dimethylformamide-tetrahydrofuran (1:1) is cooled to 0° C., admixed with 0.800 g of sodium hydride dispersion (60%) and stirred over 30 minutes. The mixture is admixed with 7.90 g of (2-iodoethoxy)triisopropylsilane and stirred at room temperature for a further 16 hours. The reaction mixture is poured onto ice-water (150 ml) and extracted with ethyl acetate (3×150 ml). The organic phases are washed successively with aqueous sodium hydrogencarbonate solution (1×100 ml), water (100 ml) and brine (100 ml), dried over sodium sulphate, filtered and concentrated by evaporation. The title compound is obtained as a colourless oil from the residue by means of flash chromatography (SiO$_2$ 60F). Rf=0.57 (1:1 EtOAc-heptane); Rt=6.71.

m) 6-(Tetrahydropyran-2-yloxymethyl)-4H-benzo[1,
4]oxazin-3-one

The solution of 5.0 g of 6-hydroxymethyl-4H-benzo[1,4]oxazin-3-one in 60 ml of dichloromethane is admixed successively with 5.20 ml of 3,4-dihydro-2H-pyran and 0.236 g of p-toluenesulphonic acid monohydrate. The reaction mixture is stirred at room temperature over 14 hours. The solution is poured onto 1M sodium hydrogencarbonate solution (300 ml) and extracted with tert-butyl methyl ether (2×400 ml). The organic phase is washed with brine (300 ml), dried over sodium sulphate, filtered and concentrated by evaporation. The title compound is obtained as a beige solid from the residue by means of crystallization (EtOAc/heptane). Rf=0.25 (1:1 EtOAc-heptane); Rt=3.45.

According to the process described in Example 185, the following compound is prepared in an analogous manner:

EXAMPLE 186

Methyl {2-[6-(4-{4-[3-(2,5-difluorophenoxy)pro-
poxy]phenyl}piperidin-3-yloxymethyl)-2,3-dihy-
drobenzo[1,4]oxazin-4-yl]ethyl}carbamate

EXAMPLE 187

6-(4-{4-[2-(2,5-Difluorobenzyloxy)ethoxy]
phenyl}piperidin-3-yloxymethyl)-4-(3-methoxypro-
pyl)-3,4-dihydro-2H-benzo[1,4]oxazine Analogously to Method B, 0.360 g of benzyl 4-{4-[2-(2,5-difluorobenzyloxy)ethoxy]phenyl}-3-[4(3-methoxypropyl)-3,4-dihydro-2H-benzo[1,4]oxazin-6-ylmethoxy]piperidine-1-carboxylate is used to prepare the title compound.

The starting materials are prepared as follows:

a) Benzyl 4-{4-[2-(2,5-difluorobenzyloxy)ethoxy]
phenyl}-3-[4(3-methoxypropyl)-3,4-dihydro-2H-
benzo[1,4]oxazin-6-ylmethoxy]piperidine-1-car-
boxylate Analogously to Method C, 0.390 g of benzyl 4-{4-[2-(2,5-difluorobenzyloxy)ethoxy]phenyl}-3-[4-(3-methoxypropyl)-3-oxo-3,4-dihydro-2H-benzo[1,4]oxazin-6-ylmethoxy]piperidine-1-carboxylate is reacted. The title compound is obtained as a slightly yellowish oil. Rf=0.26 (1:1 EtOAc-heptane). Rt=5.93.

b) Benzyl 4-{4-[2-(2,5-difluorobenzyloxy)ethoxy]phenyl}-3-[4-(3-methoxypropyl)-3-oxo-3,4-dihydro-2H-benzo[1,4]oxazin-6-ylmethoxy]piperidine-1-carboxylate Analogously to Method D, 0.430 g of benzyl 4-{4-[2-(2,5-difluorobenzyloxy)ethoxy]phenyl}-3-hydroxypiperidine-1-carboxylate and 0.261 g of 6-chloromethyl-4-(3-methoxypropyl)-4H-benzo[1,4]oxazin-3-one are reacted. The title compound is obtained as a colourless oil. Rf=0.10 (1:1 EtOAc-heptane). Rt=5.72.

c) Benzyl 4-{4-[2-(2,5-difluorobenzyloxy)ethoxy]phenyl}-3-hydroxypiperidine-1-carboxylate Analogously to Method I, 0.665 g of benzyl 3-hydroxy-4-(4-hydroxyphenyl)piperidine-1-carboxylate and 0.824 g of 2-(2,5-difluorobenzyloxy)ethyl toluene-4-sulphonate are reacted. The title compound is obtained as a colourless oil. Rf=0.21 (1:1 EtOAc-heptane). Rt=5.01.

d) Benzyl 3-hydroxy-4-(4-hydroxyphenyl)piperidine-1-carboxylate

The mixture of 6.0 g of tert-butyl 3-hydroxy-4-(4-hydroxyphenyl)piperidine-1-carboxylate, 120 ml of methanol, 40 ml of chloroform and 20 ml of 2M HCl is stirred at 60° C. over 20 hours. The reaction mixture is cooled and the organic solvent is evaporated off. The resulting aqueous solution is admixed with stirring with 80 ml of saturated sodium hydrogencarbonate solution and 80 ml of ethyl acetate. The biphasic mixture is cooled to 0° C. and admixed slowly with 3.30 ml of benzyl chloroformate and stirred over a further 2 hours. The reaction mixture is extracted with ethyl acetate-tetrahydrofuran. The organic phases are concentrated by evaporation and the title compound is obtained as a white solid from the residue by means of crystallization (ethyl acetate-heptane). Rt=5.72.

e) 2-(2,5-Difluorobenzyloxy)ethyl toluene-4-sulphonate

Analogously to Method H, 3.70 g of 2-(2,5-difluorobenzyloxy)ethanol are reacted. The title compound is obtained as a colourless oil. Rf=0.35 (1:2 EtOAc-heptane). Rt=4.92.

f) 2-(2,5-Difluorobenzyloxy)ethanol

The mixture of 1.51 g of ethylene glycol, 360 ml of toluene and 6.13 g of dibutyltin oxide is stirred on a water separator at reflux temperature over 18 hours. The reaction mixture is admixed with 3.11 g of tetrabutylammonium bromide and 10 g of 3,5-difluorobenzyl bromide and stirred at reflux for a further 3 hours. The mixture is subsequently concentrated by evaporation and the title compound is obtained as a slightly yellowish oil from the residue by means of flash chromatography (SiO$_2$ 60F). Rf=0.29 (1:1 EtOAc-heptane). Rt=3.18.

According to the process described in Example 187, the following compound is prepared in an analogous manner:

EXAMPLE 188

6-(4-{4-[2-(2-Methoxybenzyloxy)ethoxy]phenyl}piperidin-3-yloxymethyl)-4-(3-methoxypropyl)-3,4-dihydro-2H-benzo[1,4]oxazine

EXAMPLE 189

2-Cyclopropyl-1-[3-(4-{3-[4-(3-methoxypropyl)-3,4-dihydro-2H-benzo[1,4]oxazin-6-ylmethoxy]piperidin-4-yl}phenoxy)pyrrolidin-1-yl]ethanone Analogously to Method B, 0.120 g of benzyl 4-{4-[1-(2-cyclopropylacetyl)pyrrolidin-3-yloxy]phenyl}-3-[4-(3-methoxypropyl)-3,4-dihydro-2H-benzo[1,4]oxazin-6-ylmethoxy]piperidine-1-carboxylate is used to prepare the title compound.

The starting materials are prepared as follows:

a) Benzyl 4-{4-[1-(2-cyclopropylacetyl)pyrrolidin-3-yloxy]phenyl}-3-[4-(3-methoxypropyl)-3,4-dihydro-2H-benzo[1,4]oxazin-6-ylmethoxy]piperidine-1-carboxylate The solution of 0.120 g of benzyl 3-[4-(3-methoxypropyl)-3,4-dihydro-2H-benzo[1,4]oxazin-6-ylmethoxy]-4-[4-(pyrrolidin-3-yloxy)phenyl]piperidine-1-carboxylate in 4.0 ml of dichloromethane is cooled to 0° C. with stirring and admixed with 0.032 ml of triethylamine. 0.031 ml of cyclopropylacetyl chloride in 0.40 ml of dichloromethane is slowly added dropwise. Subsequently, the mixture is stirred at 0° C. over 1 hour. The reaction mixture is poured onto ice-water (20 ml) and extracted with tert-butyl methyl ether (2×20 ml). The organic phases are washed with brine (20 ml), dried over sodium sulphate and concentrated by evaporation. The title compound is obtained as a pink oil from the residue by means of flash chromatography (SiO$_2$ 60F). Rf=0.30 (200:20:1 dichloromethane-methanol-25% conc. ammonia); Rt=5.18.

According to the process described in Example 189, the following compounds are prepared in an analogous manner:

EXAMPLES

| | |
|---|---|
| 190 | Cyclohexyl-[3-(4-{3-[4-(3-methoxypropyl)-3,4-dihydro-2H-benzo[1,4]oxazin-6-ylmethoxy]piperidin-4-yl}phenoxy)pyrrolidin-1-yl]methanone |
| 191 | [3-(4-{3-[4-(3-Methoxypropyl)-3,4-dihydro-2H-benzo[1,4]oxazin-6-ylmethoxy]piperidin-4-yl}phenoxy)pyrrolidin-1-yl](tetrahydropyran-4-yl)methanone |
| 192 | [3-(4-{3-[4-(3-Methoxypropyl)-3,4-dihydro-2H-benzo[1,4]oxazin-6-ylmethoxy]piperidin-4-yl}phenoxy)azetidin-1-yl]phenylmethanone |

EXAMPLE 193

4-(3-Methoxypropyl)-6-{4-[4-(1-phenylpyrrolidin-3(S)-yloxy)phenyl]piperidin-3-yloxymethyl}-3,4-dihydro-2H-benzo[1,4]oxazine Analogously to Method B, 0.220 g of benzyl 3-[4-(3-methoxypropyl)-3,4-dihydro-2H-benzo[1,4]oxazin-6-ylmethoxy]-4-[4-(1-phenylpyrrolidin-3(S)-yloxy)phenyl]piperidine-1-carboxylate is used to prepare the title compound.

The starting materials are prepared as follows:

a) Benzyl 3-[4-(3-methoxypropyl)-3,4-dihydro-2H-benzo[1,4]oxazin-6-ylmethoxy]-4-[4-(1-phenylpyrrolidin-3(S)-yloxy)phenyl]piperidine-1-carboxylate Analogously to Method C, 0.265 g of benzyl 3-[4-(3-methoxypropyl)-3-oxo-3,4-dihydro-2H-benzo[1,4]oxazin-6-ylmethoxy]-4-[4-(1-phenylpyrrolidin-3(S)-yloxy)phenyl]piperidine-1-carboxylate is reacted. The title compound is obtained as a slightly yellowish oil. Rf=0.28 (1:1 EtOAc-heptane). Rt=6.13.

b) Benzyl 3-[4-(3-methoxypropyl)-3-oxo-3,4-dihydro-2H-benzo[1,4]oxazin-6-ylmethoxy]-4-[4-(1-phenylpyrrolidin-3(S)-yloxy)phenyl]piperidine-1-carboxylate The mixture of 0.106 g of sodium tert-butoxide, 0.500 g of benzyl 3-[4-(3-methoxypropyl)-3-oxo-3,4-dihydro-2H-benzo[1,4]oxazin-6-ylmethoxy]-4-[4-(pyrrolidin-3(S)-yloxy)phenyl]piperidine-1-carboxylate, 0.106 ml iodobenzene and 8.5 ml of dioxane is initially charged under argon in a Schlenk apparatus with stirring. The mixture is admixed with the solution of 0.028 g of 9,9-dimethyl-4,5-bis(diphenylphosphino)xanthene and tris(dibenzylidenacetone)dipalladium(0) in 2.5 ml of dioxane (prepared in a Schlenk apparatus under argon) and stirred at 60° C. for 3 hours. The reaction mixture is cooled, poured onto ice-water (70 ml) and extracted with tert-butyl methyl ether (2×70 ml). The organic phases are washed with brine (70 ml), dried over sodium sulphate and concentrated by evaporation. The title compound is obtained as a brown foam from the residue by means of flash chromatography (SiO$_2$ 60F). Rf=0.20 (1:1 EtOAc-heptane). Rt=5.88.

c) Benzyl 3-[4-(3-methoxypropyl)-3-oxo-3,4-dihydro-2H-benzo[1,4]oxazin-6-ylmethoxy]-4-[4-(pyrrolidin-3(S)-yloxy)phenyl]piperidine-1-carboxylate Analogously to Method A, 0.720 g of benzyl 4-[4-(1-tert-butoxycarbonylpyrrolidin-3(S)-yloxy)phenyl]-3-[4-(3-methoxypropyl)-3-oxo-3,4-dihydro-2H-benzo[1,4]oxazin-6-ylmethoxy]piperidine-1-carboxylate is reacted. The title compound is obtained as a yellowish oil. Rf=0.20 (200:20:1 dichloromethane-methanol-25% conc. ammonia); Rt=4.11.

d) Benzyl 4-[4-(1-tert-butoxycarbonylpyrrolidin-3(S)-yloxy)phenyl]-3-[4-(3-methoxypropyl)-3-oxo-3,4-dihydro-2H-benzo[1,4]oxazin-6-ylmethoxy]piperidine-1-carboxylate Analogously to Method D, 0.980 g of benzyl 4-[4-(1-tert-butoxycarbonylpyrrolidin-3(S)-yloxy)phenyl]-3-hydroxypiperidine-1-carboxylate and 0.572 g of 6-chloromethyl-4-(3-methoxypropyl)-4H-benzo[1,4]oxazin-3-one are reacted. The title compound is obtained as a yellowish oil. Rf=0.14 (1:1 EtOAc-heptane). Rt=5.63.

e) Benzyl 4-[4-(1-tert-butoxycarbonylpyrrolidin-3(S)-yloxy)phenyl]-3-hydroxypiperidine-1-carboxylate Analogously to Method I, 0.665 g of benzyl 3-hydroxy-4-(4-hydroxyphenyl)piperidine-1-carboxylate and 0.822 g of tert-butyl 3(R)-(toluene-4-sulphonyloxy)pyrrolidine-1-carboxylate are reacted. The title compound is obtained as a white foam. Rf=0.14 (1:1 EtOAc-heptane). Rt=4.91.

According to the process described in Example 193, the following compounds are prepared in an analogous manner:

EXAMPLES

| | | |
|---|---|---|
| 194 | 6-(4-{4-[1-(2-Fluorophenyl)pyrrolidin-3(S)-yloxy]phenyl}piperidin-3-yloxymethyl)-4-(3-methoxypropyl)-3,4-dihydro-2H-benzo[1,4]oxazine |
| 195 | 6-(4-{4-[1-(4-Fluorophenyl)pyrrolidin-3(S)-yloxy]phenyl}piperidin-3-yloxymethyl)-4-(3-methoxypropyl)-3,4-dihydro-2H-benzo[1,4]oxazine |
| 196 | 6-(4-{4-[1-(3-Fluorophenyl)pyrrolidin-3(S)-yloxy]phenyl}piperidin-3-yloxymethyl)-4-(3-methoxypropyl)-3,4-dihydro-2H-benzo[1,4]oxazine |
| 197 | 4-(3-Methoxypropyl)-6-{4-[4-(1-phenylazetidin-3-yloxy)phenyl]piperidin-3-yloxymethyl}-3,4-dihydro-2H-benzo[1,4]oxazine |
| 198 | 4-(3-Methoxypropyl)-6-{4-[4-(1-phenylpiperidin-4-yloxy)phenyl]piperidin-3-yloxymethyl}-3,4-dihydro-2H-benzo[1,4]oxazine |
| 199 | 6-(4-{4-[1-(3-Methoxyphenyl)pyrrolidin-3(S)-yloxy]phenyl}piperidin-3-yloxymethyl)-4-(3-methoxypropyl)-3,4-dihydro-2H-benzo[1,4]oxazine |
| 200 | 4-(3-Methoxypropyl)-6-{4-[4-(1-pyridin-2-ylpyrrolidin-3(S)-yloxy)phenyl]piperidin-3-yloxymethyl}-3,4-dihydro-2H-benzo[1,4]oxazine |
| 201 | 6-(4-{4-[1-(3-Chlorophenyl)pyrrolidin-3(S)-yloxy]phenyl}piperidin-3-yloxymethyl)-4-(3-methoxypropyl)-3,4-dihydro-2H-benzo[1,4]oxazine |
| 202 | 6-(4-{4-[1-(2-Chlorophenyl)pyrrolidin-3(S)-yloxy]phenyl}piperidin-3-yloxymethyl)-4-(3-methoxypropyl)-3,4-dihydro-2H-benzo[1,4]oxazine |
| 203 | 4-(3-Methoxypropyl)-6-{4-[4-(5(S)-methyl-1-phenylpyrrolidin-3(S)-yloxy)phenyl]piperidin-3-yloxymethyl}-3,4-dihydro-2H-benzo[1,4]oxazine |
| 204 | 6-(4-{4-[1-(2-Methoxyphenyl)pyrrolidin-3(S)-yloxy]phenyl}piperidin-3-yloxymethyl)-4-(3-methoxypropyl)-3,4-dihydro-2H-benzo[1,4]oxazine |
| 205 | 6-{4-[4-(1-Benzo[1,3]dioxol-5-ylpyrrolidin-3(S)-yloxy)phenyl]piperidin-3-yloxymethyl}-4-(3-methoxypropyl)-3,4-dihydro-2H-benzo[1,4]oxazine |
| 206 | 6-(4-{4-[1-(2-Fluorophenyl)azetidin-3-yloxy]phenyl}piperidin-3-yloxymethyl)-4-(3-methoxypropyl)-3,4-dihydro-2H-benzo[1,4]oxazine |
| 207 | 6-(4-{4-[1-(3-Fluorophenyl)azetidin-3-yloxy]phenyl}piperidin-3-yloxymethyl)-4-(3-methoxypropyl)-3,4-dihydro-2H-benzo[1,4]oxazine |
| 208 | 6-(4-{4-[1-(4-Fluorophenyl)azetidin-3-yloxy]phenyl}piperidin-3-yloxymethyl)-4-(3-methoxypropyl)-3,4-dihydro-2H-benzo[1,4]oxazine |
| 209 | 6-{4-[4-(1-Benzo[1,3]dioxol-5-ylazetidin-3-yloxy)phenyl]piperidin-3-yloxymethyl}-4-(3-methoxypropyl)-3,4-dihydro-2H-benzo[1,4]oxazine |

-continued 210 6-(4-{4-[1-(2,5-Difluorophenyl)azetidin-3-yloxy]phenyl}piperidin-3-yloxymethyl)-4-(3-methoxypropyl)-3,4-dihydro-2H-benzo[1,4]oxazine
211 6-(4-{4-[1-(3,4-Difluorophenyl)azetidin-3-yloxy]phenyl}piperidin-3-yloxymethyl)-4-(3-methoxypropyl)-3,4-dihydro-2H-benzo[1,4]oxazine
212 6-(4-{4-[1-(3,5-Difluorophenyl)azetidin-3-yloxy]phenyl}piperidin-3-yloxymethyl)-4-(3-methoxypropyl)-3,4-dihydro-2H-benzo[1,4]oxazine
213 6-(4-{4-[1-(4-Methoxyphenyl)azetidin-3-yloxy]-phenyl}piperidin-3-yloxymethyl)-4-(3-methoxypropyl)-3,4-dihydro-2H-benzo[1,4]oxazine
214 6-(4-{4-[1-(3-Methoxyphenyl)azetidin-3-yloxy]phenyl}piperidin-3-yloxymethyl)-4-(3-methoxypropyl)-3,4-dihydro-2H-benzo[1,4]oxazine
215 6-(4-{4-[1-(2-Methoxyphenyl)azetidin-3-yloxy]phenyl}piperidin-3-yloxymethyl)-4-(3-methoxypropyl)-3,4-dihydro-2H-benzo[1,4]oxazine

EXAMPLE 216

4-(3-Methoxypropyl)-6-{4-[4-phenylpiperidin-1-carbonyl)phenyl]piperidin-3-yloxymethyl}-4H-benzo[1,4]oxazin-3-one Analogously to Method A, 0.090 g of tert-butyl 3-[4-(3-methoxypropyl)-3-oxo-3,4-dihydro-2H-benzo[1,4]oxazin-6-ylmethoxy]-4-[4-(4-phenylpiperidine-1-carbonyl)phenyl]piperidine-1-carboxylate is used to prepare the title compound.

The starting materials are prepared as follows:

a) tert-Butyl 3-[4-(3-methoxypropyl)-3-oxo-3,4-dihydro-2H-benzo[1,4]oxazin-6-ylmethoxy]-4-[4-(4-phenylpiperidine-1-carbonyl)phenyl]piperidine-1-carboxylate A solution of 0.122 g of 4-phenylpiperidine in 2 ml of dichloromethane is admixed with 0.101 ml of triethylamine. The reaction solution is cooled to 0° and a solution of tert-butyl 4-(4-chlorocarbonylphenyl)-3-[4-(3-methoxypropyl)-3-oxo-3,4-dihydro-2H-benzo[1,4]oxazin-6-ylmethoxy]piperidine-1-carboxylate in 4 ml of dichloromethane is added dropwise. The reaction mixture is stirred at 0° C. over 40 minutes and subsequently poured onto 25 ml of saturated sodium hydrogencarbonate solution. The mixture is extracted with 80 ml of dichloromethane, the phases are separated and the organic phase is washed with 40 ml each of water and brine, dried over sodium sulphate, filtered and concentrated. The residue is purified by means of flash chromatography ($SiO_2$ 60F). The title compound is obtained as a colourless oil. Rf=0.20 (3:1 EtOAc-heptane); Rt=5.44.

b) tert-Butyl 4-(4-chlorocarbonylphenyl)-3-[4-(3-methoxypropyl)-3-oxo-3,4-dihydro-2H-benzo[1,4]oxazin-6-ylmethoxy]piperidine-1-carboxylate 0.190 ml of oxalyl chloride are added dropwise to a solution of 0.600 g of tert-butyl 4-(4-carboxyphenyl)-3-[4-(3-methoxypropyl)-3-oxo-3,4-dihydro-2H-benzo[1,4]oxazin-6-ylmethoxy]piperidine-1-carboxylate in 6 ml of dichloromethane. The reaction solution is subsequently stirred at room temperature over 1 hour and then admixed with 2 drops of N,N-dimethylformamide and stirred at room temperature for a further 35 minutes. The reaction mixture is concentrated by evaporation to dryness and used further as the crude product without purification. Reddish oil, Rt=5.50.

c) tert-Butyl 4-(4-carboxyphenyl)-3-[4-(3-methoxypropyl)-3-oxo-3,4-dihydro-2H-benzo[1,4]oxazin-6-ylmethoxy]piperidine-1-carboxylate A solution of 1,200 g of tert-butyl 4-(4-methoxycarbonylphenyl)-3-[4-(3-methoxypropyl)-3-oxo-3,4-dihydro-2H-benzo[1,4]oxazin-6-ylmethoxy]piperidine-1-carboxylate in 20 ml of dioxane is admixed with 10 ml of 2N NaOH. The reaction mixture is heated to 80° C. over 1 hour and subsequently cooled to room temperature. The phases are separated and the aqueous phase is adjusted to pH 2 with 2N HCl (9.5 ml) and extracted with tert-butyl methyl ether (2×40 ml). The organic phases are combined, washed with 50 ml of water, dried over sodium sulphate, filtered and concentrated by evaporation. The residue is recrystallized from 1:1 ethyl acetate/heptane (20 ml). The title compound is obtained as a colourless solid. Rt=4.48.

d) tert-Butyl 4-(4-methoxycarbonylphenyl)-3-[4-(3-methoxypropyl)-3-oxo-3,4-dihydro-2H-benzo[1,4]oxazin-6-ylmethoxy]piperidine-1-carboxylate Analogously to Method D, 1.180 g of tert-butyl 3-hydroxy-4-(4-methoxycarbonylphenyl)piperidine-1-carboxylate and 1.016 g of 6-chloromethyl-4-(3-methoxypropyl)-4H-benzo[1,4]oxazin-3-one are reacted. The title compound is obtained as a colourless oil. Rf=0.20 (3:1 EtOAc-heptane); Rt=5.12.

e) tert-Butyl 3-hydroxy-4-(4-methoxycarbonylphenyl)piperidine-1-carboxylate

An autoclave is initially charged under argon with 58 ml of N,N-dimethylformamide, 42 ml of methanol, 0.347 g of diphenylphosphinopropane and 0.189 g of palladium(II) acetate. The reaction mixture is stirred at room temperature over 20 minutes. Subsequently, 7.73 g of tert-butyl 3-hydroxy-4-(4-trifluoromethanesulphonyloxyphenyl)piperidine-1-carboxylate and 3.75 g of triethylamine are added and the autoclave is charged with 5 bar of carbon monoxide. The reaction mixture is subsequently stirred at 70° and 5 bar of pressure over 3 hours. Subsequently, the reaction mixture is cooled and a solution of palladium(II) acetate (0.095 g) and diphenylphosphinopropane (0.175 g) in 29 ml of N,N-dimethylformamide and 21 ml of methanol is added. The reaction mixture is subsequently stirred at 70° and 5 bar of carbon monoxide for a further 3 hours. The reaction solution is cooled and stirred with 200 ml of water and 250 ml of tert-butyl methyl ether. The phases are separated and the aqueous phase is extracted once more with 250 ml of tert-butyl methyl ether. The organic phases are combined and concentrated by evaporation to dryness. The title compound is obtained as a colourless solid from the residue by means of flash chromatography (SiO$_2$ 60F). Rf=0.20 (1:1 EtOAc-heptane); Rt=4.15.

f) tert-Butyl 3-hydroxy-4-(4-trifluoromethanesulphonyloxyphenyl)piperidine-1-carboxylate A solution of 7.50 g of tert-butyl 3-hydroxy-4-(4-hydroxyphenyl)piperidine-1-carboxylate in 225 ml of dichloromethane is admixed under argon with 9.97 g of N-phenylbis(trifluoromethanesulphonylimide) and 3.90 ml of triethylamine. The reaction solution is stirred at room temperature over 18 hours and subsequently concentrated by evaporation to dryness. The residue is purified by means of flash chromatography (SiO$_2$ 60F). The title compound is obtained as a colourless solid from the prepurified product by recrystallization from 1:10 ethyl acetate/heptane (165 ml). Rf=0.10 (1:3 EtOAc-heptane); Rt=4.85.

According to the process described in Example 216, the following compound is prepared in an analogous manner:

EXAMPLE 217

4-(3-Methoxypropyl)-6-{4-[4-(4-phenylpiperazine-1-carbonyl)phenyl]piperidin-3-yloxymethyl}-4H-benzo[1,4]oxazin-3-one

EXAMPLE 218

7-(4-{4-[3-(2-Methoxybenzyloxy)propoxy]phenyl}piperidin-3-yloxymethyl)-3,3-dimethyl-1,3-dihydroindol-2-one Analogously to Method B, 0.442 g of benzyl 3-(3,3-dimethyl-2-oxo-2,3-dihydro-1H-indol-7-ylmethoxy)-4-{4-[3-(2-methoxybenzyloxy)propoxy]phenyl}piperidine-1-carboxylate is used to prepare the title compound.

The starting materials are prepared as follows:

a) Benzyl 3-(3,3-dimethyl-2-oxo-2,3-dihydro-1H-indol-7-ylmethoxy)-4-{4-[3-(2-methoxybenzyloxy)propoxy]phenyl}piperidine-1-carboxylate The solution of 0.690 g of benzyl 3-[3,3-dimethyl-2-oxo-1-(2-trimethylsilanylethoxymethyl)-2,3-dihydro-1H-indol-7-ylmethoxy]-4-{4-[3-(2-methoxybenzyloxy)propoxy]phenyl}piperidine-1-carboxylate in 7.2 ml of tetrahydrofuran is admixed with 17.9 ml of tetrabutylammonium fluoride solution (1M in tetrahydrofuran) and stirred at reflux over 26 hours. The reaction mixture is cooled, poured onto water (100 ml) and extracted with tert-butyl methyl ether (2×100 ml). The organic phases are washed with brine (1×100 ml), dried over sodium sulphate, filtered and concentrated by evaporation. The title compound is obtained as an orange oil from the residue by means of flash chromatography (SiO$_2$ 60F). Rf=0.22 (1:1 EtOAc-heptane); Rt=5.89.

b) Benzyl 3-[3,3-dimethyl-2-oxo-1-(2-trimethylsilanylethoxymethyl)-2,3-dihydro-1H-indol-7-ylmethoxy]-4-{4-[3-(2-methoxybenzyloxy)propoxy]phenyl}piperidine-1-carboxylate Analogously to Method D, 0.600 g of benzyl 3-hydroxy-4-{4-[3-(2-methoxybenzyloxy)propoxy]phenyl}piperidine-1-carboxylate (Example 10f) and 0.574 g of 7-bromomethyl-3,3-dimethyl-1-(2-trimethylsilanylethoxymethyl)-1,3-dihydroindol-2-one are reacted. The title compound is obtained as a slightly yellowish oil. Rf=0.16 (1:2 EtOAc-heptane); Rt=6.79.

c) 7-Bromomethyl-3,3-dimethyl-1-(2-trimethylsilanylethoxymethyl)-1,3-dihydroindol-2-one The mixture of 3.10 g of 3,3,7-trimethyl-1-(2-trimethylsilanylethoxymethyl)-1,3-dihydroindol-2-one, 1.86 g of N-bromosuccinimide, 0.050 g of dibenzoyl peroxide and 0.033 g of 2,2'-azobis(2-methylpropionitrile) in 100 ml of carbon tetrachloride is kept at reflux with stirring over 2 hours. The reaction mixture is cooled and clarified by filtration, and the filtrate is concentrated by evaporation. The title compound is obtained as a beige solid from the residue by means of flash chromatography (SiO$_2$ 60F). Rf=0.42 (1:10 EtOAc-heptane); Rt=26.45 (II).

d) 3,3,7-Trimethyl-1-(2-trimethylsilanylethoxymethyl)-1,3-dihydroindol-2-one

The stirred solution of 2.00 g of 3,3,7-trimethyl-1,3-dihydroindol-2-one and 10 ml of N,N-dimethylformamide is cooled to 0° C. and admixed with 0.479 g of sodium hydride dispersion (60%). The mixture is stirred at 0° C. over 1 hour and subsequently admixed with 2.33 ml of 2-(trimethylsilyl)ethoxymethyl chloride. The ice bath is removed and the reaction mixture is stirred further at room temperature over 14 hours. The reaction mixture is poured onto ice-water (100 ml) and extracted with tert-butyl methyl ether (2×100 ml). The organic phases are washed successively with water (2×100 ml) and brine (1×100 ml), dried over sodium sulphate, filtered and concentrated by evaporation. The title compound is obtained as an orange oil from the residue by means of flash chromatography (SiO$_2$ 60F). Rf=0.51 (1:3 EtOAc-heptane); Rt=5.93.

EXAMPLE 219

Cyclohexylmethyl-[2-(4-{3-[4-(3-methoxypropyl)-3,4-dihydro-2H-benzo[1,4]oxazin-6-ylmethoxy]piperidin-4-yl}phenoxy)ethyl]amine Analogously to Method B, 0.348 g of benzyl 4-{4-[2-(cyclohexylmethylamino)ethoxy]phenyl}-3-[4-(3-methoxypropyl)-3,4-dihydro-2H-benzo[1,4]oxazin-6-ylmethoxy]piperidine-1-carboxylate is used to prepare the title compound.

The starting materials are prepared as follows:

a) Benzyl 4-{4-[2-(cyclohexylmethylamino)ethoxy]phenyl}-3-[4-(3-methoxypropyl)-3,4-dihydro-2H-benzo[1,4]oxazin-6-ylmethoxy]piperidine-1-carboxylate A solution of 0.346 g of benzyl 4-[4-(2-aminoethoxy)phenyl]-3-[4-(3-methoxypropyl)-3,4-dihydro-2H-benzo[1,4]oxazin-6-ylmethoxy]piperidine-1-carboxylate (Example 184b) and 0.068 ml of cyclohexanecarbaldehyde in 2 ml of methanol is stirred at room temperature over 3.5 hours, admixed in portions with 0.037 g of sodium borohydride and subsequently stirred for a further 2 hours. The reaction mixture is admixed with 2 ml of 1N NaOH, stirred for 30 minutes and then partitioned between ethyl acetate and water. The organic phase is washed with brine, dried over sodium sulphate and concentrated by evaporation. The title compound is obtained as a yellow oil from the residue by means of flash chromatography (SiO₂ 60F). Rf=0.48 (200:20:1 dichloromethane-methanol-25% conc. ammonia); Rt=4.97.

According to the process described in Example 219, the following compounds are prepared in a similar manner:

EXAMPLES

220 Cyclohexyl-[3-(4-{3-[4-(3-methoxypropyl)-3,4-dihydro-2H-benzo[1,4]oxazin-6-ylmethoxy]piperidin-4-yl}phenoxy)propyl]amine
221 [2-(2-Methoxyphenyl)ethyl]-[2-(4-{3-[4-(3-methoxypropyl)-3,4-dihydro-2H-benzo[1,4]oxazin-6-ylmethoxy]piperidin-4-yl}phenoxy)ethyl]amine
222 (2,5-Difluorobenzyl)-[2-(4-{3-[4-(3-methoxypropyl)-3,4-dihydro-2H-benzo[1,4]oxazin-6-ylmethoxy]piperidin-4-yl}phenoxy)ethyl]amine

EXAMPLE 223

N-(2-{4-Fluoro-2-[2-(4-{4-[3-(3-fluorophenoxy)propoxy]phenyl}piperidin-3-yloxy)ethoxy]phenyl}ethyl)acetamide Analogously to Method A, 0.27 g of tert-butyl 3-{2-[2-(2-acetylaminoethyl)-5-fluorophenoxy]ethoxy}-4-{4-[3-(3-fluorophenoxy)propoxy]phenyl}piperidine-1-carboxylate is used to prepare the title compound.

The starting materials are prepared as follows:

a) tert-Butyl 3-{2-[2-(2-acetylaminoethyl)-5-fluorophenoxy]ethoxy}-4-{4-[3-(3-fluorophenoxy)propoxy]phenyl}piperidine-1-carboxylate Analogously to Method I, 0.26 g of tert-butyl 3-{2-[2-(2-acetylaminoethyl)-5-fluorophenoxy]ethoxy}-4-(4-hydroxyphenyl)piperidine-1-carboxylate and 0.153 g of 1-(3-bromopropoxy)-3-fluorobenzene are reacted. The title compound is obtained as a yellowish oil. Rf=0.41 (EtOAc); Rt=5.66.

b) tert-Butyl 3-{2-[2-(2-acetylaminoethyl)-5-fluorophenoxy]ethoxy}-4-(4-hydroxyphenyl)piperidine-1-carboxylate A solution of 5.8 g of tert-butyl 3-{2-[2-(2-acetylaminoethyl)-5-fluorophenoxy]ethoxy}-4-(4-benzyloxyphenyl)piperidine-1-carboxylate in 200 ml of ethyl acetate is hydrogenated at room temperature in the presence of 2.03 g of 10% Pd/C over 15 hours. The reaction mixture is clarified by filtration and the filtrate is concentrated by evaporation. The title compound is obtained as a white solid from the residue by means of flash chromatography (SiO₂ 60F). Rf=0.29 (EtOAc); Rt=4.30.

c) tert-Butyl 3-{2-[2-(2-acetylaminoethyl)-5-fluorophenoxy]ethoxy}-4-(4-benzyloxyphenyl)piperidine-1-carboxylate Analogously to Method G, 6.7 g of tert-butyl 4-(4-benzyloxyphenyl)-3-[2-(toluene-4-sulphonyloxy)ethoxy]piperidine-1-carboxylate and 4.54 g of N-[2-(4-fluoro-2-hydroxyphenyl)ethyl]acetamide (Example 112b) are reacted. The title compound is obtained as a yellowish oil. Rf=0.16 (2:1 EtOAc-heptane); Rt=5.44.

d) tert-Butyl 4-(4-benzyloxyphenyl)-3-[2-(toluene-4-sulphonyloxy)ethoxy]piperidine-1-carboxylate Analogously to Method H, 6.0 g of tert-butyl 4-(4-benzyloxyphenyl)-3-(2-hydroxyethoxy)piperidine-1-carboxylate are reacted. The title compound is obtained as a yellowish solid. Rf=0.18 (1:3 EtOAc-heptane); Rt=5.44.

e) tert-Butyl 4-(4-benzyloxyphenyl)-3-(2-hydroxyethoxy)piperidine-1-carboxylate

Analogously to Example 14c, 11.1 g of tert-butyl 3-allyloxy-4-(4-benzyloxyphenyl)piperidine-1-carboxylate are reacted. The title compound is obtained as a yellowish oil. Rf=0.45 (2:1 EtOAc-heptane); Rt=4.96.

f) tert-Butyl 3-allyloxy-4-(4-benzyloxyphenyl)piperidine-1-carboxylate

Analogously to Method D, 12 g of tert-butyl 4-(4-benzyloxyphenyl)-3-hydroxypiperidine-1-carboxylate and 5.4 ml of allyl bromide are reacted. The title compound is obtained as a yellowish oil. Rf=0.31 (1:3 EtOAc-heptane); Rt=5.80.

g) tert-Butyl 4-(4-benzyloxyphenyl)-3-hydroxypiperidine-1-carboxylate

Analogously to Method I, 9.89 g of tert-butyl 3-hydroxy-4-(4-hydroxyphenyl)piperidine-1-carboxylate and 4.84 ml of benzyl chloride are reacted. The title compound is obtained as a white solid. Rf=0.53 (1:1 EtOAc-heptane); Rt=4.96.

According to the process described in Example 223, the following compounds are prepared in an analogous manner:

EXAMPLES

224 N-(2-{4-Fluoro-2-[2-(4-{4-[3-(2-fluorophenoxy)propoxy]phenyl}piperidin-3-yloxy)ethoxy]phenyl}ethyl)acetamide
225 N-{2-[4-Fluoro-2-(2-{4-[4-(3-phenoxypropoxy)phenyl]piperidin-3-yloxy}ethoxy)phenyl]ethyl}acetamide
226 Methyl (2-{2-[2-(4-{4-[3-(3-fluorophenoxy)propoxy]phenyl}piperidin-3-yloxy)ethoxy]phenyl}ethyl)carbamate
227 Methyl (2-{2-[2-(4-{4-[3-(2-fluorophenoxy)propoxy]phenyl}piperidin-3-yloxy)ethoxy]phenyl}ethyl)carbamate

EXAMPLE 228

8-(4-{4-[3-(2-Methoxybenzyloxy)propoxy]phenyl}piperidin-3-yloxymethyl)-4,4-dimethyl-3,4-dihydro-1H-quinolin-2-one Analogously to Method A, 0.060 g of tert-butyl 3-(4,4-dimethyl-2-oxo-1,2,3,4-tetrahydroquinolin-8-ylmethoxy)-4-{4-[3-(2-methoxybenzyloxy)propoxy]phenyl}piperidine-1-carboxylate is used to prepare the title compound.

The starting materials are prepared as follows:

a) tert-Butyl 3-(4,4-dimethyl-2-oxo-1,2,3,4-tetrahydroquinolin-8-ylmethoxy)-4-{4-[3-(2-methoxybenzyloxy)propoxy]phenyl}piperidine-1-carboxylate A solution of 0.225 g of tert-butyl 3-[4,4-dimethyl-2-oxo-1-(2-trimethylsilanylethoxymethyl)-1,2,3,4-tetrahydroquinolin-8-ylmethoxy]-4-{4-[3-(2-methoxybenzyloxy)propoxy]phenyl}piperidine-1-carboxylate in 2.5 ml of tetrahydrofuran is admixed with 2.5 ml of tetrabutylammonium fluoride solution (1M in tetrahydrofuran) and stirred at reflux over 6.5 hours. The reaction mixture is cooled to room temperature, poured onto water and extracted with tert-butyl methyl ether (2×). The combined organic phases are washed with brine, dried over sodium sulphate and concentrated by evaporation. The title compound is obtained as a yellow oil from the residue by means of flash chromatography ($SiO_2$ 60F). Rf=0.40 (1:1 EtOAc-heptane); Rt=5.97.

b) tert-Butyl 3-[4,4-dimethyl-2-oxo-1-(2-trimethylsilanylethoxymethyl)-1,2,3,4-tetrahydroquinolin-8-ylmethoxy]-4-{4-[3-(2-methoxybenzyloxy)propoxy]phenyl}piperidine-1-carboxylate Analogously to Method D, 0.28 g of tert-butyl 3-hydroxy-4-{4-[3-(2-methoxybenzyloxy)propoxy]phenyl}piperidine-1-carboxylate and 0.21 g of 8-chloromethyl-4,4-dimethyl-1-(2-trimethylsilanylethoxymethyl)-3,4-dihydro-1H-quinolin-2-one are reacted. The title compound is obtained as a yellowish oil. Rf=0.33 (1:2 EtOAc-heptane); Rt=6.81.

c) 8-Chloromethyl-4,4-dimethyl-1-(2-trimethylsilanylethoxymethyl)-3,4-dihydro-1H-quinolin-2-one Analogously to Method E, 0.32 g of 8-hydroxymethyl-4,4-dimethyl-1-(2-trimethylsilanylethoxymethyl)-3,4-dihydro-1H-quinolin-2-one is reacted. The title compound is obtained as a yellowish oil. Rf=0.47 (1:3 EtOAc-heptane); Rt=5.85.

d) 8-Hydroxymethyl-4,4-dimethyl-1-(2-trimethylsilanylethoxymethyl)-3,4-dihydro-1H-quinolin-2-one Analogously to Example 129c, 0.68 g of 4,4-dimethyl-8-(tetrahydropyran-2-yloxymethyl)-1-(2-trimethylsilanylethoxymethyl)-3,4-dihydro-1H-quinolin-2-one and 0.041 g of pyridinium p-toluenesulphonate are reacted. The title compound is obtained as a yellowish oil. Rf=0.55 (1:1 EtOAc-heptane); Rt=4.78.

e) 4,4-Dimethyl-8-(tetrahydropyran-2-yloxymethyl)-1-(2-trimethylsilanylethoxymethyl)-3,4-dihydro-1H-quinolin-2-one A solution of 1.4 g of 4,4-dimethyl-8-(tetrahydropyran-2-yloxymethyl)-3,4-dihydro-1H-quinolin-2-one in 10 ml of N,N-dimethylformamide is admixed at 0° C. with 0.2 g of sodium hydride dispersion (60%). After stirring for 1 hour, 0.94 ml of (2-chloromethoxyethyl)trimethylsilane are added and the reaction mixture is warmed to room temperature. After 17 hours and 22 hours, 0.1 g of sodium hydride dispersion (60%) and 0.5 ml of (2-chloromethoxyethyl)trimethylsilane are again added. After a total of 24 hours, the reaction mixture is admixed with a few drops of water and subsequently partitioned between tert-butyl methyl ether and saturated aqueous sodium bicarbonate solution. The organic phase is washed with water, dried over sodium sulphate and concentrated by evaporation. The title compound is obtained as a yellowish oil from the residue by means of flash chromatography ($SiO_2$ 60F). Rf=0.37 (2:1 EtOAc-heptane); Rt=6.01.

f) 4,4-Dimethyl-8-(tetrahydropyran-2-yloxymethyl)-3,4-dihydro-1H-quinolin-2-one

Analogously to Example 129g, 2.5 g of 8-hydroxymethyl-4,4-dimethyl-3,4-dihydro-1H-quinolin-2-one and 2.28 ml of 3,4-dihydro-2H-pyran are reacted. The title compound is obtained as a light brown oil. Rf=0.25 (1:1 EtOAc-heptane); Rt=4.28.

g) 8-Hydroxymethyl-4,4-dimethyl-3,4-dihydro-1H-quinolin-2-one

A solution of 3.72 g of methyl 4,4-dimethyl-2-oxo-1,2,3,4-tetrahydroquinoline-8-carboxylate in 100 ml of tetrahydrofuran is admixed with 1.83 g of lithium borohydride and then stirred at 50° C. over 1 hour. The reaction mixture is cooled to room temperature, diluted with tert-butyl methyl ether and stirred with saturated aqueous sodium bicarbonate solution until no more gas is formed. The phases are separated—the organic phase is washed with water, dried over sodium sulphate and concentrated by evaporation. The crude title compound is obtained as a brown-yellow oil from the residue. Rt=3.02.

h) Methyl 4,4-dimethyl-2-oxo-1,2,3,4-tetrahydroquinoline-8-carboxylate

A solution of 15.18 g of methyl 2-(3-methyl-but-2-enoylamino)benzoate and 35.07 g of aluminium trichloride in 250 ml of 1,2-dichloroethane is stirred at reflux over 30 minutes. The reaction mixture is cooled to room temperature, diluted with dichloromethane, washed with 1N HCl (2×) and brine, dried over sodium sulphate and concentrated by evaporation. The title compound is obtained as a brown solid from the residue by means of flash chromatography ($SiO_2$ 60F). Rf=0.21 (3:7 EtOAc-heptane); Rt=3.98.

i) Methyl 2-(3-methyl-but-2-enoylamino)benzoate

A solution of 12.5 ml of 3-methylbut-2-enoyl chloride in 110 ml of toluene is added dropwise at room temperature to a solution of 13.4 ml of methyl 2-aminobenzoate and 21.8 ml of triethylamine in 110 ml of toluene. After 30 minutes, the reaction mixture is diluted with toluene, washed with 1N HCl (2×), dried over sodium sulphate and concentrated by evaporation. The title compound is obtained as a white solid from the residue by means of flash chromatography ($SiO_2$ 60F). Rf=0.34 (1:10 EtOAc-heptane); Rt=4.78.

EXAMPLE 229

4-{3-[4-(3-Methoxypropyl)-3,4-dihydro-2H-benzo[1,4]oxazin-6-ylmethoxy]piperidin-4-yl}-N-(2-phenoxyethyl)benzamide Analogously to Method B, 0.110 g of benzyl 3-[4-(3-methoxypropyl)-3,4-dihydro-2H-benzo[1,4]oxazin-6-ylmethoxy]-4-[4-(2-phenoxyethylcarbamoyl)phenyl]piperidine-1-carboxylate is used to prepare the title compound.

The starting materials are prepared as follows:

a) Benzyl 3-[4-(3-methoxypropyl)-3,4-dihydro-2H-benzo[1,4]oxazin-6-ylmethoxy]-4-[4-(2-phenoxyethylcarbamoyl)phenyl]piperidine-1-carboxylate A solution of 0.36 g of benzyl 4-(4-carboxyphenyl)-3-[4-(3-methoxypropyl)-3,4-dihydro-2H-benzo[1,4]oxazin-6-ylmethoxy]piperidine-1-carboxylate and 0.125 g of 2-phenoxyethylamine in 5 ml of N,N-dimethylformamide is admixed under argon with 0.172 g of 3-dimethylaminopropyl ethyl carbodiimide hydrochloride and 0.0037 g of 4-dimethylaminopyridine. The reaction solution is stirred at room temperature over 3 days, subsequently poured onto 25 ml of water and extracted with 50 ml of tert-butyl methyl ether. The organic phase is dried over potassium carbonate, filtered and concentrated. The title compound is obtained as a yellow oil from the residue by means of flash chromatography (SiO$_2$ 60F). Rf=0.16 (2:1 EtOAc-heptane); Rt=5.18.

b) Benzyl 4-(4-carboxyphenyl)-3-[4-(3-methoxypropyl)-3,4-dihydro-2H-benzo[1,4]oxazin-6-ylmethoxy]piperidine-1-carboxylate Analogously to Example 255c, 3.40 g of benzyl 4-(4-methoxycarbonylphenyl)-3-[4-(3-methoxypropyl)-3,4-dihydro-2H-benzo[1,4]oxazin-6-ylmethoxy]piperidine-1-carboxylate are reacted. The title compound is obtained as a white foam. Rt=4.70.

c) Benzyl 4-(4-methoxycarbonylphenyl)-3-[4-(3-methoxypropyl)-3,4-dihydro-2H-benzo[1,4]oxazin-6-ylmethoxy]piperidine-1-carboxylate A solution of 3.92 g of benzyl 4-(4-methoxycarbonylphenyl)-3-[4-(3-methoxypropyl)-3-oxo-3,4-dihydro-2H-benzo[1,4]oxazin-6-ylmethoxy]piperidine-1-carboxylate (Example 255d) in 50 ml of chloroform is admixed under argon with 4.27 g of tetrabutylammonium borohydride. The reaction solution is stirred at 60° C. over 19 hours and subsequently cooled to room temperature. 10 ml of 2N HCl and 50 ml of water are subsequently added dropwise. The suspension is stirred at room temperature over 10 minutes. The reaction mixture is poured onto 150 ml of aqueous sodium hydrogencarbonate solution and extracted with 800 ml of tert-butyl methyl ether. The organic phase is washed with 100 ml of water and 50 ml of brine, dried over sodium sulphate, filtered and concentrated by evaporation. The title compound is obtained as a colourless oil from the residue by means of flash chromatography (SiO$_2$ 60F). Rf=0.19 (2:1 EtOAc-heptane); Rt=5.34.

EXAMPLE 230

(4-{3-[4-(3-Methoxypropyl)-3,4-dihydro-2H-benzo[1,4]oxazin-6-ylmethoxy]piperidin-4-yl}phenyl)(3-phenoxypyrrolidine-1-yl)methanone Analogously to Method B, 0.152 g of benzyl 3-[4-(3-methoxypropyl)-3,4-dihydro-2H-benzo[1,4]oxazin-6-ylmethoxy]-4-[4-(3-phenoxypyrrolidine-1-carbonyl)phenyl]piperidine-1-carboxylate is used to prepare the title compound.

The starting materials are prepared as follows:

a) Benzyl 3-[4-(3-methoxypropyl)-3,4-dihydro-2H-benzo[1,4]oxazin-6-ylmethoxy]-4-[4-(3-phenoxypyrrolidine-1-carbonyl)phenyl]piperidine-1-carboxylate Analogously to Example 255b, 0.207 g of benzyl 4-(4-carboxyphenyl)-3-[4-(3-methoxypropyl)-3,4-dihydro-2H-benzo[1,4]oxazin-6-ylmethoxy]piperidine-1-carboxylate (Example 243b) and 0.0832 g of (R)-3-phenoxypyrrolidine are reacted. The title compound is obtained as a colourless oil. Rf=0.17 (EtOAc); Rt=5.33.

b) (R)-3-Phenoxypyrrolidine

Analogously to Method A, 0.61 g of tert-butyl (R)-3-phenoxypyrrolidine-1-carboxylate is reacted. The title compound is obtained as a yellow oil. Rt=2.40.

c) tert-Butyl (R)-3-phenoxypyrrolidine-1-carboxylate

Analogously to Method G, 1.01 g of tert-butyl (S)-3-(toluene-4-sulphonyloxy)pyrrolidine-1-carboxylate and 0.418 g of phenol are reacted. The title compound is obtained as a colourless oil. Rf=0.47 (2:1 EtOAc-heptane); Rt=4.88.

According to the processes described in Examples 229 and 230, the following compounds are prepared in an analogous manner:

EXAMPLES

| | |
|---|---|
| 231 | 4-{3-[4-(3-Methoxypropyl)-3,4-dihydro-2H-benzo[1,4]oxazin-6-ylmethoxy]piperidin-4-yl}-N-methyl-N-(2-phenoxyethyl)benzamide |
| 232 | (4-{3-[4-(3-Methoxypropyl)-3,4-dihydro-2H-benzo[1,4]oxazin-6-ylmethoxy]piperidin-4-yl}phenyl)-(3-phenoxyazetidin-1-yl)methanone |
| 233 | (4-{3-[4-(3-Methoxypropyl)-3,4-dihydro-2H-benzo[1,4]oxazin-6-ylmethoxy]piperidin-4-yl}phenyl)-(3-phenylpyrrolidin-1-yl)methanone |

EXAMPLE 234

4-(4-{4-[3-(2-Methoxybenzyloxy)propoxy]phenyl}piperidin-3-yloxymethyl)-2-(3-methoxypropyl)-1H-benzoimidazole Analogously to Method A, 0.40 g of tert-butyl 4-{4-[3-(2-methoxybenzyloxy)propoxy]phenyl}-3-[2-(3-methoxypropyl)-1H-benzoimidazol-4-ylmethoxy]piperidine-1-carboxylate is used to prepare the title compound.

The starting materials are prepared as follows:

a) tert-Butyl 4-{4-[3-(2-methoxybenzyloxy)propoxy]phenyl}-3-[2-(3-methoxypropyl)-1H-benzoimidazol-4-ylmethoxy]piperidine-1-carboxylate Analogously to Example 228a, 0.5 g of tert-butyl 4-{4-[3-(2-methoxybenzyloxy)propoxy]phenyl}-3-[2-(3-methoxypropyl)-1-(2-trimethylsilanylethoxymethyl)-1H-benzoimidazol-4-ylmethoxy]piperidine-1-carboxylate and 5.44 ml of tetrabutylammonium fluoride solution (1M in tetrahydrofuran) are reacted. The title compound is obtained as a yellowish oil. Rf=0.40 (1:1 EtOAc-heptane); Rt=4.99.

b) tert-Butyl 4-{4-[3-(2-methoxybenzyloxy)propoxy]phenyl}-3-[2-(3-methoxypropyl)-1-(2-trimethylsilanylethoxymethyl)-1H-benzoimidazol-4-ylmethoxy]piperidine-1-carboxylate Analogously to Method D, 2.1 g of tert-butyl 3-hydroxy-4-{4-[3-(2-methoxybenzyloxy)propoxy]phenyl}piperidine-1-carboxylate and 1.81 g of 4-chloromethyl-2-(3-methoxypropyl)-1-(2-trimethylsilanylethoxymethyl)-1H-benzoimidazole are reacted. The title compound is obtained as a yellowish oil. Rf=0.37 (3:1 EtOAc-heptane); Rt=6.04.

c) 4-Chloromethyl-2-(3-methoxypropyl)-1-(2-trimethylsilanylethoxymethyl)-1H-benzoimidazole Analogously to Method E, 2.6 g of [2-(3-methoxypropyl)-1-(2-trimethylsilanylethoxymethyl)-1H-benzoimidazol-4-yl]methanol are reacted. The title compound is obtained as a yellowish oil. Rf=0.62 (2:1 EtOAc-heptane); Rt=4.33.

d) [2-(3-Methoxypropyl)-1-(2-trimethylsilanylethoxymethyl)-1H-benzoimidazol-4-yl]methanol 35 ml of diisobutylaluminium hydride (1.5M in toluene) are added dropwise at −70° C. to a solution of 4.95 g of methyl 2-(3-methoxypropyl)-1-(2-trimethylsilanylethoxymethyl)-1H-benzoimidazole-4-carboxylate in 200 ml of tetrahydrofuran. The reaction mixture is then stirred at −10° C. for 1 hour and subsequently partitioned between tert-butyl methyl ether and 2:1 water/1N potassium bisulphate solution—the organic phase is washed with saturated aqueous sodium bicarbonate solution and water, dried over sodium sulphate and concentrated by evaporation. The combined aqueous phases are reextracted with ethyl acetate (3×)—the combined organic phases are washed with saturated aqueous sodium bicarbonate solution and water, dried over sodium sulphate and concentrated by evaporation. The title compound is obtained as a yellow oil from the residues by means of flash chromatography (SiO₂ 60F). Rf=0.21 (95:5 ethyl acetate-methanol); Rt=3.91.

e) Methyl 2-(3-methoxypropyl)-1-(2-trimethylsilanylethoxymethyl)-1H-benzoimidazole-4-carboxylate Analogously to Example 228e, 4.3 g of methyl 2-(3-methoxypropyl)-3H-benzoimidazole-4-carboxylate and 3.54 ml of (2-chloromethoxyethyl)trimethylsilane are reacted. The title compound is obtained as a brown solid. Rf=0.33 (95:5 dichloromethane-methanol); Rt=4.26.

f) Methyl 2-(3-methoxypropyl)-3H-benzoimidazole-4-carboxylate

A solution of 4 g of methyl 2,3-diaminobenzoate and 8.53 g of 4-methoxybutyric acid in 70 ml of 4N HCl is stirred at reflux over 21 hours. The reaction mixture is cooled to room temperature and partitioned between ethyl acetate and water. The aqueous phase is concentrated by evaporation—the residue is diluted with 100 ml of methanol and 2 ml of conc. H₂SO₄ and stirred at reflux over 45 hours. The reaction mixture is cooled to room temperature, neutralized with saturated aqueous sodium bicarbonate solution and concentrated by evaporation. The residue is diluted with water and extracted with ethyl acetate (2×)—the combined organic phases are dried over sodium sulphate and concentrated by evaporation. The title compound is obtained as a red solid from the residue by means of flash chromatography (SiO₂ 60F). Rf=0.31 (95:5 dichloromethane-methanol); Rt=2.53.

EXAMPLE 235

[2-(2,5-Difluorophenoxy)ethyl]-(4-{3-[4-(3-methoxypropyl)-3,4-dihydro-2H-benzo[1,4]-oxazin-6-ylmethoxy]piperidin-4-yl}benzyl)amine Analogously to Method B, 0.140 g of benzyl 4-(4-{[2-(2,5-difluorophenoxy)ethylamino]methyl}phenyl)-3-[4-(3-methoxypropyl)-3,4-dihydro-2H-benzo[1,4]oxazin-6-ylmethoxy]piperidine-1-carboxylate is used to prepare the title compound.

The starting materials are prepared as follows:

a) Benzyl 4-(4-{[2-(2,5-difluorophenoxy)ethylamino]methyl}phenyl)-3-[4-(3-methoxypropyl)-3,4-dihydro-2H-benzo[1,4]oxazin-6-ylmethoxy]piperidine-1-carboxylate The solution of 0.440 g of benzyl 4-{4-[2-(2,5-difluorophenoxy)ethylcarbamoyl]phenyl}-3-[4-(3-methoxypropyl)-3-oxo-3,4-dihydro-2H-benzo[1,4]oxazin-6-ylmethoxy]piperidine-1-carboxylate in 2.0 ml of tetrahydrofuran is admixed with 13.6 ml of 9-BBN (0.5M in tetrahydrofuran) and stirred at reflux over 18 hours. The reaction mixture is cooled, admixed with 0.412 ml of ethanolamine and concentrated by evaporation. The residue is stirred at 0° C. in 40 ml of EtOAc-heptane (1:1) overnight and clarified by filtration, and the filtrate is concentrated by evaporation. The title compound is obtained as a slightly yellowish oil from the residue by means of flash chromatography (SiO₂ 60F). Rf=0.11 (1:3 EtOAc-heptane); Rt=4.76.

b) Benzyl 4-{4-[2-(2,5-difluorophenoxy)ethylcarbamoyl]phenyl}-3-[4-(3-methoxypropyl)-3-oxo-3,4-dihydro-2H-benzo[1,4]oxazin-6-ylmethoxy]piperidine-1-carboxylate The solution of 0.400 g of benzyl 4-(4-carboxyphenyl)-3-[4-(3-methoxypropyl)-3-oxo-3,4-dihydro-2H-benzo[1,4]oxazin-6-ylmethoxy]piperidine-1-carboxylate and 5.0 ml of dichloromethane is cooled to 10° C. and admixed successively with 0.113 ml of oxalyl chloride and 0.002 ml of N,N-dimethylformamide. The reaction mixture is stirred over a further 1 hour and subsequently concentrated by evaporation. The evaporation residue is dissolved in dichloromethane and added dropwise at 0° C. to the stirred solution of 0.170 g of 2-(2,5-difluorophenoxy)ethylamine and 0.182 ml of triethylamine in 5.0 ml of dichloromethane. The mixture is stirred for a further 30 minutes and then poured onto ice-water (30 ml) and extracted with ethyl acetate (2×40 ml). The organic phases are washed successively with aqueous sodium hydrogencarbonate solution (40 ml) and brine (40 ml), dried over sodium sulphate, filtered and concentrated by evaporation. The title compound is obtained as a slightly yellowish foam from the residue by means of flash chromatography (SiO₂ 60F). Rf=0.14 (3:1 EtOAc-heptane); Rt=5.00.

c) Benzyl 4-(4-carboxyphenyl)-3-[4-(3-methoxypropyl)-3-oxo-3,4-dihydro-2H-benzo[1,4]oxazin-6-ylmethoxy]piperidine-1-carboxylate The mixture of 2.45 g of benzyl 4-(4-methoxycarbonylphenyl)-3-[4-(3-methoxypropyl)-3-oxo-3,4-dihydro-2H-benzo[1,4]oxazin-6-ylmethoxy]piperidine-1-carboxylate, 16 ml of tetrahydrofuran and 16 ml of 2N NaOH is stirred at reflux over 18 hours. The reaction mixture is cooled, admixed with 20 ml of 2N HCl and extracted with tert-butyl methyl ether (3×50 ml). The organic phases are washed successively with water (40 ml) and brine (40 ml), dried over sodium sulphate, filtered and concentrated by evaporation to obtain the crude title compound as a white foam. Rt=4.45.

d) Benzyl 4-(4-methoxycarbonylphenyl)-3-[4-(3-methoxypropyl)-3-oxo-3,4-dihydro-2H-benzo[1,4]oxazin-6-ylmethoxy]piperidine-1-carboxylate Analogously to Method D, 5.25 g of benzyl 3-hydroxy-4-(4-methoxycarbonylphenyl)piperidine-1-carboxylate and 0.572 g of 6-chloromethyl-4-(3-methoxypropyl)-4H-benzo[1,4]oxazin-3-one are reacted. The title compound is obtained as a yellowish oil. Rf=0.28 (2:1 EtOAc-heptane). Rt=5.06.

e) Benzyl 3-hydroxy-4-(4-methoxycarbonylphenyl)piperidine-1-carboxylate

An autoclave is initially charged under argon with 220 ml of N,N-dimethylformamide, 160 ml of methanol, 1.49 g of diphenylphosphinopropane and 0.809 g of palladium(II) acetate. The reaction mixture is stirred at room temperature over 20 minutes. Subsequently, 33.1 g of benzyl 3-hydroxy-4-(4-trifluoromethanesulphonyloxyphenyl)piperidine-1-carboxylate and 22 ml of triethylamine are added and the autoclave is charged with 5 bar of carbon monoxide. The reaction mixture is subsequently stirred at 70° and 5 bar of pressure over 3 hours. Subsequently, the reaction mixture is cooled and a solution of palladium(II) acetate (0.404 g) and diphenylphosphinopropane (0.743 g) in 125 ml of DMF and 90 ml of methanol is added. The reaction mixture is subsequently stirred at 70° and 5 bar of carbon monoxide for a further 3 hours. The reaction solution is cooled and stirred with 800 ml of water and 250 ml of tert-butyl methyl ether. The phases are separated and the aqueous phase is extracted twice more with 250 ml of tert-butyl methyl ether. The organic phases are combined and concentrated by evaporation to dryness. The title compound is obtained as a white solid from the residue by means of flash chromatography (SiO$_2$ 60F). Rf=0.23 (1:1 EtOAc-heptane); Rt=4.25.

f) Benzyl 3-hydroxy-4-(4-trifluoromethanesulphonyloxyphenyl)piperidine-1-carboxylate A solution of 25.0 g of benzyl 3-hydroxy-4-(4-hydroxyphenyl)piperidine-1-carboxylate in 500 ml of dichloromethane is admixed under argon with 29.8 g of N-phenylbis(trifluoromethanesulphonylimide) and 11.6 ml of triethylamine. The reaction solution is stirred at room temperature over 18 hours and subsequently concentrated by evaporation to dryness. The residue is purified by means of flash chromatography (SiO$_2$ 60F). The title compound is obtained as a colourless solid from the prepurified product by recrystallization from 1:10 ethyl acetate-heptane (500 ml). Rf=0.25 (1:1 EtOAc-heptane); Rt=4.86.

g) 2-(2,5-Difluorophenoxy)ethylamine

The solution of 2.44 g of (2,5-difluorophenoxy)acetonitrile in 40 ml of tetrahydrofuran is added dropwise at 20-30° C. to the stirred mixture of 1.13 g of lithium aluminium hydride in 16 ml of diethyl ether. The reaction mixture is stirred at reflux over 2 hours and subsequently cooled to room temperature. 2 ml of water and 6.5 ml of 1N NaOH are successively added dropwise. The suspension is stirred at room temperature over 14 hours. The reaction mixture is poured onto 80 ml of water and extracted with diethyl ether (2×80 ml). The organic phases are washed successively with water (2×80 ml) and brine (1×50 ml), dried over sodium sulphate, filtered and concentrated by evaporation. The title compound is obtained as a yellowish oil from the residue by means of flash chromatography (SiO$_2$ 60F). Rf=0.24 (200:20:1 dichloromethane-methanol-25% conc. ammonia); Rt=2.37.

h) (2,5-Difluorophenoxy)acetonitrile

Analogously to Method F, 2.0 g of 2,5-difluorophenol and 2.1 ml of bromoacetonitrile are reacted. The title compound is obtained as a slightly yellowish oil. Rf=0.52 (1:2 EtOAc-heptane); Rt=3.86.

According to the process described in Example 235, the following compounds are prepared in an analogous manner:

EXAMPLES

| | |
|---|---|
| 236 | 4-(3-Methoxypropyl)-6-{4-[4-(4-phenylpiperazin-1-ylmethyl)phenyl]piperidin-3-yloxymethyl}-3,4-dihydro-2H-benzo[1,4]oxazine |
| 237 | (4-{3-[4-(3-Methoxypropyl)-3,4-dihydro-2H-benzo[1,4]oxazin-6-ylmethoxy]piperidin-4-yl}benzyl)-(1-phenylpyrrolidin-3(S)-yl)amine |
| 238 | (4-{3-[4-(3-Methoxypropyl)-3,4-dihydro-2H-benzo[1,4]oxazin-6-ylmethoxy]piperidin-4-yl}benzyl)-(1-phenylpyrrolidin-3(R)-yl)amine |

EXAMPLE 239

3-[5-(4-{4-[3-(2-Methoxybenzyloxy)propoxy]phenyl}piperidin-3-yloxymethyl)-2-methylphenoxy]propionic acid Analogously to Method B, 0.255 g of benzyl 3-[3-(2-carboxyethoxy)-4-methylbenzyloxy]-4-{4-[3-(2-methoxybenzyloxy)propoxy]phenyl}piperidine-1-carboxylate is used to prepare the title compound.

The starting materials are prepared as follows:

a) Benzyl 3-[3-(2-carboxyethoxy)-4-methylbenzyloxy]-4-{4-[3-(2-methoxybenzyloxy)propoxy]phenyl}piperidine-1-carboxylate The mixture of 0.527 g of benzyl 4-{4-[3-(2-methoxybenzyloxy)propoxy]phenyl}-3-[3-(2-methoxycarbonylethoxy)-4-methylbenzyloxy]piperidine-1-carboxylate, 20 ml of diisopropyl ether, 0.20 ml of dimethyl sulphoxide and 100 ml of pH 7.0 phosphate buffer is admixed with 15 ml of Novozyme 398 (Novo Nordisk) and stirred at 35° C. over 120 hours. The reaction mixture is extracted repeatedly with tetrahydrofuran and the organic phases are concentrated by evaporation. The title compound is obtained as a slightly yellowish oil from the residue by means of flash chromatography (SiO$_2$ 60F). Rf=0.10 (1:1 EtOAc-heptane); Rt=5.57.

b) Benzyl 4-{4-[3-(2-methoxybenzyloxy)propoxy]phenyl}-3-[3-(2-methoxycarbonylethoxy)-4-methyl-benzyloxy]piperidine-1-carboxylate The solution of 5.1 mg of sodium in 0.5 ml of ethanol is admixed with 0.626 g of benzyl 3-(3-hydroxy-4-methylbenzyloxy)-4-{4-[3-(2-methoxybenzyloxy)propoxy]phenyl}piperidine-1-carboxylate and 15 ml of methyl acrylate and stirred at room temperature over 18 hours. The reaction mixture is concentrated by evaporation, and the residue is admixed with 25 ml of 0.5M HCl (cold) and extracted with tert-butyl methyl ether (2×25 ml). The organic phases are washed with brine (25 ml), dried over sodium sulphate, filtered and concentrated by evaporation. The title compound is obtained as a slightly yellowish oil from the residue by means of flash chromatography (SiO$_2$ 60F). Rf=0.42 (1:1 EtOAc-heptane); Rt=6.00.

c) Benzyl 3-(3-hydroxy-4-methylbenzyloxy)-4-{4-[3-(2-methoxybenzyloxy)propoxy]phenyl}piperidine-1-carboxylate Analogously to Example 31b, 3.45 g of benzyl 3-(3-allyloxy-4-methylbenzyloxy)-4-{4-[3-(2-methoxybenzyloxy)propoxy]phenyl}piperidine-1-carboxylate are reacted. The title compound is obtained as a colourless oil. Rf=0.16 (1:2 EtOAc-heptane); Rt=5.64.

d) Benzyl 3-(3-allyloxy-4-methylbenzyloxy)-4-{4-[3-(2-methoxybenzyloxy)propoxy]phenyl}piperidine-1-carboxylate Analogously to Method D, 3.00 g of benzyl 3-hydroxy-4-{4-[3-(2-methoxybenzyloxy)propoxy]-phenyl}piperidine-1-carboxylate (Example 10f) and 1.31 g of 2-allyloxy-4-chloromethyl-1-methylbenzene are reacted. The title compound is obtained as a colourless oil. Rf=0.33 (1:2 EtOAc-heptane); Rt=6.27.

e) 2-Allyloxy-4-chloromethyl-1-methylbenzene

Analogously to Example 31d-f, 3-hydroxy-4-methylbenzoic acid is used to obtain the title compound. Rf=0.68 (1:2 EtOAc-heptane); Rt=5.06.

EXAMPLE 241

4-[2-(4-{4-[3-(2-Methoxybenzyloxy)propoxy]phenyl}piperidin-3-yloxy)ethoxy]-3H-isobenzofuran-1-one Analogously to Method A, 0.130 g of tert-butyl 4-{4-[3-(2-methoxybenzyloxy)propoxy]phenyl}-3-[2-(1-oxo-1,3-dihydroisobenzofuran-4-yloxy)ethoxy]piperidine-1-carboxylate is used to prepare the title compound.

The starting material is prepared as follows:

a) tert-Butyl 4-{4-[3-(2-methoxybenzyloxy)propoxy]phenyl}-3-[2-(1-oxo-1,3-dihydroisobenzofuran-4-yloxy)ethoxy]piperidine-1-carboxylate Analogously to Method G, 0.210 g of tert-butyl 4-{4-[3-(2-methoxybenzyloxy)propoxy]phenyl}-3-[2-(toluene-4-sulphonyloxy)ethoxy]piperidine-1-carboxylate (Example 14b) and 0.094 g of 4-hydroxy-3H-isobenzofuran-1-one are reacted. The title compound is obtained as a white solid. Rf=0.32 (1:1 EtOAc-heptane); Rt=5.84.

EXAMPLE 242

4-(4-{4-[3-(2-Methoxybenzyloxy)propoxy]phenyl}piperidin-3-yloxymethyl)-1H-benzimidazole Analogously to Method A, 0.620 g of tert-butyl 4-{4-[3-(2-methoxybenzyloxy)propoxy]phenyl}-3-(3-trityl-3H-benzimidazol-4-ylmethoxy)piperidine-1-carboxylate is used to prepare the title compound.

The starting materials are prepared as follows:

a) tert-Butyl 4-{4-[3-(2-methoxybenzyloxy)propoxy]phenyl}-3-(3-trityl-3H-benzimidazol-4-ylmethoxy)piperidine-1-carboxylate Analogously to Method D, 1.300 g of tert-butyl 3-hydroxy-4-{4-[3-(2-methoxybenzyloxy)propoxy]phenyl}piperidine-1-carboxylate and 1.129 g of 6-chloromethyl-1-trityl-1H-benzimidazole are reacted. The title compound is obtained as a colourless foam. Rf=0.20 (1:1 EtOAc-heptane); Rt=6.08.

b) 6-Chloromethyl-1-trityl-1H-benzimidazole

Analogously to Method E, 1.95 g of (3-trityl-3H-benzimidazol-4-yl)methanol are reacted. The title compound is obtained as a colourless oil. Rf=0.25 (1:3 EtOAc-heptane). Rt=4.64 c) (3-Trityl-3H-benzimidazol-4-yl)methanol

A suspension of 0.210 g of lithium aluminium hydride in 15 ml of anhydrous tetrahydrofuran is cooled under argon to 0° C. A solution of 2.300 g of methyl 3-trityl-3H-benzimidazole-4-carboxylate in 25 ml of anhydrous tetrahydrofuran is added dropwise to the suspension over 5 minutes and the reaction mixture is subsequently stirred at 0° C. over one hour. The reaction mixture is subsequently poured slowly onto 80 ml of 1M sodium potassium tartrate solution and admixed with ethyl acetate (100 ml). The phases are separated and the aqueous phase is extracted with (100 ml) of ethyl acetate. The combined organic phases are washed with 100 ml of water, dried over sodium sulphate, filtered and concentrated by evaporation. The title compound is obtained as a reddish foam and is used for the next stage without further purification. Rt=4.04.

d) Methyl 3-trityl-3H-benzimidazole-4-carboxylate

A suspension of 1.12 g of methyl 3H-benzimidazole-4-carboxylate in 25 ml of dichloromethane is admixed with 0.97 ml of triethylamine and a solution of 2.010 g of trityl chloride in 25 ml of dichloromethane. The reaction mixture is stirred at room temperature over 16 hours and subsequently poured onto a 100 ml of semisaturated aqueous sodium hydrogencarbonate solution. The phases are separated and the aqueous phase is extracted with 100 ml of dichloromethane. The combined organic phases are washed with 100 ml of water, dried over sodium sulphate and concentrated by evaporation. The title compound is obtained as a yellow solid from the residue by flash chromatography (SiO$_2$ 60F). Rf (1:2 EtOAc-heptane)=0.25; Rt=4.31.

e) Methyl 3H-Benzimidazole-4-carboxylate 2.000 g of methyl 2,3-diaminobenzoate are suspended in 35 ml of 4M aqueous HCl. The suspension is admixed at room temperature with 1.350 ml of formic acid and heated to reflux over one hour. The reaction solution is cooled to room temperature and the precipitated solid is filtered off. The filtercake is taken up in 50 ml of methanol and the mixture is heated to reflux until all solids have dissolved. The hot solution is treated with 0.500 g of activated carbon and subsequently clarified by filtration. The filtrate is admixed with 0.62 ml of conc. $H_2SO_4$ and heated to reflux over 24 hours. The reaction solution is cooled to room temperature and made neutral with saturated aqueous sodium carbonate solution (6 ml). The mixture is subsequently admixed with 50 ml of water and 100 ml of ethyl acetate, and the phases are separated. The aqueous phase is extracted with ethyl acetate (2×100 ml) and the combined organic phases are subsequently washed with 100 ml of saturated sodium carbonate solution and 100 ml of water, dried over sodium sulphate and concentrated by evaporation. The title compound is obtained as a beige solid. Rt=2.02.

f) Methyl 2,3-diaminobenzoate 10.10 g of methyl 2-amino-3-nitrobenzoate are suspended in 250 ml of methanol. 10% Pd/C (1.08 g) is added under argon and the reaction mixture is hydrogenated at room temperature at atmospheric pressure over 3 hours. The catalyst is filtered off through Hyflo and the filtrate is concentrated by evaporation. The title compound is isolated as a brown solid. Rt=2.15.

EXAMPLE 243

N-[1-(4-{3-[4-(3-Methoxypropyl)-3-oxo-3,4-dihydro-2H-benzo[1,4]oxazin-6-ylmethoxy]piperidin-4-yl}phenyl)pyrrolidin-3-(R)-yl]-N-methylbenzamide Analogously to Method B, 0.100 g of benzyl 4-{4-[3-(R)-(benzoylmethylamino)pyrrolidin-1-yl]phenyl}-3-[4-(3-methoxypropyl)-3-oxo-3,4-dihydro-2H-benzo[1,4]oxazin-6-ylmethoxy]piperidine-1-carboxylate is used to prepare the title compound.

a) Benzyl 4-{4-[3-(R)-(benzoylmethylamino)pyrrolidin-1-yl]phenyl}-3-[4-(3-methoxypropyl)-3-oxo-3,4-dihydro-2H-benzo[1,4]oxazin-6-ylmethoxy]piperidine-1-carboxylate A baked-out Schlenk flask is initially charged with 0.131 g of caesium carbonate, 0.027 g of palladium acetate and 0.010 g of (±)-2,2'-bis(diphenylphosphine)-1,1'-binaphthyl. Under argon, a solution of 0.199 g of benzyl 3-[4-(3-methoxypropyl)-3-oxo-3,4-dihydro-2H-benzo[1,4]oxazin-6-ylmethoxy]-4-(trifluoromethanesulphonyloxyphenyl)piperidine-1-carboxylate and 0.070 g of (R)—N-methyl-N-pyrrolidin-3-ylbenzamide in 2 ml of dried dioxane is added. The reaction mixture is stirred at room temperature over 30 minutes and subsequently at 100° C. over 16 hours. The reaction mixture is filtered through Hyflo and the filtercake is washed with tert-butyl methyl ether. The filtrate is concentrated by evaporation and the residue purified by means of flash chromatography ($SiO_2$ 60F). The title compound is obtained as a colourless foam. Rf=0.20 (3:1 EtOAc-heptane); Rt=5.18.

b) (R)—N-Methyl-N-pyrrolidin-3-ylbenzamide

Analogously to Method B, 0.774 g of (R)—N-(1-benzylpyrrolidin-3-yl)-N-methylbenzamide in methanol is used to prepare the title compound. Rf=0.08 (200:20:1 dichloromethane-methanol-25% conc. ammonia); Rt=2.04.

c) (R)—N-(1-Benzylpyrrolidin-3-yl)-N-methylbenzamide 0.778 g of (R)-(1-benzylpyrrolidin-3-yl)methylamine is dissolved in 20 ml of dichloromethane. 0.521 ml of triethylamine is added and the solution is cooled to 0° C. in an ice bath. 0.434 ml of benzoyl chloride is added dropwise and the reaction solution is subsequently stirred at 0° C. over 50 minutes. The reaction solution is diluted with 20 ml of dichloromethane and washed with 20 ml of saturated aqueous sodium hydrogencarbonate solution and 20 ml of brine, dried over sodium sulphate and concentrated by evaporation. The residue is purified by means of flash chromatography ($SiO_2$ 60F). The title compound is obtained as a colourless oil. Rf=0.75 (200:20:1 dichloromethane-methanol-25% conc. ammonia); Rt=3.08 d) (R)-(1-Benzylpyrrolidin-3-yl)methylamine

An autoclave is initially charged with 6.20 ml of methylamine solution in ethanol and a solution of 2.000 g of (S)-1-benzylpyrrolidin-3-yl toluene-4-sulphonate in 2 ml of ethanol. The reaction solution is subsequently heated to 140° C. over 15 hours. The reaction solution is cooled to room temperature and concentrated to dryness, and the residue is taken up in 10 ml of water. The aqueous solution is extracted with dichloromethane (2×10 ml). The aqueous phase is then admixed with 1 g of potassium carbonate and the suspension is stirred at room temperature over 5 minutes. The solid is filtered off and the filtrate is extracted with dichloromethane (2×10 ml). The combined organic phases are dried over sodium sulphate and concentrated by evaporation. The residue is purified by means of flash chromatography ($SiO_2$ 60F). The title compound is obtained as a yellow oil. Rf=0.14 (200:20:1 dichloromethane-methanol-25% conc. ammonia).

EXAMPLE 244

7-[2-(4-{4-[3-(2-Methoxybenzyloxy)propoxy]phenyl}piperidin-3-yloxy)ethoxy]-1H-benzimidazole Analogously to Method A, 0.620 g of tert-butyl 3-[2-(3H-benzimidazol-4-yloxy)ethoxy]-4-{4-[3-(2-methoxybenzyloxy)propoxy]phenyl}piperidine-1-carboxylate is used to prepare the title compound.

The starting material is prepared as follows:

a) tert-Butyl 3-[2-(3H-benzimidazol-4-yloxy)ethoxy]-4-{4-[3-(2-methoxybenzyloxy)propoxy]phenyl}piperidine-1-carboxylate Analogously to Method F, 0.670 g of tert-butyl 4-{4-[3-(2-methoxybenzyloxy)propoxy]phenyl-3-[2-(toluenesulphonyloxy)ethoxy]piperidine-1-carboxylate and 0.201 g of 3H-benzimidazol-4-ol are reacted. The title compound is obtained as a brown resin. Rf=0.20 (5:1 EtOAc-heptane); Rt=4.86.

EXAMPLE 245

6-(4-{4-[3-(2-Methoxybenzyloxy)propoxy]
phenyl}piperidin-3-yloxymethyl)-4-(3-methoxypropyl)-3,4-dihydro-2H-benzo[1,4]thiazine Analogously to Method C, 0.060 g of 6-(4-{4-[3-(2-methoxybenzyloxy)propoxy]phenyl}piperidin-3-yloxymethyl)-4-(3-methoxypropyl)-4H-benzo[1,4]thiazin-3-one is used to prepare the title compound.

The starting materials are prepared as follows:

a) 6-(4-{4-[3-(2-Methoxybenzyloxy)propoxy] phenyl}piperidin-3-yloxymethyl)-4-(3-methoxypropyl)-4H-benzo[1,4]thiazin-3-one Analogously to Method A, 0.105 g of tert-butyl 4-{4-[3-(2-methoxybenzyloxy)propoxy]phenyl}-3-[4-(3-methoxypropyl)-3-oxo-3,4-dihydro-2H-benzo[1,4]thiazin-6-ylmethoxy]piperidine-1-carboxylate is reacted. The title compound is obtained as colourless oil. Rf=0.32 (200:20:1 dichloromethane-methanol-conc. ammonia); Rt=4.37.

b) tert-Butyl 4-{4-[3-(2-methoxybenzyloxy)propoxy]phenyl}-3-[4-(3-methoxypropyl)-3-oxo-3,4-dihydro-2H-benzo[1,4]thiazin-6-ylmethoxy]piperidine-1-carboxylate Analogously to Method D, 0.570 g of tert-butyl 3-hydroxy-4-{4-[3-(2-methoxybenzyloxy)propoxy]phenyl}piperidine-1-carboxylate and 0.359 g of 6-chloromethyl-4-(3-methoxypropyl)-4H-benzo[1,4]thiazin-3-one are reacted. The title compound is obtained as a colourless oil. Rf=0.27 (1:1 EtOAc-heptane); Rt=6.14.

c) 6-Chloromethyl-4-(3-methoxypropyl)-4H-benzo[1,4]thiazin-3-one

Analogously to Example 2b-d, methyl 3-oxo-3,4-dihydro-2H-benzo[1,4]thiazine-6-carboxycarboxylate is used to obtain the title compound as a colourless oil. Rf=0.60 (2:1 EtOAc-heptane); Rt=4.25.

EXAMPLE 246

4-(4-{4-[3-(2-Methoxybenzyloxy)propoxy] phenyl}piperidin-3-yloxymethyl)-1-methyl]-1H-benzimidazole Analogously to Method A, 0.390 g of tert-butyl 4-{4-[3-(2-methoxybenzyloxy)propoxy]phenyl}-3-(1-methyl-1H-benzimidazol-4-ylmethoxy)piperidine-1-carboxylate is used to prepare the title compound.

The starting materials are prepared as follows:

a) tert-Butyl 4-{4-[3-(2-methoxybenzyloxy)propoxy] phenyl}-3-(1-methyl-1H-benzimidazol-4-ylmethoxy)piperidine-1-carboxylate Analogously to Method D, 0.800 g of tert-butyl 3-hydroxy-4-{4-[3-(2-methoxybenzyloxy)propoxy]phenyl}piperidine-1-carboxylate and 0.317 g of 4-chloromethyl-1-methyl-1H-benzimidazole are reacted. The title compound is obtained as a yellow resin. Rf=0.30 (15:1 dichloromethane-methanol); Rt=4.74.

b) 4-Chloromethyl-1-methyl-1H-benzimidazole

Analogously to Method E, 0.720 g of (1-methyl-1H-benzimidazol-4-yl)methanol is reacted. The title compound is obtained as a beige solid. Rf=0.40 (10:1 dichloromethane-methanol); Rt=2.18.

c) (1-Methyl-1H-benzimidazol-4-yl)methanol

Analogously to Example 242c, 1.960 g of methyl 1-methyl-1H-benzimidazole-4-carboxylate are reacted. The title compound is obtained as a yellow oil. Rf=0.40 (8:1 dichloromethane-methanol). Rt=1.20.

d) Methyl 1-methyl-1H-benzimidazole-4-carboxylate 1.39 g of methyl 3H-benzimidazole-4-carboxylate are dissolved under argon in 20 ml of N,N-dimethylformamide. The solution is cooled to 0° C. in an ice bath and admixed in portions with 0.299 g of sodium hydride (60% dispersion). 0.744 ml of methyl iodide is added and the reaction mixture is heated to 45° C. over 17 hours. The reaction mixture is subsequently poured onto 50 ml of saturated aqueous sodium hydrogencarbonate solution and extracted with 2:1 tetrahydrofuran/tert-butyl methyl ether (2×150 ml). The combined organic phases are washed with 50 ml each of saturated aqueous sodium hydrogencarbonate solution and water, dried over sodium sulphate, filtered and concentrated by evaporation. The title compound is obtained as a beige solid from the residue by means of flash chromatography (SiO$_2$ 60F). Rt=1.95.

EXAMPLE 247

Methyl 7-(4-{4-[3-(2-methoxybenzyloxy)propoxy] phenyl}piperidin-3-yloxymethyl)-1H-benzoimidazole-2-carboxylate Analogously to Method B, 0.570 g of methyl 4-(1-benzyloxycarbonyl-4-{4-[3-(2-methoxybenzyloxy)propoxy] phenyl}piperidin-3-yloxymethyl)-1H-benzoimidazole-2-carboxylate is used to prepare the title compound.

The starting materials are prepared as follows:

a) Methyl 4-(1-benzyloxycarbonyl-4-{4-[3-(2-methoxybenzyloxy)propoxy]phenyl}piperidin-3-yloxymethyl)-1H-benzoimidazole-2-carboxylate The mixture of 1.03 g of methyl 4-(1-benzyloxycarbonyl-4-{4-[3-(2-methoxybenzyloxy)propoxy]phenyl}piperidin-3-yloxymethyl)-1-(2-trimethylsilanylethoxymethyl)-1H-benzoimidazole-2-carboxylate, 10 ml of methanol and 10 ml of 2M HCl is stirred at 50° C. over 2 hours. The reaction mixture is cooled, poured onto aqueous 1M sodium hydrogencarbonate solution (70 ml) and extracted with tert-butyl methyl ether (2×100 ml). The organic phases are washed with brine, dried over sodium sulphate and concentrated by evaporation. The title compound is obtained as a white foam from the residue by means of flash chromatography (SiO$_2$ 60F). Rf=0.26 (2:1 EtOAc-heptane); Rt=5.11.

b) Methyl 4-(1-benzyloxycarbonyl-4-{4-[3-(2-methoxybenzyloxy)propoxy]phenyl}piperidin-3-yloxymethyl)-1-(2-trimethylsilanylethoxymethyl)-1H-benzoimidazole-2-carboxylate Analogously to Method D, 1.58 g of benzyl 3-hydroxy-4-{4-[3-(2-methoxybenzyloxy)propoxy]phenyl}piperidine-1-carboxylate (Example 10f) and 1.43 g of methyl 4-bromomethyl-1-(2-trimethylsilanylethoxymethyl)-1H-benzoimidazole-2-carboxylate are reacted. The title compound is obtained as a colourless oil. Rf=0.23 (1:1 EtOAc-heptane); Rt=29.5 (II).

c) Methyl 4-bromomethyl-1-(2-trimethylsilanylethoxymethyl)-1H-benzoimidazole-2-carboxylate Analogously to Example 147b, 2.00 g of methyl 4-methyl-1-(2-trimethylsilanylethoxymethyl)-1H-benzoimidazole-2-carboxylate are reacted. The title compound is obtained as a white solid. Rf=0.31 (1:2 EtOAc-heptane); Rt=5.39; m.p. 85-86° C.

d) Methyl 4-methyl-1-(2-trimethylsilanylethoxymethyl)-1H-benzoimidazole-2-carboxylate The stirred solution of 1.60 g of methyl 7-hydroxymethyl-1H-benzoimidazole-2-carboxylate and 13.0 ml of N,N-dimethylformamide is admixed at 0° C. with 0.274 g of sodium hydride dispersion (55%) and, after 60 minutes, with 1.33 ml of 2-(trimethylsilyl)ethoxymethyl chloride. The mixture is stirred at room temperature over 3 hours, subsequently poured onto ice-water (100 ml) and extracted with tert-butyl methyl ether (2×100 ml). The organic phases are washed successively with water (100 ml) and brine (100 ml), dried over sodium sulphate and concentrated. The title compound is obtained as a white solid from the residue by means of flash chromatography (SiO$_2$ 60F). Rf=0.23 (1:2 EtOAc-heptane); Rt=5.16; m.p. 59.6-59.8° C.

EXAMPLE 248

6-{4-[4-(1-Cyclohexylpyrrolidin-3-yloxy)phenyl]piperidin-3-yloxymethyl}-4-(3-methoxypropyl)-3,4-dihydro-2H-benzo[1,4]oxazine Analogously to Method B, 0.296 g of benzyl 4-[4-(1-cyclohexylpyrrolidin-3-yloxy)phenyl]-3-[4-(3-methoxypropyl)-3,4-dihydro-2H-benzo[1,4]oxazin-6-ylmethoxy]piperidine-1-carboxylate is used to prepare the title compound.

The starting materials are prepared as follows:

a) Benzyl 4-[4-(1-cyclohexylpyrrolidin-3(S)-yloxy)phenyl]-3-[4-(3-methoxypropyl)-3,4-dihydro-2H-benzo[1,4]oxazin-6-ylmethoxy]piperidine-1-carboxylate Analogously to Method C, 0.330 g of benzyl 4-[4-(1-cyclohexylpyrrolidin-3-yloxy)phenyl]-3-[4-(3-methoxypropyl)-3-oxo-3,4-dihydro-2H-benzo[1,4]oxazin-6-ylmethoxy]piperidine-1-carboxylate is used to obtain the title compound. Rf=0.25 (200:20:1 dichloromethane-methanol-25% conc. ammonia); Rt=4.76.

b) Benzyl 4-[4-(1-cyclohexylpyrrolidin-3(S)-yloxy)phenyl]-3-[4-(3-methoxypropyl)-3-oxo-3,4-dihydro-2H-benzo[1,4]oxazin-6-ylmethoxy]piperidine-1-carboxylate A solution of 0.374 g of benzyl 3-[4-(3-methoxypropyl)-3-oxo-3,4-dihydro-2H-benzo[1,4]oxazin-6-ylmethoxy]-4-[4-(pyrrolidin-3(S)-yloxy)phenyl]piperidine-1-carboxylate is admixed under argon with 0.038 ml of acetic acid and 0.078 ml of cyclohexanone. 0.199 g of sodium triacetoxyborohydride is added in portions at room temperature to this reaction solution and the reaction mixture is subsequently stirred at room temperature over one hour. The reaction mixture is concentrated by evaporation and the residue is taken up in 20 ml of ethyl acetate. The organic solution is washed with 10 ml each of saturated aqueous sodium hydrogencarbonate solution and brine, dried over sodium sulphate and concentrated by evaporation. The title compound is obtained as a colourless resin from the residue by means of flash chromatography (SiO$_2$ 60F). Rf=0.20 (200:20:1 dichloromethane-methanol-25% conc. ammonia); Rt=4.52.

EXAMPLE 249

[7-(4-{4-[3-(2-Methoxybenzyloxy)propoxy]phenyl}piperidin-3-yloxymethyl)-1H-benzoimidazol-2-yl]methanol The solution of 0.100 g of methyl 7-(4-4{-[3-(2-methoxybenzyloxy)propoxy]phenyl}piperidin-3-yloxymethyl)-1H-benzoimidazole-2-carboxylate (Example 247) and 5.0 ml of tetrahydrofuran is cooled to 0° C. and admixed with 0.028 g of lithium aluminium hydride. The mixture is kept at room temperature over 2 hours. The reaction mixture is poured onto 1M sodium hydrogencarbonate solution and extracted with ethyl acetate (2×25 ml). The organic phases are washed with brine (20 ml), dried over sodium sulphate and concentrated by evaporation. The title compound is obtained from the residue by means of flash chromatography (SiO$_2$ 60F).

EXAMPLE 250

7-(4-{4-[3-(2-Methoxybenzyloxy)propoxy]phenyl}piperidin-3-yloxymethyl)-3,3-dimethyl-2,3-dihydro-1H-indole The solution of 0.055 g of 7-(4-{4-[3-(2-methoxybenzyloxy)propoxy]phenyl}piperidin-3-yloxymethyl)-3,3-dimethyl-1,3-dihydroindol-2-one (Example 218) and 1.0 ml of toluene is admixed with 0.072 ml of Vitride and stirred at 110° C. over 1 hour. The reaction mixture is cooled to 10° C., admixed slowly with 1M NaOH and extracted with tert-butyl methyl ether (2×30 ml). The organic phases are washed successively with 1M NaOH (30 ml), water (30 ml) and brine (30 ml), dried over sodium sulphate and concentrated by evaporation. The title compound is obtained from the residue by means of flash chromatography (SiO$_2$ 60F).

EXAMPLE 251

7-(4-{4-[3-(2-Methoxybenzyloxy)propoxy]phenyl}piperidin-3-yloxymethyl)-1,3,3-trimethyl-1,3-dihydroindol-2-one Analogously to Method B, 0.200 g of benzyl 4-{4-[3-(2-methoxybenzyloxy)propoxy]phenyl}-3-(1,3,3-trimethyl-2- oxo-2,3-dihydro-1H-indol-7-ylmethoxy)piperidine-1-carboxylate is used to prepare the title compound.

The starting material is prepared as follows:

a) Benzyl 4-{4-[3-(2-methoxybenzyloxy)propoxy]phenyl}-3-(1,3,3-trimethyl-2-oxo-2,3-dihydro-1H-indol-7-ylmethoxy)piperidine-1-carboxylate Analogously to Example 30a, 0.400 g of benzyl 3-(3,3-dimethyl-2-oxo-2,3-dihydro-1H-indol-7-ylmethoxy)-4-{4-[3-(2-methoxybenzyloxy)propoxy]phenyl}piperidine-1-carboxylate (Example 218a) is reacted. The title compound is obtained as a yellowish oil. Rf=0.41 (1:1 EtOAc-heptane); Rt=5.99.

EXAMPLE 252

7-(4-{4-[3-(2-Methoxybenzyloxy)propoxy]phenyl}piperidin-3-yloxymethyl)-1,3,3-trimethyl-2,3-dihydro-1H-indole Analogously to Example 250, 0.080 g of 7-(4-{4-[3-(2-methoxybenzyloxy)propoxy]phenyl}piperidin-3-yloxymethyl)-1,3,3-trimethyl-1,3-dihydroindol-2-one (Example 251) is used to obtain the title compound.

EXAMPLE 253

6-{4-[4-(2,2-Difluoro-3-phenoxypropoxy)phenyl]piperidin-3-yloxymethyl}-4-(3-methoxypropyl)-3,4-dihydro-2H-benzo[1,4]oxazine Analogously to Method B, 0.165 g of benzyl 4-[4-(2,2-difluoro-3-phenoxypropoxy)phenyl]-3-[4-(3-methoxypropyl)-3,4-dihydro-2H-benzo[1,4]oxazin-6-ylmethoxy]piperidine-1-carboxylate is used to prepare the title compound.

The starting materials are prepared as follows:

a) Benzyl 4-[4-(2,2-difluoro-3-phenoxypropoxy)phenyl]-3-[4-(3-methoxypropyl)-3,4-dihydro-2H-benzo[1,4]oxazin-6-ylmethoxy]piperidine-1-carboxylate Analogously to Method C, 0.175 g of benzyl 4-[4-(2,2-difluoro-3-phenoxypropoxy)phenyl]-3-[4-(3-methoxypropyl)-3-oxo-3,4-dihydro-2H-benzo[1,4]oxazin-6-ylmethoxy]piperidine-1-carboxylate is reacted. The title compound is obtained as a yellowish oil. Rf=0.35 (1:1 EtOAc-heptane); Rt=5.87.

b) Benzyl 4-[4-(2,2-difluoro-3-phenoxypropoxy)phenyl]-3-[4-(3-methoxypropyl)-3-oxo-3,4-dihydro-2H-benzo[1,4]oxazin-6-ylmethoxy]piperidine-1-carboxylate Analogously to Method D, 0.260 g of benzyl 4-[4-(2,2-difluoro-3-phenoxypropoxy)phenyl]-3-hydroxypiperidine-1-carboxylate and 0.185 g of 6-chloromethyl-4-(3-methoxypropyl)-4H-benzo[1,4]oxazin-3-one are reacted. The title compound is obtained as a yellow oil. Rf=0.25 (1:1 EtOAc-heptane); Rt=5.67.

c) Benzyl 4-[4-(2,2-difluoro-3-phenoxypropoxy)phenyl]-3-hydroxypiperidine-1-carboxylate Analogously to Method G, 0.350 g of 2,2-difluoro-3-phenoxypropyl toluene-4-sulphonate and 0.452 g of benzyl 3-hydroxy-4-(4-hydroxyphenyl)piperidine-1-carboxylate are reacted. The title compound is obtained as a yellow oil. Rf=0.25 (1:1 EtOAc-heptane); Rt=5.11.

d) 2,2-Difluoro-3-phenoxypropyl toluene-4-sulphonate

Analogously to Method G, 0.095 g of phenol and 1.061 g of 1,3-bistoluenesulphonyl-2,2-difluoropropane-1,3-diol are reacted. The title compound is obtained as a yellow oil. Rf=0.25 (1:2 EtOAc-heptane); Rt=5.03.

e) 1,3-Bistoluenesulphonyl-2,2-difluoropropane-1,3-diol

Analogously to Method H, 3.850 g of 4-toluenesulphonyl chloride and 2.689 g of 2,2-difluoropropane-1,3-diol are reacted. The title compound is obtained as a white solid. Rf=0.20 (1:2 EtOAc-heptane); Rt=5.03.

EXAMPLE 254

N-{2-[4-Fluoro-2-(2-{4-[(1-phenylpyrrolidin-3(S)-yloxy)phenyl]piperidin-3-yloxy}ethoxy)phenyl]ethyl}acetamide Analogously to Method B, 0.120 g of benzyl 3-{2-[2-(acetylaminoethyl)-5-fluorophenoxy]ethoxy}-4-[4-(1-phenylpyrrolidin-3(S)-yloxy)phenyl]piperidine-1-carboxylate is used to prepare the title compound.

The starting materials are prepared as follows:

a) Benzyl 3-{2-[2-(acetylaminoethyl)-5-fluorophenoxy]ethoxy}-4-[4-(1-phenylpyrrolidin-3(S)-yloxy)phenyl]piperidine-1-carboxylate Analogously to Example 193b, 0.400 g of benzyl 3-{2-[2-(acetylaminoethyl)-5-fluorophenoxy]ethoxy}-4-[4-(pyrrolidin-3(S)-yloxy)phenyl]piperidine-1-carboxylate is reacted. The title compound is obtained as a colourless oil. Rt=5.47.

b) Benzyl 3-{2-[2-(acetylaminoethyl)-5-fluorophenoxy]ethoxy}-4-[4-(pyrrolidin-3(S)-yloxy)phenyl]piperidine-1-carboxylate Analogously to Method A, 1.300 g of benzyl 3-{2-[2-(acetylaminoethyl)-5-fluorophenoxy]ethoxy}-4-[4-(1-tert-butoxycarbonylpyrrolidin-3(S)-yloxy)phenyl]piperidine-1-carboxylate are reacted. The title compound is obtained as a yellow oil. Rt=3.85.

c) Benzyl 3-{2-[2-(acetylaminoethyl)-5-fluorophenoxy]ethoxy}-4-[4-(1-tert-butoxycarbonylpyrrolidin-3(S)-yloxy)phenyl]piperidine-1-carboxylate Analogously to Method I, 1.000 g of benzyl 3-{2-[2-(2-acetylaminoethyl)-5-fluorophenoxy]ethoxy}-4-(4-hydroxyphenylpiperidine-1-carboxylate and 0.705 g of tert-butyl 3(R)-(toluene-4-sulphonyloxy)pyrrolidine-1-carboxylate are reacted. The title compound is obtained as a yellow oil. Rt=5.29.

d) Benzyl 3-{2-[2-(2-acetylaminoethyl)-5-fluorophenoxy]ethoxy}-4-(4-hydroxyphenylpiperidine-1-carboxylate Analogously to Method A, 2.90 g of tert-butyl 3-{2-[2-(2-acetylaminoethyl)-5-fluorophenoxy]ethoxy}-4-(4-hydroxyphenyl)piperidine-1-carboxylate (Example 223) are reacted. The resulting crude product is subsequently taken up in 50 ml each of ethyl acetate and saturated aqueous sodium hydrogencarbonate solution. The reaction mixture is cooled in an ice bath and admixed with 1.00 ml of benzyl chloroformate and subsequently stirred at 0° C. for a further 30 minutes. The reaction mixture is admixed with 300 ml of water and extracted with ethyl acetate (2×250 ml). The combined organic phases are dried over sodium sulphate, filtered and concentrated by evaporation. The title compound is used further as the crude product. Rf=0.30 (EtOAc); Rt=4.33

According to the process described in Example 248, the following compound is prepared in an analogous manner:

EXAMPLE 255

6-{4-[4-(1-Benzylazetidinyloxy)phenyl]piperidin-3-yloxymethyl}-4-(3-methoxypropyl)-3,4-dihydro-2H-benzo[1,4]oxazine

EXAMPLE 256

3(S)-(4-{3-[4-(3-Methoxypropyl)-3,4-dihydro-2H-benzo[1,4]oxazin-6-ylmethoxy]piperidin-4-yl}phenoxy-1-phenylpyrrolidin-2-one Analogously to Method B, 0.140 g of benzyl 3-[4-(3-methoxypropyl)-3,4-dihydro-2H-benzo[1,4]oxazin-6-ylmethoxy]-4-[4-(2-oxo-1-phenylpyrrolidin-3(S)-yloxy)phenyl]piperidine-1-carboxylate is used to prepare the title compound.

The starting materials are prepared as follows:

a) Benzyl 3-[4-(3-methoxypropyl)-3,4-dihydro-2H-benzo[1,4]oxazin-6-ylmethoxy]-4-[4-(2-oxo-1-phenylpyrrolidin-3(S)-yloxy)phenyl]piperidine-1-carboxylate Analogously to Method I, 0.213 g of 3(R)-2-oxo-1-phenylpyrrolidinyl toluene-4-sulphonate and 0.438 g of benzyl 4-(4-hydroxyphenyl)-3-[4-(3-methoxypropyl)-3,4-dihydro-2H-benzo[1,4]oxazin-6-ylmethoxypiperidine-1-carboxylate are reacted. The title compound is obtained as a colourless oil. Rf=0.20 (1:1 EtOAc-heptane); Rt=5.44 b) 3(R)-2-Oxo-1-phenylpyrrolidinyl toluene-4-sulphonate

A solution of 0.130 g of 3(S)-hydroxy-1-phenylpyrrolidin-2-one in 4 ml of anhydrous tetrahydrofuran is cooled under argon to 0° C. in an ice bath. 0.249 g of triphenylphosphine and 0.297 g of pyridinium p-toluenesulphonate are added and a solution of 0.218 g of diisopropyl azodicarboxylate in 2 ml of tetrahydrofuran is subsequently added dropwise. The yellow reaction mixture is subsequently stirred at room temperature over 16 hours. The reaction mixture is poured onto 20 ml of saturated aqueous sodium hydrogencarbonate solution and the mixture is extracted with 2×20 ml of ethyl acetate. The combined organic phases are washed with 20 ml of brine, dried over sodium sulphate, filtered and concentrated by evaporation. The title compound is obtained as a colourless solid from the residue by means of flash chromatography (SiO₂ 60F). Rf=0.44 (1:1 EtOAc-heptane); Rt=4.42.

c) 3(S)-Hydroxy-1-phenylpyrrolidin-2-one

A Schlenk flask is initially charged with 0.123 g of 3(S)-hydroxy-pyrrolidin-2-one, 0.453 g of caesium carbonate, 0.032 g of dipalladiumtris(dibenzylidenacetone)-chloroform complex and 0.052 g of 9,9-dimethyl-4,5-bis(diphenylphosphine)xanthane under argon. 0.110 ml of bromobenzene and 2 ml dioxane are added and the reaction mixture is heated to reflux over 14 hours. The reaction mixture is subsequently cooled to room temperature, diluted with dichloromethane and filtered through Hyflo, and the filtrate is concentrated by evaporation. The title compound is obtained as a beige solid from the residue by means of flash chromatography (SiO₂ 60F). Rf=0.24 (4:1 EtOAc-heptane); Rt=2.50.

EXAMPLE 257

6-{4-[4-(1-Benzoxazol-2-ylazetidin-3-yloxy)phenyl]piperidin-3-yloxymethyl}-4-(3-methoxypropyl)-3,4-dihydro-2H-benzo[1,4]oxazine Analogously to Method B, 0.199 g of benzyl 4-[4-(1-benzoxazol-2-ylazetidin-3-yloxy)phenyl]-3-[4-(3-methoxypropyl)-3,4-dihydro-2H-benzo[1,4]oxazin-6-ylmethoxy]piperidine-1-carboxylate is used to prepare the title compound.

The starting materials are prepared as follows:

a) Benzyl 4-[4-(1-benzoxazol-2-ylazetidin-3-yloxy)phenyl]-3-[4-(3-methoxypropyl)-3,4-dihydro-2H-benzo[1,4]oxazin-6-ylmethoxy]piperidine-1-carboxylate Analogously to Method C, 0.292 g of benzyl 4-[4-(1-benzoxazol-2-ylazetidin-3-yloxy)phenyl]-3-[4-(3-methoxypropyl)-3-oxo-3,4-dihydro-2H-benzo[1,4]oxazin-6-ylmethoxy]piperidine-1-carboxylate is reacted. The title compound is obtained as a colourless resin. Rf=0.25 (2:1 EtOAc-heptane); Rt=5.25.

b) Benzyl 4-[4-(1-benzoxazol-2-ylazetidin-3-yloxy)phenyl]-3-[4-(3-methoxypropyl)-3-oxo-3,4-dihydro-2H-benzo[1,4]oxazin-6-ylmethoxy]piperidine-1-carboxylate A solution of 0.382 g of benzyl 4-[4-(azetidin-3-yloxy)phenyl]-3-[4-(3-methoxypropyl)-3-oxo-3,4-dihydro-2H-benzo[1,4]oxazin-6-ylmethoxy]piperidine-1-carboxylate in 10 ml of chloroform is admixed at 0-5° C. with 0.156 ml of 2-chlorobenzoxazole. The reaction solution is stirred at room temperature over 20 hours and subsequently poured onto an ice-water mixture. The reaction mixture is extracted with ethyl acetate (2×50 ml) and the combined organic phases are washed with 50 ml of brine, dried over sodium sulphate, filtered and concentrated. The title compound is obtained as a colourless oil from the residue by means of flash chromatography (SiO₂ 60F). Rf=0.20 (2:1 EtOAc-heptane); Rt=4.99.

c) Benzyl 4-[4-(azetidin-3-yloxy)phenyl]-3-[4-(3-methoxypropyl)-3-oxo-3,4-dihydro-2H-benzo[1,4]oxazin-6-ylmethoxy]piperidine-1-carboxylate Analogously to Method A, 14.90 g of benzyl 4-[4-(1-tert-butoxycarbonylazetidin-3-yloxy)phenyl]-3-[4-(3-methoxypropyl)-3-oxo-3,4-dihydro-2H-benzo[1,4]oxazin-6-ylmethoxy]piperidine-1-carboxylate are reacted. The title compound is obtained as a yellow oil. Rf=0.19 (200:20:1 dichloromethane-methanol-25% conc. ammonia); Rt=4.09.

d) Benzyl 4-[4-(1-tert-butoxycarbonylazetidin-3-yloxy)phenyl]-3-[4-(3-methoxypropyl)-3-oxo-3,4-dihydro-2H-benzo[1,4]oxazin-6-ylmethoxy]piperidine-1-carboxylate Analogously to Method D, 13.34 g of benzyl 4-[4-(1-tert-butoxycarbonylazetidin-3-yloxy)phenyl]-3-hydroxypiperidine-1-carboxylate and 8.267 g of 6-chloromethyl-4-(3-methoxypropyl)-4H-benzo[1,4]oxazin-3-one are reacted. The title compound is obtained as a yellow oil. Rf=0.33 (2:1 EtOAc-heptane); Rt=5.53.

e) Benzyl 4-[4-(1-tert-butoxycarbonylazetidin-3-yloxy)phenyl]-3-hydroxypiperidine-1-carboxylate Analogously to Method I, 9.170 g of benzyl 3-hydroxy-4-(4-hydroxyphenyl)piperidinecarboxylate and 11.00 g of tert-butyl 3-(toluenesulphonyloxy)azetidine-1-carboxylate are reacted. The title compound is obtained as a yellow oil. Rf=0.23 (3:1 EtOAc-heptane); Rt=5.01.

EXAMPLE 258

4-(3-Methoxypropyl)-6-{4-[4-(1-thiazol-2-ylazetidin-3-yloxy)phenyl]piperidin-3-yloxymethyl}-3,4-dihydro-2H-benzo[1,4]oxazine 0.190 g of benzyl 3-[4-(3-methoxypropyl)-3,4-dihydro-2H-benzo[1,4]oxazin-6-ylmethoxy]-4-[4-(1-thiazol-2-ylazetidin-3-yloxy)phenyl]piperidinecarboxylate is dissolved in 8 ml of dioxane. 8 ml each of methanol and 40% KOH are added and the reaction mixture is stirred at 100° C. in a sealed flask over 5 hours. The reaction mixture is subsequently cooled to room temperature, diluted with 40 ml of water and extracted with ethyl acetate (3×40 ml). The combined organic phases are washed with 40 ml of water, dried over sodium sulphate, filtered and concentrated by evaporation. The title compound is obtained from the residue by means of flash chromatography (SiO$_2$ 60F).

The starting materials are prepared as follows:

a) Benzyl 3-[4-(3-methoxypropyl)-3,4-dihydro-2H-benzo[1,4]oxazin-6-ylmethoxy]-4-[4-(1-thiazol-2-ylazetidin-3-yloxy)phenyl]piperidine-carboxylate Analogously to Method C, 0.285 g of benzyl 3-[4-(3-methoxypropyl)-3-oxo-3,4-dihydro-2H-benzo[1,4]oxazin-6-ylmethoxy]-4-[4-(1-thiazol-2-ylazetidin-3-yloxy)phenyl]piperidinecarboxylate is reacted. The title compound is obtained as a yellow resin. Rf=0.15 (5:1 EtOAc-heptane); Rt=4.57.

b) Benzyl 3-[4-(3-methoxypropyl)-3-oxo-3,4-dihydro-2H-benzo[1,4]oxazin-6-yl methoxy]-4-[4-(1-thiazol-2-ylazetidin-3-yloxy)phenyl]piperidinecarboxylate A baked-out Schlenk flask is initially charged under argon with 0.071 g of tri-tert-butylphosphine and 0.114 g of palladium trifluoroacetate. 1.3 ml of degassed toluene are added and the suspension is stirred under argon over 10 minutes. 0.700 g of benzyl 4-[4-(azetidin-3-yloxy)phenyl]-3-[4-(3-methoxypropyl)-3-oxo-3,4-dihydro-2H-benzo[1,4]oxazin-6-ylmethoxy]piperidine-1-carboxylate (Example 257c), 0.265 g of tribasic potassium phosphate and 0.290 ml of bromothiazole are added and the reaction mixture is stirred at 80-85° C. over 16 hours. The reaction mixture is cooled, diluted with 20 ml each of brine and water and subsequently extracted with 40 ml of ethyl acetate. The organic phase is dried with sodium sulphate, filtered and concentrated by evaporation. The title compound is obtained as a yellow resin from the residue by means of flash chromatography (SiO$_2$ 60F). Rf=0.15 (4:1 EtOAc-heptane); Rt=4.34.

EXAMPLE 259

4-{3-[4-(3-Methoxypropyl)-3,4-dihydro-2H-benzo[1,4]-oxazin-6-ylmethoxy]piperidin-4-yl}phenyl 3-phenylpyrrolidine-1-carboxylate Analogously to Method B, 0.241 g of benzyl 3-[4-(3-methoxypropyl)-3,4-dihydro-2H-benzo[1,4]oxazin-6-ylmethoxy]-4-[4-(3-phenylpyrrolidine-1-carbonyloxy)phenyl]piperidine-1-carboxylate is used to prepare the title compound.

The starting materials are prepared as follows:

a) Benzyl 3-[4-(3-methoxypropyl)-3,4-dihydro-2H-benzo[1,4]oxazin-6-ylmethoxy]-4-[4-(3-phenylpyrrolidine-1-carbonyloxy)phenyl]piperidine-1-carboxylate The stirred solution of 0.250 g of benzyl 4-(4-hydroxyphenyl)-3-[4-(3-methoxypropyl)-3,4-dihydro-2H-benzo[1,4]oxazin-6-ylmethoxy]piperidine-1-carboxylate in 2.5 ml of toluene is admixed at 0° C. with 0.131 ml of N,N-dimethylaniline and 0.65 ml of phosgene solution (20% in toluene). The reaction mixture is stirred at room temperature over 24 hours. The resulting suspension is diluted with tert-butyl methyl ether (20 ml) and washed successively with 0.1M HCl (20 ml), 1M sodium hydrogencarbonate solution (20 ml) and water, dried over sodium sulphate, filtered and concentrated by evaporation. The residue is dissolved in 1.0 ml of ethyl acetate and added to the stirred cold mixture of 0.177 g of 3-phenylpyrrolidine, 1.80 ml of ethyl acetate and 1M sodium hydrogencarbonate solution. The mixture is stirred at 0° C. over 1 hour. The reaction mixture is poured onto brine (50 ml) and extracted with ethyl acetate (2×50 ml). The organic phases are dried over sodium sulphate, filtered and concentrated by evaporation. The title compound is obtained as a white solid from the residue by means of flash chromatography (SiO$_2$ 60F). Rf=0.16 (1:1 EtOAc-heptane); Rt=5.87.

b) Benzyl 4-(4-hydroxyphenyl)-3-[4-(3-methoxypropyl)-3,4-dihydro-2H-benzo[1,4]oxazin-6-ylmethoxy]piperidine-1-carboxylate Analogously to Method C, 5.0 g of benzyl 4-(4-hydroxyphenyl)-3-[4-(3-methoxypropyl)-3-oxo-3,4-dihydro-2H-benzo[1,4]oxazin-6-ylmethoxy]piperidine-1-carboxylate (Example 166d) are reacted. The title compound is obtained as a colourless oil. Rf=0.33 (2:1 EtOAc-heptane); Rt=4.80.

According to the process described in Example 259, the following compound is prepared in an analogous manner:

EXAMPLE 260

4-{3-[4-(3-Methoxypropyl)-3,4-dihydro-2H-benzo[1,4]oxazin-6-ylmethoxy]piperidin-4-yl}phenyl 3,4-dihydro-2H-quinoline-1-carboxylate According to the process described in Example 270, the following compounds are prepared in an analogous manner:

EXAMPLES

| | |
|---|---|
| 261 | 4-(3-Methoxypropyl)-6-{4-[4-(1-phenylpyrrolidin-3-yloxymethyl)phenyl]piperidin-3-yloxymethyl}-3,4-dihydro-2H-benzo[1,4]oxazine |
| 277 | 6-(4-{4-[2-(2-Methoxybenzyloxy)ethoxymethyl]phenyl}piperidin-3-yloxymethyl)-4-(3-methoxypropyl)-3,4-dihydro-2H-benzo[1,4]oxazine |
| 313 | 4-(3-Methoxypropyl)-6-{4-[4-(tetrahydrofuran-3-yloxymethyl)phenyl]piperidin-3-yloxymethyl}-3,4-dihydro-2H-benzo[1,4]oxazine |
| 315 | 4-(3-Methoxypropyl)-6-{4-[4-(tetrahydropyran-4-yloxymethyl)phenyl]piperidin-3-yloxymethyl}-3,4-dihydro-2H-benzo[1,4]oxazine |
| 356 | 6-[4-(4-Cyclopropylmethoxymethylphenyl)piperidin-3-yloxymethyl]-4-(3-methoxypropyl)-3,4-dihydro-2H-benzo[1,4]oxazine |
| 357 | 6-{4-[4-(2-Cyclopropylethoxymethyl)phenyl]piperidin-3-yloxymethyl}-4-(3-methoxypropyl)-3,4-dihydro-2H-benzo[1,4]oxazine |
| 358 | 6-{4-[4-(2-Methoxyethoxymethyl)phenyl]piperidin-3-yloxymethyl}-4-(3-methoxypropyl)-3,4-dihydro-2H-benzo[1,4]oxazine |
| 359 | 4-(3-Methoxypropyl)-6-[4-(4-propoxymethylphenyl)piperidin-3-yloxymethyl]-3,4-dihydro-2H-benzo[1,4]oxazine |
| 360 | 6-[4-(4-Butoxymethylphenyl)piperidin-3-yloxymethyl]-4-(3-methoxypropyl)-3,4-dihydro-2H-benzo[1,4]oxazine |

According to the process described in Example 258, the following compound is prepared in an analogous manner:

EXAMPLE 262

4-(3-Methoxypropyl)-6-{4-[4-(1-thiazol-2-ylpyrrolidin-3(S)-yloxy)phenyl]piperidin-3-yloxymethyl}-3,4-dihydro-2H-benzo[1,4]oxazine

EXAMPLE 263

1-(4-{3-[4-(3-Methoxypropyl)-3,4-dihydro-2H-benzo[1,4]oxazin-6-ylmethoxy]piperidin-4-yl}phenoxymethyl)-3-phenylpropylamine Analogously to Method B, 0.050 g of benzyl 4-[4-(2-benzyloxycarbonylamino-4-phenylbutoxy)phenyl]-3-[4-(3-methoxypropyl)-3,4-dihydro-2H-benzo[1,4]oxazin-6-ylmethoxy]piperidine-1-carboxylate is used to prepare the title compound.

The starting materials are prepared as follows:

a) Benzyl 4-[4-(2-benzyloxycarbonylamino-4-phenylbutoxy)phenyl]-3-[4-(3-methoxypropyl)-3,4-dihydro-2H-benzo[1,4]oxazin-6-ylmethoxy]piperidine-1-carboxylate Analogously to Method I, 0.250 g of benzyl 4-(4-hydroxyphenyl)-3-[4-(3-methoxypropyl)-3,4-dihydro-2H-benzo[1,4]oxazin-6-ylmethoxy]piperidine-1-carboxylate (Example 259b) and 0.281 g of 2-benzyloxycarbonylamino-4-phenylbutyl toluene-4-sulphonate are reacted. The title compound is obtained as a colourless oil. Rf=0.27 (2:1 EtOAc-heptane); Rt=6.01.

b) 2-Benzyloxycarbonylamino-4-phenylbutyl toluene-4-sulphonate

Analogously to Method H, 0.40 g of benzyl (1-hydroxymethyl-3-phenylpropyl)carbamate is reacted. The title compound is obtained as a slightly yellowish oil. Rf=0.46 (1:1 EtOAc-heptane); Rt=5.19.

EXAMPLE 264

6-(4-{4-[2-(3-Methoxyphenoxy)ethoxy]phenyl}piperidin-3-yloxymethyl)-4-(3-methoxypropyl)-3,4-dihydro-2H-benzo[1,4]oxazine Analogously to Method B, 0.578 g of benzyl 4-{4-[2-(3-methoxyphenoxy)ethoxy]phenyl}-3-[4-(3-methoxypropyl)-3,4-dihydro-2H-benzo[1,4]oxazin-6-ylmethoxy]piperidinecarboxylate is used to prepare the title compound.

The starting materials are prepared as follows:

a) Benzyl 4-{4-[2-(3-methoxyphenoxy)ethoxy]phenyl}-3-[4-(3-methoxypropyl)-3,4-dihydro-2H-benzo[1,4]oxazin-6-ylmethoxy]piperidinecarboxylate Analogously to Method C, 0.516 g of benzyl 4-{4-[2-(3-methoxyphenoxy)ethoxy]phenyl}-3-[4-(3-methoxypropyl)-3-oxo-3,4-dihydro-2H-benzo[1,4]oxazin-6-methoxy]piperidinecarboxylate is reacted. The title compound is obtained as a colourless oil. Rf=0.45 (2:1 EtOAc-heptane); Rt=5.71.

b) Benzyl 4-{4-[2-(3-methoxyphenoxy)ethoxy]phenyl}-3-[4-(3-methoxypropyl)-3-oxo-3,4-dihydro-2H-benzo[1,4]oxazin-6-ylmethoxy]piperidinecarboxylate Analogously to Method I, 0.500 g of benzyl 4-hydroxyphenyl-3-[4-(3-methoxypropyl)-3-oxo-3,4-dihydro-2H-benzo[1,4]oxazin-6-ylmethoxy]piperidinecarboxylate and 0.414 g of 2-(3-methoxyphenoxy)ethyl toluene-4-sulphonate are reacted. The title compound is obtained as a colourless oil. Rf=0.31 (2:1 EtOAc-heptane); Rt=5.51.

c) 2-(3-Methoxyphenoxy)ethyl toluene-4-sulphonate

Analogously to Method I, 0.500 g of methoxyphenol and 4.385 g of ethylene di(p-toluenesulphonate) are reacted. The title compound is obtained as a colourless solid. Rf=0.51 (1:1 EtOAc-heptane); Rt=4.68.

EXAMPLE 265

4-(3-Methoxypropyl)-6-[4-(4-pyrrolidin-1-ylphenyl)piperidin-3-yloxymethyl]-3,4-dihydro-2H-benzo[1,4]oxazine Analogously to Method B, 0.105 g of benzyl 3-[4-(3-methoxypropyl)-3,4-dihydro-2H-benzo[1,4]oxazin-6-ylmethoxy]-4-(4-pyrrolidin-1-ylphenyl)piperidine-1-carboxylate is used to prepare the title compound.
The starting materials are prepared as follows:

a) Benzyl 3-[4-(3-methoxypropyl)-3,4-dihydro-2H-benzo[1,4]oxazin-6-ylmethoxy]-4-(4-pyrrolidin-1-ylphenyl)piperidine-1-carboxylate The mixture of 0.300 g of benzyl 3-[4-(3-methoxypropyl)-3,4-dihydro-2H-benzo[1,4]oxazin-6-ylmethoxy]-4-(4-trifluoromethanesulphonyloxyphenyl)piperidine-1-carboxylate, 0.043 ml of pyrrolidine, 0.041 g of (i)-2,2'-bis(diphenylphosphine)-1,1'-binaphthyl, 0.194 g of caesium carbonate and 0.0099 g of palladium(II) acetate in 3.0 ml of dioxane is stirred under argon at 100° C. over 20 hours. The reaction mixture is cooled, admixed with water (20 ml) and extracted with tert-butyl methyl ether (2×20 ml). The organic phases are washed successively with water (20 ml) and brine (20 ml), dried over sodium sulphate, filtered and concentrated by evaporation. The title compound is obtained as a slightly yellowish oil from the residue by means of flash chromatography ($SiO_2$ 60F). Rf=0.40 (2:1 EtOAc-heptane); Rt=4.68.

b) Benzyl 3-[4-(3-methoxypropyl)-3,4-dihydro-2H-benzo[1,4]oxazin-6-ylmethoxy]-4-(4-trifluoromethanesulphonyloxyphenyl)piperidine-1-carboxylate The stirred solution of 1.0 g of benzyl 4-(4-hydroxyphenyl)-3-[4-(3-methoxypropyl-3,4-dihydro-2H-benzo[1,4]oxazin-6-ylmethoxy]piperidine-1-carboxylate (Example 259b) in 16 ml of dichloromethane is admixed successively with 0.713 g of N-phenybis(trifluoromethanesulphonimide) and 0.279 ml of triethylamine and kept at room temperature over 16 hours. The reaction mixture is admixed with saturated aqueous sodium hydrogencarbonate solution (40 ml) and extracted with tert-butyl methyl ether (2×40 ml). The organic phases are washed successively with water (40 ml) and brine (40 ml), dried over sodium sulphate, filtered and concentrated by evaporation. The title compound is obtained as a slightly yellowish oil from the residue by means of flash chromatography ($SiO_2$ 60F). Rf=0.37 (2:1 EtOAc-heptane); Rt=5.71.

According to the process described in Example 265, the following compound is prepared in an analogous manner:

EXAMPLE 266

6-[4-(4-Azetidin-1-phenyl)piperidin-3-yloxymethyl]-4-(3-methoxypropyl)-3,4-dihydro-2H-benzo[1,4]oxazine

EXAMPLE 267

6-(4-{4-[2-(3-Ethoxyphenoxy)ethoxy]phenyl}piperidin-3-yloxymethyl)-4-(3-methoxypropyl)-3,4-dihydro-2H-benzo[1,4]oxazine Analogously to Method B, 0.578 g of benzyl 4-{4-[2-(3-ethoxyphenoxy)ethoxy]phenyl}-3-[4-(3-methoxypropyl)-3,4-dihydro-2H-benzo[1,4]oxazin-6-ylmethoxy]piperidinecarboxylate is used to prepare the title compound.
The starting materials are prepared as follows:

a) Benzyl 4-{4-[2-(3-ethoxyphenoxy)ethoxy]phenyl}-3-[4-(3-methoxypropyl)-3,4-dihydro-2H-benzo[1,4]oxazin-6-ylmethoxy]piperidinecarboxylate Analogously to Method C, 0.400 g of benzyl 4-{4-[2-(3-ethoxyphenoxy)ethoxy]phenyl}-3-[4-(3-methoxypropyl)-3-oxo-3,4-dihydro-2H-benzo[1,4]oxazin-6-ylmethoxy]piperidinecarboxylate is reacted. The title compound is obtained as a colourless oil. Rf=0.27 (1:1 EtOAc-heptane); Rt=5.87.

b) Benzyl 4-{4-[2-(3-ethoxyphenoxy)ethoxy]phenyl}-3-[4-(3-methoxypropyl)-3-oxo-3,4-dihydro-2H-benzo[1,4]oxazin-6-ylmethoxy]piperidinecarboxylate Analogously to Method I, 0.420 g of benzyl 3-[4-(3-methoxypropyl)-3-oxo-3,4-dihydro-2H-benzo[1,4]oxazin-6-ylmethoxy]-4-{4-[2-(toluene-4-sulphonyloxy)ethoxy]phenyl}piperidinecarboxylate and 0.124 g of ethoxyphenol are reacted. The title compound is obtained as a dark yellow oil. Rf=0.16 (1:1 EtOAc-heptane); Rt=5.68.

c) Benzyl 3-[4-(3-methoxypropyl)-3-oxo-3,4-dihydro-2H-benzo[1,4]oxazin-6-ylmethoxy]-4-{4-[2-(toluene-4-sulphonyloxy)ethoxy]phenyl}piperidinecarboxylate Analogously to Method I, 0.417 g of benzyl 4-hydroxyphenyl-3-[4-(3-methoxypropyl)-3-oxo-3,4-dihydro-2H-benzo[1,4]oxazin-6-ylmethoxy]piperidinecarboxylate and 0.984 g of ethylene di(p-toluenesulphonate) are reacted. The title compound is obtained as a colourless oil. Rf=0.31 (2:1 EtOAc-heptane); Rt=5.35.

EXAMPLE 268

4-(3-Methoxypropyl)-6-{4-[4-(1-phenylazetidin-3-yloxymethyl)phenyl]piperidin-3-yloxymethyl}-3,4-dihydro-2H-benzo[1,4]oxazine Analogously to Method B, 0.0497 g of benzyl 3-[4-(3-methoxypropyl)-3,4-dihydro-2H-benzo[1,4]oxazin-6-ylmethoxy]-4-[4-(1-phenylazetidin-3-yloxymethyl)phenyl]piperidine-1-carboxylate is used to prepare the title compound.
The starting materials are prepared as follows:

a) Benzyl 3-[4-(3-methoxypropyl)-3,4-dihydro-2H-benzo[1,4]oxazin-6-ylmethoxy]-4-[4-(1-phenylazetidin-3-yloxymethyl)phenyl]piperidine-1-carboxylate Analogously to Example 270a, 0.0435 g of benzyl 4-(4-chloromethylphenyl)-3-[4-(3-methoxypropyl)-3,4-dihydro-2H-benzo[1,4]oxazin-6-ylmethoxy]piperidine-1-carboxylate (Example 270b) and 0.013 g of 1-phenylazetidin-3-ol are reacted. The title compound is obtained as a yellowish oil. Rt=5.64.

b) 1-phenylazetidin-3-ol

The mixture of 1.053 g of sodium tert-butoxide, 0.500 g of 3-hydroxyazetidine hydrochloride, 0.864 g of bromobenzene and 9 ml of toluene is initially charged under argon with stirring in a Schlenk apparatus. The mixture is admixed with a solution of 0.234 g of (+,−)-2,2'-bis(diphenylphosphino)-1,1'-binaphthyl and dipalladiumtris(dibenzylidenacetone)-chloroform complex in 2 ml of toluene (prepared in a Schlenk apparatus under argon) and the reaction mixture is stirred at 70° C. for 5 hours. The reaction mixture is cooled, poured onto ice-water (50 ml) and extracted with tert-butyl methyl ether (2×100 ml). The organic phases are washed with brine (50 ml), dried over sodium sulphate and concentrated by evaporation. The title compound is obtained as a reddish oil from the residue by means of flash chromatography (SiO$_2$ 60F). Rf=0.25 (1:1 EtOAc-heptane). Rt=2.01.

EXAMPLE 269

4-(3-Methoxypropyl)-6-[4-[4-(3-phenylpyrrolidin-1-ylmethyl)phenyl]piperidin-3-yloxymethyl]-3,4-dihydro-2H-benzo[1,4]oxazine Analogously to Method B, 0.0478 g of benzyl 3-[4-(3-methoxypropyl)-3,4-dihydro-2H-benzo[1,4]oxazin-6-ylmethoxy]-4-[4-(3-phenylpyrrolidin-1-ylmethyl)phenyl]piperidin-1-carboxylate is used to obtain the title compound.

The starting material is prepared as follows:

a) Benzyl 3-[4-(3-methoxypropyl)-3,4-dihydro-2H-benzo[1,4]oxazin-6-ylmethoxy]-4-[4-(3-phenylpyrrolidin-1-ylmethyl)phenyl]piperidine-1-carboxylate The stirred solution of 0.0435 g of benzyl 4-(4-chloromethylphenyl)-3-[4-(3-methoxypropyl)-3,4-dihydro-2H-benzo[1,4]oxazin-6-ylmethoxy]piperidine-1-carboxylate (Example 270b) and 0.0155 g of 3-phenylpyrrolidine in 0.5 ml of N,N-dimethylformamide is admixed at 0° C. with 0.0076 g of sodium hydride dispersion (60% in oil). The reaction mixture is stirred at 0° C. over 15 minutes, then at room temperature for 1 hour, and subsequently diluted with 80 ml of tert-butyl methyl ether. The mixture is washed with 20 ml of water, then 10 ml of brine, dried over sodium sulphate, filtered and concentrated by evaporation. The title compound is obtained as a slightly yellowish oil from the residue by means of flash chromatography (SiO$_2$ 60F). Rt=4.72.

EXAMPLE 270

6-(4-{4-[2-(2,5-Difluorophenoxy)ethoxymethyl]phenyl}piperidin-3-yloxymethyl)-4-(3-methoxypropyl)-3,4-dihydro-2H-benzo[1,4]oxazine Analogously to Method B, 0.052 g of benzyl 4-{4-[2-(2,5-difluorophenoxy)ethoxymethyl]phenyl}-3-[4-(3-methoxypropyl)-3,4-dihydro-2H-benzo[1,4]oxazin-6-ylmethoxy]piperidine-1-carboxylate is used to prepare the title compound.

The starting materials are prepared as follows:

a) Benzyl 4-{4-[2-(2,5-difluorophenoxy)ethoxymethyl]phenyl}-3-[4-(3-methoxypropyl)-3,4-dihydro-2H benzo[1,4]oxazin-6-ylmethoxy]piperidine-1-carboxylate The stirred solution of 0.150 g of benzyl 4-(4-chloromethylphenyl)-3-[4-(3-methoxypropyl)-3,4-dihydro-2H-benzo[1,4]oxazin-6-ylmethoxy]piperidine-1-carboxylate, 0.035 g of 2-(2,5-difluorophenoxy)ethanol and 2.0 ml of N,N-dimethylformamide is admixed at 0° C. with 0.0094 g of sodium hydride dispersion (55%). The reaction mixture is stirred at room temperature over a further 1 hour and subsequently poured onto 1M sodium hydrogencarbonate solution (30 ml). The mixture is extracted with tert-butyl methyl ether (2×30 ml). The organic phases are washed successively with water (30 ml) and brine (30 ml), dried over sodium sulphate, filtered and concentrated by evaporation. The title compound is obtained as a slightly yellowish oil from the residue by means of flash chromatography (SiO$_2$ 60F). Rf=0.33 (1:1 EtOAc-heptane); Rt=5.78.

b) Benzyl 4-(4-chloromethylphenyl)-3-[4-(3-methoxypropyl)-3,4-dihydro-2H-benzo[1,4]oxazin-6-ylmethoxy]piperidine-1-carboxylate The stirred solution of 0.980 g of benzyl 4-(4-hydroxymethylphenyl)-3-[4-(3-methoxypropyl)-3,4-dihydro-2H-benzo[1,4]oxazin-6-ylmethoxy]piperidine-1-carboxylate and 20 ml of dichloromethane is admixed with 2.12 ml of 1-chloro-N,N,2-trimethylpropenylamine (chlorenamine) in portions over 24 hours. The reaction mixture is poured onto water (100 ml) and extracted with tert-butyl methyl ether (100 ml). The organic phase is washed with brine (50 ml), dried over sodium sulphate, filtered and concentrated by evaporation. The title compound is obtained as a slightly yellowish oil from the residue by means of flash chromatography (SiO$_2$ 60F). Rf=0.39 (2:1 EtOAc-heptane); Rt=5.57 c) Benzyl 4-(4-hydroxymethylphenyl)-3-[4-(3-methoxypropyl)-3,4-dihydro-2H-benzo[1,4]oxazin-6-ylmethoxy]piperidine-1-carboxylate The solution of 2.0 g of benzyl 4-(4-methoxycarbonylphenyl)-3-[4-(3-methoxypropyl)-3-oxo-3,4-dihydro-2H-benzo[1,4]oxazin-6-ylmethoxy]piperidine-1-carboxylate (Example 235d) in 16 ml of tetrahydrofuran is admixed with 52.1 ml of 9-BBN and stirred at reflux over 24 hours. The reaction mixture is cooled to room temperature, admixed with 1.58 ml of ethanolamine and concentrated by evaporation. The residue is stirred in 50 ml of ethyl acetate-hexane (1:1) over 1 hour and clarified by filtration, and the filtrate is concentrated by evaporation. The title compound is obtained as a slightly yellowish oil from the residue by means of flash chromatography (SiO$_2$ 60F). Rf=0.20 (3:1 EtOAc-heptane); Rt=4.74.

d) 2-(2,5-Difluorophenoxy)ethanol

The solution of 1.80 g of [2-(2,5-difluorophenoxy)ethoxy]triisopropylsilane and 23 ml of tetrahydrofuran is admixed with 4.37 ml of tetrabutylammonium fluoride solution (1M in tetrahydrofuran) and stirred at 60° C. over 1 hour. The reaction mixture is cooled, poured onto water (70 ml) and extracted with tert-butyl methyl ether (2×70 ml). The organic phases are washed with brine (1×50 ml), dried over sodium sulphate, filtered and concentrated by evaporation. The title compound is obtained as a colourless oil from the residue by means of flash chromatography (SiO$_2$ 60F). Rf=0.19 (2:1 EtOAc-heptane); Rt=3.17.

e) [2-(2,5-Difluorophenoxy)ethoxy]triisopropylsilane

The stirred mixture of 0.80 g of 2,5-difluorophenol, 0.82 g of potassium carbonate, 1.98 g of (2-iodoethoxy)triisopropylsilane and 10 ml of acetone is kept at reflux over 3 hours. The reaction mixture is cooled, poured onto water (100 ml) and extracted with tert-butyl methyl ether (2×100 ml). The organic phases are washed with brine (1×80 ml) dried over sodium sulphate, filtered and concentrated by evaporation.

The title compound is obtained as a colourless oil from the residue by means of flash chromatography (SiO$_2$ 60F). Rt=6.63.

EXAMPLE 271

9-(4-{4-[3-(2-Methoxybenzyloxy)propoxy] phenyl}piperidin-3-ylmethyl)-1,3,4,5-tetrahydrobenzo[b]azepin-2-one Analogously to Method A, 0.215 g of tert-butyl 4-{4-[3-(2-methoxybenzyloxy)propoxy]phenyl}-3-(2-oxo-2,3,4,5-tetrahydro-1H-benzo[b]azepin-9-ylmethoxy)piperidine-1-carboxylate is used to prepare the title compound.

The starting materials are prepared as follows:

a) tert-Butyl 4-{4-[3-(2-methoxybenzyloxy)propoxy] phenyl}-3-(2-oxo-2,3,4,5-tetrahydro-1H-benzo[b] azepin-9-ylmethoxy)piperidine-1-carboxylate A solution of 0.345 g of tert-butyl 4-{4-[3-(2-methoxybenzyloxy)propoxy]phenyl}-3-(2-oxo-1-(2-trimethylsilanylethoxymethyl)-2,3,4,5-tetrahydro-1H-benzo[b]azepin-9-ylmethoxy)piperidine-1-carboxylate in 4 ml of tetrahydrofuran is admixed with 0.85 ml of a 1M solution of tetrabutylammonium fluoride in tetrahydrofuran. The reaction solution is heated to reflux over 4 hours. A further 0.85 ml of tetrabutylammonium fluoride solution is added and the reaction solution is subsequently heated to reflux over a further 20 hours. The reaction solution is cooled and admixed with 50 ml each of water and tert-butyl methyl ether. The aqueous phase is removed and extracted with 40 ml of tert-butyl methyl ether. The combined organic phases are washed with 40 ml of brine, dried over sodium sulphate, filtered and concentrated to dryness. The title compound is obtained as a yellow oil from the residue by means of flash chromatography (SiO$_2$ 60F). Rf=0.25 (3:1 EtOAc-heptane); Rt=4.34.

b) tert-Butyl 4-{4-[3-(2-methoxybenzyloxy)propoxy]phenyl}-3-(2-oxo-1-(2-trimethylsilanylethoxymethyl)-2,3,4,5-tetrahydro-1H-benzo[b] azepin-9-ylmethoxy)piperidine-1-carboxylate Analogously to Method D, 0.400 g of tert-butyl 3-hydroxy-4-{4-[3-(2-methoxybenzyloxy)propoxy]phenyl}piperidine-1-carboxylate and 0.303 g of 9-chloromethyl-1-(2-trimethylsilanylethoxymethyl)-1,3,4,5-tetrahydrobenzo[b]azepin-2-one are reacted. The title compound is obtained as a yellowish oil. Rf=0.20 (1:1 EtOAc-heptane); Rt=6.58.

c) 9-Chloromethyl-1-(2-trimethylsilanylethoxymethyl)-1,3,415-tetrahydrobenzo[b]azepin-2-one Analogously to Method E, 0.320 g of 9-hydroxymethyl-1-(2-trimethylsilanylethoxymethyl)-1,3,4,5-tetrahydrobenzo[b]azepin-2-one is reacted with 0.100 ml of thionyl chloride and 0.080 ml of pyridine. The resulting intermediate is subsequently dissolved in 30 ml of N,N-dimethylformamide and the solution is admixed with 0.190 g of lithium chloride. The reaction mixture is subsequently stirred at 45° C. over 2 hours and subsequently concentrated by evaporation. The residue is taken up in 100 ml of tert-butyl methyl ether and the solution is washed with 80 ml of water. The aqueous phase is extracted with 60 ml of tert-butyl methyl ether and the combined organic phases are subsequently dried over sodium sulphate and concentrated by evaporation. The title compound is obtained as a yellow resin from the residue by means of flash chromatography (SiO$_2$ 60F). Rf=0.20 (1:1 EtOAc-heptane); Rt=5.38.

d) 9-Hydroxymethyl-1-(2-trimethylsilanylethoxymethyl)-1,3,4,5-tetrahydrobenzo[b]azepin-2-one A solution of 1.500 g of methyl 2-oxo-1-(trimethylsilanylethoxymethyl)-2,3,4,5-tetrahydro-1H-benzo[b]azepine-9-carboxylate in 35 ml of tetrahydrofuran is admixed with 0.205 g of lithium borohydride. The reaction mixture is stirred at 50° C. over 4 hours and subsequently poured onto 300 ml of a 1:1 mixture of saturated aqueous sodium hydrogencarbonate solution and tert-butyl methyl ether. The phases are separated and the aqueous phase is extracted with 150 ml of tert-butyl methyl ether. The combined organic phases are washed with 150 ml of water, dried over sodium sulphate and concentrated by evaporation. The title compound is obtained as a yellow resin from the residue by means of flash chromatography (SiO$_2$ 60F). Rf=0.20 (1:1 EtOAc-heptane); Rt=4.38.

e) Methyl 2-oxo-1-(trimethylsilanylethoxymethyl)-2,3,4,5-tetrahydro-1H-benzo[b]azepine-9-carboxylate 2.500 g of methyl 2-oxo-2,3,4,5-tetrahydro-1H-benzo[b]azepine-9-carboxylate are dissolved under argon in 30 ml of N,N-dimethylformamide and the solution is cooled to 0° C. in an ice bath. 0.600 g of sodium hydride dispersion (60%) is added in portions and the reaction mixture is subsequently stirred at 0° C. over a further 1 hour. 0.502 ml of 2-(trimethylsilyl)ethoxymethyl chloride is added and the reaction mixture is subsequently stirred at room temperature over 11 hours. The reaction mixture is poured onto 150 ml of saturated aqueous sodium hydrogencarbonate solution and extracted with 2×150 ml of tert-butyl methyl ether. The combined organic phases are dried over sodium sulphate and concentrated by evaporation. The title compound is obtained as a reddish oil from the residue by means of flash chromatography (SiO$_2$ 60F). Rf=0.35 (1:1 EtOAc-heptane); Rt=5.02.

f) Methyl 2-oxo-2,3,4,5-tetrahydro-1H-benzo[b] azepine-9-carboxylate

Conc. H$_2$SO$_4$ is added dropwise at 0° C. to a solution of 3.040 g of methyl 8-oxo-5,6,7,8-tetrahydronaphthalene-1-carboxylate in 550 ml of chloroform, in the course of which the temperature is kept at 0-3° C. On completion of addition, the reaction solution is warmed to 10° C. and 21.80 g of sodium azide are added in portions over the course of 45 minutes. The reaction mixture is subsequently stirred at 50° C. over 2.5 hours. The reaction mixture is cooled to room temperature and subsequently poured onto a mixture of 200 g of potassium carbonate, 1000 ml of water and 400 g of ice. The mixture is made basic with 44 ml of 50% KOH and extracted with 2×500 ml of dichloromethane. The combined organic phases are washed with 1000 ml of water and concentrated. The title compound is obtained as a reddish solid from the residue by means of flash chromatography (SiO$_2$ 60F). Rf=0.25 (1:1 EtOAc-heptane); Rt=3.38.

g) Methyl 8-oxo-5,6,7,8-tetrahydronaphthalene-1-carboxylate

A solution of 3.466 g of 8-oxo-5,6,7,8-tetrahydronaphthalene-1-carboxylic acid in 30 ml of methanol is admixed with 1.850 ml of conc. $H_2SO_4$ and the reaction solution is subsequently heated to reflux over 18 hours. The reaction solution is subsequently cooled and poured onto 200 ml of saturated aqueous sodium hydrogencarbonate solution and extracted with 2×200 ml of ethyl acetate. The combined organic phases are washed with 150 ml of saturated aqueous sodium hydrogencarbonate solution and 150 ml of water, dried over sodium sulphate and concentrated. The crude product is obtained as a brown oil and is used without further purification. Rt=3.42

According to the process described in Example 269, the following compounds are prepared in an analogous manner:

EXAMPLES

| 272 | 4-(3-Methoxypropyl)-6-{4-[4-(3-phenoxypyrrolidin-1-ylmethyl)phenyl]piperidin-3-yloxymethyl}-3,4-dihydro-2H-benzo[1,4]oxazine |
| --- | --- |
| 295 | 4-(3-Methoxypropyl)-6-{4-[4-(3-phenylazetidin-1-ylmethyl)phenyl]piperidin-3-yloxymethyl}-3,4-dihydro-2H-benzo[1,4]oxazine |

EXAMPLE 273

6-(4-{4-[3-(2-Fluorobenzyloxy)propoxy]phenyl}piperidin-3-yloxymethyl)-4-(3-methoxypropyl)-3,4-dihydro-2H-benzo[1,4]oxazine Analogously to Method B, 0.275 g of benzyl 4-{4-[3-(2-fluorobenzyloxy)propoxy]phenyl}-3-[4-(3-methoxypropyl)-3,4-dihydro-2H-benzo[1,4]oxazin-6-ylmethoxy]piperidine-1-carboxylate is used to prepare the title compound.

The starting materials are prepared as follows:

a) Benzyl 4-{4-[3-(2-fluorobenzyloxy)propoxy]phenyl}-3-[4-(3-methoxypropyl)-3,4-dihydro-2H-benzo[1,4]oxazin-6-ylmethoxy]piperidine-1-carboxylate Analogously to Method I, 0.250 g of benzyl 4-(4-hydroxyphenyl)-3-[4-(3-methoxypropyl)-3,4-dihydro-2H-benzo[1,4]oxazin-6-ylmethoxy]piperidine-1-carboxylate (Example 259b) and 0.185 g of 3-(2-fluorobenzyloxy)propyl toluene-4-sulphonate are reacted. The title compound is obtained as a slightly yellowish oil. Rf=0.27 (1:1 EtOAc-heptane); Rt=6.04.

b) 3-(2-Fluorobenzyloxy)propyl toluene-4-sulphonate

Analogously to Example 102b, the title compound is obtained as a white solid. Rf=0.27 (1:4 EtOAc-heptane); Rt=4.99.

EXAMPLE 274

[2-(4-Fluorophenyl)ethyl]-[2-(4-{3-[4-(3-methoxypropyl)-3,4-dihydro-2H-benzo[1,4]oxazin-6-ylmethoxy]piperidin-4-yl}phenoxy)ethyl]amine Analogously to Method B, 0.058 g of benzyl 4-(4-{2-[2-(4-fluorophenyl)ethylamino]ethoxy}phenyl)-3-[4-(3-methoxypropyl)-3,4-dihydro-2H-benzo[1,4]oxazin-6-ylmethoxy]piperidine-1-carboxylate is used to prepare the title compound.

The starting material is prepared as follows:

a) Benzyl 4-(4-{2-[2-(4-fluorophenyl)ethylamino]ethoxy}phenyl)-3-[4-(3-methoxypropyl)-3,4-dihydro-2H-benzo[1,4]oxazin-6-ylmethoxy]piperidine-1-carboxylate 0.361 g of benzyl 4-[4-(2-aminoethoxy]phenyl]-3-[4-(3-methoxypropyl)-3,4-dihydro-2H-benzo[1,4]oxazin-6-ylmethoxy]piperidine-1-carboxylate (Example 184) is dissolved under argon in tetrahydrofuran. 2 g of 4 Å molecular sieve are added, followed by a solution of (4-fluorophenyl)acetaldehyde in 1 ml of tetrahydrofuran. The reaction mixture is stirred at 20° C. for 2 hours. 3 ml of methanol and 0.078 g of sodium acetate are added to the mixture. A solution of 0.055 g of sodium cyanoborohydride in 3 ml of methanol is added dropwise at 0° C. and the mixture is subsequently stirred at 0° C. over 1 hour. 10 ml of saturated aqueous sodium hydrogencarbonate solution are added and the mixture is subsequently filtered through Hyflo. The filtrate is extracted with ethyl acetate (2×20 ml)—the combined organic phases are washed with 20 ml of brine, dried over sodium sulphate and concentrated by evaporation. The title compound is obtained from the residue by means of flash chromatography ($SiO_2$ 60F). Rf=0.20 (200:5:1 dichloromethane-methanol-25% conc. ammonia); Rt=4.74.

EXAMPLE 275

6-{4-[4-(1-Benzothiazol-2-ylazetidin-3-yloxy)phenyl]piperidin-3-yloxymethyl}-4-(3-methoxypropyl)-3,4-dihydro-2H-benzo[1,4]oxazine 0.207 g of benzyl 4-[4-(1-benzothiazol-2-ylazetidin-3-yloxy)phenyl]-3-[4-(3-methoxypropyl)-3,4-dihydro-2H-benzo[1,4]oxazin-6-ylmethoxy]piperidinecarboxylate is dissolved in 8 ml of dioxane. 8 ml each of methanol and 40% KOH are added and the reaction mixture is stirred in a sealed flask at 100° C. over 5 hours. The reaction mixture is subsequently cooled to room temperature, diluted with 40 ml of water and extracted with ethyl acetate (3×40 ml). The combined organic phases are washed with 40 ml of water, dried over sodium sulphate, filtered and concentrated by evaporation. The title compound is obtained from the residue by means of flash chromatography ($SiO_2$ 60F).

The starting materials are prepared as follows:

a) Benzyl 4-[4-(1-benzothiazol-2-ylazetidin-3-yloxy)phenyl]-3-[4-(3-methoxypropyl)-3,4-dihydro-2H-benzo[1,4]oxazin-6-ylmethoxy]piperidinecarboxylate Analogously to Method C, 0.660 g of benzyl 4-[4-(1-benzothiazol-2-ylazetidin-3-yloxy)phenyl]-3-[4-(3-methoxypropyl)-3-oxo-3,4-dihydro-2H-benzo[1,4]oxazin-6-ylmethoxy]piperidinecarboxylate is reacted. The title compound is obtained as a yellow resin. Rf=0.20 (4:1 EtOAc-heptane); Rt=5.02.

b) Benzyl 4-[4-(1-benzothiazol-2-ylazetidin-3-yloxy)phenyl]-3-[4-(3-methoxypropyl)-3-oxo-3,4-dihydro-2H-benzo[1,4]oxazin-6-ylmethoxy]piperidinecarboxylate A solution of 0.835 g of benzyl 4-[4-(azetidin-3-yloxy)phenyl]-3-[4-(3-methoxypropyl)-3-oxo-3,4-dihydro-2H-benzo[1,4]oxazin-6-ylmethoxy]piperidine-1-carboxylate (Example 257c) and 0.233 g of 2-chlorobenzothiazole in 16 ml of N,N-dimethylformamide is admixed with 0.345 g of potassium carbonate. The mixture is stirred at 150° C. over 1 hour, cooled to room temperature and poured onto a mixture of 100 ml of brine, 50 ml of water and 150 ml of ethyl acetate. The phases are separated and the aqueous phase is extracted with 150 ml of ethyl acetate. The combined organic phases are dried over sodium sulphate and concentrated by evaporation. The title compound is obtained as a light yellow resin from the residue by means of flash chromatography (SiO$_2$ 60F). Rf=0.35 (4:1 EtOAc-heptane); Rt=4.78.

EXAMPLE 276

[2-(2-Fluorophenyl)ethyl]-[2-(4-{3-[4-(3-methoxypropyl)-3,4-dihydro-2H-benzo[1,4]oxazin-6-ylmethoxy]piperidin-4-yl}phenoxy)ethyl]amine Analogously to Method B, 0.135 g of benzyl 4-(4-{2-[2-(2-fluorophenyl)ethylamino]ethoxy}phenyl)-3-[4-(3-methoxypropyl)-3,4-dihydro-2H-benzo[1,4]oxazin-6-ylmethoxy]piperidine-1-carboxylate is used to prepare the title compound.

The starting materials are prepared as follows:

a) Benzyl 4-(4-{2-[2-(2-fluorophenyl)ethylamino]ethoxy}phenyl)-3-[4-(3-methoxypropyl)-3,4-dihydro-2H-benzo[1,4]oxazin-6-ylmethoxy]piperidine-1-carboxylate A solution of 0.455 g of benzyl 4-(4-{2-[2-(2-fluorophenyl)acetylamino]ethoxy}phenyl)-3-[4-(3-methoxypropyl)-3,4-dihydro-2H-benzo[1,4]oxazin-6-ylmethoxy]piperidine-1-carboxylate in 5 ml of tetrahydrofuran is admixed at 0° C. with 1.84 ml of diborane-tetrahydrofuran complex (1M solution in tetrahydrofuran). The reaction solution is subsequently heated to reflux over 3 hours. The reaction solution is cooled to room temperature, quenched with 2 ml of methanol and finally admixed with 2 ml of 2M HCl. The mixture is stirred at room temperature over 30 minutes, neutralized with 20 ml of saturated aqueous sodium hydrogencarbonate solution and extracted with 3×20 ml of ethyl acetate. The combined organic phases are washed with 20 ml of brine, dried over sodium sulphate and concentrated by evaporation. The title compound is obtained from the residue by means of flash chromatography (SiO$_2$ 60F). Rf=0.52 (200:20:1 dichloromethane-methanol-25% conc. ammonia); Rt=4.83.

b) Benzyl 4-(4-{2-[2-(2-fluorophenyl)acetylamino]ethoxy}phenyl)-3-[4-(3-methoxypropyl)-3,4-dihydro-2H-benzo[1,4]oxazin-6-ylmethoxy]piperidine-1-carboxylate 0.135 g of 2-fluorophenyl acetic acid is dissolved in 5 ml of dichloromethane. 0.127 g of carbonyldiimidazole is added and the reaction solution is stirred at 20° C. over 1 hour. A solution of 0.472 g of benzyl 4-[4-(2-aminoethoxy)phenyl]-3-[4-(3-methoxypropyl)-3,4-dihydro-2H-benzo[1,4]oxazin-6-ylmethoxy]piperidine-1-carboxylate (Example 184) in 4 ml of dichloromethane is added dropwise and the solution is subsequently stirred at 20° C. over 1 hour. The reaction solution is diluted with 10 ml of dichloromethane and subsequently washed with 10 ml each of 1M NaOH and water, dried over sodium sulphate and concentrated by evaporation. The title compound is obtained as a light yellow resin from the residue by means of flash chromatography (SiO$_2$ 60F). Rf=0.20 (4:1 EtOAc-heptane); Rt=5.14.

According to the process described in Example 187, the following compounds are prepared in an analogous manner:

EXAMPLES

| 278 | 6-(4-{4-[2-(3-Fluorobenzyloxy)ethoxy]phenyl}piperidin-3-yloxymethyl)-4-(3-methoxypropyl)-3,4-dihydro-2H-benzo[1,4]oxazine |
|---|---|
| 279 | 6-(4-{4-[2-(2-Fluorobenzyloxy)ethoxy]phenyl}piperidin-3-yloxymethyl)-4-(3-methoxypropyl)-3,4-dihydro-2H-benzo[1,4]oxazine |
| 280 | 6-(4-{4-[2-(3,5-Difluorobenzyloxy)ethoxy]phenyl}piperidin-3-yloxymethyl)-4-(3-methoxypropyl)-3,4-dihydro-2H-benzo[1,4]oxazine |

EXAMPLE 281

6-(4-{4-[2-(3-Chlorophenoxy)ethoxy]phenyl}piperidin-3-yloxymethyl)-4-(3-methoxypropyl)-3,4-dihydro-2H-benzo[1,4]oxazine 0.140 g of benzyl 4-[4-(1-benzothiazol-2-ylazetidin-3-yloxy)phenyl]-3-[4-(3-methoxypropyl)-3,4-dihydro-2H-benzo[1,4]oxazin-6-ylmethoxy]piperidinecarboxylate are dissolved in 4 ml of dioxane. 4 ml each of methanol and 40% KOH are added and the reaction mixture is stirred in a sealed flask at 100° C. over 3 hours. The reaction mixture is subsequently cooled to room temperature, diluted with 40 ml of water and extracted with ethyl acetate (3×40 ml). The combined organic phases are washed with 40 ml of water, dried (sodium sulphate), filtered and concentrated by evaporation. The residue is purified by means of flash chromatography (SiO$_2$ 60F).

The starting materials are prepared as follows:

a) Benzyl 4-{4-[2-(3-chlorophenoxy)ethoxy]phenyl}-3-[4-(3-methoxypropyl)-3,4-dihydro-2H-benzo[1,4]oxazin-6-ylmethoxy]piperidine-1-carboxylate
The title compound is prepared analogously to Example 267a According to the process described in Example 100, the following compounds are prepared in an analogous manner:

EXAMPLES

| 282 | 6-[4-(4-{2-[2-(4-Fluorophenyl)ethoxy]ethoxy}phenyl)piperidin-3-yloxymethyl]-4-(3-methoxypropyl)-3,4-dihydro-2H-benzo[1,4]oxazine |
|---|---|
| 283 | 6-[4-(4-{2-[2-(3-Fluorophenyl)ethoxy]ethoxy}phenyl)piperidin-3-yloxymethyl]-4-(3-methoxypropyl)-3,4-dihydro-2H-benzo[1,4]oxazine |
| 284 | 6-[4-(4-{2-[2-(2-Fluorophenyl)ethoxy]ethoxy}phenyl)piperidin-3-yloxymethyl]-4-(3-methoxypropyl)-3,4-dihydro-2H-benzo[1,4]oxazine |

According to the process described in Example 267, the following compounds are prepared in an analogous manner:

EXAMPLES

| 285 | 6-(4-{4-[2-(4-Fluorophenoxy)ethoxy]phenyl}-piperidin-3-yloxymethyl)-4-(3-methoxypropyl)-3,4-dihydro-2H-benz[1,4]oxazine |
|---|---|
| 286 | 6-(4-{4-[2-(Benz[1,3]dioxol-5-yloxy)-ethoxy]phenyl}piperidin-3-yloxymethyl)-4-(3-methoxypropyl)-3,4-dihydro-2H-benz[1,4]oxazine |
| 287 | 4-(3-Methoxypropyl)-6-{4-[4-(2-m-tolyloxyethoxy)phenyl}piperidin-3-yloxymethyl}-3,4-dihydro-2H-benz[1,4]oxazine |
| 288 | 3-[2-(4-{3-[4-(3-Methoxypropyl)-3,4-dihydro-2H-benz[1,4]oxazin-6-ylmethoxy]piperidin-4-yl}phenoxy)ethoxy]phenyl}benzonitrile |
| 289 | 6-(4-{4-[2-(2-Fluorophenoxy)ethoxy]phenyl}-piperidin-3-yloxymethyl)-4-(3-methoxypropyl)-3,4-dihydro-2H-benz[1,4]oxazine |
| 290 | 6-(4-{4-[2-(3-Fluorophenoxy)ethoxy]phenyl}-piperidin-3-yloxymethyl)-4-(3-methoxypropyl)-3,4-dihydro-2H-benz[1,4]oxazine |

According to the process described in Example 292, the following compound is prepared in an analogous manner:

EXAMPLE 291

2-(4-{3-[4-(3-Methoxypropyl)-3,4-dihydro-2H-benzo[1,4]oxazin-6-ylmethoxy]piperidin-4-yl}phenyl)-1-(3-phenylpyrrolidin-1-yl)ethanone

EXAMPLE 292

1-(3,4-Dihydro-2H-quinolin-1-yl)-2-(4-{3-[4-(3-methoxypropyl)-3,4-dihydro-2H-benzo[1,4]oxazin-6-ylmethoxy]piperidin-4-yl}phenyl)ethanone Analogously to Method B, 0.108 g of benzyl 4-{4-[2-(3,4-dihydro-2H-quinolin-1-yl)-2-oxoethyl]phenyl}-3-[4-(3-methoxypropyl)-3,4-dihydro-2H-benzo[1,4]oxazin-6-ylmethoxy]piperidine-1-carboxylate is used to prepare the title compound.

The starting materials are prepared as follows:

a) Benzyl 4-{4-[2-(3,4-dihydro-2H-quinolin-1-yl)-2-oxoethyl]phenyl}-3-[4-(3-methoxypropyl)-3,4-dihydro-2H-benzo[1,4]oxazin-6-ylmethoxy]piperidine-1-carboxylate The solution of 0.151 g of benzyl 4-(4-carboxymethylphenyl)-3-[4-(3-methoxypropyl)-3,4-dihydro-2H-benzo[1,4]oxazin-6-ylmethoxy]piperidine-1-carboxylate in 3 ml of dichloromethane is admixed with 0.0376 g of 1,2,3,4-tetrahydroquinoline and 0.101 ml of triethylamine, cooled to 0° C. and subsequently admixed with 0.231 g of N-propylphosphonous anhydride (cyclic trimer). The reaction mixture is stirred at 0° C. for another 1.5 hours, then diluted with 70 ml of tert-butyl methyl ether. The organic phase is washed with 15 ml of water and then 15 ml of brine, dried over sodium sulphate, filtered and concentrated by evaporation. The title compound is obtained as a yellowish oil from the residue by means of flash chromatography (SiO$_2$ 60F). Rf=0.75 (EtOAc). Rt=5.62.

b) Benzyl 4-(4-carboxymethylphenyl)-3-[4-(3-methoxypropyl)-3,4-dihydro-2H-benzo[1,4]oxazin-6-ylmethoxy]piperidine-1-carboxylate The solution of 0.228 g of benzyl 4-[4-(2-diazoacetyl)phenyl]-3-[4-(3-methoxypropyl)-3,4-dihydro-2H-benzo[1,4]oxazin-6-ylmethoxy]piperidine-1-carboxylate in 3.5 ml of tetrahydrofuran is cooled to −15° C., protected from light and admixed with a solution of 0.025 g of silver trifluoroacetate in 0.153 ml of triethylamine, then 0.4 ml of water. The reaction mixture is stirred at −10° C. for 30 minutes, then at 15° C. for 24 hours, and concentrated by evaporation. The residue is dissolved in 10 ml of 0.1N NaOH and washed with 50 ml of tert-butyl methyl ether. The aqueous phase is acidified to pH 1.0 with 2N HCl and washed three times with 30 ml of tert-butyl methyl ether. The combined organic phases are dried over sodium sulphate, filtered and concentrated by evaporation. The title compound is obtained as a yellowish oil from the residue. Rt=4.72.

c) Benzyl 4-[4-(2-diazoacetyl)phenyl]-3-[4-(3-methoxypropyl)-3,4-dihydro-2H-benzo[1,4]oxazin-6-ylmethoxy]piperidine-1-carboxylate The solution of 0.232 g of benzyl 4-(4-carboxyphenyl)-3-[4-(3-methoxypropyl)-3,4-dihydro-2H-benzo[1,4]oxazin-6-ylmethoxy]piperidine-1-carboxylate (Example 229b) in 2.5 ml of dichloromethane is admixed with 0.066 ml of oxalyl chloride and stirred at room temperature over 45 minutes. 0.003 mg of N,N-dimethylformamide is added thereto and the solution is stirred for another 15 minutes and concentrated by evaporation. The residue is also twice dissolved in 2 ml and concentrated by evaporation. The residue is then dissolved in 2.5 ml of tetrahydrofuran, cooled to 5° C., and admixed with 0.085 g of triethylamine and with 4 ml of a solution of diazomethane (1.5% in diethyl ether). The yellow solution is stirred at 5° C. for 5 hours, then at 25° C. for 15 hours, and subsequently concentrated by evaporation. The residue is dissolved in 180 ml of tert-butyl methyl ether and washed with water (50 ml) and then brine (20 ml). The organic phase is dried over sodium sulphate, filtered and concentrated by evaporation. The title compound is obtained as a yellowish oil from the residue by means of flash chromatography (SiO$_2$ 60F). Rt=5.01.

EXAMPLE 293

4-(3-Methoxypropyl)-6-(4-{4-[2-(3-phenylpyrrolidin-1-yl)ethoxy]phenyl}piperidin-3-yloxymethyl)-3,4-dihydro-2H-benzo[1,4]oxazine Analogously to Method B, 0.099 g of benzyl 3-[4-(3-methoxypropyl)-3,4-dihydro-2H-benzo[1,4]oxazin-6-ylmethoxy]-4-{4-[2-(3-phenylpyrrolidin-1-yl)ethoxy]phenyl}piperidine-1-carboxylate is used to prepare the title compound.

The starting materials are prepared as follows:

a) Benzyl 3-[4-(3-methoxypropyl)-3,4-dihydro-2H-benzo[1,4]oxazin-6-ylmethoxy]-4-{4-[2-(3-phenylpyrrolidin-1-yl)ethoxy]phenyl}piperidine-1-carboxylate A solution of 0.350 g of benzyl 3-[4-(3-methoxypropyl)-3-oxo-3,4-dihydro-2H-benzo[1,4]oxazin-6-ylmethoxy]-4-{4-[2-(toluene-4-sulphonyloxy)ethoxy]phenyl}piperidinecarboxylate (Example 267c) in 5 ml of N,N-dimethylformamide is admixed with 0.112 g of 3-phenylpyrrolidine hydrochloride, 0.199 g of potassium carbonate and 0.018 g of tetrabutylammonium iodide. The reaction mixture is subsequently stirred at 80° over 2 hours. The reaction mixture is cooled and poured onto 10 ml of saturated aqueous sodium hydrogencarbonate solution and extracted with tert-butyl methyl ether (2×20 ml). The organic phase is washed with 20 ml of brine, dried over sodium sulphate and concentrated by evaporation. The title compound is obtained from the residue by means of flash chromatography (SiO$_2$ 60F). Rf=0.26 (95:5 dichloromethane-methanol); Rt=5.03.

According to the process described in Example 293, the following compound is prepared in an analogous manner:

EXAMPLE 294

6-(4-{4-[2-(3,4-Dihydro-1H-isoquinolin-2-yl)ethoxy]phenyl}piperidin-3-yloxymethyl)-4-(3-methoxypropyl)-3,4-dihydro-2H-benzo[1,4]oxazine

EXAMPLE 296

[3-(2,5-Difluorophenoxy)propyl]-(4-{3-[4-(3-methoxypropyl)-3,4-dihydro-2H-benzo[1,4]-oxazin-6-ylmethoxy]piperidin-4-yl}phenyl)amine Analogously to Method B, 0.066 g of benzyl 4-{4-[3-(2,5-difluorophenoxy)propylamino]phenyl}-3-[4-(3-methoxypropyl)-3,4-dihydro-2H-benzo[1,4]oxazin-6-ylmethoxy]piperidine-1-carboxylate is used to prepare the title compound.

The starting materials are prepared as follows:

a) Benzyl 4-{4-[3-(2,5-difluorophenoxy)propylamino]phenyl}-3-[4-(3-methoxypropyl)-3,4-dihydro-2H-benzo[1,4]oxazin-6-ylmethoxy]piperidine-1-carboxylate A baked-out Schlenk flask is initially charged with 0.350 g of chloro(di-2-norbornylphosphino)(2-dimethylaminomethylferrocen-1-yl)palladium(II). Under argon, a solution of 0.520 g of benzyl 3-[4-(3-methoxypropyl)-3,4-dihydro-2H-benzo[1,4]oxazin-6-ylmethoxy]-4-(4-trifluoromethanesulphonyloxyphenyl)piperidine-1-carboxylate (Example 265b) and 0.172 g of 3-(2,5-difluorophenoxy)propylamine in 5.3 ml of dried dioxane is added. The reaction mixture is stirred at room temperature over 30 minutes and subsequently at 100° C. over 18 hours. The reaction mixture is cooled, poured onto aqueous 1M sodium hydrogencarbonate solution (20 ml) and extracted with tert-butyl methyl ether (2×20 ml). The organic phases are washed with brine (1×20 ml), dried over sodium sulphate, filtered and concentrated by evaporation. The title compound is obtained as a colourless oil from the residue by means of flash chromatography (SiO$_2$ 60F). Rf=0.29 (2:1 EtOAc-heptane); Rt=4.91.

b) 3-(2,5-Difluorophenoxy)propylamine

Analogously to Method A, 5.22 g of tert-butyl [3-(2,5-difluorophenoxy)propyl]carbamate are reacted. The title compound is obtained as a slightly orange oil. Rf=0.11 (200:20:1 dichloromethane-methanol-25% conc. ammonia); Rt=2.66.

c) tert-Butyl [3-(2,5-difluorophenoxy)propyl]carbamate

The solution of 2.50 g of 2,5-difluorophenol, 3-(Boc-amino)-1-propanol, 7.26 g of triphenylphosphine and tetrahydrofuran (30 ml) is cooled to 0° C. and admixed dropwise with 5.65 ml of diisopropyl azodicarboxylate. The reaction mixture is stirred at room temperature for a further 2 hours and subsequently concentrated by evaporation. The title compound is obtained as a yellowish solid from the residue by means of flash chromatography (SiO$_2$ 60F). Rf=0.34 (1:2 EtOAc-heptane); Rt=4.69.

EXAMPLE 297

4-(3-Methoxypropyl)-6-[4-(4-propoxyphenyl)piperidin-3-yloxymethyl]-3,4-dihydro-2H-benzo[1,4]oxazine Analogously to Method B, 0.047 g of benzyl 3-[4-(3-methoxypropyl)-3,4-dihydro-2H-benzo[1,4]oxazin-6-ylmethoxy]-4-(4-propoxyphenyl)piperidine-1-carboxylate is used to prepare the title compound.

The starting material is prepared as follows:

a) Benzyl 3-[4-(3-methoxypropyl)-3,4-dihydro-2H-benzo[1,4]oxazin-6-ylmethoxy]-4-(4-propoxyphenyl)piperidine-1-carboxylate Analogously to Method D, 0.0618 g of benzyl 4-(4-hydroxyphenyl)-3-[4-(3-methoxypropyl)-3,4-dihydro-2H-benzo[1,4]oxazin-6-ylmethoxy]piperidine-1-carboxylate and 0.0392 g of 1-iodopropane are reacted. The title compound is obtained as a colourless oil. Rf=0.35 (1:1 EtOAc-heptane); Rt=5.88.

According to the process described in Example 297, the following compounds are prepared in an analogous manner:

EXAMPLES

| 298 | 6-{4-[4-(2-Methoxyethoxy)phenyl]piperidin-3-yloxymethyl}-4-(3-methoxypropyl)-3,4-dihydro-2H-benzo[1,4]oxazine |
|---|---|
| 299 | 6-[4-(4-Cyclopropylmethoxyphenyl)piperidin-3-yloxymethyl]-4-(3-methoxypropyl)-3,4-dihydro-2H-benzo[1,4]oxazine |
| 300 | 6-{4-[4-(3-Methoxypropoxy)phenyl]piperidin-3-yloxymethyl}-4-(3-methoxypropyl)-3,4-dihydro-2H-benzo[1,4]oxazine |
| 303 | 6-[4-(4-Isobutoxyphenyl)piperidin-3-yloxymethyl]-4-(3-methoxypropyl)-3,4-dihydro-2H-benzo[1,4]oxazine |

EXAMPLE 301

1-Ethyl-4-(4-{4-[3-(2-methoxybenzyloxy)propoxy]phenyl}piperidin-3-yloxymethyl)-1,3-benzimidazol-2-one Analogously to Method B, 0.155 g of benzyl 3-(1-ethyl-2-oxo-2,3-dihydro-1H-benzimidazol-4-ylmethoxy)-4-{4-[3-(2-methoxybenzyloxy)propoxy]phenyl}piperidine-1-carboxylate is used to prepare the title compound.

The starting materials are prepared as follows:

a) Benzyl 3-(1-ethyl-2-oxo-2,3-dihydro-1H-benzimidazol-4-ylmethoxy)-4-{4-[3-(2-methoxybenzyloxy)propoxy]phenyl}piperidine-1-carboxylate A solution of 0.310 g of benzyl 3-[1-ethyl-2-oxo-3-(2-trimethylsilanylethoxymethyl)-2,3-dihydro-1H-benzimidazol-4-ylmethoxy]-4-{4-[3-(2-methoxybenzyloxy)propoxy]phenyl}piperidine-1-carboxylate in 4 ml of tetrahydrofuran is admixed with 6 ml of tetrabutylammonium fluoride solution (1M in tetrahydrofuran). The reaction solution is heated to reflux over 48 hours, subsequently cooled to room temperature and admixed with 40 ml of water. The mixture is extracted with tert-butyl methyl ether (2×40 ml) and the combined organic phases are washed with 40 ml of brine, dried over sodium sulphate and concentrated by evaporation. The title compound is obtained as a yellow resin from the residue by means of flash chromatography ($SiO_2$ 60F). Rf=0.18 (3:1 EtOAc-heptane); Rt=5.66.

b) Benzyl 3-[1-ethyl-2-oxo-3-(2-trimethylsilanylethoxymethyl)-2,3-dihydro-1H-benzimidazol-4-ylmethoxy]-4-{4-[3-(2-methoxybenzyloxy)propoxy]phenyl}piperidine-1-carboxylate Analogously to Method D, 0.340 g of benzyl 3-hydroxy-4-{4-[3-(2-methoxybenzyloxy)propoxy]phenyl}piperidine-1-carboxylate and 0.272 g of 4-bromomethyl-1-ethyl-3-(2-trimethylsilanylethoxymethyl)-1,3-dihydrobenzimidazol-2-one are reacted. The title compound is obtained as a dark yellow resin. Rf=0.50 (1:1 EtOAc-heptane); Rt=6.67.

c) 4-Bromomethyl-1-ethyl-3-(2-trimethylsilanylethoxymethyl)-1,3-dihydrobenzimidazol-2-one The mixture of 1.00 g of 1-ethyl-4-methyl-3-(2-trimethylsilanylethoxymethyl)-1,3-dihydrobenzimidazol-2-one, 0.469 g of N-bromosuccinimide, 0.025 g of 2,2'-azobis(2-methylpropionitrile) and 0.037 g of dibenzoyl peroxide in 60 ml of carbon tetrachloride is heated to reflux with stirring. The reaction vessel is irradiated with a 150 W lamp over the reaction time. After 0.5 hour, the reaction mixture is cooled and filtered through Hyflo. The filtrate is concentrated. The title compound is obtained as a yellow resin from the residue by means of flash chromatography ($SiO_2$ 60F). Rf=0.20 (40:1 dichloromethane-diethyl ether); Rt=5.80.

d) 1-Ethyl-4-methyl-3-(2-trimethylsilanylethoxymethyl)-1,3-dihydrobenzimidazol-2-one A solution of 3.500 g of 1-ethyl-4-methyl-1,3-dihydrobenzimidazol-2-one in 40 ml of anhydrous N,N-dimethylformamide is admixed at 0° C. with 0.874 g of sodium hydride dispersion (60%). The reaction mixture is stirred at 0° C. over a further 30 minutes and 4.06 ml of 2-(trimethylsilanyl)ethoxymethyl chloride are added dropwise. The reaction mixture is stirred at 20° C. over 14 hours, poured onto 150 ml of saturated aqueous sodium hydrogencarbonate solution and extracted with tert-butyl methyl ether (2×200 ml). The combined organic phases are dried over sodium sulphate and concentrated by evaporation. The title compound is obtained as a brown oil from the residue by means of flash chromatography ($SiO_2$ 60F). Rf=0.20 (1:3 EtOAc-heptane); Rt=5.62.

e) 1-Ethyl-4-methyl-1,3-dihydrobenzimidazol-2-one

A solution of 17.10 g of 4-methyl-1,3-dihydrobenzimidazol-2-one in 250 ml of anhydrous N,N-dimethylformamide is admixed at 0° C. with 4.070 g of sodium hydride dispersion (60%). The reaction mixture is stirred at 0° C. over a further 30 minutes and 7.5 ml of ethyl iodide are added dropwise. The reaction mixture is stirred at 30° C. over 14 hours, poured onto 500 ml of saturated aqueous sodium hydrogencarbonate solution and extracted with ethyl acetate (2×500 ml). The combined organic phases are washed with 500 ml of brine, dried over sodium sulphate and concentrated by evaporation. The title compound is obtained as a brown solid from the residue by means of flash chromatography ($SiO_2$ 60F). Rf=0.20 (200:5:1 dichloromethane-methanol-25% conc. ammonia); Rt=3.17.

According to the process described in Example 276, the following compound is prepared in an analogous manner:

EXAMPLE 302

[2-(3-Fluorophenyl)ethyl]-[2-(4-{3-[4-(3-methoxypropyl)-3,4-dihydro-2H-benzo[1,4]oxazin-6-ylmethoxy]piperidin-4-yl}phenoxy)ethyl]amine

EXAMPLE 304

6-{1 (R or S)-[4-(4-Methoxyphenyl)piperidin-3-yloxy]ethyl}-4-(3-methoxypropyl)-3,4-dihydro-2H-benzo[1,4]oxazine (diastereomer I)

Analogously to Method B, 0.180 g of benzyl 4-(4-methoxyphenyl)-3-{1(R or S)-[4-(3-methoxypropyl)-3,4-dihydro-2H-benzo[1,4]oxazin-6-yl]ethoxy}piperidine-1-carboxylate (diastereomer I) is used to prepare the title compound.

The starting materials are prepared as follows:

a) Benzyl 4-(4-methoxyphenyl)-3-{1(R or S)-[4-(3-methoxypropyl)-3,4-dihydro-2H-benzo[1,4]oxazin-6-yl]ethoxy}piperidine-1-carboxylate (diastereomer I)

Analogously to Method C, 0.200 g of benzyl 4-(4-methoxyphenyl)-3-{1 (R or S)-[4-(3-methoxypropyl)-3-oxo-3,4-dihydro-2H-benzo[1,4]oxazin-6-yl]ethoxy}piperidine-1-carboxylate (diastereomer I) is used to obtain the title compound as a slightly yellowish oil. Rf=0.38 (2:1 EtOAc-heptane); Rt=23.82 (II).

b) Benzyl 4-(4-methoxyphenyl)-3-{1 (R or S)-[4-(3-methoxypropyl)-3-oxo-3,4-dihydro-2H-benzo[1,4]oxazin-6-yl]ethoxy}piperidine-1-carboxylate (diastereomer I) benzyl 4-(4-methoxyphenyl)-3-{1 (S or R)-[4-(3-methoxypropyl)-3-oxo-3,4-dihydro-2H-benzo[1,4]oxazin-6-yl]ethoxy}piperidine-1-carboxylate (diastereomer II)

The solution of 0.800 g of 6-(1-hydroxyethyl)-4-(3-methoxypropyl)-4H-benzo[1,4]oxazin-3-one and 25 ml of diethyl ether is admixed at 0° C. with 0.231 g of sodium hydride (60% dispersion) and stirred over one hour. The mixture is admixed with 2.44 ml of trichloroacetonitrile and stirred at room temperature over 18 hours. The resulting mixture is concentrated by evaporation. The residue is admixed with 0.986 g of benzyl 3-hydroxy-4-(4-methoxyphenyl)piperidine-1-carboxylate and 75 ml of dichloromethane and cooled to −25° C. The resulting mixture is admixed with 0.509 ml of trifluoromethanesulphonic acid and stirred at −25° C. over a further 1 hour. The resulting reaction mixture is poured onto cold saturated sodium hydrogencarbonate solution (100 ml) and extracted with tert-butyl methyl ether (2×100 ml). The organic phases are washed successively with water (100 ml) and brine (50 ml), dried over sodium sulphate, filtered and concentrated by evaporation. The title compounds are obtained as yellowish oils from the residue by means of flash chromatography (SiO$_2$ 60F).

Diastereomer I: Rf=0.40 (3:1 EtOAc-heptane); Rt=22.38 (II).

Diastereomer II: Rf=0.37 (3:1 EtOAc-heptane); Rt=22.04 (II).

c) 6-(1-Hydroxyethyl)-4-(3-methoxypropyl)-4H-benzo[1,4]oxazin-3-one

The solution of 1.0 g of 4-(3-methoxypropyl)-3-oxo-3,4-dihydro-2H-benzo[1,4]oxazine-6-carbaldehyde and 30 ml of tetrahydrofuran is cooled to 0° C. and admixed dropwise with 1.4 ml of methylmagnesium bromide (35% in THF). The reaction mixture is stirred at 0° C. for a further 15 minutes, subsequently quenched with saturated ammonium chloride solution (50 ml) and extracted with tert-butyl methyl ether (2×50 ml). The organic phases are washed successively with ice-water (50 ml) and brine (50 ml), dried over sodium sulphate, filtered and concentrated by evaporation. The title compound is obtained as a slightly yellowish oil from the residue by means of flash chromatography (SiO$_2$ 60F). Rf=0.16 (3:1 EtOAc-heptane); Rt=2.96.

d) 4-(3-Methoxypropyl)-3-oxo-3,4-dihydro-2H-benzo[1,4]oxazine-6-carbaldehyde The solution of 6.08 g of 6-hydroxymethyl-4-(3-methoxypropyl)-4H-benzo[1,4]oxazin-3-one and 300 ml of dichloromethane is admixed with 20.9 g of manganese dioxide and stirred over 8 hours. The reaction mixture is filtered and the filtrate is concentrated by evaporation. The title compound is obtained as a slightly yellowish oil from the residue by means of flash chromatography (SiO$_2$ 60F). Rf=0.59 (4:1 EtOAc-heptane); Rt=3.24.

EXAMPLE 305

6-{1 (S or R)-[4-(4-Methoxyphenyl)piperidin-3-yloxy]ethyl}-4-(3-methoxypropyl)-3,4-dihydro-2H-benzo[1,4]oxazine (diastereomer II)

Analogously to Method B, 0.300 g of benzyl 4-(4-methoxyphenyl)-3-{1 (S or R)-[4-(3-methoxypropyl)-3,4-dihydro-2H-benzo[1,4]oxazin-6-yl]ethoxy}piperidine-1-carboxylate (diastereomer II) is used to prepare the title compound.

The starting material is prepared as follows:

a) Benzyl 4-(4-methoxyphenyl)-3-{1 (S or R)-[4-(3-methoxypropyl)-3,4-dihydro-2H-benzo[1,4]oxazin-6-yl]ethoxy}piperidine-1-carboxylate (diastereomer II)

Analogously to Method C, 0.325 g of benzyl 4-(4-methoxyphenyl)-3-{1(S or R)-[4-(3-methoxypropyl)-3-oxo-3,4-dihydro-2H-benzo[1,4]oxazin-6-yl]ethoxy}piperidine-1-carboxylate (diastereomer II) is reacted. The title compound is obtained as a slightly yellowish oil. Rf=0.38 (2:1 EtOAc-heptane); Rt=23.65 (II).

EXAMPLE 306

4-(3-Ethoxypropyl)-6-(4-{4-[3-(2-methoxybenzyloxy)propoxy]phenyl}piperidin-3-yloxymethyl)-3,4-dihydro-2H-benzo[1,4]oxazine Following Examples 2 and 5, the title compound is prepared starting from 6-hydroxymethyl-4H-benzo[1,4]oxazin-3-one (Example 2d) and 1-chloro-3-ethoxypropane.

EXAMPLE 307

4-(3-Methoxypropyl)-6-{4-[4-(tetrahydrofuran-3-yloxy)phenyl]piperidin-3-yloxymethyl}-3,4-dihydro-2H-benzo[1,4]oxazine Analogously to Method B, 0.0312 g of benzyl 3-[4-(3-methoxypropyl)-3,4-dihydro-2H-benzo[1,4]oxazin-6-ylmethoxy]-4-[4-(tetrahydrofuran-3-yloxy)phenyl]piperidine-1-carboxylate is used to prepare the title compound.

The starting material is prepared as follows:

a) Benzyl 3-[4-(3-methoxypropyl)-3,4-dihydro-2H-benzo[1,4]oxazin-6-ylmethoxy]-4-[4-(tetrahydrofuran-3-yloxy)phenyl]piperidine-1-carboxylate Analogously to Method D, 0.065 g of benzyl 4-(4-hydroxyphenyl)-3-[4-(3-methoxypropyl)-3,4-dihydro-2H-benzo[1,4]oxazin-6-ylmethoxy]piperidine-1-carboxylate and 0.0288 g of tetrahydrofuran-3-yl toluene-4-sulphonate are reacted. The title compound is obtained as an orange oil. Rf=0.22 (2:1 EtOAc-heptane). Rt=5.25.

According to the process described in Example 307, the following compounds are prepared in an analogous manner:

EXAMPLES

| 311 | 4-(3-Methoxypropyl)-6-{4-[4-(tetrahydropyran-4-yloxy)phenyl]piperidin-3-yloxymethyl}-3,4-dihydro-2H-benzo[1,4]oxazine |
| 312 | 6-[4-(4-Cyclohexyloxyphenyl)piperidin-3-yloxymethyl]-4-(3-methoxypropyl)-3,4-dihydro-2H-benzo[1,4]oxazine |

EXAMPLE 308

6-[4-(4-Isopropoxyphenyl)piperidin-3-yloxymethyl]-4-(3-methoxypropyl)-3,4-dihydro-2H-benzo[1,4]oxazine Analogously to Method B, 0.0302 g of benzyl 4-(4-isopropoxyphenyl)-3-[4-(3-methoxypropyl)-3,4-dihydro-2H-benzo[1,4]oxazin-6-ylmethoxy]piperidine-1-carboxylate is used to prepare the title compound.

The starting material is prepared as follows:

a) Benzyl 4-(4-isopropoxyphenyl)-3-[4-(3-methoxypropyl)-3,4-dihydro-2H-benzo[1,4]oxazin-6-ylmethoxy]piperidine-1-carboxylate Analogously to Method F, 0.05 g of benzyl 4-(4-hydroxyphenyl)-3-[4-(3-methoxypropyl)-3,4-dihydro-2H-benzo[1,4]oxazin-6-ylmethoxy]piperidine-1-carboxylate and 0.0316 g of 2-iodopropane are reacted at 50° C. The title compound is obtained as an orange oil. Rf=0.34 (1:1 EtOAc-heptane). Rt=5.78.

According to the process described in Example 308, the following compounds are prepared in an analogous manner:

EXAMPLES

| 309 | 6-[4-(4-Cyclopentyloxyphenyl)piperidin-3-yloxymethyl]-4-(3-methoxypropyl)-3,4-dihydro-2H-benzo[1,4]oxazine |
| 310 | 6-[4-(4-Ethoxyphenyl)piperidin-3-yloxymethyl]-4-(3-methoxypropyl)-3,4-dihydro-2H-benzo[1,4]oxazine |

EXAMPLE 314

6-[4-(4-Imidazol-1-ylmethylphenyl)piperidin-3-yloxymethyl]-4-(3-methoxypropyl)-3,4-dihydro-2H-benzo[1,4]oxazine 0.0978 g of benzyl 4-(4-imidazol-1-ylmethylphenyl)-3-[4-(3-methoxypropyl)-3,4-dihydro-2H-benzo[1,4]oxazin-6-ylmethoxy]piperidine-1-carboxylate is dissolved in 3 ml of dioxane. 3 ml each of methanol and 40% KOH are added and the reaction mixture is stirred in a sealed flask at 100° C. over 5 hours. The reaction mixture is subsequently cooled to room temperature, diluted with 10 ml of water and extracted with ethyl acetate (3×30 ml). The combined organic phases are washed with 10 ml of water, then 10 ml of brine, dried over sodium sulphate, filtered and concentrated. The title compound is obtained from the residue by means of flash chromatography (SiO$_2$ 60F).

The starting material is prepared as follows:

a) Benzyl 4-(4-imidazol-1-ylmethylphenyl)-3-[4-(3-methoxypropyl)-3,4-dihydro-2H-benzo[1,4]oxazin-6-ylmethoxy]piperidine-1-carboxylate Analogously to Example 269a, 0.103 g of benzyl 4-(4-chloromethylphenyl)-3-[4-(3-methoxypropyl)-3,4-dihydro-2H-benzo[1,4]oxazin-6-ylmethoxy]piperidine-1-carboxylate (Example 270b) and 0.013 g of imidazole are reacted. The title compound is obtained as a yellowish oil. Rf=0.47 (200:10:1 dichloromethane-methanol-25% conc. ammonia). Rt=4.34.

EXAMPLE 316

4-[6-(4-{4-[3-(2-Methoxybenzyloxy)propoxy]phenyl}piperidin-3-yloxymethyl)-2,3-dihydrobenzo[1,4]oxazin-4-yl]butylamine Analogously to Method B, 0.238 g of benzyl 3-[4-(4-aminobutyl)-3,4-dihydro-2H-benzo[1,4]oxazin-6-ylmethoxy]-4-{4-[3-(2-methoxybenzyloxy)propoxy]phenyl}piperidine-1-carboxylate is used to prepare the title compound.

The starting materials are prepared as follows:

a) Benzyl 3-[4-(4-aminobutyl)-3,4-dihydro-2H-benzo[1,4]oxazin-6-ylmethoxy]-4-{4-[3-(2-methoxybenzyloxy)propoxy]phenyl}piperidine-1-carboxylate Analogously to Method C, 0.250 g of benzyl 3-[4-(4-aminobutyl)-3-oxo-3,4-dihydro-2H-benzo[1,4]oxazin-6-ylmethoxy]-4-{4-[3-(2-methoxybenzyloxy)propoxy]phenyl}piperidine-1-carboxylate is reacted. The title compound is obtained as a yellowish oil. Rf=0.19 (200:20:1 dichloromethane-methanol-conc. ammonia); Rt=5.20.

b) Benzyl 3-[4-(4-aminobutyl)-3-oxo-3,4-dihydro-2H-benzo[1,4]oxazin-6-ylmethoxy]-4-{4-[3-(2-methoxybenzyloxy)propoxy]phenyl}piperidine-1-carboxylate Following Examples 56b and 56c, the title compound is obtained as a yellowish oil starting from 1.90 g of benzyl 4-{4-[3-(2-methoxybenzyloxy)propoxy]phenyl}-3-{3-oxo-4-[4-(toluene-4-sulphonyloxy)butyl]-3,4-dihydro-2H-benzo[1,4]oxazin-6-ylmethoxy}piperidine-1-carboxylate. Rf=0.17 (200:20:1 dichloromethane-methanol-conc. ammonia); Rt=5.04.

c) Benzyl 4-{4-[3-(2-methoxybenzyloxy)propoxy]phenyl}-3-{3-oxo-4-[4-(toluene-4-sulphonyloxy)butyl]-3,4-dihydro-2H-benzo[1,4]oxazin-6-ylmethoxy}piperidine-1-carboxylate Analogously to Method H, 1.81 g of benzyl 3-[4-(4-hydroxybutyl)-3-oxo-3,4-dihydro-2H-benzo[1,4]oxazin-6-ylmethoxy]-4-{4-[3-(2-methoxybenzyloxy)propoxy]phenyl}piperidine-1-carboxylate are reacted. The title compound is obtained as a yellowish oil. Rf=0.41 (2:1 EtOAc-heptane); Rt=6.01.

d) Benzyl 3-[4-(4-hydroxybutyl)-3-oxo-3,4-dihydro-2H-benzo[1,4]oxazin-6-ylmethoxy]-4-{4-[3-(2-methoxybenzyloxy)propoxy]phenyl}piperidine-1-carboxylate Analogously to Example 94e, 2.26 g of benzyl 4-{4-[3-(2-methoxybenzyloxy)propoxy]phenyl}-3-[3-oxo-4-(4-triisopropylsilanyloxybutyl)-3,4-dihydro-2H-benzo[1,4]oxazin-6-ylmethoxy]piperidine-1-carboxylate are reacted. The title compound is obtained as a yellowish oil. Rf=0.11 (2:1 EtOAc-heptane); Rt=5.44.

e) Benzyl 4-{4-[3-(2-methoxybenzyloxy)propoxy]phenyl}-3-[3-oxo-4-(4-triisopropylsilanyloxybutyl)-3,4-dihydro-2H-benzo[1,4]oxazin-6-ylmethoxy]piperidine-1-carboxylate Analogously to Method D, 1.30 g of benzyl 3-hydroxy-4-{4-[3-(2-methoxybenzyloxy)propoxy]-phenyl}piperidine-1-carboxylate (Example 10f) and 1.30 g of 6-chloromethyl-4-(4-triisopropylsilanyloxybutyl)-4H-benzo[1,4]oxazin-3-one are reacted. The title compound is obtained as a yellowish oil. Rf=0.42 (1:1 EtOAc-heptane); Rt=7.54.

f) 6-Chloromethyl-4-(4-triisopropylsilanyloxybutyl)-4H-benzo[1,4]oxazin-3-one Analogously to Method E, 1.75 g of 6-hydroxymethyl-4-(4-triisopropylsilanyloxybutyl)-4H-benzo[1,4]oxazin-3-one are reacted. The title compound is obtained as a yellowish oil. Rf=0.64 (1:1 EtOAc-heptane); Rt=6.57.

g) 6-Hydroxymethyl-4-(4-triisopropylsilanyloxybutyl)-4H-benzo[1,4]oxazin-3-one The stirred solution of 3.70 g of 6-hydroxymethyl-4H-benzo[1,4]oxazin-3-one (Example 2d) and 95 ml of N,N-dimethylformamide is cooled to 0° C., admixed with 0.808 g of sodium hydride (60% dispersion) and stirred over 1 hour. After 7.57 g of (4-bromobutoxy)triisopropylsilane have been added, the mixture is stirred at 0° C. over a further 18 hours and the resulting reaction mixture is poured onto aqueous 1M sodium hydrogencarbonate solution (200 ml). The mixture is extracted with tert-butyl methyl ether (2×200 ml). The organic phases are washed successively with water (3×200 ml) and brine (200 ml), dried over sodium sulphate, filtered and concentrated by evaporation. The title compound is obtained as a slightly yellowish oil from the residue by means of flash chromatography ($SiO_2$ 60F). Rf=0.43 (1:1 EtOAc-heptane); Rt=5.86.

EXAMPLE 317

6-[4-(4-Ethoxymethylphenyl)piperidin-3-yloxymethyl]-4-(3-methoxypropyl)-3,4-dihydro-2H-benzo[1,4]oxazine Analogously to Method B, 0.0503 g of benzyl 4-(4-ethoxymethylphenyl)-3-[4-(3-methoxypropyl)-3,4-dihydro-2H-benzo[1,4]oxazin-6-ylmethoxy]piperidine-1-carboxylate is used to prepare the title compound.

The starting material is prepared as follows:

a) Benzyl 4-(4-ethoxymethylphenyl)-3-[4-(3-methoxypropyl)-3,4-dihydro-2H-benzo[1,4]oxazin-6-ylmethoxy]piperidine-1-carboxylate Analogously to Method D, 0.100 g of benzyl 4-(4-hydroxymethylphenyl)-3-[4-(3-methoxypropyl)-3,4-dihydro-2H-benzo[1,4]oxazin-6-ylmethoxy]piperidine-1-carboxylate (Example 270c) and 0.0395 g of ethyl iodide are reacted. The title compound is obtained as a yellow oil. Rf=0.49 (2:1 EtOAc-heptane); Rt=5.60.

According to the process described in Examples 304 and 305, the following compounds are prepared in an analogous manner:

EXAMPLES

| | |
|---|---|
| 318 | 6-[1(R or S)-(4-{4-[3-(2-Methoxybenzyloxy)propoxy]phenyl}piperidin-3-yloxy)ethyl]-4-(3-methoxypropyl)-3,4-dihydro-2H-benzo[1,4]oxazine (diastereomer I) |
| 319 | 6-[1(S or R)-(4-{4-[3-(2-Methoxybenzyloxy)propoxy]phenyl}piperidin-3-yloxy)ethyl]-4-(3-methoxypropyl)-3,4-dihydro-2H-benzo[1,4]oxazine (diastereomer II) |
| 328 | 6-{1(R or S)-[4-(4-Methoxyphenyl)piperidin-3-yloxy]propyl}-4-(3-methoxypropyl)-3,4-dihydro-2H-benzo[1,4]oxazine (diastereomer I) |
| 329 | 6-{1(S or R)-[4-(4-Methoxyphenyl)piperidin-3-yloxy]propyl}-4-(3-methoxypropyl)-3,4-dihydro-2H-benzo[1,4]oxazine (diastereomer II) |

EXAMPLE 320

(2,5-Difluorophenyl)-[3-(4-{3-[4-(3-methoxypropyl)-3,4-dihydro-2H-benzo[1,4]oxazin-6-ylmethoxy]piperidin-4-yl}phenoxy)propyl]amine Analogously to Method B, 0.220 g of benzyl 4-{4-[3-(2,5-difluorophenylamino)propoxy]phenyl}-3-[4-(3-methoxypropyl)-3,4-dihydro-2H-benzo[1,4]oxazin-6-ylmethoxy]piperidinecarboxylate is used to prepare the title compound.

The starting materials are prepared as follows:

a) Benzyl 4-{4-[3-(2,5-difluorophenylamino)propoxy]phenyl}-3-[4-(3-methoxypropyl)-3,4-dihydro-2H-benzo[1,4]oxazin-6-ylmethoxy]piperidinecarboxylate A solution of 0.303 g of benzyl 4-{4-hydroxyphenyl}-3-[4-(3-methoxypropyl)-3,4-dihydro-2H-benzo[1,4]oxazin-6-ylmethoxy]piperidinecarboxylate, 0.104 g of 3-(2,5-difluorophenylamino)propan-1-ol and 0.176 g of triphenylphosphine in 8 ml of tetrahydrofuran is admixed with 0.136 ml of diisopropyl azodicarboxylate. The reaction solution is left to stand at room temperature over 3 hours and subsequently concentrated by evaporation. The title compound is obtained as a colourless oil from the residue by means of flash chromatography ($SiO_2$ 60F). Rf=0.29 (1:1 EtOAc-heptane); Rt=6.02.

b) 3-(2,5-Difluorophenylamino)propan-1-ol

A solution of 0.185 g of N-(2,5-difluorophenyl)-3-hydroxypropionamide in 3 ml of tetrahydrofuran is added dropwise at room temperature to a suspension of 0.074 g of lithium aluminium hydride in 6 ml of anhydrous tetrahydrofuran. The reaction mixture is stirred at room temperature over 12 hours and subsequently hydrolysed with 0.13 ml of water followed by 0.13 ml of 1M NaOH. The mixture is filtered through Hyflo and the filtrate is washed with 10 ml of brine. The organic phase is dried over sodium sulphate and concentrated by evaporation. The title compound is obtained as a yellow liquid from the residue by means of flash chromatography ($SiO_2$ 60F). Rf=0.28 (1:1 EtOAc-heptane); Rt=3.39.

c) N-(2,5-Difluorophenyl)-3-hydroxypropionamide 4 ml of a solution of diethylaluminum chloride (1M in hexane) is added dropwise at 0° C. to a solution of 0.519 g of 2,5-difluoroaniline in 10 ml of anhydrous dichloromethane. The reaction solution is stirred at room temperature for a further 20 minutes and subsequently cooled back to 0° C. A solution of 0.147 g of propiolactone in 8 ml of dichloromethane is added dropwise and the reaction mixture is stirred at room temperature over a further 2 hours. The reaction mixture is subsequently hydrolysed at 0° C. with 30 ml of 0.2M HCl and the phases are separated. The aqueous phase is re-extracted with 2×50 ml of dichloromethane and the combined organic phases are washed with 50 ml of water, dried over sodium sulphate and concentrated by evaporation. The title compound is obtained as a beige solid from the residue by means of flash chromatography ($SiO_2$ 60F). Rf=0.15 (1:1 EtOAc-heptane); Rt=2.62.

EXAMPLE 321

4-{4-[3-(2-Methoxybenzyloxy)propoxy]phenyl}-3-
[2-(3-methoxypropoxy)benzyloxy]piperidine Analogously to Method A, 0.171 g of tert-butyl 4-{4-[3-(2-methoxybenzyloxy)propoxy]phenyl}-3-[2-(3-methoxypropoxy)benzyloxy]piperidine-1-carboxylate is used to prepare the title compound.

The starting materials are prepared as follows:

a) tert-Butyl 4-{4-[3-(2-methoxybenzyloxy)propoxy]
phenyl}-3-[2-(3-methoxypropoxy)benzyloxy]piperi-
dine-1-carboxylate Analogously to Method D, 0.200 g of tert-butyl 3-hydroxy-4-{4-[3-(2-methoxybenzyloxy)propoxy]phenyl}piperidine-1-carboxylate and 0.113 g of 1-chloromethyl-2-(3-methoxypropoxy)benzene are reacted. The title compound is obtained as a yellowish oil. Rf=0.44 (1:2 EtOAc-heptane); Rt=6.25.

b) 1-Chloromethyl-2-(3-methoxypropoxy)benzene

Analogously to Method E, 1.25 g of 2-[(3-methoxypropoxy)phenyl]methanol, 0.955 g of thionyl chloride and 0.505 g of pyridine are reacted. The title compound is obtained as a yellowish oil. Rf=0.52 (1:4 EtOAc-heptane); Rt=4.61.

c) 2-(3-Methoxypropoxy)phenyl]methanol 2 g of 2-hydroxymethylphenol are dissolved in 40 ml of N,N-dimethylformamide and admixed with 4.499 g of potassium carbonate, then with 2.078 g of 1-chloro-3-methoxypropane. The reaction mixture is stirred at 100° C. for 18 hours, then cooled to room temperature and filtered. The solution is diluted with 250 ml of tert-butyl methyl ether, washed with 40 ml of water and 30 ml of brine, dried over sodium sulphate, filtered and concentrated by evaporation. The title compound is obtained as a colourless oil from the residue by means of flash chromatography (SiO$_2$ 60F). Rf=0.22 (1:1 EtOAc-heptane); Rt=3.21.

EXAMPLE 322

6-[4-(4-Benzyloxyphenyl)piperidin-3-yloxymethyl]-
4-(3-methoxypropyl)-3,4-dihydro-2H-benzo[1,4]
oxazine 0.090 g of benzyl 4-(4-benzyloxyphenyl)-3-[4-(3-methoxypropyl)-3,4-dihydro-2H-benzo[1,4]oxazin-6-ylmethoxy]piperidine-1-carboxylate is dissolved in 3 ml of dioxane. 3 ml each of methanol and 40% KOH are added and the reaction mixture is stirred in a sealed flask at 100° C. over 3.5 hours. The reaction mixture is subsequently cooled to room temperature, diluted with 10 ml of water and extracted with tert-butyl methyl ether (3×30 ml). The combined organic phases are washed with 10 ml of water, then 10 ml of brine, dried over sodium sulphate, filtered and concentrated by evaporation. The title compound is obtained from the residue by means of flash chromatography (SiO$_2$ 60F).

The starting material is prepared as follows:

a) Benzyl 4-(4-benzyloxyphenyl)-3-[4-(3-methoxypropyl)-3,4-dihydro-2H-benzo[1,4]oxazin-6-yl-
methoxy]piperidine-1-carboxylate Analogously to Example 308a, 0.103 g of benzyl 4-(4-hydroxyphenyl)-3-[4-(3-methoxypropyl)-3,4-dihydro-2H-benzo[1,4]oxazin-6-ylmethoxy]piperidine-1-carboxylate and 0.0533 g of benzyl bromide are reacted. The title compound is obtained as a colourless oil. Rf=0.23 (1:1 EtOAc-heptane); Rt=5.95.

EXAMPLE 323

[2-(4-{3-[4-(3-Methoxypropyl)-3,4-dihydro-2H-
benzo[1,4]oxazin-6-ylmethoxy]piperidin-4-
yl}phenoxy)ethyl]dimethylamine Analogously to Method B, 0.147 g of benzyl 4-[4-(2-dimethylaminoethoxy)phenyl]-3-[4-(3-methoxypropyl)-3,4-dihydro-2H-benzo[1,4]oxazin-6-ylmethoxy]piperidine-1-carboxylate is used to prepare the title compound.

The starting material is prepared as follows:

a) Benzyl 4-[4-(2-dimethylaminoethoxy)phenyl-3-
[4-(3-methoxypropyl)-3,4-dihydro-2H-benzo[1,4]
oxazin-6-ylmethoxy]piperidine-1-carboxylate A solution of 0.193 g of benzyl 3-[4-(3-methoxypropyl)-3,4-dihydro-2H-benzo[1,4]oxazin-6-ylmethoxy]-4-{4-[2-(toluene-4-sulphonyloxy)ethoxy]phenyl}piperidine-1-carboxylate (Example 267c), 0.131 g of triethylamine and 1.769 g of dimethylamine (33% in ethanol) is stirred at room temperature for 3 days and then concentrated by evaporation. The title compound is obtained as a yellowish oil from the residue by means of flash chromatography (SiO$_2$ 60F). Rf=0.20 (200:10:1 dichloromethane-methanol-conc. ammonia); Rt=4.40.

EXAMPLE 324

6-[4-(4-Methoxyphenyl)piperidin-3-yloxymethyl]-4-
(3-methoxypropyl)-2,2-dimethyl-4H-benzo[1,4]ox-
azin-3-one Analogously to Method B, 0.807 g of benzyl 4-(4-methoxyphenyl)-3-[4-(3-methoxypropyl)-2,2-dimethyl-3-oxo-3,4-dihydro-2H-benzo[1,4]oxazin-6-ylmethoxy]piperidine-1-carboxylate is used to prepare the title compound.

The starting materials are prepared as follows:

a) Benzyl 4-(4-methoxyphenyl)-3-[4-(3-methoxypropyl)-2,2-dimethyl-3-oxo-3,4-dihydro-2H-benzo[1,4]
oxazin-6-ylmethoxy]piperidine-1-carboxylate Analogously to Method D, 0.500 g of benzyl 3-hydroxy-4-(4-methoxyphenyl)piperidine-1-carboxylate and 0.505 g of 6-chloromethyl-4-(3-methoxypropyl)-2,2-dimethyl-4H-benzo[1,4]oxazin-3-one are reacted. The title compound is obtained as an orange oil. Rf=0.17 (1:1 EtOAc-heptane); Rt=5.51.

b) 6-Chloromethyl-4-(3-methoxypropyl)-2,2-dimethyl-4H-benzo[1,4]oxazin-3-one Analogously to Method E, 2.500 g of 6-hydroxymethyl-4-(3-methoxypropyl)-2,2-dimethyl-4H-benzo[1,4]oxazin-3-one are reacted. The title compound is obtained as a beige solid. Rt=4.64.

c) 6-Hydroxymethyl-4-(3-methoxypropyl)-2,2-dimethyl-4H-benzo[1,4]oxazin-3-one A suspension of 2.270 g of 6-hydroxymethyl-2,2-dimethyl-4H-benzo[1,4]oxazin-3-one in 180 ml of acetonitrile is admixed with 2.410 ml of 1-chloro-3-methoxypropane, 9.844 g of potassium fluoride on alumina and 0.036 g of potassium iodide. The reaction mixture is heated to reflux over 30 hours and filtered through Hyflo, and the filtrate is concentrated. The title compound is obtained as a beige solid from the residue by means of flash chromatography (SiO$_2$ 60F). Rf=0.20 (3:1 EtOAc-heptane); Rt=3.25.

d) 6-Hydroxymethyl-2,2-dimethyl-4H-benzo[1,4]oxazin-3-one

A solution of 75.60 g of methyl 2,2-dimethyl-3-oxo-3,4-dihydro-2H-benzo[1,4]oxazine-6-carboxylate in 2700 ml of anhydrous tetrahydrofuran is cooled to −40° C. 858 ml of diisobutylaluminium hydride solution (1M in toluene) are added dropwise at −45-−40° C. The reaction mixture is subsequently stirred at −40° C. for a further 2 hours and finally warmed slowly to −20° C. The reaction mixture is poured onto 360 ml of 32% HCl. The phases are separated and the organic phase is washed with 1000 ml of 1M aqueous sodium potassium tartrate solution. The combined aqueous phases are re-extracted with 1000 ml of tetrahydrofuran and the combined organic phases are dried over sodium sulphate and concentrated by evaporation. The residue is taken up in 500 ml of tert-butyl methyl ether and the suspension is stirred at 45° C. over 1 hour. The title compound is obtained as a beige solid by filtration. Rt=2.69.

EXAMPLE 325

[3-(4-{3-[4-(3-Methoxypropyl)-3,4-dihydro-2H-benzo[1,4]oxazin-6-ylmethoxy]piperidin-4-yl}phenoxy)propyl]dimethylamine Analogously to Method B, 0.160 g of benzyl 4-[4-(3-dimethylaminopropoxy)phenyl]-3-[4-(3-methoxypropyl)-3,4-dihydro-2H-benzo[1,4]oxazin-6-ylmethoxy]piperidine-1-carboxylate is used to prepare the title compound.

The starting materials are prepared as follows:

a) Benzyl 4-[4-(3-dimethylaminopropoxy)phenyl]-3-[4-(3-methoxypropyl)-3,4-dihydro-2H-benzo[1,4]oxazin-6-ylmethoxy]piperidine-1-carboxylate A solution of 0.21 g of benzyl 3-[4-(3-methoxypropyl)-3,4-dihydro-2H-benzo[1,4]oxazin-6-ylmethoxy]-4-{4-[3-(toluene-4-sulphonyloxy)propoxy]phenyl}piperidine-1-carboxylate, 0.140 g of triethylamine and 1.892 g of dimethylamine (33% in ethanol) is stirred at room temperature for 3 days and then concentrated by evaporation. The title compound is obtained as a yellowish oil from the residue by means of flash chromatography (SiO$_2$ 60F). Rf=0.21 (200:10:1 dichloromethane-methanol-conc. ammonia); Rt=4.49.

b) Benzyl 3-[4-(3-methoxypropyl)-3,4-dihydro-2H-benzo[1,4]oxazin-6-ylmethoxy]-4-{4-[3-(toluene-4-sulphonyloxy)propoxy]phenyl}piperidine-1-carboxylate Analogously to Method I, 0.204 g of benzyl 4-(4-hydroxyphenyl)-3-[4-(3-methoxypropyl)-3,4-dihydro-2H-benzo[1,4]oxazin-6-ylmethoxy]piperidine-1-carboxylate and 0.514 g of 1,3-propanediyl di-p-toluenesulphonate are reacted. The title compound is obtained as an orange oil. Rf=0.37 (2:1 EtOAc-heptane); Rt=5.72.

EXAMPLE 326

6-[4-(4-Methoxyphenyl)piperidin-3-yloxymethyl]-4-(3-methoxypropyl)-2,2-dimethyl-4H-benzo[1,4]oxazine Analogously to Method C, 0.300 g of 6-[4-(4-methoxyphenyl)piperidin-3-yloxymethyl]-4-(3-methoxypropyl)-2,2-dimethyl-4H-benzo[1,4]oxazin-3-one (Example 324) is used to prepare the title compound.

EXAMPLE 327

4-(3-Methoxypropyl)-6-[4-(4-phenoxymethyl)phenyl)piperidin-3-yloxymethyl]-3,4-dihydro-2H-benzo[1,4]oxazine Analogously to Method B, 0.116 g of benzyl 3-[4-(3-methoxypropyl)-3,4-dihydro-2H-benzo[1,4]oxazin-6-ylmethoxy]-4-(4-phenoxymethylphenyl)piperidine-1-carboxylate is used to prepare the title compound.

The starting material is prepared as follows:

a) Benzyl 3-[4-(3-methoxypropyl)-3,4-dihydro-2H-benzo[1,4]oxazin-6-ylmethoxy]-4-(4-phenoxymethylphenyl)piperidine-1-carboxylate 0.0819 g of diisopropyl azodicarboxylate is added dropwise to a solution of 0.180 g of benzyl 4-(4-hydroxymethylphenyl)-3-[4-(3-methoxypropyl)-3,4-dihydro-2H-benzo[1,4]oxazin-6-ylmethoxy]piperidine-1-carboxylate (Example 270c), 0.0304 g of phenol and 0.102 g of triphenylphosphine. The solution is stirred at room temperature for 1 hour and concentrated by evaporation. The title compound is obtained as a colourless oil from the residue by means of flash chromatography (SiO$_2$ 60F). Rf=0.25 (1:2 EtOAc-heptane); Rt=5.99.

According to the process described in Example 327, the following compounds are prepared in an analogous manner:

EXAMPLES

334: 4-(3-Methoxypropyl)-6-[4-(4-o-tolyloxymethylphenyl)piperidin-3-yloxymethyl]-3,4-dihydro-2H-benzo[1,4]oxazine
335: 6-{4-[4-(3-Fluorophenoxymethyl)phenyl]piperidin-3-yloxymethyl}-4-(3-methoxypropyl)-3,4-dihydro-2H-benzo[1,4]oxazine
336 6-{4-[4-(2-Fluorophenoxymethyl)phenyl]piperidin-3-yloxymethyl}-4-(3-methoxypropyl)-3,4-dihydro-2H-benzo[1,4]oxazine
337 6-{4-[4-(4-Fluorophenoxymethyl)phenyl]piperidin-3-yloxymethyl}-4-(3-methoxypropyl)-3,4-dihydro-2H-benzo[1,4]oxazine -continued

| | |
|---|---|
| 338 | 6-{4-[4-(2,4-Difluorophenoxymethyl)phenyl]piperidin-3-yloxymethyl}-4-(3-methoxypropyl)-3,4-dihydro-2H-benzo[1,4]oxazine |
| 339 | 6-{4-[4-(2-Methoxyphenoxymethyl)phenyl]piperidin-3-yloxymethyl}-4-(3-methoxypropyl)-3,4-dihydro-2H-benzo[1,4]oxazine |
| 342 | 4-(3-Methoxypropyl)-6-[4-(4-m-tolyloxymethylphenyl)piperidin-3-yloxymethyl]-3,4-dihydro-2H-benzo[1,4]oxazine |
| 343 | 4-(3-Methoxypropyl)-6-[4-(4-p-tolyloxymethylphenyl)piperidin-3-yloxymethyl]-3,4-dihydro-2H-benzo[1,4]oxazine |

EXAMPLE 330

6-[4-(4-isopropoxymethylphenyl)piperidin-3-yloxymethyl]-4-(3-methoxypropyl)-3,4-dihydro-2H-benzo[1,4]oxazine Analogously to Method B, 0.0351 g of benzyl 4-(4-isopropoxymethylphenyl)-3-[4-(3-methoxypropyl)-3,4-dihydro-2H-benzo[1,4]oxazin-6-ylmethoxy]piperidine-1-carboxylate is used to prepare the title compound.
The starting material is prepared as follows:

a) Benzyl 4-(4-isopropoxymethylphenyl)-3-[4-(3-methoxypropyl)-3,4-dihydro-2H-benzo[1,4]oxazin-6-ylmethoxy]piperidine-1-carboxylate The solution of 0.200 g of benzyl 4-(4-hydroxymethylphenyl)-3-[4-(3-methoxypropyl)-3,4-dihydro-2H-benzo[1,4]oxazin-6-ylmethoxy]piperidine-1-carboxylate (Example 270c) in 8 ml of carbon tetrachloride at 0° C. is admixed with 0.019 g of sodium hydride and then stirred for 20 minutes. The reaction mixture is admixed with 0.326 g of trichloroacetonitrile and stirred at 0° C. for 3 hours. Afterwards, a solution of 0.0322 g of 2-propanol in 5 ml of dichloromethane is added and the reaction mixture is cooled to −30° C. and admixed slowly with 0.108 g of trifluoromethanesulphonic acid. The reaction solution is stirred at −20° C. for 19 hours and subsequently poured onto 25 ml of aqueous saturated sodium hydrogencarbonate solution. The mixture is extracted twice with 50 ml of tert-butyl methyl ether. The combined organic phases are washed with 30 ml of brine, dried over sodium sulphate, filtered and concentrated by evaporation. The title compound is obtained as a yellowish oil from the residue by means of flash chromatography (SiO$_2$ 60F). Rf=0.15 (1:2 EtOAc-heptane); Rt=5.92.
According to the process described in Example 2, the following compound is prepared in an analogous manner:

EXAMPLE 331

6-(4-{4-[3-(2-Methoxybenzyloxy)propoxy]phenyl}piperidin-3-yloxymethyl)-4-(3-methoxypropyl)-2,2-dimethyl-4H-benzo[1,4]oxazin-3-one

EXAMPLE 332

6-(4-{4-[3-(2-Methoxybenzyloxy)propoxy]phenyl}piperidin-3-yloxymethyl)-4-(3-methoxypropyl)-2,2-dimethyl-4H-benzo[1,4]oxazine Analogously to Method C, 0.250 g of 6-(4-{4-[3-(2-methoxybenzyloxy)propoxy]phenyl}piperidin-3-yloxymethyl)-4-(3-methoxypropyl)-2,2-dimethyl-4H-benzo[1,4]oxazin-3-one (Example 331) is used to prepare the title compound.

EXAMPLE 333

{4-[6-(4-{4-[3-(2-Methoxybenzyloxy)propoxy]phenyl}piperidin-3-yloxymethyl)-2,3-dihydrobenzo[1,4]oxazin-4-yl]butyl}methylamine Analogously to Method B, 0.200 g of benzyl 3-{4-[4-(benzyloxycarbonylmethylamino)butyl]-3,4-dihydro-2H-benzo[1,4]oxazin-6-ylmethoxy}-4-{4-[3-(2-methoxybenzyloxy)propoxy]phenyl}piperidine-1-carboxylate is used to prepare the title compound.
The starting materials are prepared as follows:

a) Benzyl 3-{4-[4-(benzyloxycarbonylmethylamino)butyl]-3,4-dihydro-2H-benzo[1,4]oxazin-6-ylmethoxy}-4-{4-[3-(2-methoxybenzyloxy)propoxy]phenyl}piperidine-1-carboxylate Analogously to Method C, 0.280 g of benzyl 3-{4-[4-(benzyloxycarbonylmethylamino)butyl]-3-oxo-3,4-dihydro-2H-benzo[1,4]oxazin-6-ylmethoxy}-4-{4-[3-(2-methoxybenzyloxy)propoxy]phenyl}piperidine-1-carboxylate is used to obtain the title compound as a yellowish oil. Rf=0.23 (1:1 EtOAc-heptane); Rt=6.40.

b) Benzyl 3-{4-[4-(benzyloxycarbonylmethylamino)butyl]-3-oxo-3,4-dihydro-2H-benzo[1,4]oxazin-6-ylmethoxy}-4-{4-[3-(2-methoxybenzyloxy)propoxy]phenyl}piperidine-1-carboxylate The stirred solution of 0.351 g of benzyl 3-[4-(4-benzyloxycarbonylaminobutyl)-3-oxo-3,4-dihydro-2H-benzo[1,4]oxazin-6-ylmethoxy]-4-{4-[3-(2-methoxybenzyloxy)propoxy]phenyl}piperidine-1-carboxylate and 8 ml of N,N-dimethylformamide is admixed at 0° C. with 0.031 g of sodium hydride (60% dispersion). After 1 hour, 0.144 ml of methyl iodide is added and the mixture is kept at 75° C. over 18 hours. The mixture is cooled, poured onto aqueous 1M sodium hydrogencarbonate solution (40 ml) and extracted with ethyl acetate (2×40 ml). The organic phases are washed with brine (40 ml), dried over sodium sulphate, filtered and concentrated by evaporation. The title compound is obtained as a slightly yellowish oil from the residue by means of flash chromatography (SiO$_2$ 60F). Rf=0.17 (1:1 EtOAc-heptane); Rt=6.18.

c) Benzyl 3-[4-(4-benzyloxycarbonylaminobutyl)-3-oxo-3,4-dihydro-2H-benzo[1,4]oxazin-6-ylmethoxy]-4-{4-[3-(2-methoxybenzyloxy)propoxy]phenyl}piperidine-1-carboxylate The stirred solution of 0.300 g of benzyl 3-[4-(4-aminobutyl)-3-oxo-3,4-dihydro-2H-benzo[1,4]oxazin-6-ylmethoxy]-4-{4-[3-(2-methoxybenzyloxy)propoxy]phenyl}piperidine-1-carboxylate (Example 316b) and 3 ml of ethyl acetate is admixed at 0° C. with 3 ml of aqueous 1M sodium hydrogencarbonate solution and 0.072 ml of benzyl chloroformate. After 1 hour, the reaction mixture is poured onto water (40 ml) and extracted with ethyl acetate (2×40 ml). The organic phases are washed with brine (40 ml), dried over sodium sulphate, filtered and concentrated by evaporation. The title compound is obtained as a slightly yellowish oil from the residue by means of flash chromatography (SiO$_2$ 60F). Rf=0.21 (1:1 EtOAc-heptane); Rt=5.90.

EXAMPLE 340

6-[4-(3-Fluoro-4-methoxyphenyl)piperidin-3-yloxymethyl]-4-(3-methoxypropyl)-3,4-dihydro-2H-benzo[1,4]oxazine Analogously to Method B, 0.015 g of benzyl 4-(3-fluoro-4-methoxyphenyl)-3-[4-(3-methoxypropyl)-3,4-dihydro-2H-benzo[1,4]oxazin-6-ylmethoxy]piperidine-1-carboxylate is used to prepare the title compound.

The starting materials are prepared as follows:

a) Benzyl 4-(3-fluoro-4-methoxyphenyl)-3-[4-(3-methoxypropyl)-3,4-dihydro-2H-benzo[1,4]oxazin-6-ylmethoxy]piperidine-1-carboxylate Analogously to Method C, 0.027 g of benzyl 4-(3-fluoro-4-methoxyphenyl)-3-[4-(3-methoxypropyl)-3-oxo-3,4-dihydro-2H-benzo[1,4]oxazin-6-ylmethoxy]piperidine-1-carboxylate is reacted. The title compound is obtained as a colourless resin. Rf=0.26 (2:1 EtOAc-heptane); Rt=5.40.

b) Benzyl 4-(3-fluoro-4-methoxyphenyl)-3-[4-(3-methoxypropyl)-3-oxo-3,4-dihydro-2H-benzo[1,4]oxazin-6-ylmethoxy]piperidine-1-carboxylate Analogously to Method D, 0.050 g of benzyl 4-(3-fluoro-4-methoxyphenyl)-3-hydroxypiperidine-1-carboxylate and 0.042 g of 6-chloromethyl-4-(3-methoxypropyl)-4H-benzo[1,4]oxazin-3-one are reacted. The title compound is obtained as a colourless resin. Rf=0.26 (2:1 EtOAc-heptane); Rt=5.10.

c) Benzyl 4-(3-fluoro-4-methoxyphenyl)-3-hydroxypiperidine-1-carboxylate

A solution of 0.069 g of benzyl 4-(3-fluoro-4-hydroxyphenyl)-3-hydroxypiperidine-1-carboxylate in 5 ml of acetone is admixed with 0.034 g of potassium carbonate and 0.019 ml of dimethyl sulphate. The reaction mixture is stirred at reflux over 5 hours, cooled and filtered through Hyflo. The filtercake is washed with 2×5 ml of acetone and the filtrate is concentrated by evaporation. The residue is taken up in 30 ml of tert-butyl methyl ether, washed with 10 ml of brine, dried over sodium sulphate and concentrated by evaporation. The title compound is obtained as a colourless oil from the residue by means of flash chromatography (SiO$_2$ 60F). Rf=0.38 (2:1 EtOAc-heptane); Rt=4.32.

d) Benzyl 4-(3-fluoro-4-hydroxyphenyl)-3-hydroxypiperidine-1-carboxylate

A solution of 0.581 g of benzyl 3-hydroxy-4-(4-hydroxyphenyl)piperidine-1-carboxylate in 5 ml of acetonitrile is admixed with 0.320 g of N,N'-difluoro-2,2'-bipyridinium bis(tetrafluoroborate) and the suspension is subsequently heated at reflux over 15 hours. The reaction mixture is poured onto 10 ml of saturated aqueous sodium thiosulphate solution and the mixture is extracted with 2×50 ml of ethyl acetate. The combined organic phases are washed with 10 ml each of 0.5 M HCl and brine, dried over sodium sulphate and concentrated. The title compound is obtained as a colourless solid from the residue by means of flash chromatography (SiO$_2$ 60F). Rf=0.33 (2:1 EtOAc-heptane); Rt=3.80.

EXAMPLE 341

8-(4-{4-[3-(2-Methoxybenzyloxy)propoxy]phenyl}piperidin-3-yloxymethyl)-4,4-dimethyl-1,4-dihydrobenzo[d][1,3]oxazin-2-one Analogously to Method A, 0.31 g of tert-butyl 3-(4,4-dimethyl-2-oxo-1,4-dihydro-2H-benzo[d][1,3]oxazin-8-ylmethoxy)-4-{4-[3-(2-methoxybenzyloxy)propoxy]phenyl}piperidine-1-carboxylate is used to prepare the title compound.

The starting materials are prepared as follows:

a) tert-Butyl 3-(4,4-dimethyl-2-oxo-1,4-dihydro-2H-benzo[d][1,3]oxazin-8-ylmethoxy)-4-{4-[3-(2-methoxybenzyloxy)propoxy]phenyl}piperidine-1-carboxylate Analogously to Example 228a, 0.45 g of tert-butyl 3-[4,4-dimethyl-2-oxo-1-(2-trimethylsilanylethoxymethyl)-1,4-dihydro-2H-benzo[d][1,3]oxazin-8-ylmethoxy]-4-{4-[3-(2-methoxybenzyloxy)propoxy]phenyl}piperidine-1-carboxylate and 4.47 ml of tetrabutylammonium fluoride solution (1M in tetrahydrofuran) are reacted. The title compound is obtained as a yellowish oil. Rf=0.15 (9:1 dichloromethane-methanol); Rt=5.87.

b) tert-Butyl 3-[4,4-dimethyl-2-oxo-1-(2-trimethylsilanylethoxymethyl)-1,4-dihydro-2H-benzo[d][1,3]oxazin-8-ylmethoxy]-4-{4-[3-(2-methoxybenzyloxy)propoxy]phenyl}piperidine-1-carboxylate Analogously to Method D, 0.30 g of tert-butyl 3-hydroxy-4-{4-[3-(2-methoxybenzyloxy)propoxy]phenyl}piperidine-1-carboxylate and 0.28 g of 8-bromomethyl-4,4-dimethyl-1-(2-trimethylsilanylethoxymethyl)-1,4-dihydrobenzo[d][1,3]oxazin-2-one are reacted. The title compound is obtained as a yellow oil. Rf=0.60 (1:1 EtOAc-heptane); Rt=6.68.

c) 8-Bromomethyl-4,4-dimethyl-1-(2-trimethylsilanylethoxymethyl)-1,4-dihydrobenzo[d][1,3]oxazin-2-one Analogously to Example 147b, 0.55 g of 4,4,8-trimethyl-1-(2-trimethylsilanylethoxymethyl)-1,4-dihydrobenzo[d][1,3]oxazin-2-one is reacted. The title compound is obtained as a yellow oil. Rf=0.39 (99:1 dichloromethane-methanol); Rt=5.75.

d) 4,4,8-Trimethyl-1-(2-trimethylsilanylethoxymethyl)-1,4-dihydrobenzo[d][1,3]oxazin-2-one Analogously to Example 218d, 0.50 g of 4,4,8-trimethyl-1,4-dihydrobenzo[d][1,3]oxazin-2-one is reacted. The title compound is obtained as a yellow oil. Rf=0.21 (1:6 EtOAc-heptane); Rt=5.62.

e) 4,4,8-Trimethyl-1,4-dihydrobenzo[d][1,3]oxazin-2-one

A mixture of 2.88 g of 2-(2-amino-3-methylphenyl)propan-2-ol and 2.14 g of urea is stirred in a sealed vessel at 150° C. over 6 hours. The reaction mixture is cooled to room temperature, admixed with diethyl ether, clarified by filtration and concentrated by evaporation. The title compound is obtained as a beige solid from the residue by means of flash chromatography (SiO$_2$ 60F). Rf=0.22 (1:2 EtOAc-heptane); Rt=3.46.

EXAMPLE 344

6-{4-[4-(Benzo[1,3]dioxol-5-yloxymethyl)phenyl]piperidin-3-yloxymethyl}-4-(3-methoxypropyl)-3,4-dihydro-2H-benzo[1,4]oxazine Analogously to Method B, 0.137 g of benzyl 4-[4-(benzo[1,3]dioxol-5-yloxymethyl)phenyl]-3-[4-(3-methoxypropyl)-3,4-dihydro-2H-benzo[1,4]oxazin-6-ylmethoxy]piperidine-1-carboxylate is used to prepare the title compound.

The starting material is prepared as follows:

a) Benzyl 4-[4-(benzo[1,3]dioxol-5-yloxymethyl)phenyl]-3-[4-(3-methoxypropyl)-3,4-dihydro-2H-benzo[1,4]oxazin-6-ylmethoxy]piperidine-1-carboxylate Analogously to Method I, 0.150 g of benzyl 4-(4-chloromethylphenyl)-3-[4-(3-methoxypropyl)-3,4-dihydro-2H-benzo[1,4]oxazin-6-ylmethoxy]piperidine-1-carboxylate (Example 270b) and 0.0548 g of benzo[1,3]dioxol-5-ol are reacted. The title compound is obtained as a yellowish oil. Rf=0.18 (1:2 EtOAc-heptane); Rt=5.78.

EXAMPLE 345

3-(4-{3-[4-(3-Methoxypropyl)-3,4-dihydro-2H-benzo[1,4]oxazin-6-ylmethoxy]piperidin-4-yl}phenoxy)propan-1-ol Analogously to Method B, 0.218 g of benzyl 4-[4-(3-hydroxypropoxy)phenyl]-3-[4-(3-methoxypropyl)-3,4-dihydro-2H-benzo[1,4]oxazin-6-ylmethoxy]piperidine-1-carboxylate is used to prepare the title compound.

The starting material is prepared as follows:

a) Benzyl 4-[4-(3-hydroxypropoxy)phenyl]-3-[4-(3-methoxypropyl)-3,4-dihydro-2H-benzo[1,4]oxazin-6-ylmethoxy]piperidine-1-carboxylate Analogously to Method I, 0.200 g of benzyl 4-(4-hydroxyphenyl)-3-[4-(3-methoxypropyl)-3,4-dihydro-2H-benzo[1,4]oxazin-6-ylmethoxy]piperidine-1-carboxylate (Example 259b) and 0.045 ml of 3-bromopropanol is used to obtain the title compound as a colourless oil. Rf=0.19 (1:3 EtOAc-heptane); Rt=4.90.

EXAMPLE 346

6-{4-[4-(1H-indol-4-yloxymethyl)phenyl]piperidin-3-yloxymethyl}-4-(3-methoxypropyl)-3,4-dihydro-2H-benzo[1,4]oxazine Analogously to Method B, 0.1232 g of benzyl 4-[4-(1H-indol-4-yloxymethyl)phenyl]-3-[4-(3-methoxypropyl)-3,4-dihydro-2H-benzo[1,4]oxazin-6-ylmethoxy]piperidine-1-carboxylate is used to prepare the title compound.

The starting material is prepared as follows:

a) Benzyl 4-[4-(1H-indol-4-yloxymethyl)phenyl]-3-[4-(3-methoxypropyl)-3,4-dihydro-2H-benzo[1,4]oxazin-6-ylmethoxy]piperidine-1-carboxylate Analogously to Method I, 0.150 g of benzyl 4-(4-chloromethylphenyl)-3-[4-(3-methoxypropyl)-3,4-dihydro-2H-benzo[1,4]oxazin-6-ylmethoxy]piperidine-1-carboxylate (Example 270b) and 0.0529 g of 4-hydroxyindole are reacted. The title compound is obtained as a violet oil. Rf=0.10 (1:2 EtOAc-heptane); Rt=5.58.

According to the process described in Example 346, the following compounds are prepared in an analogous manner:

EXAMPLES

| 347 | N-[3-(4-{3-[4-(3-Methoxypropyl)-3,4-dihydro-2H-benzo[1,4]oxazin-6-ylmethoxy]piperidin-4-yl}benzyloxy)phenyl]acetamide |
|---|---|
| 350 | 5-(4-{3-[4-(3-Methoxypropyl)-3,4-dihydro-2H-benzo[1,4]oxazin-6-ylmethoxy]piperidin-4-yl}benzyloxy)-3,4-dihydro-1H-quinolin-2-one |
| 352 | 4-(3-Methoxypropyl)-6-{4-[4-(3-methyl-1H-indol-4-yloxymethyl)phenyl]piperidin-3-yloxymethyl}-3,4-dihydro-2H-benzo[1,4]oxazine |

EXAMPLE 348

2-[3-(4-{3-[4-(3-Methoxypropyl)-3,4-dihydro-2H-benzo[1,4]oxazin-6-ylmethoxy]piperidin-4-yl}benzyloxy)phenyl]-N-methylacetamide Analogously to Method B, 0.063 g of benzyl 3-[4-(3-methoxypropyl)-3,4-dihydro-2H-benzo[1,4]oxazin-6-ylmethoxy]-4-[4-(3-methylcarbamoylmethylphenoxymethyl)phenyl]piperidine-1-carboxylate is used to prepare the title compound.

The starting materials are prepared as follows:

a) Benzyl 3-[4-(3-methoxypropyl)-3,4-dihydro-2H-benzo[1,4]oxazin-6-ylmethoxy]-4-[4-(3-methylcarbamoylmethylphenoxymethyl)phenyl]piperidine-1-carboxylate A solution of 0.101 g of benzyl 4-[4-(3-ethoxycarbonylmethylphenoxymethyl)phenyl]-3-[4-(3-methoxypropyl)-3,4-dihydro-2H-benzo[1,4]oxazin-6-ylmethoxy]piperidine-1-carboxylate, 0.3 ml of methylamine (33% in ethanol) and 1 ml of tetrahydrofuran is stirred at 55° C. for 40 hours and concentrated by evaporation. The title compound is obtained as a colourless oil from the residue by means of flash chromatography (SiO$_2$ 60F). Rf=0.23 (EtOAc); Rt=5.11.

b) Benzyl 4-[4-(3-ethoxycarbonylmethylphenoxymethyl)phenyl]-3-[4-(3-methoxypropyl)-3,4-dihydro-2H-benzo[1,4]oxazin-6-ylmethoxy]piperidine-1-carboxylate 0.1122 g of diisopropyl azodicarboxylate is added dropwise to a solution of 0.246 g of benzyl 4-(4-hydroxymethylphenyl)-3-[4-(3-methoxypropyl)-3,4-dihydro-2H-benzo[1,4]oxazin-6-ylmethoxy]piperidine-1-carboxylate (Example 270c), 0.1061 g of ethyl (3-hydroxyphenyl)acetate, 0.1396 g of triphenylphosphine and 5 ml of tetrahydrofuran. The solution is stirred at room temperature for 1 hour and concentrated by evaporation. The title compound is obtained as a colourless oil from the residue by means of flash chromatography (SiO$_2$ 60F). Rf=0.28 (1:1 EtOAc-heptane); Rt=5.91.

EXAMPLE 349

4-(3-Methoxypropyl)-6-{4-[4-(1-methyl-1H-indol-4-yloxymethyl)phenyl]piperidin-3-yloxymethyl}-3,4-dihydro-2H-benzo[1,4]oxazine Analogously to Method B, 0.0978 g of benzyl 3-[4-(3-methoxypropyl)-3,4-dihydro-2H-benzo[1,4]oxazin-6-ylmethoxy]-4-[4-(1-methyl-1H-indol-4-yloxymethyl)phenyl]piperidine-1-carboxylate is used to prepare the title compound.

The starting material is prepared as follows:

a) Benzyl 3-[4-(3-methoxypropyl)-3,4-dihydro-2H-benzo[1,4]oxazin-6-ylmethoxy]-4-[4-(1-methyl-1H-indol-4-yloxymethyl)phenyl]piperidine-1-carboxylate The solution of 0.100 g of benzyl 4-[4-(1H-indol-4-yloxymethyl)phenyl]-3-[4-(3-methoxypropyl)-3,4-dihydro-2H-benzo[1,4]oxazin-6-ylmethoxy]piperidine-1-carboxylate (Example 346a), 0.0424 g of methyl iodide and 1.5 ml of N,N-dimethylformamide is admixed with stirring at −10° C. with 0.012 g of sodium hydride dispersion (60%). The reaction mixture is stirred at −10° C. for 1.5 hours, then poured onto saturated aqueous sodium hydrogencarbonate solution (45 ml) and extracted with tert-butyl methyl ether (2×75 ml). The combined organic phases are washed with 75 ml of brine, dried over sodium sulphate and concentrated by evaporation. The title compound is obtained as a violet oil from the residue. Rt=5.90.

EXAMPLE 351

2-[3-(4-{3-[4-(3-Methoxypropyl)-3,4-dihydro-2H-benzo[1,4]oxazin-6-ylmethoxy]piperidin-4-yl}benzyloxy)phenyl]acetamide Analogously to Method B, 0.109 g of benzyl 4-[4-(3-carbamoylmethylphenoxymethyl)phenyl]-3-[4-(3-methoxypropyl)-3,4-dihydro-2H-benzo[1,4]oxazin-6-ylmethoxy]piperidine-1-carboxylate is used to prepare the title compound.

The starting material is prepared as follows:

a) Benzyl 4-[4-(3-carbamoylmethylphenoxymethyl)phenyl]-3-[4-(3-methoxypropyl)-3,4-dihydro-2H-benzo[1,4]oxazin-6-ylmethoxy]piperidine-1-carboxylate A solution of 0.114 g of benzyl 4-[4-(3-ethoxycarbonylmethylphenoxymethyl)phenyl]-3-[4-(3-methoxypropyl)-3,4-dihydro-2H-benzo[1,4]oxazin-6-ylmethoxy]piperidine-1-carboxylate (Example 348b), 5 ml of ammonia (7N in methanol) and 1 ml tetrahydrofuran is stirred in a Supelco bottle at 80° C. for 50 hours. After concentration by evaporation, the title compound is obtained as a yellow oil. Rt=4.96.

EXAMPLE 353

6-(4-{4-[3-(1H-Imidazol-4-yl)phenoxymethyl]phenyl}piperidin-3-yloxymethyl)-4-(3-methoxypropyl)-3,4-dihydro-2H-benzo[1,4]oxazine Analogously to Method B, 0.0365 g of benzyl 4-{4-[3-(1H-imidazol-4-yl)phenoxymethyl]phenyl}-3-[4-(3-methoxypropyl)-3,4-dihydro-2H-benzo[1,4]oxazin-6-ylmethoxy]piperidine-1-carboxylate is used to prepare the title compound.

The starting materials are prepared as follows:

a) Benzyl 4-{4-[3-(1H-imidazol-4-yl)phenoxymethyl]phenyl}-3-[4-(3-methoxypropyl)-3,4-dihydro-2H-benzo[1,4]oxazin-6-ylmethoxy]piperidine-1-carboxylate Analogously to Method I, 0.107 g of benzyl 4-(4-chloromethylphenyl)-3-[4-(3-methoxypropyl)-3,4-dihydro-2H-benzo[1,4]oxazin-6-ylmethoxy]piperidine-1-carboxylate (Example 270b) and 0.0444 g of 3-(1H-imidazol-4-yl)phenol are reacted. The title compound is obtained as an orange oil. Rf=0.19 (200:10:1 dichloromethane-methanol-conc. ammonia); Rt=4.89.

b) 3-(1H-Imidazol-4-yl)phenol

A solution of 0.170 g of 3-(1-trityl-1H-imidazol-4-yl)phenol, 4.5 ml of methanol, 1.5 ml of chloroform and 1.5 ml of 2N HCl is stirred at 55° C. for 2 hours. After cooling, the reaction mixture is admixed with 35 ml of aqueous saturated sodium hydrogencarbonate solution and extracted twice with 75 ml of dichloromethane. The combined organic phases are washed with 35 ml of brine, dried over sodium sulphate and concentrated by evaporation. The title compound is obtained as a white solid from the residue by means of flash chromatography ($SiO_2$ 60F). Rf=0.14 (200:10:1 dichloromethane-methanol-conc. ammonia); Rt=2.08.

c) 3-(1-Trityl-1H-imidazol-4-yl)phenol

A solution of 0.389 g of 4-bromo-1-trityl-1H-imidazole, 0.152 g of 3-hydroxyphenylboric acid and 10 ml of toluene is admixed with 3 ml of ethanol and 10 ml of aqueous 2N sodium carbonate solution. The mixture is purged with argon for 15 minutes and then 0.026 g of tetrakis(triphenylphosphine)palladium(0) is added. The reaction mixture is stirred at 100° C. for 48 hours, then cooled and poured onto 75 ml of aqueous saturated sodium hydrogencarbonate solution. The mixture is extracted three times with 75 ml of dichloromethane. The combined organic phases are washed with 75 ml of brine, dried over sodium sulphate and concentrated by evaporation. The title compound is obtained as a white solid from the residue by means of flash chromatography ($SiO_2$ 60F). Rf=0.13 (1:2 EtOAc-heptane); Rt=4.33.

d) 4-Bromo-1-trityl-1H-imidazole 0.3787 g of triethylamine is added dropwise over 15 minutes to a solution of 0.500 g of 4-bromoimidazole, 1.043 g of trityl chloride and 25 ml of dichloromethane. The reaction mixture is stirred at room temperature for 11 hours and then poured onto 50 ml of aqueous saturated sodium hydrogencarbonate solution. The mixture is extracted twice with 75 ml of dichloromethane. The combined organic phases are washed with 50 ml of brine, dried over sodium sulphate and concentrated by evaporation. The title compound is obtained as a white solid from the residue by means of flash chromatography ($SiO_2$ 60F). Rf=0.38 (1:3 EtOAc-heptane); Rt=5.02.

EXAMPLE 354

4-(3-Methoxypropyl)-6-[4-(4-phenoxyphenyl)piperidin-3-yloxymethyl]-3,4-dihydro-2H-benzo[1,4]oxazine Analogously to Method B, 0.068 g of benzyl 3-[4-(3-methoxypropyl)-3,4-dihydro-2H-benzo[1,4]oxazin-6-ylmethoxy]-4-(4-phenoxyphenyl)piperidine-1-carboxylate is used to prepare the title compound.

The starting materials are prepared as follows:

a) Benzyl 3-[4-(3-methoxypropyl)-3,4-dihydro-2H-benzo[1,4]oxazin-6-ylmethoxy]-4-(4-phenoxyphenyl)piperidine-1-carboxylate Analogously to Method C, 0.090 g of benzyl 3-[4-(3-methoxypropyl)-3-oxo-3,4-dihydro-2H-benzo[1,4]oxazin-6-ylmethoxy]-4-(4-phenoxyphenyl)piperidine-1-carboxylate is reacted. The title compound is obtained as a colourless resin. Rf=0.24 (1:3 EtOAc-heptane); Rt=5.98.

b) Benzyl 3-[4-(3-methoxypropyl)-3-oxo-3,4-dihydro-2H-benzo[1,4]oxazin-6-ylmethoxy]-4-(4-phenoxyphenyl)piperidine-1-carboxylate Analogously to Method D, 0.100 g of benzyl 3-hydroxy-4-(4-phenoxyphenyl)piperidine-1-carboxylate and 0.0753 g of 6-chloromethyl-4-(3-methoxypropyl)-4H-benzo[1,4]oxazin-3-one are reacted. The title compound is obtained as a colourless resin. Rf=0.31 (1:1 EtOAc-heptane); Rt=5.74.

c) Benzyl 3-hydroxy-4-(4-phenoxyphenyl)piperidine-1-carboxylate

A suspension of 0.200 g of benzyl 3-hydroxy-4-(4-hydroxyphenyl)piperidine-1-carboxylate, 0.0906 g of phenylboric acid, 0.113 g of copper(II) acetate, 0.309 g of triethylamine, 0.700 g of 3 angstrom molecular sieves (powder) and 6 ml of dichloromethane is stirred vigorously at room temperature for 28 hours. The reaction mixture is clarified by filtration and concentrated by evaporation. The title compound is obtained as a yellowish solid from the residue by means of flash chromatography (SiO$_2$ 60F). Rf=0.44 (1:1 EtOAc-heptane); Rt=5.03.

EXAMPLE 355

N-methyl-5-(4-{3-[4-(3-Methoxypropyl)-3,4-dihydro-2H-benzo[1,4]oxazin-6-ylmethoxy]piperidin-4-yl}phenyl)pentanamide Analogously to Method B, 0.095 g of benzyl 3-[4-(3-methoxypropyl)-3,4-dihydro-2H-benzo[1,4]oxazin-6-ylmethoxy]-4-[4-(4-methylcarbamoylbut-1-ynyl)phenyl]piperidine-1-carboxylate is used to prepare the title compound.

The starting material is prepared as follows:

a) Benzyl 3-[4-(3-methoxypropyl)-3,4-dihydro-2H-benzo[1,4]oxazin-6-ylmethoxy]-4-[4-(4-methylcarbamoylbut-1-ynyl)phenyl]piperidine-1-carboxylate The mixture of 0.124 g of benzyl 3-[4-(3-methoxypropyl)-3,4-dihydro-2H-benzo[1,4]oxazin-6-ylmethoxy]-4-(4-trifluoromethanesulphonyloxyphenyl)piperidine-1-carboxylate (Example 265b), 0.0305 g of N-methylpent-4-ynecarboxamide, 0.0797 g of N,N-diisopropylethylamine, 0.0136 g of bis(triphenylphosphine)palladium(II) chloride, 0.0038 g of copper(I) iodide and 1.0 ml of N,N-dimethylformamide is stirred under argon at 45° C. over 36 hours. The reaction mixture is cooled, poured onto saturated aqueous sodium hydrogencarbonate solution (20 ml) and extracted with ethyl acetate (2×50 ml). The combined organic phases are washed with brine (30 ml), dried over sodium sulphate and concentrated by evaporation. The title compound is obtained as a yellowish oil from the residue by means of flash chromatography (SiO$_2$ 60F). Rf=0.23 (EtOAc); Rt=4.86.

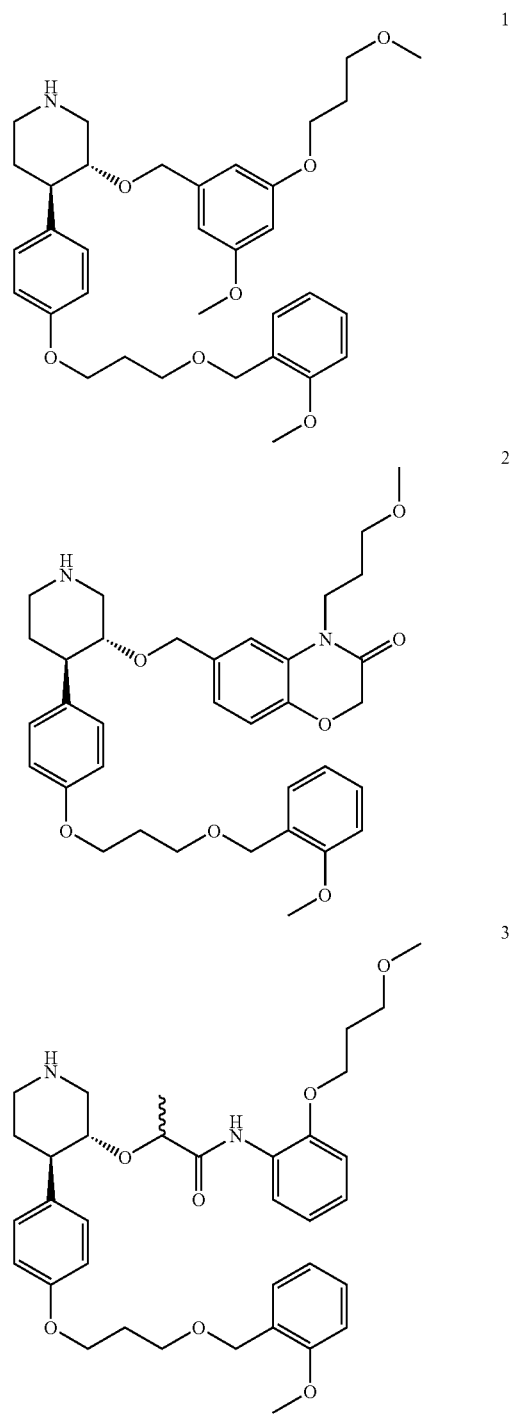

215
-continued
5
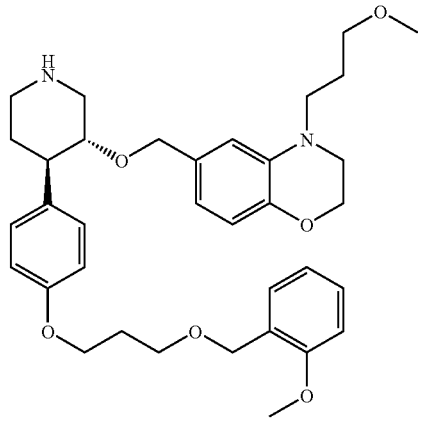
6
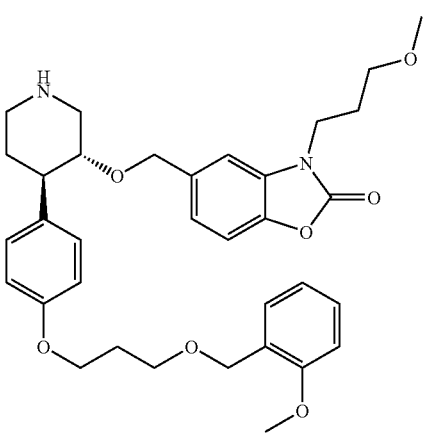
7
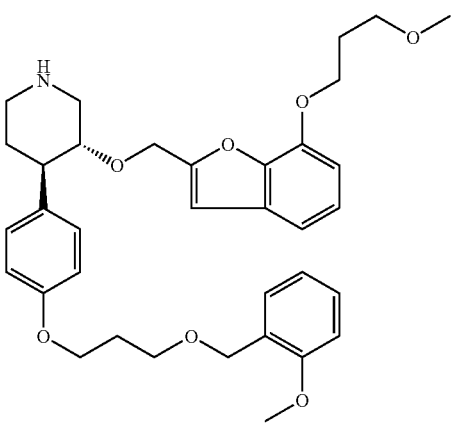
216
-continued
8
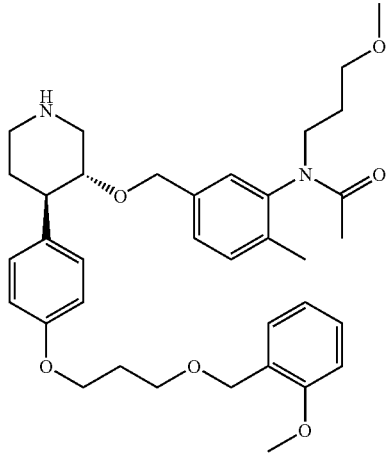
9
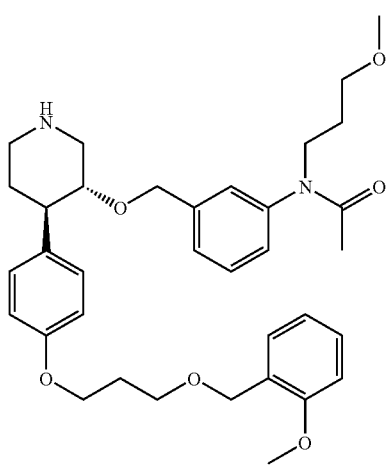
10
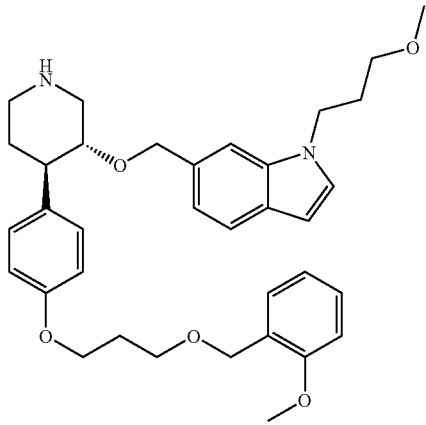

217
-continued
11
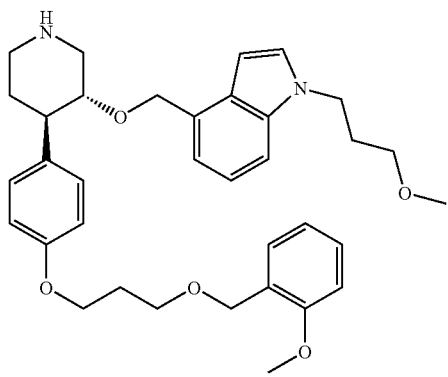
12
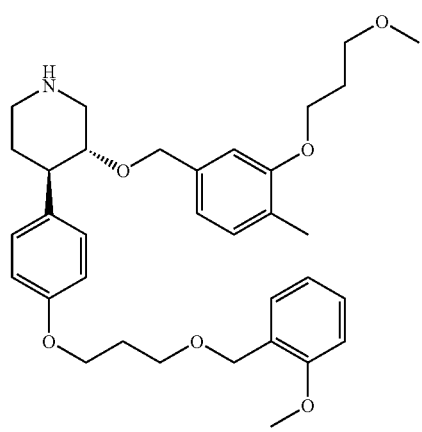
13
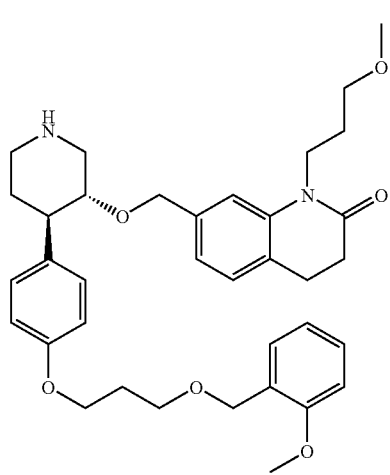
218
-continued
14
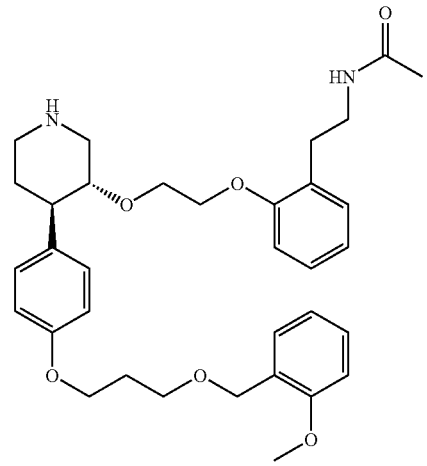
16
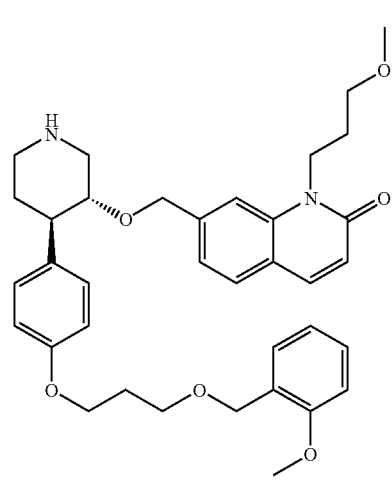
17
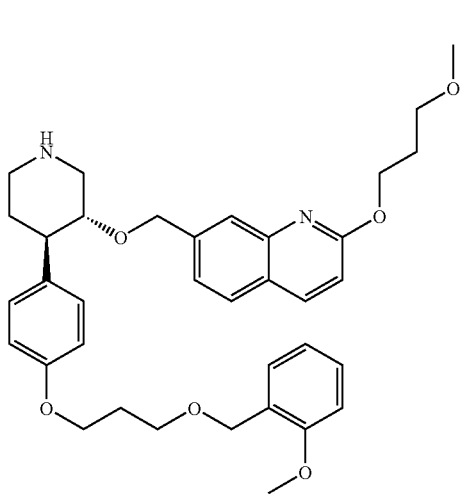

-continued
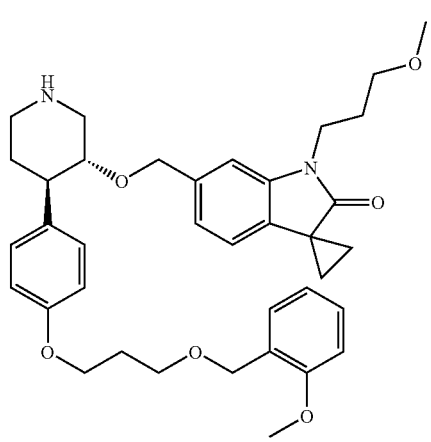
18
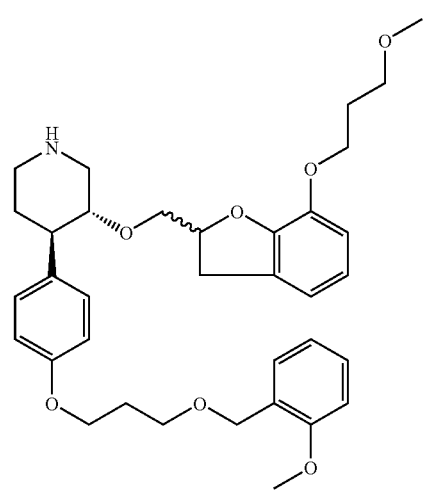
19
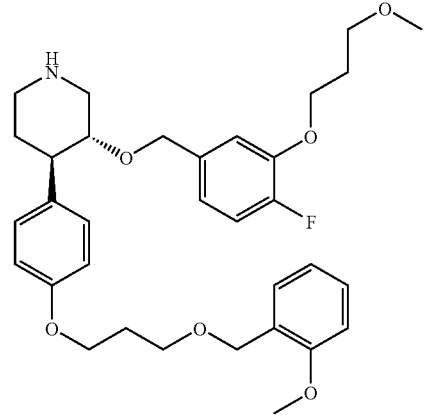
20
-continued
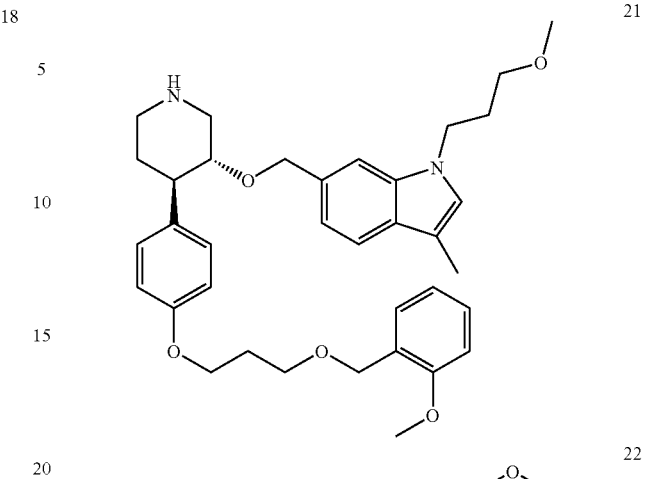
21
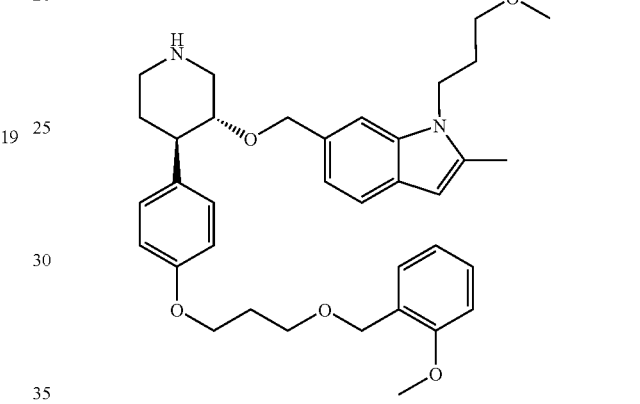
22
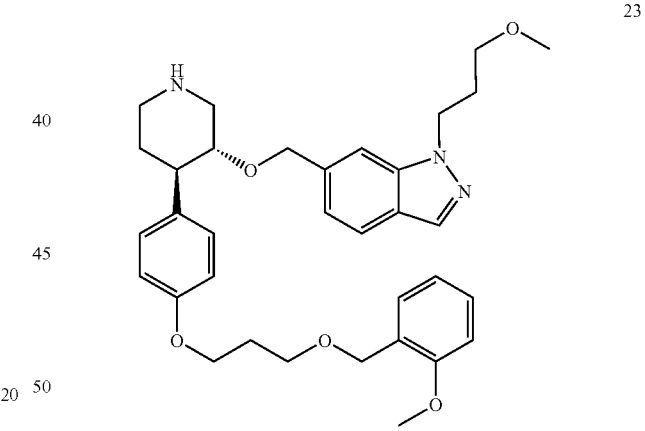
23
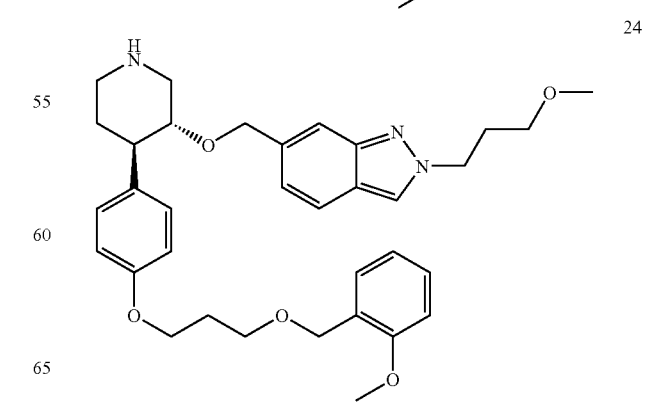
24

221
-continued
| 25 |
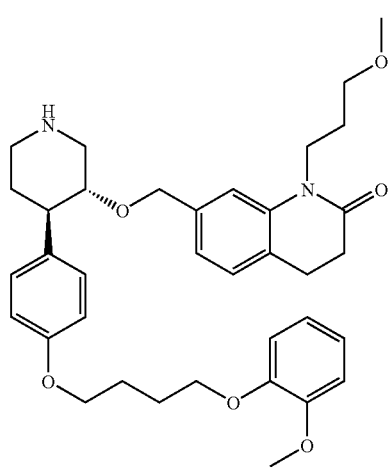
26
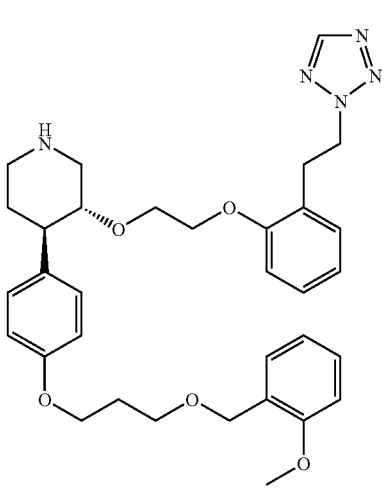
222
-continued
28
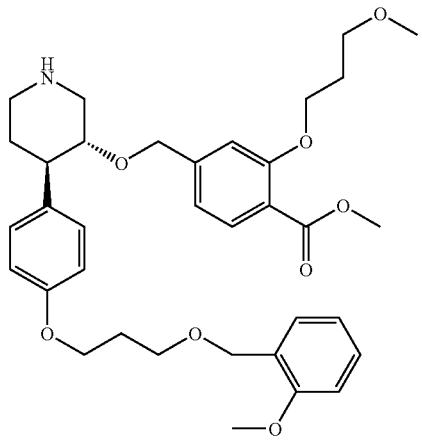
29
27
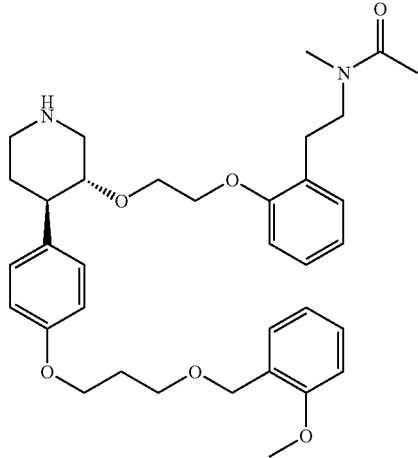
30

| 31 | 34 |
|---|---|
| 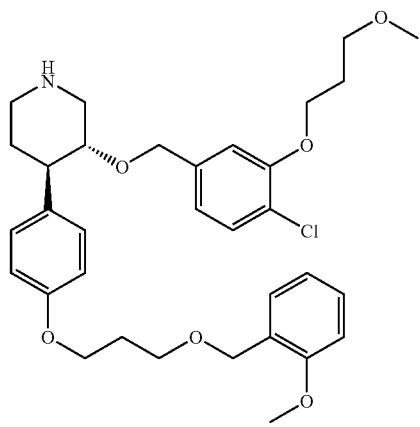 | 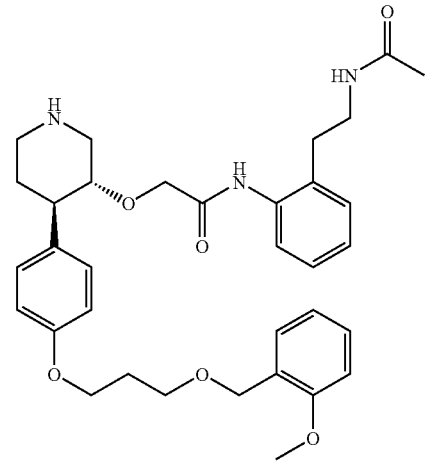 |
| 32 | 35 |
| 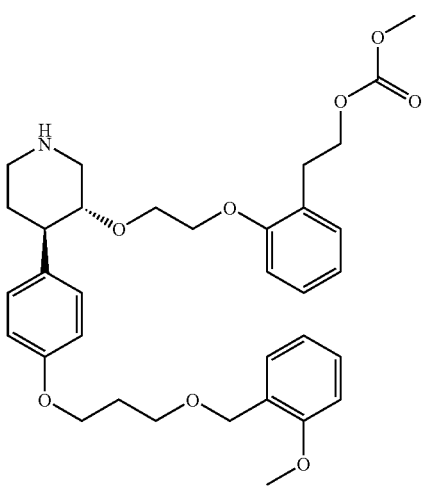 | 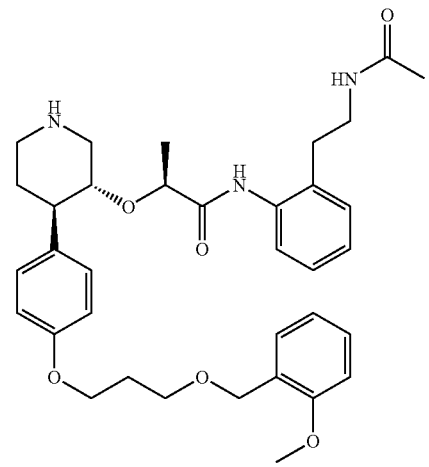 |
| 33 | 36 |
| 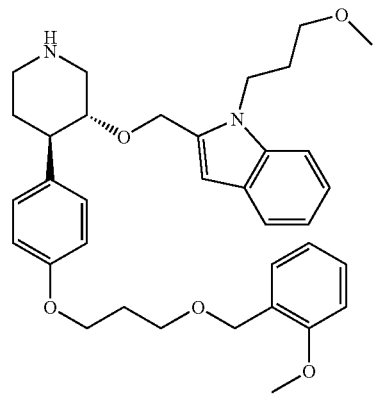 | 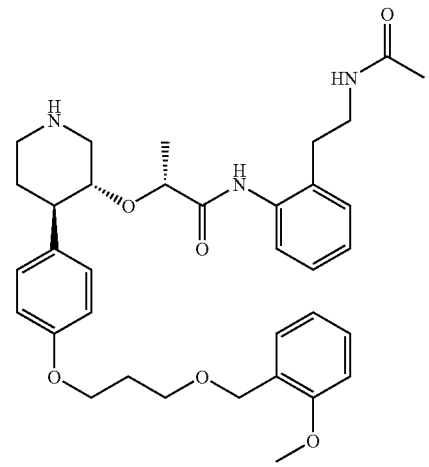 |

-continued
37
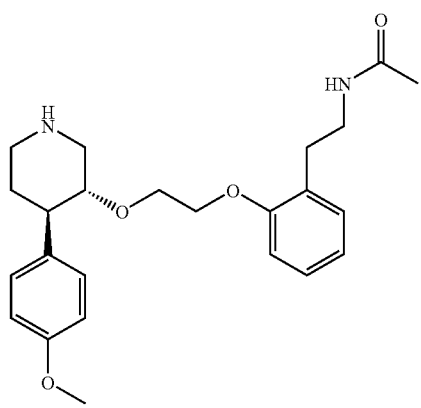
38
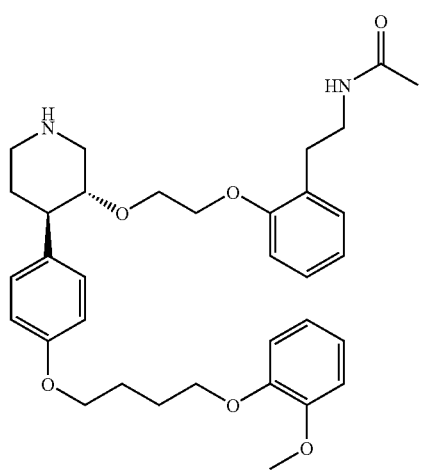
39
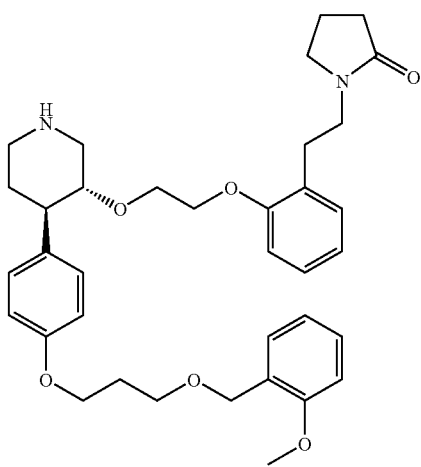
-continued
40
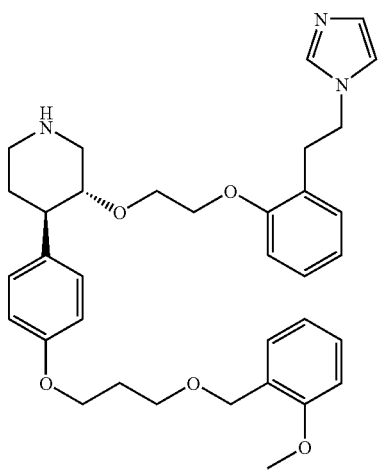
41
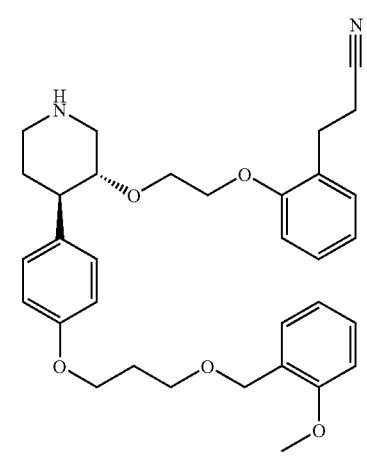
42
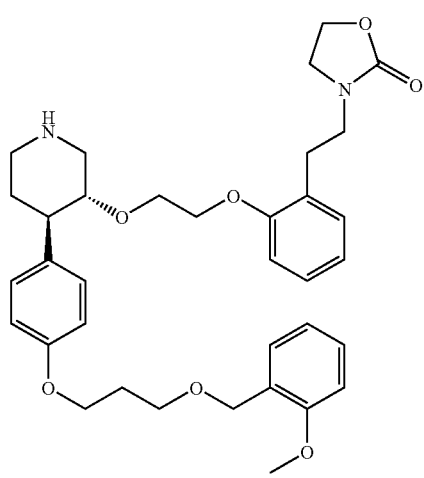

227
-continued
43
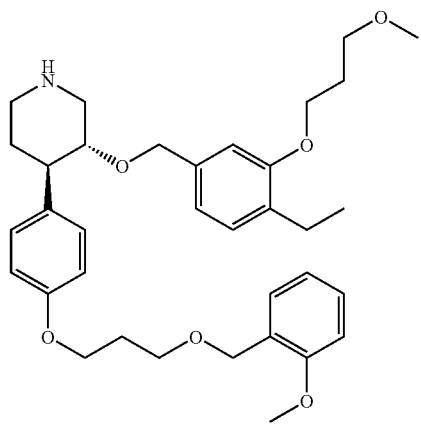
44
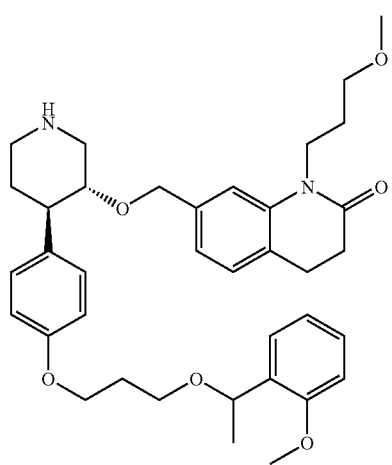
45
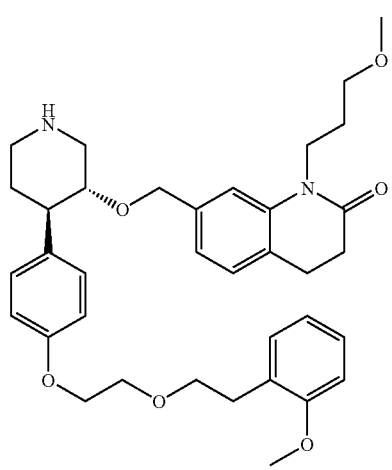
228
-continued
46
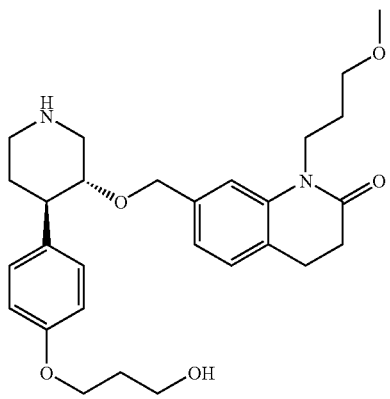
47
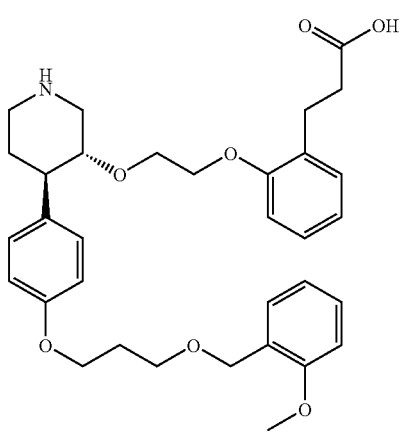
48
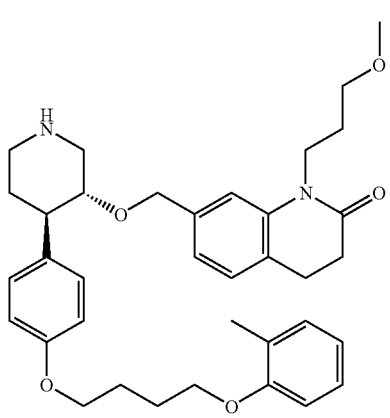

-continued
49
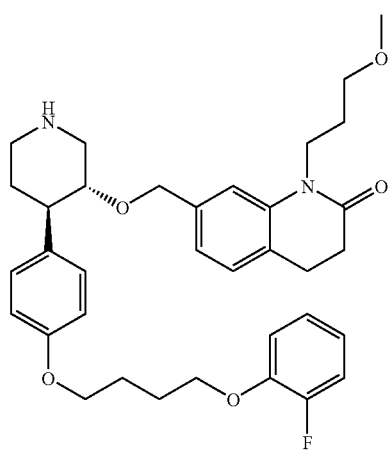
50
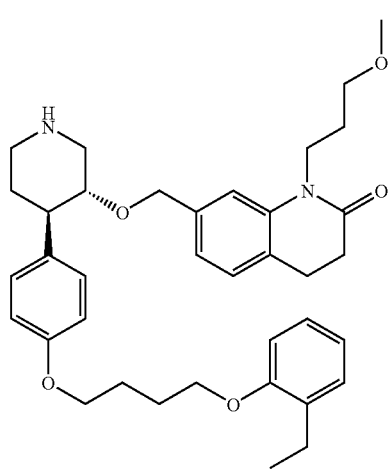
51
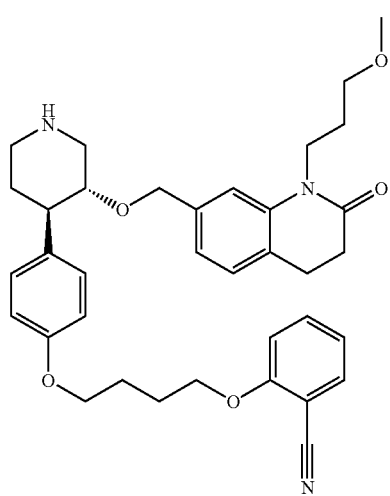
-continued
52
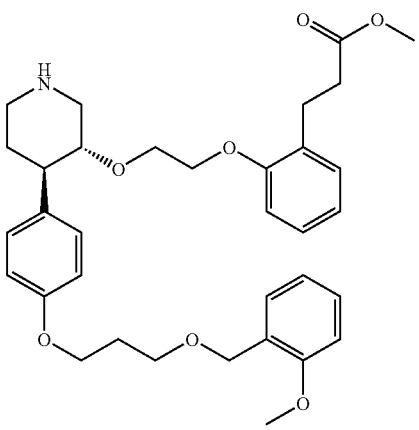
53
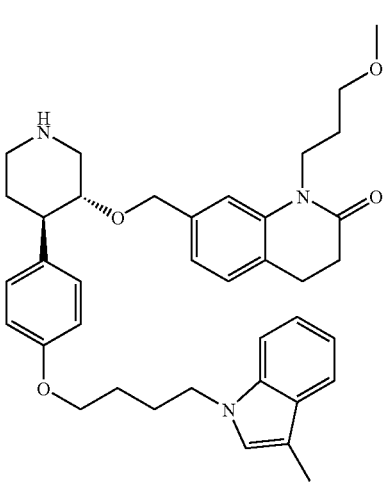
55
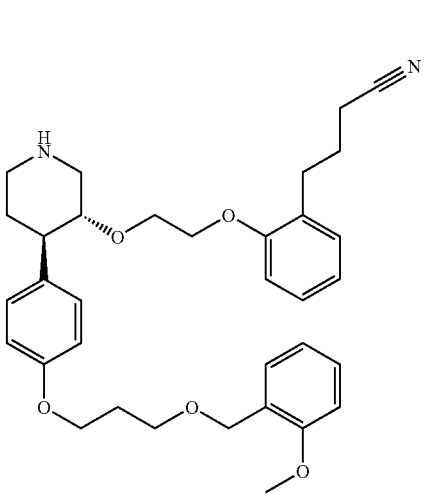

-continued
56
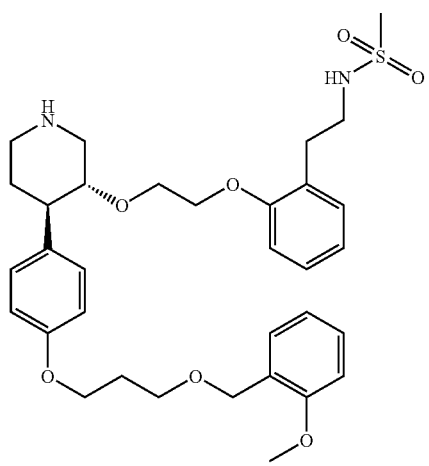
57
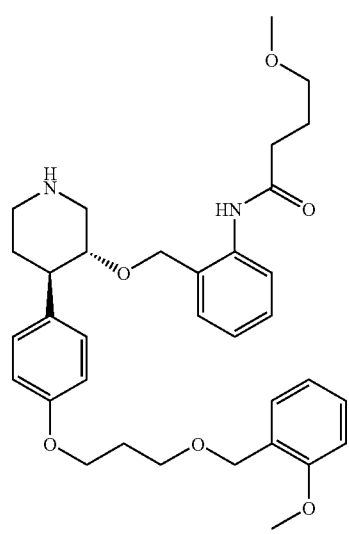
58
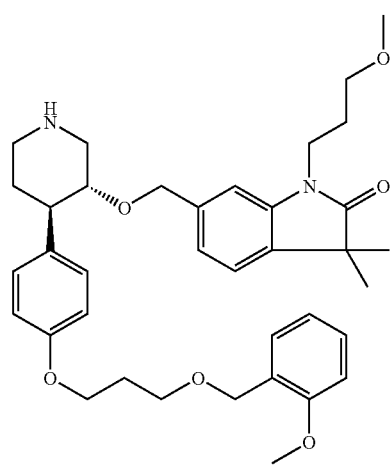
-continued
59
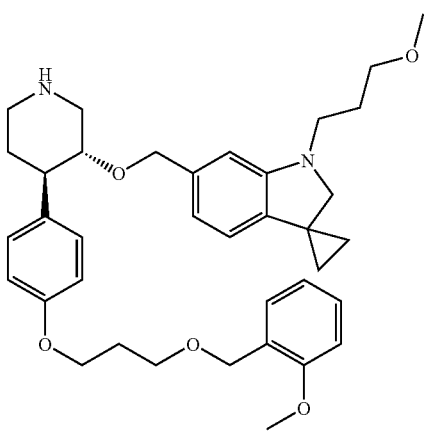
60
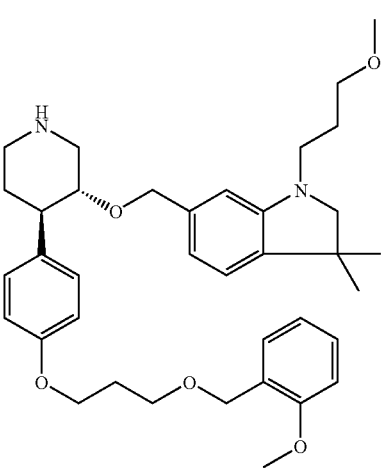
61
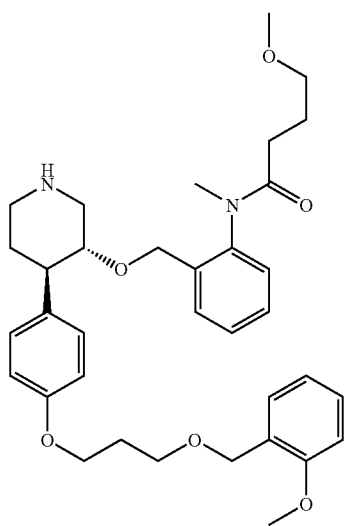

62
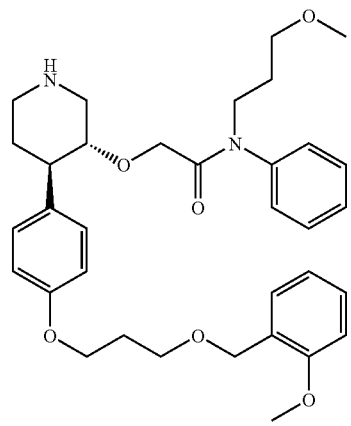
63
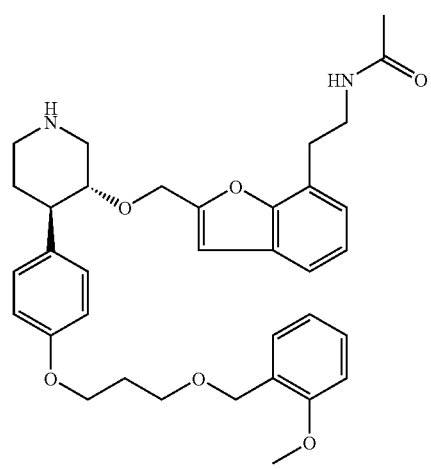
64
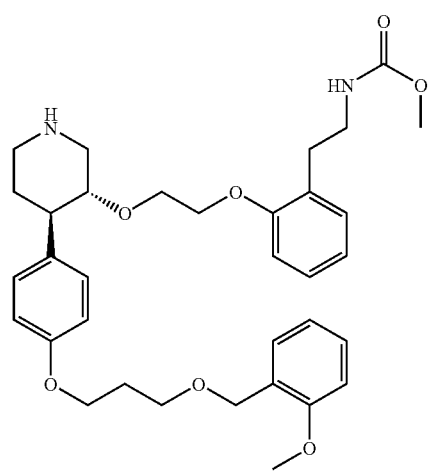
65
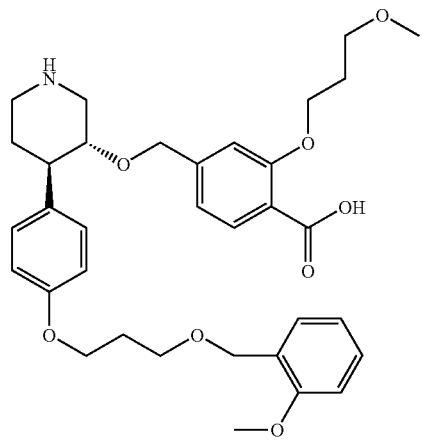
66
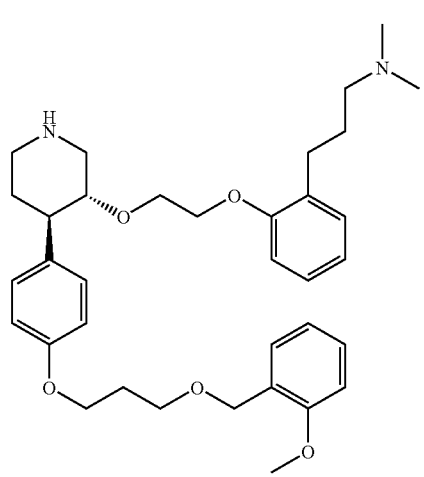
67
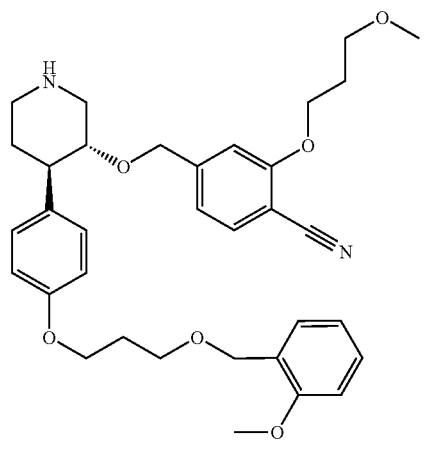

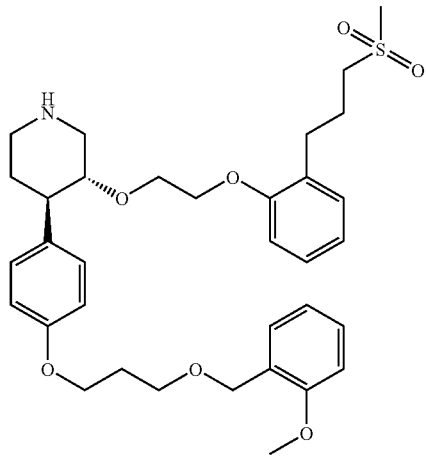
68
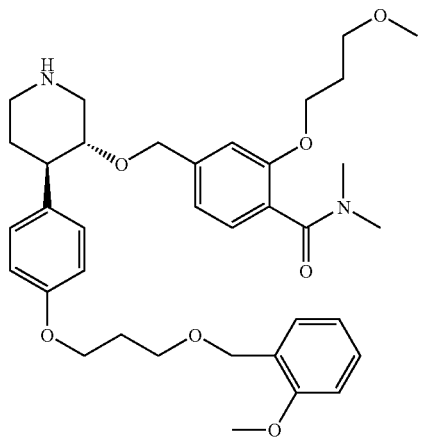
71
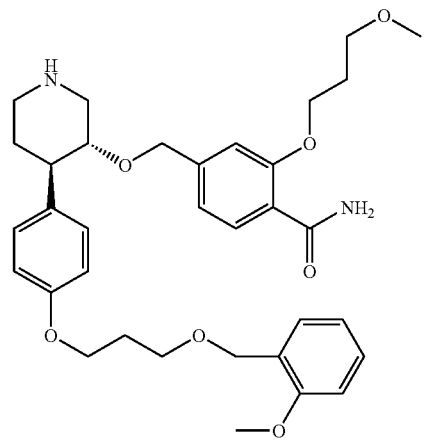
69
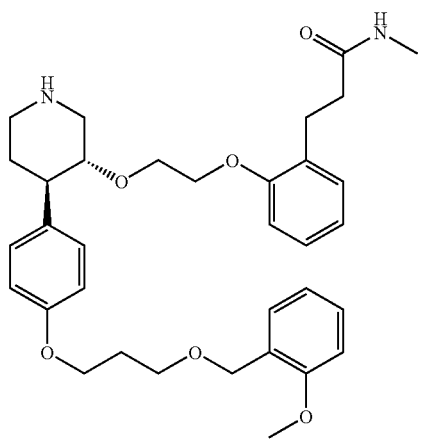
72
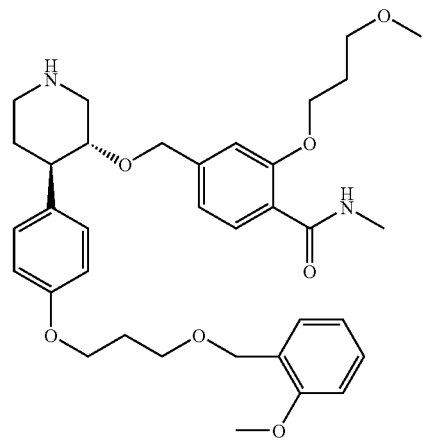
70
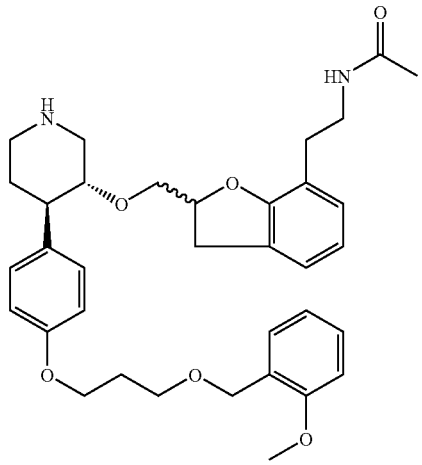
73

237
-continued
74
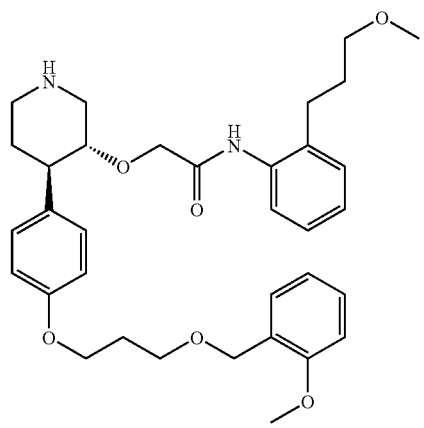
75
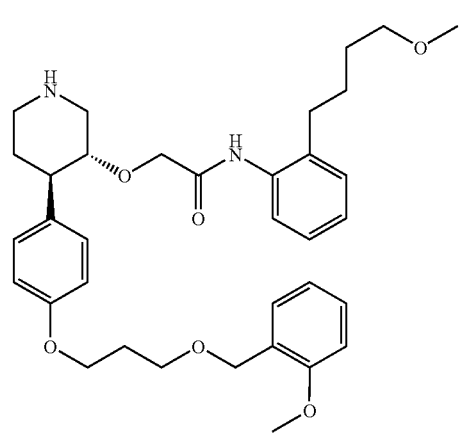
76
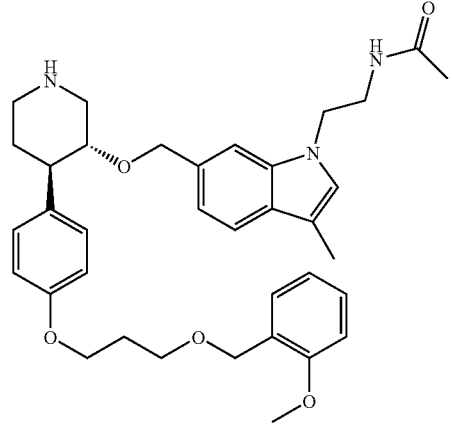
238
-continued
77
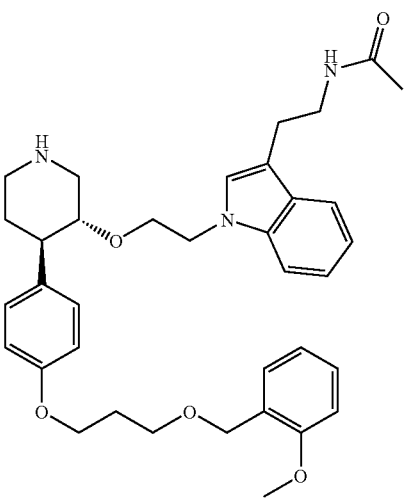
78
79
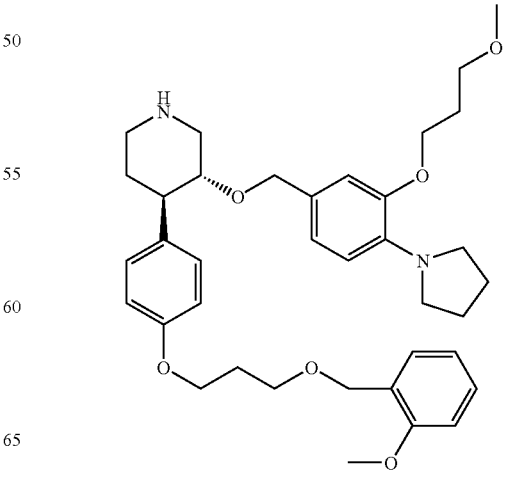

239
80
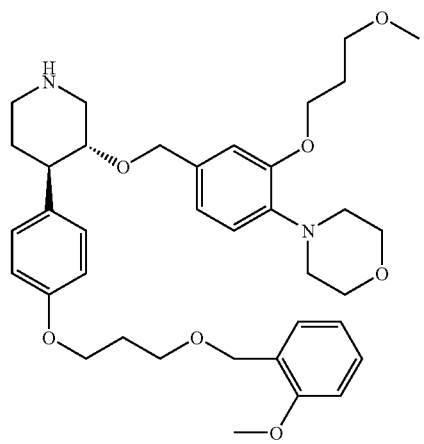
81
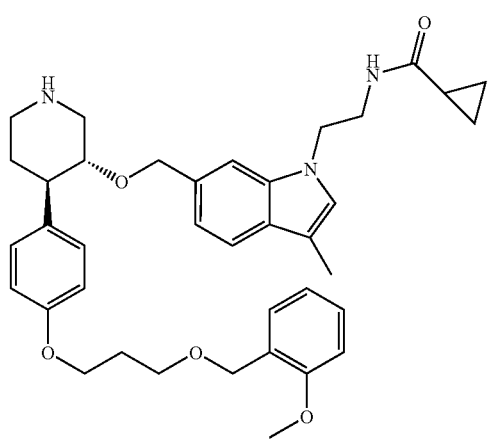
82
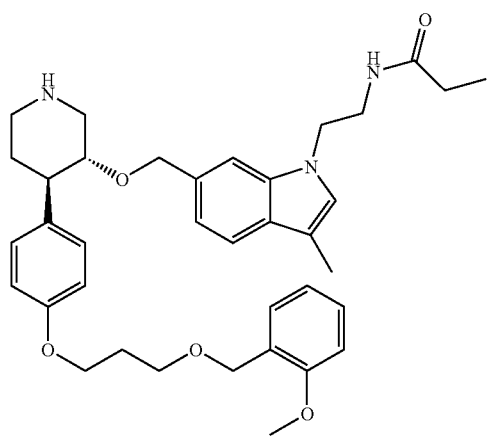
240
83
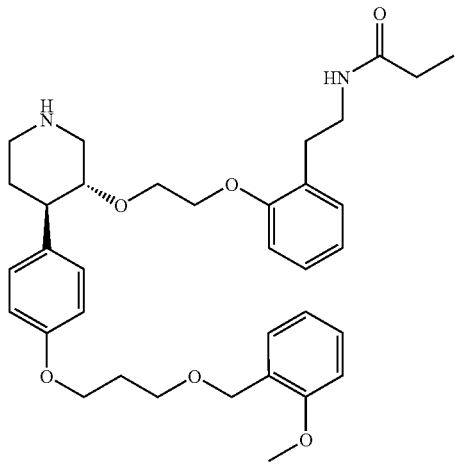
84
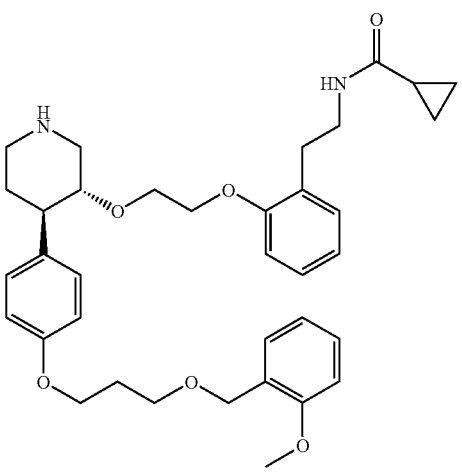
85
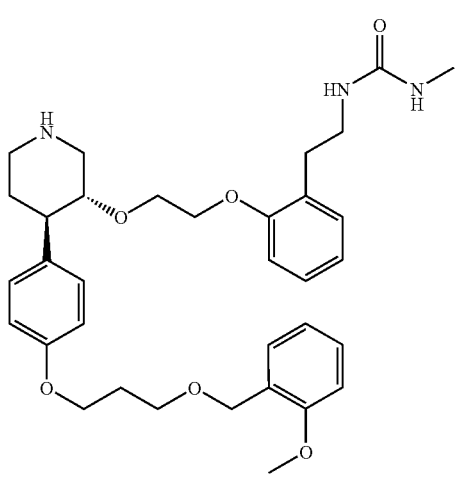

86
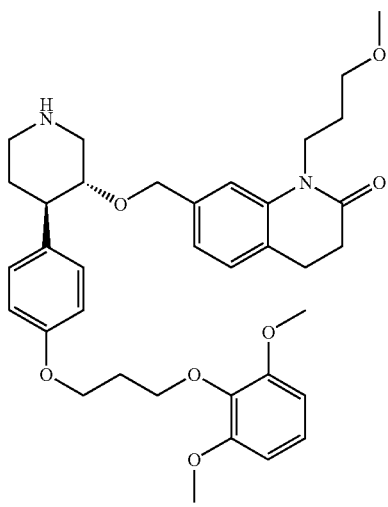
87
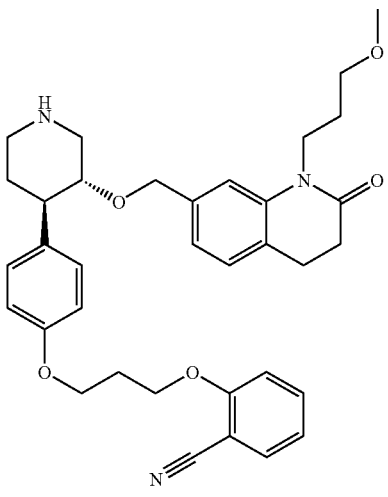
88
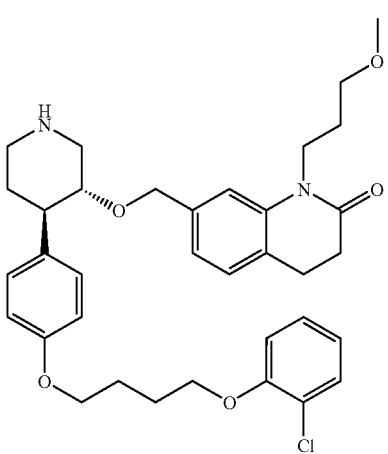
89
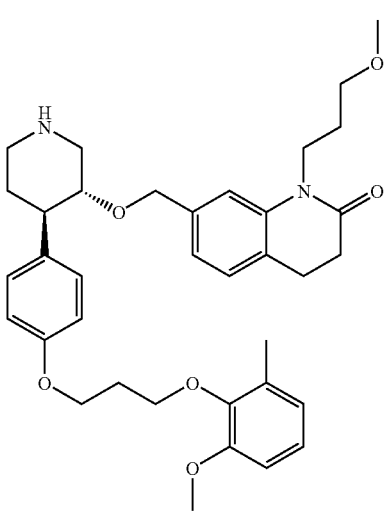
90
91

-continued
92
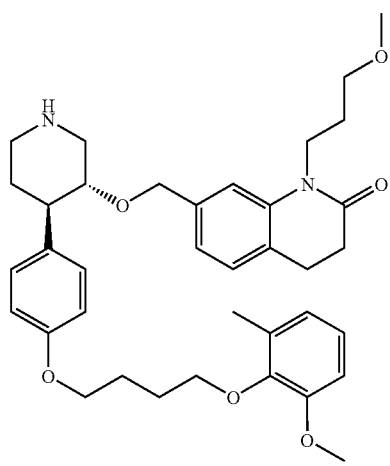
93
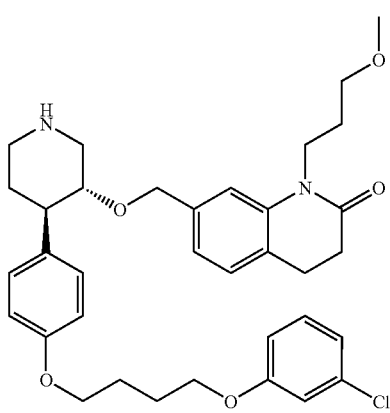
94
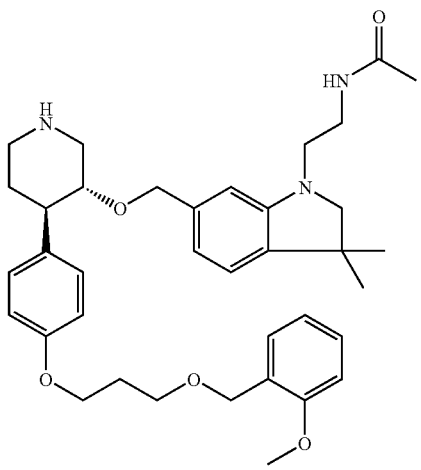
-continued
95
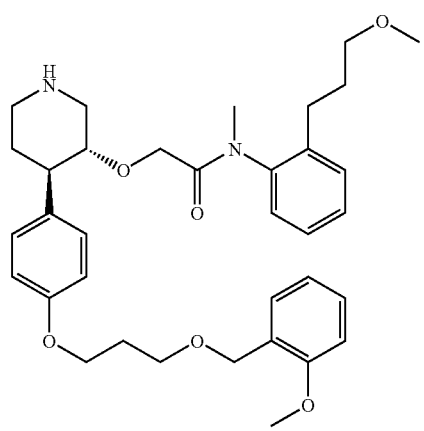
96
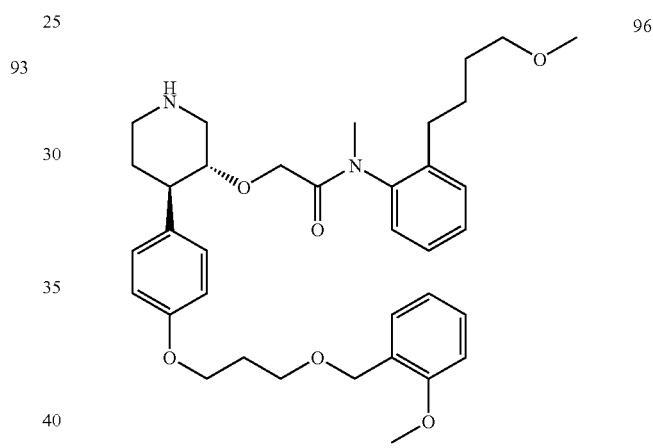
97
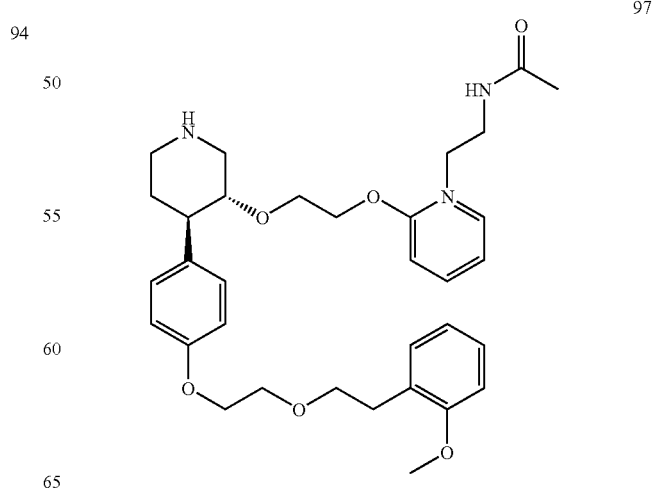

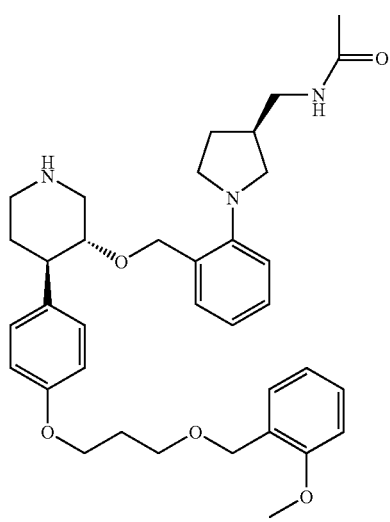
98
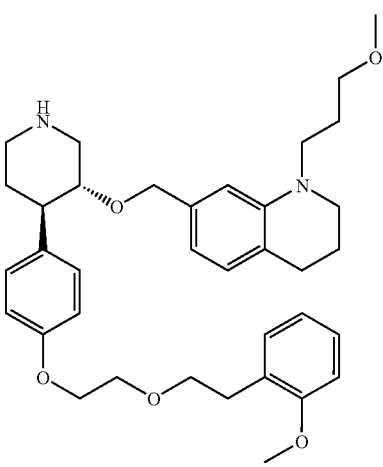
101
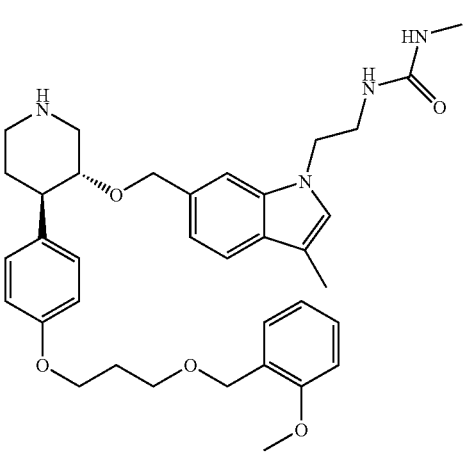
99
102
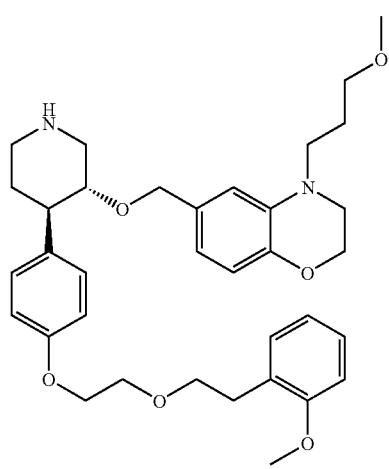
100
103

-continued
104
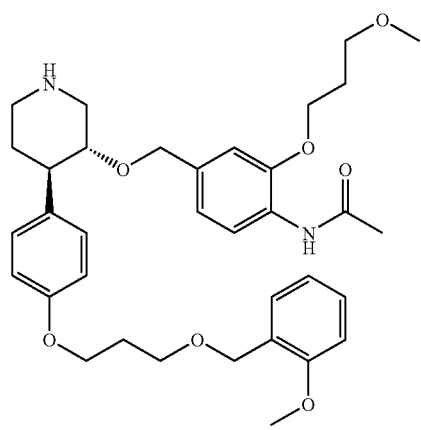
105
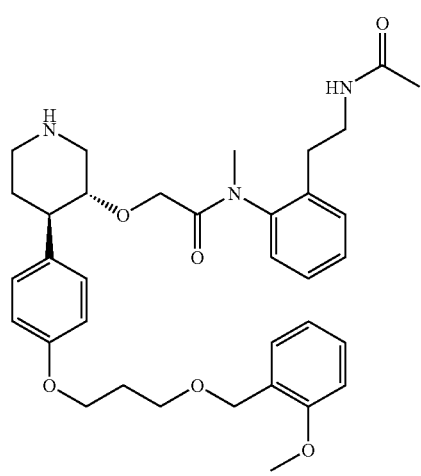
106
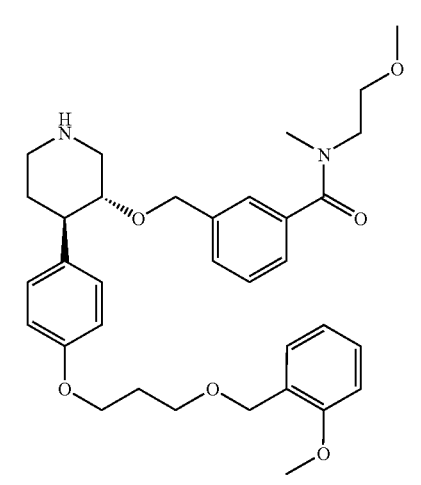
-continued
107
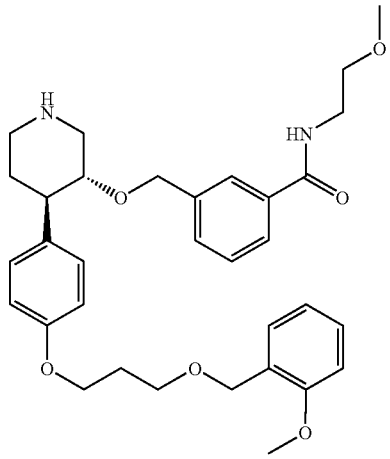
108
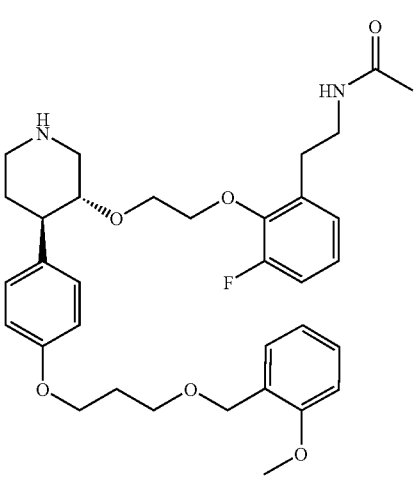
109
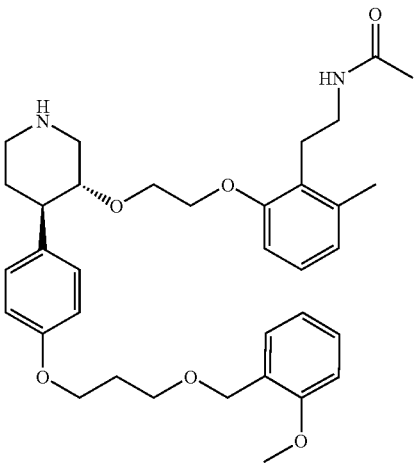

110
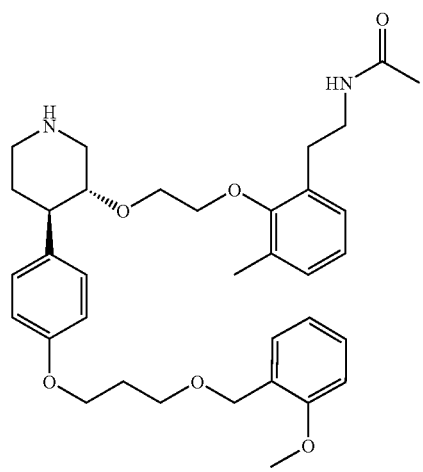
111
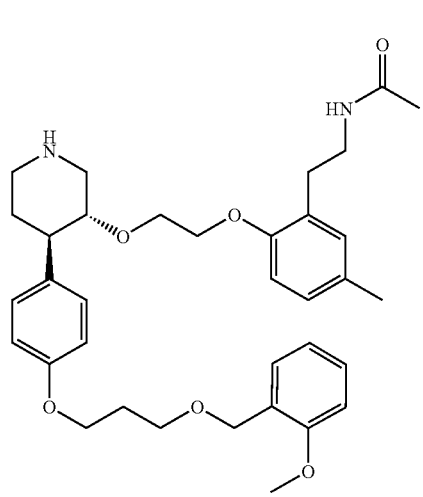
112
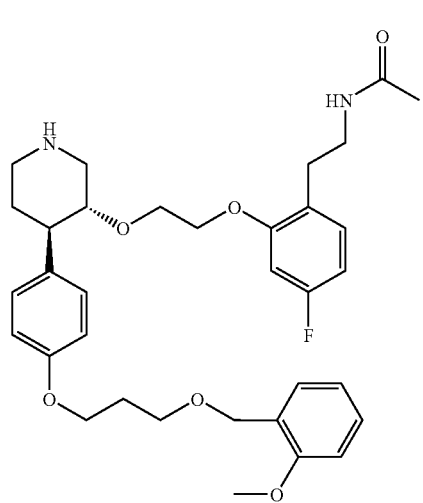
113
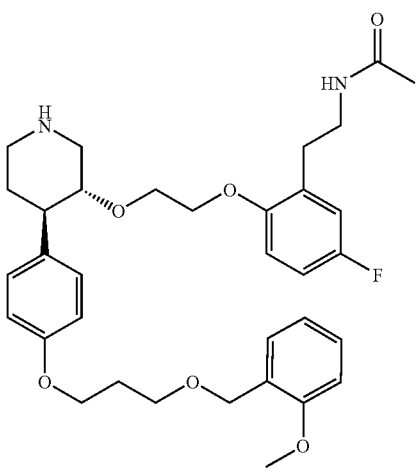
114
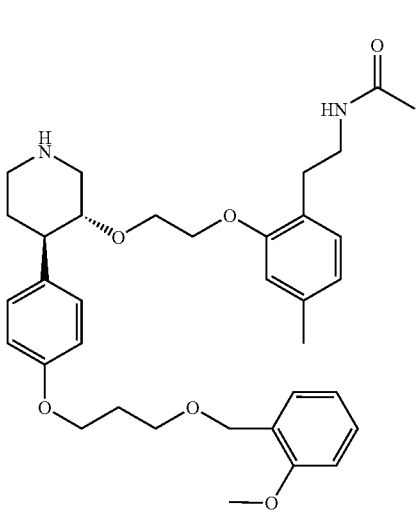
115
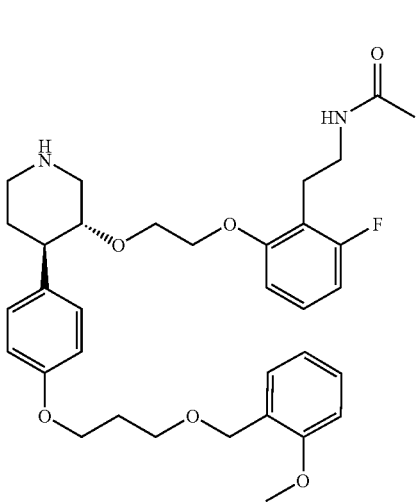

251 252
116
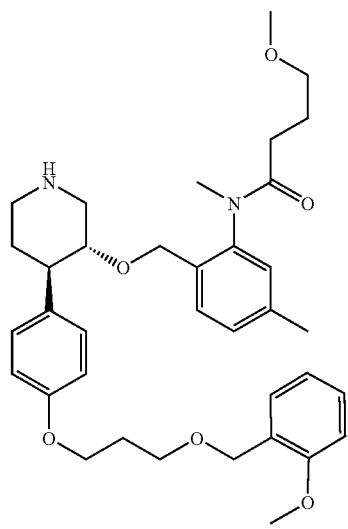
119
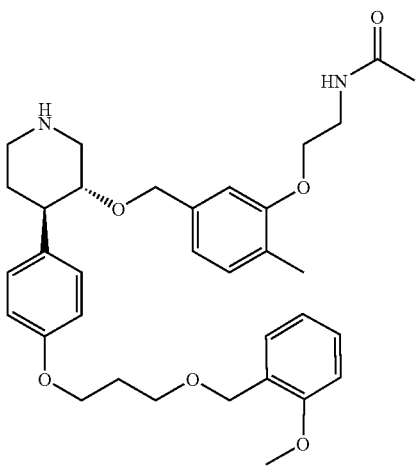
117
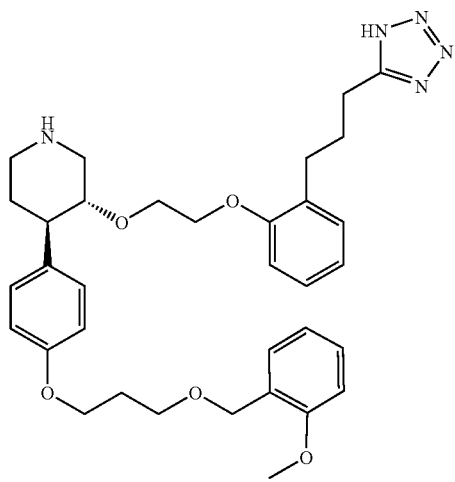
120
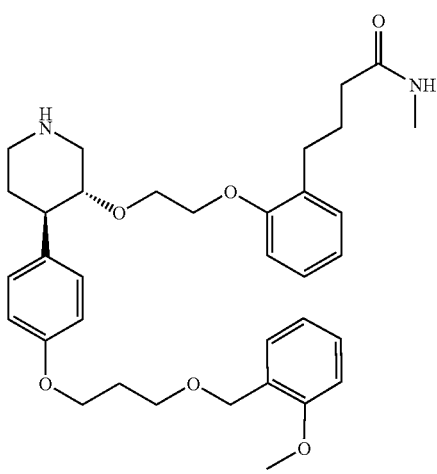
118
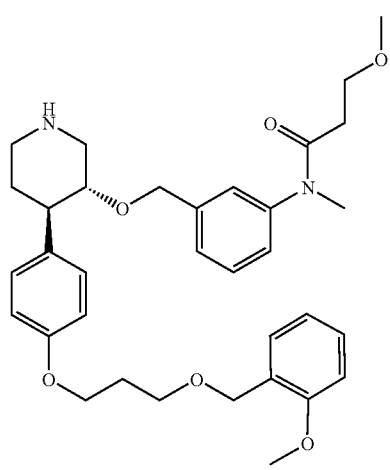
121
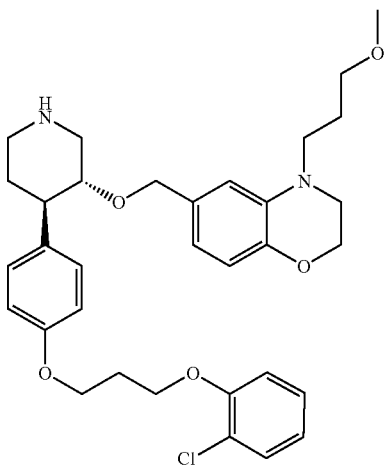

122 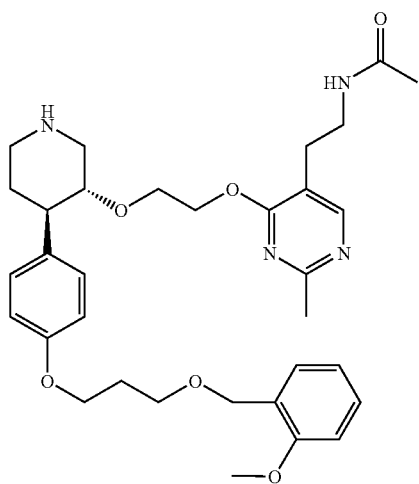
125 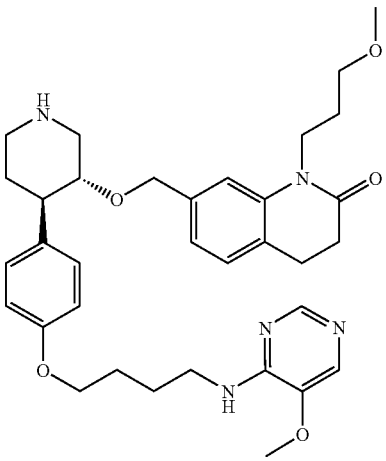
123 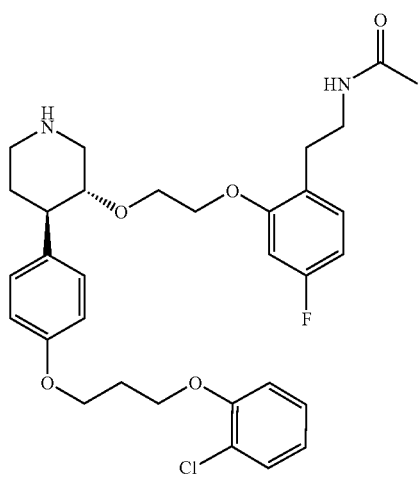
126 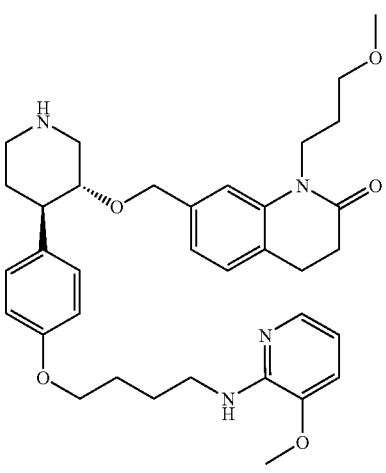
124 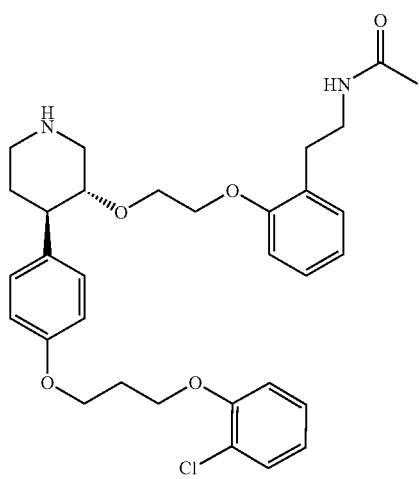
127 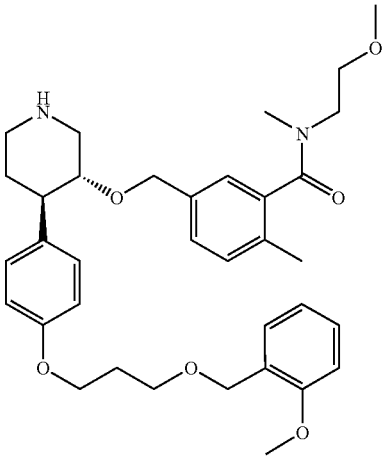

128
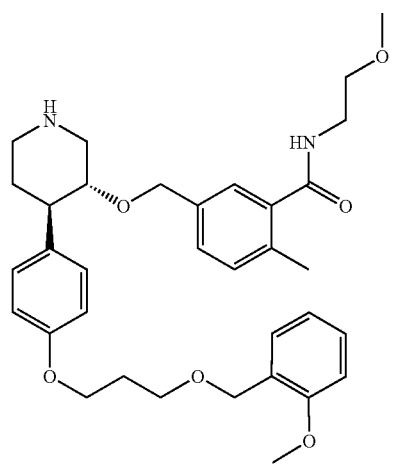
129
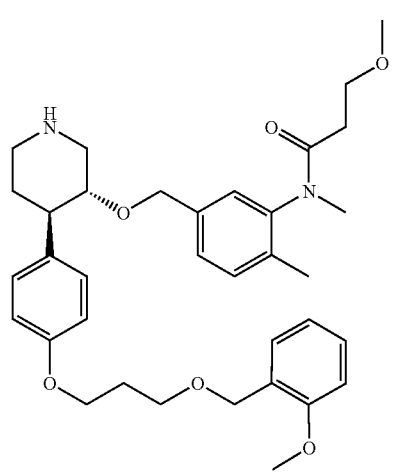
130
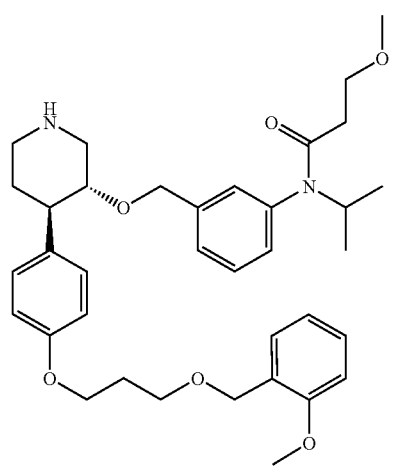
133
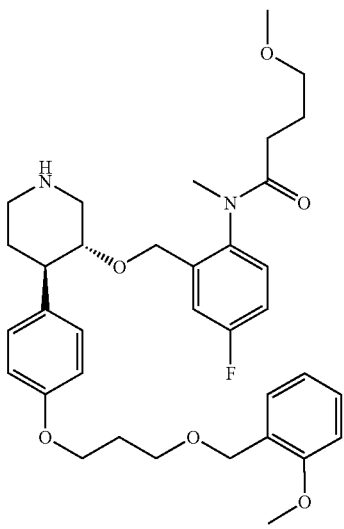
134
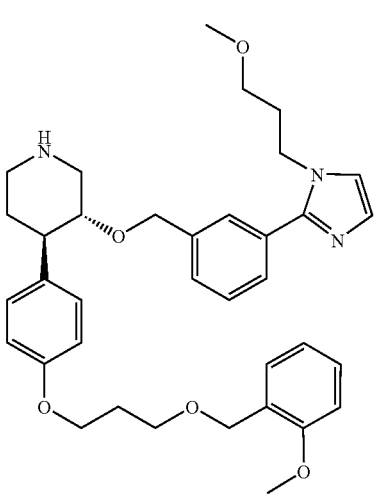
135
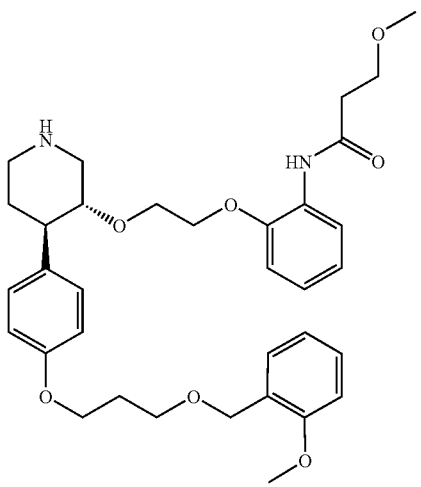

-continued

-continued
142
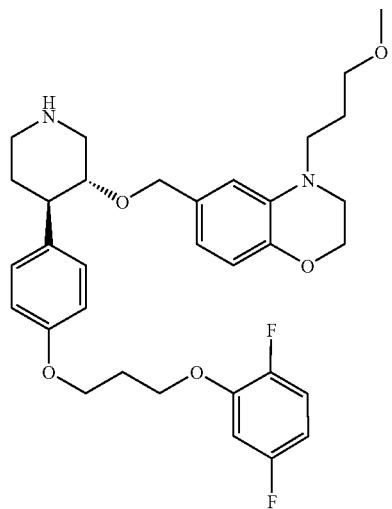
143
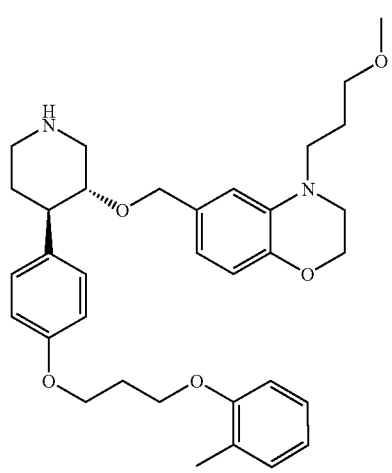
144
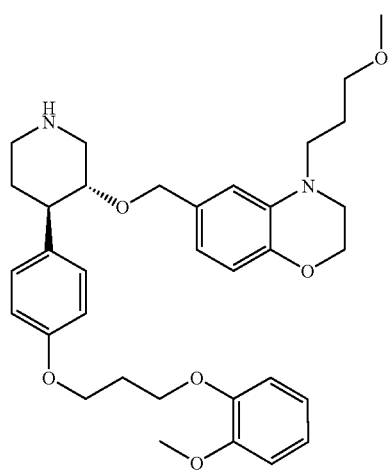
-continued
145
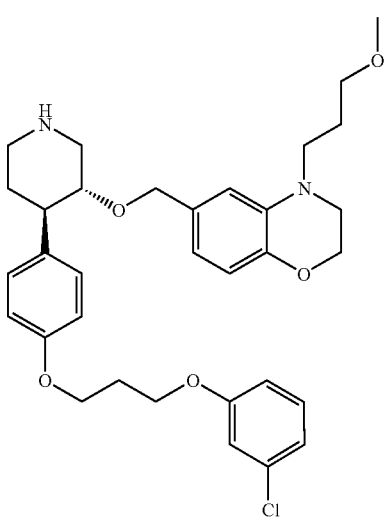
146
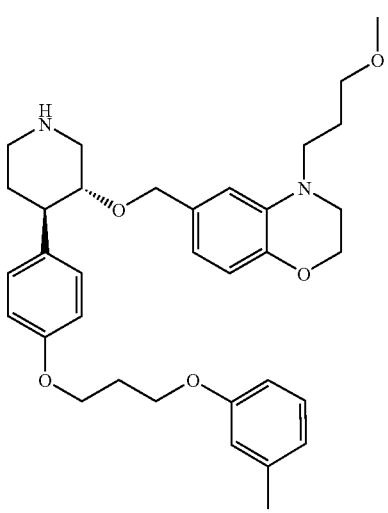
147
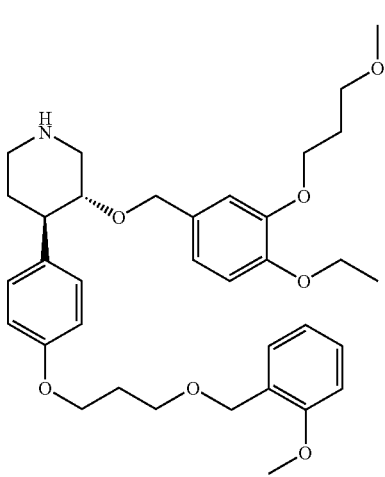

148 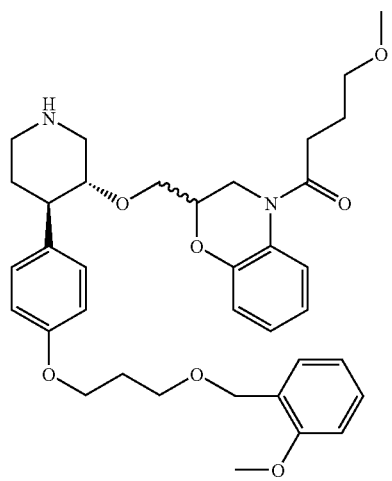
151 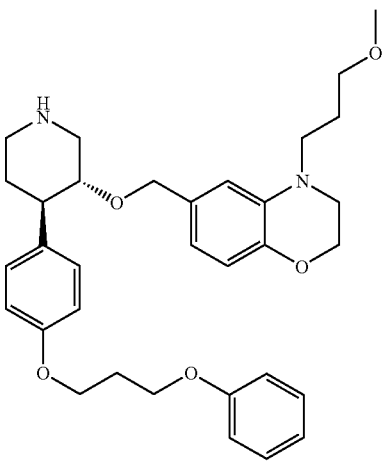
149 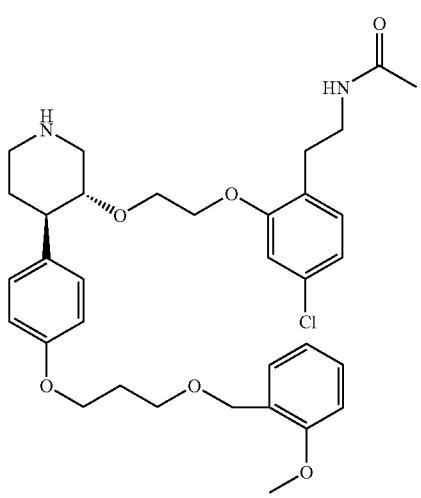
152 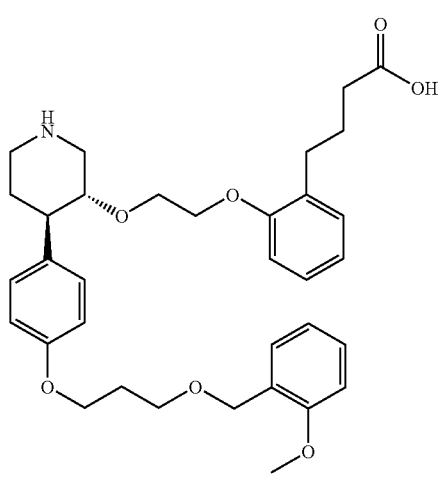
150 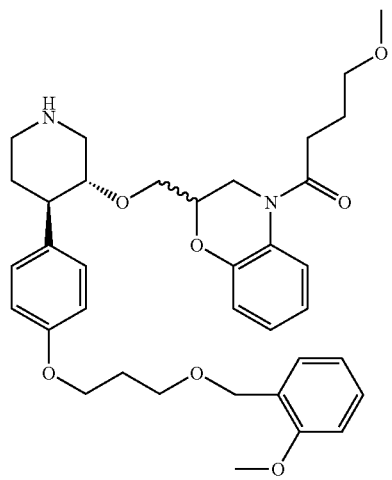
153 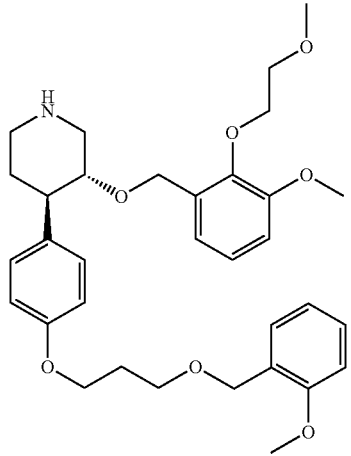

154
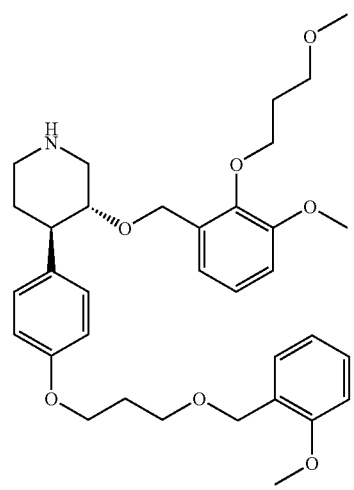
155
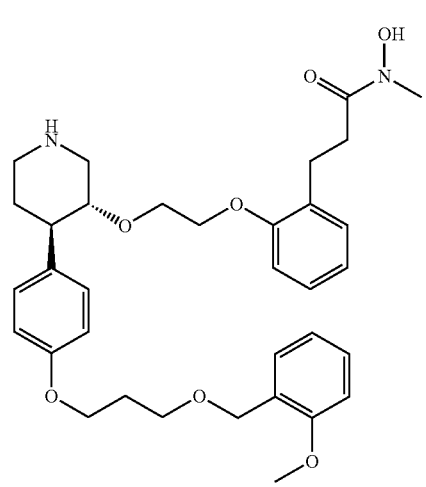
156
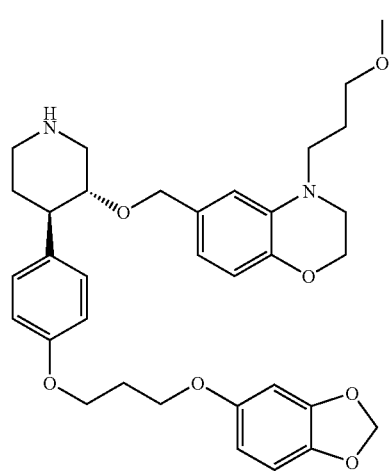
157
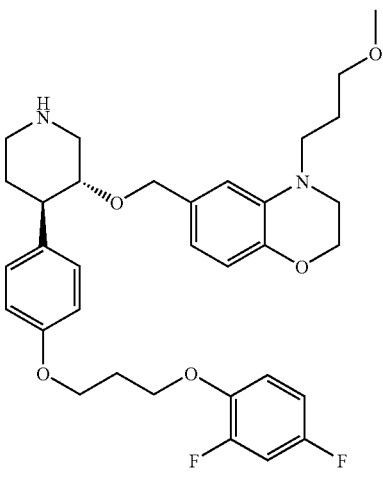
158
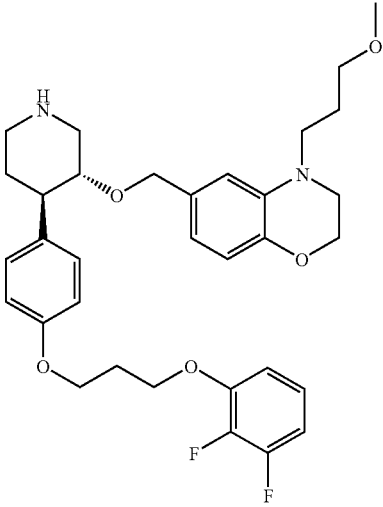
159
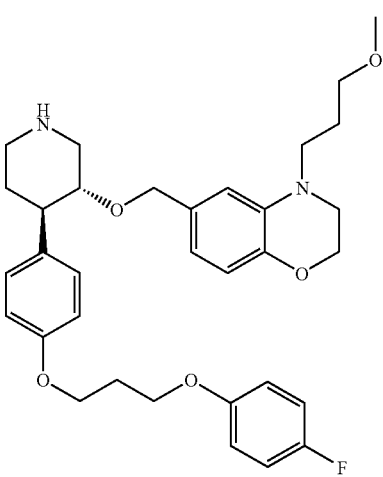

160
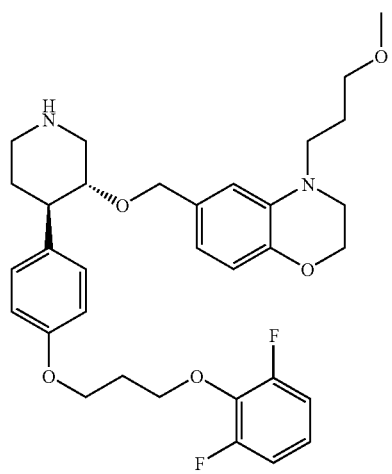
163
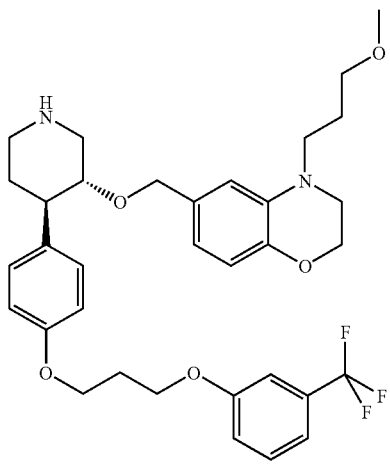
161
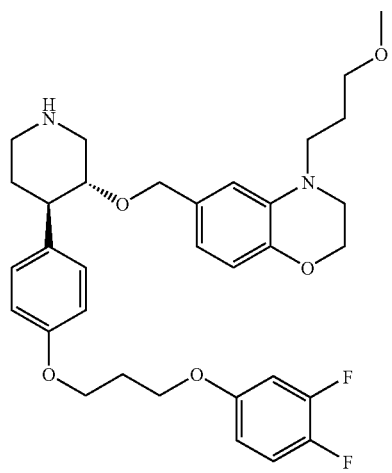
164
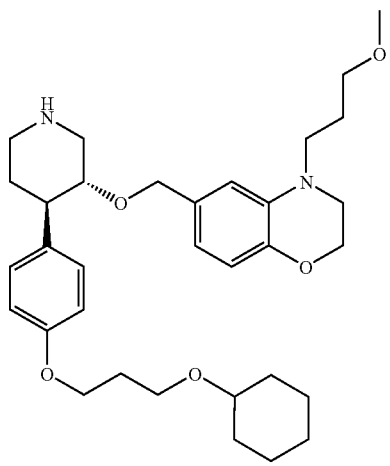
162
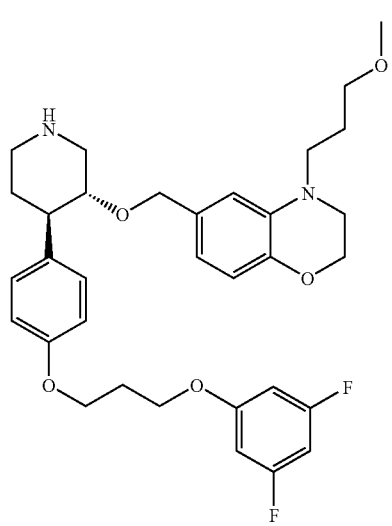
166
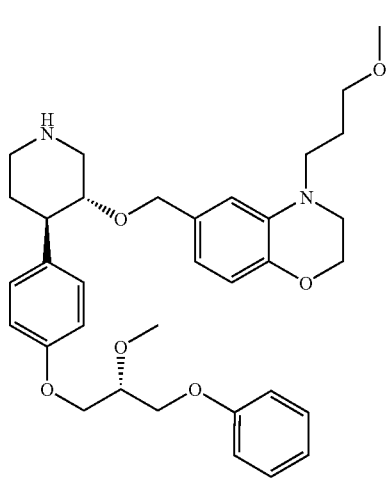

267
-continued
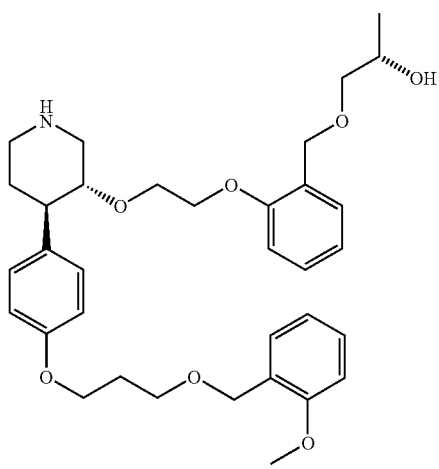
167
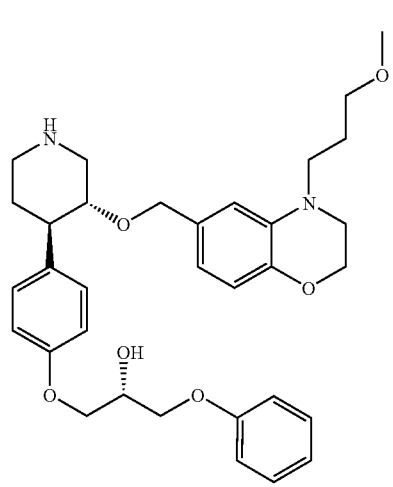
168
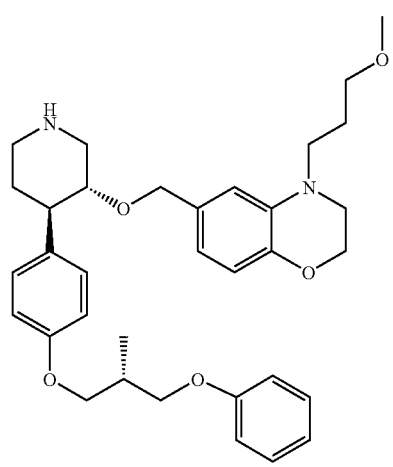
169
268
-continued
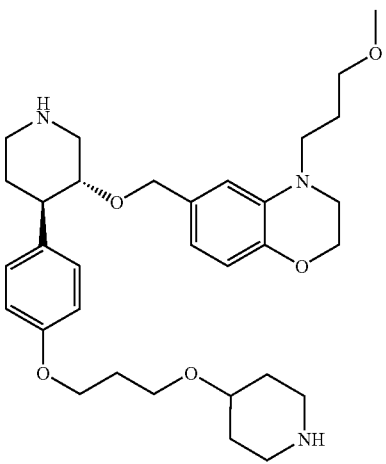
170
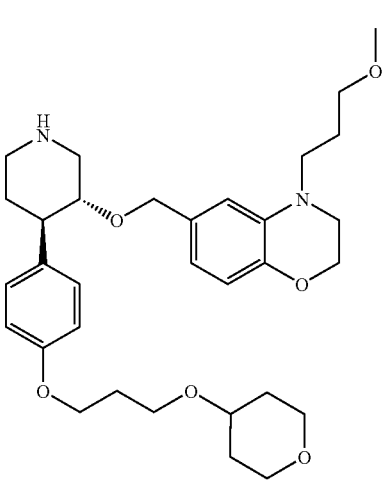
171
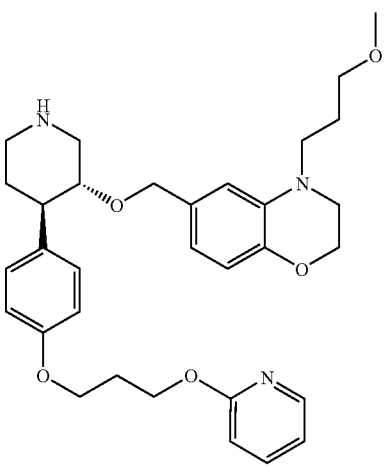
172

-continued
173
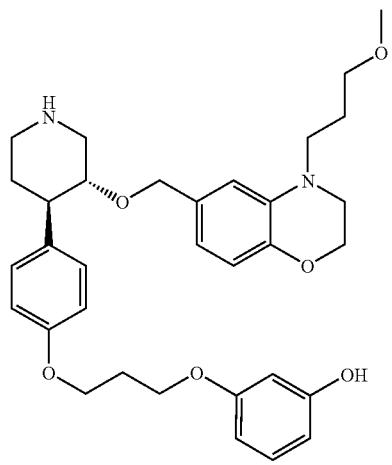
174
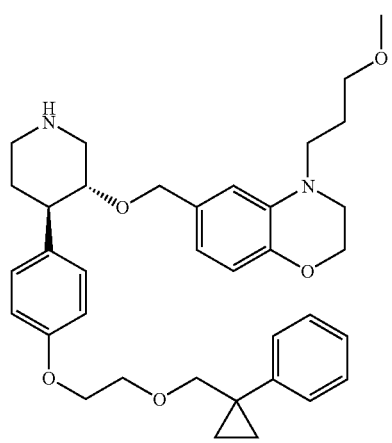
175
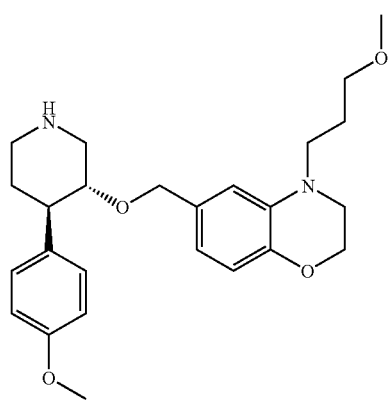
-continued
176
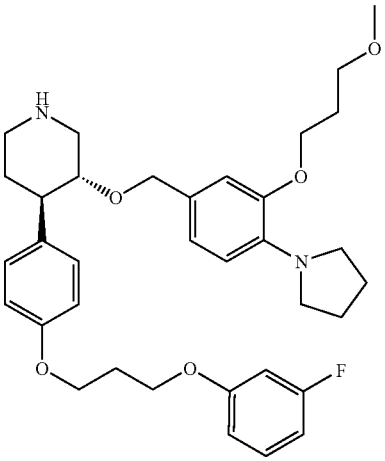
177
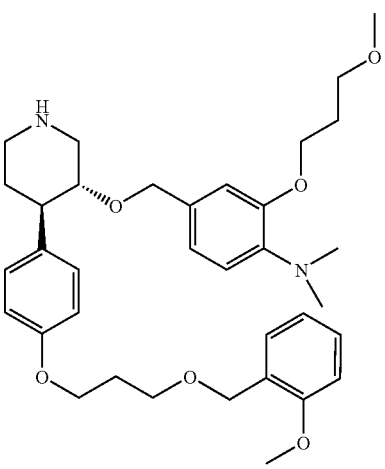
178
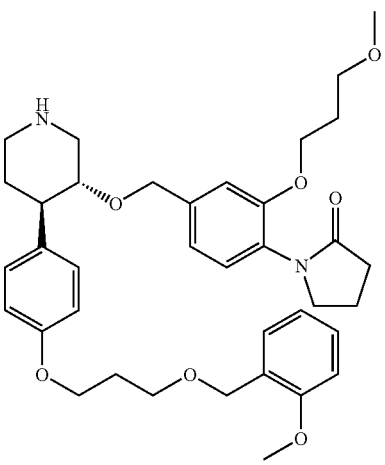

179
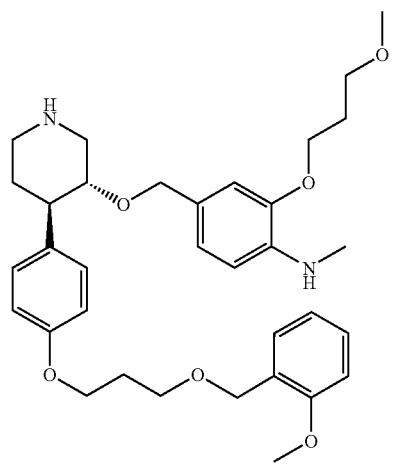
180
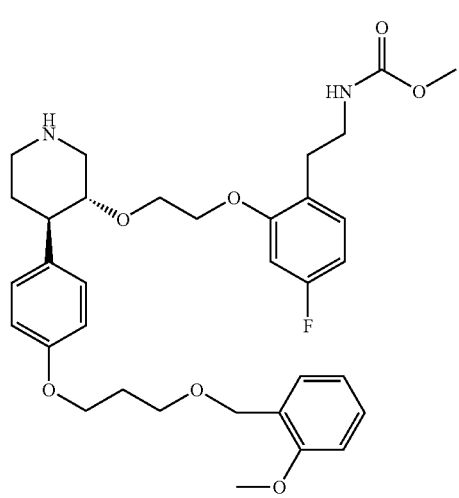
181
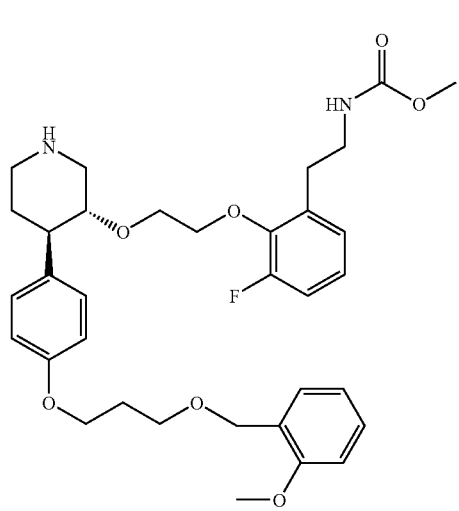
182
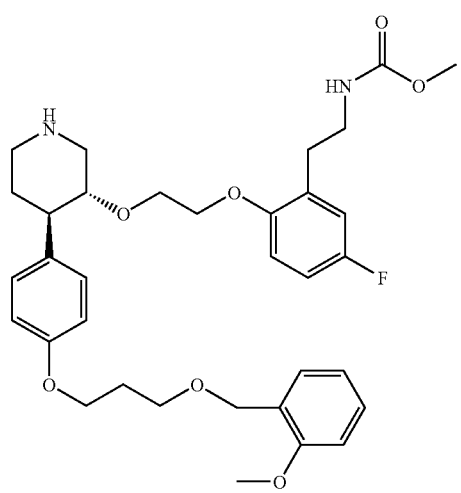
183
184
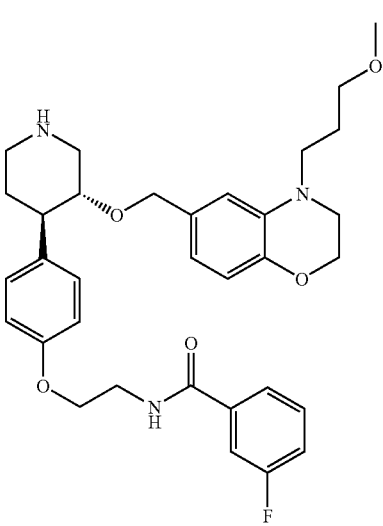

273
-continued
185
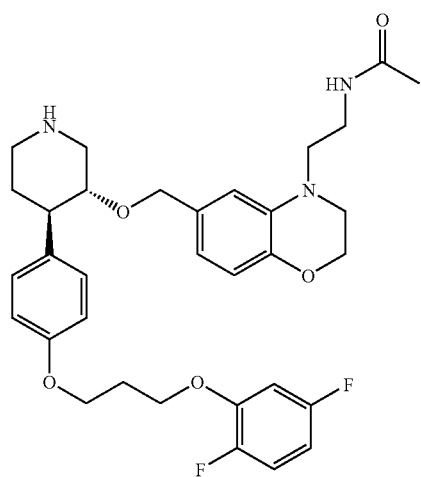
186
187
274
-continued
188
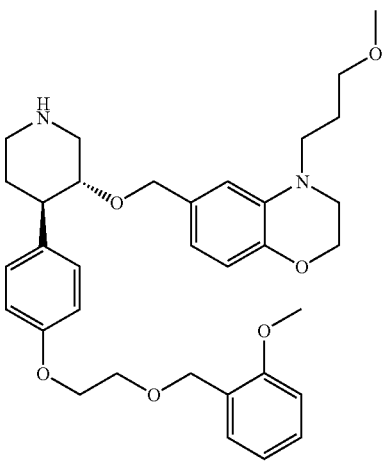
189
190

275 276
-continued
191
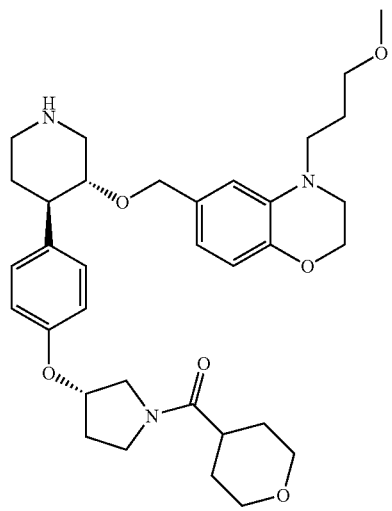
192
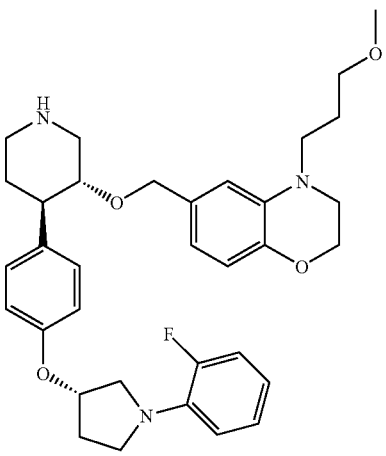
193
-continued
194
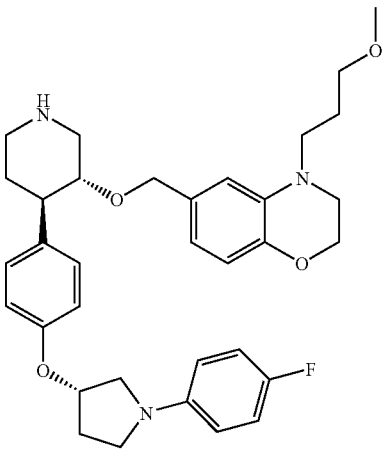
195
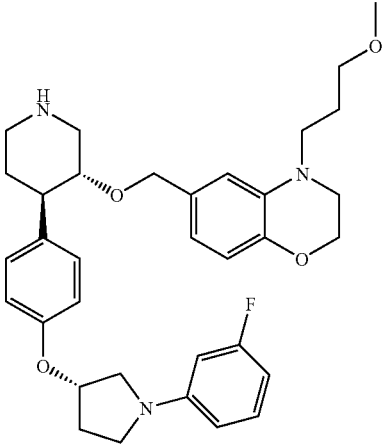
196

277
278
| | |
|---|---|
| 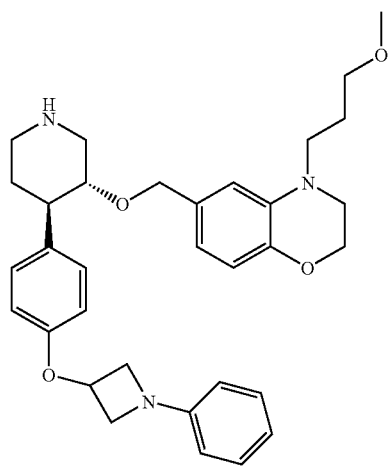 197 | 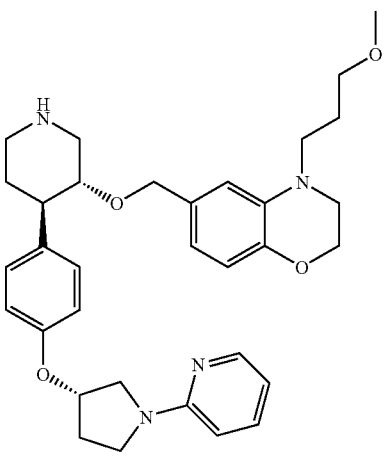 200 |
| 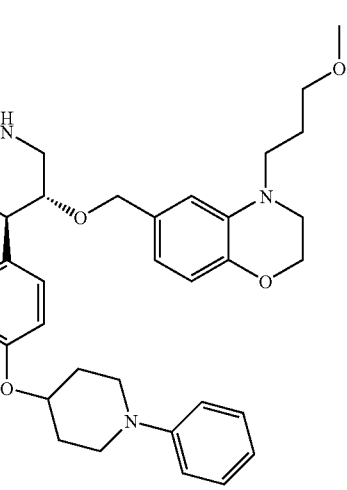 198 | 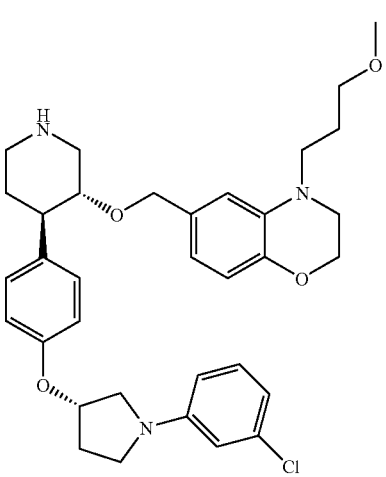 201 |
| 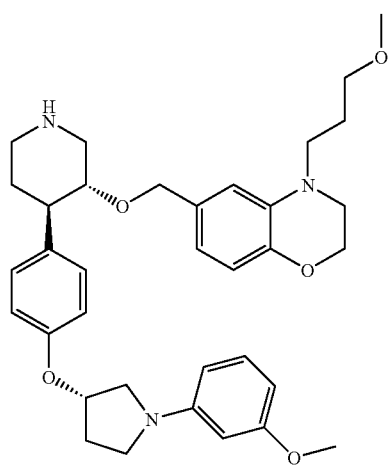 199 | 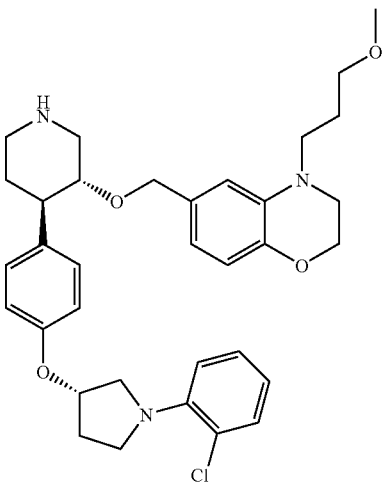 202 |

279 | 280
-continued | -continued
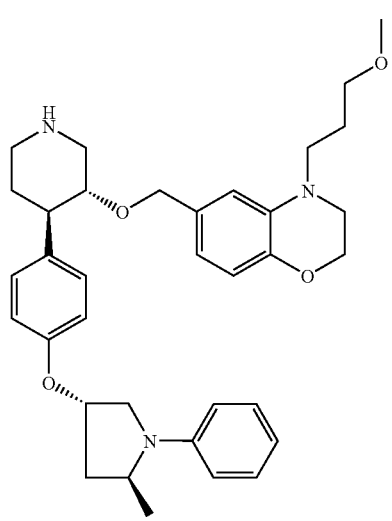
203
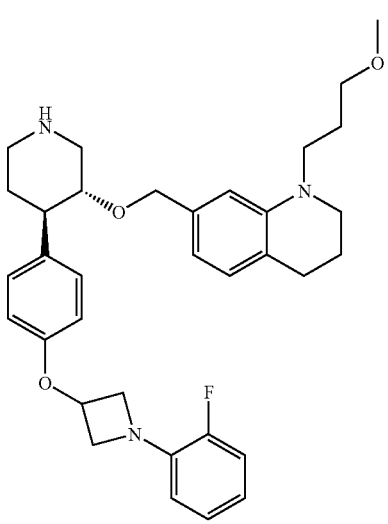
206
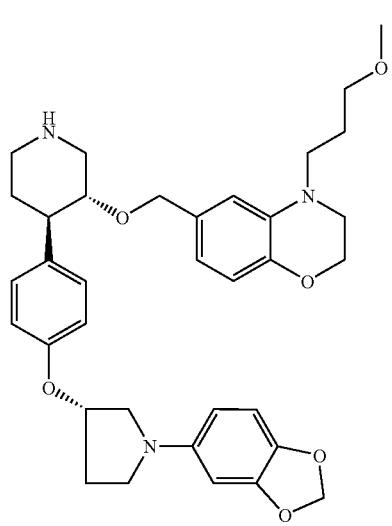
204
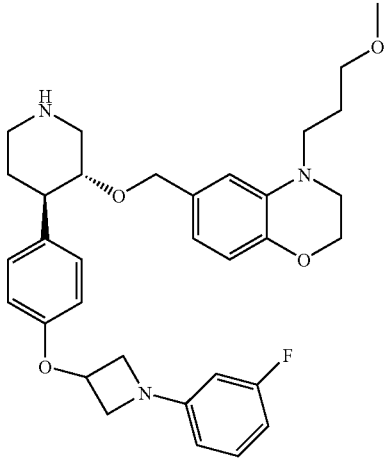
207
205
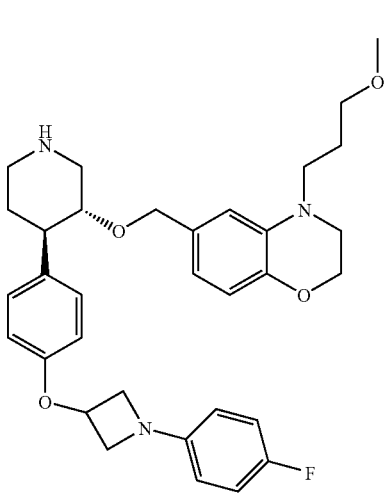
208

-continued
209
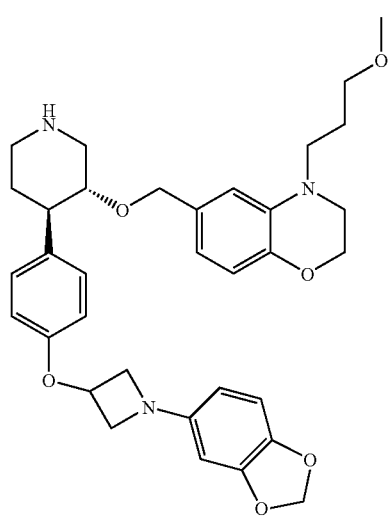
210
211
-continued
212
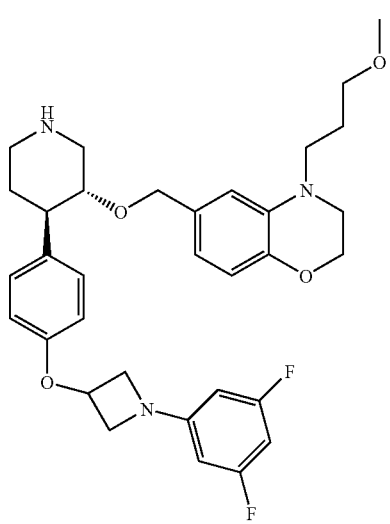
213
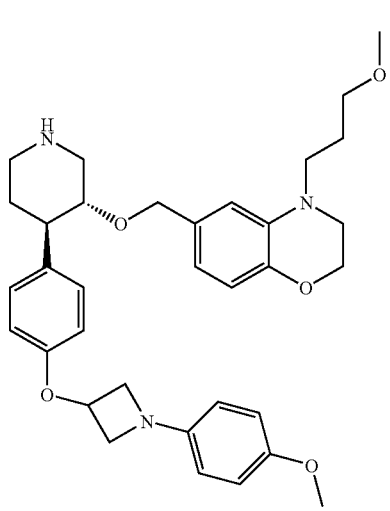
214
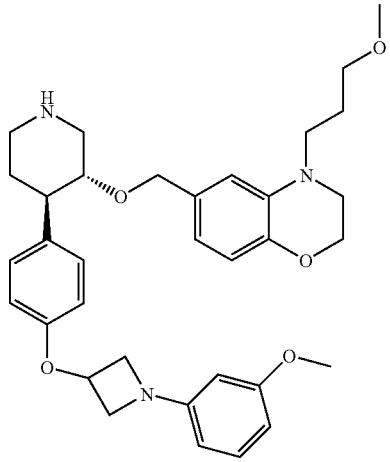

-continued
215
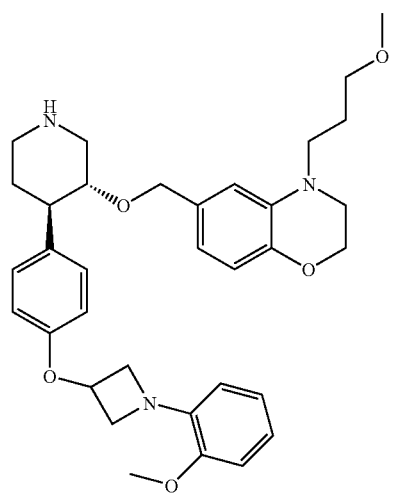
216
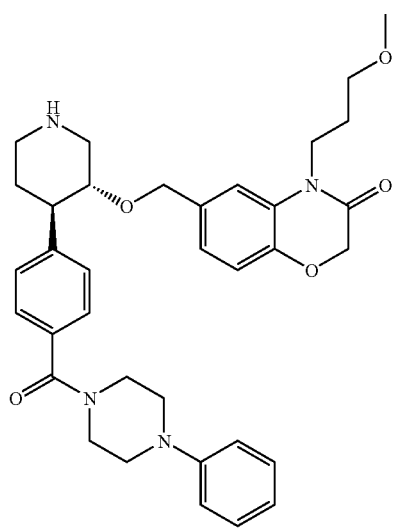
217
-continued
218
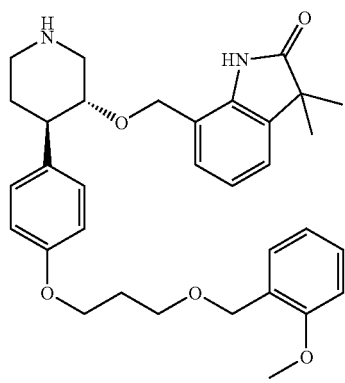
219
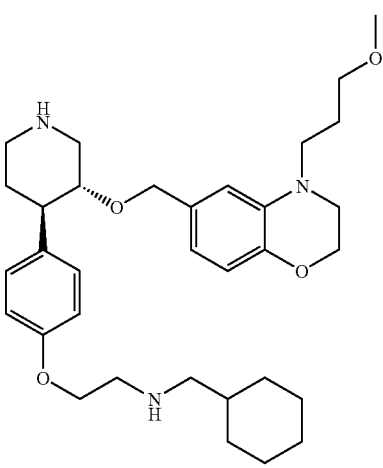
220
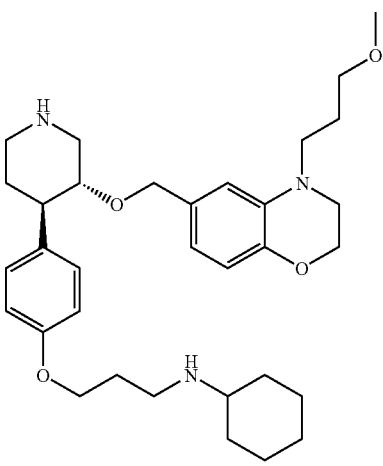

221
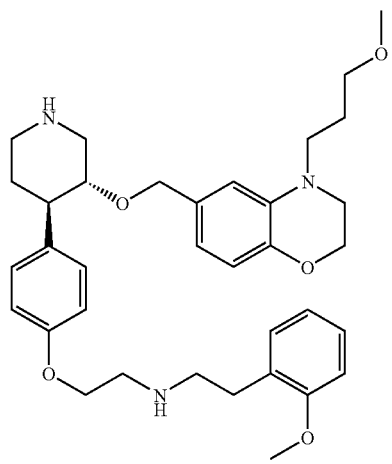
222
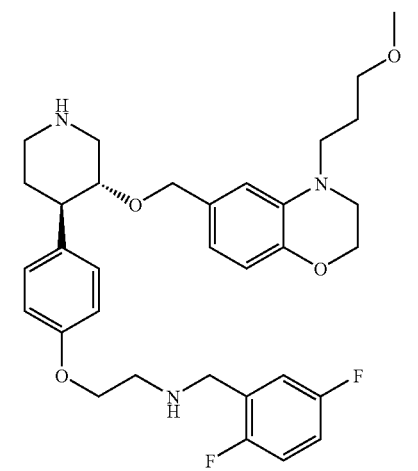
223
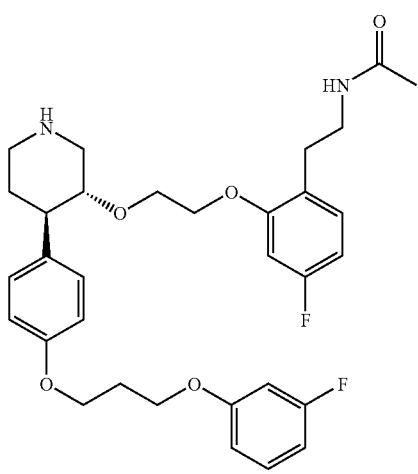
224
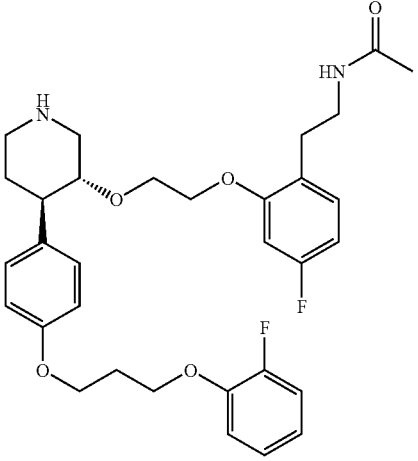
225
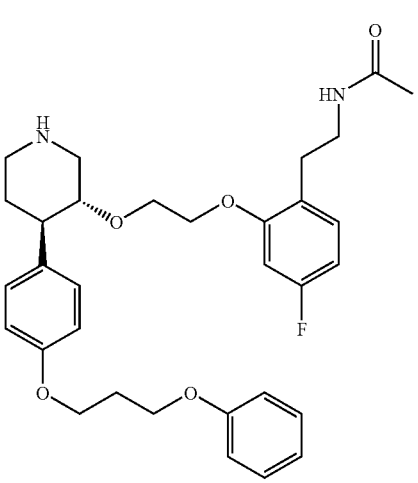
226
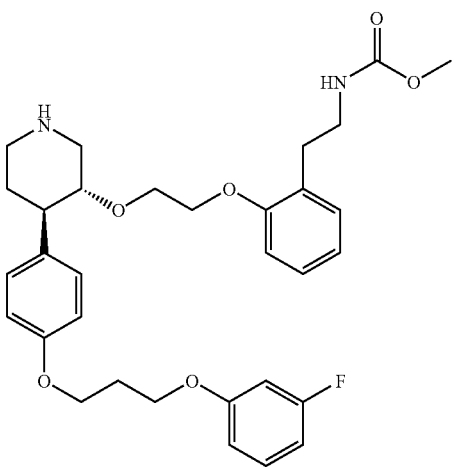

-continued

| 227 | 230 |
| 228 | 231 |
| 229 | 232 |

233
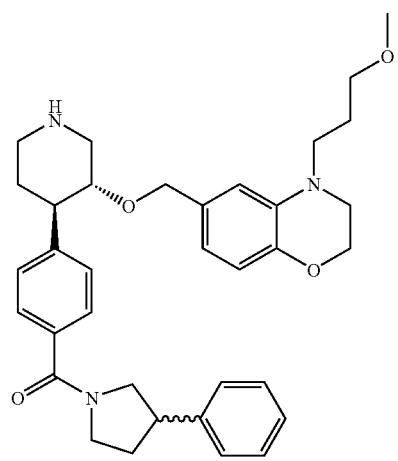
234
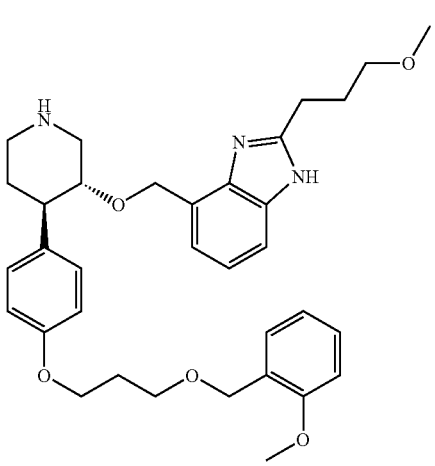
235
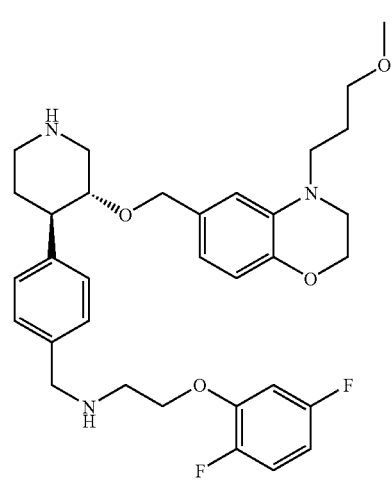
236
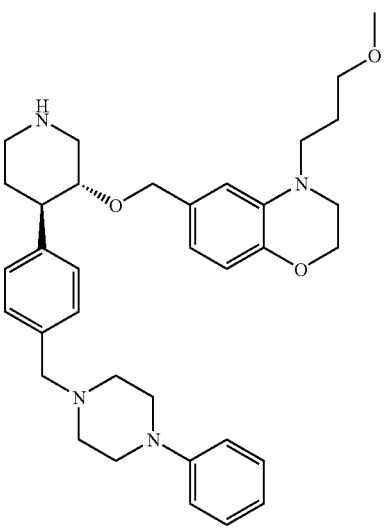
237
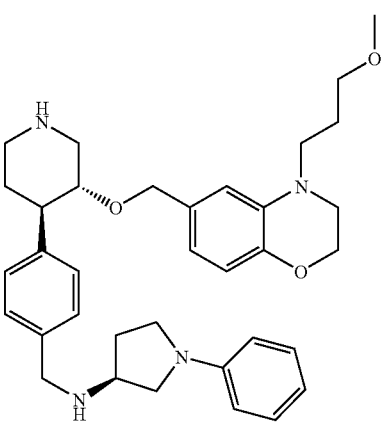
238
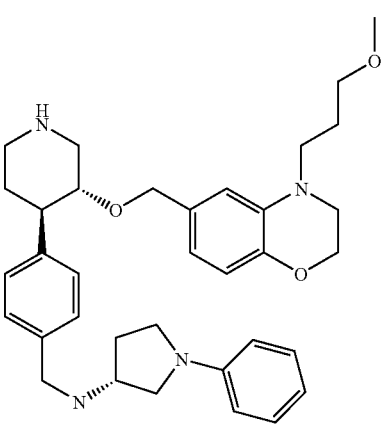

-continued
239
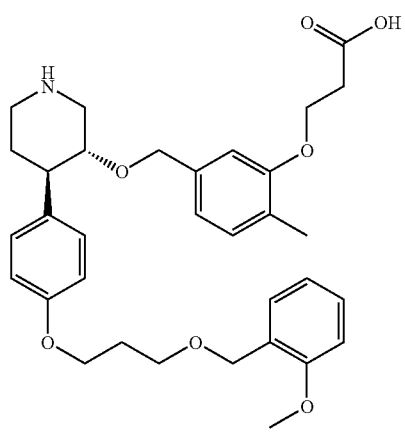
241
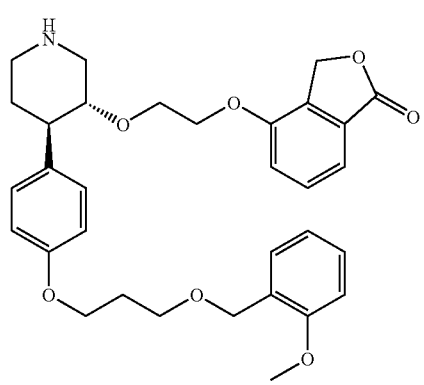
242
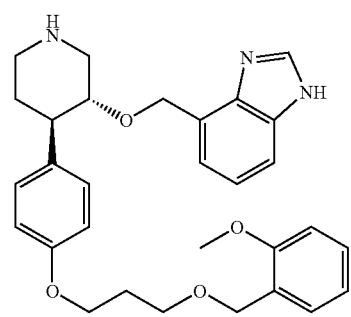
-continued
243
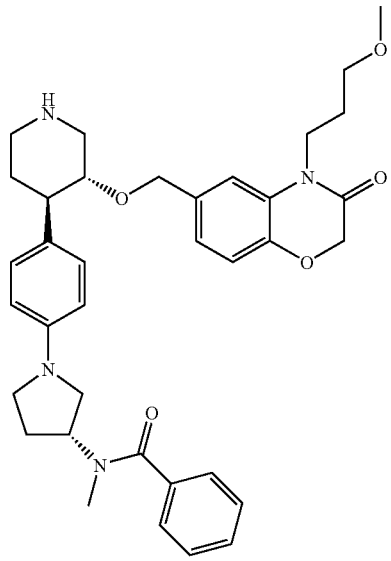
244
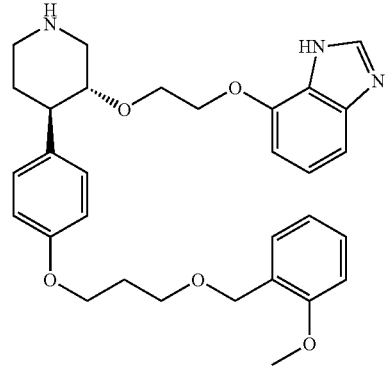
245
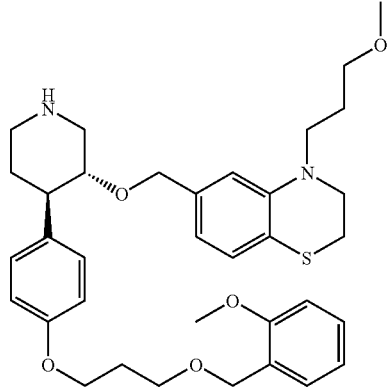
246
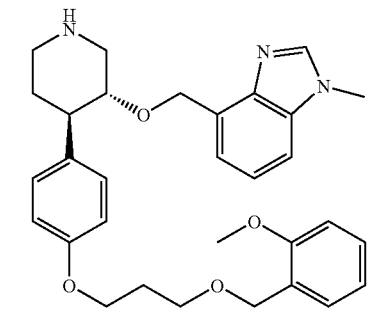

247 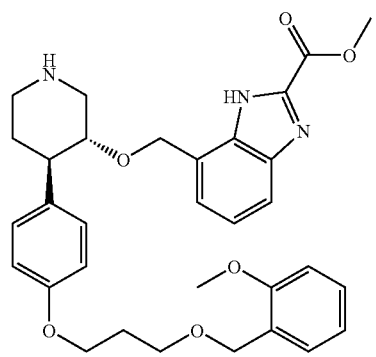
248 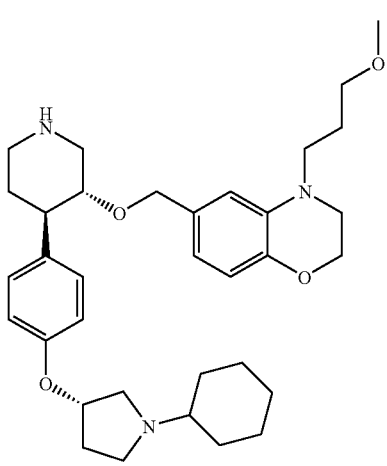
249 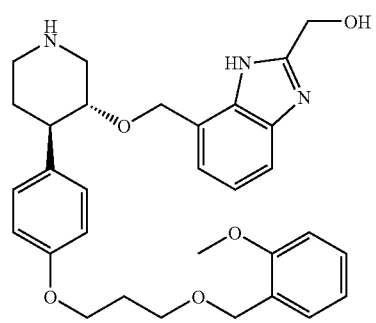
250 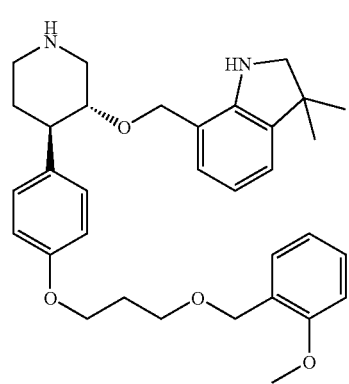
251 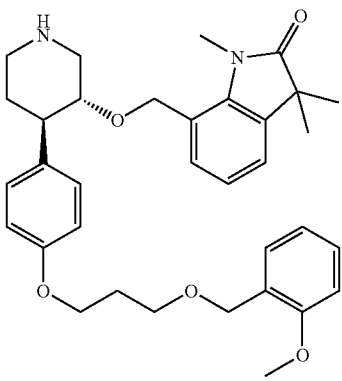
252 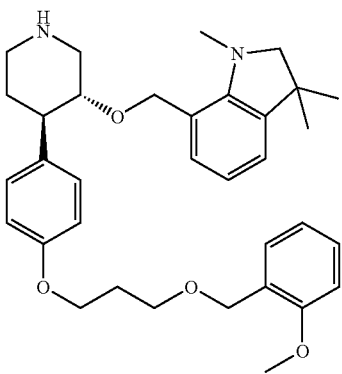
253 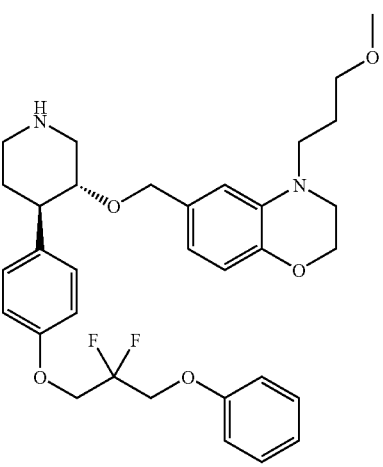

| 254 | 257 |
| 255 | 258 |
| 256 | 259 |

260
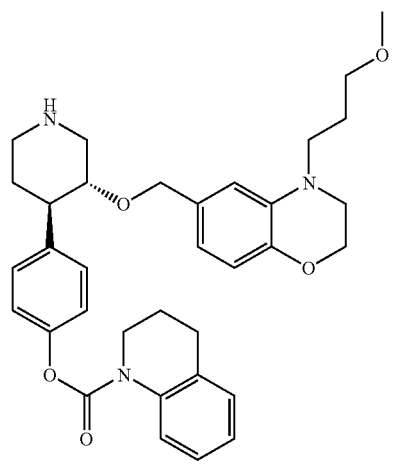
261
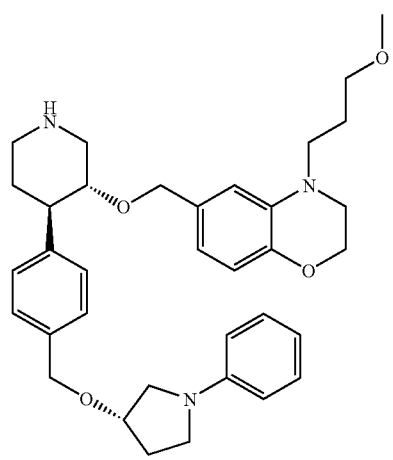
262
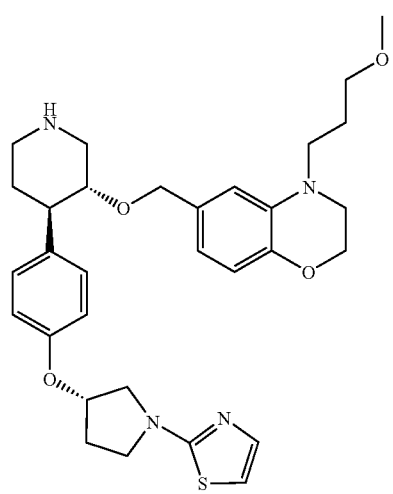
263
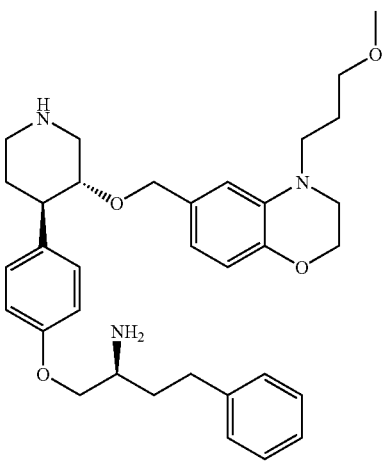
264
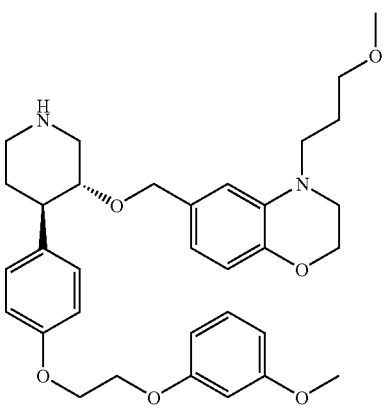
265
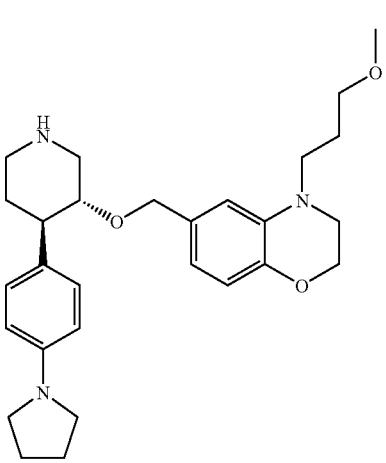

266
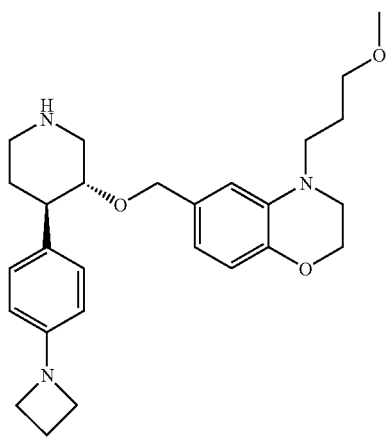
267
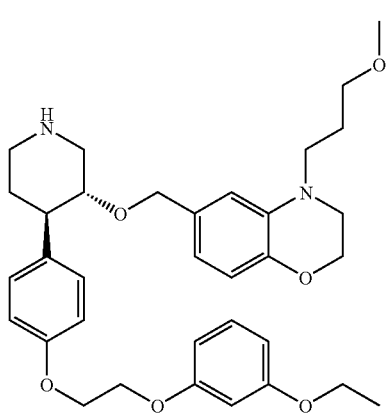
268
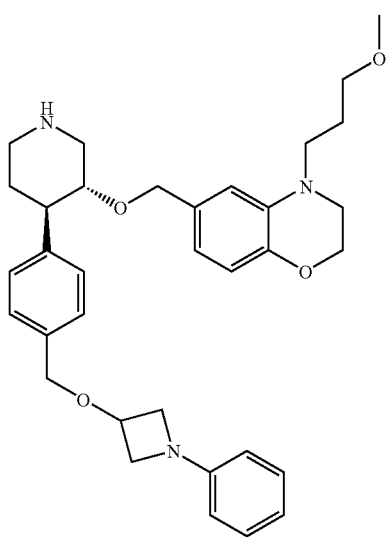
269
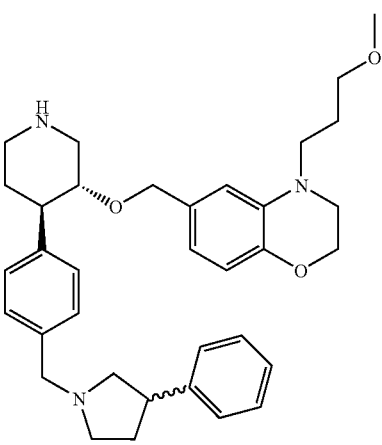
270
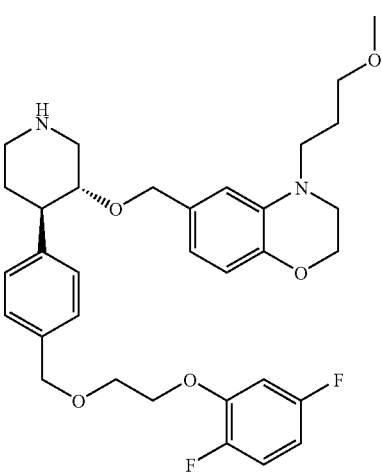
271
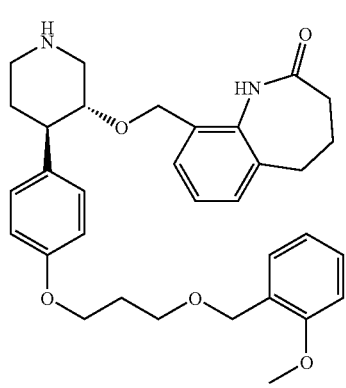

-continued
272
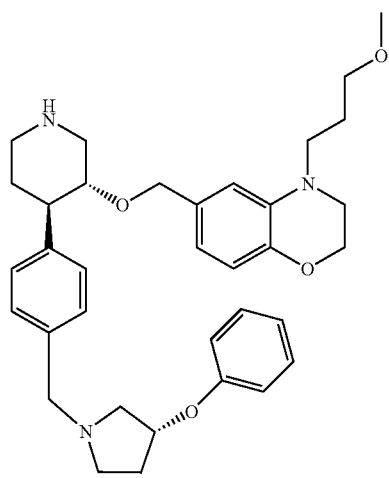
273
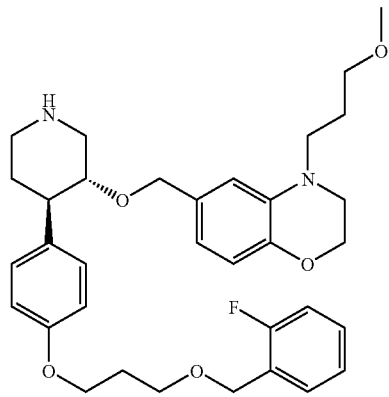
274
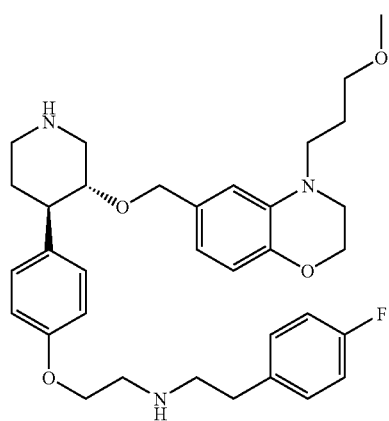
-continued
275
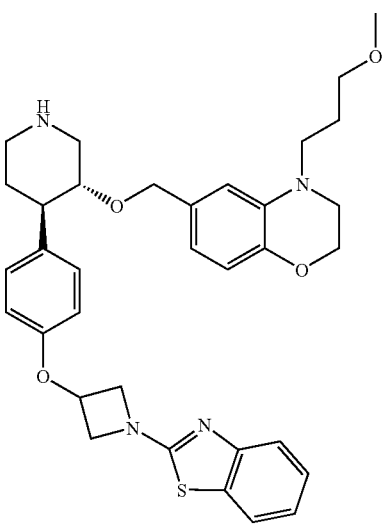
276
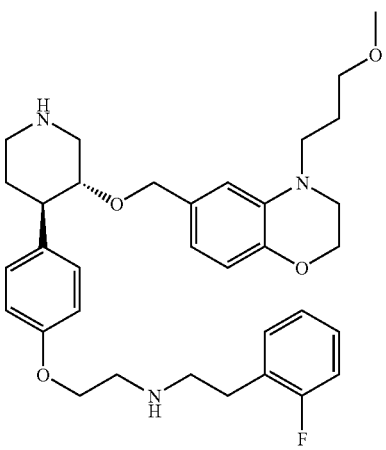
277
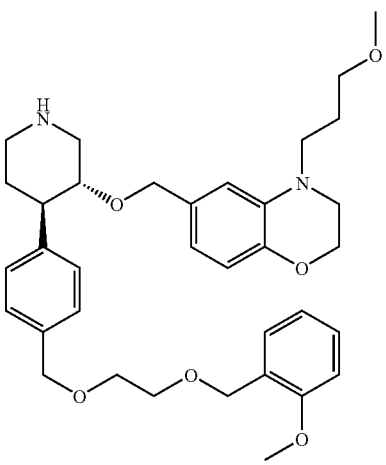

278
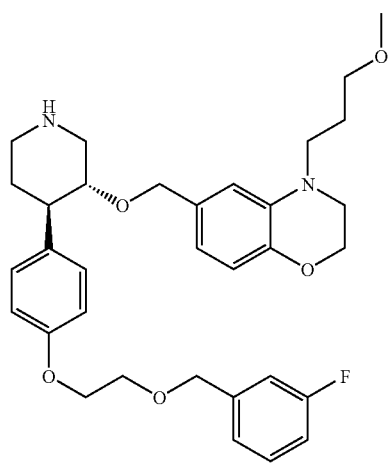
279
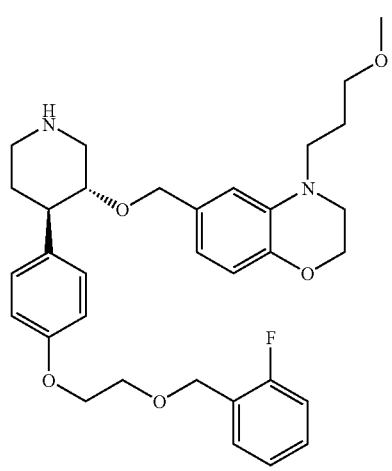
280
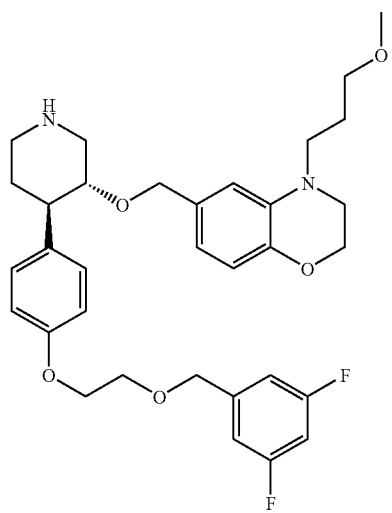
281
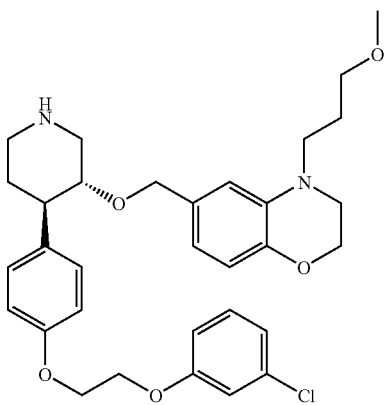
282
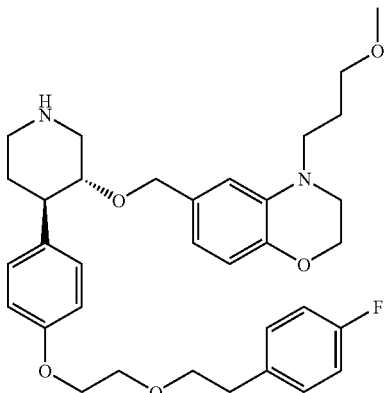
283
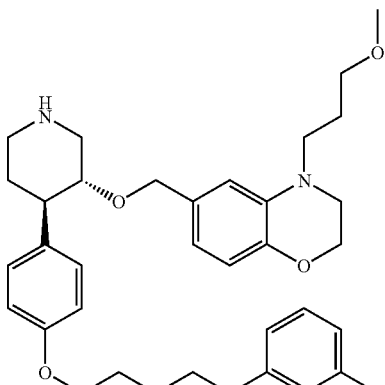
284
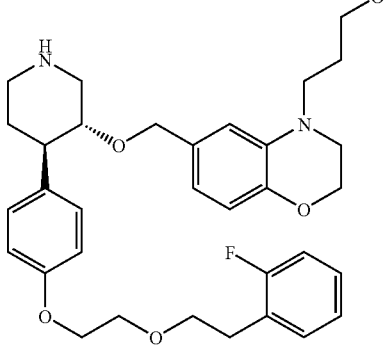

305
-continued
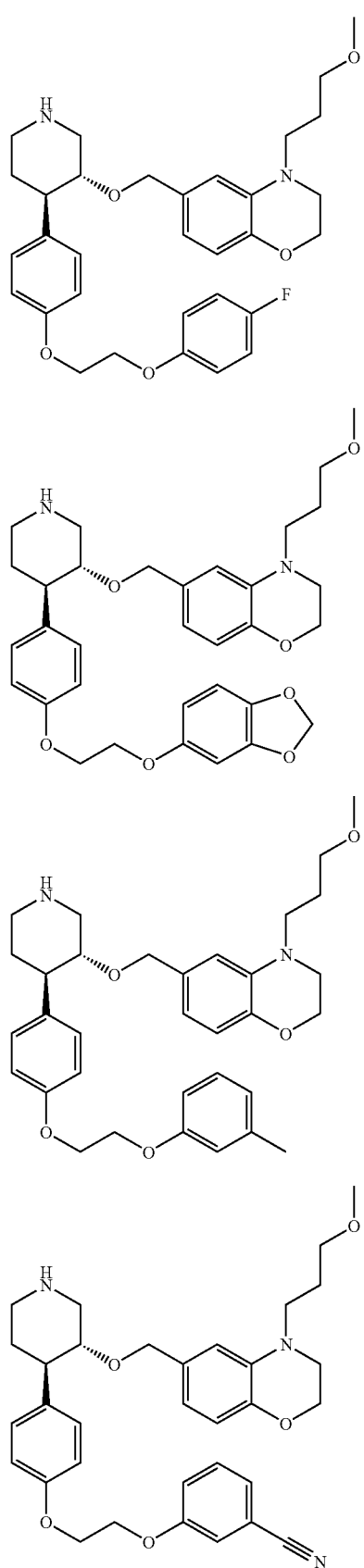
306
-continued
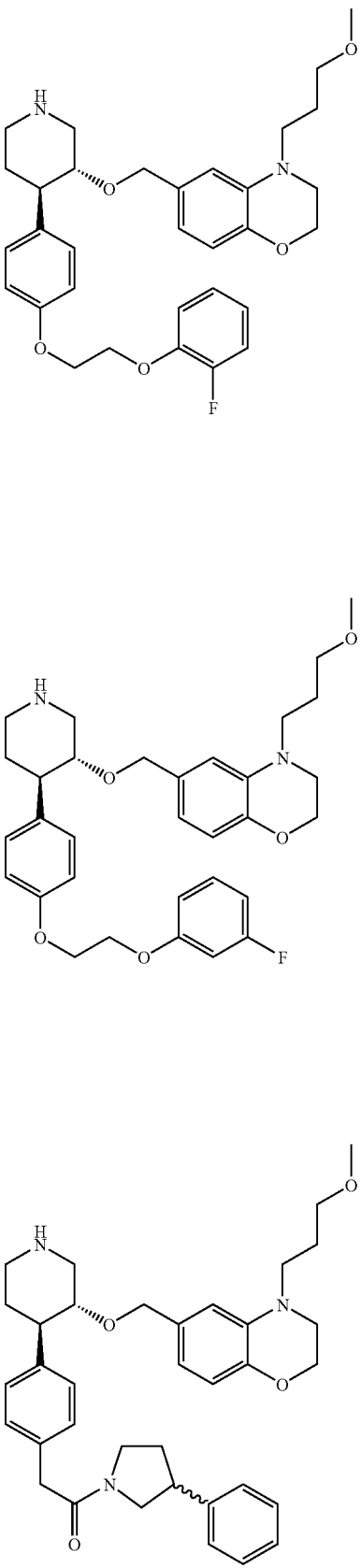

292
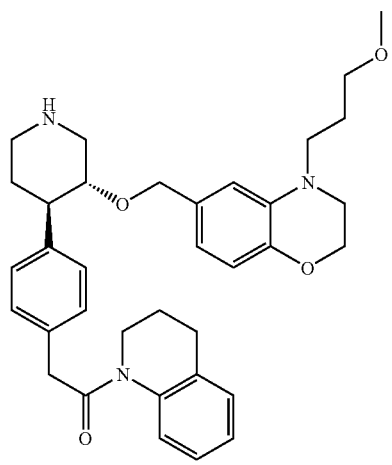
293
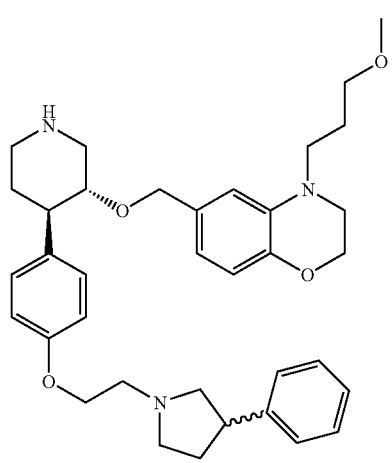
294
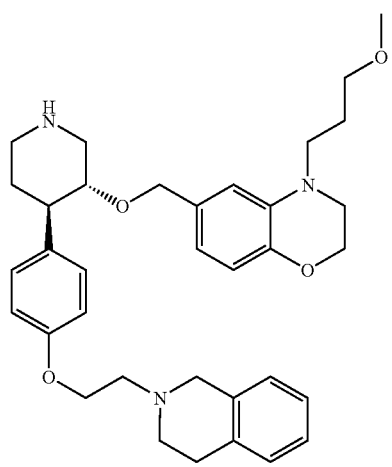
295
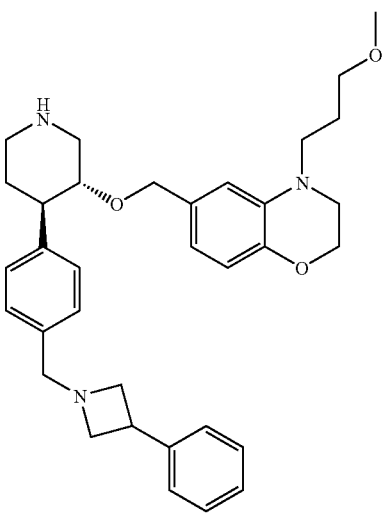
296
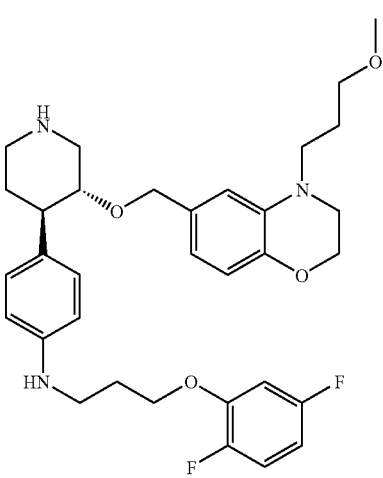
297
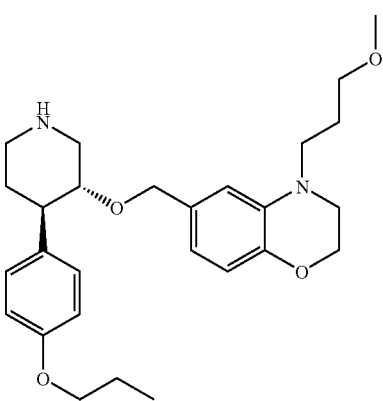

298 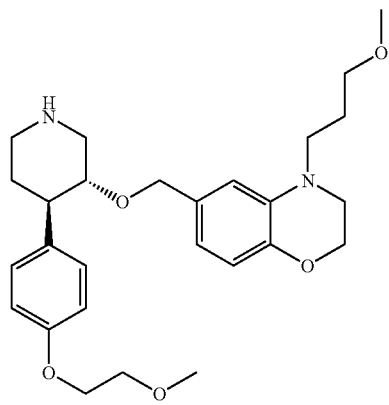
299 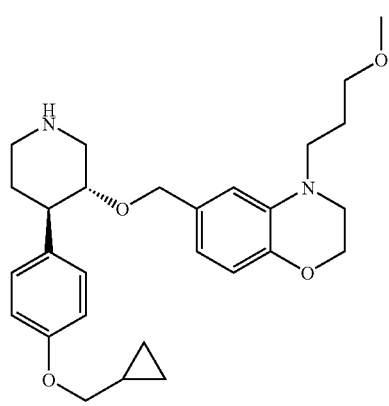
300 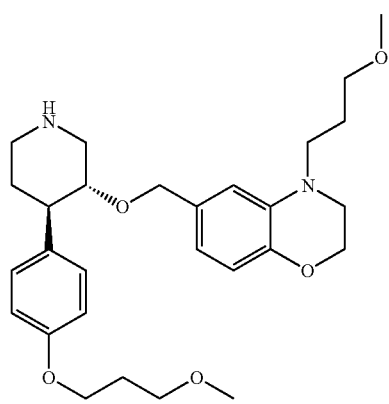
301 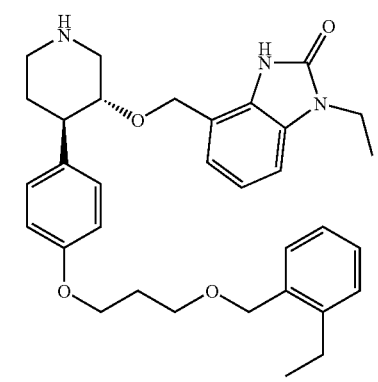
302 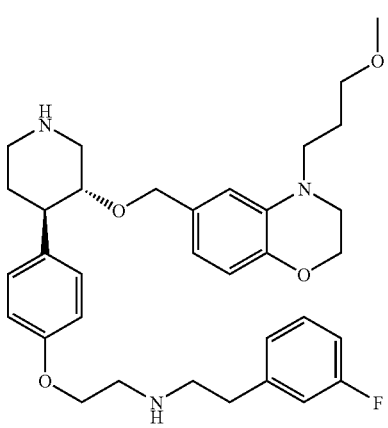
303 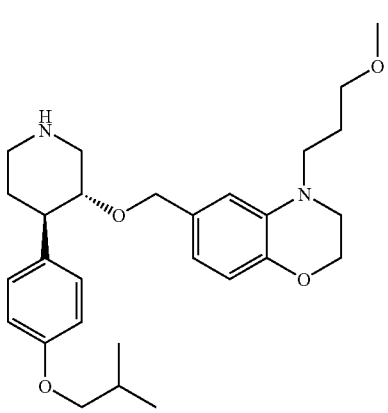
304 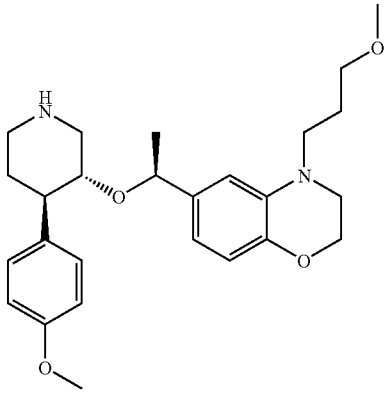
305 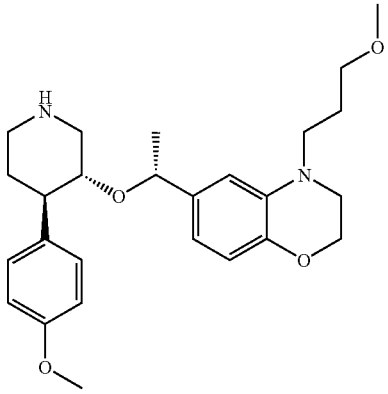

-continued
306
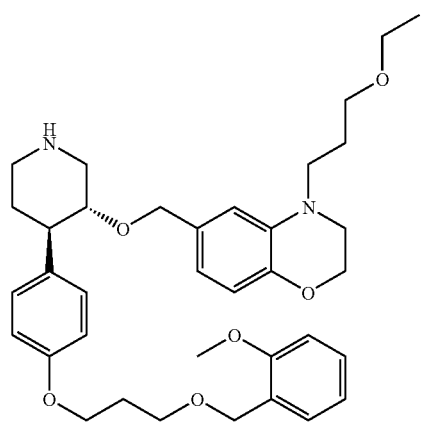
307
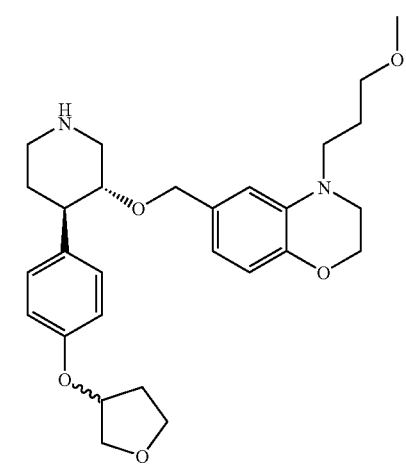
308
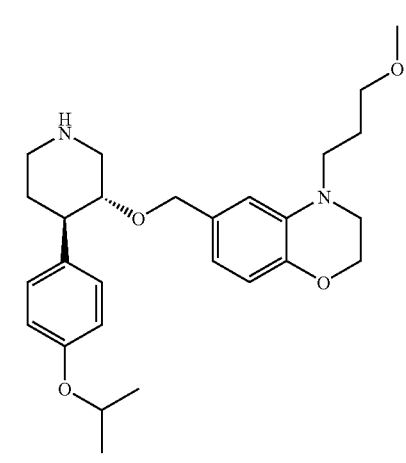
-continued
309
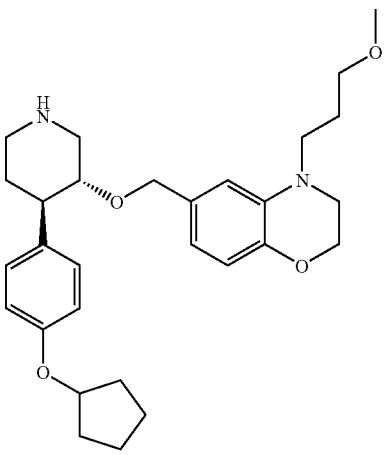
310
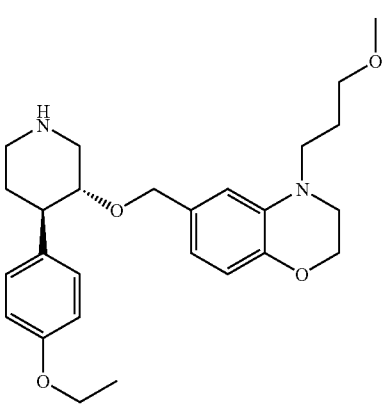
311
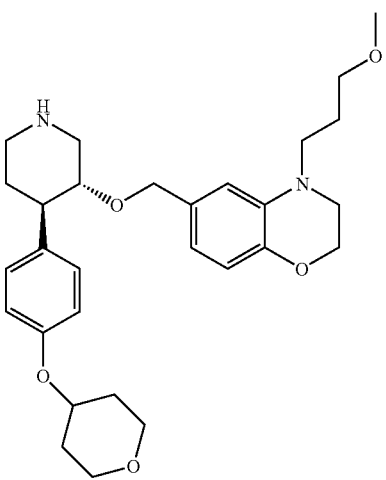

-continued
312
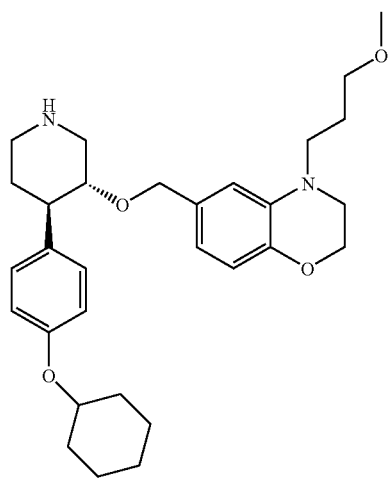
313
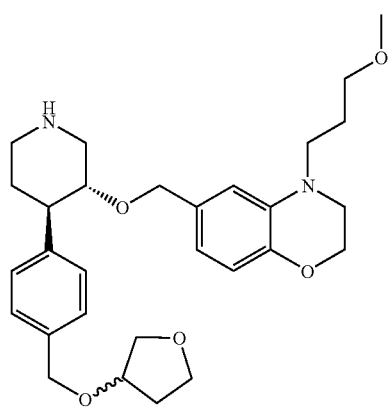
314
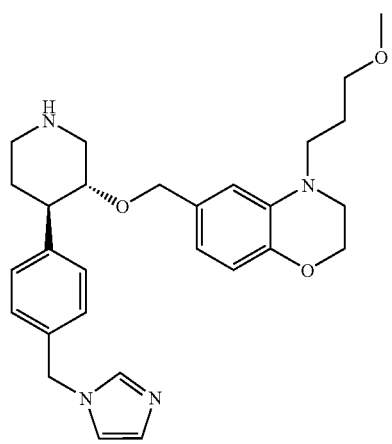
-continued
315
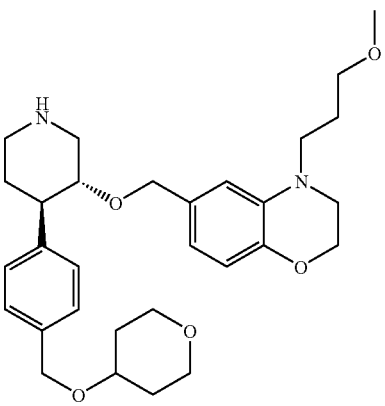
316
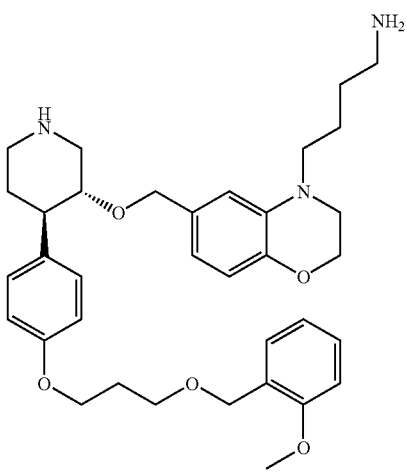
317
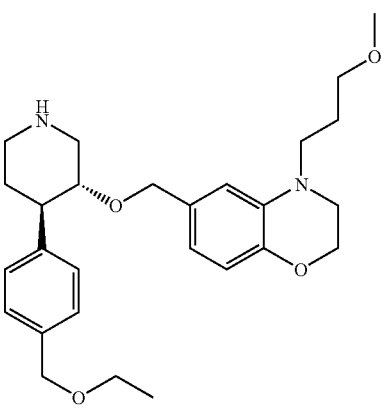

315                                316
-continued                        -continued
318
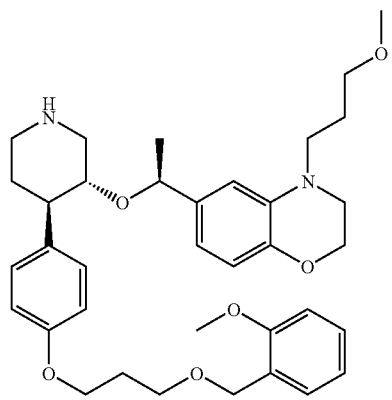
321
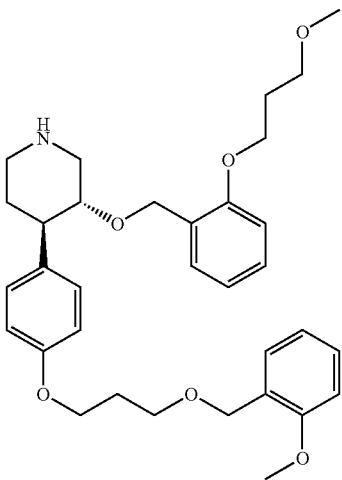
319
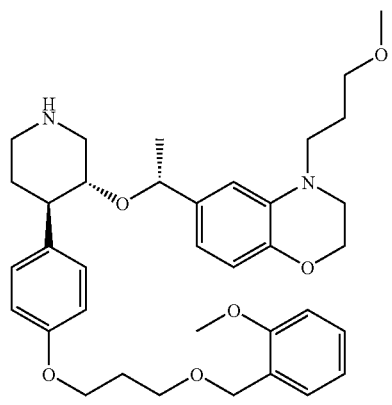
322
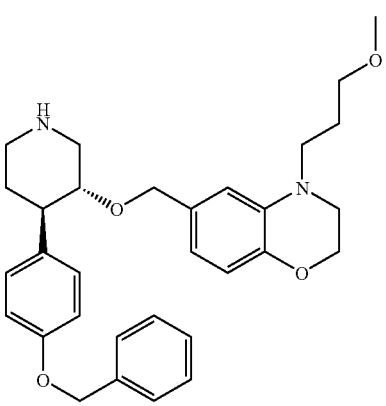
320
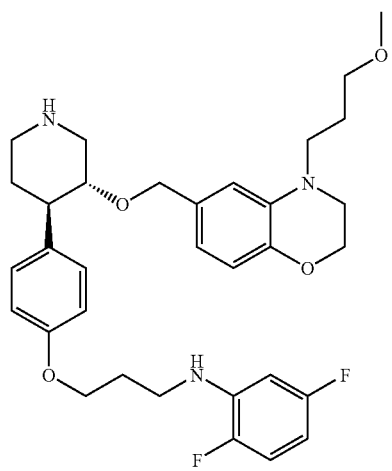
323
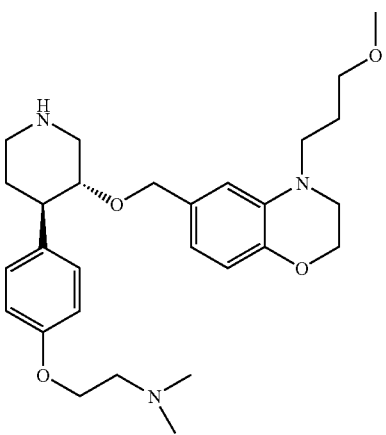

-continued
324
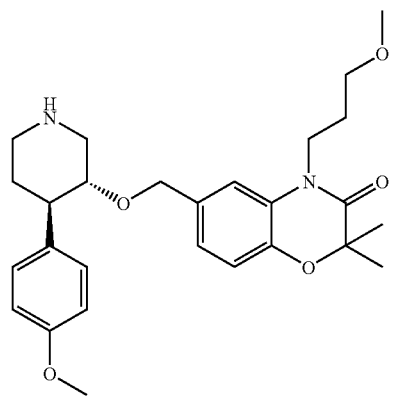
325
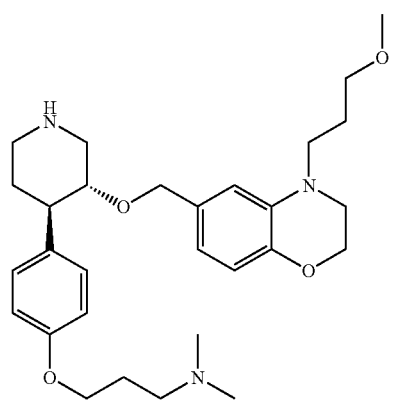
326
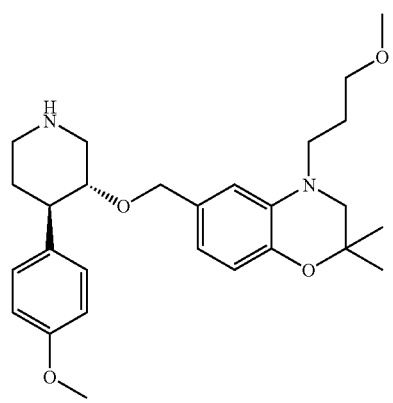
327
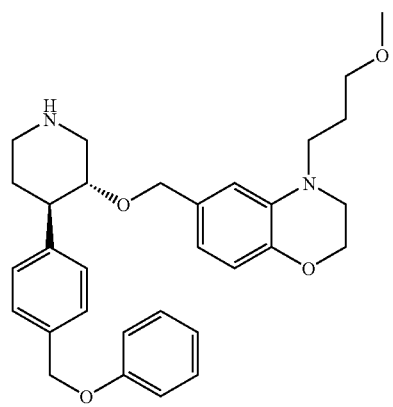
-continued
328
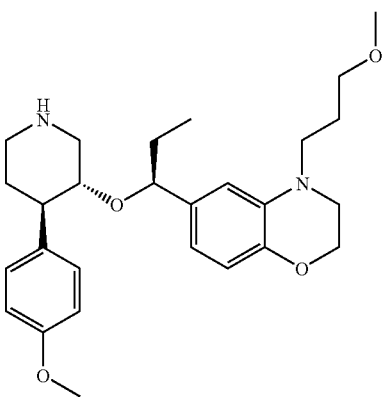
329
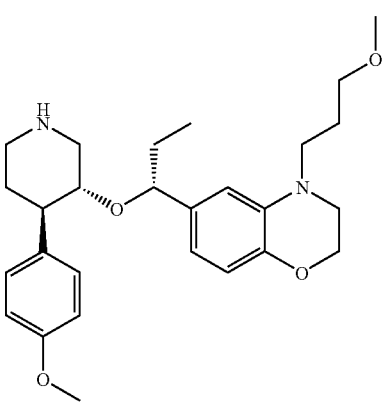
330
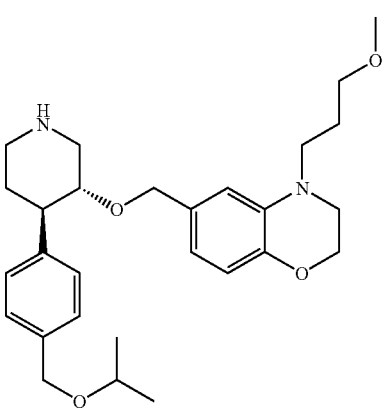

| 331 | 334 |
|---|---|
| 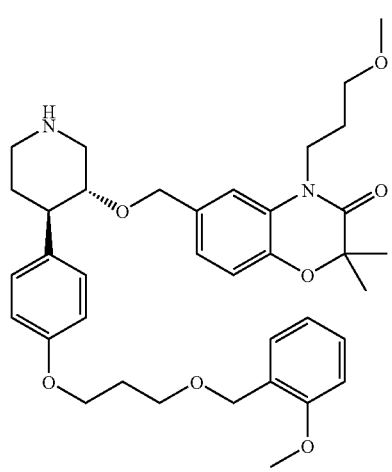 | 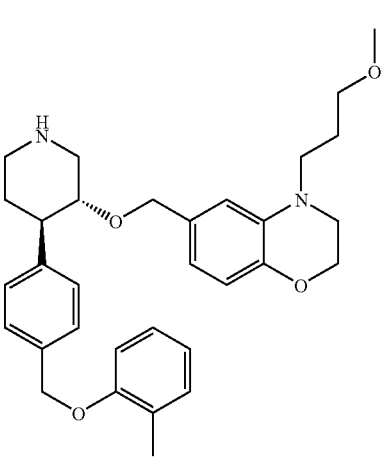 |
| 332 | 335 |
|---|---|
| 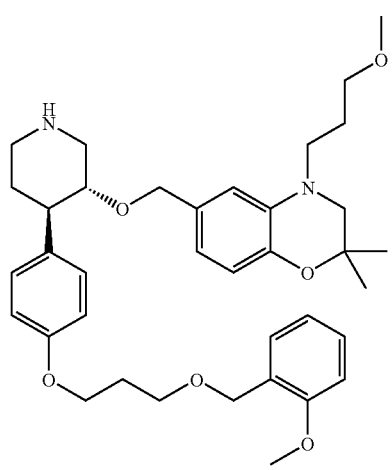 | 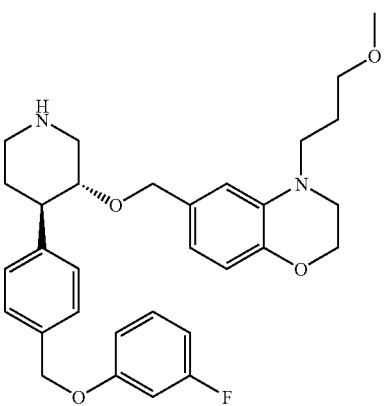 |
| 333 | 336 |
|---|---|
| 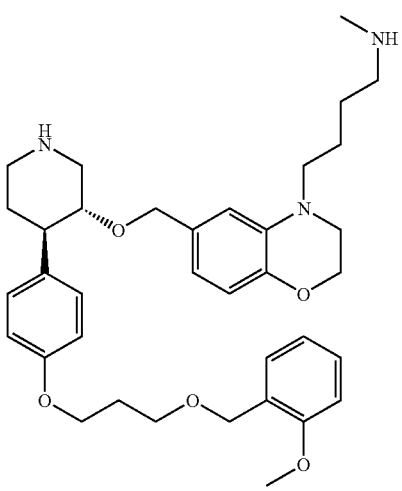 | 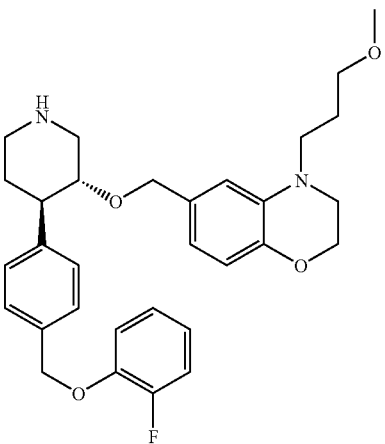 |

| 337 | 340 |
|---|---|
| 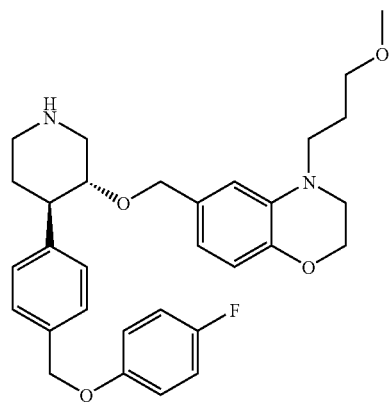 | 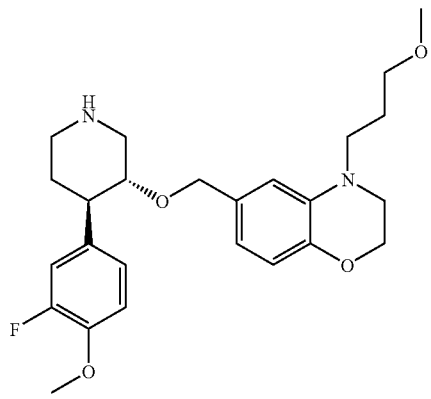 |
| 338 | 341 |
| 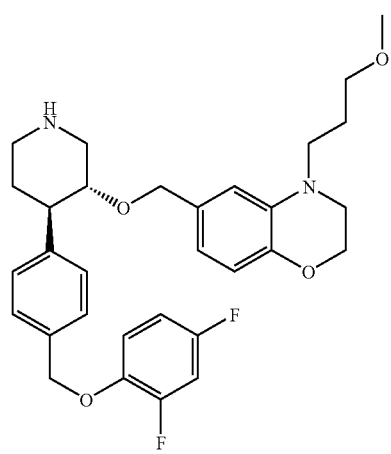 | 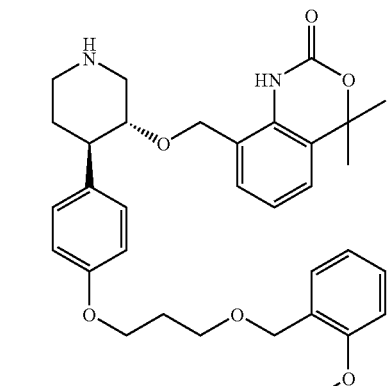 |
|  | 342 |
|  | 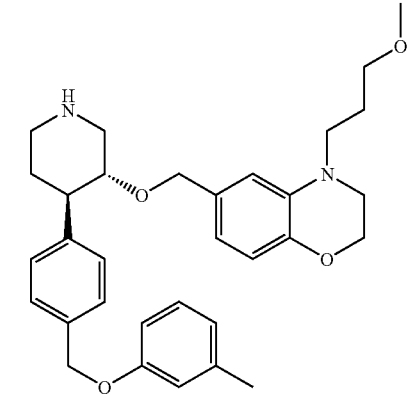 |
| 339 | 343 |
| 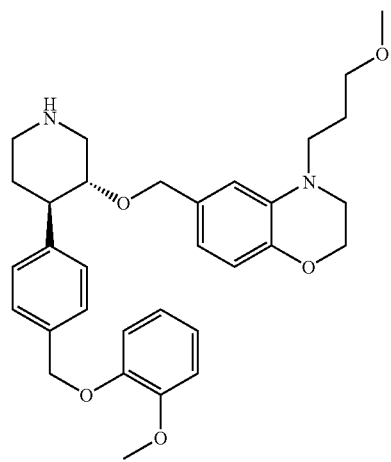 | 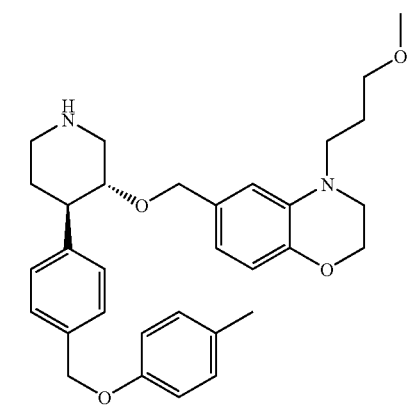 |

344
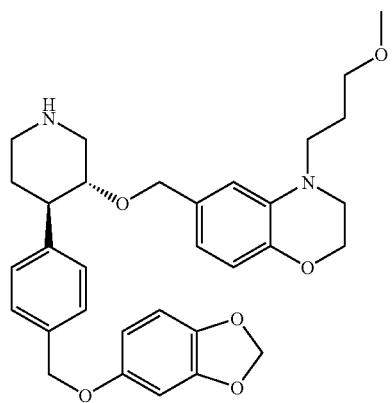
345
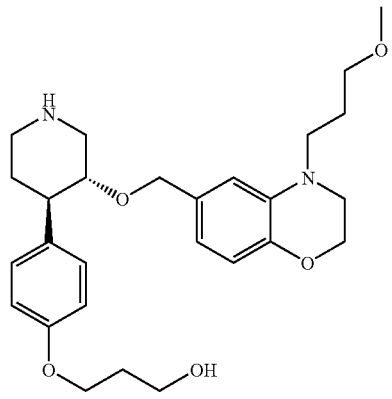
346
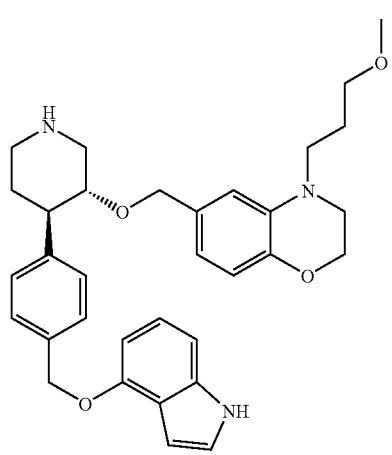
347
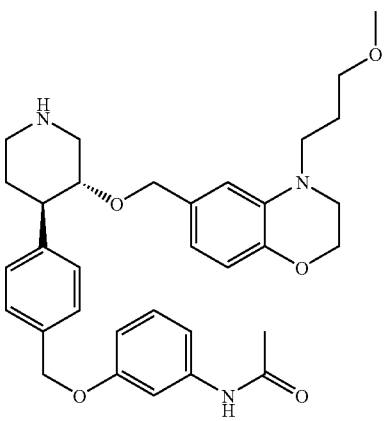
348
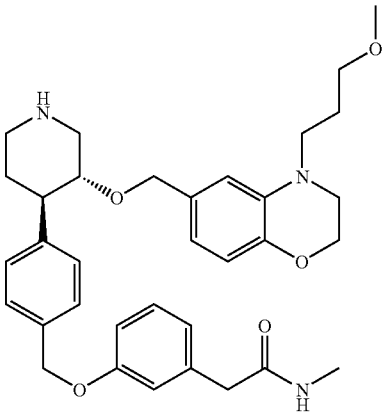
349
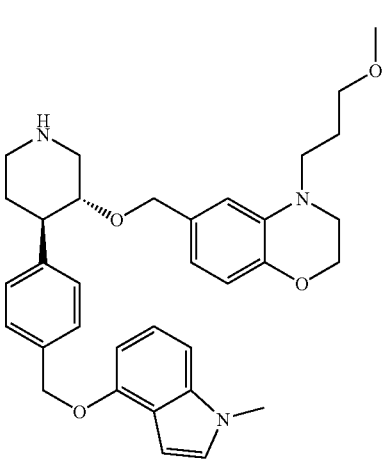

325
350
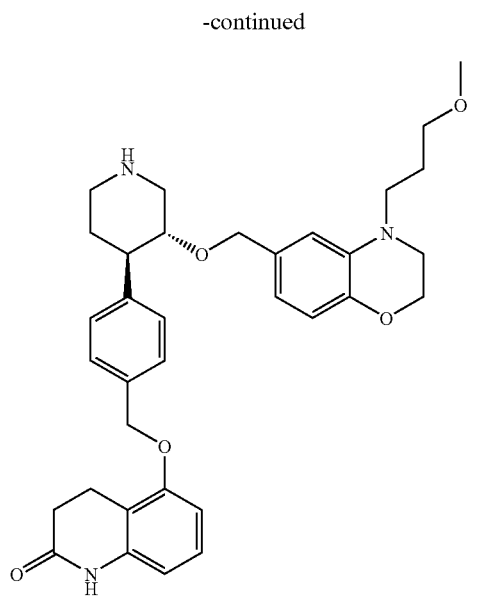
351
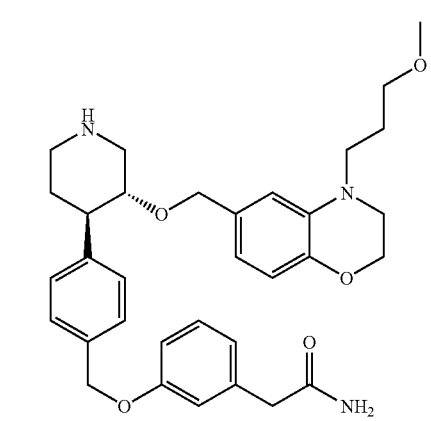
352
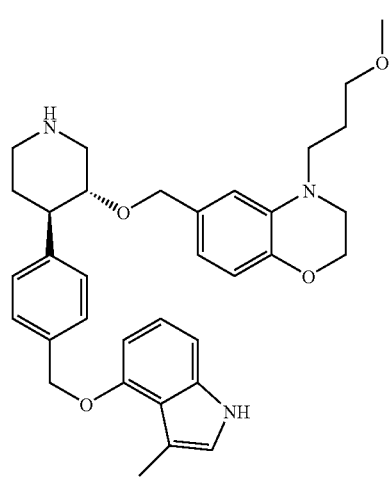
326
353
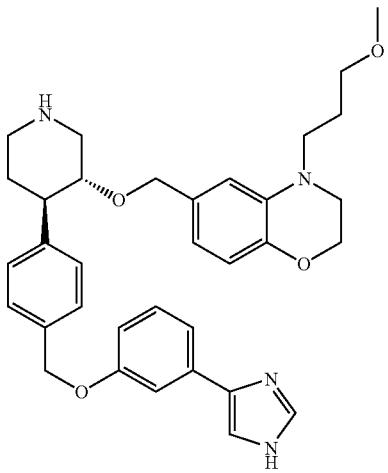
354
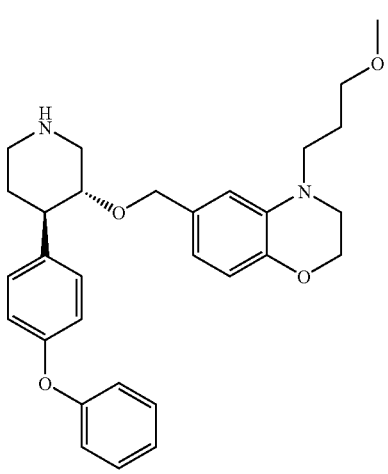
355
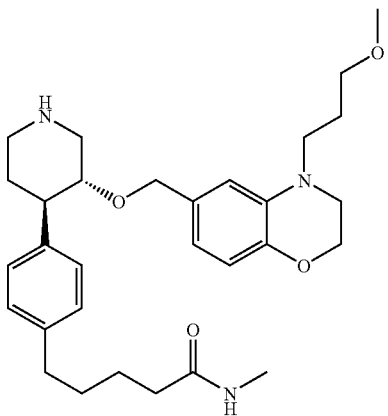

356 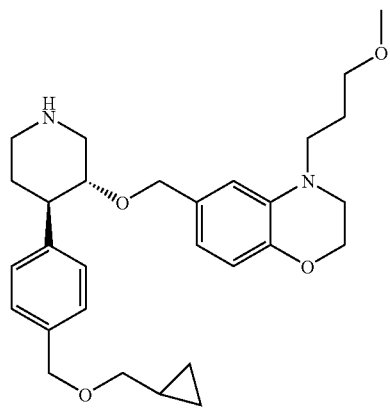

357 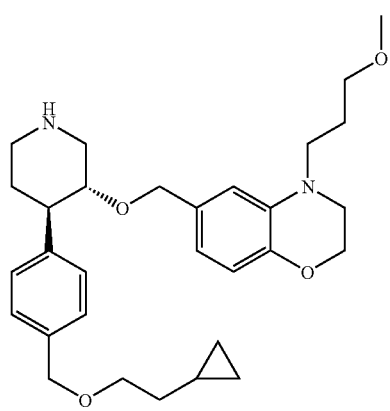

358 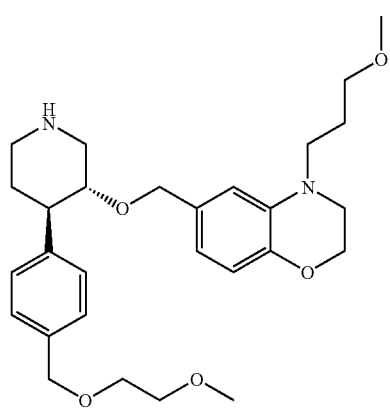

359 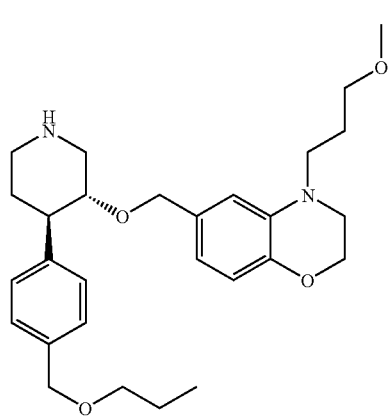

360 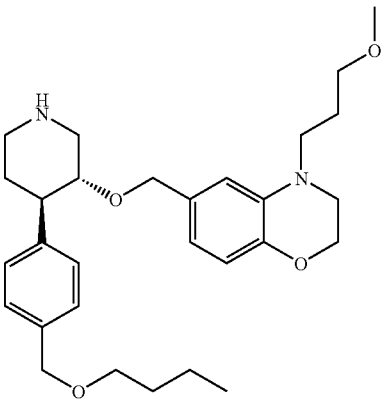

| No. | Appearance | R$_f$ (system) | Rt (method) |
|---|---|---|---|
| 1 | yellowish oil | 0.28 (A) | 4.59 (I) |
| 2 | white foam | 0.44 (B) | 4.20 (I) |
| 3 | yellow oil | 0.25 (B) | 4.65 (I) |
| 5 | yellowish oil | 0.44 (C) | 4.53 (I) |
| 6 | yellowish oil | 0.20 (A) | 4.26 (I) |
| 7 | yellowish oil | 0.29 (A) | 4.67 (I) |
| 8 | yellowish oil | 0.25 (A) | 4.16 (I) |
| 9 | yellowish oil | 0.20 (A) | 4.06 (I) |
| 10 | yellowish oil | 0.15 (A) | 19.39 (II) |
| 11 | yellowish oil | 0.15 (A) | 19.04 (II) |
| 12 | yellow oil | 0.47 (A) | 4.84 (I) |
| 13 | yellowish oil | 0.30 (A) | 4.15 (I) |
| 14 | brown oil | 0.10 (A) | 4.25 (I) |
| 16 | yellowish oil | 0.13 (A) | 4.00 (I) |
| 17 | yellowish oil | 0.16 (A) | 4.59 (I) |
| 18 | yellowish oil | 0.31 (A) | 4.23 (I) |
| 19 | yellowish oil | 0.31 (A) | 4.71 (I) |
| 20 | yellowish oil | 0.20 (A) | 4.67 (I) |
| 21 | yellowish oil | 0.23 (A) | 4.96 (I) |
| 22 | yellowish oil | 0.30 (A) | 4.92 (I) |
| 23 | colourless oil | 0.15 (A) | 4.30 (I) |
| 24 | yellowish oil | 0.11 (A) | 4.16 (I) |
| 25 | colourless oil | 0.29 (A) | 3.99 (I) |
| 26 | colourless oil | 0.14 (A) | 4.07 (I) |
| 27 | colourless oil | 0.20 (A) | 4.49 (I) |
| 28 | colourless oil | 0.18 (A) | 4.27 (I) |
| 29 | yellowish oil | 0.17 (A) | 4.48 (I) |
| 30 | colourless oil | 0.24 (A) | 4.35 (I) |
| 31 | yellowish oil | 0.20 (A) | 4.91 (I) |
| 32 | colourless oil | 0.32 (A) | 4.69 (I) |
| 33 | yellow oil | 0.33 (A) | 4.86 (I) |
| 34 | yellow oil | 0.26 (D) | 3.81 (I) |
| 35 | yellow foam | 0.21 (D) | 4.00 (I) |
| 36 | yellow oil | 0.22 (D) | 3.84 (I) |
| 37 | orange oil | 0.10 (A) | 3.28 (I) |
| 38 | orange oil | 0.10 (A) | 4.27 (I) |
| 39 | colourless oil | 0.10 (A) | 4.43 (I) |
| 40 | colourless oil | 0.08 (A) | 3.66 (I) |
| 41 | colourless oil | 0.24 (A) | 4.48 (I) |
| 42 | colourless oil | 0.15 (A) | 4.33 (I) |
| 43 | yellowish oil | 0.27 (A) | 5.16 (I) |
| 44 | brown oil | 0.24 (A) | 4.36 (I) |
| 45 | yellowish oil | 0.21 (A) | 4.15 (I) |
| 46 | yellowish oil | 0.13 (A) | 2.81 (I) |
| 47 | yellowish solid | 0.32 (U) | 4.26 (I) |
| 48 | yellowish oil | 0.24 (A) | 4.63 (I) |
| 49 | colourless oil | 0.26 (A) | 4.32 (I) |
| 50 | colourless oil | 0.28 (A) | 4.89 (I) |
| 51 | colourless oil | 0.26 (A) | 4.06 (I) |
| 52 | colourless oil | 0.35 (A) | 4.69 (I) |
| 53 | colourless oil | 0.20 (A) | 4.69 (I) |
| 55 | colourless oil | 0.24 (A) | 4.69 (I) |
| 56 | colourless oil | 0.17 (A) | 4.35 (I) |

-continued

| No. | Appearance | R$_f$(system) | Rt (method) |
|---|---|---|---|
| 57 | yellowish oil | 0.23 (A) | 4.13 (I) |
| 58 | yellowish oil | 0.28 (A) | 4.35 (I) |
| 59 | yellowish oil | 0.19 (A) | 4.46 (I) |
| 60 | yellowish oil | 0.30 (A) | 4.77 (I) |
| 61 | yellowish oil | 0.12 (A) | 4.32 (I) |
| 62 | yellow oil | 0.25 (A) | 4.38 (I) |
| 63 | yellow oil | 0.20 (A) | 4.21 (I) |
| 64 | colourless oil | 0.20 (A) | 4.51 (I) |
| 65 | yellowish oil | 0.47 (E) | 4.08 (I) |
| 66 | colourless oil | 0.22 (A) | 3.83 (I) |
| 67 | colourless oil | 0.26 (A) | 4.67 (I) |
| 68 | colourless oil | 0.22 (A) | 4.42 (I) |
| 69 | yellowish oil | 0.14 (A) | 3.90 (I) |
| 70 | yellowish oil | 0.14 (A) | 4.10 (I) |
| 71 | yellowish oil | 0.14 (A) | 4.10 (I) |
| 72 | colourless oil | 0.16 (A) | 4.26 (I) |
| 73 | yellow oil | 0.10 (A) | 4.27 (I) |
| 74 | yellowish oil | 0.10 (A) | 4.31 (I) |
| 75 | yellowish oil | 0.10 (A) | 4.43 (I) |
| 76 | white foam | 0.08 (A) | 4.34 (I) |
| 77 | yellow oil | 0.12 (A) | 4.24 (I) |
| 78 | yellow oil | 0.12 (A) | 4.49 (I) |
| 79 | yellowish oil | 0.29 (A) | 3.75 (I) |
| 80 | yellowish oil | 0.36 (A) | 3.82 (I) |
| 81 | brown foam | 0.20 (A) | 4.52 (I) |
| 82 | yellow oil | 0.35 (A) | 4.44 (I) |
| 83 | colourless oil | 0.25 (A) | 4.41 (I) |
| 84 | colourless oil | 0.32 (A) | 4.46 (I) |
| 85 | colourless oil | 0.10 (A) | 4.33 (I) |
| 86 | yellowish oil | 0.36 (A) | 3.95 (I) |
| 87 | yellowish oil | 0.31 (A) | 4.09 (I) |
| 88 | yellowish oil | 0.35 (A) | 4.31 (I) |
| 89 | yellowish oil | 0.36 (A) | 3.90 (I) |
| 90 | yellowish oil | 0.40 (A) | 4.49 (I) |
| 91 | yellowish oil | 0.43 (A) | 4.28 (I) |
| 92 | yellowish oil | 0.43 (A) | 4.48 (I) |
| 93 | yellowish oil | 0.35 (A) | 4.34 (I) |
| 94 | yellowish oil | 0.19 (A) | 4.39 (I) |
| 95 | yellow oil | 0.16 (A) | 4.44 (I) |
| 96 | yellow oil | 0.08 (A) | 4.56 (I) |
| 97 | yellow oil | 0.23 (A) | 4.27 (I) |
| 98 | yellow oil | 0.20 (A) | 3.46 (I) |
| 99 | yellow foam | 0.04 (A) | 4.34 (I) |
| 100 | yellowish oil | 0.24 (C) | 4.53 (I) |
| 101 | yellowish oil | 0.64 (A) | 4.32 (I) |
| 102 | yellow oil | 0.30 (A) | 4.34 (I) |
| 103 | yellowish oil | 0.42 (A) | 5.00 (I) |
| 104 | yellowish oil | 0.43 (A) | 4.13 (I) |
| 105 | yellowish solid | 0.24 (A) | 3.99 (I) |
| 106 | yellow oil | 0.15 (A) | 4.09 (I) |
| 107 | yellow oil | 0.15 (A) | 3.95 (I) |
| 108 | yellow oil | 0.11 (A) | 4.28 (I) |
| 109 | yellow oil | 0.18 (A) | 4.45 (I) |
| 110 | yellow oil | 0.56 (A) | 4.36 (I) |
| 111 | yellow oil | 0.30 (A) | 4.49 (I) |
| 112 | yellow oil | 0.48 (A) | 4.33 (I) |
| 113 | yellow oil | 0.32 (A) | 4.30 (I) |
| 114 | yellow oil | 0.54 (A) | 4.48 (I) |
| 115 | yellow oil | 0.19 (A) | 4.36 (I) |
| 116 | brown oil | 0.34 (A) | 4.48 (I) |
| 117 | yellowish solid | 0.34 (I) | 4.23 (I) |
| 118 | yellow oil | 0.16 (A) | 4.06 (I) |
| 119 | yellowish oil | 0.27 (A) | 4.13 (I) |
| 120 | yellow oil | 0.14 (A) | 4.30 (I) |
| 121 | yellow oil | 0.29 (A) | 4.70 (I) |
| 122 | yellow oil | 0.20 (A) | 3.14 (I) |
| 123 | yellow oil | 0.27 (A) | 4.48 (I) |
| 124 | yellow oil | 0.54 (A) | 4.43 (I) |
| 125 | yellow oil | 0.15 (A) | 2.89 (I) |
| 126 | yellow oil | 0.28 (A) | 2.94 (I) |
| 127 | yellowish oil | 0.36 (A) | 4.20 (I) |
| 128 | yellowish oil | 0.34 (A) | 4.05 (I) |
| 129 | yellow oil | 0.27 (A) | 4.16 (I) |
| 130 | colourless oil | 0.23 (A) | 4.20 (I) |
| 133 | yellow oil | 0.19 (A) | 4.35 (I) |
| 134 | colourless oil | 0.25 (A) | 3.54 (I) |
| 135 | yellow oil | 0.50 (F) | 4.17 (I) |

-continued

| No. | Appearance | R$_f$(system) | Rt (method) |
|---|---|---|---|
| 136 | yellow oil | 0.08 (A) | 4.04 (I) |
| 137 | yellowish oil | 0.25 (A) | 4.75 (I) |
| 138 | colourless oil | 0.28 (A) | 4.11 (I) |
| 139 | yellowish oil | 0.20 (H) | 4.42 (I) |
| 140 | yellowish oil | 0.17 (A) | 4.54 (I) |
| 141 | yellowish oil | 0.41 (A) | 4.42 (I) |
| 142 | yellowish oil | 0.41 (A) | 4.52 (I) |
| 143 | yellowish oil | 0.22 (A) | 4.76 (I) |
| 144 | yellowish oil | 0.27 (A) | 4.30 (I) |
| 145 | yellowish oil | 0.08 (A) | 4.84 (I) |
| 146 | yellowish oil | 0.33 (G) | 4.70 (I) |
| 147 | yellowish oil | 0.35 (A) | 4.53 (I) |
| 148 | yellowish oil | 0.16 (H) | 17.78 (II) |
| 149 | yellow oil | 0.50 (A) | 4.48 (I) |
| 150 | yellowish oil | 0.26 (H) | 18.03 (II) |
| 151 | yellow oil | 0.23 (A) | 4.52 (I) |
| 152 | yellowish solid | 0.08 (A) | 4.37 (I) |
| 153 | colourless oil | 0.30 (A) | 4.39 (I) |
| 154 | colourless oil | 0.29 (A) | 4.49 (I) |
| 155 | orange oil | 0.28 (A) | 4.20 (I) |
| 156 | orange oil | 0.34 (C) | 4.38 (I) |
| 157 | orange oil | 0.31 (C) | 4.54 (I) |
| 158 | yellow oil | 0.30 (C) | 4.55 (I) |
| 159 | yellow oil | 0.33 (C) | 4.54 (I) |
| 160 | orange oil | 0.20 (A) | 4.47 (I) |
| 161 | orange oil | 0.10 (A) | 4.55 (I) |
| 162 | orange oil | 0.11 (A) | 4.62 (I) |
| 163 | orange oil | 0.07 (A) | 4.81 (I) |
| 164 | yellow oil | 0.23 (A) | 4.81 (I) |
| 166 | yellow oil | 0.29 (C) | 4.34 (I) |
| 167 | yellowish oil | 0.11 (A) | 4.22 (I) |
| 168 | yellowish oil | 0.35 (A) | 3.88 (I) |
| 169 | colourless oil | 0.37 (A) | 4.75 (I) |
| 170 | yellow oil | 0.15 (K) | 2.95 (I) |
| 171 | yellow oil | 0.21 (A) | 3.73 (I) |
| 172 | yellow oil | 0.22 (A) | 3.56 (I) |
| 173 | yellowish oil | 0.55 (A) | 3.84 (I) |
| 174 | yellowish oil | 0.23 (A) | 4.72 (I) |
| 175 | yellowish oil | 0.34 (A) | 3.58 (I) |
| 176 | yellowish oil | 0.32 (A) | 3.82 (I) |
| 177 | yellowish oil | 0.30 (A) | 3.58 (I) |
| 178 | orange oil | 0.30 (A) | 4.10 (I) |
| 179 | yellowish oil | 0.09 (A) | 3.59 (I) |
| 180 | yellow oil | 0.37 (A) | 4.54 (I) |
| 181 | yellow-orange oil | 0.10 (A) | 4.42 (I) |
| 182 | yellow oil | 0.17 (A) | 4.40 (I) |
| 183 | yellow-orange oil | 0.20 (A) | 4.45 (I) |
| 184 | brown-orange oil | 0.33 (A) | 3.72 (I) |
| 185 | yellow foam | 0.19 (A) | 4.14 (I) |
| 186 | yellow foam | 0.32 (A) | 4.33 (I) |
| 187 | yellowish oil | 0.35 (A) | 4.43 (I) |
| 188 | yellowish oil | 0.21 (A) | 4.38 (I) |
| 189 | yellowish oil | 0.18 (A) | 3.50 (I) |
| 190 | yellow oil | 0.10 (P) | 3.85 (I) |
| 191 | yellow oil | 0.20 (P) | 3.13 (I) |
| 192 | brown oil | 0.20 (S) | 3.59 (I) |
| 193 | yellow oil | 0.19 (A) | 4.57 (I) |
| 194 | yellow resin | 0.26 (A) | 4.57 (I) |
| 195 | yellow resin | 0.37 (A) | 4.46 (i) |
| 196 | yellow resin | 0.26 (A) | 4.59 (I) |
| 197 | yellow oil | 0.21 (A) | 4.43 (I) |
| 198 | yellow oil | 0.37 (A) | 3.26 (I) |
| 199 | yellow oil | 0.37 (A) | 4.40 (I) |
| 200 | dark yellow oil | 0.22 (A) | 2.91 (I) |
| 201 | orange oil | 0.17 (A) | 4.84 (I) |
| 202 | brown oil | 0.20 (A) | 4.65 (I) |
| 203 | yellow oil | 0.26 (A) | 3.88 (I) |
| 204 | yellow oil | 0.20 (Q) | 3.23 (I) |
| 205 | brown oil | 0.40 (R) | 3.99 (I) |
| 206 | yellow oil | 0.29 (A) | 4.58 (I) |
| 207 | yellow oil | 0.29 (A) | 4.60 (I) |
| 208 | yellow oil | 0.29 (A) | 4.42 (I) |
| 209 | yellow oil | 0.18 (A) | 4.04 (I) |
| 210 | yellowish oil | 0.30 (A) | 4.66 (I) |
| 211 | yellowish oil | 0.24 (A) | 4.61 (I) |
| 212 | yellowish oil | 0.28 (A) | 4.74 (I) |
| 213 | yellow oil | 0.26 (A) | 3.75 (I) |

-continued

| No. | Appearance | R_f (system) | Rt (method) |
|---|---|---|---|
| 214 | yellow oil | 0.27 (A) | 4.38 (I) |
| 215 | yellow oil | 0.25 (A) | 3.89 (I) |
| 216 | yellow foam | 0.20 (A) | 3.75 (I) |
| 217 | yellow resin | 0.20 (A) | 3.27 (I) |
| 218 | white foam | 0.33 (A) | 4.33 (I) |
| 219 | yellow oil | 0.18 (A) | 3.36 (I) |
| 220 | yellowish oil | 0.25 (A) | 3.14 (I) |
| 221 | colourless oil | 0.22 (A) | 3.30 (I) |
| 222 | colourless oil | 0.23 (A) | 3.13 (I) |
| 223 | yellowish oil | 0.22 (A) | 4.29 (I) |
| 224 | yellowish oil | 0.21 (A) | 4.19 (I) |
| 225 | yellowish oil | 0.12 (A) | 4.23 (I) |
| 226 | yellowish oil | 0.60 (N) | 4.58 (I) |
| 227 | yellowish oil | 0.20 (A) | 4.47 (I) |
| 228 | yellowish oil | 0.22 (A) | 4.31 (I) |
| 229 | orange oil | 0.30 (A) | 3.74 (I) |
| 230 | orange oil | 0.35 (A) | 3.83 (I) |
| 231 | orange oil | 0.37 (A) | 3.85 (I) |
| 232 | yellowish oil | 0.16 (A) | 3.85 (I) |
| 233 | yellowish oil | 0.21 (A) | 3.88 (I) |
| 234 | yellowish oil | 0.3 (T) | 3.42 (I) |
| 235 | yellowish oil | 0.14 (A) | 3.30 (I) |
| 236 | yellowish oil | 0.25 (A) | 3.30 (I) |
| 237 | yellow oil | 0.27 (A) | 3.45 (I) |
| 238 | yellow oil | 0.22 (A) | 3.45 (I) |
| 239 | yellowish oil | 0.37 (J) | 4.18 (I) |
| 241 | yellow oil | 0.36 (A) | 4.12 (I) |
| 242 | yellow oil | 0.25 (L) | 3.24 (I) |
| 243 | yellow oil | 0.10 (D) | 3.43 (I) |
| 244 | yellow foam | 0.05 (M) | 3.31 (I) |
| 245 | yellow oil | 0.27 (A) | 4.80 (I) |
| 246 | colourless oil | 0.10 (O) | 3.32 (I) |
| 247 | white foam | 0.23 (A) | 3.74 (I) |
| 248 | yellow resin | 0.11 (A) | 3.14 (I) |
| 249 | yellow oil | 0.39 (I) | 3.26 (I) |
| 250 | colourless resin | 0.09 (A) | 3.53 (I) |
| 251 | yellowish oil | 0.27 (A) | 4.25 (I) |
| 252 | colourless oil | 0.16 (A) | 4.02 (I) |
| 253 | yellow oil | 0.15 (Q) | 4.45 (I) |
| 254 | yellow oil | 0.16 (A) | 4.16 (I) |
| 255 | yellow oil | 0.15 (A) | 3.12 (I) |
| 256 | colourless resin | 0.34 (A) | 3.93 (I) |
| 257 | colourless foam | 0.15 (A) | 3.74 (I) |
| 258 | brown-yellow resin | 0.20 (A) | 2.91 (I) |
| 259 | yellowish oil | 0.18 (A) | 4.33 (I) |
| 260 | yellowish oil | 0.19 (A) | 4.46 (I) |
| 261 | yellowish oil | 0.11 (C) | 4.29 (I) |
| 262 | yellow resin | 0.20 (A) | 2.87 (I) |
| 263 | yellowish oil | 0.20 (A) | 3.28 (I) |
| 264 | colourless oil | 0.28 (A) | 4.18 (I) |
| 265 | yellowish oil | 0.37 (A) | 3.77 (I) |
| 266 | yellowish oil | 0.29 (A) | 2.76 (I) |
| 267 | colourless oil | 0.33 (A) | 4.41 (I) |
| 268 | yellowish oil | 0.09 (C) | 4.15 (I) |
| 269 | yellowish oil | 0.09 (C) | 3.34 (I) |
| 270 | yellowish oil | 0.27 (C) | 4.37 (I) |
| 271 | brown resin | 0.15 (A) | 4.02 (I) |
| 272 | yellowish oil | 0.07 (C) | 3.35 (I) |
| 273 | yellowish oil | 0.21 (A) | 4.55 (I) |
| 274 | yellow oil | 0.22 (A) | 3.37 (I) |
| 275 | yellowish solid | 0.15 (A) | 3.63 (I) |
| 276 | colourless oil | 0.26 (A) | 3.32 (I) |
| 277 | yellowish oil | 0.14 (C) | 4.34 (I) |
| 278 | yellowish oil | 0.34 (A) | 4.35 (I) |
| 279 | yellowish oil | 0.38 (A) | 4.34 (I) |
| 280 | yellowish oil | 0.39 (A) | 4.44 (I) |
| 281 | yellowish oil | 0.25 (A) | 4.50 (I) |
| 282 | yellow oil | 0.20 (A) | 4.46 (I) |
| 283 | yellow oil | 0.20 (A) | 4.47 (I) |
| 284 | yellow oil | 0.20 (A) | 4.48 (I) |
| 285 | yellowish-beige oil | 0.23 (A) | 4.40 (I) |
| 286 | yellow oil | 0.19 (A) | 4.21 (I) |
| 287 | yellow oil | 0.15 (A) | 4.62 (I) |
| 288 | yellowish oil | 0.23 (A) | 4.15 (I) |
| 289 | yellowish-beige oil | 0.23 (A) | 4.34 (I) |
| 290 | yellowish-beige oil | 0.23 (A) | 4.43 (I) |
| 291 | yellowish oil | 0.11 (C) | 3.95 (I) |
| 292 | yellowish oil | 0.18 (C) | 4.06 (I) |
| 293 | colourless oil | 0.14 (A) | 3.39 (I) |
| 294 | colourless oil | 0.13 (A) | 3.22 (I) |
| 295 | orange oil | 0.06 (A) | 3.27 (I) |
| 296 | yellowish oil | 0.16 (A) | 3.58 (I) |
| 297 | yellowish oil | 0.17 (C) | 4.13 (I) |
| 298 | yellowish oil | 0.14 (C) | 3.49 (I) |
| 299 | colourless oil | 0.13 (C) | 4.04 (I) |
| 300 | yellow oil | 0.14 (C) | 3.72 (I) |
| 301 | yellow resin | 0.10 (A) | 4.03 (I) |
| 302 | colourless oil | 0.20 (A) | 3.36 (I) |
| 303 | yellowish oil | 0.11 (C) | 4.43 (I) |
| 304 | yellowish oil | 0.25 (A) | 15.21 (II) |
| 305 | yellowish oil | 0.23 (A) | 13.97 (II) |
| 306 | yellow oil | 0.25 (A) | 4.70 (I) |
| 307 | yellowish oil | 0.34 (A) | 3.44 (I) |
| 308 | colourless oil | 0.19 (C) | 3.94 (I) |
| 309 | yellowish oil | 0.13 (C) | 4.42 (I) |
| 310 | yellowish oil | 0.14 (C) | 3.83 (I) |
| 311 | yellowish oil | 0.31 (A) | 3.54 (I) |
| 312 | yellowish oil | 0.41 (A) | 4.61 (I) |
| 313 | yellow oil | 0.14 (A) | 3.44 (I) |
| 314 | colourless oil | 0.18 (A) | 2.68 (I) |
| 315 | colourless oil | 0.20 (C) | 3.52 (I) |
| 316 | yellowish oil | 0.18 (I) | 3.66 (I) |
| 317 | yellowish oil | 0.35 (A) | 3.75 (I) |
| 318 | yellowish oil | 0.33 (A) | 20.17 (II) |
| 319 | yellowish oil | 0.31 (A) | 19.20 (II) |
| 320 | yellow oil | 0.29 (C) | 4.48 (I) |
| 321 | orange oil | 0.21 (C) | 4.56 (I) |
| 322 | yellowish oil | 0.11 (C) | 4.21 (I) |
| 323 | yellowish oil | 0.06 (C) | 2.62 (I) |
| 324 | yellow-orange oil | 0.25 (A) | 3.56 (I) |
| 325 | yellowish oil | 0.05 (C) | 2.70 (I) |
| 326 | yellow-orange oil | 0.35 (A) | 3.96 (I) |
| 327 | yellowish oil | 0.17 (C) | 4.45 (I) |
| 328 | yellowish oil | 0.38 (A) | 16.76 (II) |
| 329 | yellowish oil | 0.41 (A) | 15.37 (II) |
| 330 | yellowish oil | 0.18 (C) | 4.13 (I) |
| 331 | yellow-orange oil | 0.30 (C) | 4.49 (I) |
| 332 | yellow-orange oil | 0.30 (C) | 4.85 (I) |
| 333 | yellowish oil | 0.15 (I) | 3.81 (I) |
| 334 | orange oil | 0.18 (C) | 4.79 (I) |
| 335 | yellowish oil | 0.21 (C) | 4.53 (I) |
| 336 | yellowish oil | 0.27 (C) | 4.44 (I) |
| 337 | yellowish oil | 0.27 (C) | 4.49 (I) |
| 338 | yellowish oil | 0.12 (C) | 4.47 (I) |
| 339 | yellowish oil | 0.13 (C) | 4.28 (I) |
| 340 | colourless oil | 0.30 (A) | 3.51 (I) |
| 341 | yellow oil | 0.23 (A) | 4.14 (I) |
| 342 | orange oil | 0.25 (C) | 4.73 (I) |
| 343 | orange oil | 0.25 (C) | 4.76 (I) |
| 344 | orange oil | 0.14 (C) | 4.29 (I) |
| 345 | yellowish oil | 0.29 (A) | 3.15 (I) |
| 346 | white foam | 0.13 (C) | 4.05 (I) |
| 347 | colourless oil | 0.10 (C) | 3.64 (I) |
| 348 | colourless oil | 0.25 (A) | 3.41 (I) |
| 349 | orange oil | 0.33 (S) | 4.51 (I) |
| 350 | colourless foam | 0.18 (C) | 3.62 (I) |
| 351 | yellowish oil | 0.27 (A) | 3.44 (I) |
| 352 | white solid | 0.19 (C) | 4.25 (I) |
| 353 | white solid | 0.13 (A) | 3.25 (I) |
| 354 | colourless resin | 0.10 (C) | 4.46 (I) |
| 355 | yellowish oil | 0.23 (C) | 3.35 (I) |
| 356 | yellowish oil | 0.30 (A) | 4.04 (I) |
| 357 | yellowish oil | 0.32 (A) | 4.40 (I) |
| 358 | yellowish oil | 0.39 (A) | 3.46 (I) |
| 359 | yellowish oil | 0.39 (V) | 4.56 (I) |
| 360 | yellowish oil | 0.39 (V) | 4.28 (I) |

Thin-Layer Chromatography Eluent Systems:

| | | |
|---|---|---|
| A | dichloromethane-methanol-ammonia conc. 25% | = 200:20:1 |
| B | dichloromethane-methanol-ammonia conc. 25% | = 200:20:0.5 |
| C | dichloromethane-methanol-ammonia conc. 25% | = 200:10:1 |
| D | dichloromethane-methanol-ammonia conc. 25% | = 90:10:1 |
| E | dichloromethane-methanol-water-acetic acid conc. | = 750:270:50:5 |
| F | dichloromethane-methanol | = 1:4 |
| G | dichloromethane-methanol-ammonia conc. 25% | = 200:5:1 |
| H | dichloromethane-methanol | = 9:1 |
| I | dichloromethane-methanol-ammonia conc. 25% | = 40:10:1 |
| J | dichloromethane-methanol-ammonia conc. 25% | = 80:10:1 |
| K | dichloromethane-methanol-ammonia conc. 25% | = 60:10:1 |
| L | dichloromethane-methanol-ammonia conc. 25% | = 90:20:1 |
| M | dichloromethane-methanol-ammonia conc. 25% | = 200:40:1 |
| N | dichloromethane-methanol-ammonia conc. 25% | = 200:20:1 + 10% methanol |
| O | dichloromethane-methanol-ammonia conc. 25% | = 200:100:2 |
| P | dichloromethane-methanol-ammonia conc. 25% | = 95:5:1 |
| Q | dichloromethane-methanol-ammonia conc. 25% | = 200:15:2 |
| R | dichloromethane-methanol-ammonia conc. 25% | = 200:20:2 |
| S | dichloromethane-methanol-ammonia conc. 25% | = 200:15:1 |
| T | dichloromethane-methanol-ammonia conc. 25% | = 200:50:1 |
| U | dichloromethane-methanol-water-acetic acid conc. | = 150:54:10:1 |
| V | dichloromethane-methanol-ammonia conc. 25% | = 200:10:0.5 |

The invention claimed is:
1. A compound of the formula (I)

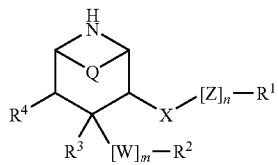

(I)

where
R$^1$ is substituted or unsubstituted dihydro-2H-benzo[1,4]oxazinyl;
R$^2$ is phenyl substituted by 1-3 halogen, hydroxyl, cyano, trifluoromethyl, $C_{1-6}$-alkyl, halo-$C_{1-6}$-alkyl, hydroxy-$C_{1-6}$-alkyl, $C_{1-6}$-alkoxy-$C_{1-6}$-alkyl, cyano-$C_{1-6}$-alkyl, carboxy-$C_{1-6}$-alkyl, $C_{1-6}$-alkanoyloxy-$C_{1-6}$-alkyl, $C_{1-6}$-alkoxycarbonyloxy-$C_{1-6}$-alkyl, $C_{1-6}$-alkoxycarbonyl, or $C_{1-6}$-alkoxy groups, or a $C_{1-6}$-alkylenedioxy group, and/or by an L1-T1-L2-T2-L3-T3-L4-T4-L5-U radical;
L1, L2, L3, L4 and L5 are each independently a bond, $C_{1-8}$-alkylene, $C_{2-8}$-alkenylene or $C_{2-8}$-alkynylene, or are absent;
T1, T2, T3 and T4 are each independently
(a) a bond, or are absent, or are one of the groups
(b) —CH(OH)—
(c) —CH(OR$^6$)—
(d) —CH(NR$^5$R$^6$)—
(e) —CO—
(f) —CR$^7$R$^8$—
(g) —O— or —NR$^6$—
(h) —S(O)$_{0-2}$—
(I) —SO$_2$NR$^6$—
(j) —NR$^6$SO$_2$—
(k) —CONR$^6$—
(l) —NR$^6$CO—
(m) —O—CO—
(n) —CO—O—
(o) —O—CO—O—
(p) —O—CO—NR$^6$—
(q) —N(R$^6$)—CO—N(R$^6$)—
(r) —N(R$^6$)—CO—O—
(s) pyrrolidinylene, piperidinylene or piperazinylene
(t) —C(R$^{11}$)(R$^{12}$)—,
where the bonds starting from (b)-(t) lead to a saturated or aromatic carbon atom of the adjacent group if the bond starts from a heteroatom, and where not more than two (b)-(f) groups, three (g)-(h) groups and one (i)-(t) group are present;
R$^3$ is hydroxyl, $C_{1-6}$-alkoxy or $C_{2-6}$-alkenyloxy;
R$^4$ is hydrogen;
R$^5$ and R$^6$ are each independently hydrogen, $C_{1-6}$-alkyl, $C_{2-6}$-alkenyl, aryl-$C_{1-6}$-alkyl or acyl, or, together with the nitrogen atom to which they are bonded, are a 5- or 6-membered heterocyclic ring which may contain an additional nitrogen, oxygen or sulphur atom or a —SO— or —SO$_2$— group, and the additional nitrogen atom may optionally be substituted by $C_{1-6}$-alkyl radicals;
R$^7$ and R$^8$, together with the carbon atom to which they are bonded, are a 3-7-membered ring which may contain one or two —O— or —S— atoms or —SO— or —SO$_2$— groups;
R$^9$ is hydrogen, $C_{1-6}$-alkyl, $C_{1-6}$-alkoxy-$C_{1-6}$-alkyl, acyl or arylalkyl;
R$^{10}$ is carboxyalkyl, alkoxycarbonylalkyl, alkyl or hydrogen;
R$^{11}$ is hydrogen or $C_{1-6}$-alkyl;
R$^{12}$ is hydrogen or $C_{1-6}$-alkyl;
U is hydrogen, $C_{1-6}$-alkyl, $C_{3-8}$-cycloalkyl, cyano, optionally substituted $C_{3-8}$-cycloalkyl, aryl, or heterocyclyl;
Q is absent;
X is a bond, oxygen or sulphur, or is a >CH—R$^{11}$, >CHOR$^9$, —O—CO—, >CO, >C=NOR$^{10}$, —O—CHR$^{11}$— or —O—CHR$^{11}$—CO—NR$^9$— group and the bond starting from an oxygen or sulphur atom leads to a saturated carbon atom of the Z group or to R$^1$;
W is oxygen or sulphur;
Z is $C_{1-6}$-alkylene, $C_{2-6}$-alkenylene, hydroxy-$C_{1-6}$-alkylidene, —O—, —S—, —O-alk-, —S-alk-, -alk-O—, -alk-S— or -alk-NR$^9$—, where alk is $C_{1-6}$-alkylene; and where
(a) if Z is —O— or —S—, X is >CH—R$^{11}$ and either R$^2$ contains an L1-T1-L2-T2-L3-T3-L4-T4-L5-U substituent or R$^4$ is a substituent other than hydrogen as defined above;
(b) if Z is —O-alk- or —S-alk-, X is >CH—R$^{11}$; and
(c) if X is a bond, Z is $C_{2-6}$-alkenylene, -alk-O— or -alk-S—,
n is 0 or 1;
m is 0;
or a pharmaceutically acceptable salt thereof.
2. A compound according to claim 1, of the formula (IA)

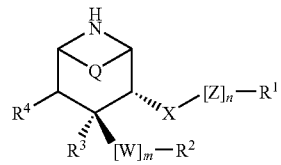

IA where R$^1$, R$^2$, R$^3$, R$^4$, Q, W, X, Z, n and m are each as defined for the compounds of the formulae (I) according to claim 11.

3. A compound according to claim 1 where
   $R^2$ is phenyl substituted by halogen, hydroxyl, cyano, trifluoromethyl, $C_{1-6}$-alkyl, halo-$C_{1-6}$-alkyl, hydroxy-$C_{1-6}$-alkyl, $C_{1-6}$-alkoxy-$C_{1-6}$-alkyl, cyano-$C_{1-6}$-alkyl, carboxy-$C_{1-6}$-alkyl, $C_{1-6}$-alkanoyloxy-$C_{1-6}$-alkyl, $C_{1-6}$-alkoxycarbonyloxy-$C_{1-6}$-alkyl, $C_{1-6}$-alkoxycarbonyl, $C_{1-6}$-alkoxy, $C_{1-6}$-alkylenedioxy, or by an L1-T1-L2-T2-L3-T3-L4-T4-L5-U radical; or naphthyl or acenaphthyl;
   L1, L2, L3, L4 and L5 are each independently a bond, $C_{1-8}$-alkylene, $C_{2-8}$-alkenylene or $C_{2-8}$-alkynylene, or are absent;
   T1, T2, T3 and T4 are each independently
   (a) a bond, or are absent, or are one of the groups
   (b) —CH(OH)—
   (c) —CH(OR$^6$)—
   (d) —CH(NR$^5$R$^6$)—
   (e) —CO—
   (f) —CR$^7$R$^8$—
   (g) —O— or —NR$^6$—
   (h) —S(O)$_{0-2}$—
   (I) —SO$_2$NR$^6$—
   (j) —NR$^6$SO$_2$—
   (k) —CONR$^6$—
   (l) —NR$^6$CO—
   (m) —O—CO—
   (n) —CO—O—
   (o) —O—CO—O—
   (p) —O—CO—NR$^6$—
   (q) —N(R$^6$)—CO—N(R$^6$)—
   (r) —N(R$^6$)—CO—O—
   (s) pyrrolidinylene, piperidinylene or piperazinylene
   (t) —C(R$^{11}$)(R$^{12}$)—,
   where the bonds starting from (b)-(t) lead to a saturated or aromatic carbon atom of the adjacent group if the bond starts from a heteroatom, and where not more than two (b)-(f) groups, three (g)-(h) groups and one (i)-(t) group are present;
   $R^3$ is hydroxyl, $C_{1-6}$-alkoxy or $C_{2-6}$-alkenyloxy;
   $R^4$ is hydrogen;
   $R^5$ and $R^6$ are each independently hydrogen, $C_{1-6}$-alkyl or acyl, or, together with the nitrogen atom to which they are bonded, are a 5- or 6-membered heterocyclic ring which may contain an additional nitrogen, oxygen or sulphur atom;
   $R^7$ and $R^8$, together with the carbon atom to which they are bonded, are a 3-7-membered ring which may contain one or two —O— or —S— atoms;
   $R^9$ is hydrogen, $C_{1-6}$-alkyl, acyl or arylalkyl;
   U is hydrogen, $C_{1-6}$-alkyl, $C_{3-8}$-cycloalkyl, cyano, aryl or heterocyclyl;
   Q is absent;
   X is oxygen, sulphur or a >CH$_2$, >CHOR$^9$, —O—CO—, >CO or —O—CH—R$^{11}$—CO—NR$^9$— group;
   W is oxygen or sulphur if $R^3$ is hydrogen;
   Z is $C_{1-6}$-alkylene or -alk-O—;
   n is 0 or 1;
   m is 0;
   or a pharmaceutically acceptable salt thereof.

4. A compound according to claim 1, wherein $R^1$ is 3,4-dihydro-2H-benzo[1,4]oxazinyl which is substituted by at least one substituent selected from $C_{1-6}$-alkoxy-$C_{1-6}$-alkoxy, $C_{1-6}$-alkoxy-$C_{1-6}$-alkyl, N-acetyl-$C_{1-6}$-alkoxy-$C_{1-6}$-alkylamino, $C_{1-6}$-alkanoylamido-$C_{1-6}$-alkyl, N—$C_{1-6}$-alkyl-$C_{1-6}$-alkanoylamido-$C_{1-6}$-alkyl, $C_{1-6}$-alkoxy-$C_{1-6}$-alkoxy-$C_{1-6}$-alkyl, triazol-1-yl-$C_{1-6}$-alkyl, tetrazol-1-yl-$C_{1-6}$-alkyl, tetrazol-2-yl-$C_{1-6}$-alkyl, tetrazol-5-yl-$C_{1-6}$-alkyl, $C_{1-6}$-alkoxycarboxyl-$C_{1-6}$-alkyl, pyrrolidinonyl-$C_{1-6}$-alkyl, imidazolyl-$C_{1-6}$-alkyl, cyano-$C_{1-6}$-alkyl, carboxy-$C_{1-6}$-alkyl, carboxy-$C_{1-6}$-alkoxy, $C_{1-6}$-alkoxycarbonyl-$C_{0-6}$-alkyl, $C_{1-6}$-alkylsulphonamidyl-$C_{1-6}$-alkyl, $C_{1-6}$-alkoxy-$C_{1-6}$-alkanoylamido, $C_{1-6}$-alkoxy-$C_{1-6}$-alkanoylamido-$C_{1-6}$-alkyl, N—($C_{1-6}$-alkyl)-$C_{1-6}$-alkoxy-$C_{1-6}$-alkanoylamido, N—$C_{1-6}$-alkylcarbamoyl-$C_{1-6}$-alkyl, $C_{3-8}$-cycloalkanoylamido-$C_{1-6}$-alkyl, $C_{1-6}$-alkylaminocarbonylamino-$C_{1-6}$-alkyl, $C_{1-6}$-alkanoylamidomethylpyrrolidinyl, N—($C_{1-6}$-alkoxy-$C_{1-6}$-alkyl)carbamoyl, N—($C_{1-6}$-alkoxy-$C_{1-6}$-alkyl)-N—($C_{1-6}$-alkyl)carbamoyl, N—($C_{1-6}$-alkoxy-$C_{1-6}$-alkyl)imidazol-2-yl, hydroxy-$C_{1-6}$-alkyl, hydroxy-$C_{1-6}$-alkoxy, hydroxy-$C_{1-6}$-alkoxy-$C_{1-6}$-alkyl, $C_{1-6}$-alkoxycarbonylamido-$C_{1-6}$-alkyl, amino-$C_{1-6}$-alkyl and $C_{1-6}$-alkylamino-$C_{1-6}$-alkyl.

5. A compound according to claim 1, wherein $R^2$ is phenyl substituted by $C_{1-6}$-alkoxybenzyloxy-$C_{1-6}$-alkoxy, $C_{1-6}$-alkoxyphenyl-$C_{1-6}$-alkoxy-$C_{1-6}$-alkoxy, $C_{1-6}$-alkylphenoxy-$C_{1-6}$-alkoxy, halobenzyloxy-$C_{1-6}$-alkoxy, halophenoxy-$C_{1-6}$-alkoxy, halophenoxy-$C_{1-6}$-alkoxy-$C_{1-6}$-alkyl, N-(halophenyl)pyrrolidin-3-yloxy or indol-4-yloxy-$C_{1-6}$-alkyl.

6. A compound according to claim 1, wherein X is oxygen, —O—CH$_2$—CO—NH—, —O—CH$_2$—CO—N(CH$_3$)— or —O—CH(CH$_3$)—CO—NH—.

7. A compound according to claim 1, wherein Z is methylene, —(CH$_2$)$_2$—O— or —CH(CH$_3$)—.

8. A pharmaceutical composition comprising a compound of the formula (I) or salt according to claim 1, and a pharmaceutically inert excipient.

9. A method for treatment of hypertension, heart failure, glaucoma, cardiac infarction, kidney failure or restenoses, which comprises administering an effective amount of a compound or salt according to claim 1 to a patient in need thereof.

10. A method for the preparation of a pharmaceutical composition, which comprises admixing a compound or salt according to claim 1 with a pharmaceutically inert excipient.

11. A compound according to claim 2 where
   $R^2$ is phenyl substituted by halogen, hydroxyl, cyano, trifluoromethyl, $C_{1-6}$-alkyl, halo-$C_{1-6}$-alkyl, hydroxy-$C_{1-6}$-alkyl, $C_{1-6}$-alkoxy-$C_{1-6}$-alkyl, cyano-$C_{1-6}$-alkyl, carboxy-$C_{1-6}$-alkyl, carboxy-$C_{1-6}$-alkanoyloxy-$C_{1-6}$-alkyl, $C_{1-6}$-alkoxycarbonyloxy-$C_{1-6}$-alkyl, $C_{1-6}$-alkoxycarbonyl, $C_{1-6}$-alkoxy, $C_{1-6}$-alkylenedioxy, or by an L1-T1-L2-T2-L3-T3-L4-T4-L5-U radical; or naphthyl or acenaphthyl;
   L1, L2, L3, L4 and L5 are each independently a bond, $C_{1-8}$-alkylene, $C_{2-8}$-alkenylene or $C_{2-8}$-alkynylene, or are absent;
   T1, T2, T3 and T4 are each independently
   (a) a bond, or are absent, or are one of the groups
   (b) —CH(OH)—
   (c) —CH(OR$^6$)—
   (d) —CH(NR$^5$R$^6$)—
   (e) —CO—
   (f) —CR$^7$R$^8$—
   (g) —O— or —NR$^6$—
   (h) —S(O)$_{0-2}$—
   (I) —SO$_2$NR$^6$—
   (j) —NR$^6$SO$_2$—
   (k) —CONR$^6$—
   (l) —NR$^6$CO—
   (m) —O—CO—
   (n) —CO—O—
   (o) —O—CO—O—
   (p) —O—CO—NR$^6$—
   (q) —N(R$^6$)—CO—N(R$^6$)—
   (r) —N(R$^6$)—CO—O—

(s) pyrrolidinylene, piperidinylene or piperazinylene
(t) —C(R$^1$)(R$^{12}$)—,
where the bonds starting from (b)-(t) lead to a saturated or aromatic carbon atom of the adjacent group if the bond starts from a heteroatom, and where not more than two (b)-(f) groups, three (g)-(h) groups and one (i)-(t) group are present;
R$^3$ is hydroxyl, C$_{1-6}$-alkoxy or C$_{2-6}$-alkenyloxy;
R$^4$ is hydrogen;
R$^5$ and R$^6$ are each independently hydrogen, C$_{1-6}$-alkyl or acyl, or, together with the nitrogen atom to which they are bonded, are a 5- or 6-membered heterocyclic ring which may contain an additional nitrogen, oxygen or sulphur atom;
R$^7$ and R$^8$, together with the carbon atom to which they are bonded, are a 3-7-membered ring which may contain one or two —O— or —S— atoms;
R$^9$ is hydrogen, C$_{1-6}$-alkyl, acyl or arylalkyl;
U is hydrogen, C$_{1-6}$-alkyl, C$_{3-8}$-cycloalkyl, cyano, aryl or heterocyclyl;
Q is absent;
X is oxygen, sulphur or a >CH$_2$, >CHOR$^9$, —O—CO—, >CO or —O—CH—R$^{11}$—CO—NR$^9$— group;
W is oxygen or sulphur if R$^3$ is hydrogen;
Z is C$_{1-6}$-alkylene or -alk-O—;
n is 0 or 1;
m is 0;
or a pharmaceutically acceptable salt thereof.

12. A pharmaceutical composition comprising a compound of the formula (IA) or salt according to claim 2, and a pharmaceutically inert excipient.

13. A method for treatment of hypertension, heart failure, glaucoma, cardiac infarction, kidney failure or restenoses, which comprises administering an effective amount of a compound or salt according to claim 2 to a patient in need thereof.

14. A method for the preparation of a pharmaceutical composition, which comprises admixing a compound or salt according to claim 2 with a pharmaceutically inert excipient.

* * * * *